US010544191B2

(12) United States Patent
Fasan

(10) Patent No.: US 10,544,191 B2
(45) **Date of Patent: *Jan. 28, 2020**

(54) METHODS AND COMPOSITIONS FOR RIBOSOMAL SYNTHESIS OF MACROCYCLIC PEPTIDES

(71) Applicant: University of Rochester, Rochester, NY (US)

(72) Inventor: Rudi Fasan, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/107,387

(22) PCT Filed: Dec. 23, 2014

(86) PCT No.: PCT/US2014/072016

§ 371 (c)(1),
(2) Date: Jun. 22, 2016

(87) PCT Pub. No.: WO2015/100277

PCT Pub. Date: Jul. 2, 2015

(65) Prior Publication Data

US 2016/0355552 A1 Dec. 8, 2016

Related U.S. Application Data

(60) Provisional application No. 61/920,181, filed on Dec. 23, 2013.

(51) Int. Cl.
*C07K 7/54* (2006.01)
*C12P 21/02* (2006.01)

(52) U.S. Cl.
CPC ................ *C07K 7/54* (2013.01); *C12P 21/02* (2013.01)

(58) Field of Classification Search
None
See application file for complete search history.

(56) References Cited

U.S. PATENT DOCUMENTS

| | | | | |
|---|---|---|---|---|
| 5,525,488 A * | 6/1996 | Mason | C07K 14/575 | 435/252.3 |
| 7,378,263 B2 * | 5/2008 | Schultz | C12N 9/93 | 435/15 |
| 7,514,210 B2 | 4/2009 | Holliger et al. | | |
| 8,986,953 B2 * | 3/2015 | Fasan | C07K 1/026 | 435/69.1 |
| 2003/0129686 A1 | 7/2003 | Glass et al. | | |
| 2006/0166319 A1 * | 7/2006 | Chan | C12N 9/93 | 435/69.1 |
| 2009/0004105 A1 | 1/2009 | Cheng et al. | | |
| 2013/0330773 A1 | 12/2013 | Fasan et al. | | |

FOREIGN PATENT DOCUMENTS

| | | |
|---|---|---|
| EP | 2141175 A1 | 1/2010 |
| EP | 2647721 A1 | 10/2013 |

OTHER PUBLICATIONS

Frost et al., "Design, synthesis, and diversification of ribosomally derived peptide macrocycles" 23 Current Opinion in Structural Biology 571-580 (Jul. 12, 2013).*

Smith et al. "Modular Assembly of Macrocyclic Organo-Peptide Hybrids Using Synthetic and Genetically Encoded Precursors." 50 Angewandte Chemi 5075-5080 (2011).*

Frost John R., et al., "Macrocyclization of Organo-Peptide Hybrids through a Dual Bio-orthogonal Ligation: Insights from Structure-Reactivy Studies," ChemBioChem, Jan. 2013, vol. 14, Issue 1, (pp. 147-160).

ISA/US International Search Report and Written Opinion of the International Searching Authority for corresponding International Applicaition No. PCT/US2014/072016 dated Jun. 18, 2015 (16 pages).

Toshimasa Hamamoto et al, "Synthesis of a cyclic peptide/protein using the NEXT-A reaction followed by cyclization", Chemical Communications, vol. 47, No. 32, (Jan. 1, 2011), p. 9116.

Smith, Jessica, et al., "Emerging Strategies to Access Peptide Macrocylces from Genetically Encoded Polypeptides", The Journal of Organic Chemistry, vol. 78, No. 8, (Mar. 21, 2013) pp. 3525-3531.

Bionda, Nina, et al., "Bioinspired Strategy for the Ribosomal Synthesis of Thioether-Bridged Macrocyclic Peptides in Bacteria", ACS Chemical Biology, vol. 9, No. 9, (Jul. 31, 2014), pp. 2008-2013.

European Search Report for corresponding International Application No. PCT/2014/072016 dated Jun. 30, 2017 (10 pages).

* cited by examiner

*Primary Examiner* — Nancy J Leith
(74) *Attorney, Agent, or Firm* — Harris Beach PLLC; Laura W. Smalley

(57) ABSTRACT

Methods and compositions are provided for generating macrocyclic peptides from genetically encoded, ribosomally produced polypeptide precursors. Also provided are nucleic acid molecules, polypeptides, and methods for generating combinatorial libraries of macrocyclic peptides. These methods can be used to produce vast libraries of conformationally constrained peptide ligands as well as facilitate the functional screening of these libraries to identify compound(s) with desired activity properties.

18 Claims, 89 Drawing Sheets

Figure 1A:
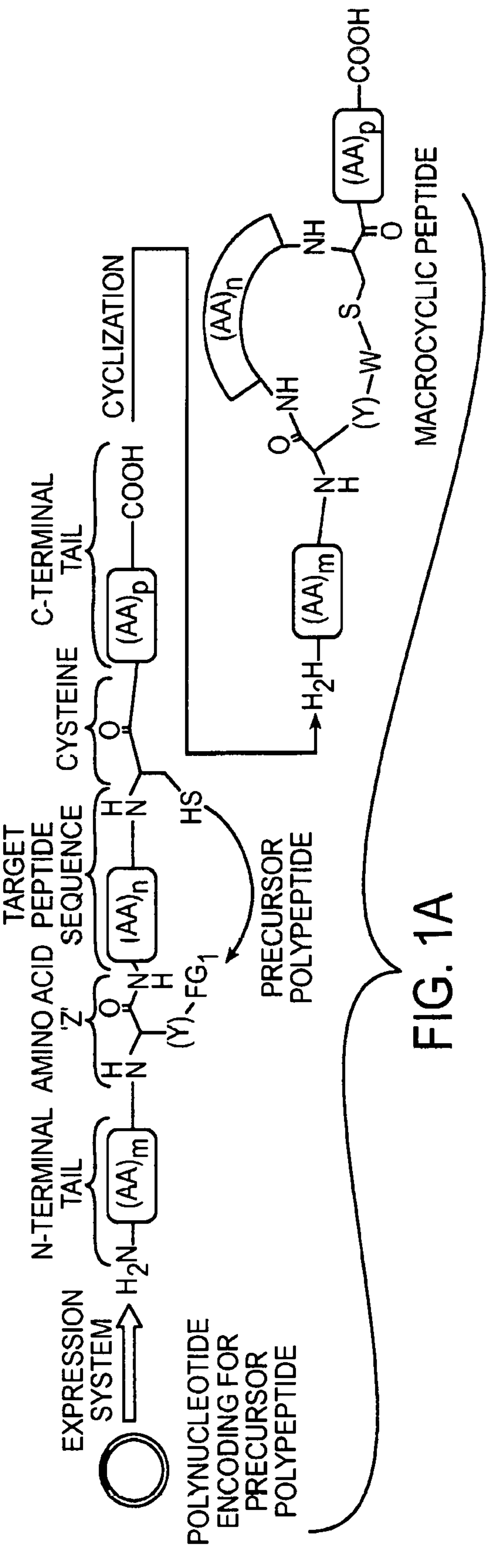

Specification includes a Sequence Listing.

SCHEME 1. SYNTHESIS OF 4-(2-BROMOETHOXY)-PHENYLALANINE (1).

SCHEME 2. SYNTHESIS OF $N^{\varepsilon}$-((2-BROMOETHOXY)CARBONYL)-LYSINE (2).

SCHEME 3. SYNTHESIS OF 4-(1-BROMOETHYL)-PHENYLALANINE (3).

p-2beF (1)

2becK (2)

p-1beF (3)

SCHEME 4. SYNTHESIS OF $N^{\varepsilon}$-((2-CHLOROETHOXY)CARBONYL)-LYSINE (4).

2cecK(4)

SCHEME 5. SYNTHESIS OF $N^{\varepsilon}$- (2-BUTA-2, 3-DIENOYL)-LYSINE (5).

bdnK (5)

SCHEME 6. SYNTHESIS OF O-(2,3-DIBROMOPROPYL)-TYROSINE (6).

OdbpY (6)

Precursor polypeptide: MG(p-2beF)TCSKLAEYGT-GyrA (12mer-Z2C(p-2beF))

Macrocyclic peptide product:

Precursor polypeptide: MG(p-2beF)TGCKLAEYGT-GyrA (12mer-Z3C(2-beF))

Macrocyclic peptide:

Precursor polypeptide: MG(p-2beF)TGS<u>C</u>LAEYGT-GyrA (12mer-Z4C(2-beF))

Macrocyclic peptide product:

Precursor polypeptide: MG(p-2beF)TGSKLCEYGT-GyrA (12mer-Z6C(2-beF))

Macrocyclic peptide product:

Precursor polypeptide: MG(p-2beF)TGSKLAECGT-GyrA (12mer-Z8C(2-beF))

Macrocyclic peptide product:

Precursor polypeptide: MG(p-2beF)TGSKYLNAECGT-GyrA (14mer-Z10C(2-beF))

Macrocyclic peptide product:

Precursor polypeptide: MG(2becK)CGSKLAEYGT-GyrA (12mer-Z1C(2becK))

Macrocyclic peptide product:

Precursor polypeptide: MG(2becK)TGSCLAEYGT-GyrA (12mer-Z4C(2becK))

Macrocyclic peptide product:

Precursor polypeptide: MG(2becK)TGSKLCEYGT-GyrA (12mer-Z6C(2becK))

Macrocyclic peptide product:

Precursor polypeptide: MG(2cecK)TCSKLAEYGT-GyrA (12mer-Z2C(2cecK))

Macrocyclic peptide:

Precursor polypeptide: MG(2cecK)TGSKLCEYGT-GyrA (12mer-Z6C(2cecK))

Macrocyclic peptide:

Precursor polypeptide: MG(p-1beF)TGS<u>C</u>LAEYGT-GyrA (12mer-Z4C(p-1beF))

Macrocyclic peptide product:

Precursor polypeptide: MG(bdnK)TGSKLCEYGT-GyrA (12mer-Z6C(bdnK))

Macrocyclic peptide:

Precursor polypeptide: MG(p-2beF)HPQFCGD-GyrA (Strep1-Z5C(p-2beF))

Macrocyclic peptide product:

Precursor polypeptide: MG(p-2beF)HPQGPPCGD-GyrA (Strep2-Z7C(p-2beF))

Macrocyclic peptide product:

Precursor polypeptide: MG(p-2beF)FTNVHPQFANCD-GyrA (Strep3-Z11C(p-2beF))

Macrocyclic peptide product:

Precursor polypeptide: $(DnaE_C)$-C(p2beF)TNCHPQFANA$(DnaE_N)$-CBD (cStrep3(C)-Z3C(p-2beF))

Bicyclic peptide product:

Precursor polypeptide: ($DnaE_C$)-S(p-2beF)TN<u>C</u>HPQFANA($DnaE_N$)-CBD (cStrep3(S)-Z3C(p-2beF))

Bicyclic peptide product:

Precursor polypeptide:(DnaE$_C$)-C(p-2beF)TNVHPQFCNA(DnaE$_N$)-CBD (cStrep3(C)-Z8C(p-2beF))

Bicyclic peptide product:

Precursor polypeptide:($DnaE_C$)-S(p-2beF)TNVHPQFCNAKGDA($DnaE_N$)-CBD (cStrep4(S)-Z8C(p-2beF))

Bicyclic peptide product:

Precursor polypeptide: ($DnaE_C$)-S(p-2beF)TNVHPQF<u>C</u>NAKGDTQA($DnaE_N$)-CBD (cStrep4(S)-Z8C(p-2beF))

Bicyclic peptide product:

Precursor polypeptide: MGSECGTNIA(p-2beF)-GyrA (10mer-C6Z(p-2beF))

Macrocyclic peptide product:

Precursor polypeptide: MG<u>C</u>EAGTNIA(p-2beF)-GyrA (10mer-C8Z(p-2beF))

Macrocyclic peptide product:

Precursor polypeptide: MG(p-2beF)HPQFCENLYFQSCNTSK(p-2beF)-GyrA (Strep6_Z4C7C4Z(p-2beY))

Polycyclic peptide product:

Precursor polypeptide: MGCAYDSG(ObdpY)HPQFCGT-GyrA (Strep7_C5Z4C(ObdpY))

Polycyclic peptide product:

METHODS AND COMPOSITIONS FOR RIBOSOMAL SYNTHESIS OF MACROCYCLIC PEPTIDES

CROSS-REFERENCE TO RELATED APPLICATIONS

This application is a national stage application under 35 U.S.C. § 371 of PCT Application No. PCT/US14/72016, filed Dec. 23, 2014, which claims priority to and the benefit of U.S. provisional patent application Ser. No. 61/920,181, entitled Methods and Compositions for Ribosomal Synthesis of Macrocyclic Peptides, filed Dec. 23, 2013, which is incorporated herein by reference in its entirety.

STATEMENT REGARDING FEDERALLY SPONSORED RESEARCH OR DEVELOPMENT

This invention was made with government support under grant no. R21CA187502 awarded by the National Institutes of Health and grant no. CHE-1112342 awarded by the National Science Foundation. The government has certain rights in this invention.

1. TECHNICAL FIELD

The present invention relates to methods and compositions for generating macrocyclic peptides from genetically encoded, ribosomally produced polypeptide precursors. The invention also relates to nucleic acid molecules, polypeptides, and methods for generating macrocyclic peptides and combinatorial libraries of macrocyclic peptides.

2. BACKGROUND

Peptides molecules represent valuable tools for investigating biological systems, studying the binding and activity properties of biomolecules (e.g., enzymes, cell receptors, antibodies, kinases), exploring the etiopathological causes of diseases, and for validating pharmacological targets. Peptides are also attractive ligands for targeting protein-protein interactions and modulating the function of biological molecules such as enzymes and nucleic acids. The synthesis of combinatorial libraries of small peptides followed by screening of these chemical libraries in biological assays can enable the identification of compounds that exhibit a variety of biological and pharmacological properties. Bioactive peptides identified in this manner can constitute valuable lead compounds or facilitate the development of lead compounds towards the discovery of new drugs.

While many peptides exhibit interesting biological activity, linear peptides do not generally represent suitable pharmacological agents as they are generally only poorly adsorbed, do not cross biological membranes readily, and are prone to proteolytic degradation. In addition, linear peptides fail to bind proteins that recognize discontinuous epitopes. The use of molecular constraints to restrict the conformational freedom of the molecule backbone can be used to overcome these limitations. In many cases, conformationally constrained peptides exhibit enhanced enzymatic stability (Fairlie, Tyndall et al. 2000; Wang, Liao et al. 2005), membrane permeability (Walensky, Kung et al. 2004; Rezai, Bock et al. 2006; Rezai, Yu et al. 2006), and protein binding affinity (Tang, Yuan et al. 1999; Dias, Fasan et al. 2006) and selectivity (Henchey, Porter et al. 2010), compared to their linear counterparts. Constraints that lock-in the active conformation of a peptide molecule can result in increased affinity due to the reduced conformational entropy loss upon binding to the receptor. Many bioactive and therapeutically relevant peptides isolated from natural sources occur indeed in cyclized form or contain intramolecular bridges that reduce the conformational flexibility of these molecules (e.g., immunosuppressant cyclosporin A, antitumor dolastatin 3 and diazonamide A, anti-HIV luzopeptin E2, and the antimicrobial vancomycin). Since macrocyclic peptides constitute promising molecular scaffolds for the development of bioactive compounds and therapeutic agents (Katsara, Tselios et al. 2006; Driggers, Hale et al. 2008; Obrecht, Robinson et al. 2009; Mars ault and Peterson 2011), methods for generating macrocyclic peptides and combinatorial libraries thereof, are of high synthetic value and practical utility, in particular in the context of drug discovery.

While cyclic peptides can be prepared synthetically via a variety of known methods (White and Yudin 2011), the possibility to generate macrocyclic peptides starting from genetically encoded polypeptide precursors offers several advantages (Frost, Smith et al. 2013; Smith, Frost et al. 2013). Among these, there are: (a) the high combinatorial potential inherent to the ribosomal synthesis of genetically encoded polypeptides, which can enable the production of very large collections of peptide sequences ($10^8$-$10^{10}$ members or higher) in a cost- and time-effective manner; (b) the possibility to link these peptide libraries to powerful, high-throughput screening platforms such as phage display, mRNA display, or yeast display, in order to identify peptide ligands with the desired property (e.g., high binding affinity toward a target protein); (c) the ease by which these chemical libraries can be deconvoluted in order to identify the library members of interest (i.e., via sequencing of the peptide-encoding DNA or RNA sequence).

Various methods have been developed for producing biological libraries of conformationally constrained peptides (Frost, Smith et al. 2013; Smith, Frost et al. 2013). For example, libraries of disulfide-constrained cyclic peptides have been prepared using phage display and fusing randomized polypeptide sequences flanked by two cysteines to a phage particle as described, e.g., in U.S. Pat. No. 7,235,626. Disulfide bridges are however potentially reactive and this chemical linkage is unstable under reducing conditions or in a reductive environment such as the intracellular milieu. Alternatively, ribosomally produced peptides have also been constrained through the use of cysteine- or amine-reactive cross-linking agents (Millward, Takahashi et al. 2005; Seebeck and Szostak 2006; Heinis, Rutherford et al. 2009; Schlippe, Hartman et al. 2012). A drawback of these methods is the risk of producing multiple undesired products via reaction of the cross-linking agents with multiple sites within the randomized peptide sequence or the carrier protein in a display system. In addition, these methods do not allow for the formation of macrocyclic peptides inside the polypeptide-producing cell host. Other methods have been described that are useful for preparing head-to-tail cyclic peptides by using natural (i.e., naturally occurring) or engineered (i.e., non-naturally occurring, artificial or synthetic) split inteins, as described in U.S. Pat. Nos. 7,354,756, 7,252,952 and 7,105,341. An advantage of these strategies is the possibility to couple the intracellular formation of cyclic peptide libraries with an cell-based reporter or selection system, which can facilitate the identification of functional peptide ligands (Horswill, Savinov et al. 2004; Cheng, Naumann et al. 2007; Naumann, Tavassoli et al. 2008; Young, Young et al. 2011). However, the peptide cyclization efficiency was found to be highly dependent on the peptide sequence (Scott, Abel-Santos et al. 2001). In addition, only head-to-tail cyclic peptides can be obtained through these strategies, which limits the extent of structural diversity of the ligand libraries generated through these methods. Finally, methods have also been reported for generating cyclic peptides through the enzymatic modification of linear peptide precursors (Hamamoto, Sisido et al. 2011; Touati, Angelini et al. 2011). However, the need for exogenous reagents and/or enzyme catalysts for mediating peptide cyclization and, in some cases, moderate cyclization efficiency limit the scope and utility of these approaches toward the generation and screening of cyclic peptide libraries.

Efficient and versatile methods for generating macrocyclic peptides from ribosomally produced polypeptides would thus be highly desirable in the art. The methods and compositions described herein provide a solution to this need, enabling the ribosomal synthesis of cyclic peptides in vitro (i.e., in a cell-free system) and in vivo (i.e., inside a cell or on a surface of a cell) and in various 'configurations', namely in the form of macrocyclic peptides, lariat-shaped peptides, or as cyclic peptides fused to a N-terminus or C-terminus of a protein of interest, such as a carrier protein of a display system.

Citation or identification of any reference in Section 2, or in any other section of this application, shall not be considered an admission that such reference is available as prior art to the present invention.

3. SUMMARY

A method is provided for making a macrocyclic peptide, the method comprising:

a. providing an artificial nucleic acid molecule encoding for a polypeptide of structure:

$(AA)_m$-Z-$(AA)_n$-Cys-$(AA)_p$ (I)

or $(AA)_m$-Cys-$(AA)_n$-Z-$(AA)_p$ (II)

or $(AA)_m$-Cys-$(AA)_n$-Z2-$(AA)_o$-Cys-$(AA)_p$ (V)

wherein:

i. $(AA)_m$ is an N-terminal amino acid or peptide sequence, ii. Z is a non-canonical amino acid carrying a side-chain functional group $FG_1$, $FG_1$ being a functional group selected from the group consisting of —$(CH_2)_n$X, where X is F, Cl, Br, or I and n is an integer number from 1 to 10; —C(O)$CH_2$X, where X is F, Cl, Br, or I; —CH(R')X, where X is F, Cl, Br, or I; —C(O)CH(R')X, where X is F, Cl, Br, or I; —$OCH_2CH_2$X, where X is F, Cl, Br, or I; —C(O)CH═C═C(R')(R''); —$SO_2$C(R')═C(R')(R''); —C(O)C(R')═C(R')(R''); —C(R')═C(R')C(O)OR'; —C(R')═C(R')C(O)N(R')(R''); —C(R')═C(R')—CN; —C(R')═C(R')—$NO_2$; —C≡C—C(O)OR'; —C≡C—C(O)N(R')(R''); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R and R' is independently H, an aliphatic, a substituted aliphatic, an aryl, or a substituted aryl group.

iii. Z2 is a non-canonical amino acid carrying two side-chain functional groups $FG_1$ and $FG_2$, wherein each of $FG_1$ and $FG_2$ is a functional group independently selected from the group consisting of —$(CH_2)_n$X, where X is F, Cl, Br, or I and n is an integer number from 1 to 10; —C(O)$CH_2$X, where X is F, Cl, Br, or I; —CH(R')X, where X is F, Cl, Br, or I; —C(O)CH(R')X, where X is F, Cl, Br, or I; —$OCH_2CH_2$X, where X is F, Cl, Br, or I; —C(O)CH═C═C(R')(R''); —$SO_2$C(R')═C(R')(R''); —C(O)C(R')═C(R')(R''); —C(R')═C(R')C(O)OR'; —C(R')═C(R')C(O)N(R')(R''); —C(R')═C(R')—CN; —C(R')═C(R')—$NO_2$; —C≡C—C(O)OR'; —C≡C—C(O)N(R')(R''); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R' and R' is independently H, an aliphatic, a substituted aliphatic, an aryl, or a substituted aryl group, iv. $(AA)_n$ is a target peptide sequence, v. $(AA)_o$ is a second target peptide sequence, and vi. $(AA)_p$ is a C-terminal amino acid or peptide sequence;

b. introducing the nucleic acid molecule into an expression system and expressing the nucleic acid molecule in the expression system, thereby producing the polypeptide; and c. allowing the functional group $FG_1$, and whenever present, $FG_2$, to react with the side-chain sulfhydryl group (—SH) of the cysteine (Cys) residue(s), thereby producing the macrocyclic peptide.

In certain embodiments, $FG_1$ and $FG_2$ can be either the same group among those groups listed above or two different groups among those groups listed above.

In one embodiment of the method, Z is an amino acid of structure:

(III)

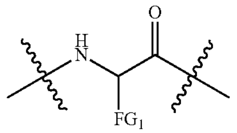

or (IV)

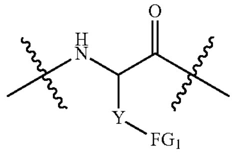

wherein $FG_1$ is a functional group selected from the group consisting of —$(CH_2)_n$X, where X is F, Cl, Br, or I and n is an integer number from 1 to 10; —C(O)$CH_2$X, where X is F, Cl, Br, or I; —CH(R')X, where X is F, Cl, Br, or I; —C(O)CH(R')X, where X is F, Cl, Br, or I; —$OCH_2CH_2$X, where X is F, Cl, Br, or I; —C(O)CH═C═C(R')(R''); —$SO_2$C(R')═C(R')(R''); —C(O)C(R')═C(R')(R''); —C(R')═C(R')C(O)OR'; —C(R')═C(R')C(O)N(R')(R''); —C(R')═C(R')—CN; —C(R')═C(R')—$NO_2$; —C≡C—C(O)OR'; —C≡C—C(O)N(R')(R''); unsubstituted or substituted oxirane, unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide; where each R and R'' is independently H, an aliphatic, a substituted aliphatic, an aryl, or a substituted aryl group;

wherein Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups.

In another embodiment of the method, Z is an amino acid of structure (IV) and Y is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, and $C_5$-$C_{24}$ aryloxy groups.

In another embodiment of the method, Y is a linker group selected from the group consisting of $—CH_2—C_6H_4—$, $—CH_2—C_6H_4—O—$, $—CH_2—C_6H_4—NH—$, $—(CH_2)_4—$, $—(CH_2)_4NH—$, $—(CH_2)_4NHC(O)—$, and $—(CH_2)_4NHC(O)O—$.

In another embodiment of the method, the amino acid Z is selected from the group consisting of 4-(2-bromoethoxy)-phenylalanine, 3-(2-bromoethoxy)-phenylalanine, 4-(2-chloroethoxy)-phenylalanine, 3-(2-chloroethoxy)-phenylalanine, 4-(1-bromoethyl)-phenylalanine, 3-(1-bromoethyl)-phenylalanine, 4-(aziridin-1-yl)-phenylalanine, 3-(aziridin-1-yl)-phenylalanine, 4-acrylamido-phenylalanine, 3-acrylamido-phenylalanine, 4-(2-fluoro-acetamido)-phenylalanine, 3-(2-fluoro-acetamido)-phenylalanine, 4-(2-chloro-acetamido)-phenylalanine, 3-(2-chloro-acetamido)-phenylalanine, 3-(2-fluoro-acetyl)-phenylalanine, 4-(2-fluoro-acetyl)-phenylalanine, $N^ε$-((2-bromoethoxy)carbonyl)-lysine, $N^ε$-((2-chloroethoxy)carbonyl)-lysine, $N^ε$-(buta-2,3-dienoyl)-lysine, $N^ε$-acryl-lysine, $N^ε$-crotonyl-lysine, $N^ε$-(2-fluoro-acetyl)-lysine, and $N^ε$-(2-chloro-acetyl)-lysine.

In another embodiment of the method, Z2 is an amino acid of structure:

(VI)

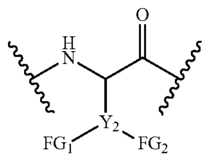

or (VII)

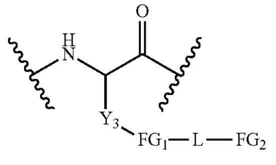

wherein each of $FG_1$ and $FG_2$ is a functional group independently selected from the group consisting of $—(CH_2)_nX$, where X is F, Cl, Br, or I and n is an integer number from 1 to 10; $—C(O)CH_2X$, where X is F, Cl, Br, or I; $—CH(R')X$, where X is F, Cl, Br, or I; $—C(O)CH(R')X$, where X is F, Cl, Br, or I; $—OCH_2CH_2X$, where X is F, Cl, Br, or I; $—C(O)CH=C=C(R')(R'')$; $—SO_2C(R')=C(R')(R'')$; $—C(O)C(R')=C(R')(R'')$; $C(R')=C(R')C(O)OR'$; $—C(R')=C(R')C(O)N(R')(R'')$; $—C(R')=C(R')—CN$; $—C(R')=C(R')—NO_2$, $—C≡C—C(O)OR'$; $—C≡C—C(O)N(R')(R'')$; unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R and R' is independently H, an aliphatic, a substituted aliphatic, an aryl, or a substituted aryl group;

wherein $Y_2$, $Y_3$, and L are linker groups selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups.

In certain embodiments, $FG_1$ and $FG_2$ can be either the same group among those groups listed above or two different groups among those groups listed above.

In another embodiment of the method, Z2 is an amino acid of structure (VI) and $Y_2$ is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, and $C_5$-$C_{24}$ aryloxy groups.

In another embodiment of the method, Y is a linker group selected from the group consisting of $—CH_2—C_6H_4—$, $—CH_2—C_6H_4—O—$, $—CH_2—C_6H_4—NH—$, $—CH_2—C_6H_4—OCH_2—$, $—(CH_2)_4NH—$, $—(CH_2)_4NHC(O)—$, $—(CH_2)_4NHC(O)O—$, $—(CH_2)_4NHC(O)OCH_2—$,

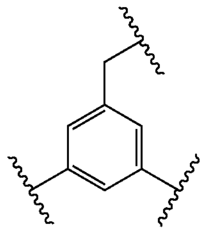

, and

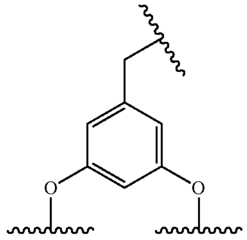

.

In another embodiment of the method, the amino acid Z2 is selected from the group consisting of 3,5-bis(2-bromoethoxy)-phenylalanine, 3,5-bis(2-chloroethoxy)-phenylalanine, 3,5-bis(1-bromoethyl)-phenylalanine, 3,5-bis(aziridin-1-yl)-phenylalanine, 3,5-bis-acrylamido-phenylalanine, 3,5-bis(2-fluoro-acetamido)-phenylalanine, 3,5-bis(2-fluoro-acetyl)-phenylalanine, 4-((1,3-dibromopropan-2-yl)oxy)-phenylalanine, 4-((1,3-dichloropropan-2-yl)oxy)-phenylalanine, $N^ε$-4(1,3-dibromopropan-2-yl)oxy)carbonyl)-lysine, $N^ε$-4(1,3-dichloropropan-2-yl)oxy)carbonyl)-lysine, 4-(2,3-dibromopropoxy)-phenylalanine, 3-(2,3-dibromopropoxy)-phenylalanine, 4-(2,3-dichloropropoxy)-phenylalanine, 3-(2,3-dichloropropoxy)-phenylalanine, $N^ε$-((2,3-dibromopropoxy)carbonyl)-lysine, and $N^ε$-((2,3-dichloropropoxy)carbonyl)-lysine.

In another embodiment of the method, the codon encoding for Z or Z2 is an amber stop codon TAG, an ochre stop codon TAA, an opal stop codon TGA, or a four base codon.

In another embodiment of the method, the expression system comprises:

an aminoacyl-tRNA synthetase polypeptide or an engineered variant thereof that is at least 90% identical to SEQ ID NO:77, 78, 79, or 80; and a transfer RNA molecule encoded by a polynucleotide that is at least 90% identical to SEQ ID NO:101, 105, 109, 113, or 117.

In another embodiment of the method, (a) the engineered variant of the aminoacyl-tRNA synthetase polypeptide of SEQ ID NO:77 comprises an amino acid substitution at a position selected from the group consisting of position: X32, X63, X65, X70, X107, X108, X109, X155, X158, X159, X160, X161, X162, X163, X164, X167, and X286 of SEQ ID NO:77, (b) the engineered variant of the aminoacyl-tRNA synthetase polypeptide of SEQ ID NO:78 comprises an amino acid substitution at a position selected from the group consisting of position: X302, X305, X306, X309, X346, X348, X364, X384, X401, X405, and X417 of SEQ ID NO:78, (c) the engineered variant of the aminoacyl-tRNA synthetase polypeptide of SEQ ID NO:79 comprises an amino acid substitution at a position selected from the group consisting of position: X76, X266, X270, X271, X273, X274, X313, X315, and X349 of SEQ ID NO:79, or (d) the engineered variant of the aminoacyl-tRNA synthetase polypeptide of SEQ ID NO:80 comprises an amino acid substitution at a position selected from the group consisting of position: X37, X182, X183, X186, and X265 of SEQ. ID NO. 204.

In another embodiment of the method, (a) the engineered variant of the aminoacyl-tRNA synthetase polypeptide of SEQ ID NO:77 comprises at least one of the features selected from the group consisting of: X32 is Tyr, Leu, Ala, Gly, Thr, His, Glu, Val, or Gln; X65 is Leu, His, Tyr, Val, Ser, Thr, Gly, or Glu; X67 is Ala or Gly; X70 is His, Ala, Cys, or Ser; X107 is Glu, Pro, Asn, or Thr; X108 is Phe, Trp, Ala, Ser, Arg, Gly, Tyr, His, Trp, or Glu; X109 is Gln, Met, Asp, Lys, Glu, Pro, His, Gly, Met, or Leu; X155 is Gln, Glu, or Gly; X158 is Asp, Gly, Glu, Ala, Pro, Thr, Ser, or Val; X159 is Ile, Cys, Pro, Leu, Ser, Trp, His, or Ala; X160 is His or Gln; X161 is Tyr or Gly; X162 is Leu, Arg, Ala, Gln, Gly, Lys, Ser, Glu, Tyr, or His; X163 is Gly or Asp; X164 is Val or Ala; X167 is Ala or Val; X286 is Asp or Arg;

(b) the engineered variant of the aminoacyl-tRNA synthetase polypeptide of SEQ ID NO:78 comprises at least one of the features selected from the group consisting of: X302 is Ala or Thr; X305 is Leu or Met; X306 is Tyr, Ala, Met, Ile, Leu, Thr, Gly; X309 is Leu, Ala, Pro, Ser, or Arg; X346 is Asn, Ala, Ser, or Val; X348 is Cys, Ala, Thr, Leu, Lys, Met, or Trp; X364 is Thr or Lys; X384 is Tyr or Phe; X405 is Ile or Arg; X401 is Val or Leu; and X417 is Trp, Thr, or Leu;

(c) the engineered variant of the aminoacyl-tRNA synthetase polypeptide of SEQ ID NO:79 comprises at least one of the features selected from the group consisting of: X76 is Asp or Gly; X266 is Leu, Val, or Met; X270 is Leu or Ile; X271 is Tyr, Phe, Leu, Met, or Ala; X274 is Leu, Ala, Met, or Gly; X313 is Cys, Phe, Ala, Val, or Ile; X315 is Met or Phe; and X349 is Tyr, Phe, or Trp; or (d) the engineered variant of the aminoacyl-tRNA synthetase polypeptide of SEQ ID NO:80 comprises at least one of the features selected from the group consisting of: X37 is Tyr, Ile, Gly, Val, Leu, Thr, or Ser; X182 is Asp, Gly, Ser, or Thr; X183 is Phe, Met, Tyr, or Ala; X186 is Leu, Ala, Met, or Val; and X265 is Asp or Arg.

In another embodiment of the method, the expression system comprises:

an aminoacyl-tRNA synthetase selected from the group consisting of SEQ ID NOs. 77, 78, 79, 80, 81, 82, 83, 84, 85, 86, 87, 88, 89, 90, 91, 92, 93, 94, 95, 96, 97, 98, 99 and 100; and a transfer RNA molecule encoded by a polynucleotide selected from the group consisting of SEQ ID NO:101, 102, 103, 104, 105, 106, 107, 108, 109, 110, 111, 112, 113, 114, 115, 116, 117, 118, 119, and 120.

In another embodiment of the method, the N-terminal tail polypeptide, $(AA)_m$, or the C-terminal tail polypeptide, $(AA)_p$, or both, of the precursor polypeptides of formula (I), (II), or (V) comprise(s):

a polypeptide affinity tag, a DNA-binding polypeptide, a protein-binding polypeptide, an enzyme, a fluorescent protein, an intein protein, or a combination thereof.

In another embodiment of the method, the polypeptide comprised within the N-terminal tail polypeptide, $(AA)_m$, or the C-terminal tail polypeptide, $(AA)_p$, or both, of the precursor polypeptides of formula (I), (II), and (V), is a polypeptide selected from the group of polypeptides consisting of SEQ ID NOs 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, and 158.

In another embodiment of the method, the intein polypeptide comprised within the N-terminal tail polypeptide, $(AA)_m$, or the C-terminal tail polypeptide, $(AA)_p$, or both, of the precursor polypeptides of formula (I), (II), or (V), is a selected from the group consisting of a naturally occurring intein, an engineered variant of a naturally occurring intein, a fusion of the N-terminal and C-terminal fragments of a naturally occurring split intein and a fusion of the N-terminal and C-terminal fragments of an engineered split intein.

In another embodiment of the method, the intein is selected from the group consisting of Mxe GyrA (SEQ ID NO:1), eDnaB (SEQ ID NO:2), Hsp-NRC1 CDC21 (SEQ ID NO:3), Ceu ClpP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FG-SCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8 (SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:46), Ter RIR1-1 (SEQ ID NO:47), Pab RIR1-1 (SEQ ID NO:48), Pfu RIR1-1 (SEQ ID NO:49), Chy RIR1 (SEQ ID NO:50), Mth RIR1 (SEQ ID NO:51), Pab RIR1-3 (SEQ ID NO:52), Pfu RIR1-2 (SEQ ID NO:53), Ter RIR1-2 (SEQ ID NO:54), Ter RIR1-4 (SEQ ID NO:55), CIV RIR1 (SEQ ID NO:56), Ctr VMA (SEQ ID NO:57), Sce VMA (SEQ ID NO:58), Tac-ATCC25905 VMA (SEQ ID NO:59), Ssp DnaB (SEQ ID NO:60), engineered variant(s) thereof, and engineered variant(s) thereof wherein the N-terminal cysteine or serine residue of the engineered variant is mutated to any natural (or naturally occurring) amino acid residue other than cysteine or serine, or wherein the C-terminal asparagine residue of the engineered variant is mutated to any natural (or naturally occurring) amino acid residue other than asparagine.

In another embodiment of the method, the intein is a fusion product of a split intein selected from the group consisting of Ssp DnaE (SEQ ID NO:61-SEQ ID NO:62), Neq Pol (SEQ ID NO:63-SEQ ID NO:64), Asp DnaE (SEQ ID NO:65-SEQ ID NO:66), Npu-PCC73102 DnaE (SEQ ID NO:67-SEQ ID NO:68), Nsp-PCC7120 DnaE (SEQ ID NO:69-SEQ ID NO:70), Oli DnaE (SEQ ID NO:71-SEQ ID NO:72), Ssp-PCC7002 DnaE (SEQ ID NO:73-SEQ ID NO:74), Tvu DnaE (SEQ ID NO:75-SEQ ID NO:76), engineered variant(s) thereof, and engineered variant(s) thereof wherein the N-terminal cysteine or serine residue of the split intein N-domain of the engineered variant is mutated to any of the natural (or naturally occurring) amino acid residues other than cysteine or serine, or wherein the C-terminal asparagine residue of the split intein C-domain of the engineered variant is mutated to any of the natural (or naturally occurring) amino acid residues other than asparagine.

In another embodiment of the method, the N-terminal tail polypeptide, $(AA)_m$, of the precursor polypeptide of formula (I), (II), or (V) comprises the C-domain of a split intein, and the C-terminal tail polypeptide, $(AA)_p$, comprises the corresponding N-domain of the split intein.

In another embodiment of the method, the split intein C-domain is selected from the group consisting of Ssp DnaE-c (SEQ ID NO:62), Neq Pol-c (SEQ ID NO:64), Asp DnaE-c (SEQ ID NO:66), Npu-PCC73102 DnaE-c (SEQ ID NO:68), Nsp-PCC7120 DnaE-c (SEQ ID NO:70), Oli DnaE-c (SEQ ID NO:72), Ssp-PCC7002 DnaE-c (SEQ ID NO:74), Tvu DnaE-c (SEQ ID NO:76), and engineered variant(s) thereof; and the split intein N-domain is selected from the group consisting of Ssp DnaE-n (SEQ ID NO:61), Neq Pol-n (SEQ ID NO:63), Asp DnaE-n (SEQ ID NO:65), Npu-PCC73102 DnaE-n (SEQ ID NO:67), Nsp-PCC7120 DnaE-n (SEQ ID NO:69), Oli DnaE-n (SEQ ID NO:71), Ssp-PCC7002 DnaE-n (SEQ ID NO:73), Tvu DnaE-n (SEQ ID NO:75), and engineered variant(s) thereof.

In another embodiment of the method, the expression system is selected from the group consisting of a prokaryotic cell, an eukaryotic cell, and a cell-free expression system.

In another embodiment of the method, the prokaryotic cell is *Escherichia coli.*

In another embodiment of the method, the eukaryotic cell is a yeast, a mammalian, an insect or a plant cell.

In another embodiment of the method, any of polypeptides $(AA)_n$, $(AA)_o$, $(AA)_m$, or $(AA)_p$, is fully or partially genetically randomized so that a plurality of macrocyclic peptides is obtained upon a thioether bond-forming reaction between the cysteine (Cys) residue and the side-chain functional group $FG_1$ in Z or between the cysteine (Cys) residues and the side-chain functional groups $FG_1$ and $FG_2$ in Z2.

In another embodiment of the method, the method comprises fully or partially randomizing any of polypeptides $(AA)_n$, $(AA)_o$, $(AA)_m$, or $(AA)_p$, wherein, upon a thioether bond-forming reaction between the cysteine (Cys) residue and the side-chain functional group $FG_1$ in Z or between the cysteine (Cys) residues and the side-chain functional groups $FG_1$ and $FG_2$ in Z2, a plurality of macrocyclic peptides is produced.

Artificial, engineered and recombinant nucleic acid molecules and peptide sequences (or amino acid sequences) for use in this method are also provided.

A recombinant host cell is provided comprising a polypeptide of structure:

$$(AA)_m\text{-}Z\text{-}(AA)_n\text{-}Cys\text{-}(AA)_p \quad (I)$$

or $$(AA)_m\text{-}Cys\text{-}(AA)_n\text{-}Z\text{-}(AA)_p \quad (II)$$

or $$(AA)_m\text{-}Cys\text{-}(AA)_n\text{-}Z2\text{-}(AA)_o\text{-}Cys\text{-}(AA)_p \quad (V)$$

wherein:

i. $(AA)_m$ is an N-terminal amino acid or peptide sequence, ii. Z is an amino acid of structure:

(III)

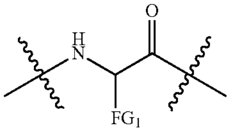

or (IV)

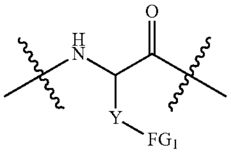

wherein $FG_1$ is a functional group selected from the group consisting of —$(CH_2)_nX$, where X is F, Cl, Br, or I and n is an integer number from 1 to 10; —$C(O)CH_2X$, where X is F, Cl, Br, or I; —CH(R')X, where X is F, Cl, Br, or I; —C(O)CH(R')X, where X is F, Cl, Br, or I; —$OCH_2CH_2X$, where X is F, Cl, Br, or I; —C(O)CH═C═C(R')(R"); —$SO_2C(R')$═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$; —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide; where each R' and R" is independently H, an aliphatic, a substituted aliphatic, an aryl, or a substituted aryl group;

wherein Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups, iii. Z2 is an amino acid of structure:

(VI)

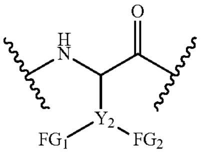

or (VII)

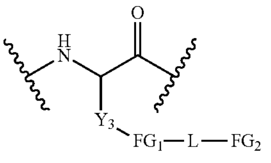

wherein each of $FG_1$ and $FG_2$ is a functional group independently selected from the group consisting of $—(CH_2)_nX$, where X is F, Cl, Br, or I and n is an integer number from 1 to 10; $—C(O)CH_2X$, where X is F, Cl, Br, or I; —CH(R')X, where X is F, Cl, Br, or I; —C(O)CH(R')X, where X is F, Cl, Br, or I; $—OCH_2CH_2X$, where X is F, Cl, Br, or I; —C(O)CH═C═C(R')(R"); $—SO_2C(R')═C(R')(R")$; —C(O)C(R')═C(R')(R"); —C(R')═C(R')C(O)OR'; —C(R')═C(R')C(O)N(R')(R"); —C(R')═C(R')—CN; $—C(R')═C(R')—NO_2$; —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R' and R' is independently H, an aliphatic, a substituted aliphatic, an aryl, or a substituted aryl group; and wherein $Y_2$, $Y_3$, L are linker groups selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups, iv. $(AA)_n$ is a target peptide sequence, v. $(AA)_o$ is a second target peptide sequence, v. $(AA)_p$ is a C-terminal amino acid or peptide sequence.

In certain embodiments, $FG_1$ and $FG_2$ can be either the same group among those groups listed above or two different groups among those groups listed above.

In one embodiment of the cell, the amino acid Z is selected from the group consisting of 4-(2-bromoethoxy)-phenylalanine, 3-(2-bromoethoxy)-phenylalanine, 4-(2-chloroethoxy)-phenylalanine, 3-(2-chloroethoxy)-phenylalanine, 4-(1-bromoethyl)-phenylalanine, 3-(1-bromoethyl)-phenylalanine, 4-(aziridin-1-yl)-phenylalanine, 3-(aziridin-1-yl)-phenylalanine, 4-acrylamido-phenylalanine, 3-acrylamido-phenylalanine, 4-(2-fluoro-acetamido)-phenylalanine, 3-(2-fluoro-acetamido)-phenylalanine, 4-(2-chloro-acetamido)-phenylalanine, 3-(2-chloro-acetamido)-phenylalanine, 3-(2-fluoro-acetyl)-phenylalanine, 4-(2-fluoro-acetyl)-phenylalanine, $N^{\varepsilon}$-((2-bromoethoxy)carbonyl)-lysine, $N^{\varepsilon}$-((2-chloroethoxy)carbonyl)-lysine, $N^{\varepsilon}$-(buta-2,3-dienoyl)-lysine, $N^{\varepsilon}$-acryl-lysine, $N^{\varepsilon}$-crotonyl-lysine, $N^{\varepsilon}$-(2-fluoro-acetyl)-lysine, and $N^{\varepsilon}$-(2-chloro-acetyl)-lysine.

In another embodiment of the cell, the amino acid Z2 is selected from the group consisting of 3,5-bis(2-bromoethoxy)-phenylalanine, 3,5-bis(2-chloroethoxy)-phenylalanine, 3,5-bis(1-bromoethyl)-phenylalanine, 3,5-bis(aziridin-1-yl)-phenylalanine, 3,5-bis-acrylamido-phenylalanine, 3,5-bis(2-fluoro-acetamido)-phenylalanine, 3,5-bis(2-fluoro-acetyl)-phenylalanine, 4-((1,3-dibromopropan-2-yl)oxy)-phenylalanine, 4-((1,3-dichloropropan-2-yl)oxy)-phenylalanine, $N^{\varepsilon}$-(((1,3-dibromopropan-2-yl)oxy)carbonyl)-lysine, $N^{\varepsilon}$-(((1,3-dichloropropan-2-yl)oxy)carbonyl)-lysine, 4-(2,3-dibromopropoxy)-phenylalanine, 3-(2,3-dibromopropoxy)-phenylalanine, 4-(2,3-dichloropropoxy)-phenylalanine, 3-(2,3-dichloropropoxy)-phenylalanine, $N^{\varepsilon}$-((2,3-dibromopropoxy)carbonyl)-lysine, and $N^{\varepsilon}$-((2,3-dichloropropoxy)carbonyl)-lysine.

In another embodiment of the cell, the polypeptide comprised within the N-terminal tail polypeptide, $(AA)_m$, or the C-terminal tail polypeptide, $(AA)_p$, or both, of the precursor polypeptides of formula (I), (II), and (V), is a polypeptide selected from the group of polypeptides consisting of SEQ ID NOs 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, and 158.

In another embodiment of the cell, the cell comprises a macrocyclic peptide produced by a thioether bond-forming reaction between the cysteine (Cys) residue and the $FG_1$ functional group in the amino acid Z or between the cysteine (Cys) residues and the $FG_1$ and $FG_2$ functional groups in the amino acid Z2.

In another embodiment of the cell, the N-terminal tail polypeptide, $(AA)_m$, or the C-terminal tail polypeptide, $(AA)_p$, or both, in the precursor polypeptides of formula (I), formula (II), or formula (V) comprise(s) an intein selected from the group consisting of a naturally occurring intein, an engineered variant of a naturally occurring intein, a fusion of the N-terminal and C-terminal fragments of a naturally occurring split intein and a fusion of the N-terminal and C-terminal fragments of an engineered split intein.

In another embodiment of the cell, the intein is selected from the group consisting of Mxe GyrA (SEQ ID NO:1), eDnaB (SEQ ID NO:2), Hsp-NRC1 CDC21 (SEQ ID NO:3), Ceu ClpP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FGSCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8 (SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:46), Ter RIR1-1 (SEQ ID NO:47), Pab RIR1-1 (SEQ ID NO:48), Pfu RIR1-1 (SEQ ID NO:49), Chy RIR1 (SEQ ID NO:50), Mth RIR1 (SEQ ID NO:51), Pab RIR1-3 (SEQ ID NO:52), Pfu RIR1-2 (SEQ ID NO:53), Ter RIR1-2 (SEQ ID NO:54), Ter RIR1-4 (SEQ ID NO:55), CIV RIR1 (SEQ ID NO:56), Ctr VMA (SEQ ID NO:57), Sce VMA (SEQ ID NO:58), Tac-ATCC25905 VMA (SEQ ID NO:59), Ssp DnaB (SEQ ID NO:60), engineered variant(s) thereof, and engineered variant(s) thereof wherein the N-terminal cysteine or serine residue of the engineered variant is mutated to any natural (or naturally occurring) amino acid residue other than cysteine or serine, or wherein the C-terminal asparagine residue of the engineered variant is mutated to any natural (or naturally occurring) amino acid residue other than asparagine In another embodiment of the cell, the intein is a fusion product of a split intein selected from the group consisting of Ssp DnaE (SEQ ID NO:61-SEQ ID NO:62), Neq Pol (SEQ ID NO:63-SEQ ID NO:64), Asp DnaE (SEQ ID NO:65-SEQ ID NO:66), Npu-PCC73102 DnaE (SEQ ID NO:67-SEQ ID NO:68), Nsp-PCC7120 DnaE (SEQ ID NO:69-SEQ ID NO:70), Oli DnaE (SEQ ID NO:71-SEQ ID NO:72), Ssp-PCC7002 DnaE (SEQ ID NO:73-SEQ ID NO:74), Tvu DnaE (SEQ ID NO:75-SEQ ID NO:76), engineered variant(s) thereof, engineered variant(s) thereof, wherein the N-terminal cysteine or serine residue of the split intein N-domain of the engineered variant is mutated to any natural (or naturally occurring) amino acid residue other than cysteine or serine, or wherein the C-terminal asparagine residue of the split intein C-domain of the engineered variant is mutated to any natural (or naturally occurring) amino acid residue other than asparagine.

In another embodiment of the cell, the cell comprises a macrocyclic peptide produced by a thioether bond-forming reaction between the cysteine (Cys) residue and the $FG_1$ functional group in the amino acid Z or between the cysteine (Cys) residues and the $FG_1$ and $FG_2$ functional groups in the amino acid Z2, and an intein-catalyzed N-terminal splicing, C-terminal splicing, or self-splicing reaction.

In another embodiment of the cell, the N-terminal tail polypeptide, $(AA)_m$, comprises the C-domain of a naturally occurring split intein, or of an engineered variant thereof, and the C-terminal tail polypeptide, $(AA)_p$, comprises the N-domain of said split intein.

In another embodiment of the cell, the split intein C-domain is selected from the group consisting of Ssp DnaE-c (SEQ ID NO:62), Neq Pol-c (SEQ ID NO:64), Asp DnaE-c (SEQ ID NO:66), Npu-PCC73102 DnaE-c (SEQ ID NO:68), Nsp-PCC7120 DnaE-c (SEQ ID NO:70), Oli DnaE-c (SEQ ID NO:72), Ssp-PCC7002 DnaE-c (SEQ ID NO:74), Tvu DnaE-c (SEQ ID NO:76), and engineered variant(s) thereof; and the split intein N-domain is selected from the group consisting of Ssp DnaE-n (SEQ ID NO:61), Neq Pol-n (SEQ ID NO:63), Asp DnaE-n (SEQ ID NO:65), Npu-PCC73102 DnaE-n (SEQ ID NO:67), Nsp-PCC7120 DnaE-n (SEQ ID NO:69), Ohi DnaE-n (SEQ ID NO:71), Ssp-PCC7002 DnaE-n (SEQ ID NO:73), Tvu DnaE-n (SEQ ID NO:75), and engineered variant(s) thereof.

In another embodiment of the cell, the cell comprises a polycyclic peptide produced by a thioether bond-forming reaction between the cysteine (Cys) residue and the $FG_1$ functional group in the amino acid Z or between the cysteine (Cys) residues and the $FG_1$ and $FG_2$ functional groups in the amino acid Z2, and a split intein-catalyzed trans-splicing reaction.

4. BRIEF DESCRIPTION OF THE DRAWINGS

Embodiments are described herein with reference to the accompanying drawings, in which similar reference characters denote similar elements throughout the several views. It is to be understood that in some instances, various aspects of the embodiments may be shown exaggerated or enlarged to facilitate an understanding of the invention.

Figure 1B:
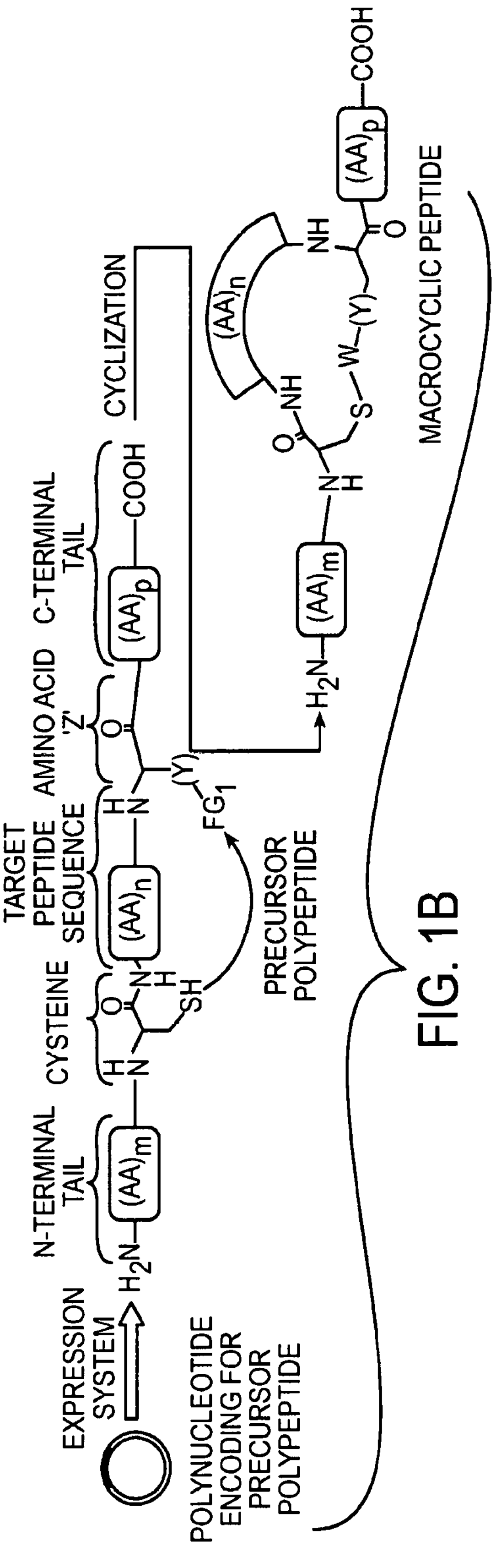

FIGS. 1A-B. Schematic representation of two general methods for making macrocyclic peptides from ribosomally produced precursor polypeptides of general formula (I) (panel A) or general formula (II) (panel B). W corresponds to the linker group resulting from the bond-forming reaction between the functional group $FG_1$ and the cysteine residue.

Figure 2A:
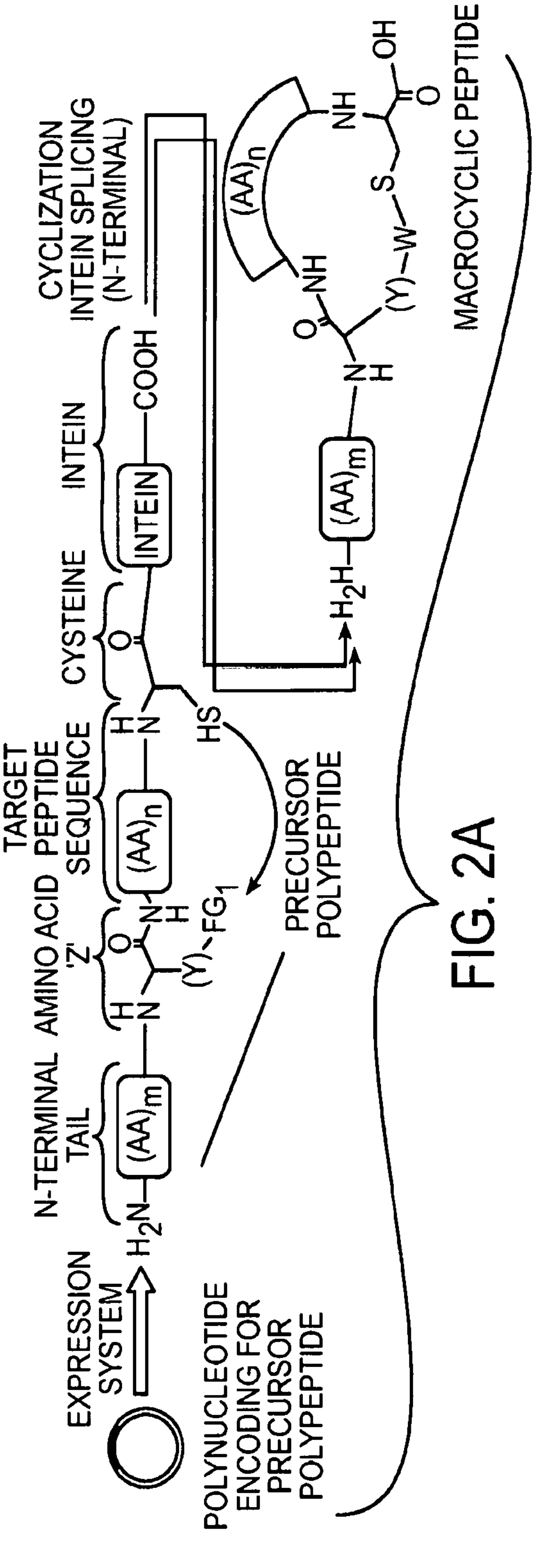
Figure 2B:
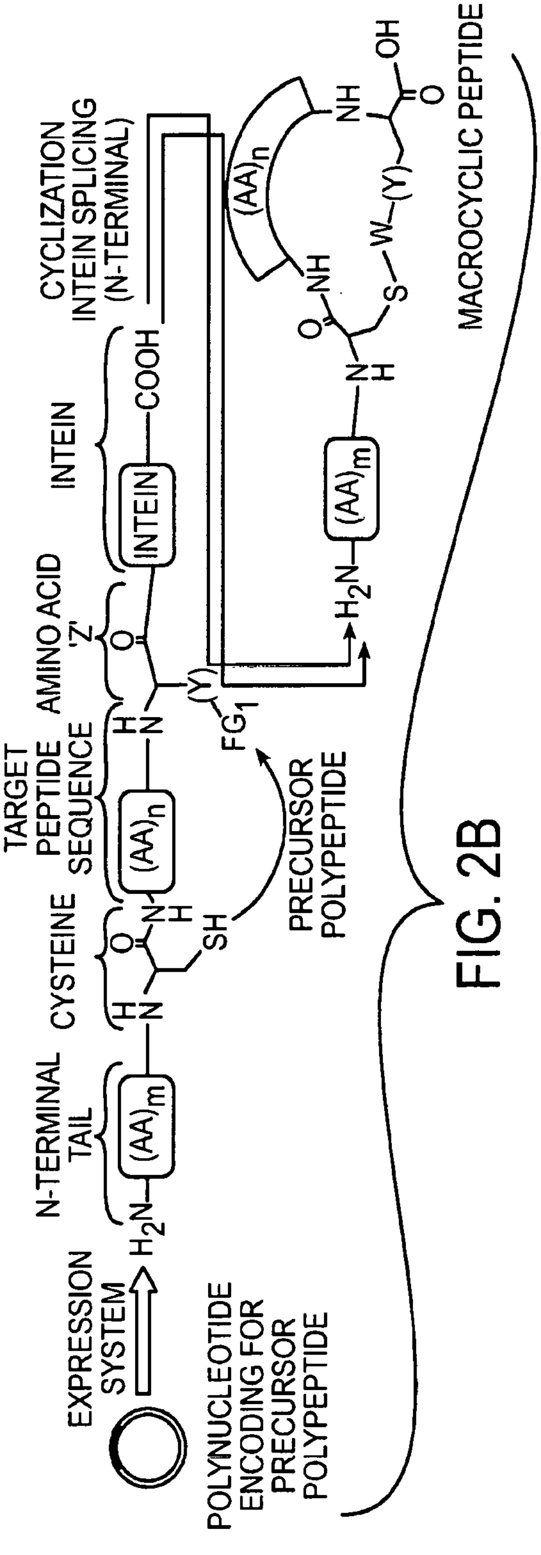

FIGS. 2A-B. Schematic representation of a variation of the general methods of FIGS. 1A-B, wherein an intein protein is comprised within the C-terminal tail of a precursor polypeptide of general formula (I) (panel A) or of general formula (II) (panel B). W corresponds to the linker group resulting from the bond-forming reaction between the functional group $FG_1$ and the cysteine residue.

Figure 3A:
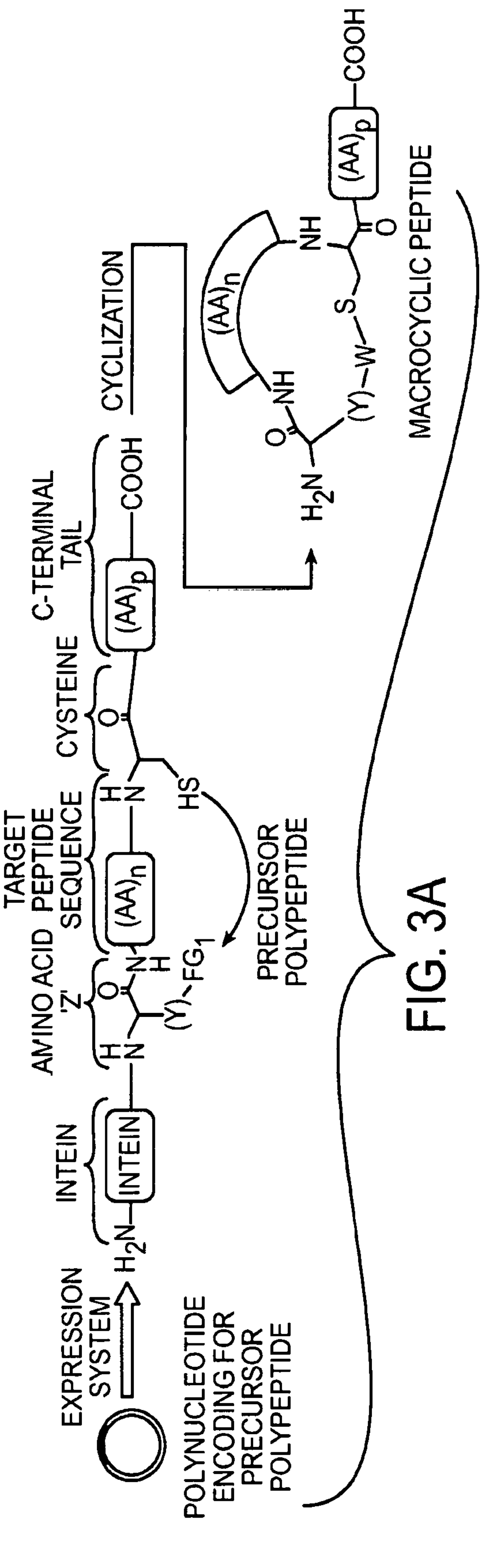
Figure 3:
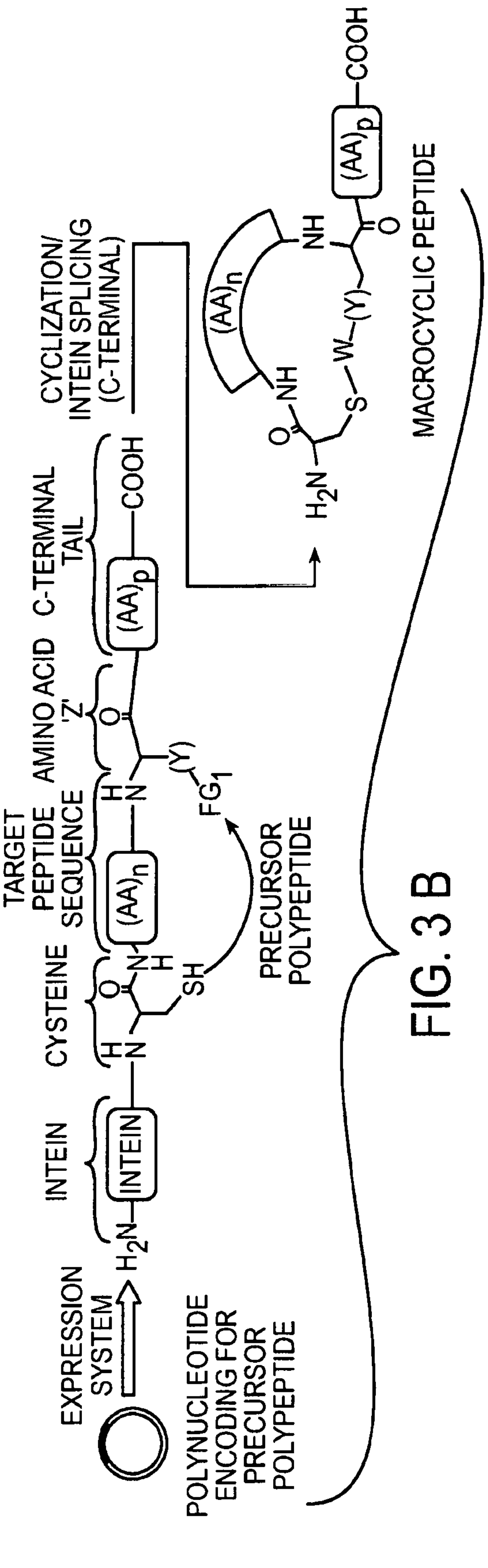

FIGS. 3A-B. Schematic representation of another variation of the general methods of FIGS. 1A-B, wherein an intein protein is comprised within the N-terminal tail of a precursor polypeptide of general formula (I) (panel A) or of general formula (II) (panel B). W corresponds to the linker group resulting from the bond-forming reaction between the functional group $FG_1$ and the cysteine residue.

Figure 4A:
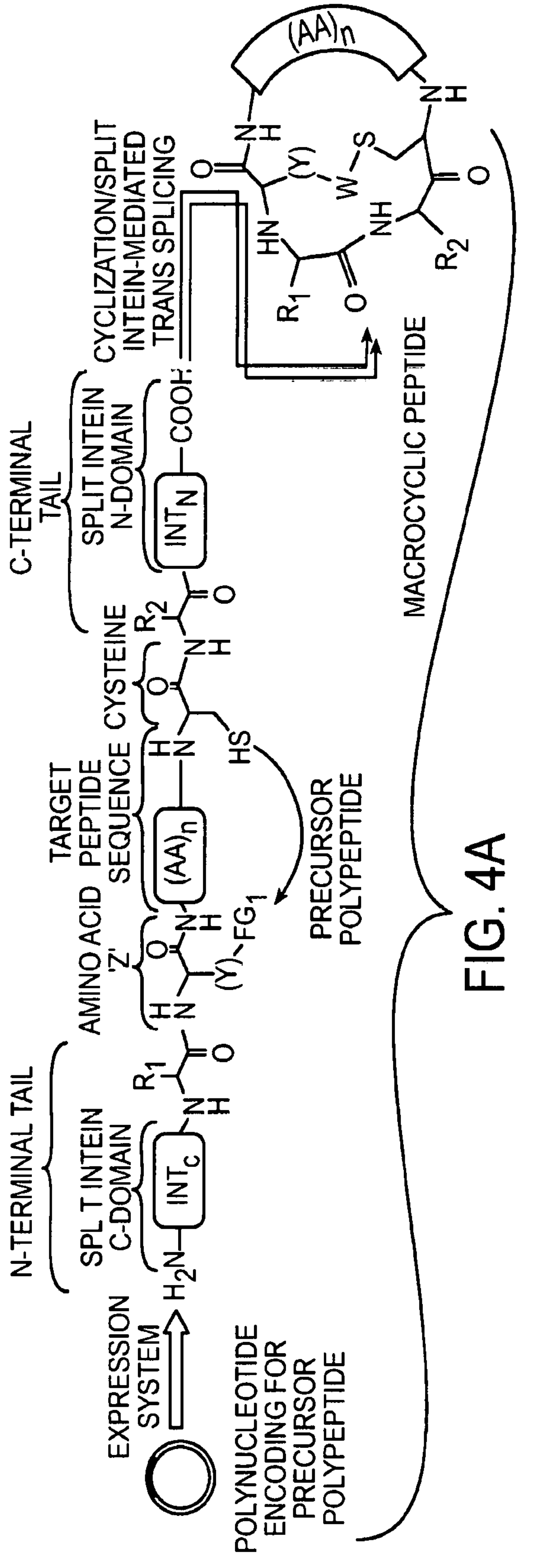
Figure 4B:
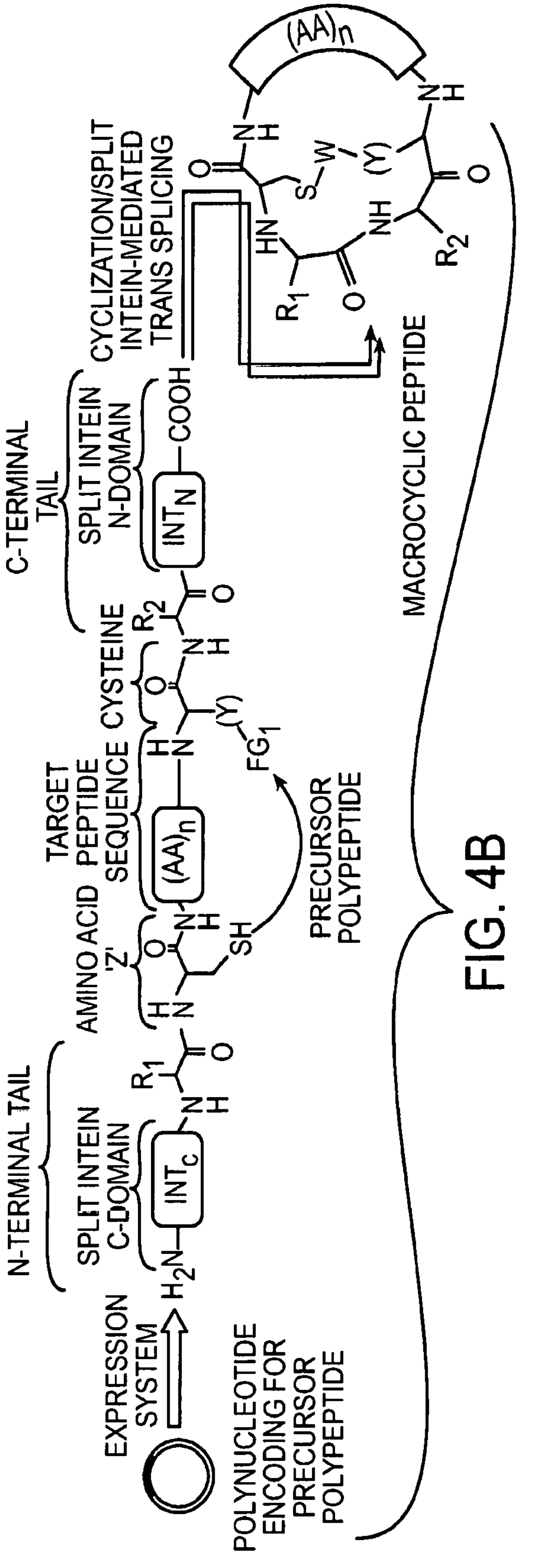

FIGS. 4A-B. Schematic representation of another variation of the general methods of FIGS. 1A-B, wherein the C- and N-domains of a split intein is comprised within the N-terminal tail and C-terminal tail, respectively, of a precursor polypeptide of general formula (I) (panel A) or of general formula (II) (panel B). W corresponds to the linker group resulting from the bond-forming reaction between the functional group $FG_1$ and the cysteine residue.

Figure 5:
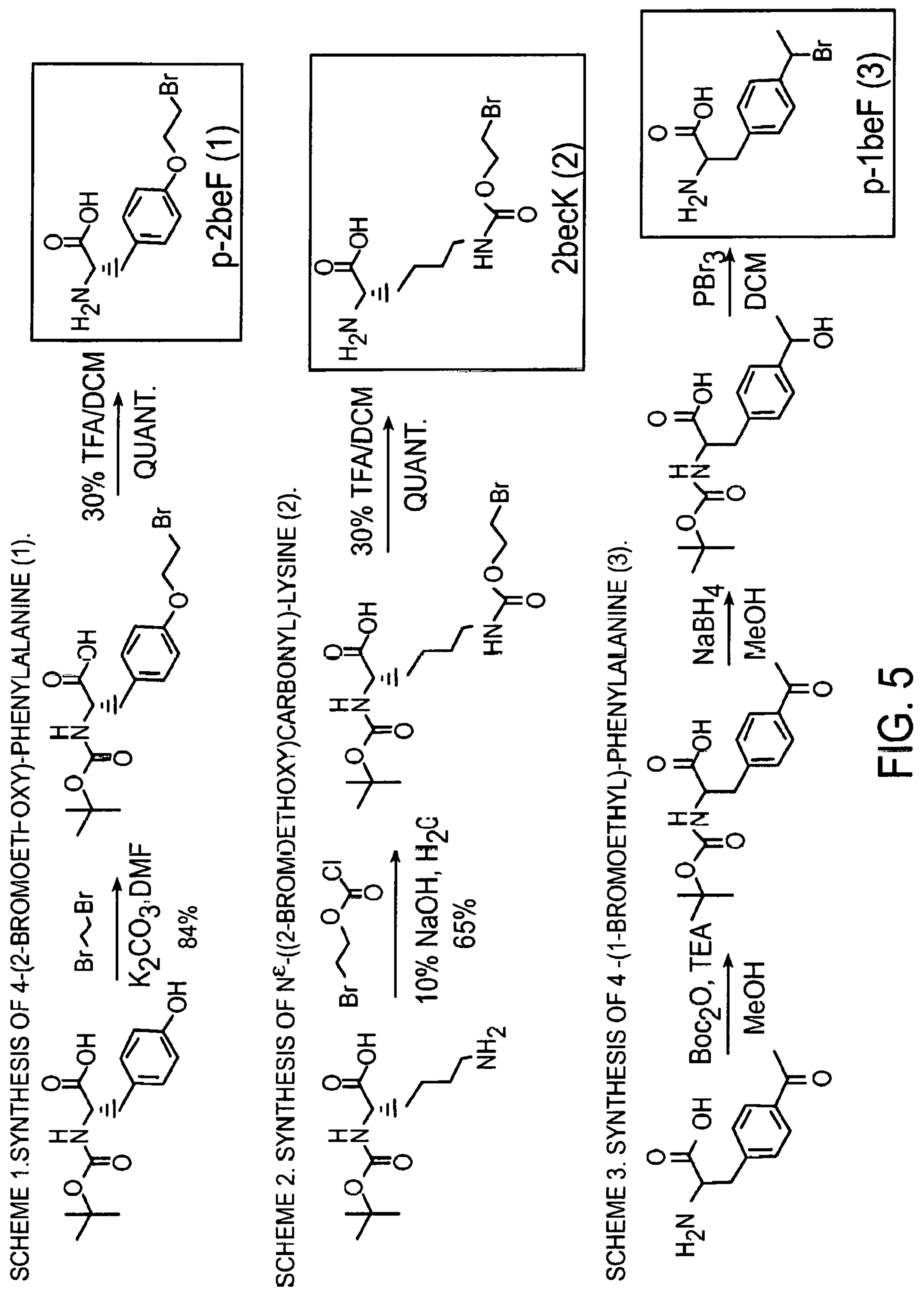

FIG. 5. Synthetic routes for the synthesis of the cysteine-reactive unnatural amino acids p-2beF, 2becK, and p-1beF.

Figure 6:
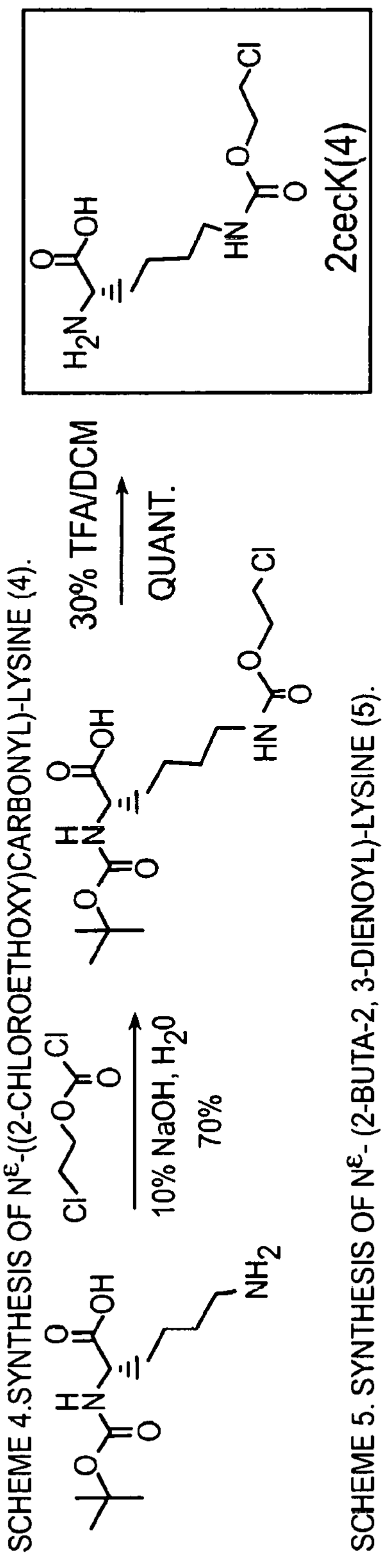
Figure 6:
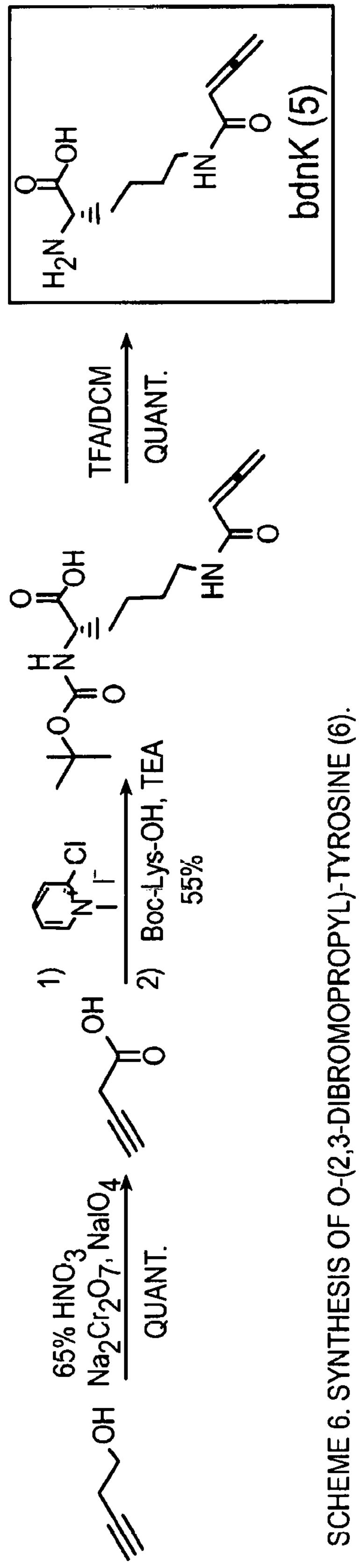
Figure 6:
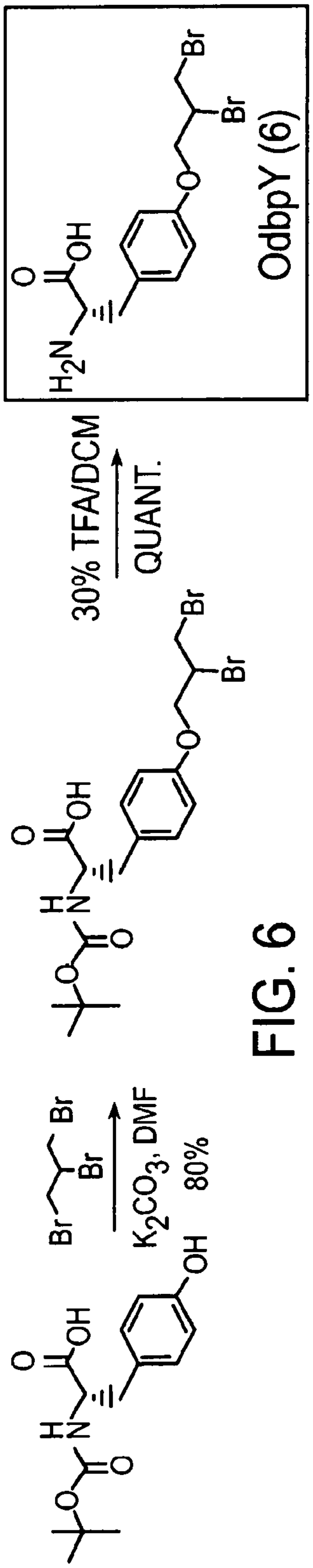

FIG. 6. Synthetic routes for the synthesis of the cysteine-reactive unnatural amino acids 2cecK, bdnK, and OdbpY.

Figure 7A:
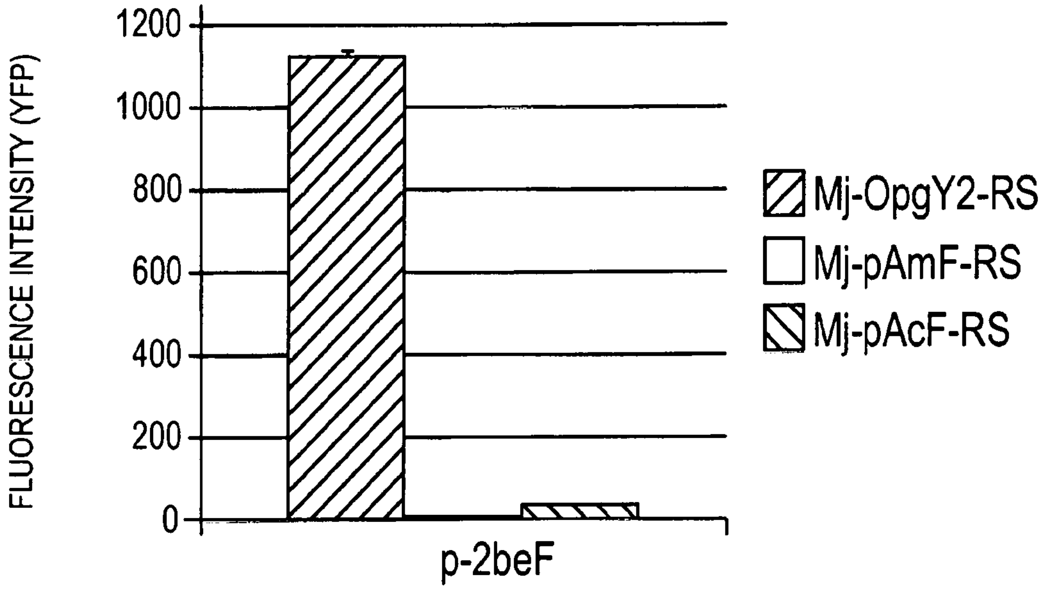
Figure 7B:
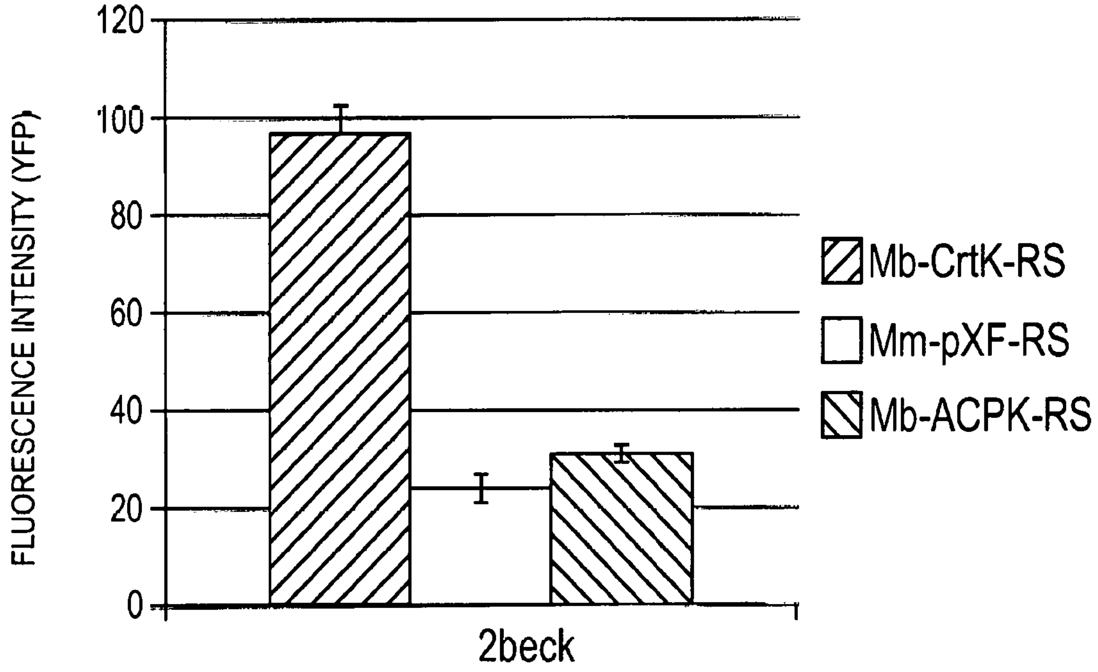

FIGS. 7A-B. Fluorescence-based assay for screening of AARS/tRNA pairs. The graphs indicate the relative efficiency of incorporation of the unnatural amino acid p-2beF (A) and 2becK (B) into the reporter protein YFP(TAG) by different amber stop codon suppressor AARS/tRNA pairs.

Figure 8:
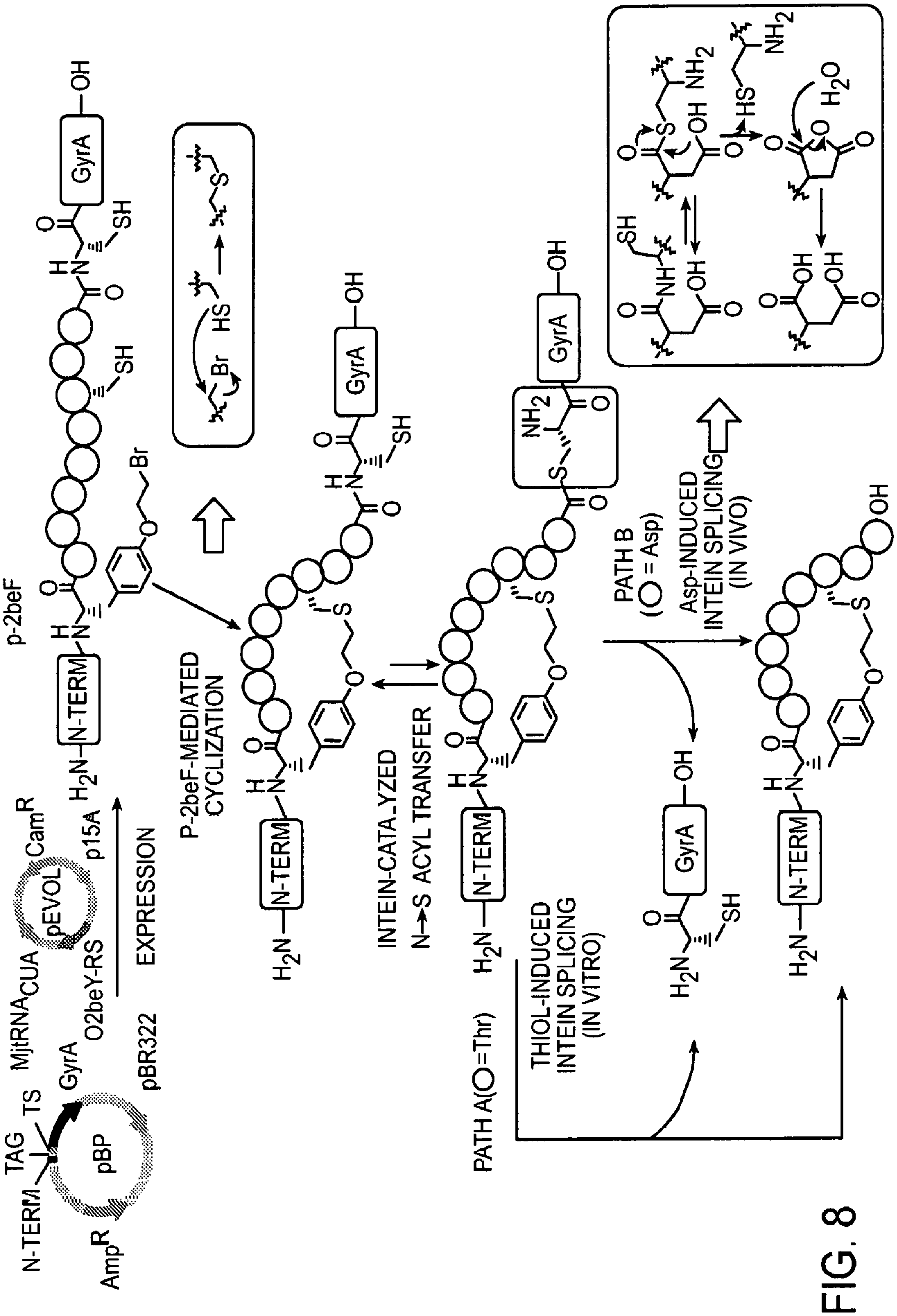

FIG. 8. Strategy for ribosomal synthesis of thioether-bridged macrocyclic peptides via p-2beF-mediated cyclization. The linear precursor polypeptide comprises an N-terminal tail (N-term), the unnatural amino acid p-2beF, a variable target sequence containing the reactive cysteine (black circle) and GyrA intein. Depending on the nature of the 'I-1' residue, the macrocyclic peptide can be released in vitro via thiol-induced Intein splicing (path A) or directly in vivo (path B).

Figure 9A:
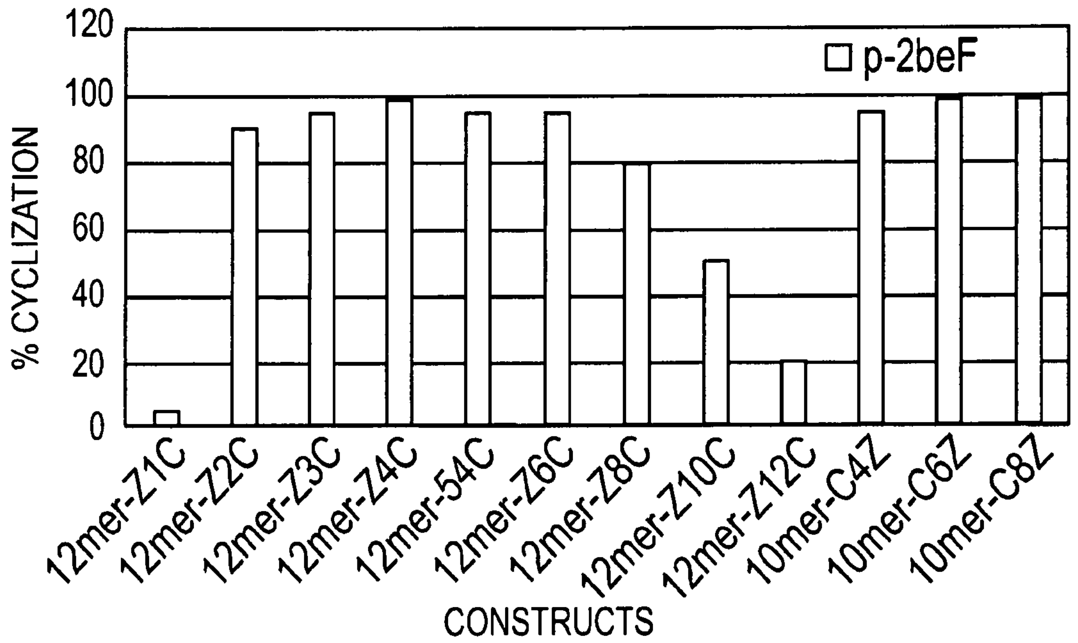
Figure 9B:
Figure 10A:
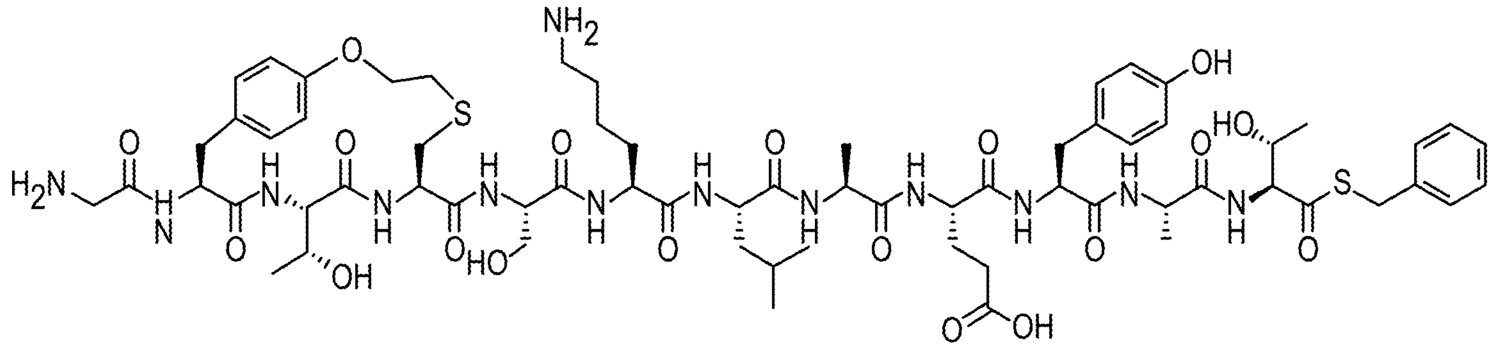
Figure 10B:
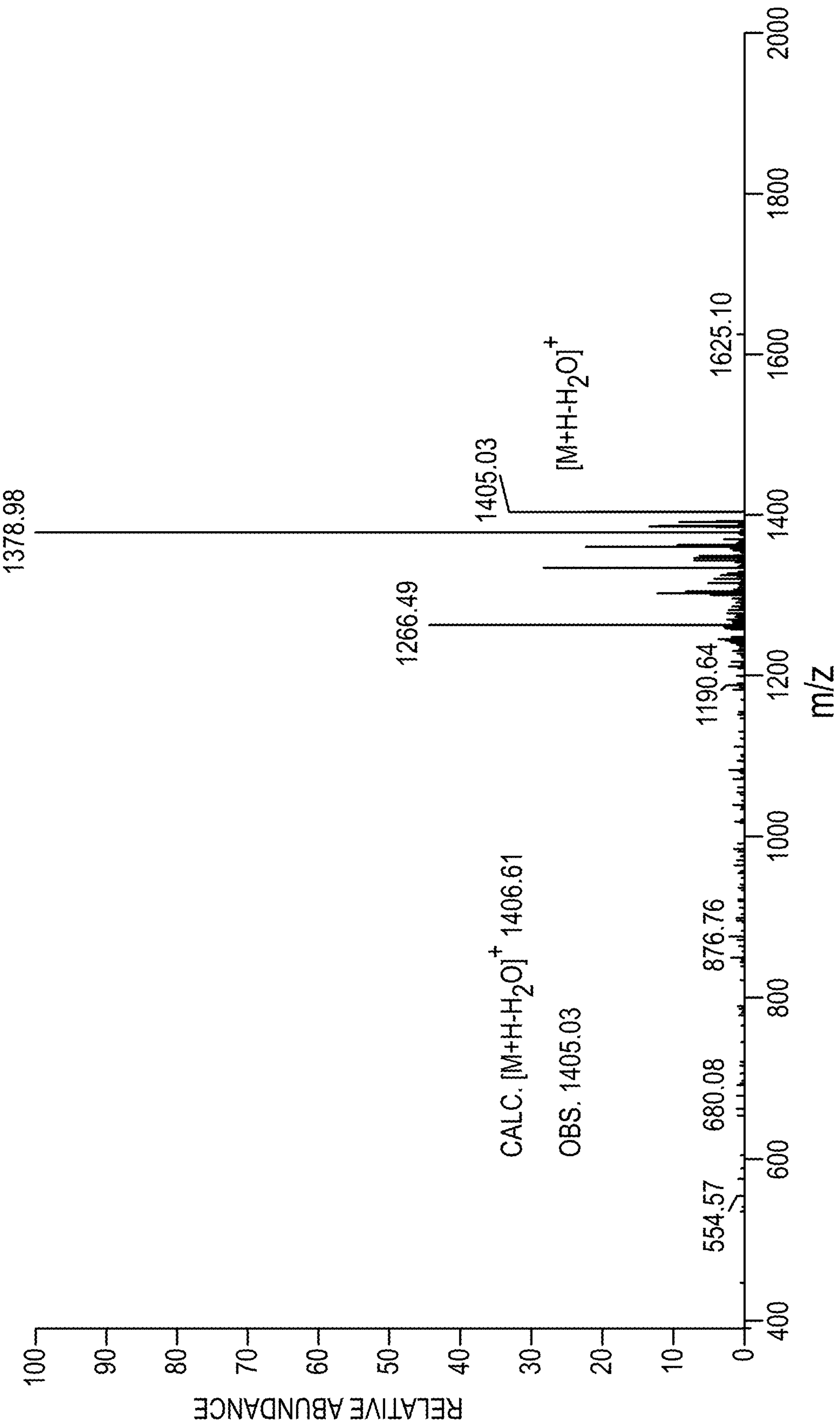
Figure 10C:
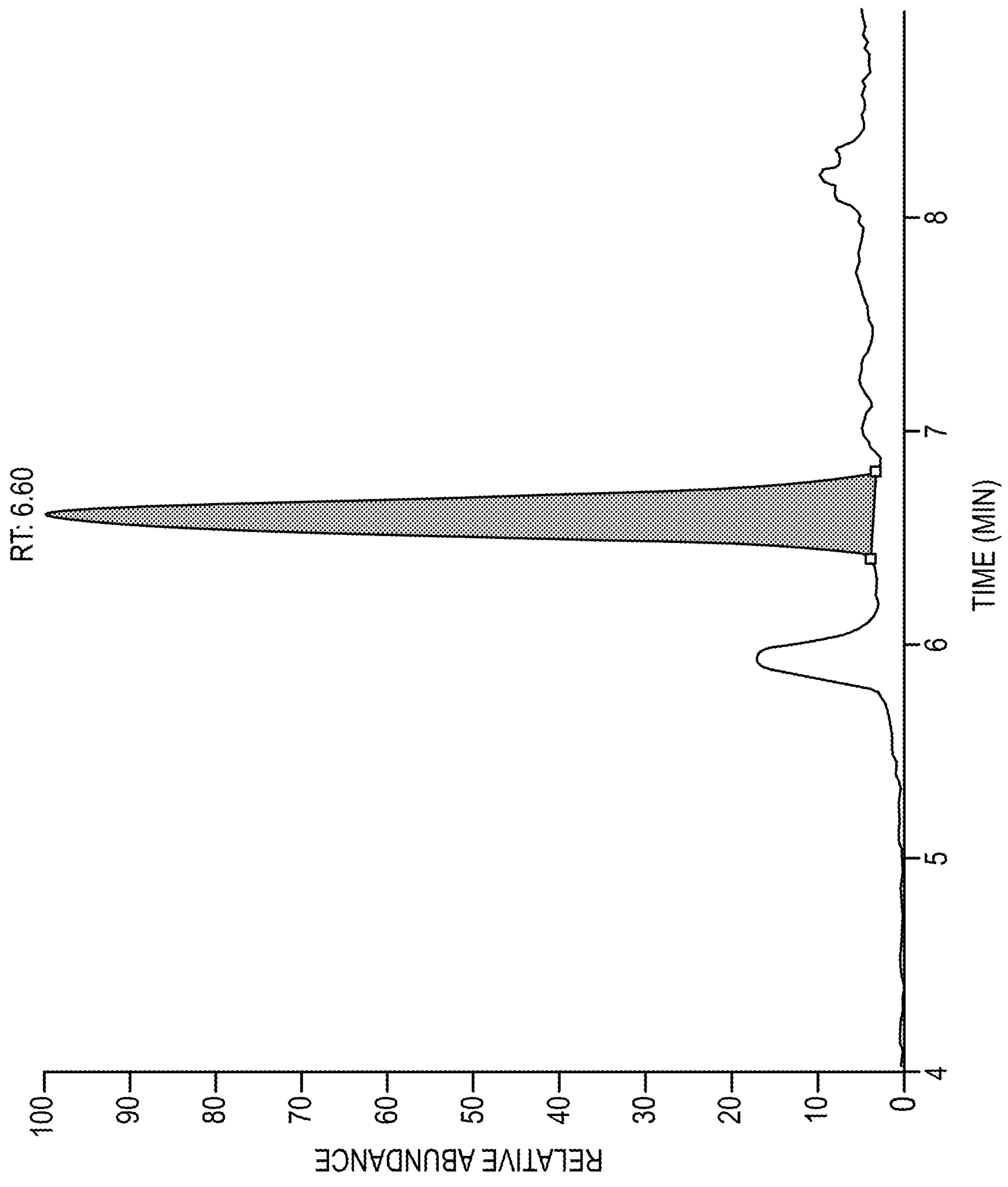
Figure 11A:
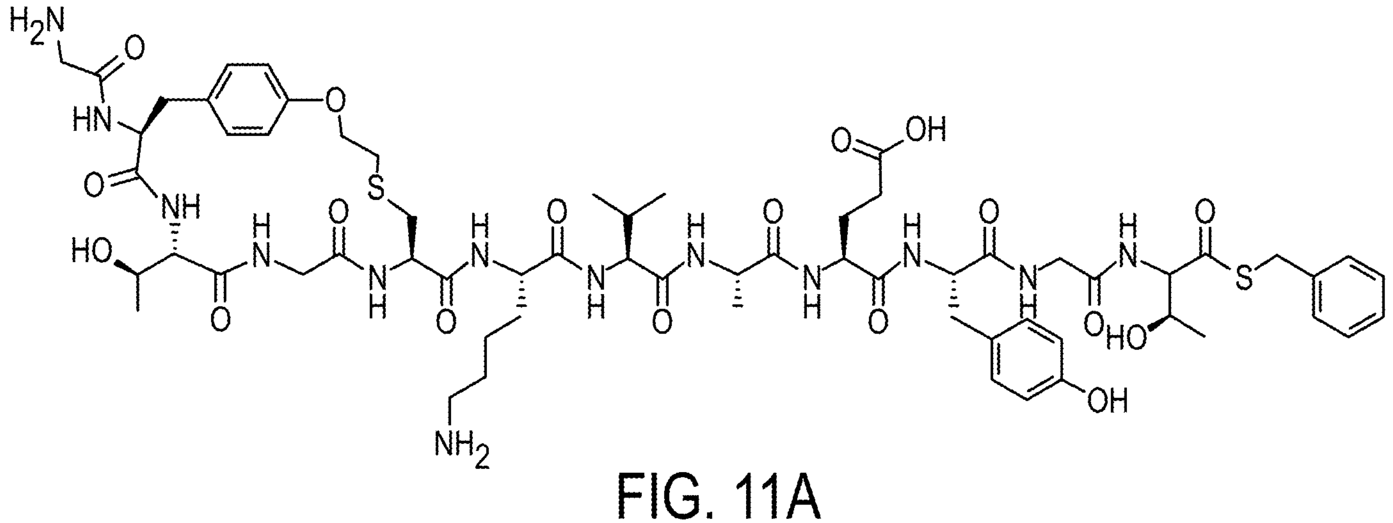
Figure 11B:
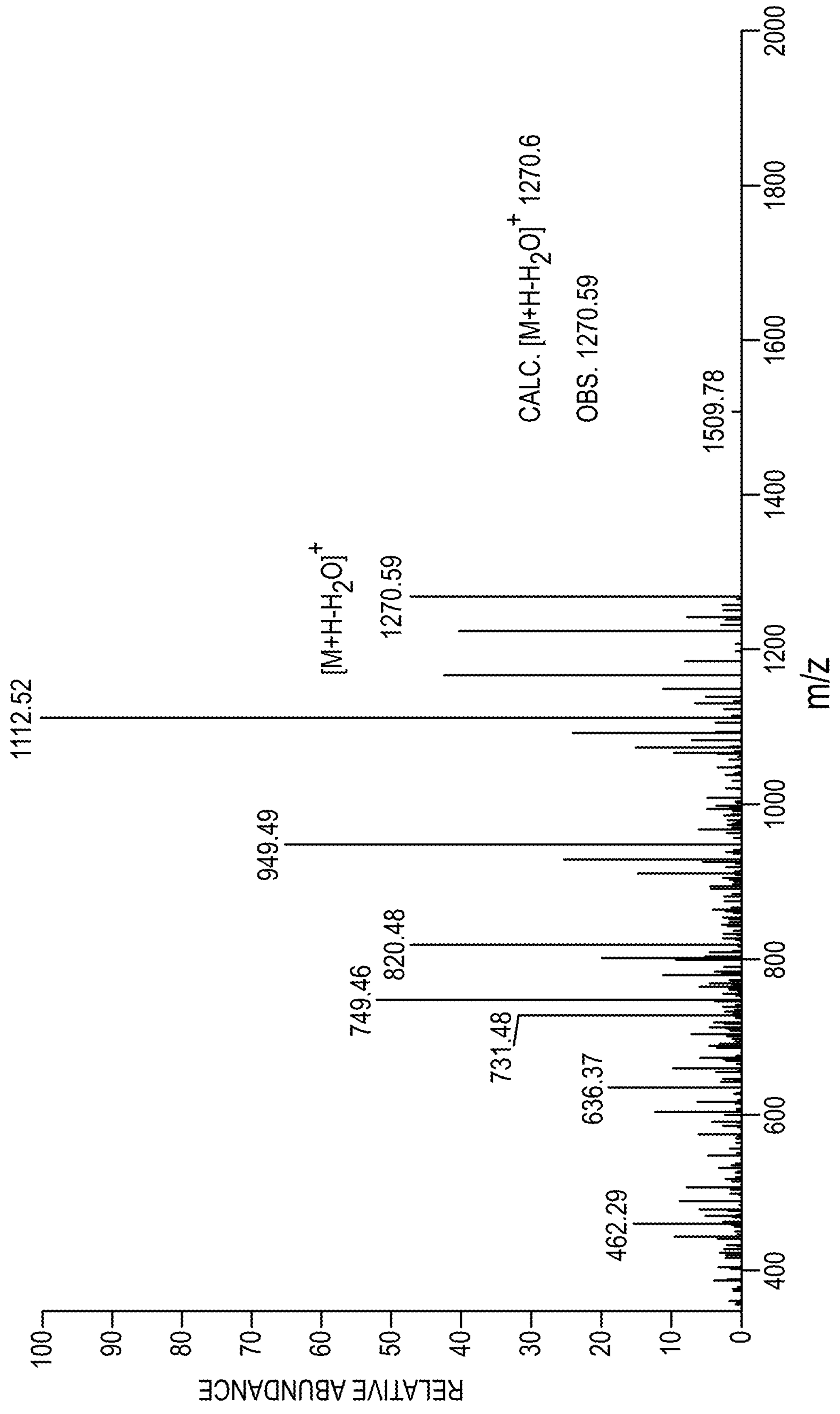
Figure 11C:
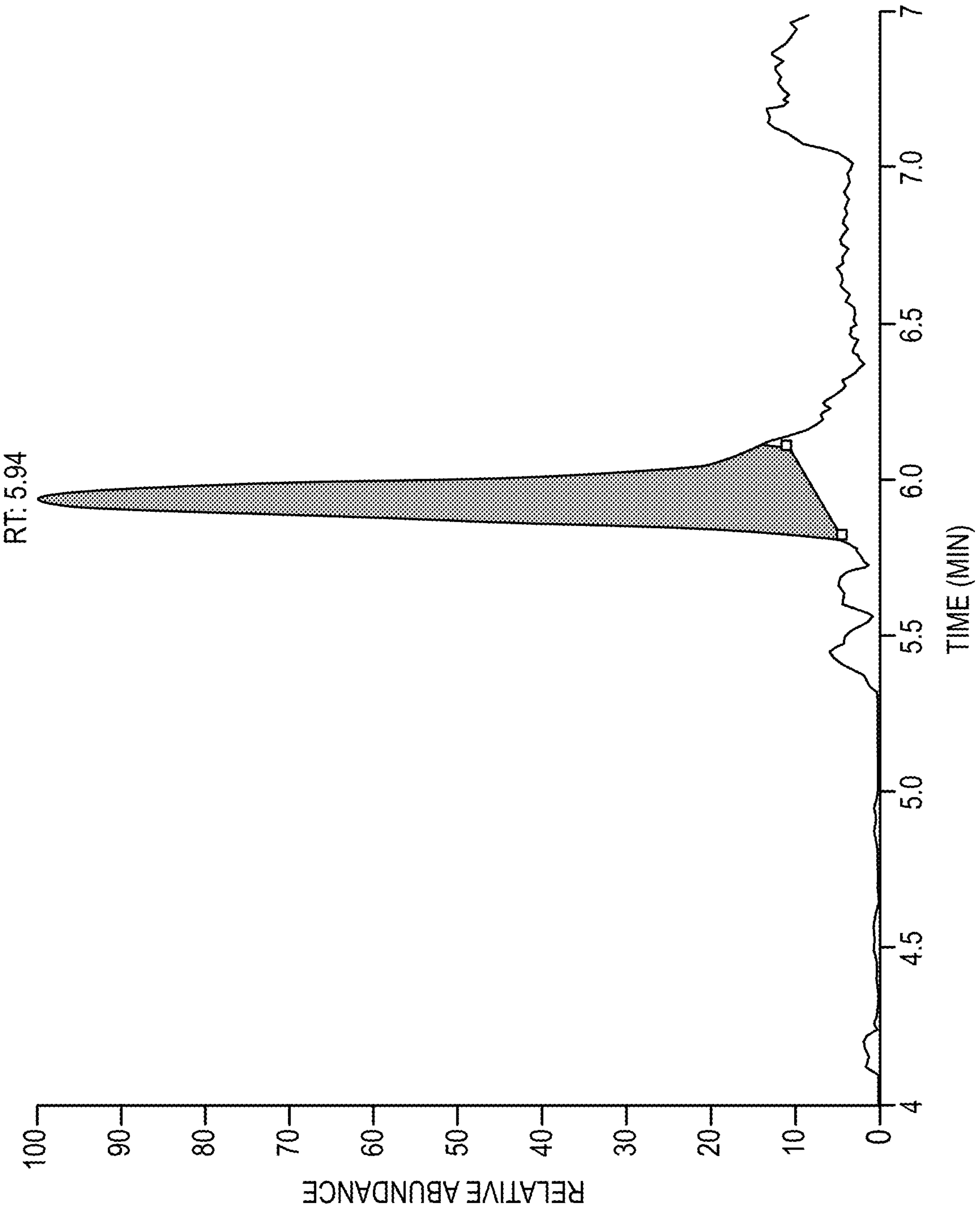
Figure 12A:
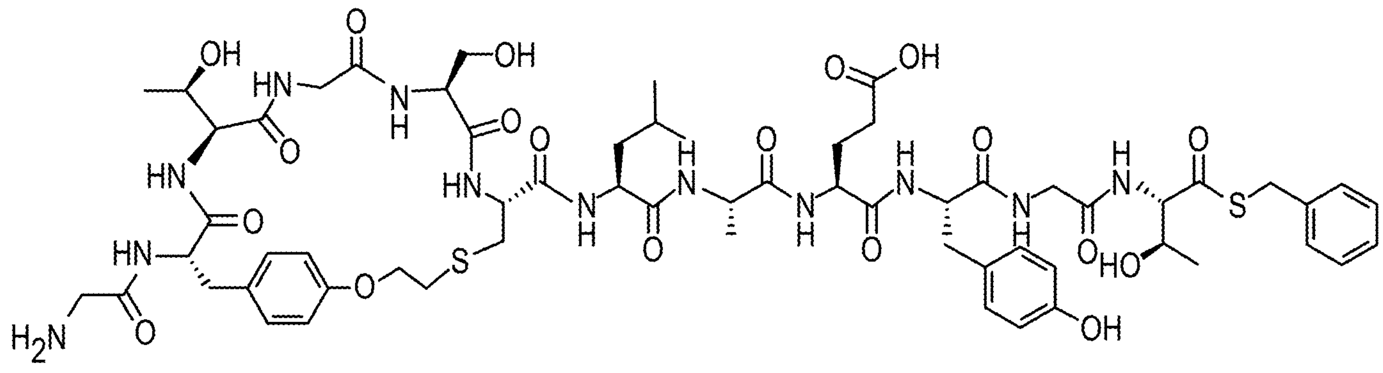
Figure 12B:
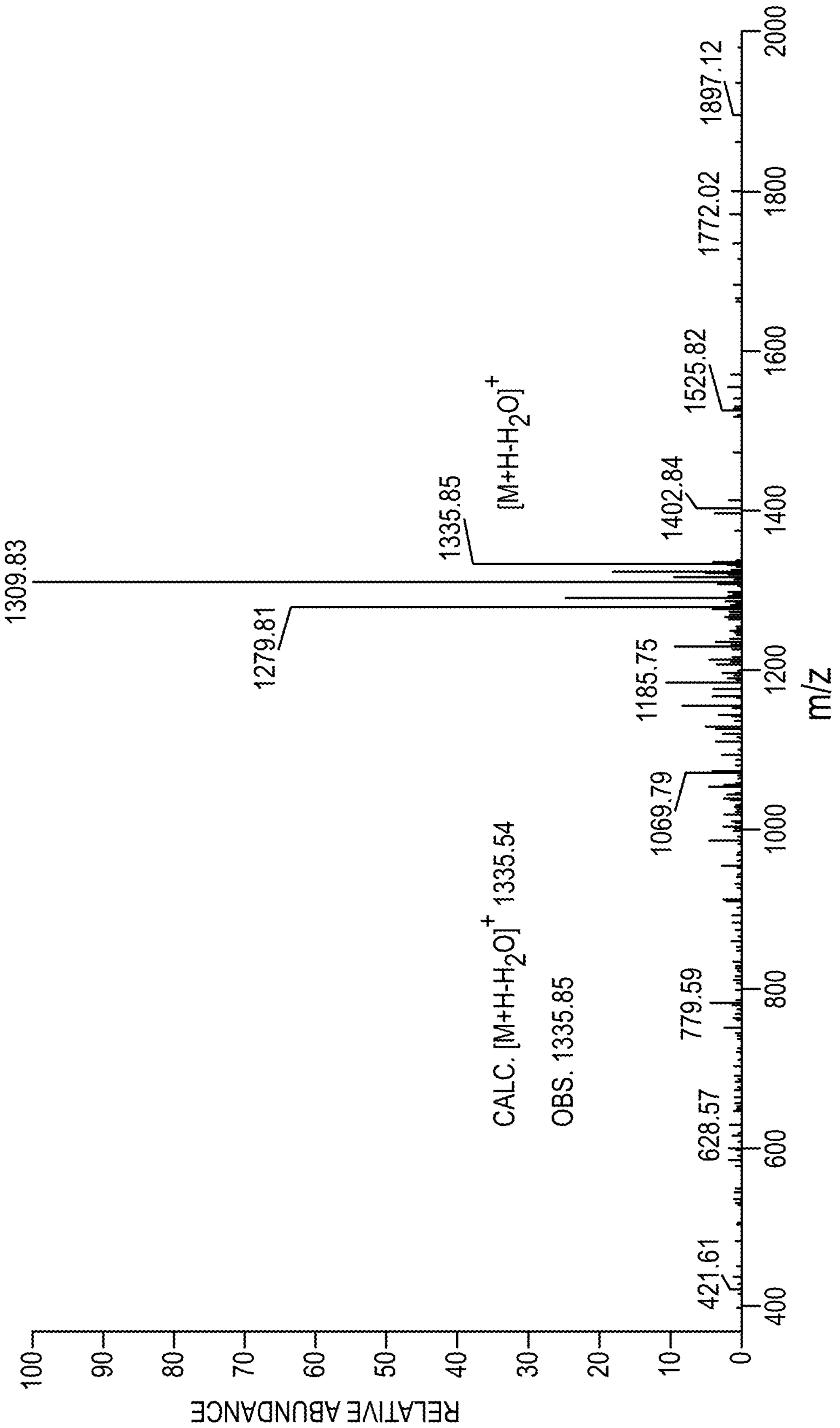
Figure 12C:
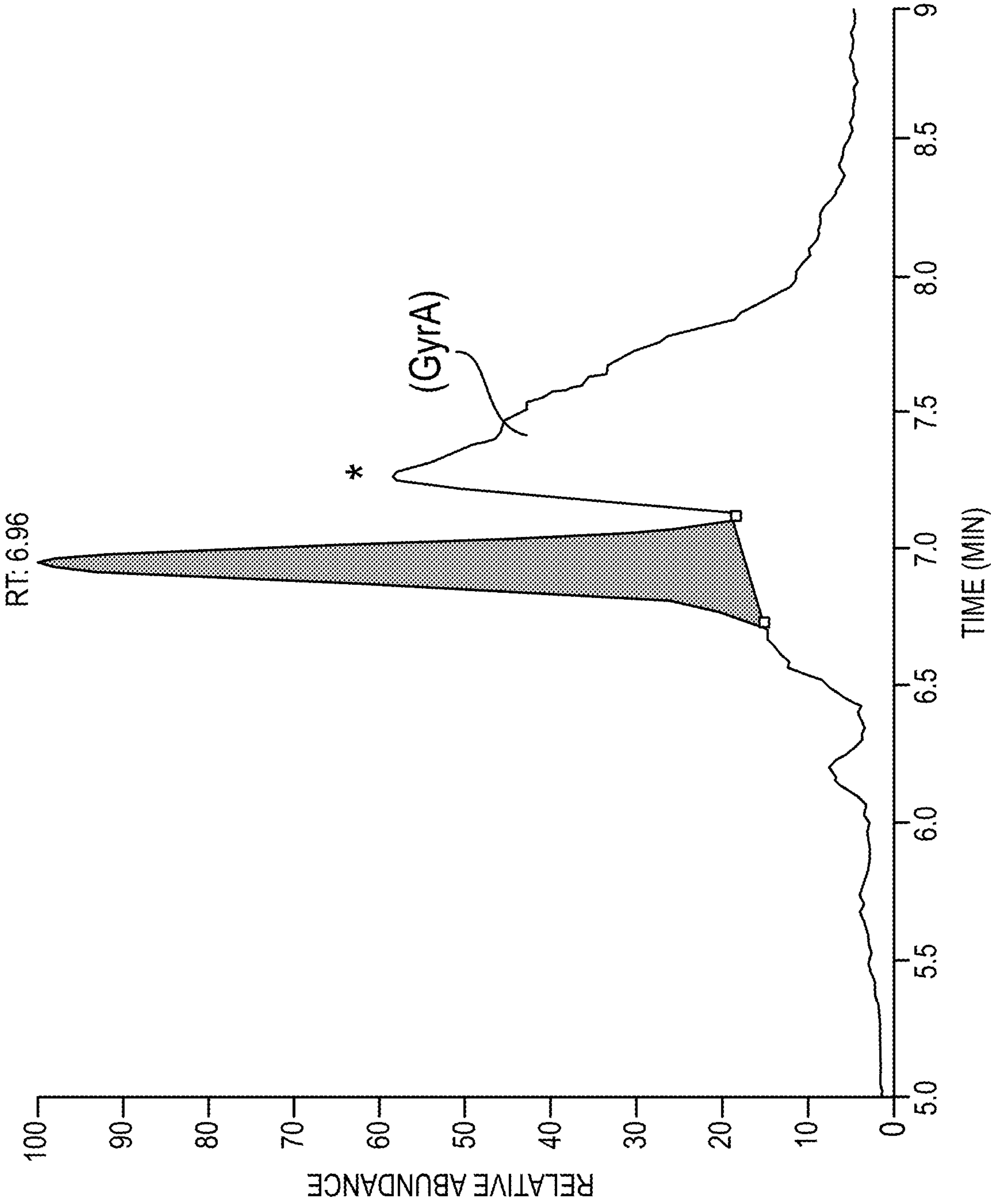
Figure 13A:
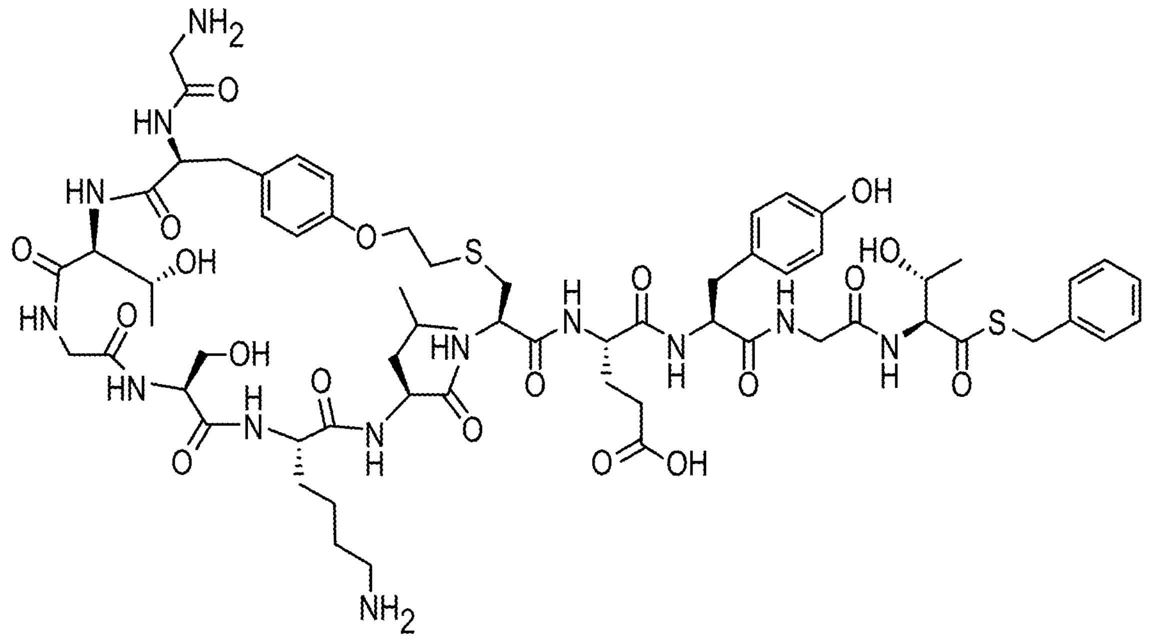
Figure 13B:
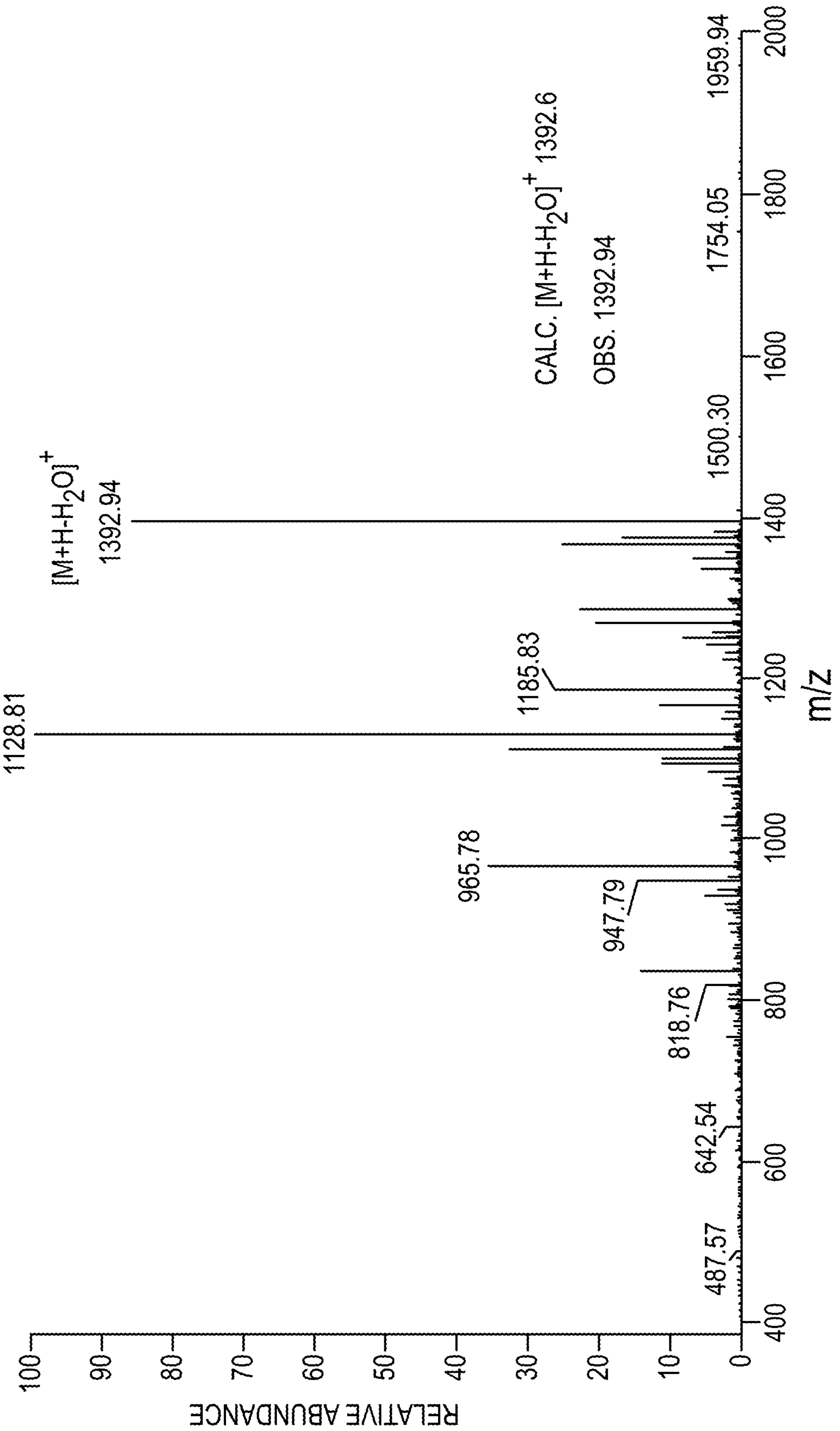
Figure 13C:
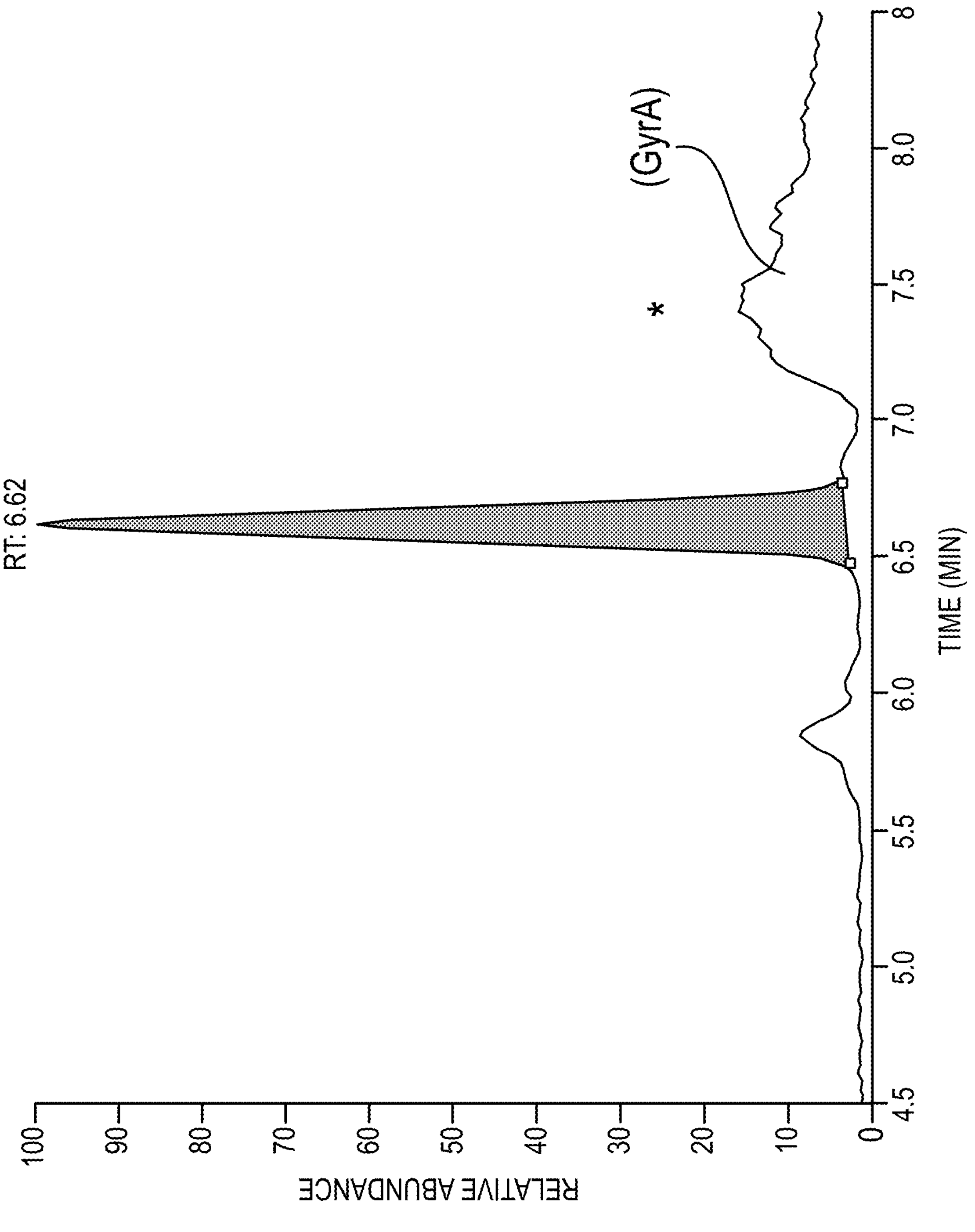
Figure 14A:
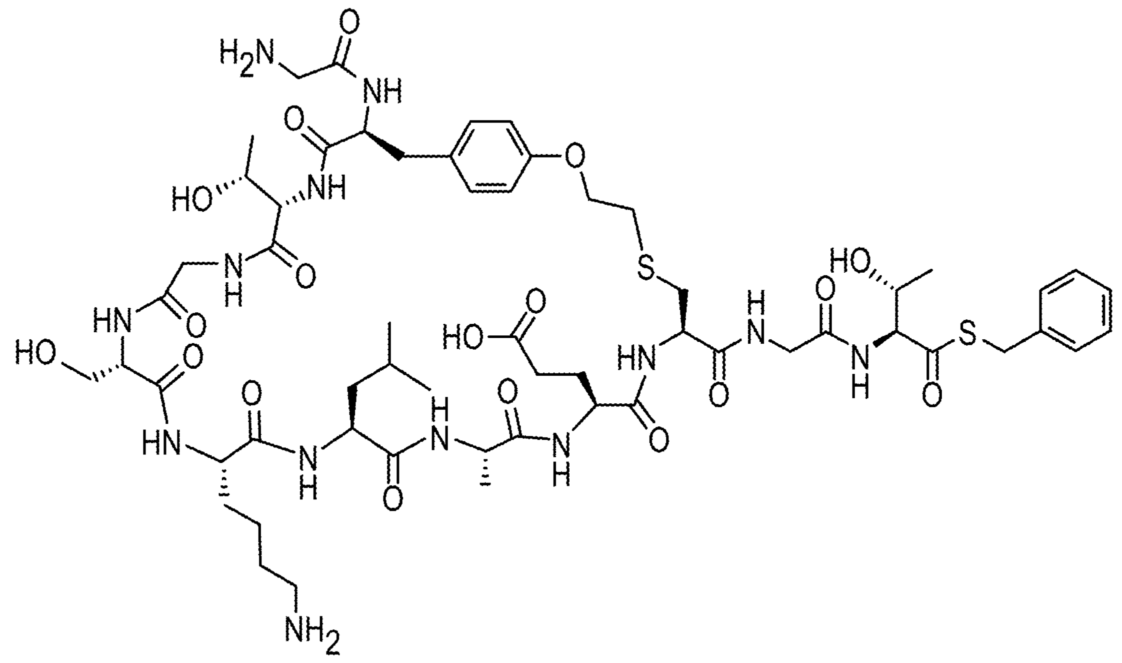
Figure 14B:
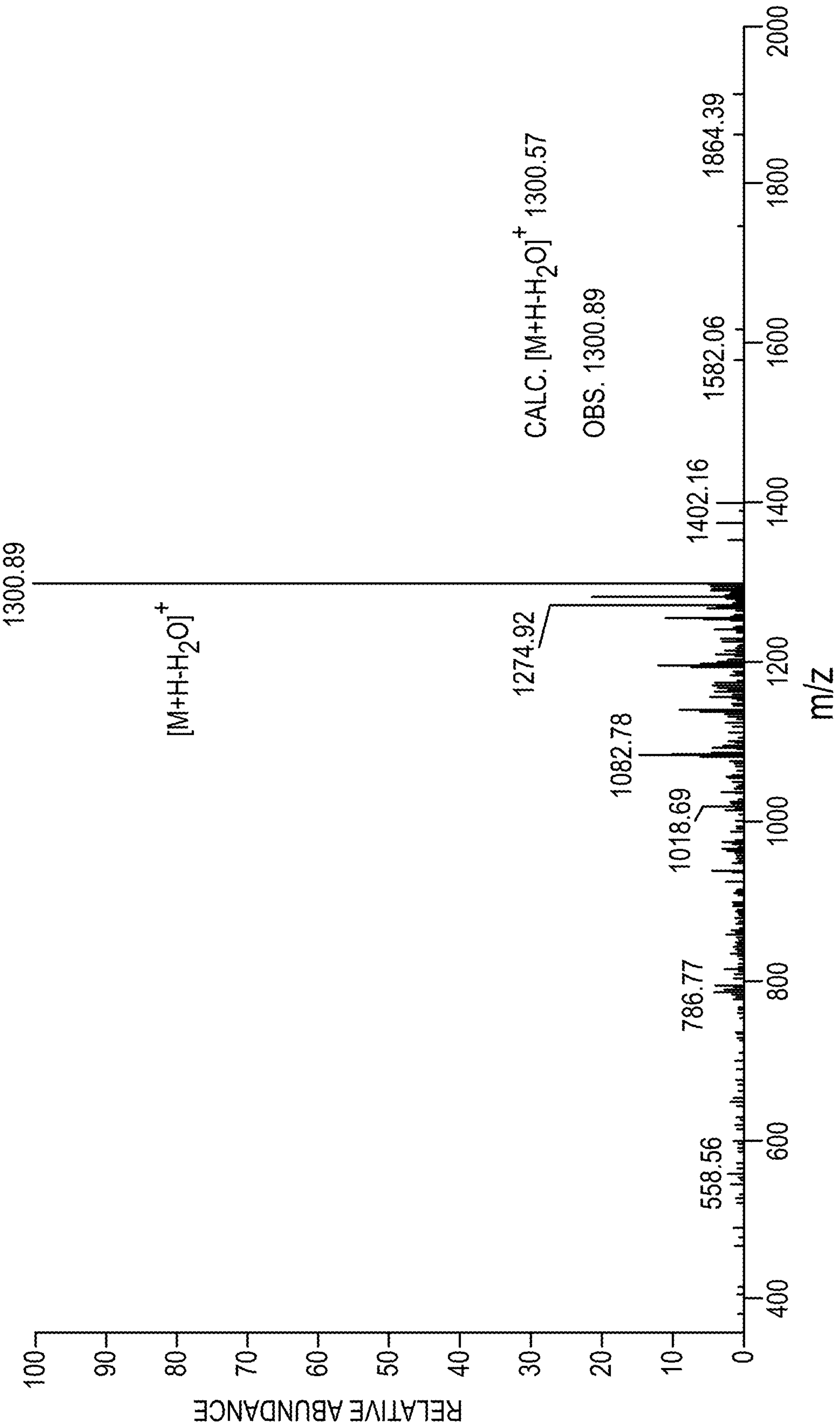
Figure 14C:
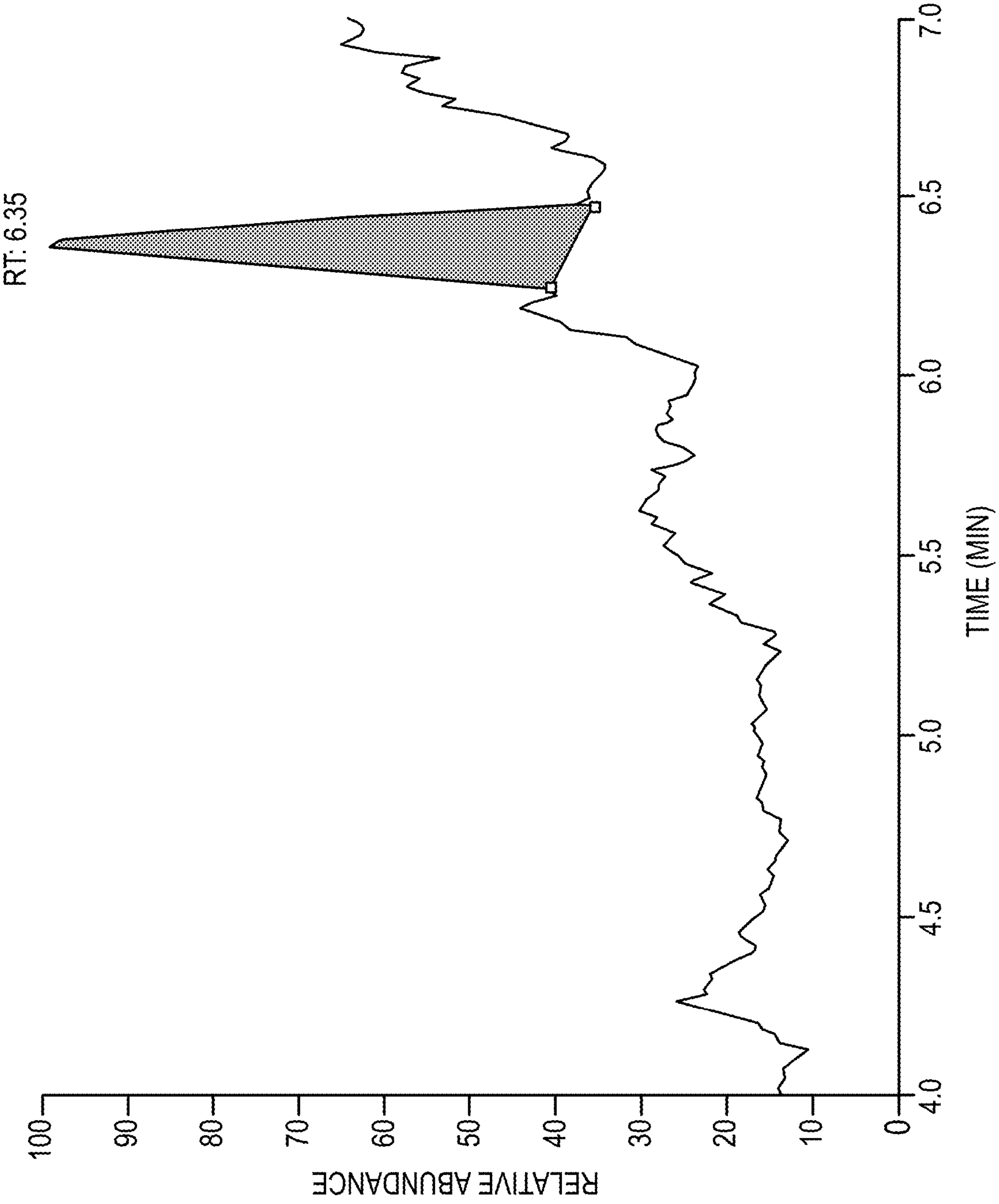
Figure 15A:
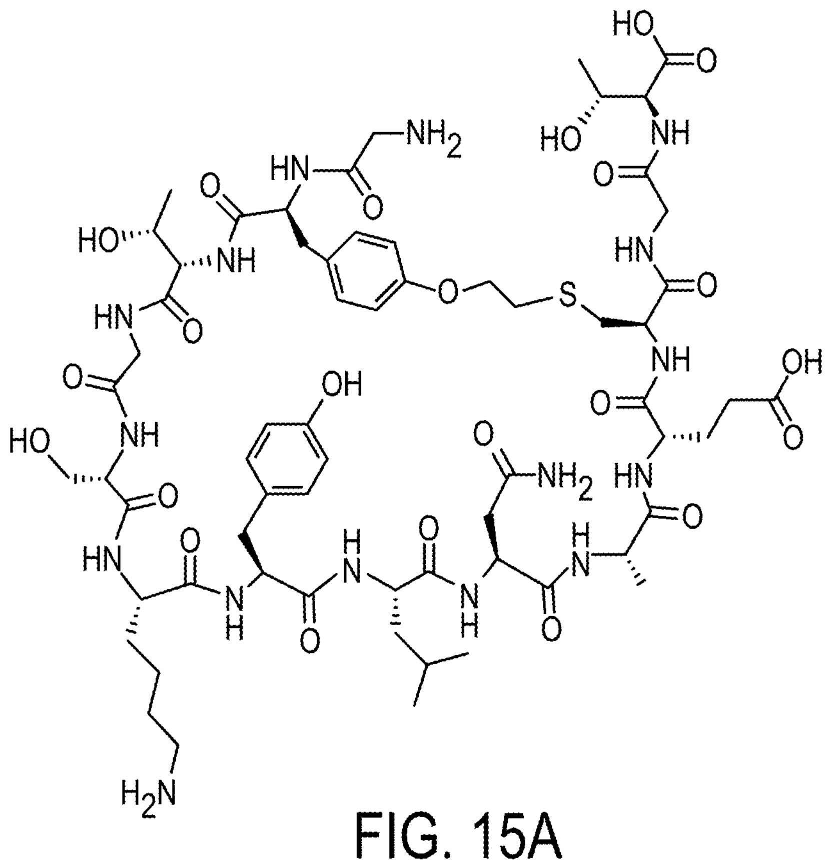
Figure 15B:
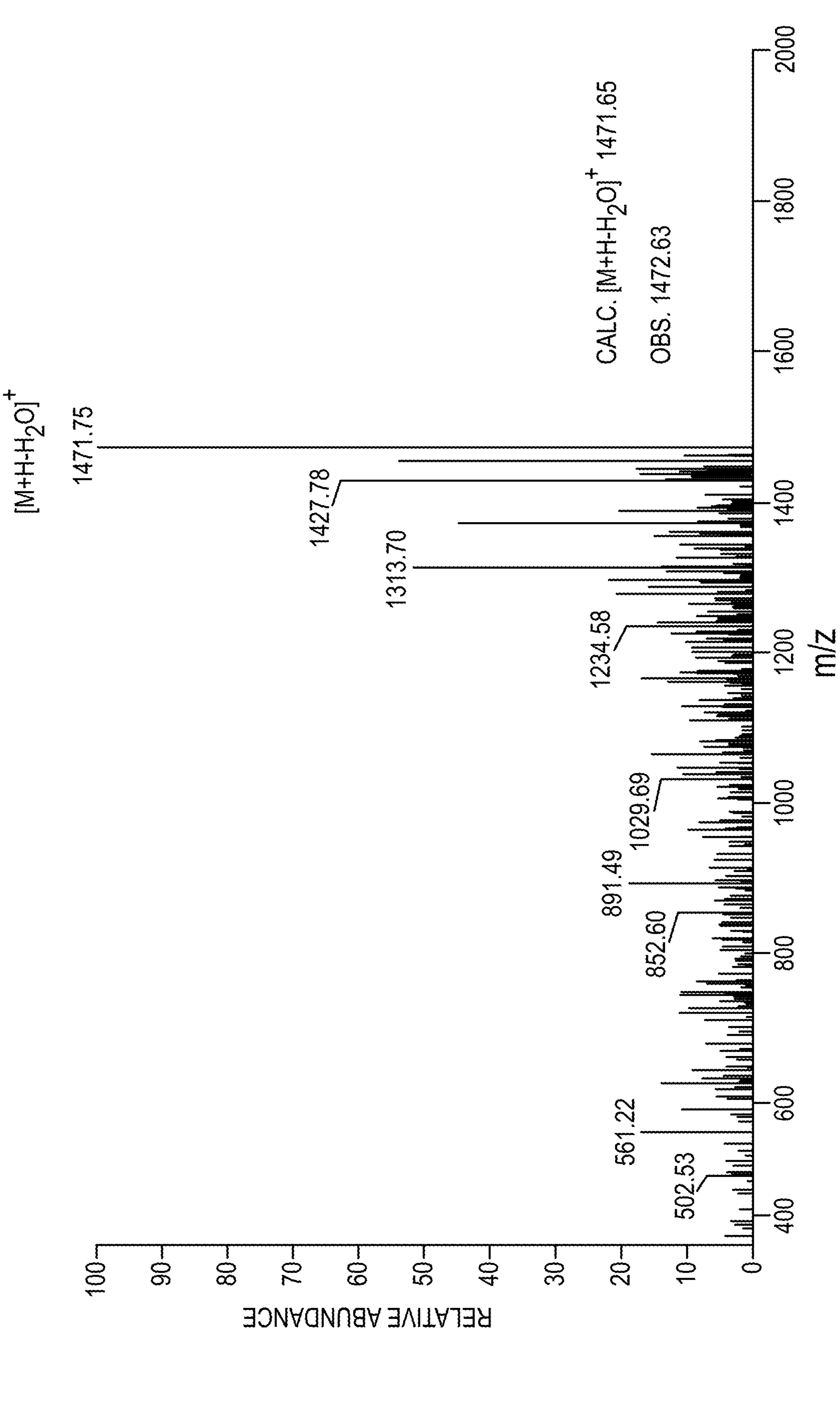
Figure 15C:
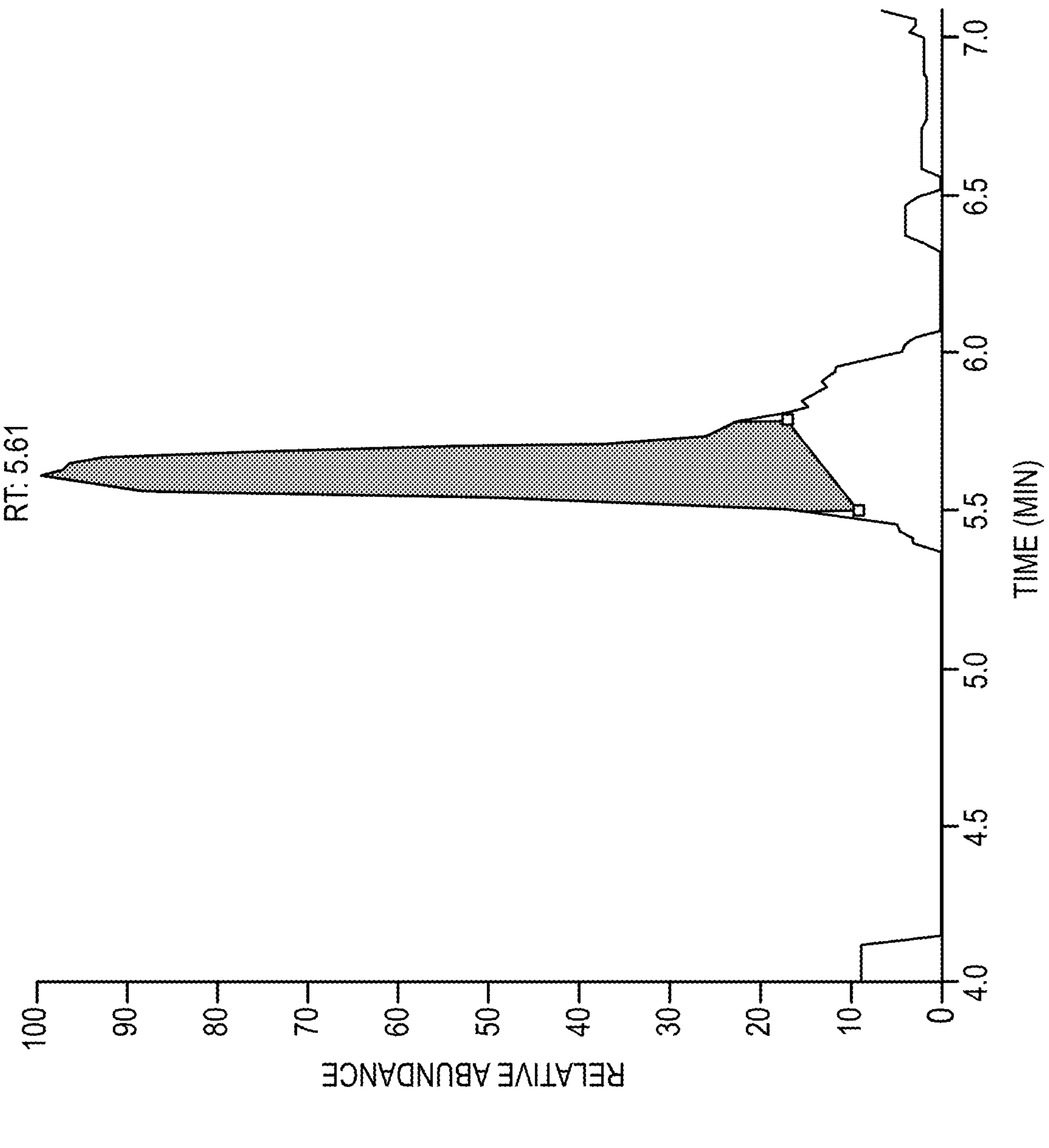

FIGS. 9A-B. Dependence of macrocyclization efficiency on relative position of the Cys residue with respect to the unnatural amino acid 'Z'. (A) Percentage of cyclization for the different p-2beF-containing constructs as determined by LCMS after in vitro splicing of the GyrA intein. (B) (Percentage of cyclization for the different 2becK- and 2cecK-containing constructs as determined by LCMS after in vitro splicing of the GyrA intein. In each case, proteins were isolated after expression in *E. coli* for 12 hours at 27° C. (see Examples for details).

FIGS. 10A-C, 11A-C, 12A-C, 13A-C, 14A-C and 15A-C. Representative examples of macrocyclic peptides produced from p-2beF-containing precursor polypeptides according to the methods disclosed herein. In each multi-part figure, (A) shows the sequence of the precursor polypeptide and the chemical structure of the macrocyclic peptide product, (B)

shows the MS/MS spectrum of the macrocyclic peptide, and (C) shows the LC-MS extracted-ion chromatogram of the macrocyclic peptide.

Figure 16A:
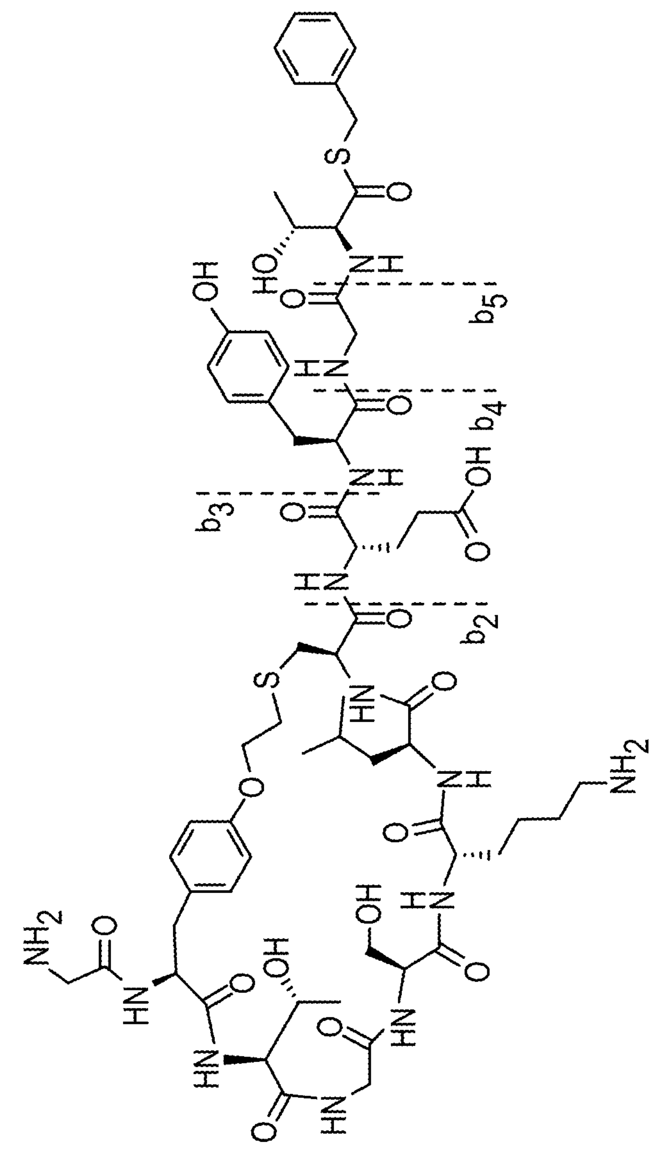
Figure 16B:
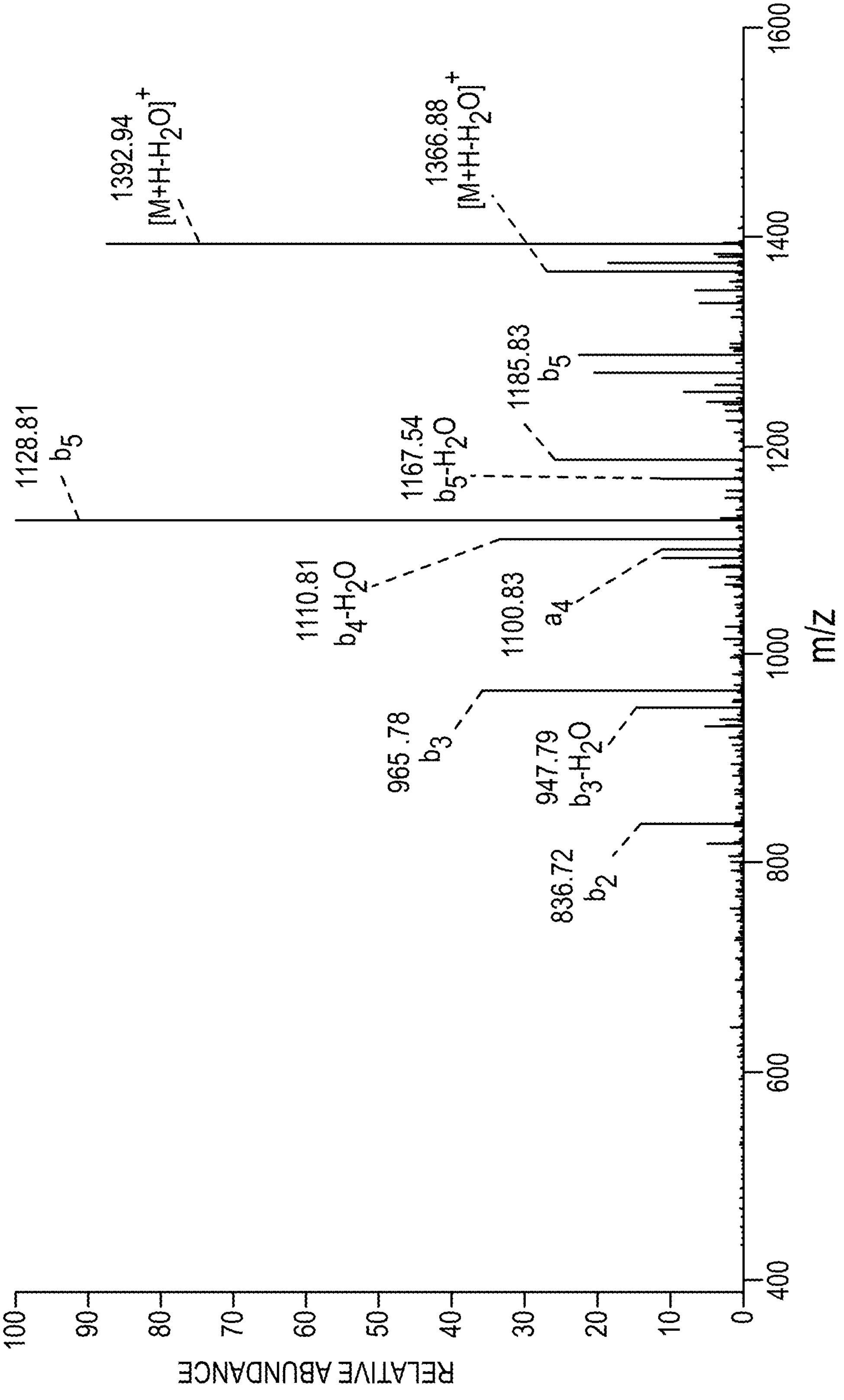
Figure 17A:
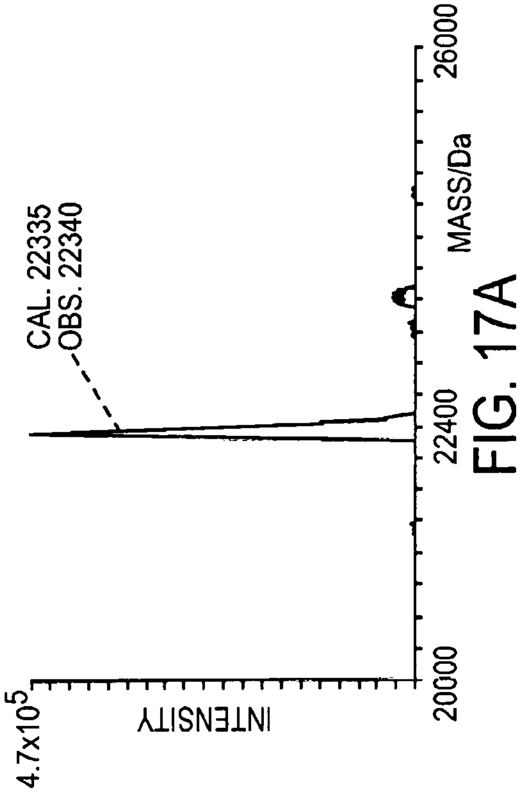
Figure 17B:
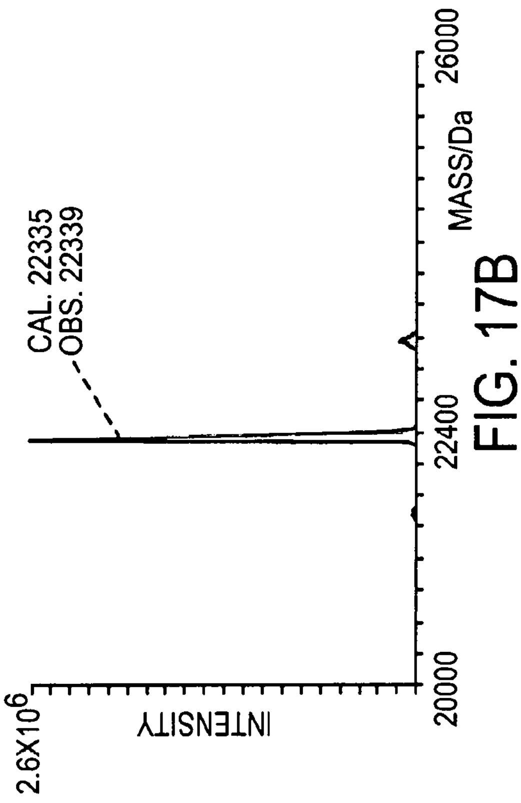
Figure 17C:
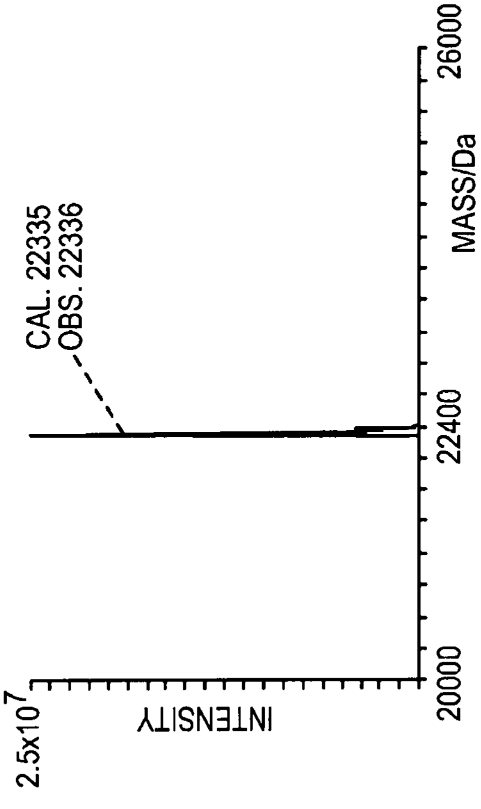
Figure 17D:
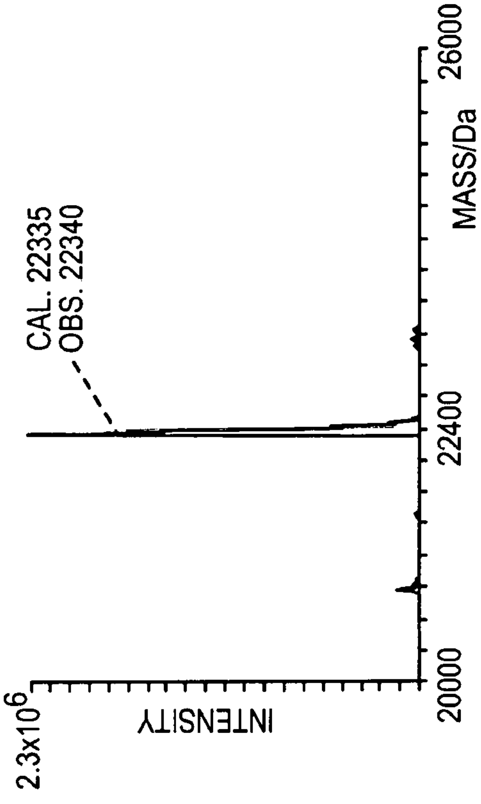
Figure 18A:
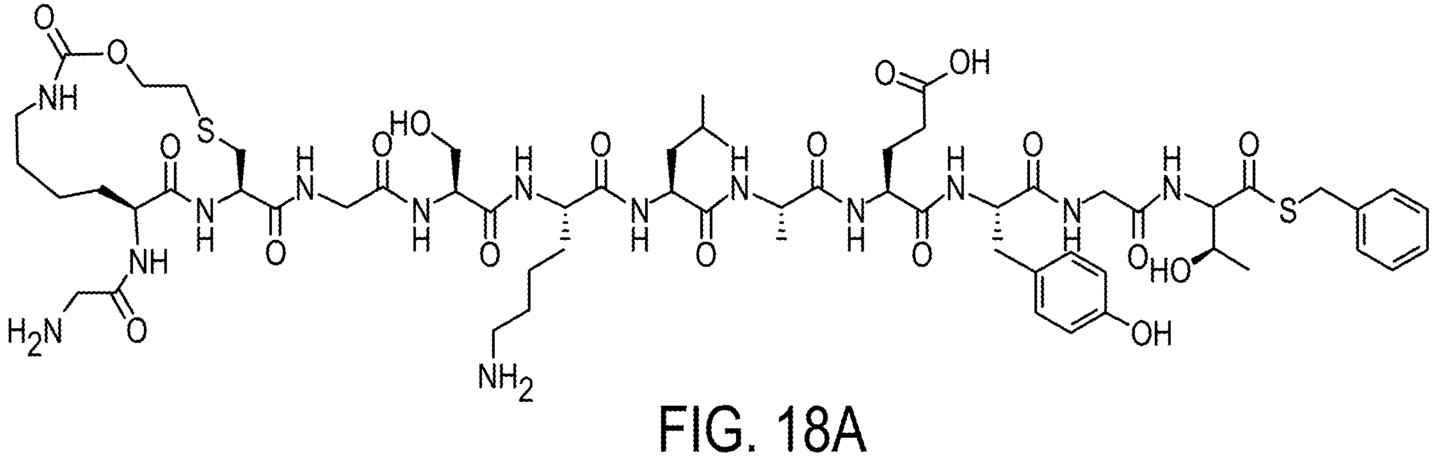
Figure 18B:
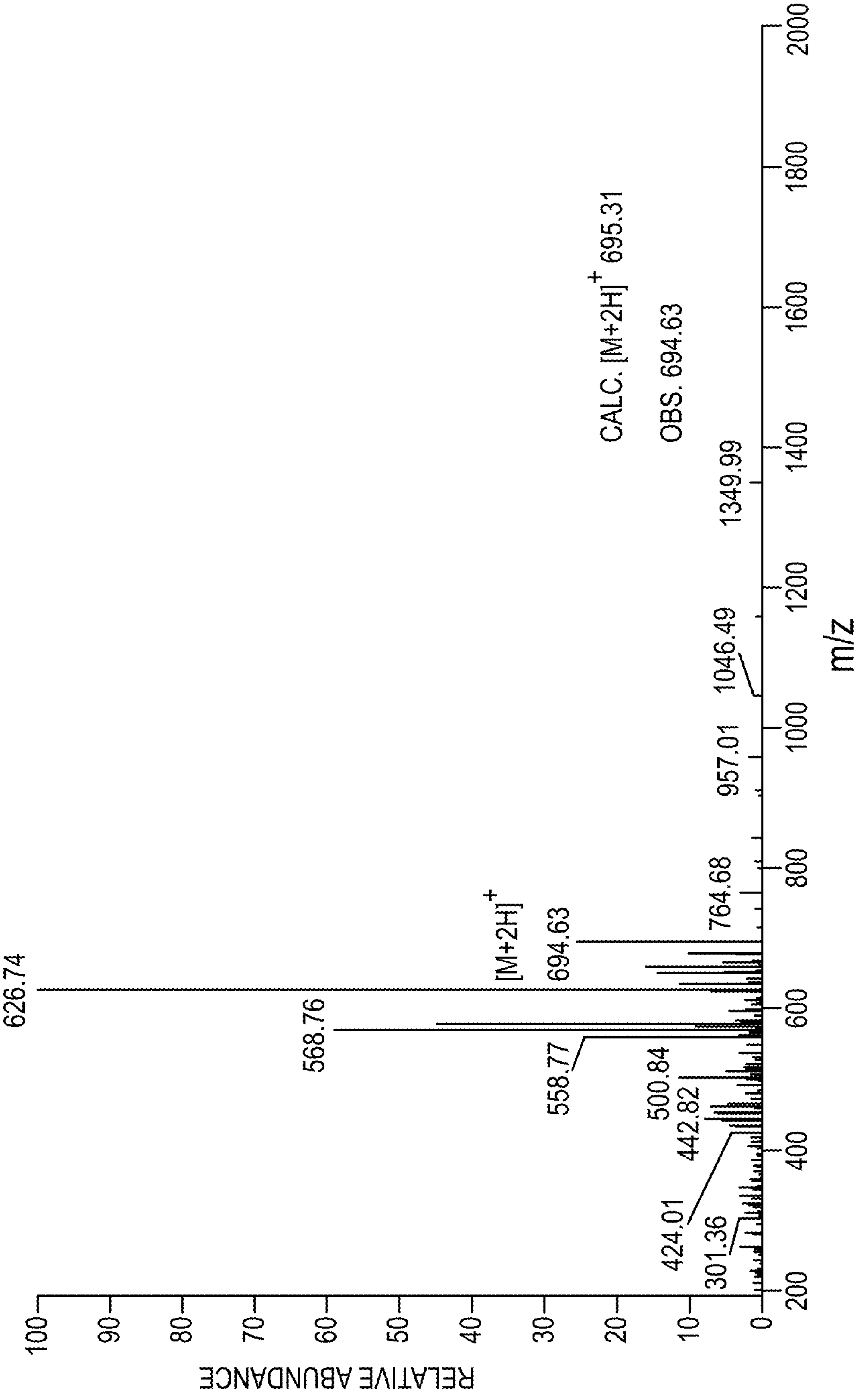
Figure 18C:
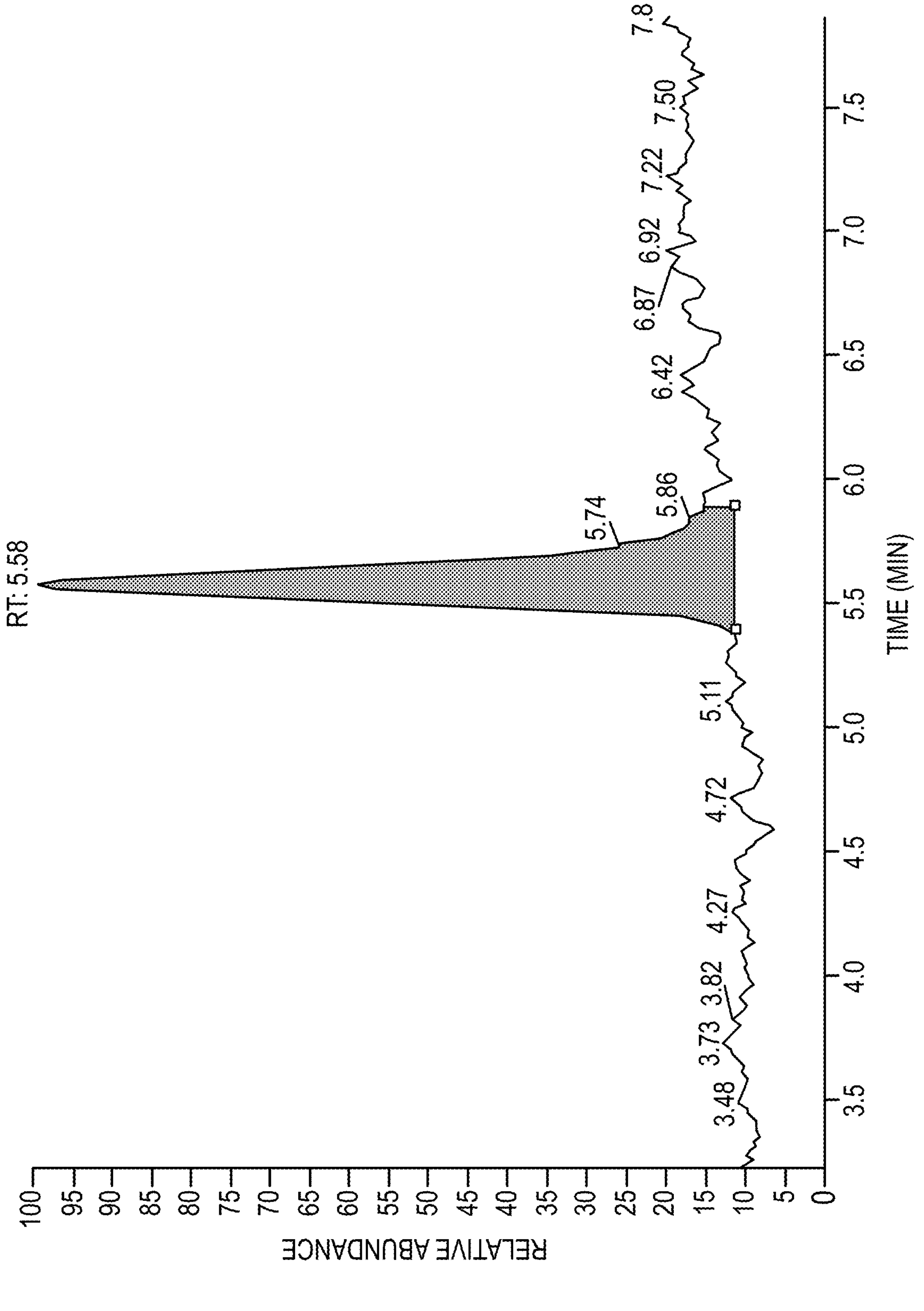
Figure 19A:
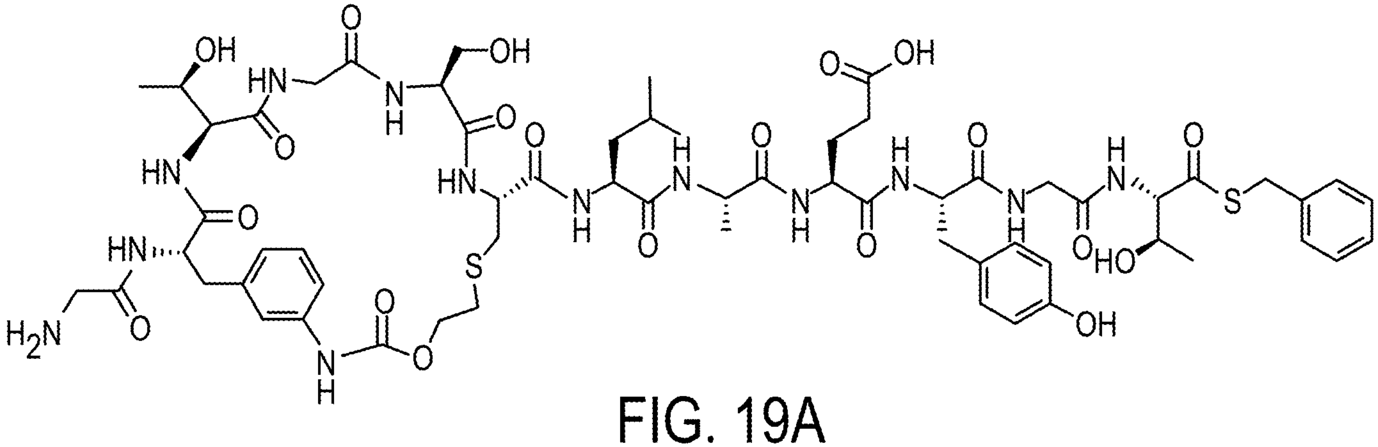
Figure 19B:
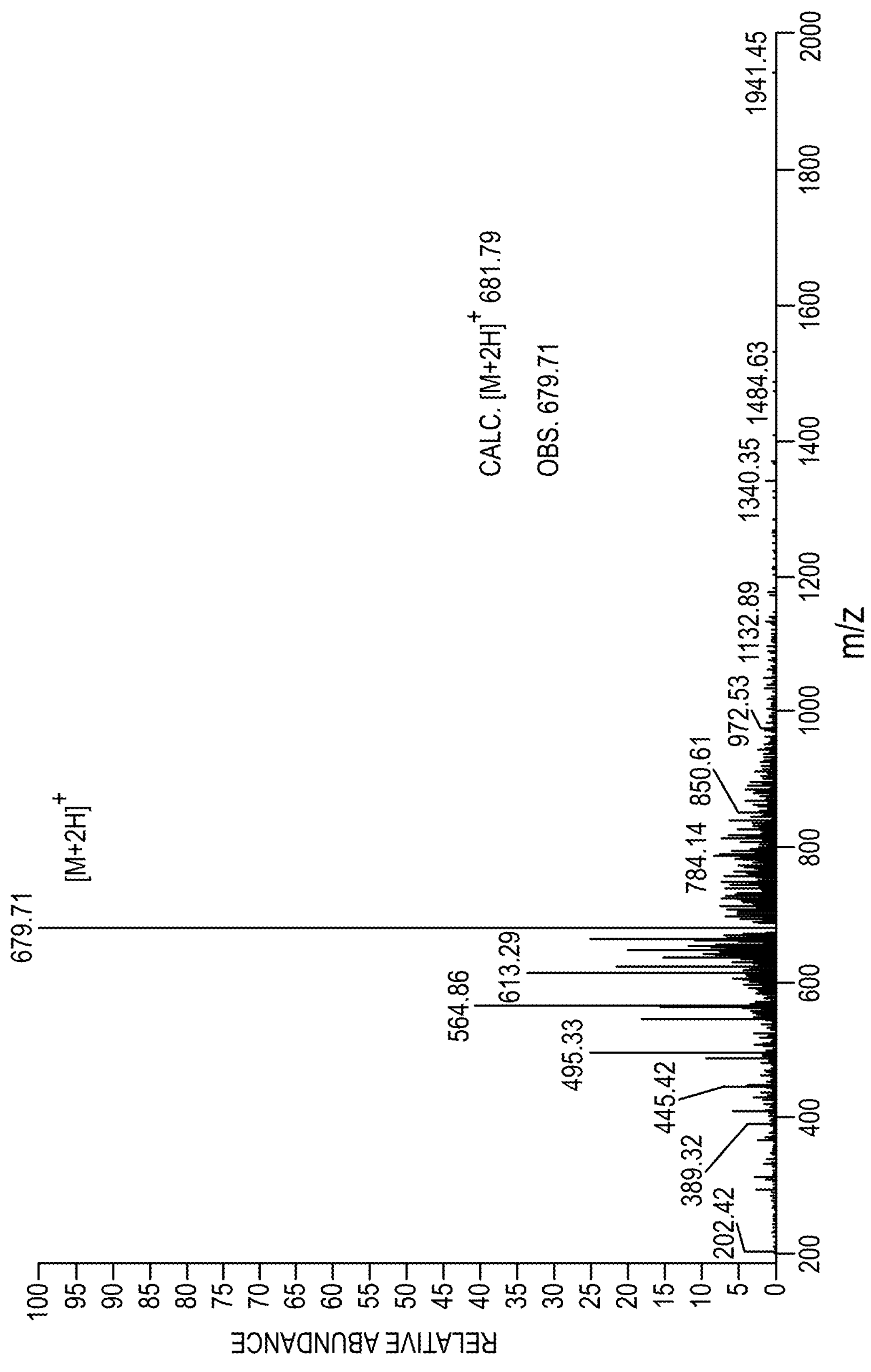
Figure 20A:
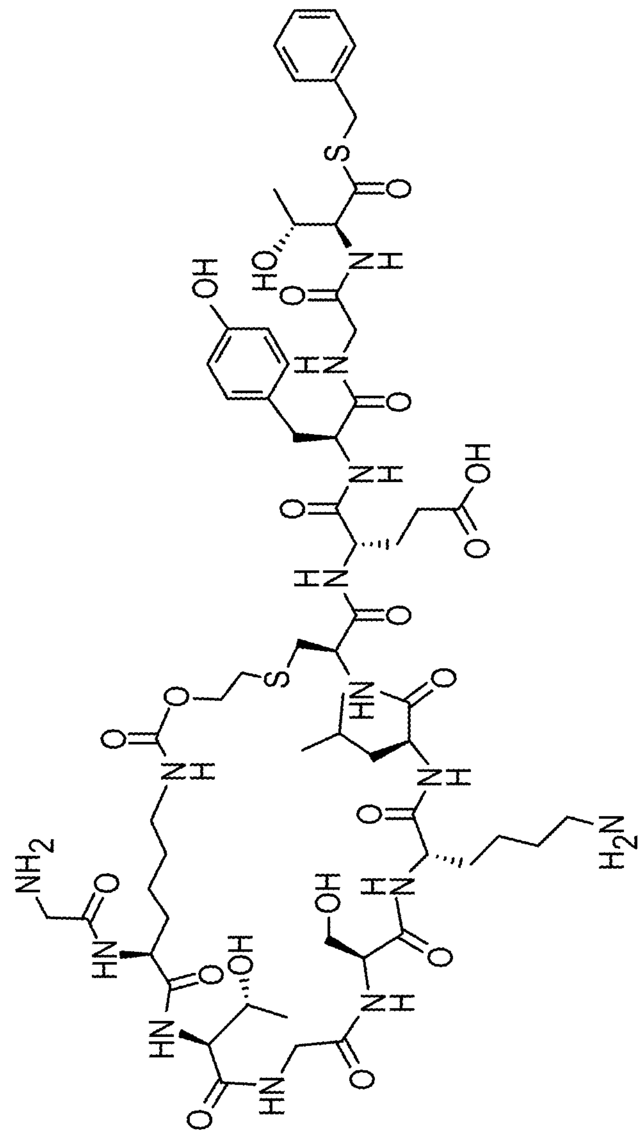
Figure 20B:
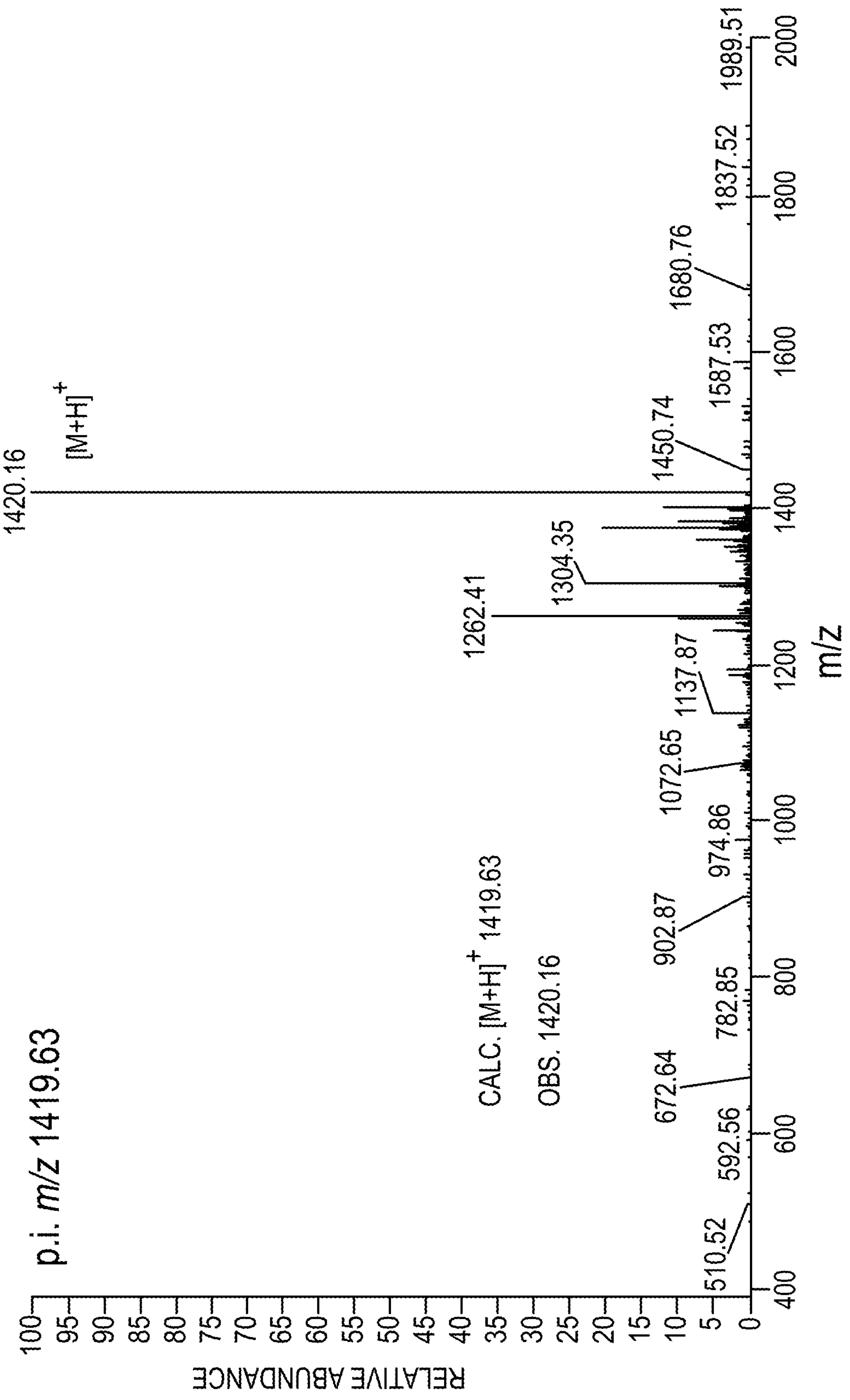
Figure 20C:
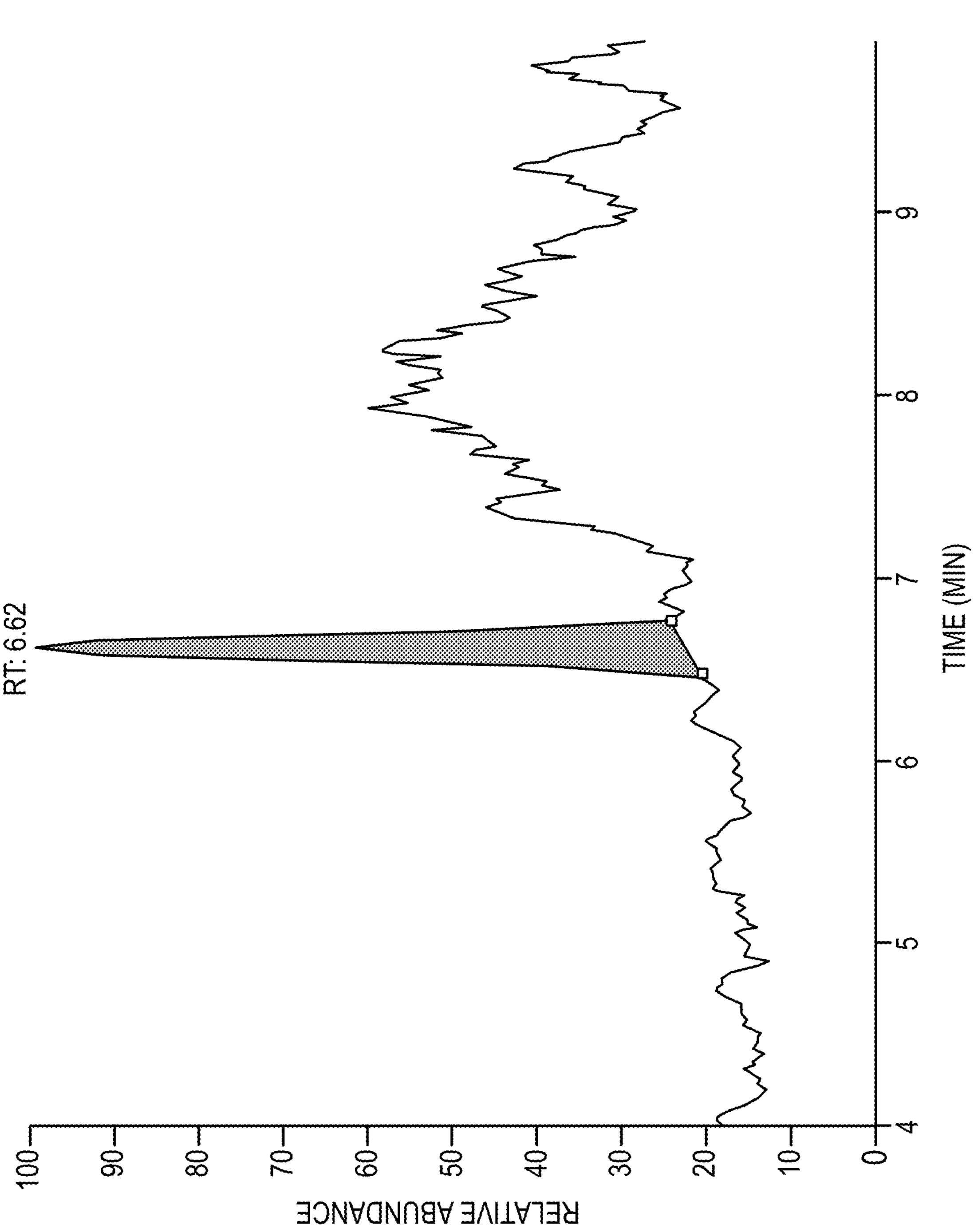
Figure 21A:
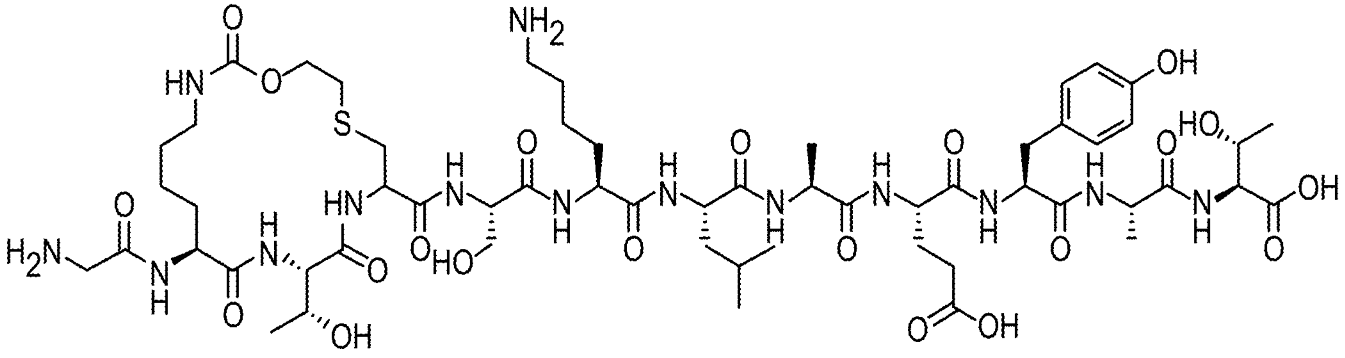
Figure 21B:
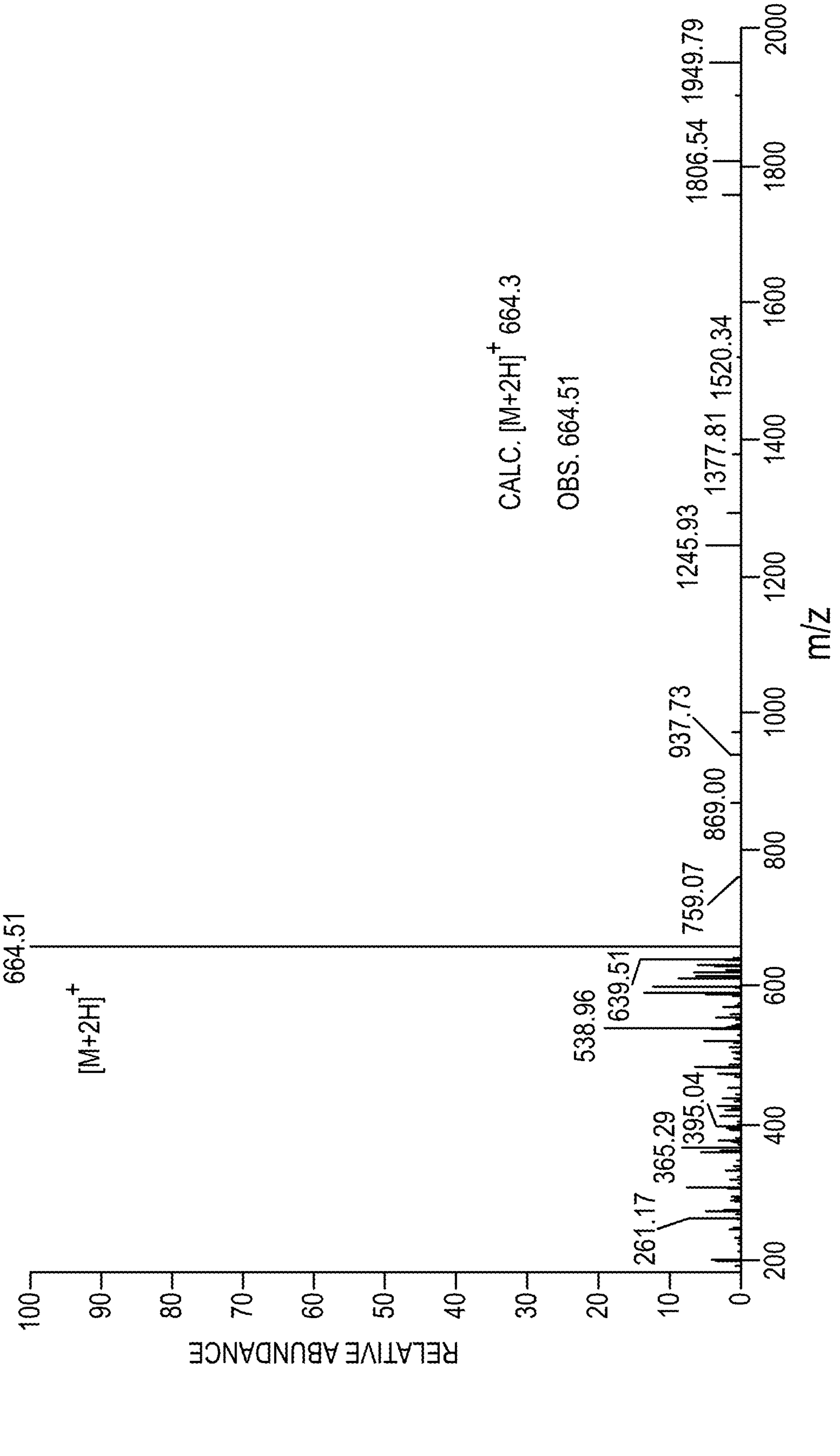
Figure 21C:
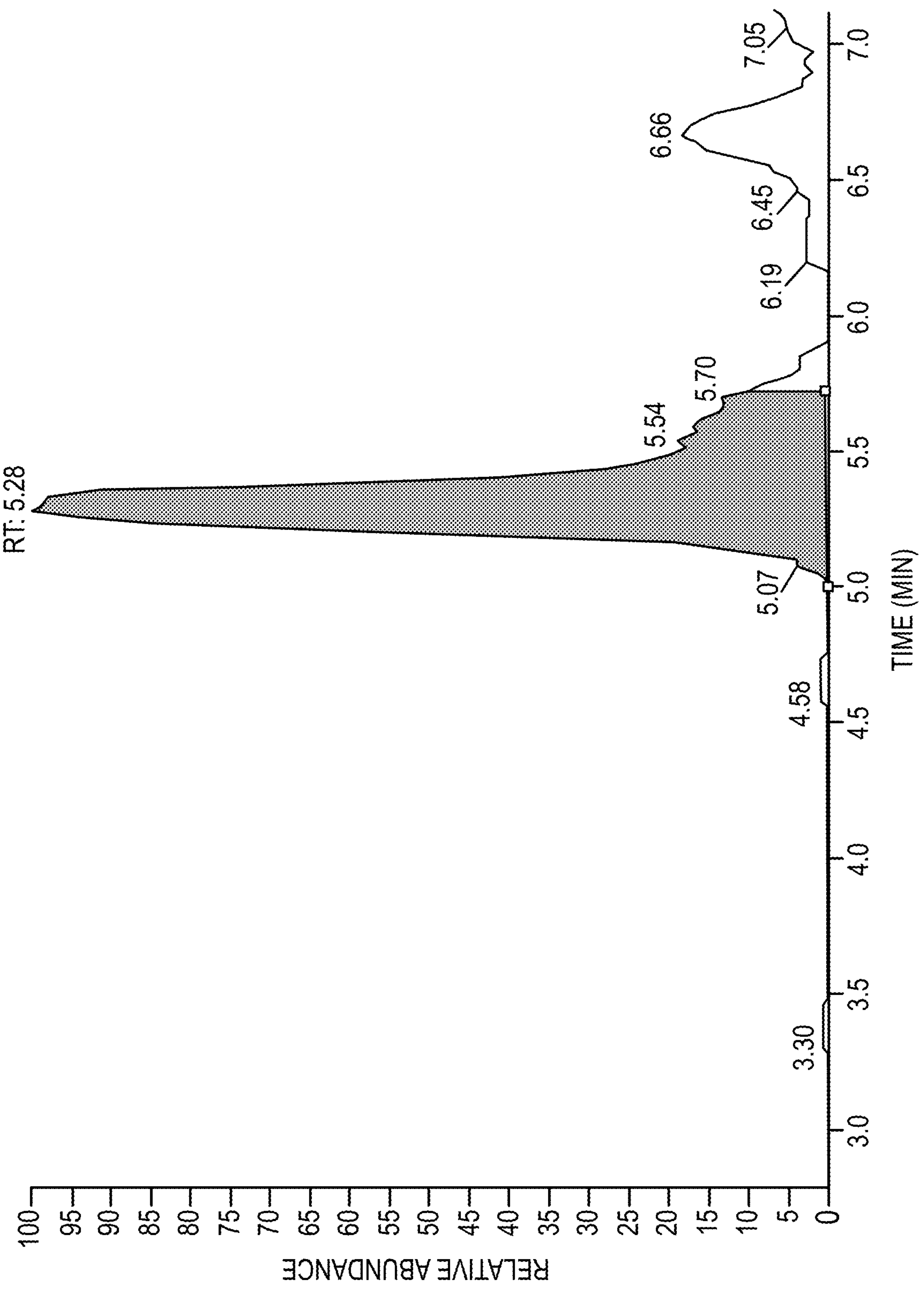
Figure 22A:
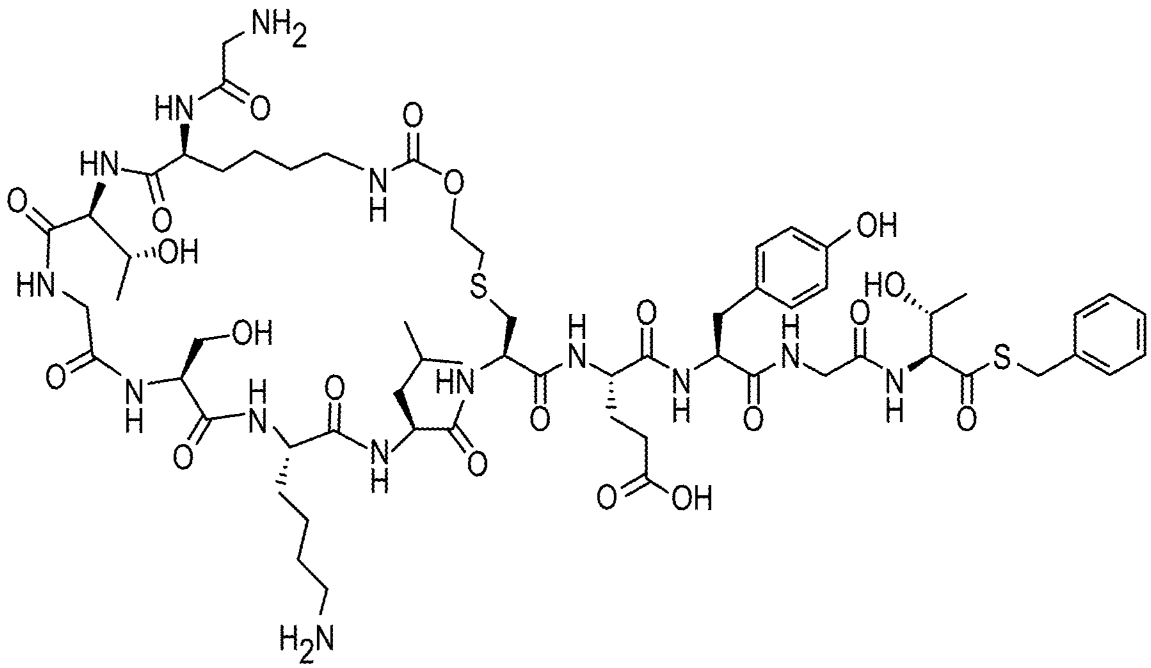
Figure 22B:
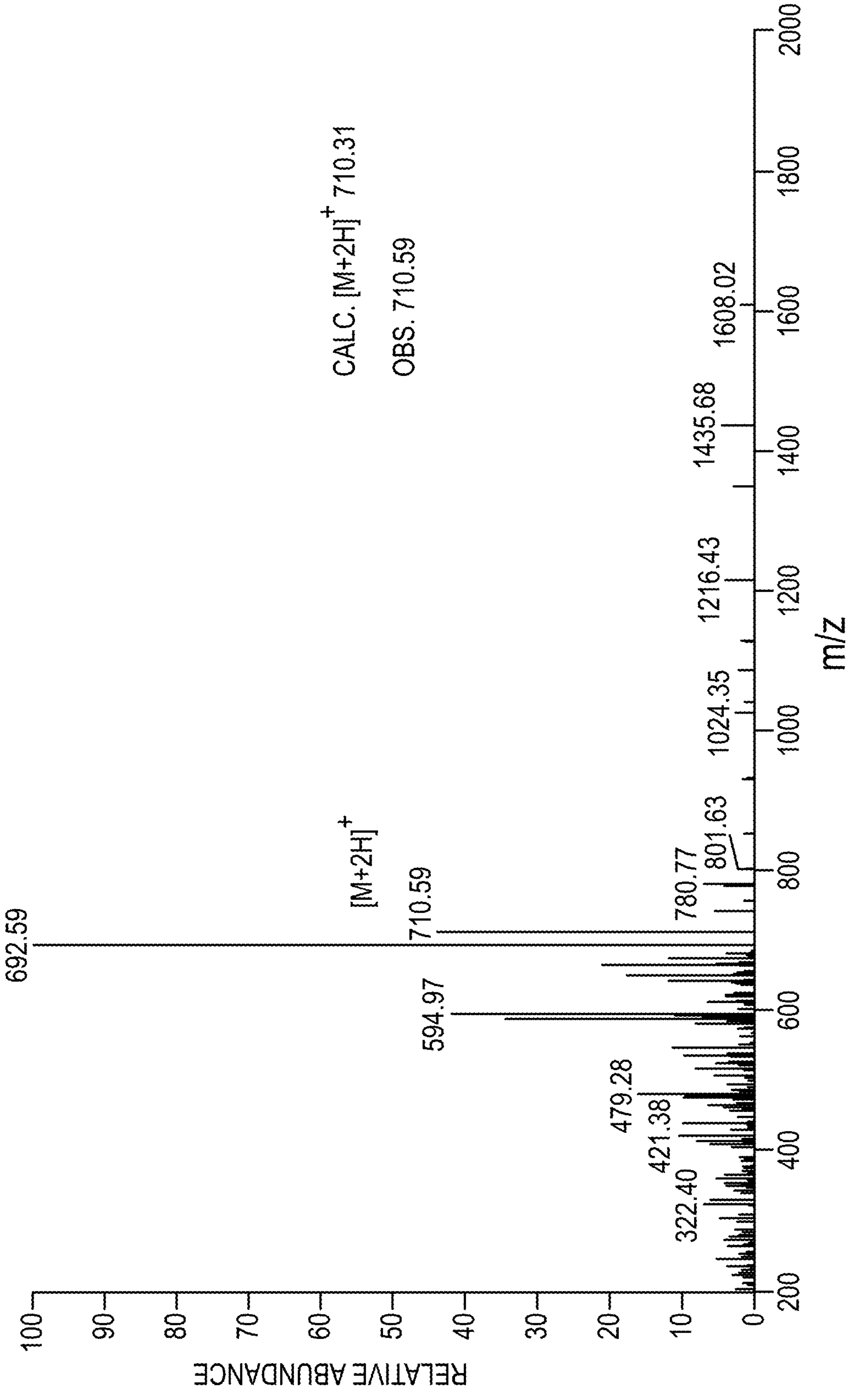
Figure 22C:
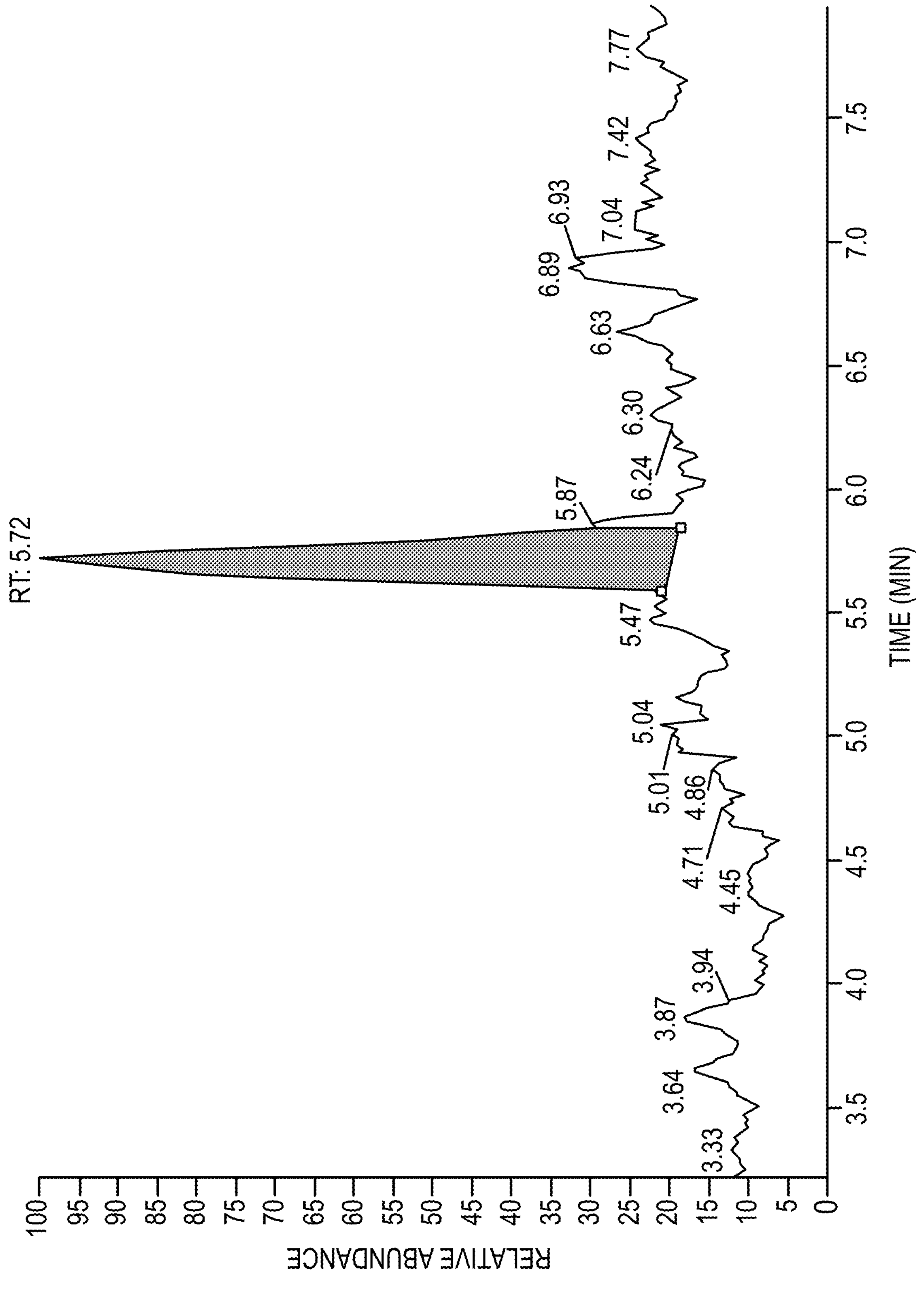
Figure 23A:
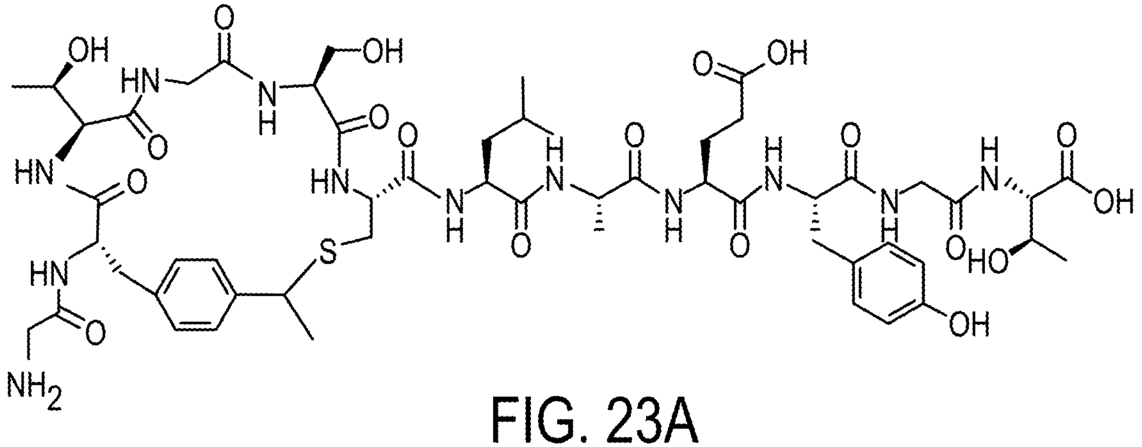
Figure 23B:
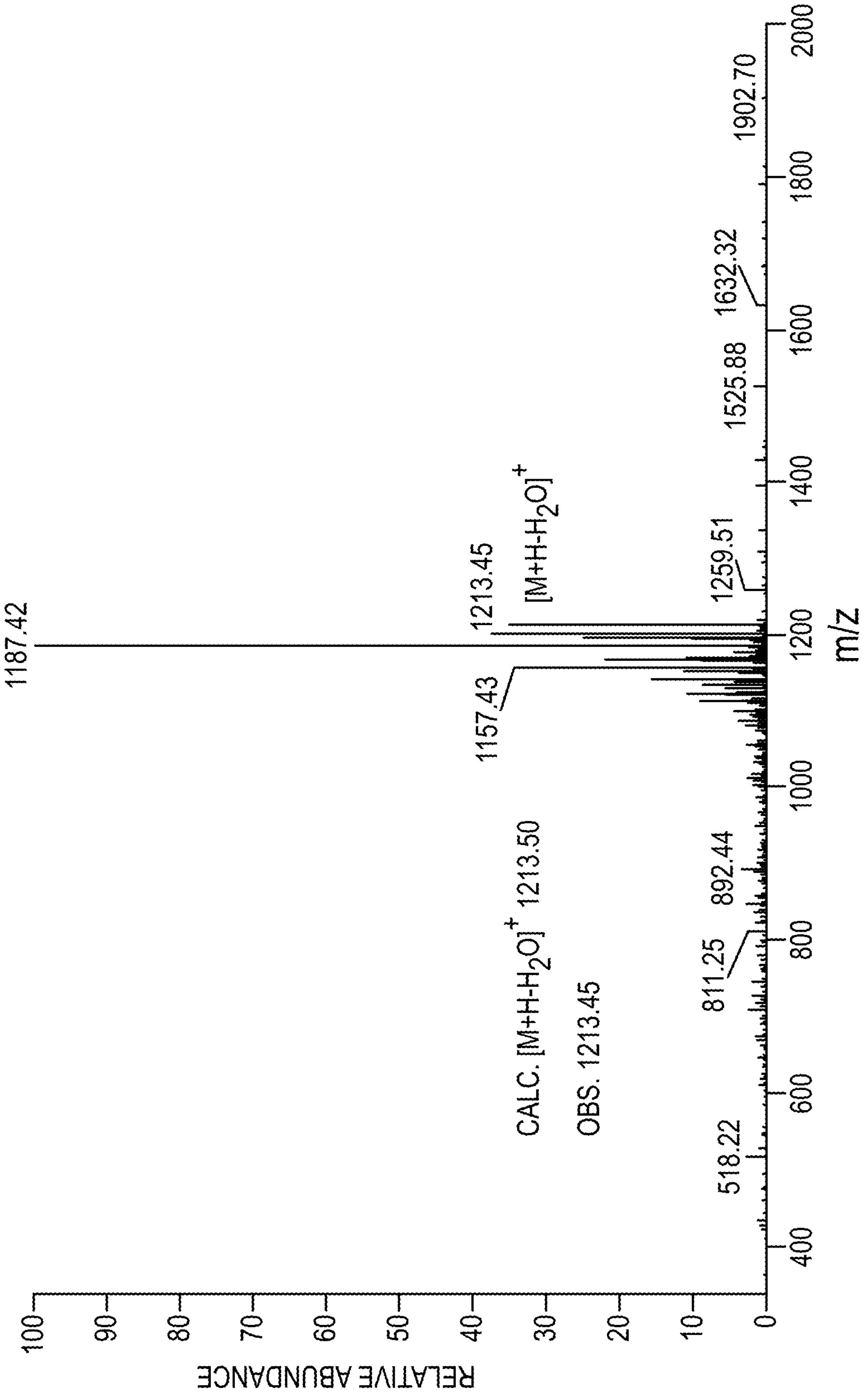
Figure 23C:
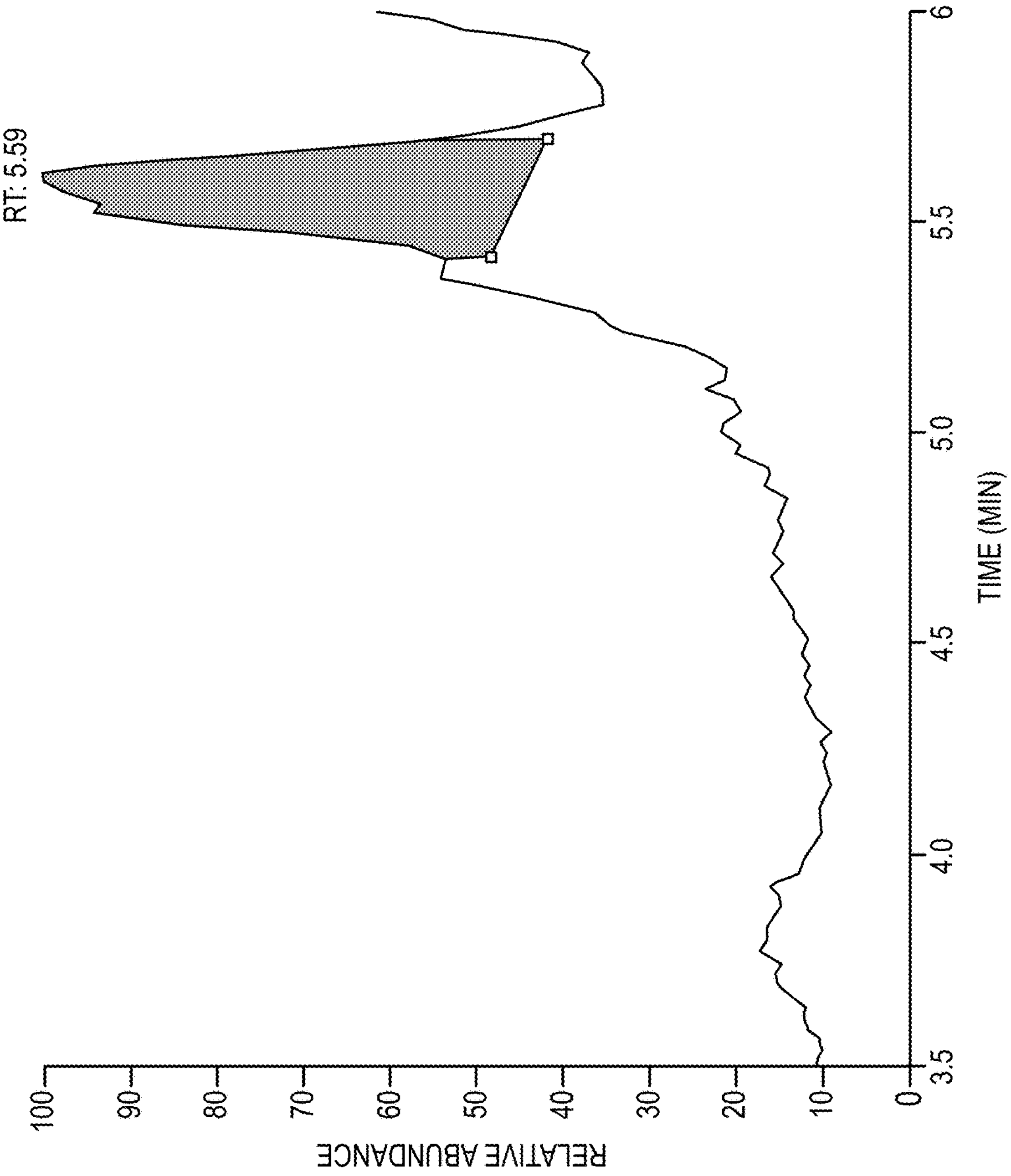
Figure 24A:
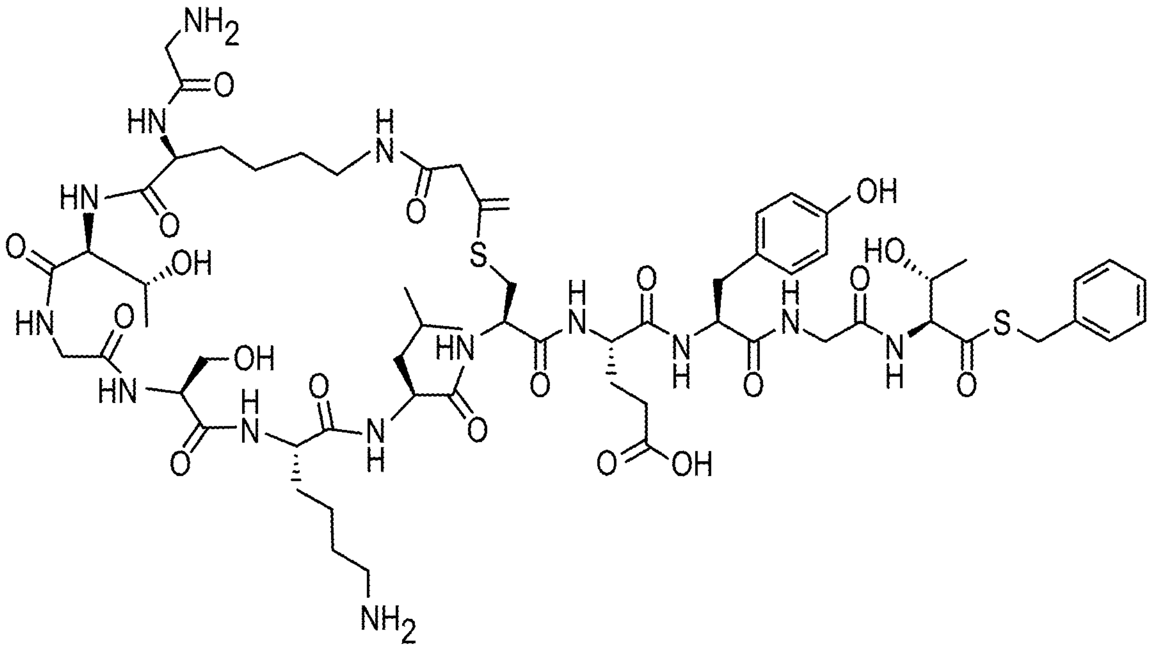
Figure 24B:
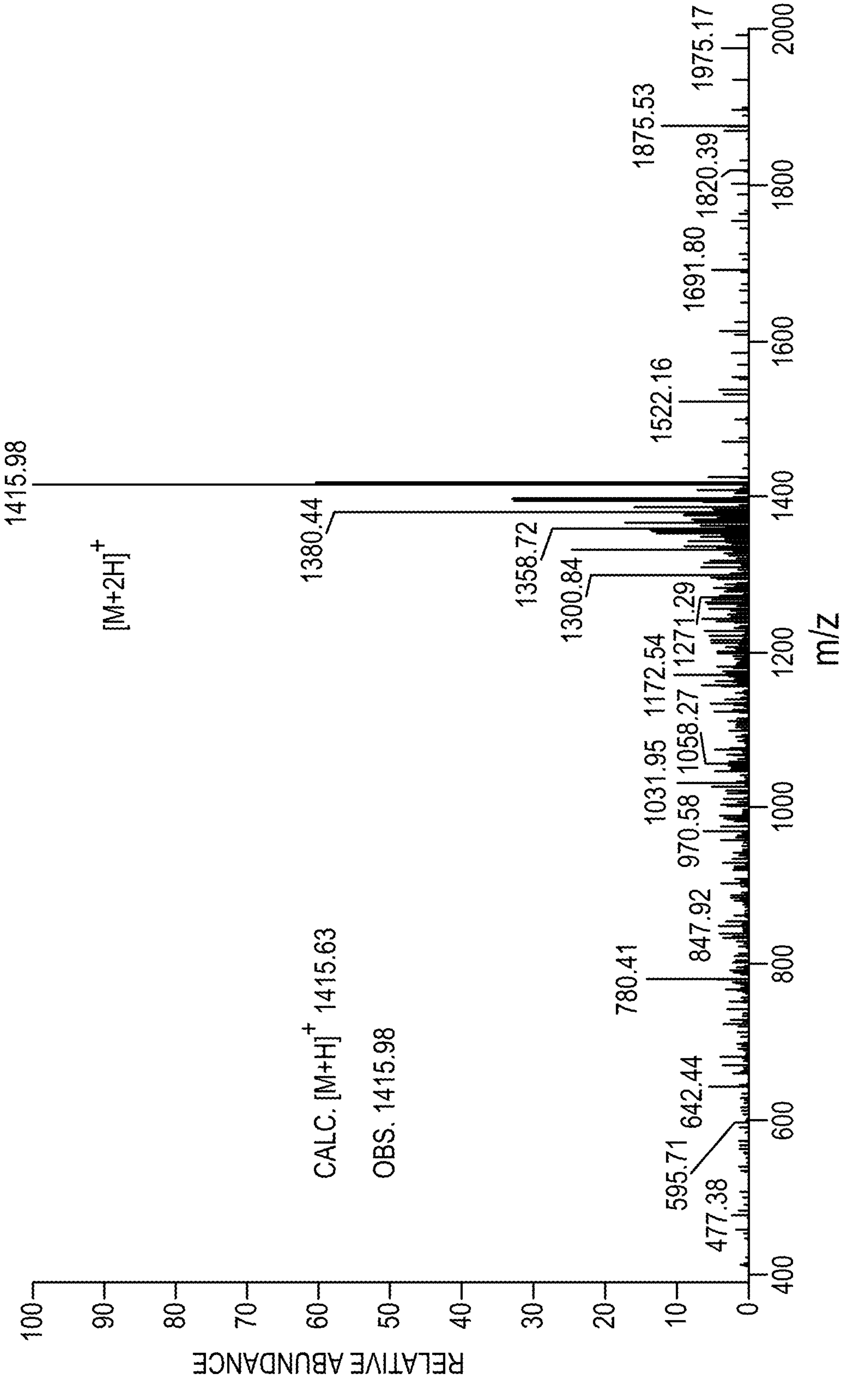
Figure 24C:
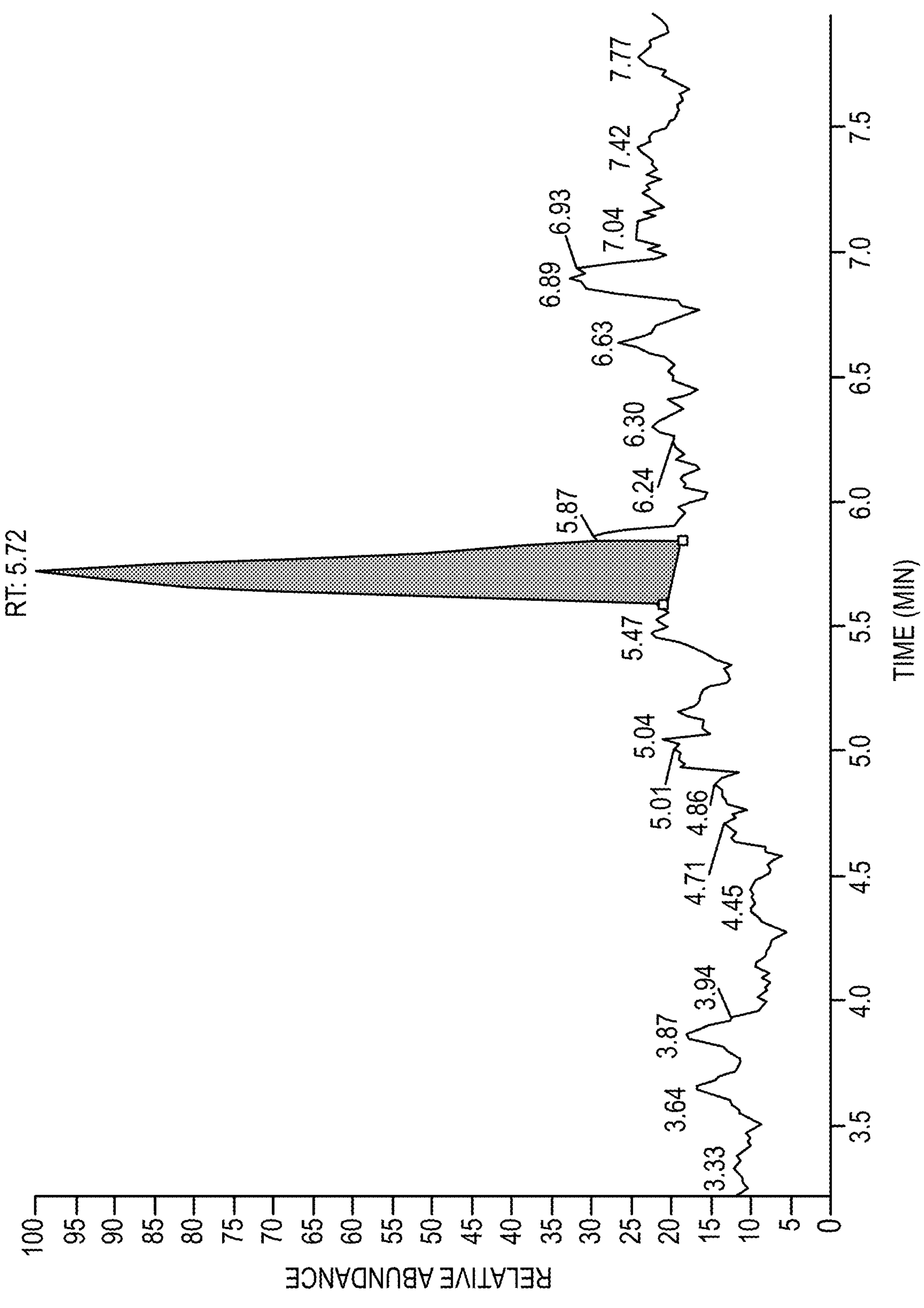
Figure 25A:
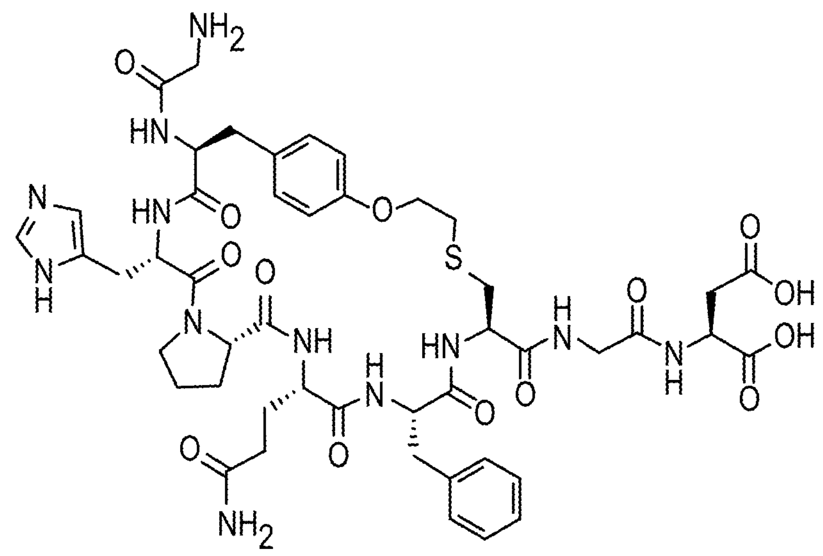
Figure 25B:
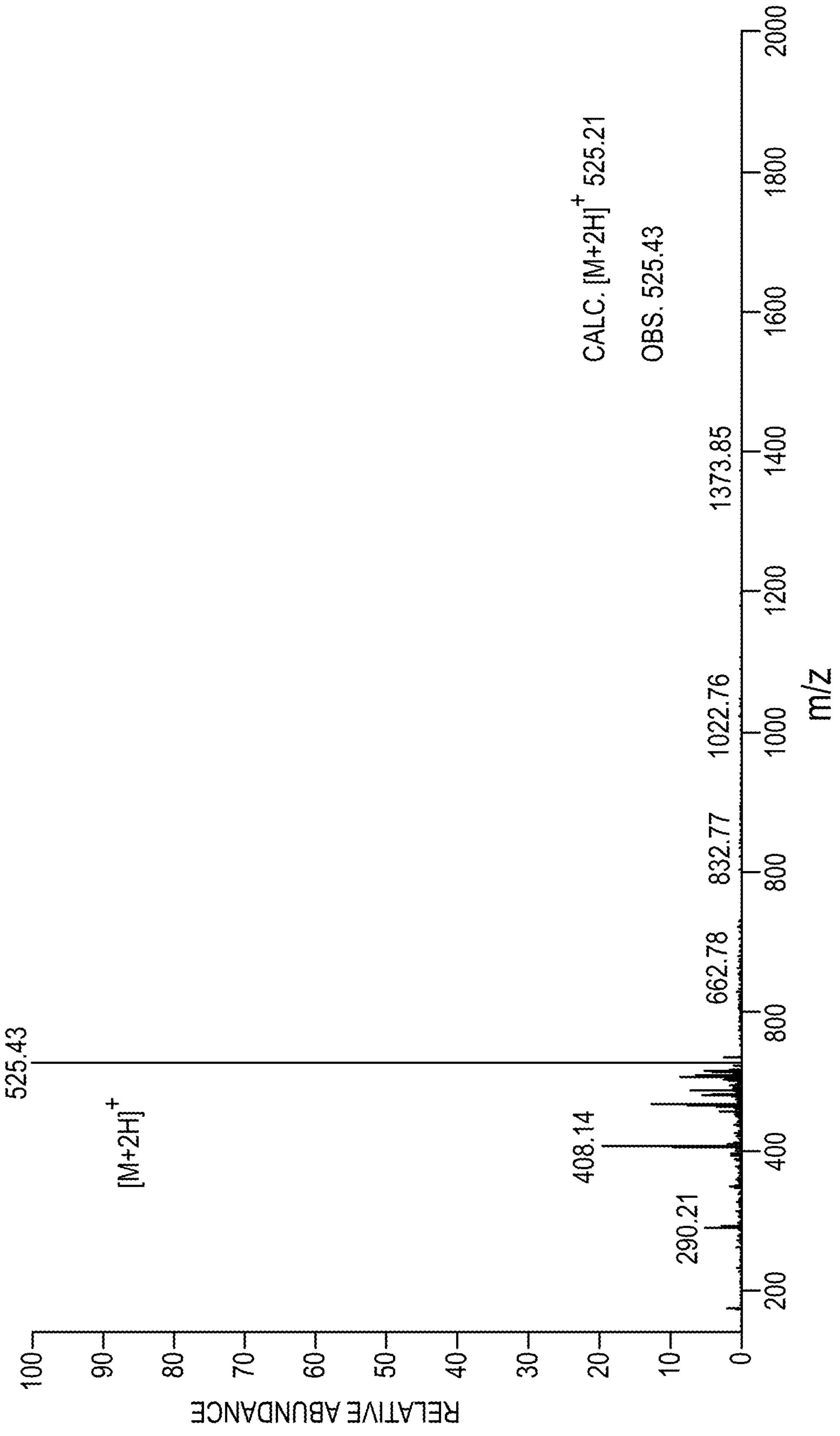
Figure 25C:
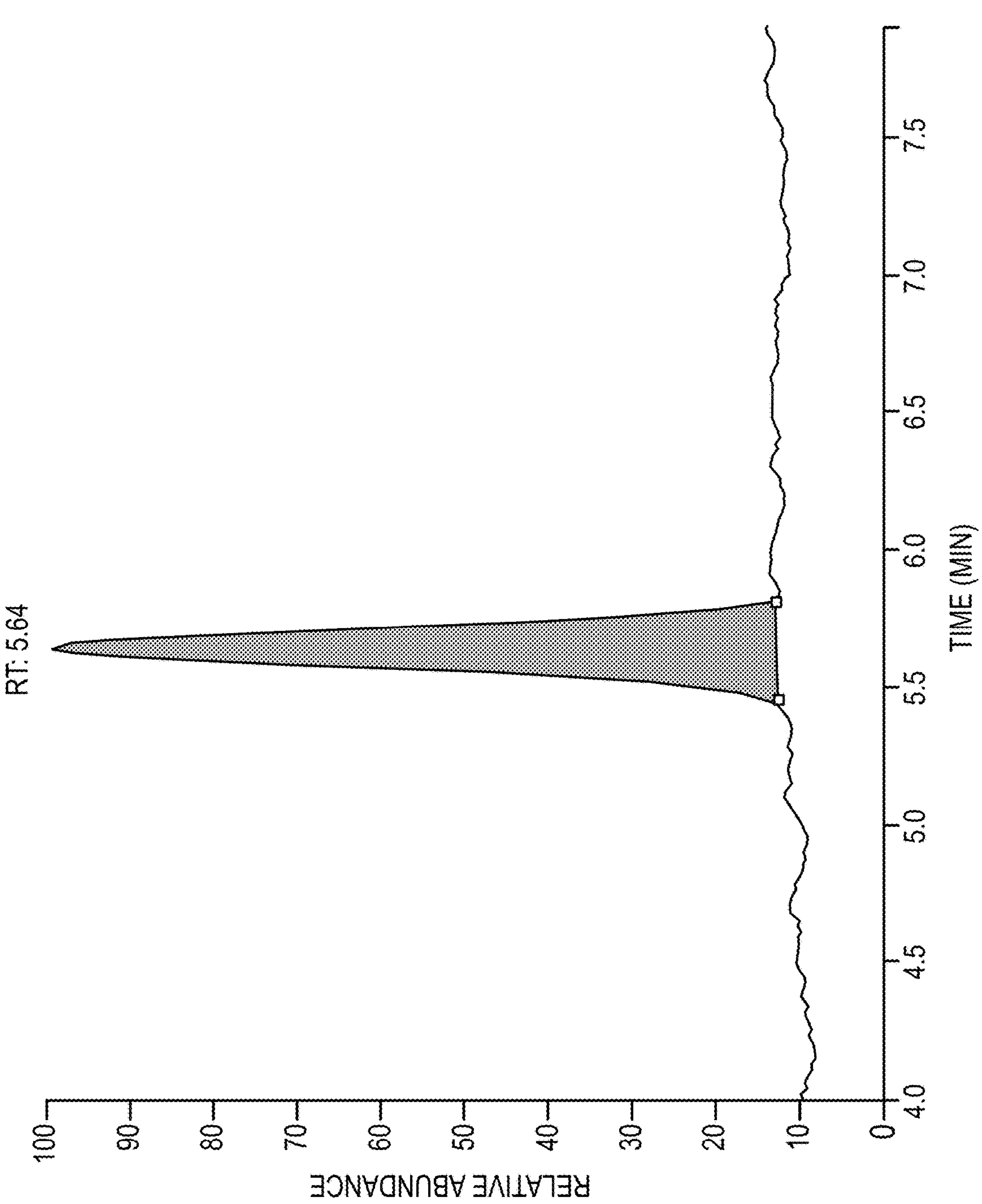
Figure 26A:
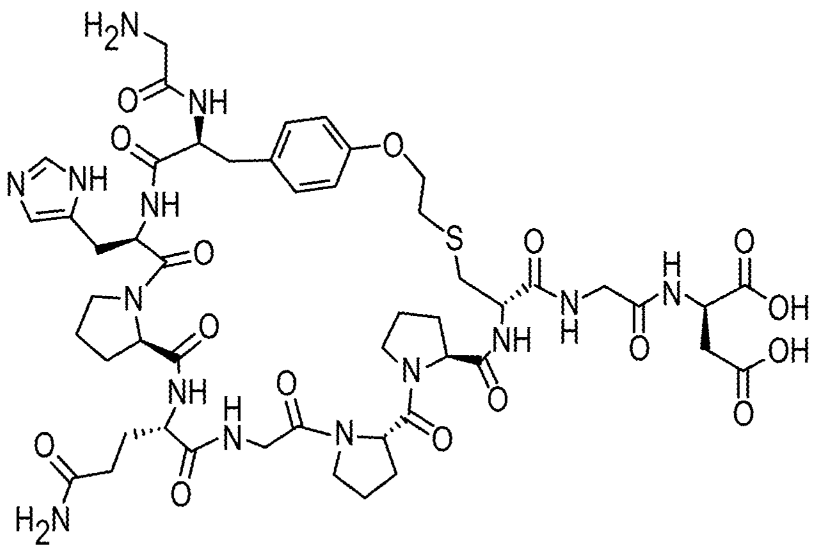
Figure 26B:
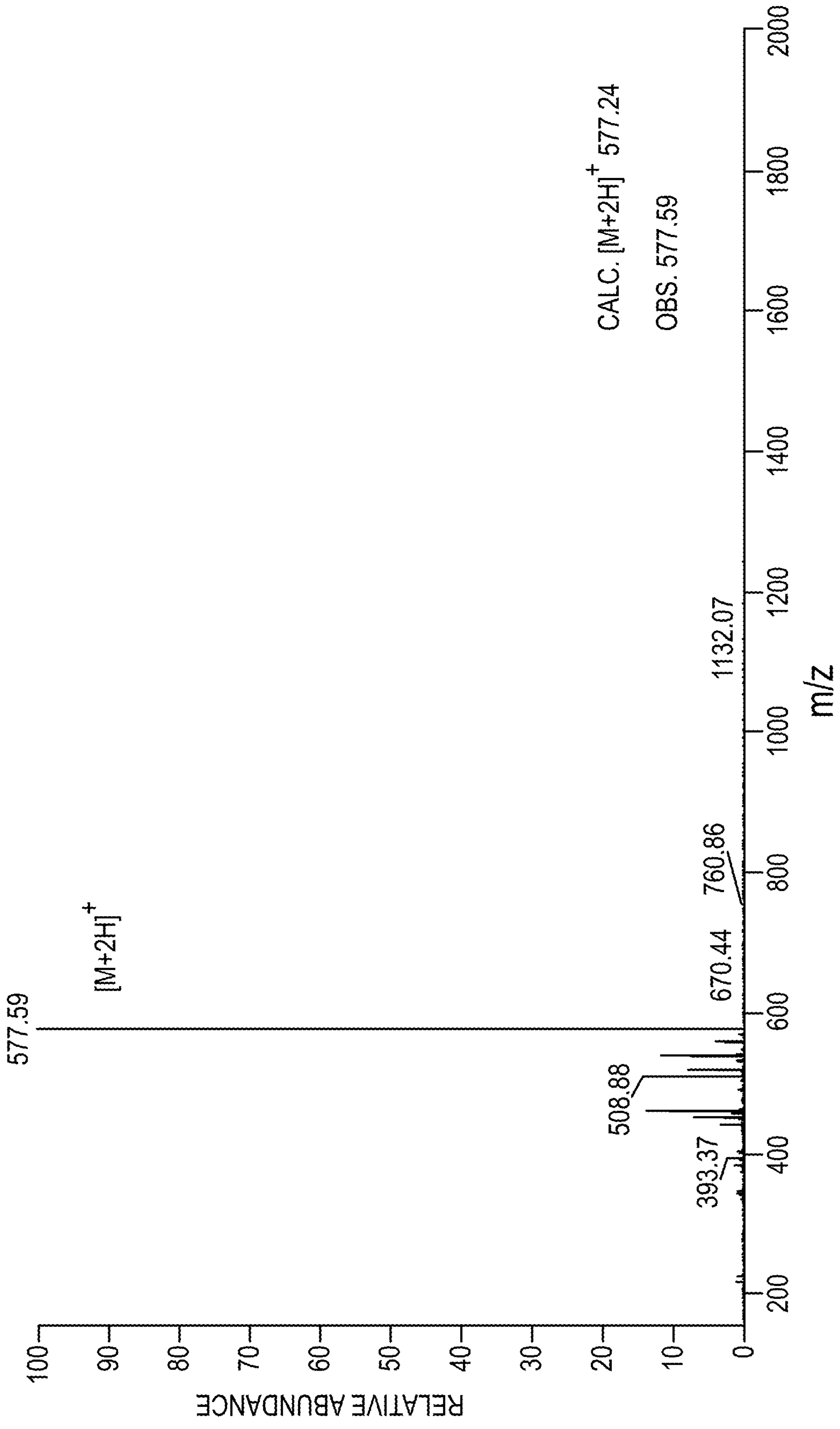
Figure 26C:
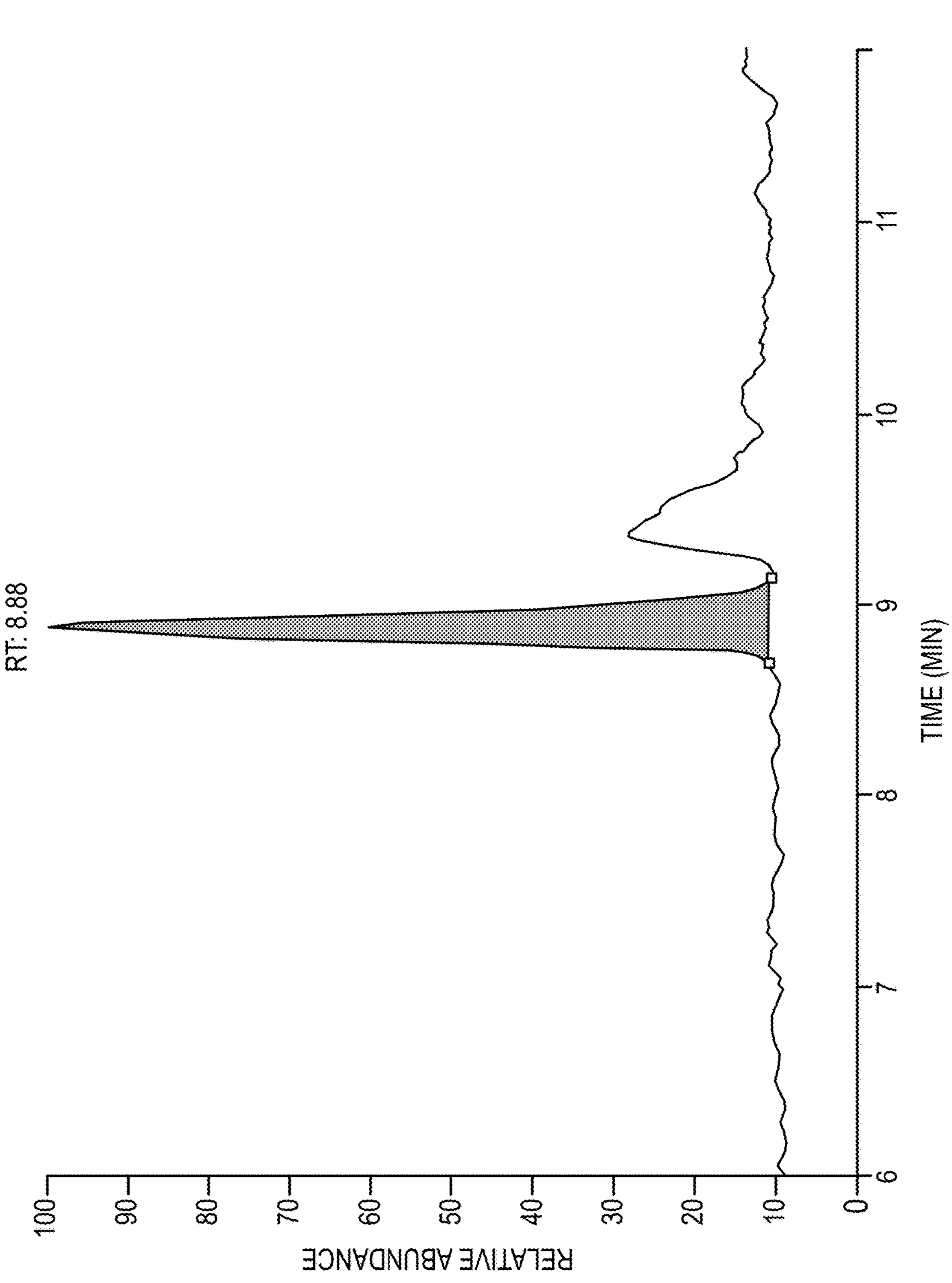
Figure 27A:
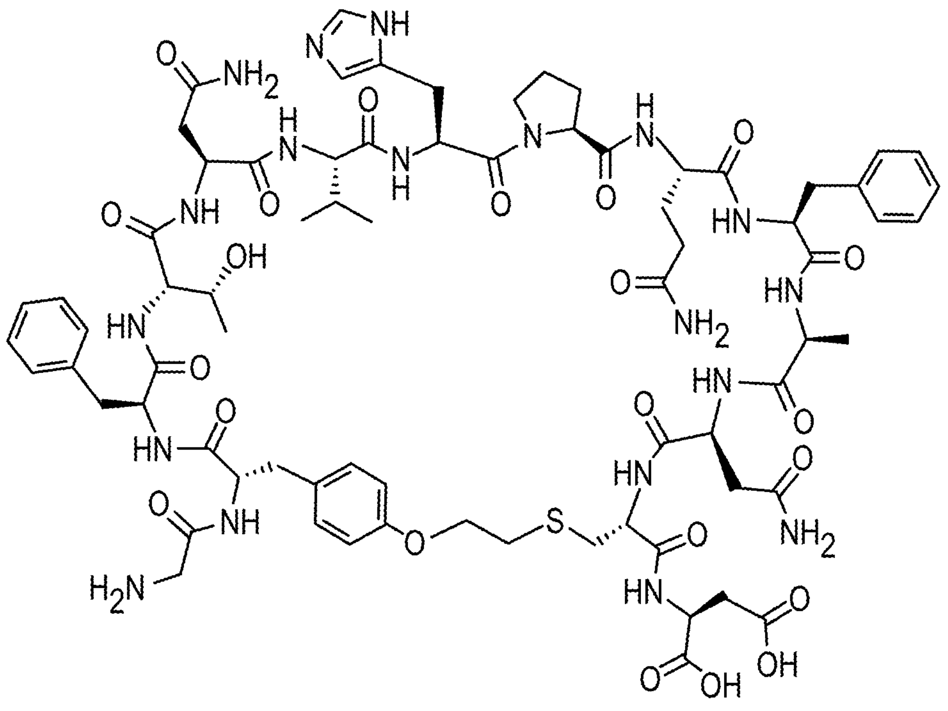
Figure 27B:
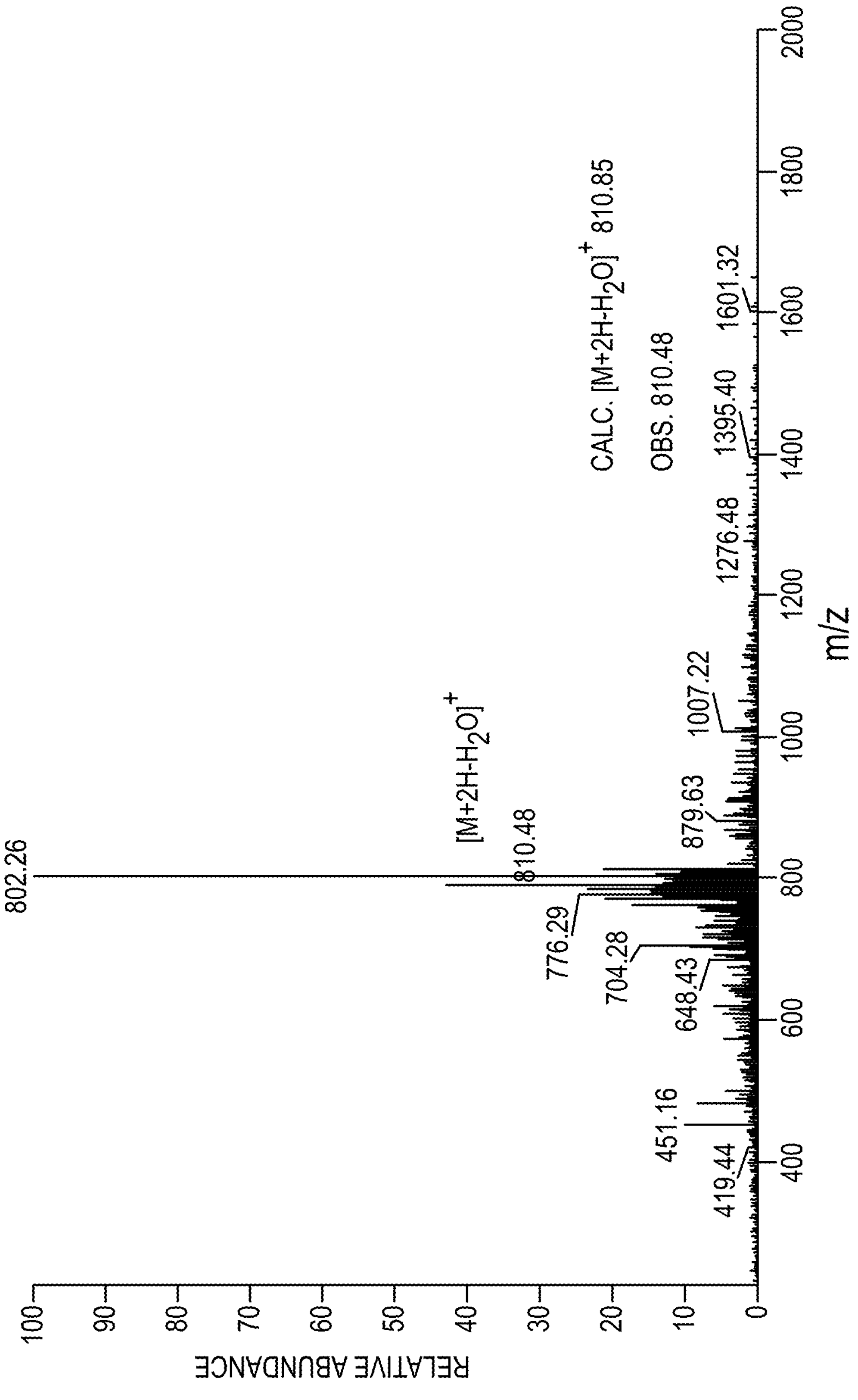
Figure 27C:
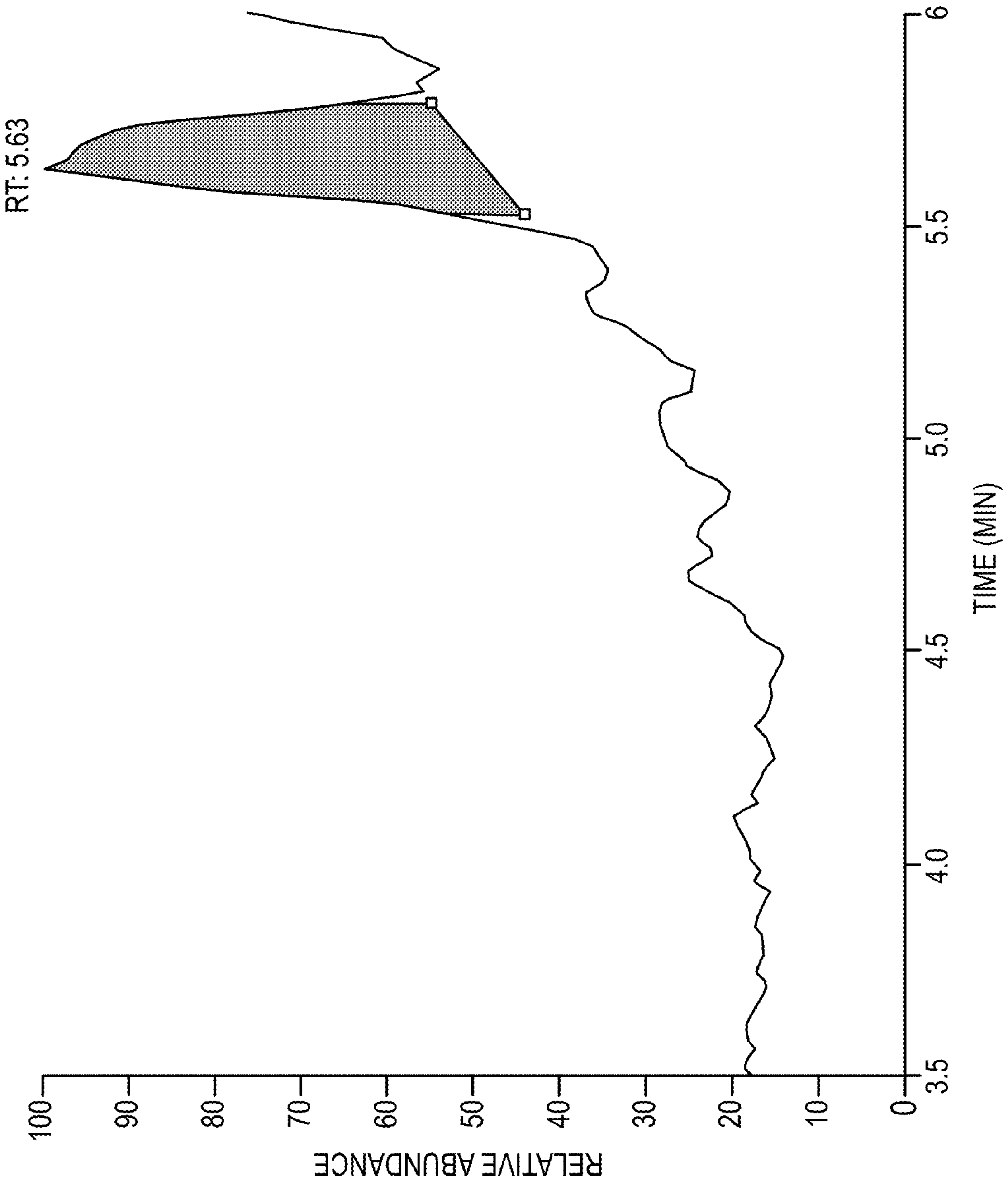
Figure 28A:
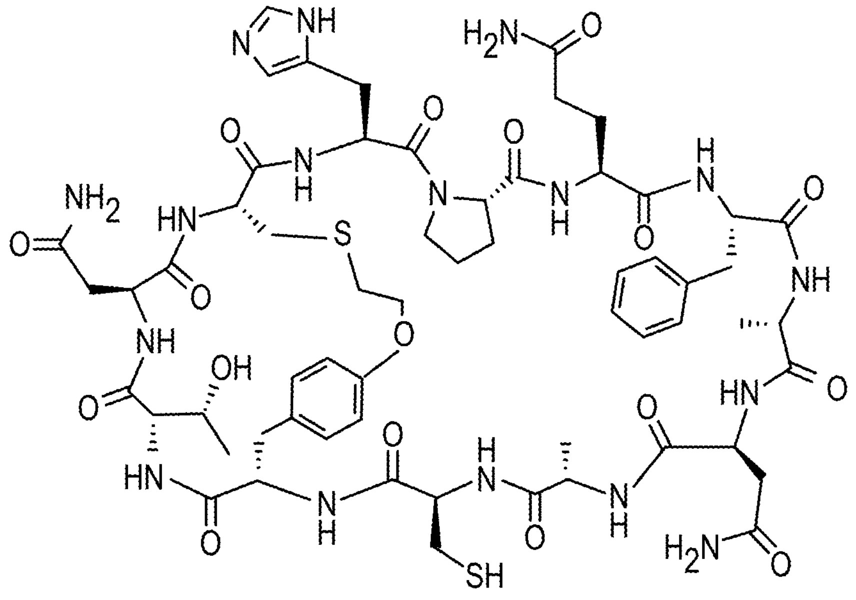
Figure 28B:
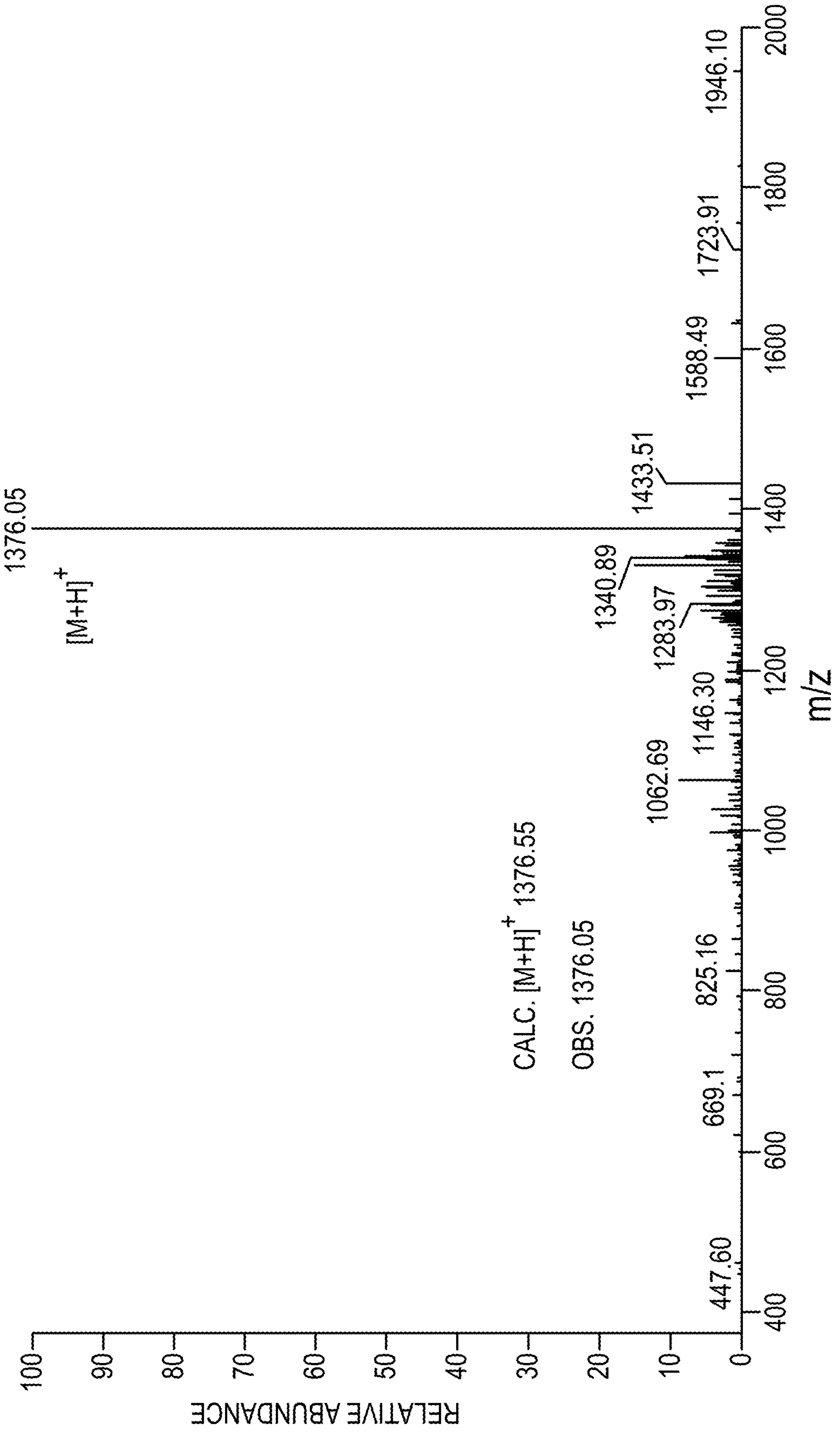
Figure 28C:
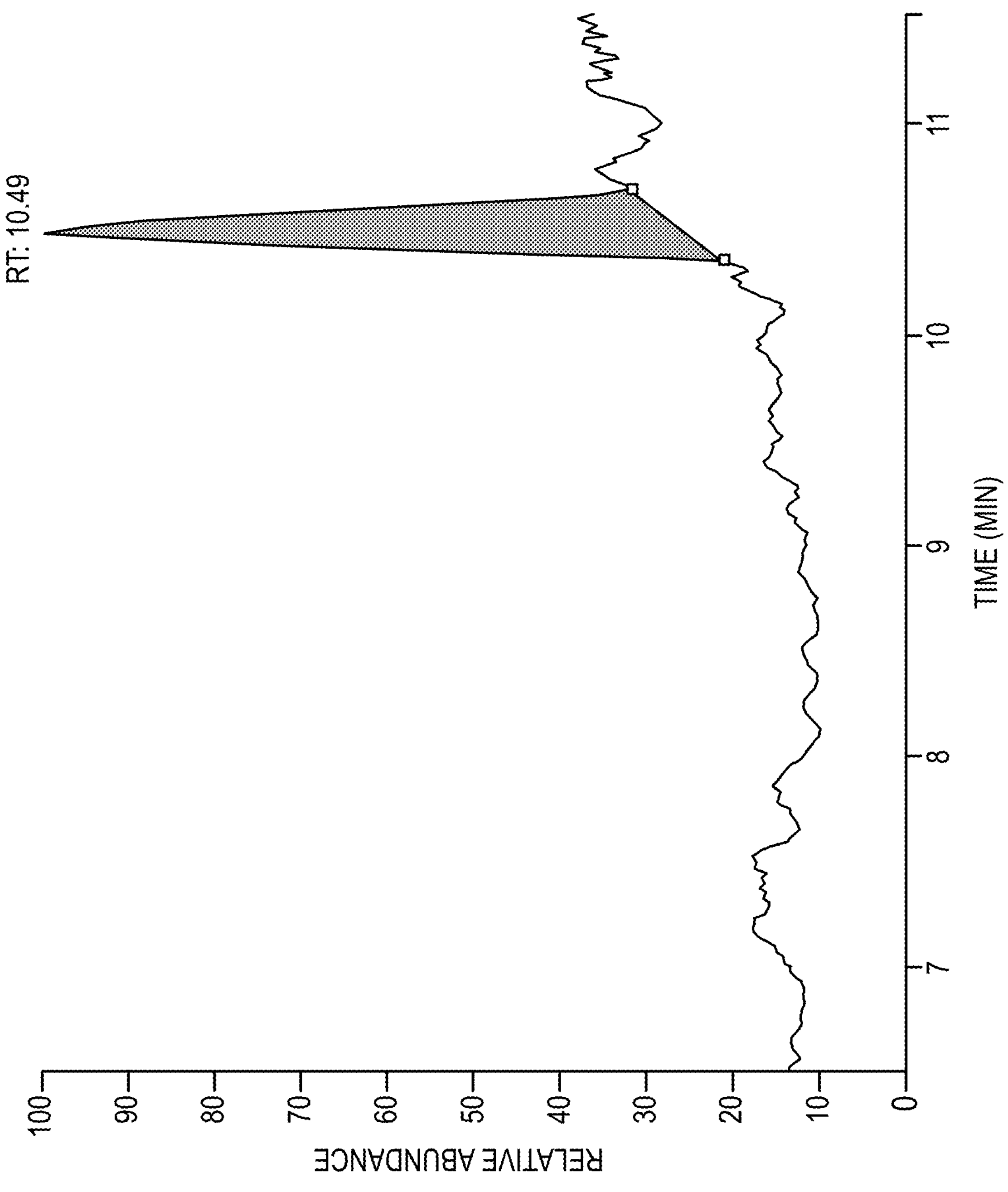
Figure 29A:
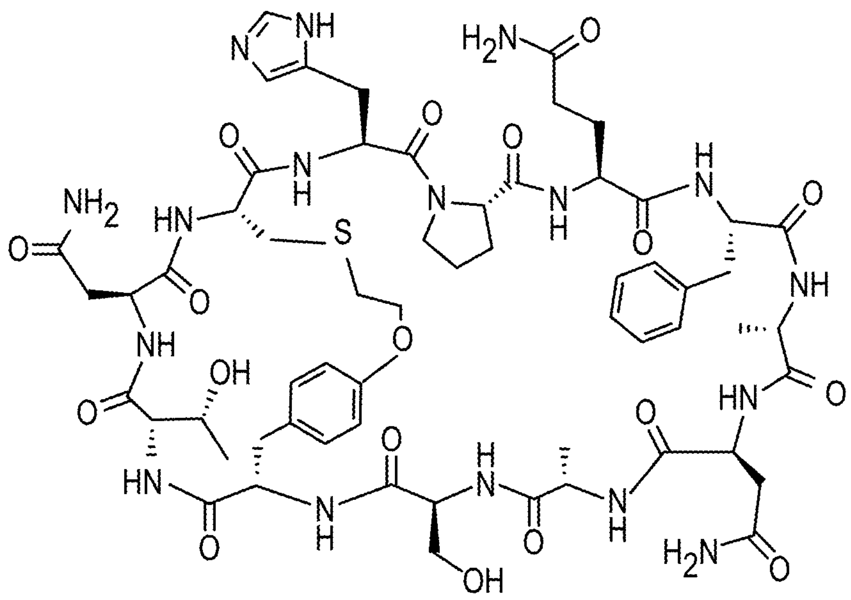
Figure 29B:
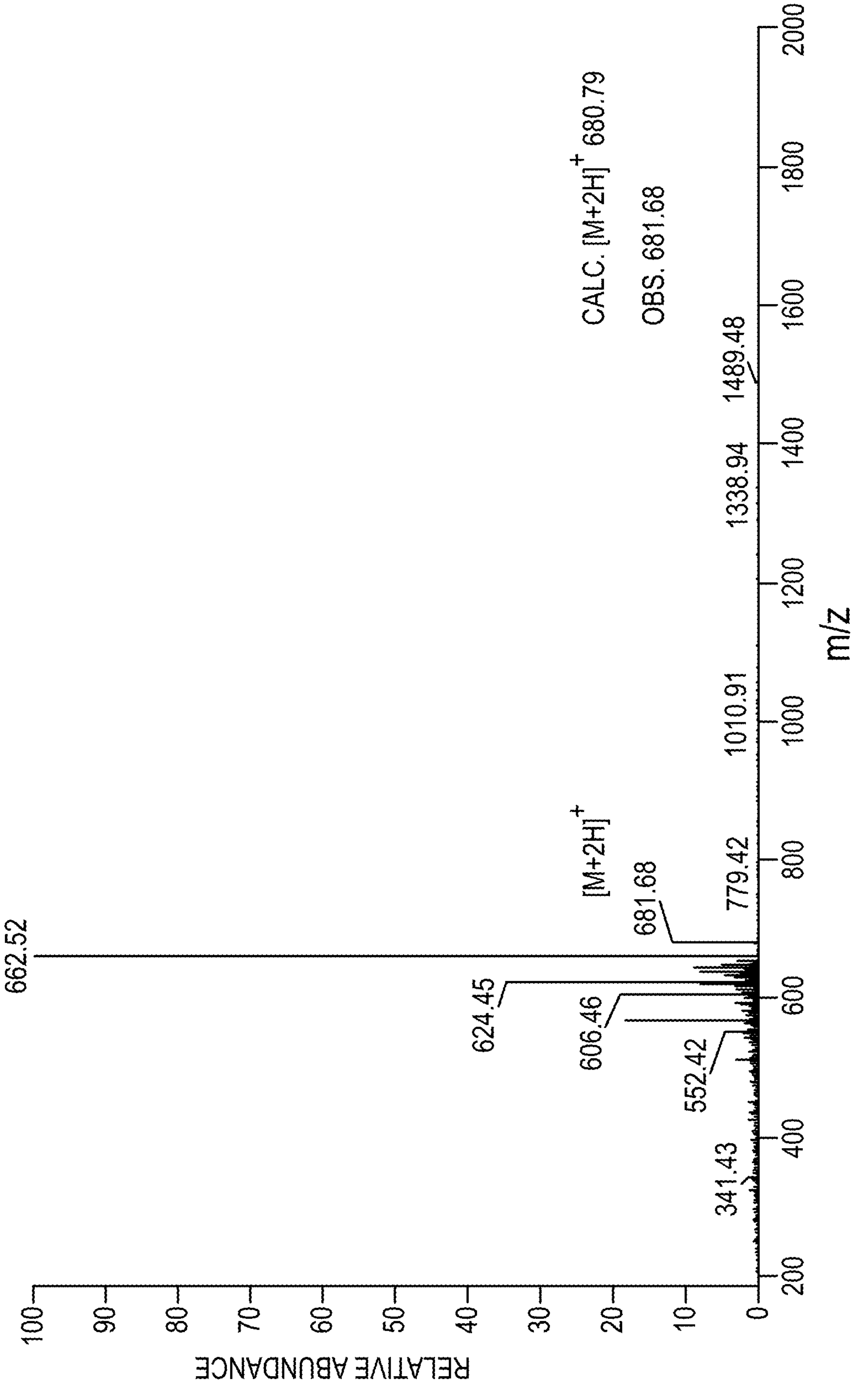
Figure 29C:
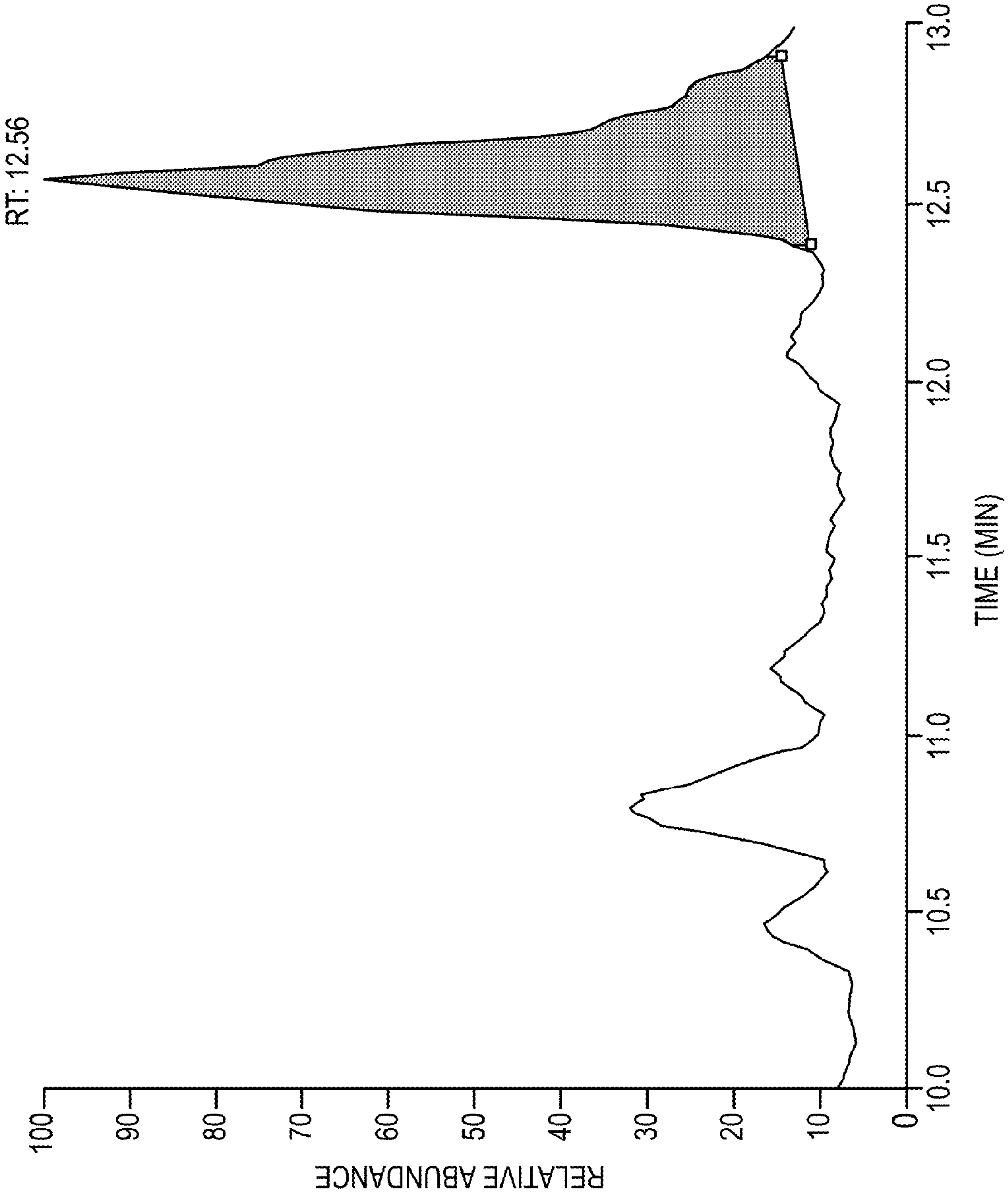
Figure 30A:
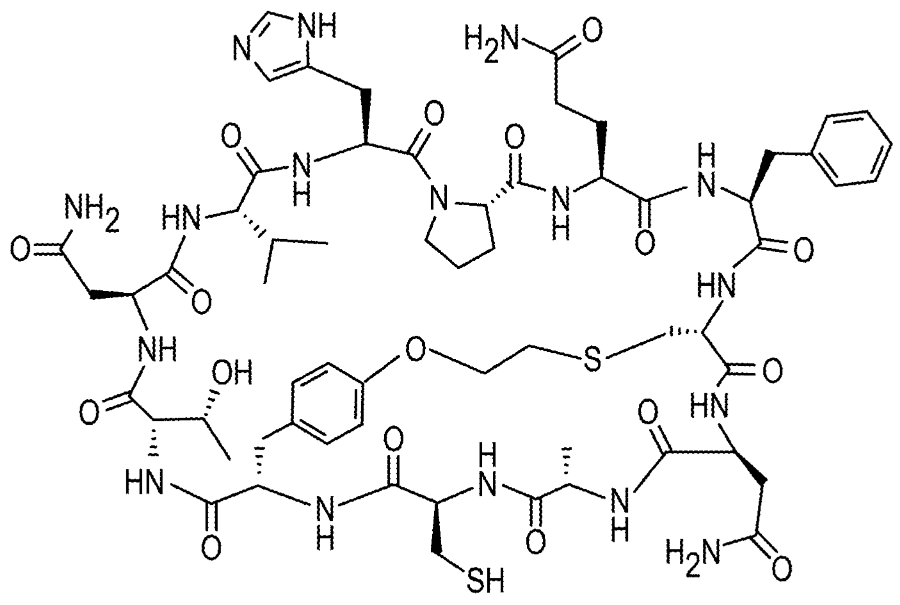
Figure 30B:
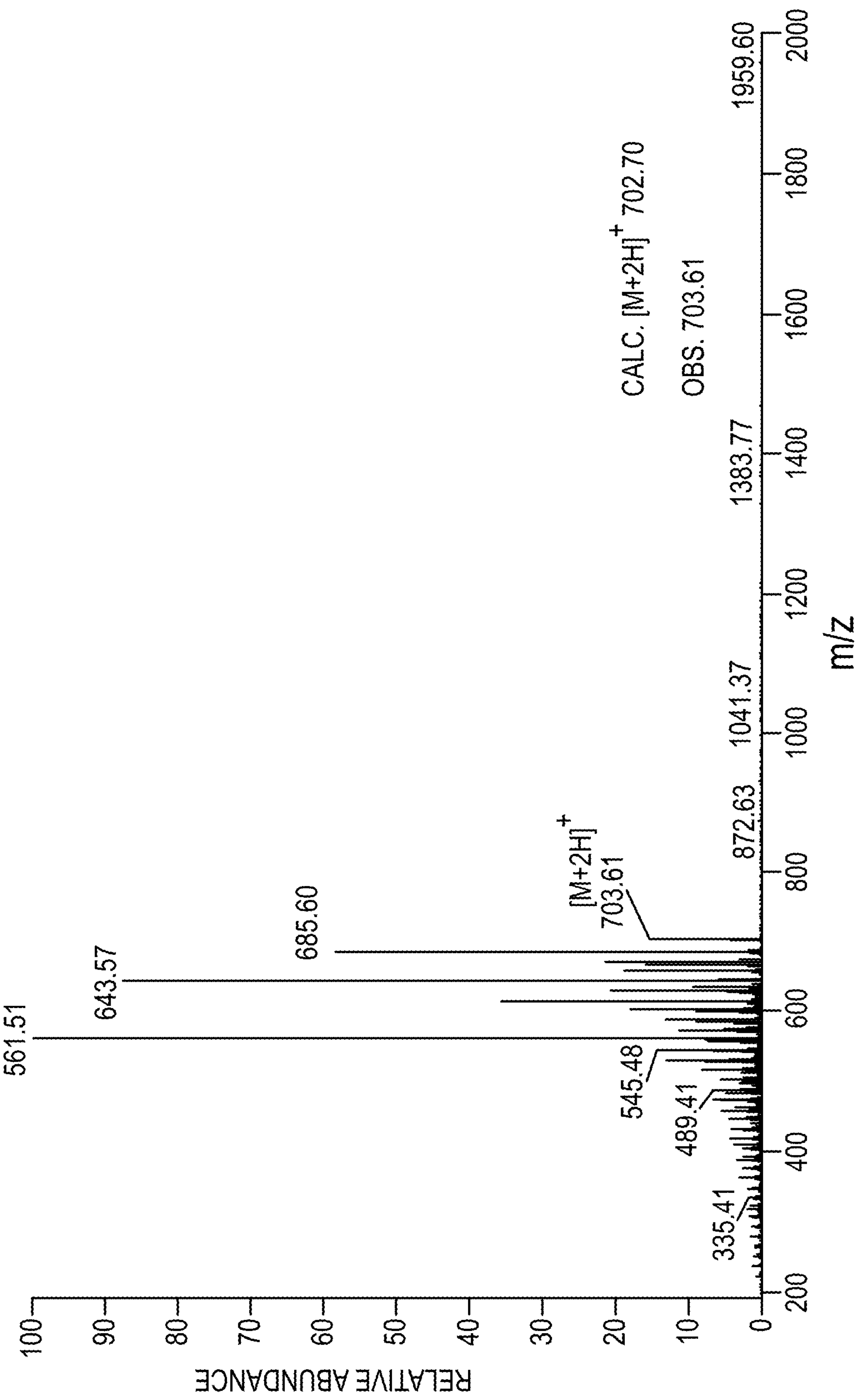
Figure 30C:
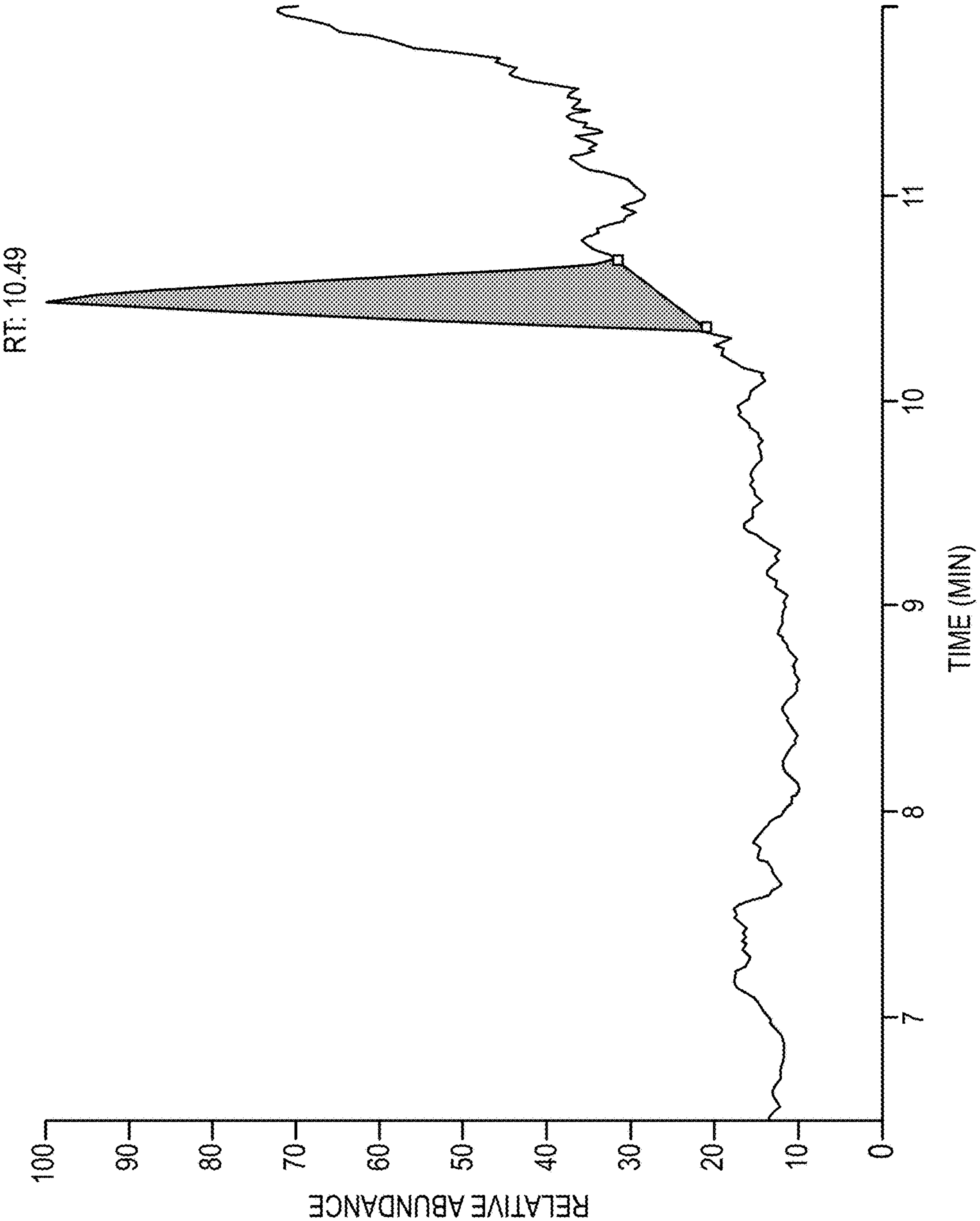
Figure 31A:
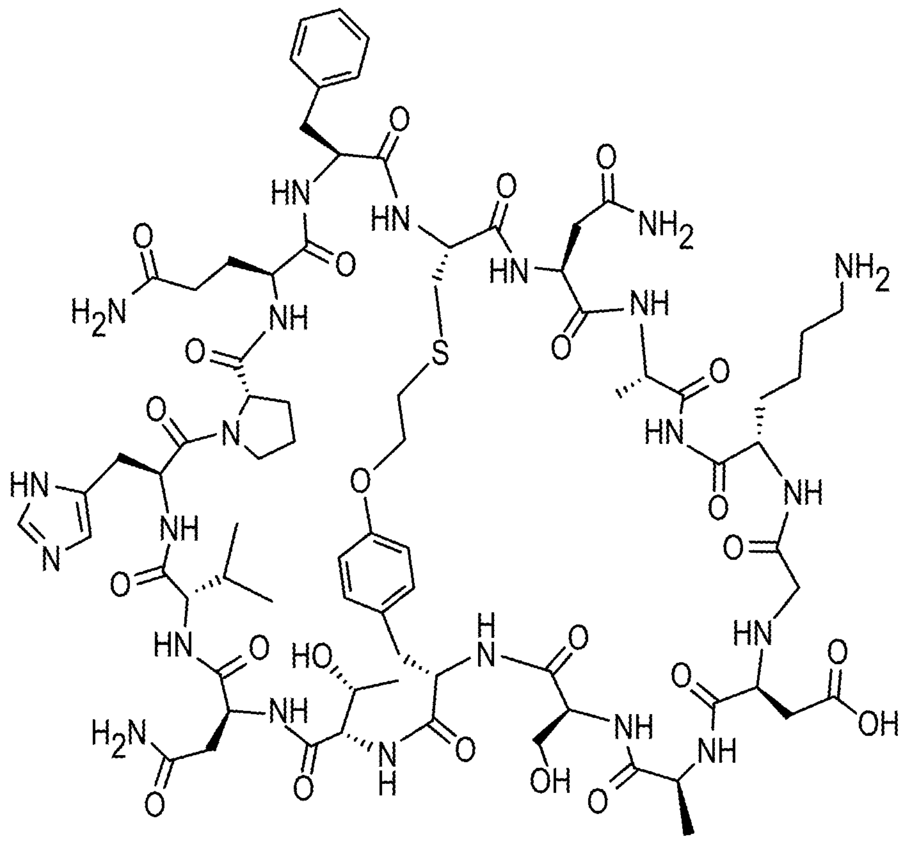
Figure 31B:
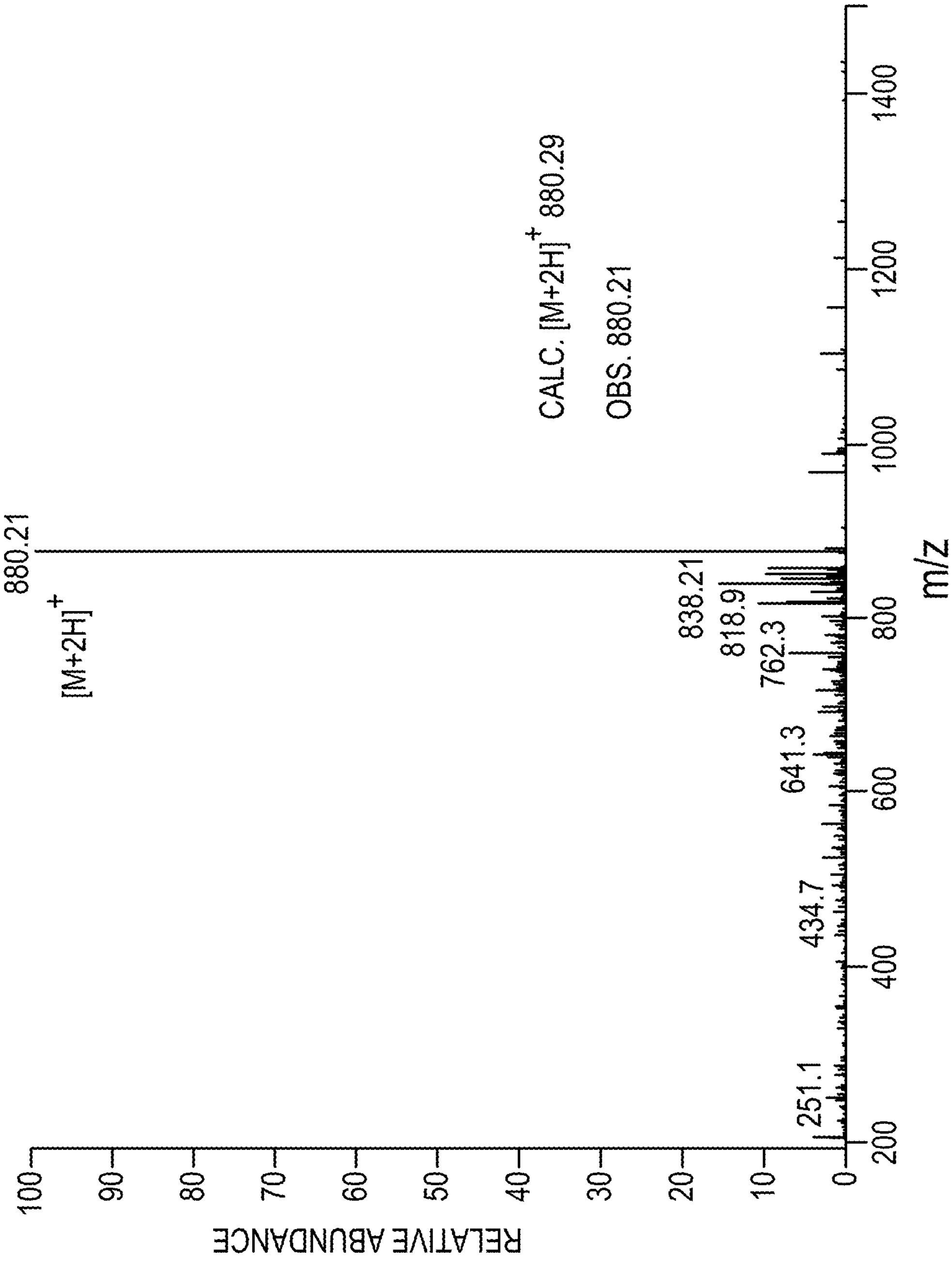
Figure 31C:
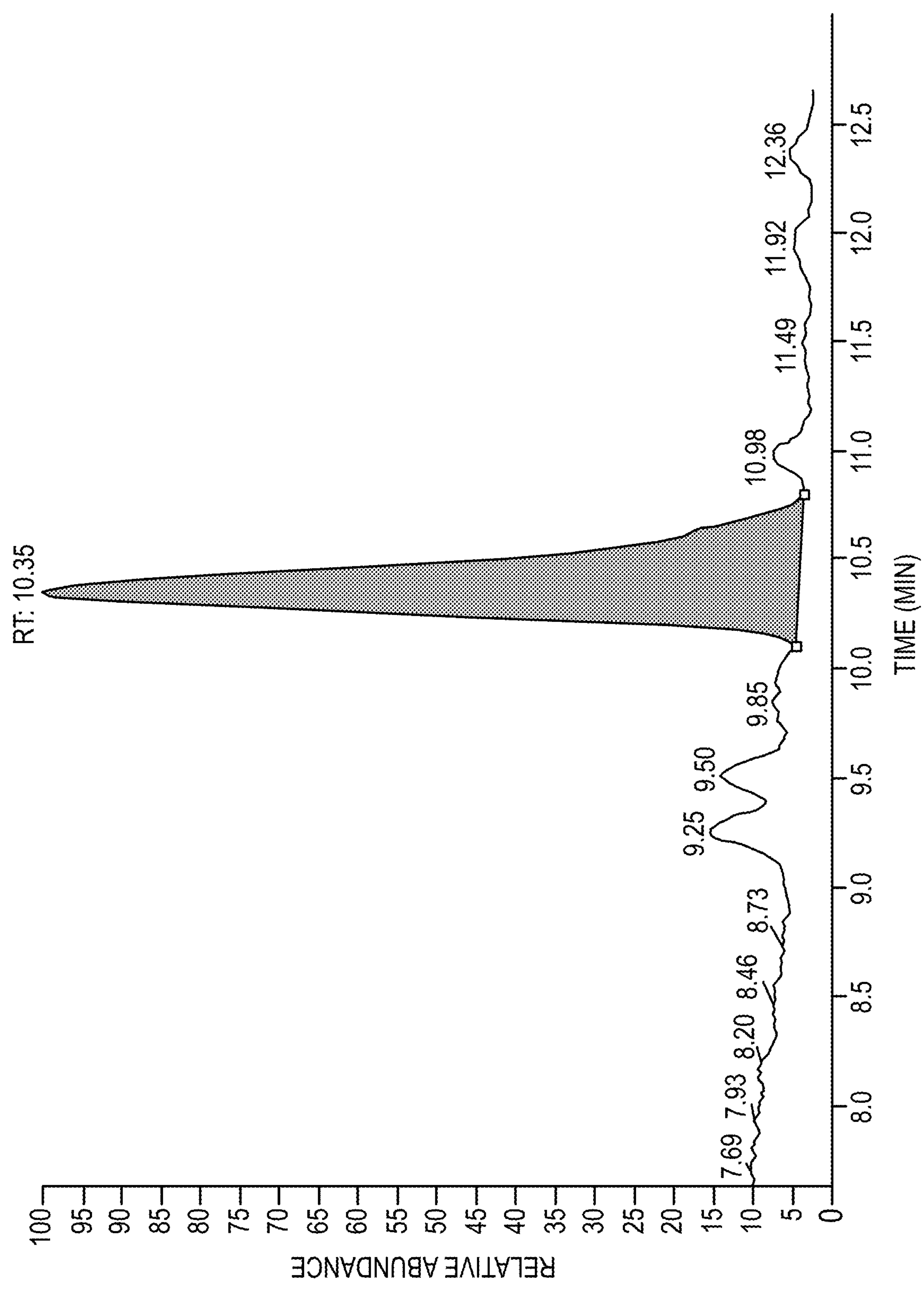
Figure 32A:
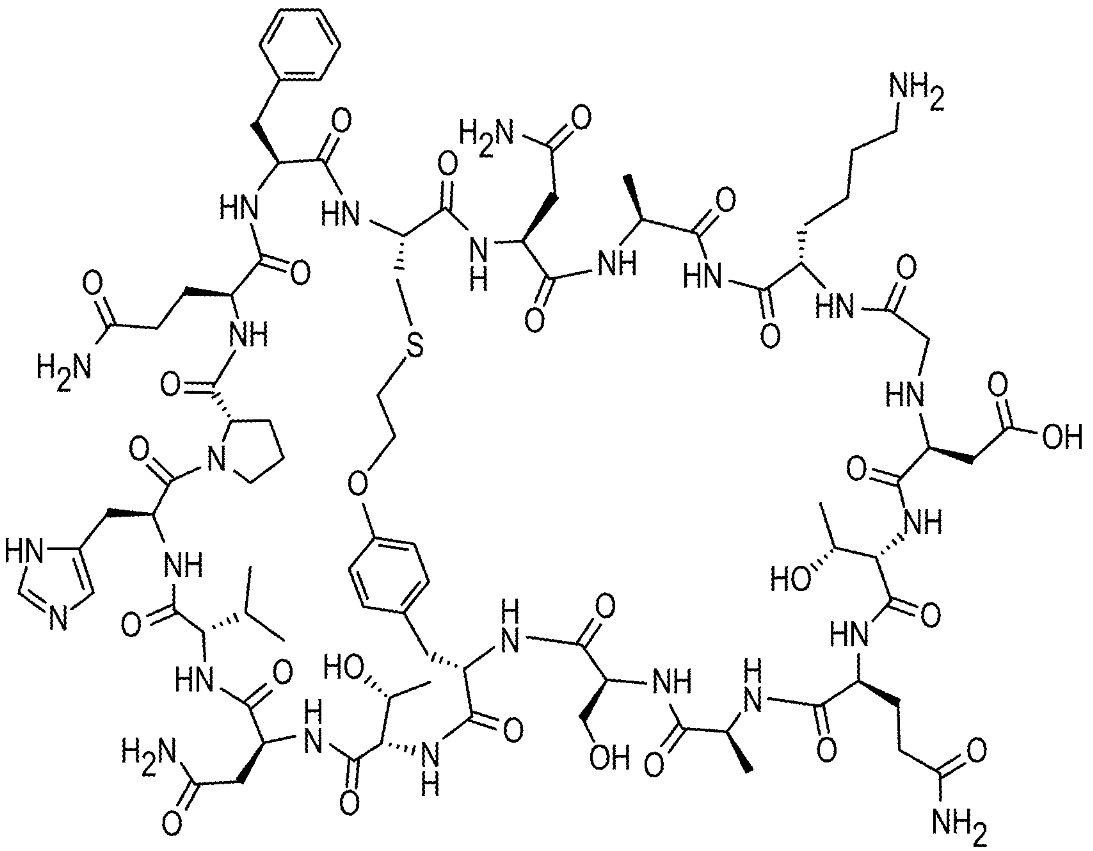
Figure 32B:
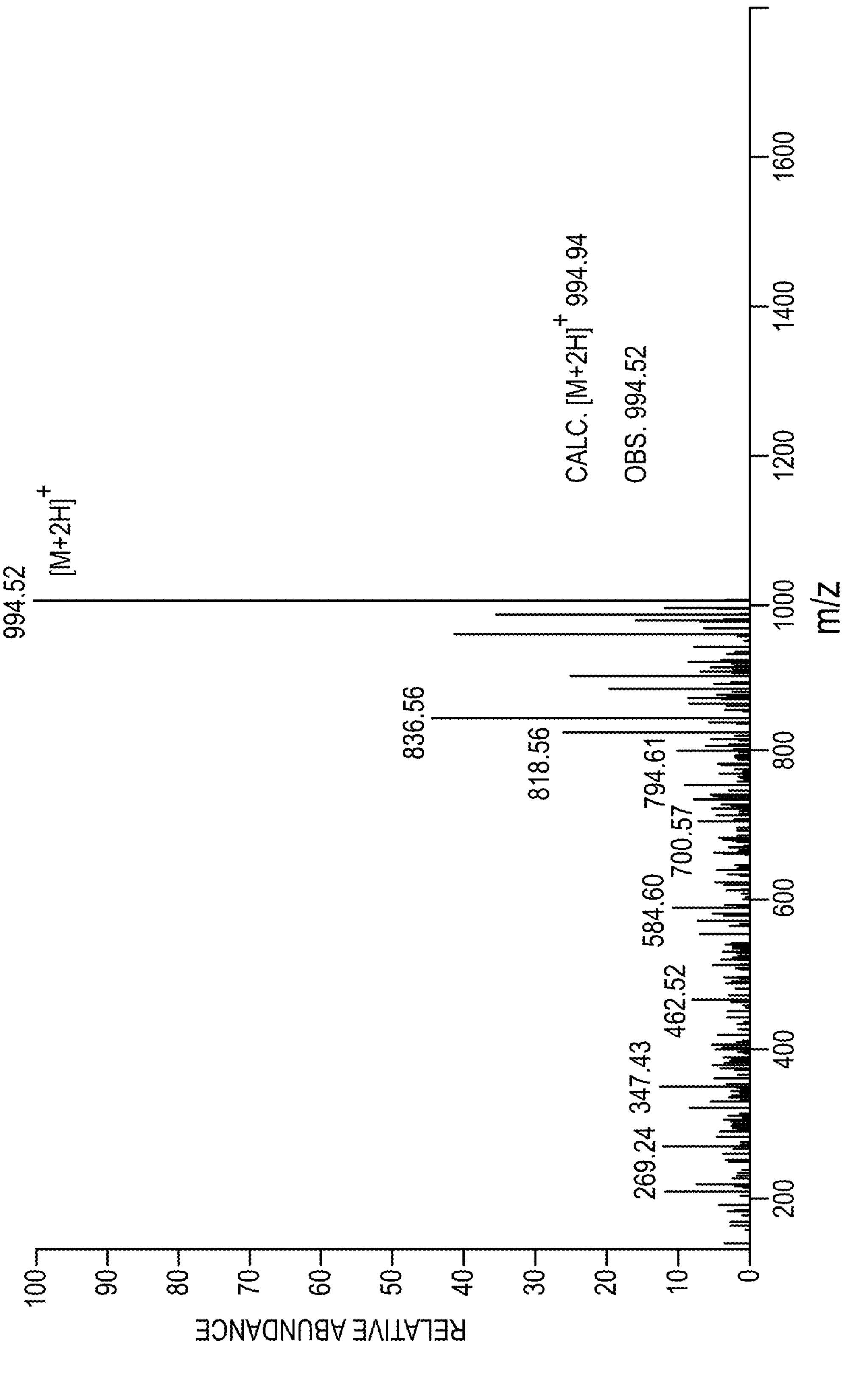
Figure 32C:
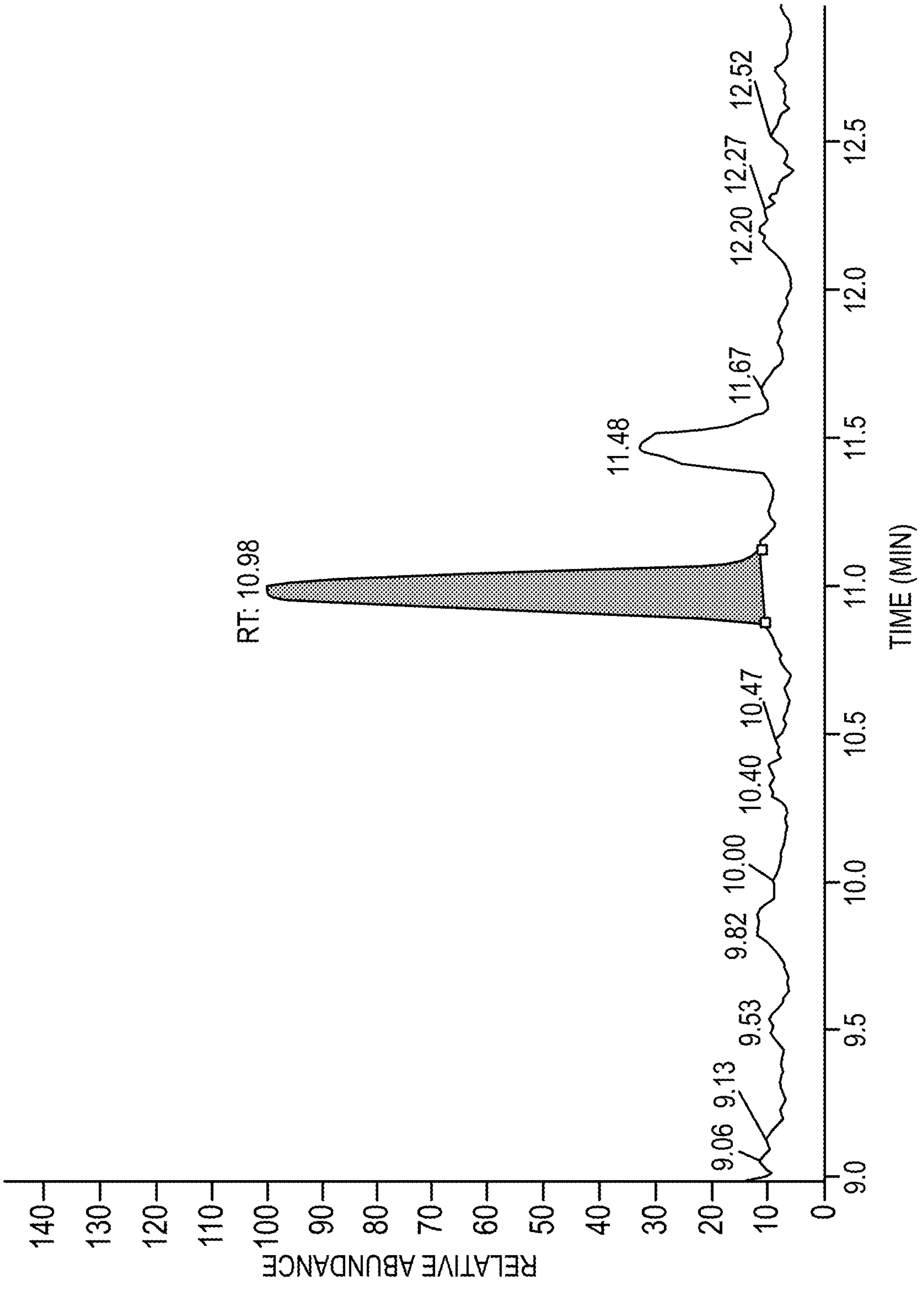
Figure 33A:
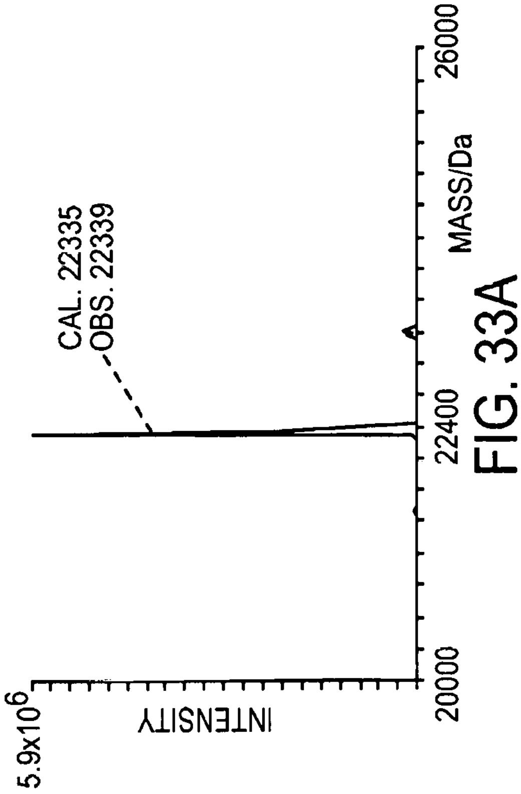
Figure 33B:
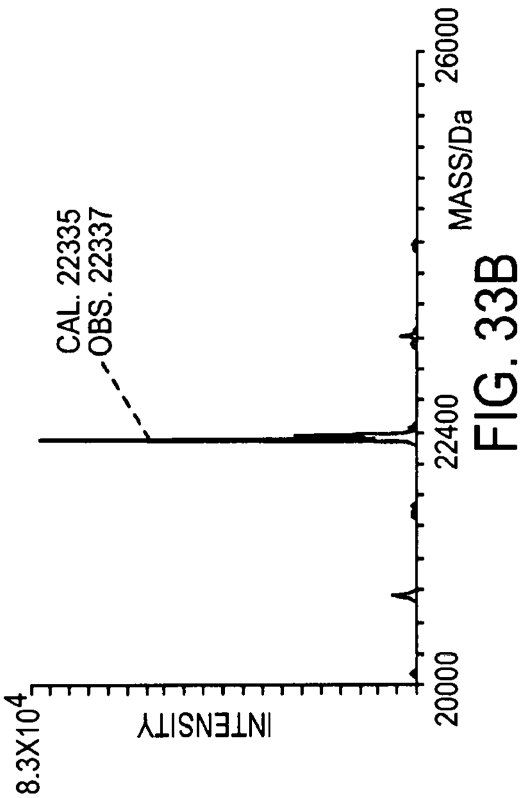
Figure 33C:
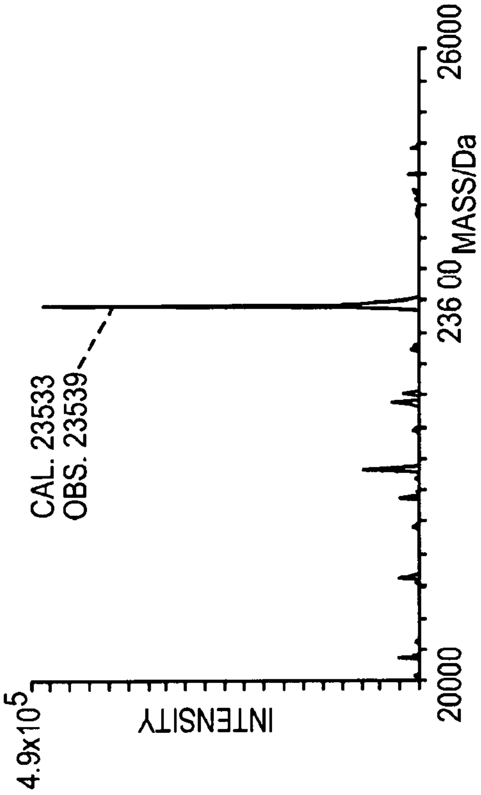
Figure 33D:
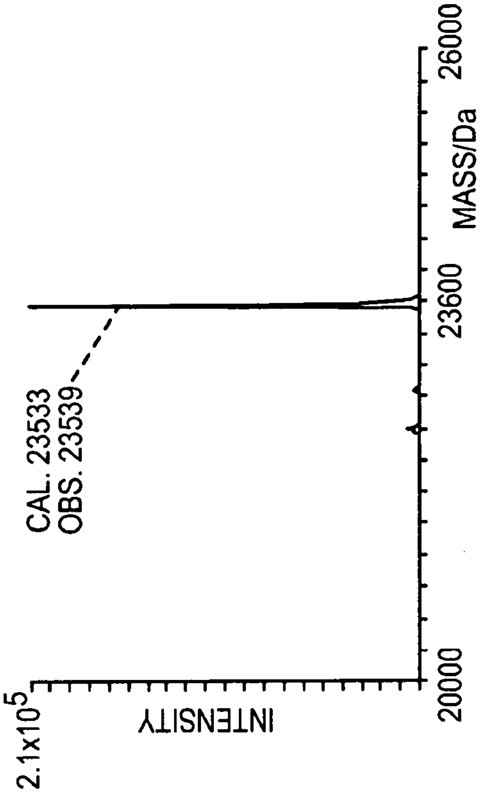
Figure 34A:
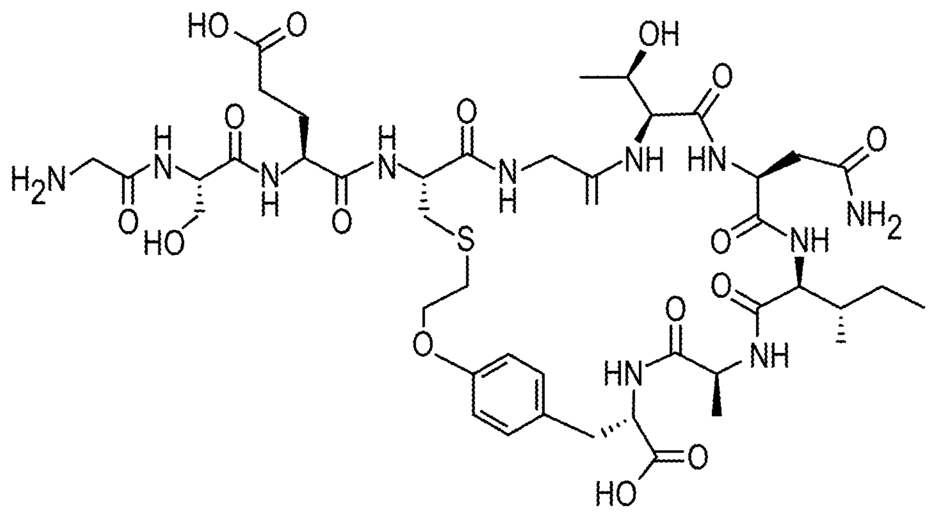
Figure 34B:
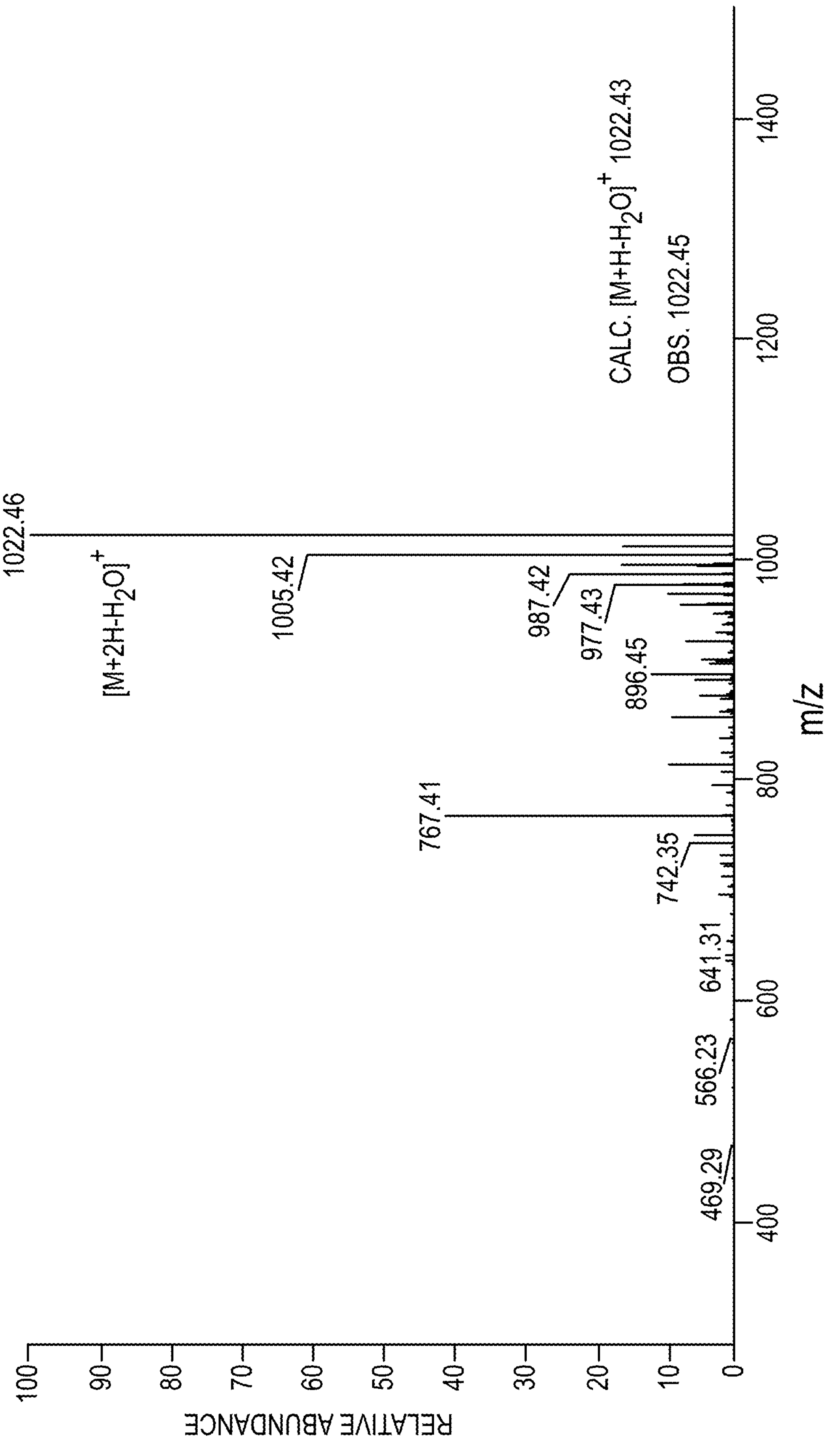
Figure 34C:
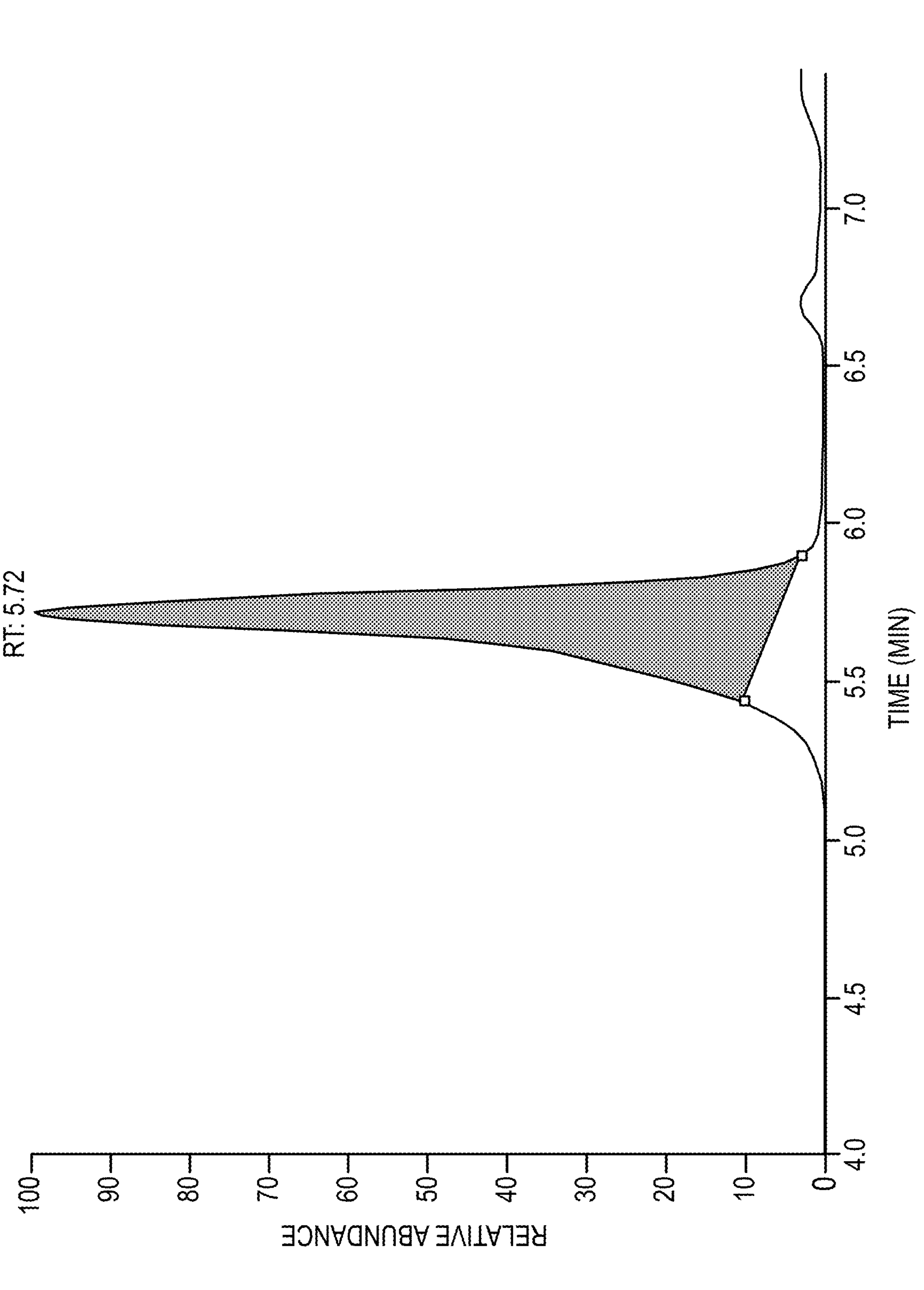
Figure 35A:
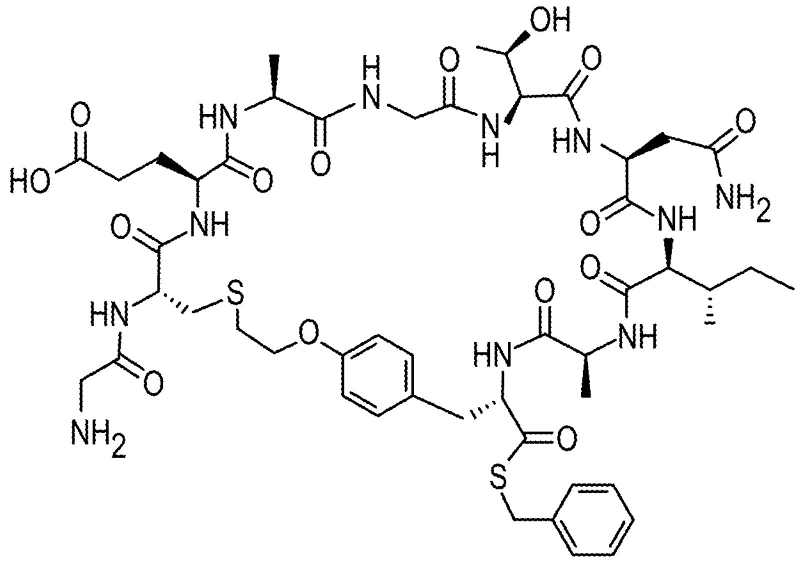
Figure 35B:
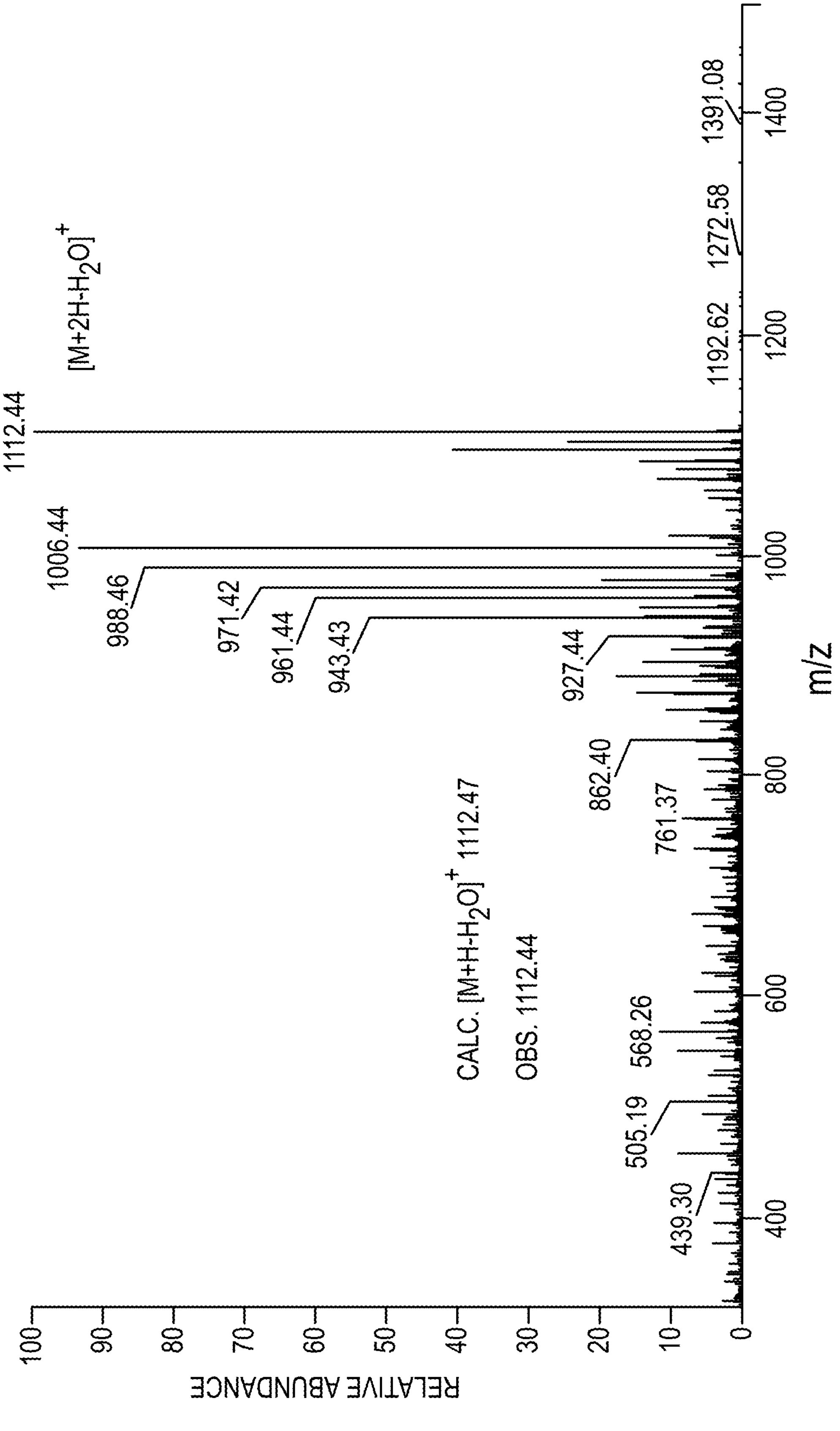
Figure 35C:
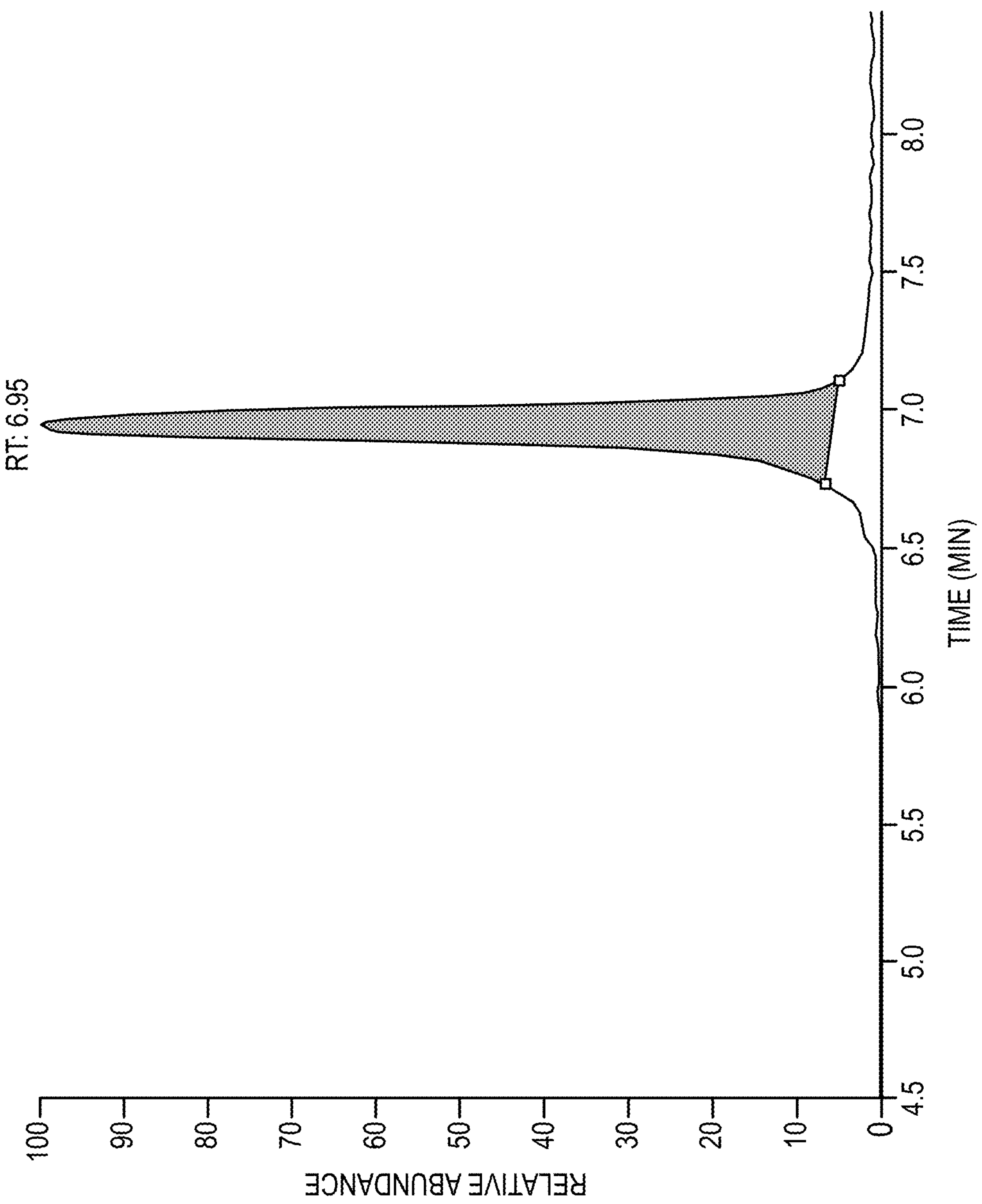

FIGS. 16A-B. (A) macrocyclic peptide obtained from construct 12mer-Z6C(2-beF). (B) Representative MS/MS spectrum corresponding to the macrocyclic peptide obtained from construct 12mer-Z6C(2-beF). The assignment of the a and b fragments is indicated.

FIGS. 17*a-d*. Deconvoluted LC-MS mass spectra of proteins isolated after benzyl mercaptan-induced splicing of purified construct (a) 12mer-Z1C, (b) 12mer-Z4C, (c) 10mer-C6Z, and (d) 10mer-C8Z.

FIGS. 18A-C, 19A-B, 20A-C, 21A-C, 22A-C, 23A-C, and 24A-C. Representative examples of macrocyclic peptides produced from 2becK-, 2cecK, p-1beF-, and bdnK-containing precursor polypeptides according to the methods disclosed herein. In each multi-part figure, (A) shows the sequence of the precursor polypeptide and the chemical structure of the macrocyclic peptide product, (B) shows the MS/MS spectrum of the macrocyclic peptide, and (C) shows the LC-MS extracted-ion chromatogram of the macrocyclic peptide.

FIGS. 25A-C, 26A-C, and 27A-C. Macrocyclic peptides isolated via streptavidin-affinity chromatography from bacterial lysate. In each multi-part figure, (A) shows the sequence of the precursor polypeptide and the chemical structure of the macrocyclic peptide product, (B) shows the MS/MS spectrum of the macrocyclic peptide, and (C) shows the LC-MS extracted-ion chromatogram of the macrocyclic peptide.

FIGS. 28A-C, 29A-C, 30A-C, 31A-C, and 32A-C. Bicyclic peptides isolated via streptavidin-affinity chromatography from bacterial lysate. In each multi-part figure, (A) shows the sequence of the precursor polypeptide and the chemical structure of the bicyclic peptide product, (B) shows the MS/MS spectrum of the bicyclic peptide, and (C) shows the LC-MS extracted-ion chromatogram of the bicyclic peptide.

FIGS. 33*a-d*. Deconvoluted LC-MS mass spectra of proteins isolated from the cell lysate using Ni-NTA beads: (a) Strep1-Z5C(p-2beF) construct, (b) Strep2-Z7C(p-2beF) construct; and using chitin beads: (c) cStrep3(C)-Z3C(p-2beF) construct, (d) cStrep3(S)-Z3C(p-2beF) construct FIGS. 34A-C and 35A-C. Representative examples of macrocyclic peptides produced from p-2beF-containing precursor polypeptides of general formula (II). In each multi-part figure, (A) shows the sequence of the precursor polypeptide and the chemical structure of the macrocyclic peptide product, (B) shows the MS/MS spectrum of the macrocyclic peptide, and (C) shows the LC-MS extracted-ion chromatogram of the macrocyclic peptide.

Figure 36A:
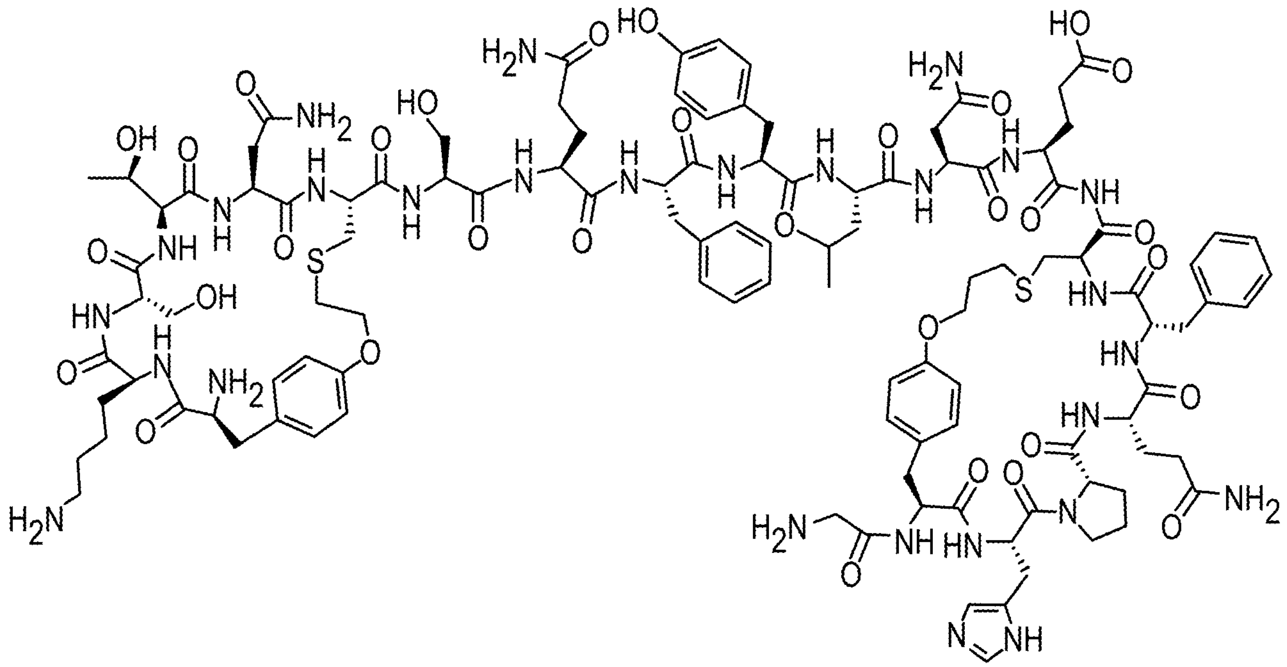
Figure 36B:
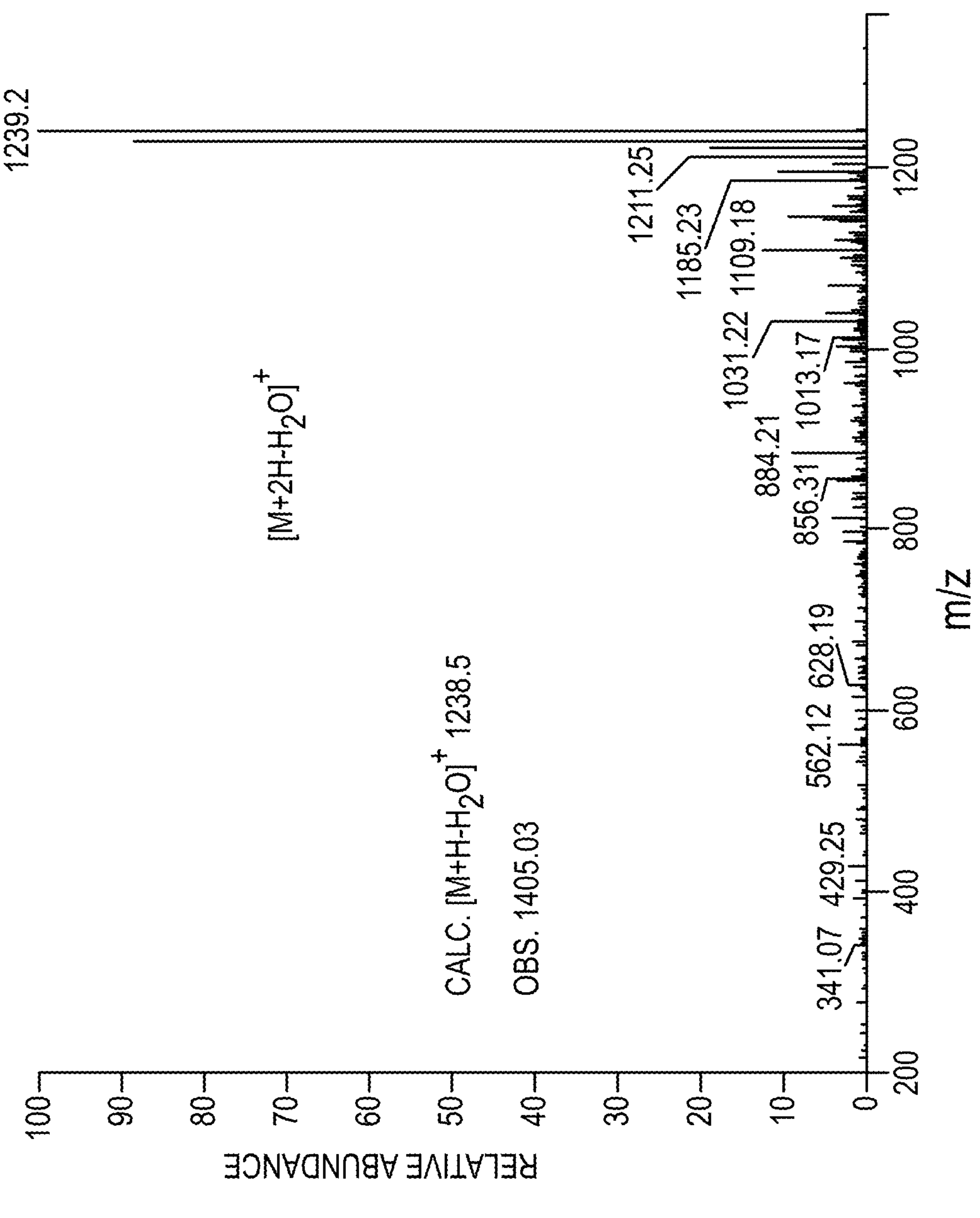
Figure 36C:
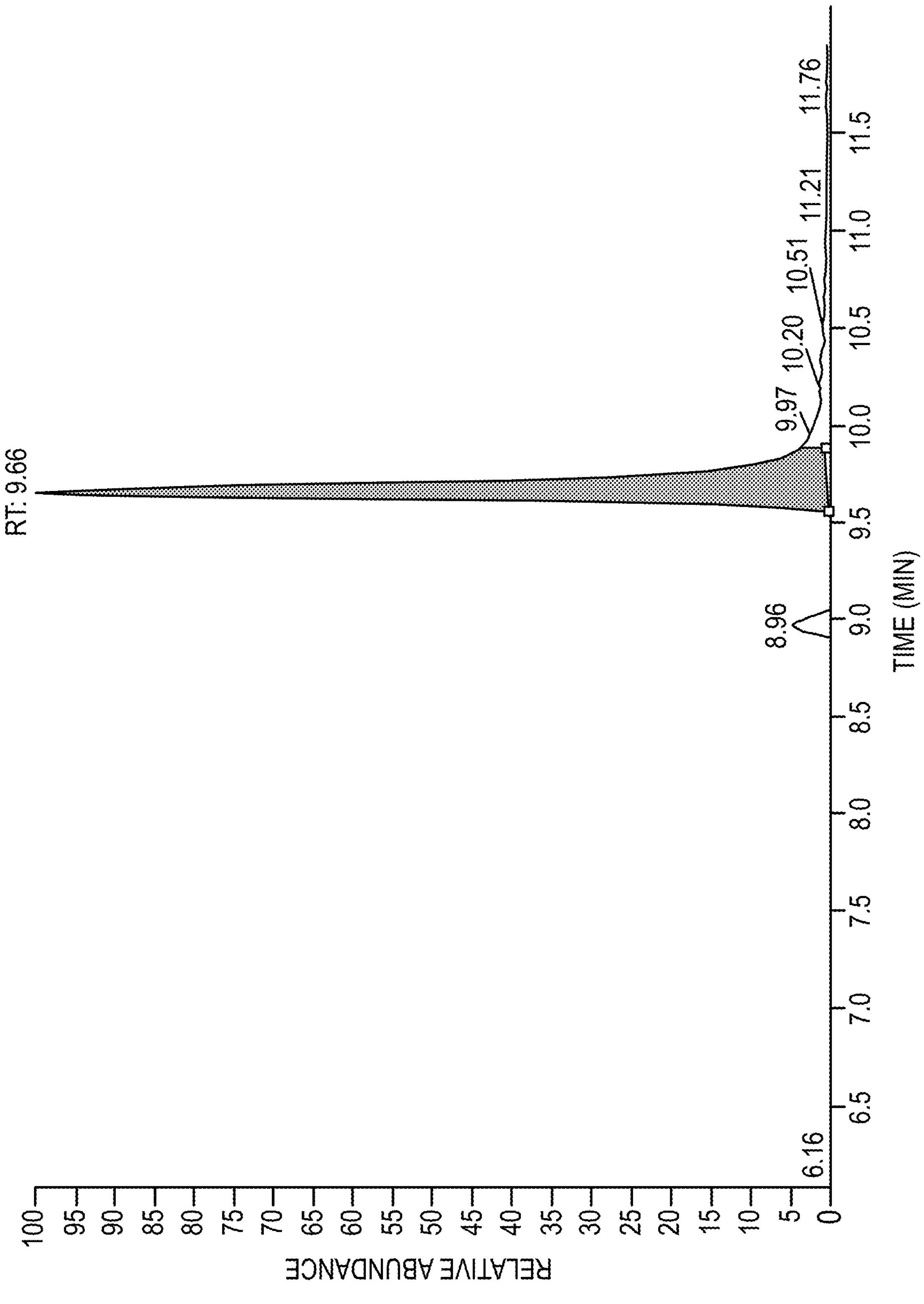

FIGS. 36A-C. Representative example of a polycyclic peptide produced from a precursor polypeptide containing two Cys/Z pairs, where Z is p-2beF. In the multi-part figure, (A) shows the sequence of the precursor polypeptide and the chemical structure of the polycyclic peptide product, (B) shows the MS/MS spectrum of the polycyclic peptide, and (C) shows the LC-MS extracted-ion chromatogram of the macrocyclic peptide.

Figure 37A:
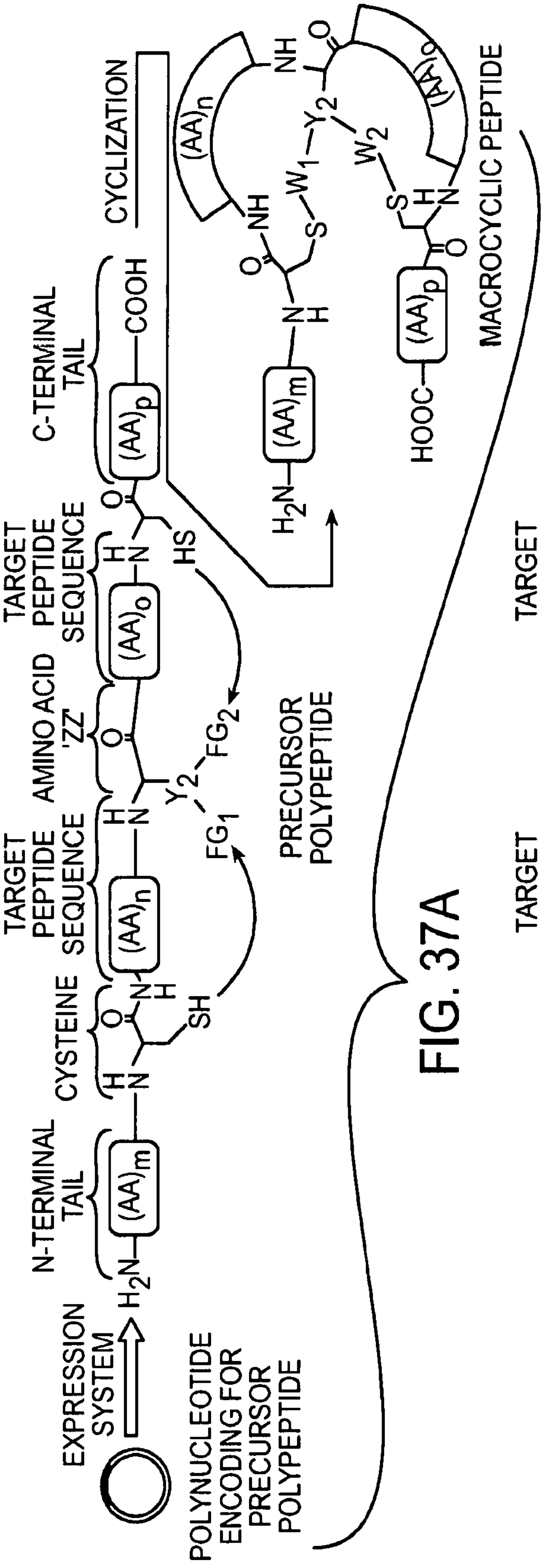
Figure 37B:
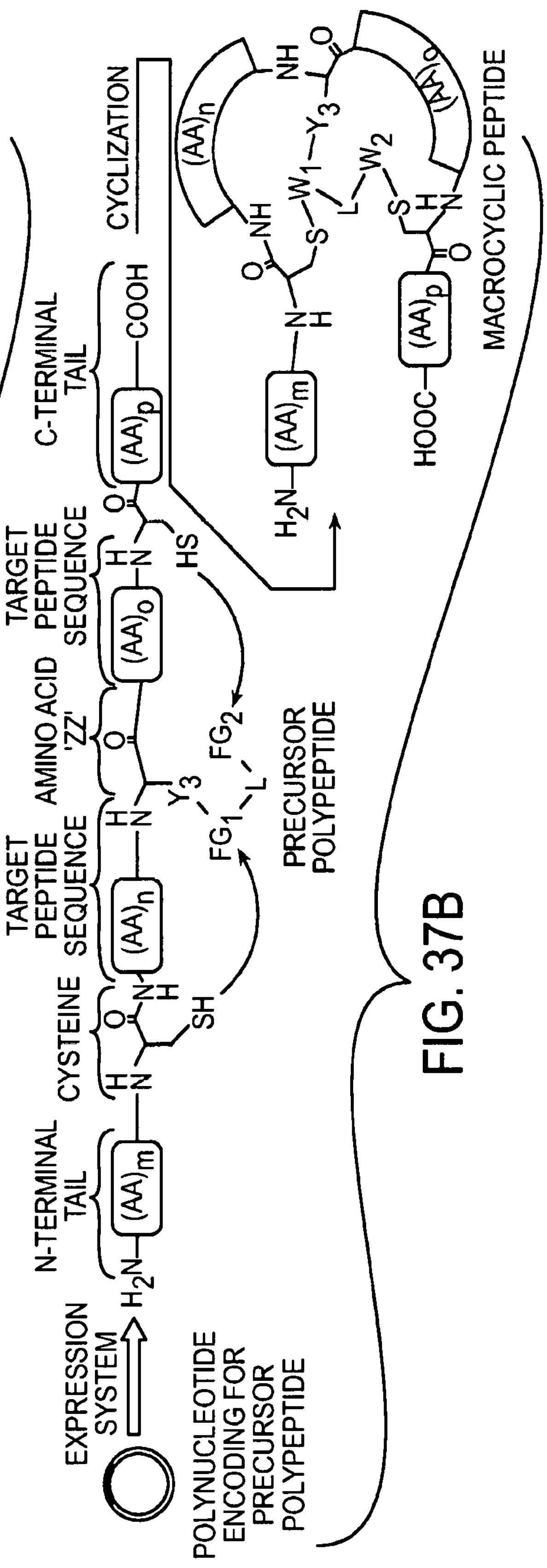

FIGS. 37A-B. Schematic representation of the general methods for making polycyclic peptides from ribosomally produced precursor polypeptides of general formula (V) containing a bifunctional cysteine-reactive amino acid (Z2) of general formula (VI) (panel A) or (VII) (panel B). $W_1$ and $W_2$ correspond to the linker groups resulting from the bond-forming reaction between the cysteine residues and functional group $FG_1$ and $FG_2$, respectively.

Figure 38A:
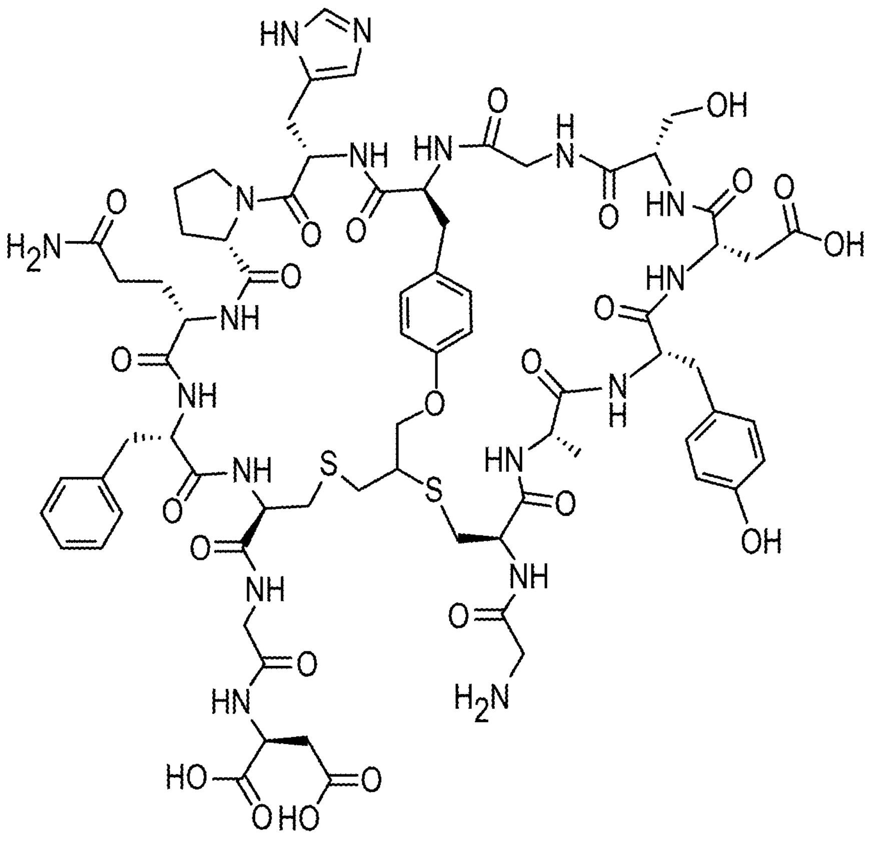
Figure 38B:
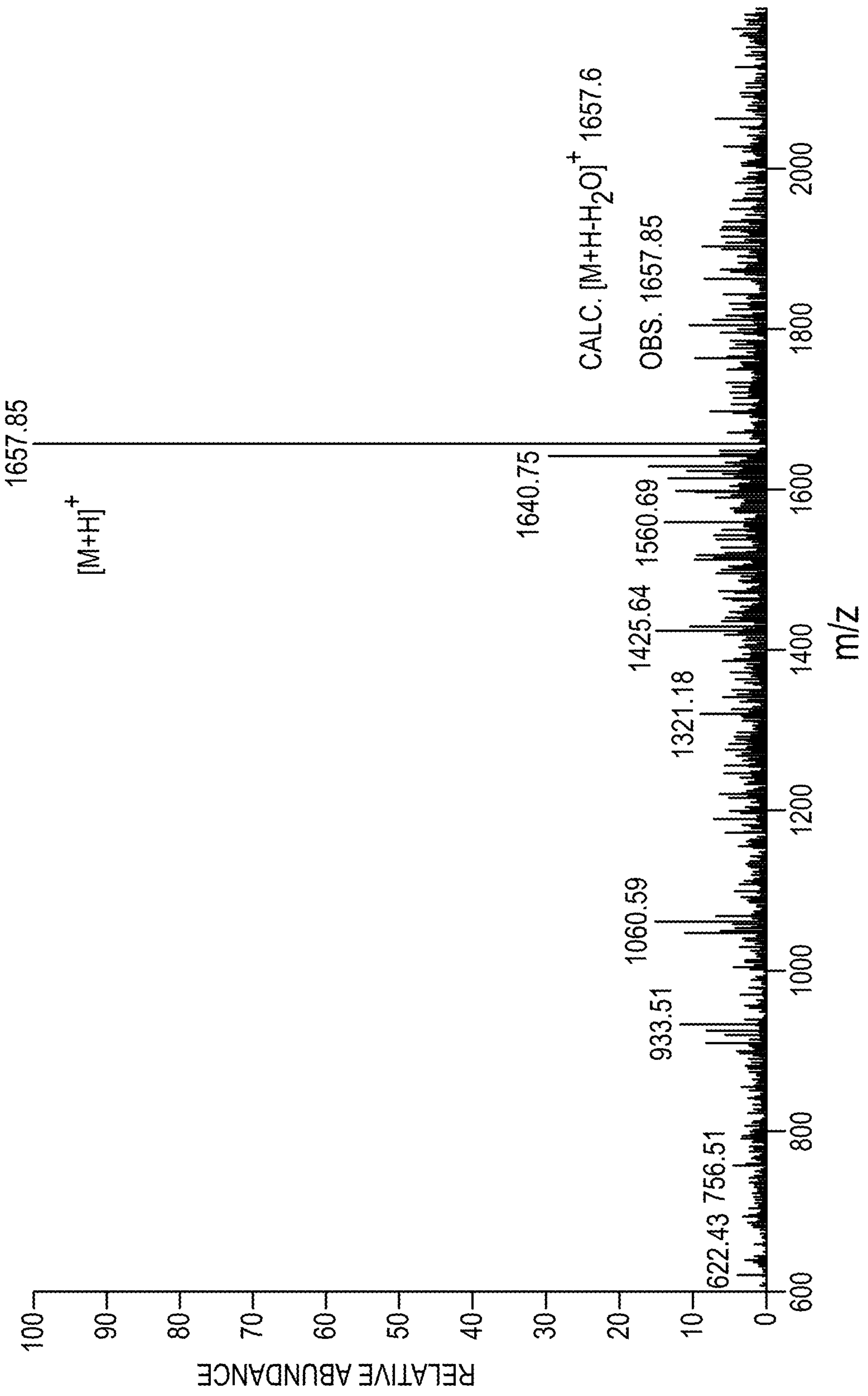
Figure 38C:
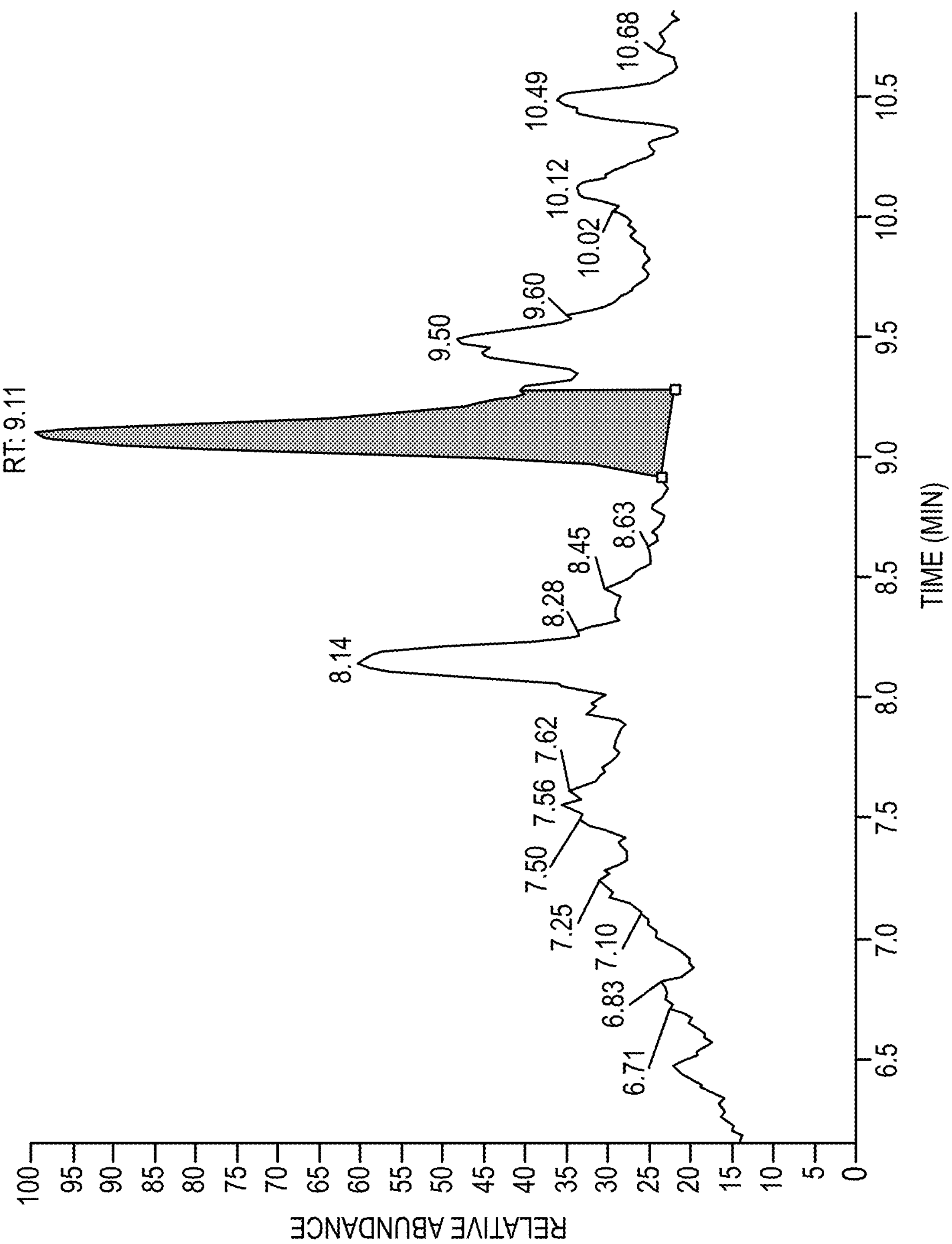

FIGS. 38A-C. Representative example of a polycyclic peptide produced from a precursor polypeptide containing two cysteines and a bifunctional cysteine-reactive amino acid (ObdpY). In the multi-part figure, (A) shows the sequence of the precursor polypeptide and the chemical structure of the polycyclic peptide product, (B) shows the MS/MS spectrum of the polycyclic peptide, and (C) shows the LC-MS extracted-ion chromatogram of the macrocyclic peptide.

Figure 39A:
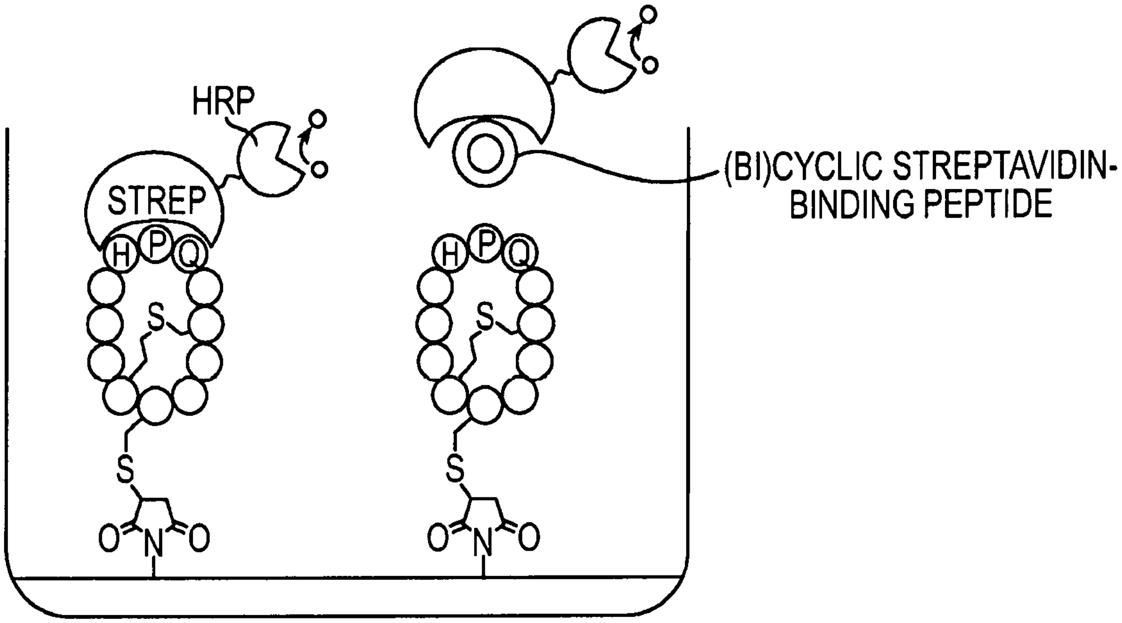
Figure 39B:
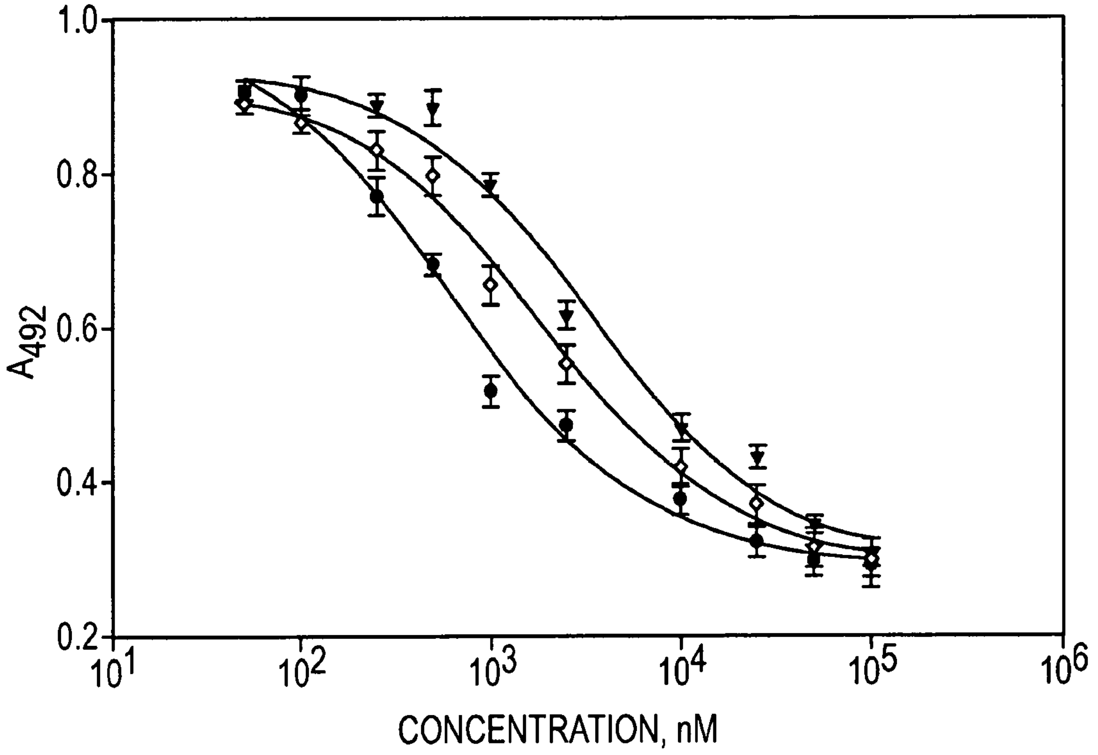

FIGS. 39A-B. Competitive binding assay for measuring streptavidin binding affinity of HPQ-containing cyclic and bicyclic peptides. (A) Schematic illustration of the in-solution inhibition assay. $IC_{50}$ values are obtained from the dose-dependent decrease in horseradish peroxidase (HRP) activity at increasing concentration of the cyclic or bicyclic streptavidin-binding peptide. (B) Inhibition curve.

5. DETAILED DESCRIPTION

For clarity of disclosure, and not by way of limitation, the detailed description is divided into the subsections set forth below.

5.1 Definitions

Unless defined otherwise herein, all technical and scientific terms used herein have the same meaning as commonly understood by one of ordinary skill in the art to which the disclosure pertains.

The singular forms "a," "an," and "the" used herein include plural referents unless the content clearly dictates otherwise.

The term "plurality" refers to two or more referents unless the content clearly dictates otherwise. The term "at least one" refers to one or more referents.

The term "functional group" as used herein refers to a contiguous group of atoms that, together, may undergo a chemical reaction under certain reaction conditions. Examples of functional groups are, among many others, —OH, $—NH_2$, —SH, —(C═O)—, $—N_3$, —C≡CH.

The term "aliphatic" or "aliphatic group" as used herein means a straight or branched $C_{1-15}$ hydrocarbon chain that is completely saturated or that contains at least one unit of unsaturation, or a monocyclic $C_{3-3}$ hydrocarbon, or bicyclic $C_{8-12}$ hydrocarbon that is completely saturated or that contains at least one unit of unsaturation, but which is not aromatic (also referred to herein as "cycloalkyl"). For example, suitable aliphatic groups include, but are not limited to, linear or branched alkyl, alkenyl, alkynyl groups or hybrids thereof such as (cycloalkyl)alkyl, (cycloalkenyl) alkyl, or (cycloalkynyl)alkyl. The alkyl, alkenyl, or alkynyl group may be linear, branched, or cyclic and may contain up to 15, up to 8, or up to 5 carbon atoms. Alkyl groups include, but are not limited to, methyl, ethyl, propyl, cyclopropyl, butyl, cyclobutyl, pentyl, and cyclopentyl groups. Alkenyl groups include, but are not limited to, propenyl, butenyl, and pentenyl groups. Alkynyl groups include, but are not limited to, propynyl, butynyl, and pentynyl groups.

The term "aryl" and "aryl group" as used herein refers to an aromatic substituent containing a single aromatic or multiple aromatic rings that are fused together, directly linked, or indirectly linked (such as linked through a methylene or an ethylene moiety). An aryl group may contain from 5 to 24 carbon atoms, 5 to 18 carbon atoms, or 5 to 14 carbon atoms.

The terms "heteroatom" means nitrogen, oxygen, or sulphur, and includes, but is not limited to, any oxidized forms of nitrogen and sulfur, and the quaternized form of any basic nitrogen. Heteroatom further includes, but is not limited to, Se, Si, or P.

The term "heteroaryl" as used herein refer to an aryl group in which at least one carbon atom is replaced with a heteroatom. In various embodiments, a heteroaryl group is a 5- to 18-membered, a 5- to 14-membered, or a 5- to 10-membered aromatic ring system containing at least one heteroatom selected from the group consisting of oxygen, sulphur, and nitrogen atoms. Heteroaryl groups include, but are not limited to, pyridyl, pyrrolyl, furyl, thienyl, indolyl, isoindolyl, indolizinyl, imidazolyl, pyridonyl, pyrimidyl, pyrazinyl, oxazolyl, thiazolyl, purinyl, quinolinyl, isoquinolinyl, benzofuranyl, and benzoxazolyl groups.

A heterocyclic group may be any monocyclic or polycyclic ring system which contains at least one heteroatom and may be unsaturated or partially or fully saturated. The term "heterocyclic" thus includes, but is not limited to, heteroaryl groups as defined above as well as non-aromatic heterocyclic groups. In various embodiments, a heterocyclic group is a 3- to 18-membered, a 3- to 14-membered, or a 3- to 10-membered, ring system containing at least one heteroatom selected from the group consisting of oxygen, sulphur, and nitrogen atoms. Heterocyclic groups include, but are not limited to, the specific heteroaryl groups listed above as well as pyranyl, piperidinyl, pyrrolidinyl, dioaxanyl, piperazinyl, morpholinyl, thiomorpholinyl, morpholinosulfonyl, tetrahydroisoquinolinyl, and tetrahydrofuranyl groups.

A halogen atom may be a fluorine, chlorine, bromine, or iodine atom.

By "optionally substituted", it is intended that in the any of the chemical groups listed above (e.g., alkyl, alkenyl, alkynyl, heteroalkyl, heteroalkenyl, heteroalkynyl, aryl, heteroaryl, heterocyclic, triazolyl groups), at least one of the hydrogen atoms is optionally replaced with an atom or chemical group other than hydrogen. Specific examples of such substituents include, but are not limited to, halogen atoms, hydroxyl (—OH), sulfhydryl (—SH), substituted sulfhydryl, carbonyl carboxy (—COOH), amino (—$NH_2$), nitro (—$NO_2$), sulfo (~$SO_2$—OH), cyano (—C≡N), thiocyanato (—S—C≡N), phosphono (—P(O)$OH_2$), alkyl, alkenyl, alkynyl, heteroalkyl, heteroalkenyl, heteroalkynyl, aryl, heteroaryl, heterocyclic, alkylthiol, alkyloxy, alkylamino, arylthiol, aryloxy, or arylamino groups. Where "optionally substituted" modifies a series of groups separated by commas (e.g., "optionally substituted A, B, or C"; or "A, B, or C optionally substituted with"), it is intended that each of the groups (e.g., A, B, or C) is optionally substituted.

The term "heteroatom-containing aliphatic" as used herein refer to an aliphatic moiety where at least one carbon atom is replaced with a heteroatom, e.g., oxygen, nitrogen, sulphur, selenium, phosphorus, or silicon, and typically oxygen, nitrogen, or sulphur.

The terms "alkyl" and "alkyl group" as used herein refer to a linear, branched, or cyclic saturated hydrocarbon typically containing 1 to 24 carbon atoms, or 1 to 12 carbon atoms, such as methyl, ethyl, n-propyl, isopropyl, n-butyl, isobutyl, t-butyl, octyl, decyl and the like.

The term "heteroatom-containing alkyl" as used herein refers to an alkyl moiety where at least one carbon atom is replaced with a heteroatom, e.g., oxygen, nitrogen, sulphur, phosphorus, or silicon, and typically oxygen, nitrogen, or sulphur.

The terms "alkenyl" and "alkenyl group" as used herein refer to a linear, branched, or cyclic hydrocarbon group of 2 to 24 carbon atoms, or of 2 to 12 carbon atoms, containing at least one double bond, such as ethenyl, n-propenyl, isopropenyl, n-butenyl, isobutenyl, octenyl, decenyl, and the like.

The term "heteroatom-containing alkenyl" as used herein refer to an alkenyl moiety where at least one carbon atom is replaced with a heteroatom.

The terms "alkynyl" and "alkynyl group" as used herein refer to a linear, branched, or cyclic hydrocarbon group of 2 to 24 carbon atoms, or of 2 to 12 carbon atoms, containing at least one triple bond, such as ethynyl, n-propynyl, and the like.

The term "heteroatom-containing alkynyl" as used herein refer to an alkynyl moiety where at least one carbon atom is replaced with a heteroatom.

The term "heteroatom-containing aryl" as used herein refer to an aryl moiety where at least one carbon atom is replaced with a heteroatom.

The terms "alkoxy" and "alkoxy group" as used herein refer to an aliphatic group or a heteroatom-containing aliphatic group bound through a single, terminal ether linkage. In various embodiments, aryl alkoxy groups contain 1 to 24 carbon atoms, or contain 1 to 14 carbon atoms.

The terms "aryloxy" and "aryloxy group" as used herein refer to an aryl group or a heteroatom-containing aryl group bound through a single, terminal ether linkage. In various embodiments, aryloxy groups contain 5 to 24 carbon atoms, or contain 5 to 14 carbon atoms.

The term "substituent" refers to a contiguous group of atoms. Examples of "substituents" include, but are not limited to: alkoxy, aryloxy, alkyl, heteroatom-containing alkyl, alkenyl, heteroatom-containing alkenyl, alkynyl, heteroatom-containing alkynyl, aryl, heteroatom-containing aryl, alkoxy, heteroatom-containing alkoxy, aryloxy, heteroatom-containing aryloxy, halo, hydroxyl (—OH), sulfhydryl (—SH), substituted sulfhydryl, carbonyl (—CO—), thiocarbonyl, (—CS—), carboxy (—COOH), amino (—$NH_2$), substituted amino, nitro (—$NO_2$), nitroso (—NO), sulfo (~$SO_2$—OH), cyano (—C≡N), cyanato (—O—C≡N), thiocyanato (—S—C≡N), formyl (—CO—H), thioformyl (—CS—H), phosphono (—P(O)$OH_2$), substituted phosphono, and phospho (—$PO_2$).

The term "contact" as used herein with reference to interactions of chemical units indicates that the chemical units are at a distance that allows short range non-covalent interactions (such as Van der Waals forces, hydrogen bonding, hydrophobic interactions, electrostatic interactions, dipole-dipole interactions) to dominate the interaction of the chemical units. For example, when a protein is 'contacted' with a chemical species, the protein is allowed to interact with the chemical species so that a reaction between the protein and the chemical species can occur.

The term "bioorthogonal" as used herein with reference to a reaction, reagent, or functional group, indicates that such reaction, reagent, or functional group does not exhibit significant or detectable reactivity towards biological molecules such as those present in a bacterial, yeast or mammalian cell. The biological molecules can be, e.g., proteins, nucleic acids, fatty acids, or cellular metabolites.

In general, the term "mutant" or "variant" as used herein with reference to a molecule such as polynucleotide or polypeptide, indicates that such molecule has been mutated from the molecule as it exists in nature. In particular, the term "mutate" and "mutation" as used herein indicates any modification of a nucleic acid and/or polypeptide which results in an altered nucleic acid or polypeptide. Mutations include, but are not limited to, any process or mechanism resulting in a mutant protein, enzyme, polynucleotide, or gene. A mutation can occur in a polynucleotide or gene sequence, by point mutations, deletions, or insertions of single or multiple nucleotide residues. A mutation in a polynucleotide includes, but is not limited to, mutations arising within a protein-encoding region of a gene as well as mutations in regions outside of a protein-encoding sequence, such as, but not limited to, regulatory or promoter sequences. A mutation in a coding polynucleotide such as a gene can be "silent", i.e., not reflected in an amino acid alteration upon expression, leading to a "sequence-conservative" variant of the gene. A mutation in a polypeptide includes, but is not limited to, mutation in the polypeptide sequence and mutation resulting in a modified amino acid. Non-limiting examples of a modified amino acid include, but are not limited to, a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like.

The term "engineer" refers to any manipulation of a molecule that result in a detectable change in the molecule, wherein the manipulation includes, but is not limited to, inserting a polynucleotide and/or polypeptide heterologous to the cell and mutating a polynucleotide and/or polypeptide native to the cell.

The term "nucleic acid molecule" as used herein refers to any chain of at least two nucleotides bonded in sequence. For example, a nucleic acid molecule can be a DNA or a RNA.

The term "peptide", "polypeptide", and "protein" as used herein refers to any chain of at least two amino acids bonded in sequence, regardless of length or post-translational modification.

The term "peptide-containing molecule" as used herein refers to a molecule that contains at least two amino acids.

The term "non-natural" and "unnatural" as used herein means being directly or indirectly made or caused to be made through human action. Thus, a "non-natural amino acid" is an amino acid that has been produced through human manipulation and does not occur in nature. The term "non-canonical amino acid" is equivalent in meaning to the terms "non-natural amino acid" or "unnatural amino acid".

The term "cyclic" and "macrocyclic" as used herein means having constituent atoms forming a ring. Thus, a "macrocyclic peptide" is a peptide molecule that contains at least one ring formed by atoms comprised in the molecule. As such, the term "macrocyclic peptide" comprises peptides that contain at least two rings separated from each other via a polypeptide sequence (also referred to herein as "polycyclic peptides") and peptides that contain at least two rings fused to each other (also referred to herein as "polycyclic peptides"). The term "macrocyclic peptide" also comprises peptides that contain two rings fused to each other (referred to herein also as "bicyclic peptides").

The terms "cyclization" or "macrocyclization" as used herein refer to a process or reaction whereby a cyclic molecule is formed or is made to be formed.

The term "peptidic backbone" as used herein refers to a sequence of atoms corresponding to the main backbone of a natural protein.

The term "precursor polypeptide" or "polypeptide precursor" as used herein refers to a polypeptide that is capable of undergoing macrocyclization according to the methods disclosed herein.

The term "ribosomal polypeptide", "ribosomally produced polypeptide" or "ribosomally derived polypeptide" as used herein refers to a polypeptide that is produced by action of a ribosome, and specifically, by the ribosomal translation of a messenger RNA encoding for such polypeptide. The ribosome can be a naturally occurring ribosome, e.g., a ribosome derived from an archea, procaryotic or eukaryotic organism, or an engineered (i.e., non-naturally occurring, artificial or synthetic) variant of a naturally occurring ribosome.

The term "intein" and "intein domain" as used herein refers to a naturally occurring or artificially constructed polypeptide sequence embedded within a precursor protein that can catalyze a splicing reaction during post-translational processing of the protein. The NEB Intein Registry (neb.com/neb/inteins.html) provides a list of known inteins.

The term "split intein" as used herein refers to an intein that has at least two separate components not fused to one another.

The term "splicing" as used herein refers to the process involving the cleavage of the main backbone of an intein-containing polypeptide by virtue of a reaction or process catalyzed by an intein or portions of an intein. "N-terminal splicing" refers to the cleavage of a polypeptide chain fused to the N-terminus of an intein, such reaction typically involving the scission of the thioester (or ester) bond formed via intein-catalyzed N→S (or N→O acyl) transfer, by action of a nucleophilic functional group or a chemical species containing a nucleophilic functional group. "C-terminal splicing" refers to the cleavage of a polypeptide chain fused to the C-terminus of an intein. "Self-splicing" as used herein refers to the process involving the cleavage of an intein from a polypeptide, within which the intein is embedded. "Trans-splicing" as used herein refers to a self-splicing process involving split inteins.

The term "affinity tag" as used herein refers to a polypeptide that is able to bind reversibly or irreversibly to an organic molecule, a metal ion, a protein, or a nucleic acid molecule.

The terms "vector" and "vector construct" as used herein refer to a vehicle by which a DNA or RNA sequence (e.g., a foreign gene) can be introduced into a host cell, so as to transform the host and promote expression (e.g., transcription and translation) of the introduced sequence. A common type of vector is a "plasmid", which generally is a self-contained molecule of double-stranded DNA that can be readily accept additional (foreign) DNA and which can readily introduced into a suitable host cell. A large number of vectors, including plasmid and fungal vectors, have been described for replication and/or expression in a variety of eukaryotic and prokaryotic hosts. Non-limiting examples include, but are not limited to, pKK plasmids (Clonetech), pUC plasmids, pET plasmids (Novagen, Inc., Madison, Wis.), pRSET or pREP plasmids (Invitrogen, San Diego, Calif.), or pMAL plasmids (New England Biolabs, Beverly, Mass.), and many appropriate host cells, using methods disclosed or cited herein or otherwise known to those skilled in the relevant art. The terms "express" and "expression" refer to allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g., the resulting protein, may also be said to be "expressed" by the cell. A polynucleotide or polypeptide is expressed recombinantly, for example, when it is expressed or produced in a foreign host cell under the control of a foreign or native promoter, or in a native host cell under the control of a foreign promoter.

The term "fused" as used herein means being connected through at least one covalent bond. The term "bound" as used herein means being connected through non-covalent interactions. Examples of non-covalent interactions are van der Waals, hydrogen bond, electrostatic, and hydrophobic interactions. Thus, a "DNA-binding peptide" refers to a peptide capable of connecting to a DNA molecule via non-covalent interactions. The term "tethered" as used herein means being connected through non-covalent interactions or through covalent bonds. Thus, a "polypeptide tethered to a solid support" refers to a polypeptide that is connected to a solid support (e.g., surface, resin bead) either via non-covalent interactions or through covalent bonds.

5.2 Methods for Producing Macrocyclic Peptides from Ribosomal Polypeptides

Methods and compositions are provided for making artificial macrocyclic peptides from genetically encoded, ribosomally produced artificial polypeptides. These methods are based on the use of artificial precursor polypeptides comprising (a) a non-canonical amino acid residue carrying a thiol-reactive functional group (referred to as $FG_1$); and (b) a cysteine residue that is positioned either upstream or downstream of the non-canonical amino acid in the polypeptide sequence. These methods are based on the ability of the $FG_1$-bearing amino acid and cysteine residue to react with each other after ribosomal synthesis of the polypeptide, so that a macrocyclic peptide carrying a side-chain-to-side-chain covalent (thioether) linkage is formed. Schematic representations of these embodiments are provided in FIGS. 1A-B.

Methods and compositions are also provided for making macrocyclic peptides from genetically encoded, ribosomally produced, intein-fused polypeptides. These methods are based on the use of artificial precursor polypeptides comprising (a) a non-canonical amino acid residue with a thiol-reactive functional group (referred to as $FG_1$); (b) a cysteine residue positioned upstream or downstream of the non-canonical amino acid within the polypeptide sequence; and (c) an intein protein positioned upstream or downstream of the non-canonical amino acid or of the cysteine residue within the polypeptide sequence. These methods exploit the ability of this non-canonical amino acid and cysteine residue to react with each other after ribosomal synthesis of the precursor polypeptide, so that a macrocyclic peptide carrying a side-chain-to-side-chain covalent (thioether) linkage is formed. These methods also exploit the ability of the intein to undergo N-terminal splicing, C-terminal splicing, or self-splicing, so that the macrocyclic peptide is released upon intein splicing. Schematic representations of these embodiments are provided in FIGS. 2A-B and 3A-B.

Methods and compositions are also provided for making artificial macrocyclic peptides from genetically encoded, ribosomally produced, split intein-fused polypeptides. These methods are based on the use of artificial precursor polypeptides comprising (a) a non-canonical amino acid residue with a thiol-reactive functional group (referred to as $FG_1$); (b) a cysteine residue positioned upstream or downstream of the non-canonical amino acid within the polypeptide sequence; and (c) a split intein domain positioned upstream or downstream of the non-canonical amino acid or the cysteine residue within the polypeptide sequence. These methods exploit the ability of this non-canonical amino acid and cysteine residue to react with each other after ribosomal synthesis of the precursor polypeptide, so that a macrocyclic peptide carrying a side-chain-to-side-chain covalent (thioether) linkage is formed. These methods also exploit the ability of the split intein to undergo trans-splicing, so that the bicyclic peptide is released upon split intein trans-splicing. Schematic representations of these embodiments are provided in FIGS. 4A-B.

Methods and compositions are also provided for making artificial macrocyclic peptides from genetically encoded, ribosomally produced, split intein-fused polypeptides. These methods are based on the use of artificial precursor polypeptides comprising (a) a non-canonical amino acid residue with two thiol-reactive functional groups (referred to as $FG_1$ and $FG_2$); (b) two cysteine residues positioned upstream and downstream of the non-canonical amino acid within the polypeptide sequence. These methods are based on the ability of the $FG_1/FG_2$-bearing amino acid to react with the two cysteine residues after ribosomal synthesis of the polypeptide, so that a bicyclic peptide carrying two side-chain-to-side-chain covalent (thioether) linkages is formed. Schematic representations of these embodiments are provided in FIGS. 37A-B.

Artificial, engineered and recombinant nucleic acid molecules and peptide sequences (or amino acid sequences) for use in these methods are also provided.

In some embodiments, a method is provided for making an artificial macrocyclic peptide, the method comprising:

a. providing a nucleic acid molecule encoding for a polypeptide of structure:

$$(AA)_m\text{-}Z\text{-}(AA)_n\text{-}Cys\text{-}(AA)_p \qquad (I)$$

or $$(AA)_m\text{-}Cys\text{-}(AA)_n\text{-}Z\text{-}(AA)_p \qquad (II)$$

wherein:

i. $(AA)_m$ is an N-terminal amino acid or peptide sequence, ii. Z is a non-canonical amino acid carrying a side-chain functional group $FG_1$, this $FG_1$ being a functional group selected from the group consisting of $—(CH_2)_n—X$, where X is F, Cl, Br, or I and n is an integer number from 1 to 10; $—C(O)CH_2X$, where X is F, Cl, Br, or I; —CH(R')X, where X is F, Cl, Br, or I; —C(O)CH(R')X, where X is F, Cl, Br, or I; $—OCH_2CH_2X$, where X is F, Cl, Br, or —C(O)CH═C═C(R')(R"), $—SO_2C(R')═C(R')(R")$, —C(O)C(R')═C(R')(R"), —C(R')═C(R')C(O)OR', —C(R')═C(R')C(O)N(R')(R"), —C(R')═C(R')—CN, $—C(R')═C(R')—NO_2$, —C≡C—C(O)OR', —C≡C—C(O)N(R')(R"), unsubstituted or substituted oxirane, unsubstituted or substituted aziridine, 1,2-oxathiolane 2,2-dioxide, 4-fluoro-1,2-oxathiolane 2,2-dioxide, and 4,4-difluoro-1,2-oxathiolane 2,2-dioxide, where each R and R' is independently H, an aliphatic, a substituted aliphatic, an aryl, or a substituted aryl group.

iii. $(AA)_n$ is a target peptide sequence, iv. $(AA)_p$ is a C-terminal amino acid or peptide sequence;

b. introducing the nucleic acid molecule into an expression system and expressing the nucleic acid molecule in the expression system, thereby producing the polypeptide; and c. allowing the functional group $FG_1$ to react with the cysteine (Cys) side-chain sulfhydryl group (—SH), thereby producing the macrocyclic peptide.

In other embodiments, a method is provided for making an artificial macrocyclic peptide, the method comprising:

a. providing a nucleic acid molecule encoding for a polypeptide of structure:

$$(AA)_m\text{-}Cys\text{-}(AA)_n\text{-}Z2\text{-}(AA)_o\text{-}Cys\text{-}(AA)_p \qquad (V)$$

wherein:

i. $(AA)_m$ is an N-terminal amino acid or peptide sequence, ii. Z2 is a non-canonical amino acid carrying two side-chain functional groups $FG_1$ and $FG_2$, these $FG_1$ and $FG_2$ being a functional group independently selected from the group consisting of —$(CH_2)_n$X, where X is F, Cl, Br, or I and n is an integer number from 1 to 10; —C(O)$CH_2$X, where X is F, Cl, Br, or I; —CH(R')X, where X is F, Cl, Br, or I; —C(O)CH(R')X, where X is F, Cl, Br, or I; —$OCH_2CH_2$X, where X is F, Cl, Br, or I; —C(O)CH═C═C(R')(R"), —$SO_2$C(R')═C(R')(R"), —C(O)C(R')═C(R')(R"), —C(R')═C(R')C(O)OR', —C(R')═C(R')C(O)N(R')(R"), —C(R')═C(R')—CN, —C(R')═C(R')—$NO_2$, —C≡C—C(O)OR', —C≡C—C(O)N(R')(R"), unsubstituted or substituted oxirane, unsubstituted or substituted aziridine, 1,2-oxathiolane 2,2-dioxide, 4-fluoro-1,2-oxathiolane 2,2-dioxide, and 4,4-difluoro-1,2-oxathiolane 2,2-dioxide, where each R' and R' is independently H, an aliphatic, a substituted aliphatic, an aryl, or a substituted aryl group.

iii. $(AA)_n$ is a target peptide sequence, iv. $(AA)_o$ is a second target peptide sequence, v. $(AA)_p$ is a C-terminal amino acid or peptide sequence;

b. introducing the nucleic acid molecule into an expression system and expressing the nucleic acid molecule in the expression system, thereby producing the polypeptide; and c. allowing the functional group $FG_1$ and $FG_2$ to react with the side-chain sulfhydryl group (—SH) of the cysteines (Cys), thereby producing the macrocyclic peptide.

According to the method, $(AA)_m$ is a N-terminal sequence comprising at least one amino acid, where AA corresponds to a generic amino acid residue and m corresponds to the number of amino acid residues composing such sequence. $(AA)_m$ is also referred to as "N-terminal tail". $(AA)_p$ is a C-terminal sequence that has 0 or at least one amino acid, where AA corresponds to a generic amino acid residue and p corresponds to the number of amino acid residues composing such sequence. $(AA)_p$ is also referred to as "C-terminal tail". $(AA)_n$ (and $(AA)_o$, when present) is a peptide sequence of variable length (also referred to as "target peptide sequence"), where AA corresponds to a generic amino acid residue and n corresponds to the number of amino acid residues composing such peptide sequence. Cys is a cysteine amino acid residue. Z is an amino acid that carries a side-chain functional group $FG_1$, which can react with the side-chain sulfhydryl group (—SH) of the cysteine residue to form a stable thioether bond.

As disclosed herein, the ability of an artificial polypeptide of formula (I) or (II) (also referred herein to as "precursor polypeptide") to produce a macrocyclic peptide is conferred by the ability of the nucleophilic sulfhydryl group carried by the cysteine residue to react intramolecularly with the electrophilic functional group $FG_1$ carried by the amino acid Z, thereby forming a covalent, inter-side-chain thioether bond. Depending on the nature of $FG_1$, this reaction proceeds via a thiol-mediated nucleophilic substitution reaction, a thiol-mediated Michael-type addition reaction, or a radical thiol-ene or thiol-yne reaction. Whereas the electrophilic functional group $FG_1$ in the precursor polypeptide could in principle react intermolecularly with free cysteine or other thiol-containing molecules contained in the expression system (e.g., glutathione), it was discovered by the inventors that appropriate functional groups $FG_1$ can be found so that the desired intramolecular thioether-bond forming reaction occurs exclusively or preferentially over the undesired intermolecular side-reactions. This result can be achieved because of the spatial proximity between the nucleophilic cysteine residue and the electrophilic Z amino acid, resulting in an increased effective concentration of the reacting species (i.e., —SH and $FG_1$ groups, respectively) in the intramolecular settings as compared to the intermolecular settings, which in turn favors the intramolecular peptide cyclization reaction over undesired intermolecular reactions. Similar considerations can be made in the context of certain embodiments, wherein a precursor polypeptide of formula (V) along with a bifunctional cysteine-reactive amino acid capable of forming thioether bonds with two cysteine residues within the polypeptide (residue Z2) is used.

A first advantage of the methods described herein is that they provide a highly versatile approach for the preparation of structurally diverse artificial macrocyclic peptides. Indeed, they offer multiple opportunities toward the structural and functional diversification of these compounds, e.g., through variation of the length and composition of the target peptide sequence ($(AA)_n$), variation of the structure of the amino acid Z, variation of the position of the amino acid Z relative to the cysteine residue (e.g., precursor polypeptide (I) versus (II)), variation of the length and composition of the N-terminal tail ($(AA)_m$), and variation of the length and composition of the C-terminal tail ($(AA)_p$). Further structural diversification can be achieved by combining multiple Z/Cys pairs within the same precursor polypeptide or by using bifunctional cysteine-reactive amino acids (Z2) in order to obtain polycyclic and bicyclic peptides. Accordingly, and because of the genetically encoded and ribosomal nature of the precursor polypeptides, the methods and compositions described herein can be used to produce vast libraries of structurally and functionally diverse macrocyclic peptides, which can be screened to identify compounds that can modulate, inhibit or promote interactions between biomolecules (e.g., enzymes, proteins, nucleic acids) for a variety of applications, including drug discovery.

A second advantage of the methods disclosed herein is that they produce peptide molecules whose conformational flexibility is restrained by virtue of at least one intramolecular thioether linkage. As illustrated in Example 8, this feature can confer these molecules with advantageous properties such as, for example, enhanced binding affinity, increased stability against proteolysis, and/or more favorable membrane-crossing properties, as compared to linear peptides or peptides lacking the intramolecular thioether linkage. In addition, the thioether linkage is redox and chemically stable in biological milieu, including the intracellular environment.

A third advantage of the methods disclosed herein is they allow for the preparation of macrocyclic peptides from genetically encoded, ribosomally produced polypeptides. Accordingly, these macrocyclic peptides can be produced as fused to a genetically encoded affinity tag, DNA-binding protein/peptide, protein-binding protein/peptide, fluorescent protein, or enzyme, which can be achieved via the introduction of one or more of these elements within the N-terminal tail and/or within the C-terminal tail of the precursor polypeptide. On one hand, these tags/proteins/enzymes can be useful to facilitate the purification and/or immobilization of the macrocyclic peptides for functional screening as demonstrated in Examples 4, 5 and 8. On the other hand, very large libraries of macrocyclic peptides can be rapidly and cost-effectively produced utilizing precursor polypeptides in which the target peptide sequence ($(AA)_n$), N-terminal tail ($(AA)_m$), and/or C-terminal tail ($(AA)_m$), is partially or fully randomized genetically. These features of the method can allow one to produce macrocyclic peptides as fused to a carrier protein of a display system such as phage display, mRNA display, ribosome display, yeast display, and the like. So, for example, the methods described herein allow one to generate combinatorial libraries of macrocyclic peptides that are fused to the pIII protein of M13 bacteriophage. These phage-displayed macrocyclic peptide libraries can be then 'panned' against a target biomolecule of interest according to procedures well known in the art (Lane and Stephen 1993; Giebel, Cass et al. 1995; Sidhu, Lowman et al. 2000) in order to identify macrocyclic peptide binders or inhibitors of such biomolecule.

A fourth advantage of the methods described herein is that they also enable the production of macrocyclic peptides inside a cell-based expression host such as a bacterial, yeast, insect, or mammalian cell. Intracellular production of the macrocyclic peptide can then be coupled to an (intra)cellular reporter system, phenotypic screen, or selection system, in order to identify a macrocyclic peptide capable of inhibiting or activating a certain cellular process, biomolecule, or enzymatic reaction linked to the reporter output, phenotype, or cell survival, respectively.

A fifth advantage of the methods disclosed herein is that the production of the macrocyclic peptides can be carried out under physiological conditions (e.g., in aqueous buffer, neutral pH, physiological temperature) and in complex biological media (e.g., inside a cell, in cell lysate) and in the presence of biological molecules (proteins, nucleic acids, cell metabolites) and biological material. One implication of this is that the production of macrocyclic peptides according to the methods disclosed herein can be coupled to one of the several techniques known in the art for the display and high-throughput screening of biological peptide libraries.

Because of the aforementioned advantageous features, the methods described herein can be useful to greatly accelerate and facilitate the discovery of bioactive peptide-based compounds as potential drug molecules and chemical probes or the identification of lead structures for the development of new chemical probes and drugs.

In some embodiments, Z is an amino acid of structure:

(III)

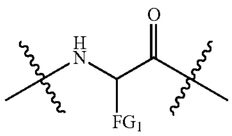

or (IV)

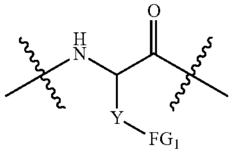

wherein $FG_1$ is a functional group selected from the group consisting of $—(CH_2)_nX$, where X is F, Cl, Br, or I and n is an integer number from 1 to 10; $—C(O)CH_2X$, where X is F, Cl, Br, or I; —CH(R')X, where X is F, Cl, Br, or I; —C(O)CH(R')X, where X is F, Cl, Br, or I; $—OCH_2CH_2X$, where X is F, Cl, Br, or I; —C(O)CH═C═C(R')(R''), $—SO_2C(R')═C(R')(R'')$, —C(O)C(R')═C(R')(R''), —C(R')═C(R')C(O)OR', —C(R')═C(R')C(O)N(R')(R''), —C(R')═C(R')—CN, $—C(R')═C(R')—NO_2$, —C≡C—C(O)OR', —C≡C—C(O)N(R')(R''), unsubstituted or substituted oxirane, unsubstituted or substituted aziridine, 1,2-oxathiolane 2,2-dioxide, 4-fluoro-1,2-oxathiolane 2,2-dioxide, and 4,4-difluoro-1,2-oxathiolane 2,2-dioxide, where each R' and R'' is independently H, an aliphatic, a substituted aliphatic, an aryl, or a substituted aryl group; and wherein Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups.

In some embodiments, Z is an amino acid of structure (IV) wherein Y is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, $C_5$-$C_{24}$ aryloxy groups.

In some embodiments, Z is an amino acid of structure (IV) wherein Y is a linker group selected from $—CH_2—C_6H_4—$, $—CH_2—C_6H_4—O—$, $—CH_2—C_6H_4—NH—$, $—(CH_2)_4—$, $—(CH_2)_4NH—$, $—(CH_2)_4NHC(O)—$, and $—(CH_2)_4NHC(O)O—$.

In specific embodiments, the amino acid Z is selected from the group consisting of 4-(2-bromoethoxy)-phenylalanine, 3-(2-bromoethoxy)-phenylalanine, 4-(2-chloroethoxy)-phenylalanine, 3-(2-chloroethoxy)-phenylalanine, 4-(1-bromoethyl)-phenylalanine, 3-(1-bromoethyl)-phenylalanine, 4-(aziridin-1-yl)-phenylalanine, 3-(aziridin-1-yl)-phenylalanine, 4-acrylamido-phenylalanine, 3-acrylamido-phenylalanine, 4-(2-fluoro-acetamido)-phenylalanine, 3-(2-fluoro-acetamido)-phenylalanine, 4-(2-chloro-acetamido)-phenylalanine, 3-(2-chloro-acetamido)-phenylalanine, 3-(2-fluoro-acetyl)-phenylalanine, 4-(2-fluoro-acetyl)-phenylalanine, $N^ε$-((2-bromoethoxy)carbonyl)-lysine, $N^ε$-((2-chloroethoxy)carbonyl)-lysine, $N^ε$-(buta-2,3-dienoyl)-lysine, $N^ε$-acryl-lysine, $N^ε$-crotonyl-lysine, $N^ε$-(2-fluoro-acetyl)-lysine, and $N^ε$-(2-chloro-acetyl)-lysine.

In some embodiments, Z2 is an amino acid of structure:

(VI)

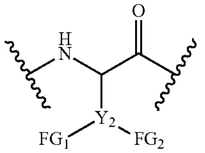

or (VII)

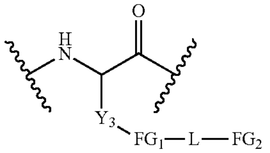

wherein $FG_1$ and $FG_2$ are a functional group independently selected from the group consisting of $—(CH_2)_nX$, where X is F, Cl, Br, or I and n is an integer number from 1 to 10; $—C(O)CH_2X$, where X is F, Cl, Br, or I; —CH(R')X, where X is F, Cl, Br, or I; —C(O)CH(R')X, where X is F, Cl, Br, or I; $—OCH_2CH_2X$, where X is F, Cl, Br, or I; —C(O)CH═C═C(R')(R''), $—SO_2C(R')═C(R')(R'')$, —C(O)C(R')═C(R')(R''), —C(R')═C(R')C(O)OR', —C(R')═C(R')C(O)N(R')(R''), —C(R')═C(R')—CN, $—C(R')═C(R')—NO_2$, —C≡C—C(O)OR', —C≡C—C(O)N(R')(R''), unsubstituted or substituted oxirane, unsubstituted or substituted aziridine, 1,2-oxathiolane 2,2-dioxide, 4-fluoro-1,2-oxathiolane 2,2-dioxide, and 4,4-difluoro-1,2-oxathiolane 2,2-dioxide, where each R and R' is independently H, an aliphatic, a substituted aliphatic, an aryl, or a substituted aryl group; and wherein $Y_2$, $Y_3$, and L are linker groups selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, aryloxy groups.

In some embodiments, Z2 is an amino acid of structure (VI) wherein $Y_2$ is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, $C_5$-$C_{24}$ aryloxy groups.

In some embodiments, Z2 is an amino acid of structure (VI) wherein $Y_2$ is a linker group selected from the group consisting of $—CH_2—C_6H_4—$, $—CH_2—C_6H_4—O—$, $—CH_2—C_6H_4—NH—$, $—CH_2—C_6H_4—OCH_2—$, $—(CH_2)_4NH—$, $—(CH_2)_4NHC(O)—$, $—(CH_2)_4NHC(O)O—$, $—(CH_2)_4NHC(O)OCH_2—$,

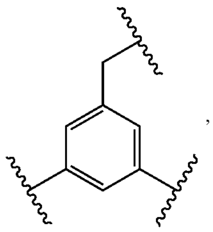

, and

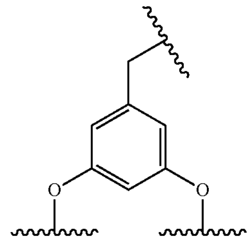

In specific embodiments, the amino acid Z2 is selected from the group consisting of of 3,5-bis(2-bromoethoxy)-phenylalanine, 3,5-bis(2-chloroethoxy)-phenylalanine, 3,5-bis(1-bromoethyl)-phenylalanine, 3,5-bis(aziridin-1-yl)-phenylalanine, 3,5-bis-acrylamido-phenylalanine, 3,5-bis(2-fluoro-acetamido)-phenylalanine, 3,5-bis(2-fluoro-acetyl)-phenylalanine, 4-((1,3-dibromopropan-2-yl)oxy)-phenylalanine, 4-((1,3-dichloropropan-2-yl)oxy)-phenylalanine, $N^{\varepsilon}$-4(1,3-dibromopropan-2-yl)oxy)carbonyl)-lysine, $N^{\varepsilon}$-4(1,3-dichloropropan-2-yl)oxy)carbonyl)-lysine, 4-(2,3-dibromopropoxy)-phenylalanine, 3-(2,3-dibromopropoxy)-phenylalanine, 4-(2,3-dichloropropoxy)-phenylalanine, 3-(2,3-dichloropropoxy)-phenylalanine, $N^{\varepsilon}$-((2,3-dibromopropoxy)carbonyl)-lysine, and $N^{\varepsilon}$-((2,3-dichloropropoxy)carbonyl)-lysine.

Artificial nucleic acid molecules for use according to the methods provided herein include, but are not limited to, those that encode for a polypeptide of general formula (I), (II), or (V) as defined above. The codon encoding for the amino acid Z (or Z2) in these polypeptides can be one of the 61 sense codons of the standard genetic code, a stop codon (TAG, TAA, TGA), or a four-base frameshift codon (e.g., TAGA, AGGT, CGGG, GGGT, CTCT). In some embodiments, the codon encoding for the amino acid Z (or Z2) within the nucleotide sequence encoding for the precursor polypeptide of formula (I), (II) or (V) is an amber stop codon (TAG), an ochre stop codon (TAA), an opal stop codon (TGA), or a four-base frameshift codon (see Example 2). In other embodiments, the codon encoding for Z (or Z2) in the nucleotide sequence encoding for these precursor polypeptides is the amber stop codon, TAG, or the 4-base codon, TAGA.

The non-canonical amino acid Z (or Z2) can be introduced into the precursor polypeptide through direct incorporation during ribosomal synthesis of the precursor polypeptide, or generated post-translationally through enzymatic or chemical modification of the precursor polypeptide, or by a combination of these procedures. In some embodiments, the amino acid Z (or Z2) is introduced into the precursor polypeptide during ribosomal synthesis of the precursor polypeptide via either stop codon suppression or four-base frameshift codon suppression. In other embodiments, the amino acid Z (or Z2) is introduced into the precursor polypeptide during ribosomal synthesis of the precursor polypeptide via amber (TAG) stop codon suppression or via 4-base TAGA codon suppression.

Several methods are known in the art for introducing a non-canonical amino acid into a recombinant or in vitro translated artificial polypeptide, any of which can be applied for preparing artificial precursor polypeptides suitable for the methods disclosed herein. These art-known methods include, but are not limited to, methods for suppression of a stop codon or of a four-based frameshift codon with a non-canonical amino acid using engineered (i.e., non-naturally occurring, artificial or synthetic) tRNA/aminoacyl-tRNA synthetase (AARS) pairs (Wang, Xie et al. 2006; Wu and Schultz 2009; Liu and Schultz 2010; Fekner and Chan 2011; Lang and Chin 2014). Examples of tRNA/aminoacyl-tRNA synthetase (AARS) pairs used for this purpose include, but are not limited to, engineered variants of *Methanococcus jannaschii* AARS/tRNA pairs (e.g., TyrRS/$tRNA^{Tyr}$), of *Saccharomyces cerevisiae* AARS/tRNA pairs (e.g., AspRS/$tRNA^{Asp}$, GlnRS/$tRNA^{Gln}$, TyrRS/$tRNA^{Tyr}$, and PheRS/$tRNA^{Phe}$), of *Escherichia coli* AARS/tRNA pairs (e.g., TyrRS/$tRNA^{Tyr}$, LeuRS/$tRNA^{Lue}$), of *Methanosarcina mazei* AARS/tRNA pairs (PylRS/$tRNA^{Pyl}$), and of *Methanosarcina mazei* AARS/tRNA pairs (PylRS/$tRNA^{Pyl}$) (Wang, Xie et al. 2006; Wu and Schultz 2009; Liu and Schultz 2010; Fekner and Chan 2011; Lang and Chin 2014). Alternatively, natural or engineered four-codon suppressor tRNAs and their cognate aminoacyl-tRNA synthetases can be used for the same purpose (Anderson, Wu et al. 2004; Rodriguez, Lester et al. 2006; Neumann, Slusarczyk et al. 2010; Neumann, Wang et al. 2010). Alternatively, a non-canonical amino acid can be incorporated into a polypeptide using chemically (Dedkova, Fahmi et al. 2003) or enzymatically (Bessho, Hodgson et al. 2002; Hartman, Josephson et al. 2006) aminoacylated tRNA molecules and using a cell-free protein expression system in the presence of the aminoacylated tRNA molecules (Kourouklis, Murakami et al. 2005; Murakami, Ohta et al. 2006). Alternatively, a non-canonical amino acid can be incorporated into a polypeptide by exploiting the promiscuity of wild-type aminoacyl-tRNA synthetase enzymes using a cell-free protein expression system, in which one or more natural amino acids are replaced with structural analogs(Josephson, Hartman et al. 2005; Hartman, Josephson et al. 2007). Any of these methods can be used to introduce an unnatural amino acid of the type (III), (IV), (VI) or (VII) into the precursor polypeptide for the purpose of generating macrocyclic peptides according to the methods disclosed herein.

In some embodiments, the non-canonical amino acid Z (or Z2) is incorporated into the precursor polypeptide via stop codon or four-base codon suppression methods using an engineered AARS/tRNA pair derived from *Methanococcus jannaschii* tyrosyl-tRNA synthetase (MjTyrRS) and its cognate tRNA ($MjtRNA^{Tyr}$), an engineered AARS/tRNA pair derived from *Methanosarcina mazei* pyrrolysyl-tRNA synthetase (MmPylRS) and its cognate tRNA ($tRNA^{Pyl}$), an engineered AARS/tRNA pair derived from *Methanosarcina mazei* pyrrolysyl-tRNA synthetase (MmPylRS) and its cognate tRNA (tRNA$^{Pyl}$), or an engineered AARS/tRNA pair derived from *Escherichia coli* tyrosyl-tRNA synthetase (EcTyrRS) and its cognate tRNA (EctRNA$^{Tyr}$).

In the characterization of the aminoacyl-tRNA synthetase enzymes disclosed herein, these enzymes can be described in reference to the amino acid sequence of a naturally occurring aminoacyl-tRNA synthetase or another engineered aminoacyl-tRNA synthetase. As such, the amino acid residue is determined in the aminoacyl-tRNA synthetase enzyme beginning from the first amino acid after the initial methionine (M) residue (i.e., the first amino acid after the initial methionine M represents residue position 1). It will be understood that the initiating methionine residue may be removed by biological processing machinery such as in a host cell or in vitro translation system, to generate a mature protein lacking the initiating methionine residue. The amino acid residue position at which a particular amino acid or amino acid change is present is sometimes described herein as "Xn", or "position n", where n refers to the residue position.

In some embodiments, the stop codon/frameshift codon suppression system used for incorporating the amino acid Z (or Z2) into the precursor polypeptide comprises an engineered variant of *Methanococcus jannaschii* tRNA$^{Tyr}$ as encoded by a nucleotide of sequence SEQ ID NO: 101, 102, 103, or 104; and an engineered variant of *Methanococcus jannaschii* tyrosyl-tRNA synthetase (SEQ ID NO: 77), said variant comprising an amino acid change at at least one of the following amino acid positions of SEQ ID NO:77: X32, X63, X65, X70, X107, X108, X109, X155, X158, X159, X160, X161, X162, X163, X164, X167, and X286.

In other embodiments, the stop codon/frameshift codon suppression system used for incorporating the amino acid Z (or Z2) into the precursor polypeptide consists of a *Methanococcus jannaschii* tRNA$^{Tyr}$ variant selected from the group of tRNA molecules encoded by the nucleotide sequence of SEQ ID NOs: 101, 102, 103, and 104; and a *Methanococcus jannaschii* tyrosyl-tRNA synthetase variant selected from the group of polypeptides of SEQ ID NOs: 77, 81, 82, 83, 84, 85, 86, 87, 88, 89, and 90.

In some embodiments, the stop codon/frameshift codon suppression system used for incorporating the amino acid Z (or Z2) into the precursor polypeptide comprises an engineered variant of *Methanosarcina* species tRNA$^{Pyl}$ or *Desulfitobacterium hafniense* tRNA$^{Pyl}$ as encoded by a nucleotide of sequence SEQ ID NO: 105, 106, 107, 108, 109, 110, 111, or 112; and an engineered variant of *Methanosarcina mazei* pyrrolysyl-tRNA synthetase (SEQ ID NO: 78), said variant comprising an amino acid change at least one of the following amino acid positions of SEQ ID NO:78: X302, X305, X306, X309, X346, X348, X364, X384, X401, X405, and X417.

In some embodiments, the stop codon/frameshift codon suppression system used for incorporating the amino acid Z (or Z2) into the precursor polypeptide comprises an engineered variant of *Methanosarcina* species tRNA$^{Pyl}$ or *Desulfitobacterium hafniense* tRNA$^{Pyl}$ as encoded by a nucleotide of sequence SEQ ID NO: 105, 106, 107, 108, 109, 110, 111, or 112; and an engineered variant of *Methanosarcina barkeri* pyrrolysyl-tRNA synthetase (SEQ ID NO: 79), said variant comprising an amino acid change at at least one of the following amino acid positions of SEQ ID NO: 79: X76, X266, X270, X271, X273, X274, X313, X315, and X349.

In other embodiments, the stop codon/frameshift codon suppression system used for incorporating the amino acid Z (or Z2) into the precursor polypeptide consists of a tRNA$^{Pyl}$ variant selected from the group of tRNA molecules encoded by the nucleotide sequence of SEQ ID NO: 105, 106, 107, 108, 109, 110, 111, and 112; and a pyrrolysyl-tRNA synthetase variant selected from the group of polypeptides of SEQ ID NOs: 78, 79, 91, 92, 93, 94, 95, and 96.

In some embodiments, the stop codon/frameshift codon suppression system used for incorporating the amino acid Z (or Z2) into the precursor polypeptide comprises an engineered variant of *Escherichia coli* tRNA$^{Tyr}$ or *Bacillus stearothermophilus* tRNA$^{Tyr}$ as encoded by a nucleotide of sequence SEQ ID NO: 113, 114, 115, 116, 117, 118, 119, or 120; and an engineered variant of *Escherichia coli* tyrosyl-tRNA synthetase (SEQ ID NO: 80), said variant comprising an amino acid change at least one of the following amino acid positions of SEQ ID NO: 80: X37, X182, X183, X186, and X265.

In other embodiments, the stop codon/frameshift codon suppression system used for incorporating the amino acid Z (or Z2) into the precursor polypeptide consists of a tRNA$^{Tyr}$ variant selected from the group of tRNA molecules encoded by the nucleotide sequence of SEQ ID NO: 113, 114, 115, 116, 117, 118, 119, and 120; and a *E. coli* tyrosyl-tRNA synthetase variant selected from the group of polypeptides of SEQ ID NOs: 80, 97, 98, 99, and 100.

In some embodiments, the aminoacyl-tRNA synthetase used for incorporating the amino acid Z (or Z2) into the precursor polypeptide can have additionally at least one amino acid residue differences at positions not specified by an X above as compared to the sequence SEQ ID NO: 77, 78, 79, or 80. In some embodiments, the differences can be 1-2, 1-5, 1-10, 1-20, 1-30, 1-40, 1-50, 1-75, 1-100, 1-150, or 1-200 amino acid residue differences at other positions not defined by X above.

In some embodiments, the suppressor tRNA molecule used for incorporating the amino acid Z (or Z2) into the precursor polypeptide can have additionally at least one nucleotide difference as compared to the sequence encoded by the gene of SEQ ID NO: 101, 102, 103, 104, 105, 106, 107, 108, 109, 110, 111, 112, 113, 114, 115, 116, 117, 118, 119, or 120. In some embodiments, the differences can be 1-2, 1-5, 1-10, 1-20, 1-30, 1-40, 1-50, or 1-60 nucleotide differences as compared to the sequences encoded by these genes.

In another embodiment of the method, the engineered variant of *Methanococcus jannaschii* tyrosyl-tRNA synthetase (SEQ ID NO: 77) comprises at least one of the features selected from the group consisting of: X32 is Tyr, Leu, Ala, Gly, Thr, His, Glu, Val, or Gln; X65 is Leu, His, Tyr, Val, Ser, Thr, Gly, or Glu; X67 is Ala or Gly; X70 is His, Ala, Cys, or Ser; X107 is Glu, Pro, Asn, or Thr; X108 is Phe, Trp, Ala, Ser, Arg, Gly, Tyr, His, Trp, or Glu; X109 is Gln, Met, Asp, Lys, Glu, Pro, His, Gly, Met, or Leu; X155 is Gln, Glu, or Gly; X158 is Asp, Gly, Glu, Ala, Pro, Thr, Ser, or Val; X159 is Ile, Cys, Pro, Leu, Ser, Trp, His, or Ala; X160 is His or Gln; X161 is Tyr or Gly; X162 is Leu, Arg, Ala, Gln, Gly, Lys, Ser, Glu, Tyr, or His; X163 is Gly or Asp; X164 is Val or Ala; X167 is Ala or Val; X286 is Asp or Arg.

In another embodiment of the method, the engineered variant of *Methanosarcina mazei* pyrrolysyl-tRNA synthetase (SEQ ID NO: 78) comprises at least one of the features selected from the group consisting of: X302 is Ala or Thr; X305 is Leu or Met; X306 is Tyr, Ala, Met, Ile, Leu, Thr, Gly; X309 is Leu, Ala, Pro, Ser, or Arg; X346 is Asn, Ala, Ser, or Val; X348 is Cys, Ala, Thr, Leu, Lys, Met, or Trp; X364 is Thr or Lys; X384 is Tyr or Phe; X405 is Ile or Arg; X401 is Val or Leu; X417 is Trp, Thr or Leu.

In another embodiment of the method, the engineered variant of *Methanosarcina barkeri* pyrrolysyl-tRNA synthetase (SEQ ID NO: 79) comprises at least one of the features selected from the group consisting of: X76 is Asp or Gly; X266 is Leu, Val, or Met; X270 is Leu or Ile; X271 is Tyr, Phe, Leu, Met, or Ala; X274 is Leu, Ala, Met, or Gly; X313 is Cys, Phe, Ala, Val, or Ile; X315 is Met or Phe; X349 is Tyr, Phe, or Trp.

In another embodiment of the method, the engineered variant of *Escherichia coli* tyrosyl-tRNA synthetase (SEQ ID NO: 80) comprises at least one of the features selected from the group consisting of: X37 is Tyr, Ile, Gly, Val, Leu, Thr, or Ser; X182 is Asp, Gly, Ser, or Thr; X183 is Phe, Met, Tyr, or Ala; X186 is Leu, Ala, Met, or Val; X265 is Asp or Arg.

An aspect of the methods disclosed herein is the identification and selection of a suitable aminoacyl-tRNA synthetase for incorporating an amino acid Z (or Z2) as defined above, into the artificial precursor polypeptide. Various methods are known in the art to evaluate and quantify the relative efficiency of a given wild-type or engineered aminoacyl-tRNA synthetase to incorporate a non-canonical amino acid into a protein (Young, Young et al. 2011). Any of these methods can be used to guide the identification and choice of a suitable aminoacyl-tRNA synthetase for incorporating a desired amino acid Z (or Z2) into the precursor polypeptide. For example, such efficiency can be measured via a fluorescence assay based on the expression of a reporter fluorescent protein (e.g., green fluorescent protein), whose encoding gene has been modified to contain a codon to be suppressed (e.g., amber stop codon). Expression of the reporter fluorescent protein is then induced in a suitable expression system (e.g., an *E. coli* or yeast cell) in the presence of the aminoacyl-tRNA synthetase to be tested, a cognate suppressor tRNA (e.g., amber stop codon suppressor tRNA), and the desired non-canonical amino acid. Under these conditions, the relative amount of the expressed (i.e., ribosomally produced) fluorescent protein is linked to the relative efficiency of the aminoacyl-tRNA synthetase to charge the cognate suppressor tRNA with the non-canonical amino acid, which can thus be quantified via fluorimetric means. A demonstration of how this procedure can be applied for selecting an aminoacyl-tRNA synthetase/suppressor tRNA pair for incorporating a desired amino acid Z (or Z2) into the precursor polypeptide is provided in Example 3.

If necessary, the ability of a given aminoacyl-tRNA synthetase/suppressor tRNA pair to incorporate a target non-canonical amino acid into a protein can be improved by means of rational design or directed evolution. While the fluorescence-based method described above can be used to screen several hundreds of engineered aminoacyl-tRNA synthetase variants and/or suppressor tRNA variants for this purpose, higher throughput procedures are also known in the art, which are, for example, based on selection systems (Wang, Xie et al. 2006; Wu and Schultz 2009; Liu and Schultz 2010; Fekner and Chan 2011). One such system involves introducing a library of mutated aminoacyl-tRNA synthetases and/or of mutated suppressor tRNAs into a suitable cell-based expression host (e.g., *E. coli* or yeast cells), whose survival under a suitable selective medium or growth conditions is dependent upon the functionality of the aminoacyl-tRNA synthetase/suppressor tRNA pair. This can be achieved, for example, by introducing a stop codon or four-base codon that is to be suppressed, into a gene encoding for a protein or enzyme essential for survival of the cell, such as a protein or enzyme conferring resistance to an antibiotic. In this case, the ability of the aminoacyl-tRNA synthetase/suppressor tRNA pair to incorporate the desired non-canonical amino acid into the selection marker protein is linked to the survival of the host, thereby enabling the rapid isolation of suitable aminoacyl-tRNA synthetase/suppressor tRNA pair(s) for the incorporation of a particular non-canonical amino acid from very large engineered libraries. The selectivity of these aminoacyl-tRNA synthetase/suppressor tRNA pair toward the desired non-canonical amino acid over the twenty natural amino acids can be further improved by iterative rounds of positive and negative selection as described in (Wang, Xie et al. 2006; Wu and Schultz 2009; Liu and Schultz 2010; Fekner and Chan 2011). Procedures such as those described above can be thus applied to generate and isolate an engineered aminoacyl-tRNA synthetase/suppressor tRNA pair suitable for incorporation of the amino acid Z as defined above, into the precursor polypeptide.

Engineered aminoacyl-tRNA synthetase/tRNA pairs for the incorporation of the amino acid Z (or Z2) into the precursor polypeptide can be prepared via mutagenesis of the polynucleotide encoding for the aminoacyl-tRNA synthetase enzymes of SEQ ID NOs: 77, 78, 79, 80, or an engineered variant thereof; and via mutagenesis of the tRNA-encoding polynucleotides of SEQ ID NOs: 101, 102, 103, 104, 105, 106, 107, 108, 109, 110, 111, 112, 113, 114, 115, 116, 117, 118, 119, 120, or an engineered variant thereof. Many mutagenesis methods are known in the art and these include, but are not limited to, site-directed mutagenesis, site-saturation mutagenesis, random mutagenesis, cassette-mutagenesis, DNA shuffling, homologous recombination, non-homologous recombination, site-directed recombination, and the like. Detailed description of art-known mutagenesis methods can be found, among other sources, in U.S. Pat. Nos. 5,605,793; 5,830,721; 5,834,252; WO 95/22625; WO 96/33207; WO 97/20078; WO 97/35966; WO 98/27230; WO 98/42832; WO 99/29902; WO 98/41653; WO 98/41622; WO 98/42727; WO 00/18906; WO 00/04190; WO 00/42561; WO 00/42560; WO 01/23401; WO 01/64864.

As described above, the engineered aminoacyl-tRNA synthetases and cognate suppressor tRNA obtained from mutagenesis of SEQ ID NO:77 to 80, and from mutagenesis of SEQ ID NO:101 to 120, can be screened for identifying aminoacyl-tRNA synthetase/suppressor tRNA pairs being able, or having improved ability as compared to the corresponding wild-type enzyme/tRNA molecule, to incorporate the amino acid Z (or Z2) into the precursor polypeptide.

In some embodiments, the engineered aminoacyl-tRNA synthetase used in the method comprises an amino acid sequence that is at least 80%, 85%, 90%, 95%, 99% or more identical to the sequence SEQ ID NOs: 77, 78, 79, or 80.

In some embodiments, the engineered suppressor tRNA used in the method is encoded by a polynucleotide comprising a nucleotide sequence that is at least 80%, 85%, 90%, 95%, 99% or more identical to the sequence SEQ ID NOs: 101, 102, 103, 104, 105, 106, 107, 108, 109, 110, 111, 112, 113, 114, 115, 116, 117, 118, 119, or 120.

The target peptide sequence, $(AA)_n$, in the precursor polypeptide of formula (I), (II) and (V) and the second target peptide sequence, $(AA)_o$, in the precursor polypeptide of formula (V), can be a polypeptide comprising 1 to 1,000 amino acid residues. In some embodiments, $(AA)_m$ (and $(AA)_o$) consists of a polypeptide comprising 1 to 50 amino acid residues and, in other embodiments, $(AA)_n$ (and $(AA)_o$) consists of a polypeptide comprising 1 to 20 amino acid residues.

The N-terminal tail, $(AA)_m$, in the precursor polypeptide of formula (I), (II), and (V) can be a polypeptide comprising 1 to 10,000 amino acid residues. In some embodiments, $(AA)_m$ consists of a polypeptide comprising 1 to 1,000 amino acid residues and, in other embodiments, $(AA)_m$ consists of a polypeptide comprising 1 to 600 amino acid residues.

The C-terminal tail, $(AA)_p$, in the precursor polypeptide of formula (I), (II), and (V) may not be present, and when present, it can be a polypeptide comprising 1 to 10,000 amino acid residues. When present, $(AA)_m$ consists, in some embodiments, of a polypeptide comprising 1 to 1,000 amino acid residues and, in other embodiments, $(AA)_m$ consists of a polypeptide comprising 1 to 600 amino acid residues.

The N-terminal tail, $(AA)_m$, the C-terminal tail, $(AA)_p$, or both, in the precursor polypeptides of formula (I), (II), and (V) can comprise a polypeptide affinity tag, a DNA-binding polypeptide, a protein-binding polypeptide, an enzyme, a fluorescent protein, an intein protein, or a combination of these polypeptides.

Introduction of a polypeptide affinity tag within the N-terminal tail and/or C-terminal tail of the precursor polypeptide results in macrocyclic peptides fused to such polypeptide affinity tag. Such affinity tags can be useful for isolating, purifying, and/or immobilizing onto a solid support the macrocyclic peptides generated according to the methods disclosed herein. Accordingly, in some embodiments, the N-terminal tail, C-terminal tail, or both, of the precursor polypeptides comprise at least one polypeptide affinity tags selected from the group consisting of a polyarginine tag (e.g., RRRRR) (SEQ ID NO:121), a polyhistidine tag (e.g., HHHHHH) (SEQ ID NO:122), an Avi-Tag (SGLNDIFEAQKIEWHELEL) (SEQ ID NO:123), a FLAG tag (DYKDDDDK) (SEQ ID NO:124), a Strep-tag II (WSHPQFEK) (SEQ ID NO:125), a c-myc tag (EQKLISEEDL) (SEQ ID NO:126), a S tag (KETAAAKFERQHMDS) (SEQ ID NO:127), a calmodulin-binding peptide (KRRWKKNFIAVSAANRFKKISSSGAL) (SEQ ID NO:128), a streptavidin-binding peptide (MDEKTTGWRGGHVVEGLAGELEQLRARLEHHPQGQREP) (SEQ ID NO:129), a chitin-binding domain (SEQ ID NO:130), a glutathione S-transferase (GST; SEQ ID NO:131), a maltose-binding protein (MBP; SEQ ID NO:132), streptavidin (SEQ ID NO:133), and engineered variants thereof. These aspects are illustrated in Example 2.

The N-terminal tail, $(AA)_m$, the C-terminal tail, $(AA)_p$, or both, in the precursor polypeptides of formula (I), (II), and (V) can comprise a reporter protein or enzyme. This approach will result in the formation of macrocyclic peptides fused to a reporter protein or enzyme, which can be useful to facilitate the functional screening of said macrocyclic peptides. Accordingly, in some embodiments, the N-terminal tail, $(AA)_m$ and/or the C-terminal tail, $(AA)_p$, in the precursor polypeptides of formula (I), (II), and (V) comprise at least one polypeptide selected from the group consisting of green fluorescent protein (SEQ ID NO:134), luciferase (SEQ ID NO:135), alkaline phosphatase (SEQ ID NO:136), and engineered variants thereof.

The N-terminal tail, $(AA)_m$, the C-terminal tail, $(AA)_p$, or both, in the precursor polypeptides of formula (I), (II), or (V) can comprise a protein or enzyme that is part of a display system such as, for example, a phage display (e.g., M13, T7, or lambda phage display), a yeast display, a bacterial display, a DNA display, a plasmid display, a CIS display, a ribosome display, or a mRNA display system. As mentioned above, this approach can be useful for generating large libraries of macrocyclic peptides which are physically linked to, or compartmentalized with the polynucleotide sequence that encodes for the corresponding precursor polypeptides. In turn, this approach can be useful toward isolating functional macrocyclic peptides that are able to bind, inhibit or activate a certain target biomolecule (e.g., protein, enzyme, DNA or RNA molecule) or target biomolecular interaction.

Accordingly, in some embodiments, the N-terminal tail, $(AA)_m$, comprises a polypeptide selected from the group consisting of M13 phage coat protein pVI (SEQ ID NO:137), T7 phage protein 10A (SEQ ID NO:138), T7 phage protein 10B (SEQ ID NO:139), *E. coli* NlpA (SEQ ID NO:140), *E. coli* OmpC (SEQ ID NO:141), *E. coli* FadL (SEQ ID NO:142), *E. coli* Lpp-OmpA (SEQ ID NO:143), *E. coli* PgsA (SEQ ID NO:144), *E. coli* EaeA (SEQ ID NO:145), *S. cerevisiae* Aga2p (SEQ ID NO:146), *S. cerevisiae* Flo 1p (SEQ ID NO:147), human NF-κB p50 protein (SEQ ID NO:148), M13 phage coat protein pIII leader sequence (SEQ ID NO:149), M13 phage coat protein pVIII leader sequence (SEQ ID NO:150), M13 phage protein pVI (SEQ ID NO:151), Snap-tag (SEQ ID NO:152), Clip-Tag (SEQ ID NO:153), and engineered variants thereof.

In other embodiments, the C-terminal tail, $(AA)_p$, comprises a polypeptide selected from the group consisting of M13 phage coat protein pIII (SEQ ID NO:154), M13 phage coat protein pVIII (SEQ ID NO:155), RepA protein (SED ID NO: 156), *S. cerevisiae* Aga1p (SEQ ID NO:157), Snap-tag (SEQ ID NO:152), Clip-Tag (SEQ ID NO:153), P2A protein (SED ID NO: 158), and engineered variants thereof.

In other embodiments, the C-terminal tail, $(AA)_p$, comprises a molecule selected from the group consisting of puromycin, puromycin analog, a puromycin-DNA conjugate, and a puromycin-RNA conjugate.

The N-terminal tail, $(AA)_m$, the C-terminal tail, $(AA)_p$, or both, in the precursor polypeptides of formula (I), (II), or (V) can comprise an intein protein. Inteins are polypeptides that are found as in-frame insertions in various natural proteins and can undergo a self-catalyzed intramolecular rearrangement leading to self-excision (self-splicing) of the intein and ligation of the flanking polypeptides together. The mechanism of intein splicing is well known (Xu and Perler 1996; Paulus 2000) and it involves the formation of a (thio)ester bond at the junction between the intein and the polypeptide fused the N-terminus of the intein (commonly referred to as "N-extein") by action of a catalytic cysteine or serine residue at the first position of the intein sequence. This reversible N(backbone)→S(side-chain) or a N(backbone)→O(side-chain) acyl transfer is followed by a trans(thio)esterification step whereby the N-extein acyl unit is transferred to the side-chain thiol/hydroxyl group of a cysteine, serine, or threonine residue at the first position of the polypeptide fused the C-terminus of the intein ("C-extein"). The last step of the intein self-splicing process involves cleavage of the peptide bond connecting the intein to the C-extein via an intramolecular transamidation reaction by action of a conserved catalytic asparagine residue at the C-terminal position of the intein sequence (Paulus 2000).

Knowledge of the splicing mechanism of intein has enabled the preparation of engineered inteins with altered splicing behavior (Perler 2005; Xu and Evans 2005; Elleuche and Poggeler 2010). For example, it is known that removal of the conserved asparagine residue at the C-terminus of the intein sequence can result in an engineered intein protein capable of only N-terminal splicing (i.e., cleavage of the peptide bond between the N-extein and the intein), which can occurs spontaneously (i.e., via hydrolysis of N-terminal (thio)ester bond) or upon incubation with a thiol reagent (e.g., thiophenol, benzylmercaptan, dithiothreitol, sodium 2-sulfanylethanesulfonate), depending on the nature of the intein and of the C-terminal amino acid(s) in the N-extein sequence. Similarly, removal of the conserved cysteine or serine residue at the N-terminus of the intein sequence can result in an engineered intein protein capable of only C-terminal splicing (i.e., cleavage of the peptide bond between the intein and C-extein), which can occurs spontaneously or promoted via a change in pH or temperature, depending on the nature of the intein and of the N-terminal amino acid(s) in the C-extein sequence. Furthermore, certain intein proteins occur as split inteins, having an N-domain and C-domain. Upon association of the N-domain with the C-domain, split inteins acquires the ability to self-splice according to a mechanism analogous to single-polypeptide intein proteins (Mootz 2009). As for the latter, the N-terminal cysteine or serine residue and C-terminal asparagine residue can be mutated, resulting in altered splicing behavior as described above (Perler 2005; Xu and Evans 2005; Mootz 2009; Elleuche and Poggeler 2010).

According to the methods described herein, introduction of a natural or engineered intein protein within the N-terminal tail, $(AA)_m$, or C-terminal tail, $(AA)_p$, of the precursor polypeptide of formula (I), (II), or (V) results in the formation of a macrocyclic peptide that is fused to either the C-terminus or the N-terminus, respectively, of such natural or engineered intein. This aspect enables one to control and modulate the release of the macrocyclic peptide from the intein-fused polypeptide based on the self-splicing and altered splicing behavior of natural and engineered intein proteins as summarized above. This aspect can be useful to facilitate the isolation and characterization of the macrocyclic peptide from a complex mixture such as, for example, the lysate of a cell expressing the precursor polypeptide or a cell-free translation system. This aspect can also be useful to facilitate the accumulation, and if desired, control the formation of a target macrocyclic peptide, prepared according the methods described herein, inside a cell-based expression host. In turn, this capability can facilitate the functional screening of in vivo (i.e., in-cell) produced macrocyclic peptide libraries, prepared according the methods disclosed herein, using an intracellular reporter system or a selection system as described above. These aspects are illustrated by Examples 4-8.

Nucleotide sequences encoding for intein proteins that can be used can be derived from naturally occurring inteins and engineered variants thereof. A rather comprehensive list of such inteins is provided by the Intein Registry (neb.com/neb/inteins.html). Inteins that can be used include, but are not limited to, any of the naturally occurring inteins from organisms belonging to the Eucarya, Eubacteria, and Archea. Among these, for example, inteins of the GyrA group (e.g., Mxe GyrA, Mfl GyrA, Mgo GyrA, Mkas GyrA, Mle-TN GyrA, Mma GyrA), DnaB group (e.g., Ssp DnaB, Mtu-CDC1551 DnaB, Mtu-H37Rv DnaB, Rma DnaB), RecA group (e.g., Mtu-H37Rv RecA, Mtu-So93 RecA), RIR1 group (e.g., Mth RIR1, Chy RIR1, Pfu RIR1-2, Ter RIR1-2, Pab RIR1-3), and Vma group (e.g., Sce Vma, Ctr Vma), intein Mxe GyrA (SEQ ID NO:1) and the engineered 'mini Ssp DnaB ('eDnaB', SEQ ID NO:2) can be used.

Intein proteins suitable in the methods described herein include, but are not limited to, engineered variants of natural inteins (or genetic fusion of split inteins), which have been modified by mutagenesis in order, for example, to prevent or minimize splicing at the N-terminal or C-terminal end of the intein. Examples of these modifications include, but are not limited to, mutation of the conserved cysteine or serine residue at the N-terminus of the intein (e.g., via substitution to an alanine) with the purpose, for example, of preventing cleavage at the N-terminus of the intein. Examples of these modifications include, but are not limited to, mutation of the conserved asparagine residue at the C-terminus of the intein (e.g., via substitution to an alanine) with the purpose, for example, of preventing cleavage at the C-terminus of the C-terminus of the intein. Examples of these modifications are provided in Example 2. Intein variants useful for the methods disclosed herein also include, but are not limited to, engineered inteins whose internal endonuclease domain, which is not essential for the splicing mechanism, is removed. For example, a variant of Ssp DnaB ('eDnaB', SEQ ID NO:2) lacking the internal endonuclease domain is used for the preparation of the precursor polypeptides. Inteins to be comprised in the precursor polypeptide can also be engineered with the purpose, for example, of altering the splicing properties of the intein in order to increase or reduce the splicing efficiency or in order to make the intein-catalyzed splicing process dependent upon variation of certain parameters such as pH or temperature.

Accordingly, in some embodiments, the N-terminal tail, $(AA)_m$, the C-terminal tail, $(AA)_p$, or both, in the precursor polypeptides of formula (I), (II), and (V) comprise an intein protein, or an engineered variant thereof. In some embodiments, the N-terminal tail, $(AA)_m$, the C-terminal tail, $(AA)_p$, or both, in the precursor polypeptides of formula (I), (II), and (V) comprise an intein protein selected from the group consisting of Mxe GyrA (SEQ ID NO:1), eDnaB (SEQ ID NO:2), Hsp-NRC1 CDC21 (SEQ ID NO:3), Ceu ClpP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FGSCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8 (SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:46), Ter RIR1-1 (SEQ ID NO:47), Pab RIR1-1 (SEQ ID NO:48), Pfu RIR1-1 (SEQ ID NO:49), Chy RIR1 (SEQ ID NO:50), Mth RIR1 (SEQ ID NO:51), Pab RIR1-3 (SEQ ID NO:52), Pfu RIR1-2 (SEQ ID NO:53), Ter RIR1-2 (SEQ ID NO:54), Ter RIR1-4 (SEQ ID NO:55), CIV RIR1 (SEQ ID NO:56), Ctr VMA (SEQ ID NO:57), Sce VMA (SEQ ID NO:58), Tac-ATCC25905 VMA (SEQ ID NO:59), Ssp DnaB (SEQ ID NO:60), engineered variants thereof, and engineered variants thereof wherein the N-terminal cysteine or serine residue of the engineered variant is mutated to any of the natural amino acid residues other than cysteine or serine, or wherein the C-terminal asparagine residue of the engineered variant is mutated to any of the natural amino acid residues other than asparagine.

In some embodiments, the N-terminal tail, $(AA)_m$, the C-terminal tail, $(AA)_p$, or both, in the precursor polypeptides of formula (I), (II), and (V) comprise the N-domain, C-domain, or both the N-domain and C-domain of a split intein, or an engineered variant thereof. In some embodiments, the N-terminal tail, $(AA)_m$, the C-terminal tail, $(AA)_p$, or both, in the precursor polypeptides of formula (I), (II), and (V) comprise the N-domain, C-domain, or both the N-domain and C-domain of a split intein selected from the group consisting of Ssp DnaE (SEQ ID NO:61-SEQ ID NO:62), Neq Pol (SEQ ID NO:63-SEQ ID NO:64), Asp DnaE (SEQ ID NO:65-SEQ ID NO:66), Npu-PCC73102 DnaE (SEQ ID NO:67-SEQ ID NO:68), Nsp-PCC7120 DnaE (SEQ ID NO:69-SEQ ID NO:70), Oli DnaE (SEQ ID NO:71-SEQ ID NO:72), Ssp-PCC7002 DnaE (SEQ ID NO:73-SEQ ID NO:74), Tvu DnaE (SEQ ID NO:75-SEQ ID NO:76), engineered variants thereof, and engineered variants wherein the N-terminal cysteine or serine residue of the split intein N-domain of the engineered variant is mutated to any of the natural amino acid residues other than cysteine or serine, or wherein the C-terminal asparagine residue of the split intein C-domain of the engineered variant is mutated to any of the natural amino acid residues other than asparagine.

In some embodiments, the N-terminal tail, $(AA)_m$, in the precursor polypeptides of formula (I), (II), and (V) comprises the C-domain of a split intein and the C-terminal tail, $(AA)_p$, of said precursor polypeptides comprises the corresponding N-domain of the split intein. In some embodiments, the N-terminal tail, $(AA)_m$, in the precursor polypeptides of formula (I), (II), and (V) comprises the C-domain of a split intein selected from the group consisting of Ssp DnaE-c (SEQ ID NO:62), Neq Pol-c (SEQ ID NO:64), Asp DnaE-c (SEQ ID NO:66), Npu-PCC73102 DnaE-c (SEQ ID NO:68), Nsp-PCC7120 DnaE-c (SEQ ID NO:70), Oli DnaE-c (SEQ ID NO:72), Ssp-PCC7002 DnaE-c (SEQ ID NO:74), Tvu DnaE-c (SEQ ID NO:76), and engineered variants thereof; and the C-terminal tail, $(AA)_p$, comprises the corresponding N-domain of the split intein selected from the group consisting of Ssp DnaE-n (SEQ ID NO:61), Neq Pol-n (SEQ ID NO:63), Asp DnaE-n (SEQ ID NO:65), Npu-PCC73102 DnaE-n (SEQ ID NO:67), Nsp-PCC7120 DnaE-n (SEQ ID NO:69), Oli DnaE-n (SEQ ID NO:71), Ssp-PCC7002 DnaE-n (SEQ ID NO:73), Tvu DnaE-n (SEQ ID NO:75), and engineered variants thereof.

5.3 Polynucleotides and Host Cells for Expression of Precursor Polypeptides

In another aspect, polynucleotide molecules are provided encoding for precursor polypeptides of formula (I), (II), and (V) as defined above. Polynucleotide molecules are provided for encoding for the aminoacyl-tRNA synthetases and cognate tRNA molecules for the ribosomal incorporation of the amino acid Z into the precursor polypeptides of formula (I) and (II) and for the ribosomal incorporation of the amino acid Z2 into the precursor polypeptides of formula (V). Polynucleotide molecules are provided encoding for polypeptide sequences that can be introduced within the N-terminal tail ($(AA)_m$) or C-terminal tail ($(AA)_p$) of the precursor polypeptides of formula (I), (II) and (V), such as peptide and protein affinity tags, reporter proteins and enzymes, carrier proteins of a display system, and intein proteins, as described above. Since the correspondence of all the possible three-base codons to the various amino acids is known, providing the amino acid sequence of the polypeptide provides also a description of all the polynucleotide molecules encoding for such polypeptide. Thus, a person skilled in the art will be able, given a certain polypeptide sequence, to generate any number of different polynucleotides encoding for the same polypeptide. In some embodiments, the codons are selected to fit the host cell in which the polypeptide is being expressed. For example, codons used in bacteria can be used to express the polypeptide in a bacterial host. The polynucleotides may be linked to one or more regulatory sequences controlling the expression of the polypeptide-encoding gene to form a recombinant polynucleotide capable of expressing the polypeptide.

Numerous methods for making nucleic acids encoding for polypeptides having a predetermined or randomized sequence are known to those skilled in the art. For example, oligonucleotide primers having a predetermined or randomized sequence can be prepared chemically by solid phase synthesis using commercially available equipments and reagents. Polynucleotide molecules can then be synthesized and amplified using a polymerase chain reaction, digested via endonucleases, ligated together, and cloned into a vector according to standard molecular biology protocols known in the art (e.g., Sambrook et al. *Molecular Cloning: A Laboratory Manual* (Third Edition), Cold Spring Harbor Press, 2001). These methods, in combination with the mutagenesis methods mentioned above, can be used to generate polynucleotide molecules that encode for the aforementioned polypeptides as well as suitable vectors for the expression of these polypeptides in a host expression system.

The precursor polypeptides can be produced by introducing said polynucleotides into an expression vector, by introducing the resulting vectors into an expression host, and by inducing the expression of the encoded precursor polypeptides in the presence of the amino acid Z (or Z2) and, whenever necessary, also in the presence of a suitable stop codon or frameshift codon suppression system for mediating the incorporation of the amino acid Z (or Z2) into the precursor polypeptides.

Nucleic acid molecules can be incorporated into any one of a variety of expression vectors suitable for expressing a polypeptide. Suitable vectors include, but are not limited to, chromosomal, nonchromosomal, artificial and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated viruses, retroviruses and many others. Any vector that transduces genetic material into a cell, and, if replication is desired, which is replicable and viable in the relevant host can be used. A large number of expression vectors and expression hosts are known in the art, and many of these are commercially available. A person skilled in the art will be able to select suitable expression vectors for a particular application, e.g., the type of expression host (e.g., in vitro systems, prokaryotic cells such as bacterial cells, and eukaryotic cells such as yeast, insect, or mammalian cells) and the expression conditions selected.

Expression hosts that may be used for the preparation of the precursor polypeptides and macrocyclic peptides include, but are not limited to, any systems that support the transcription, translation, and/or replication of a nucleic acid. In some embodiments, the expression host system is a cell. Host cells for use in expressing the polypeptides encoded by the expression vector of this disclosure are well known in the art and include, but are not limited to, bacterial cells (e.g., *Escherichia coli, Streptomyces*); fungal cells such as yeast cells (e.g., *Saccharomyces cerevisiae, Pichia pastoris*); insect cells; plant cells; and animal cells, such as mammalian cells and human cells. These systems also include, but are not limited to, lysates of prokaryotic cells (e.g., bacterial cells) and lysates of eukaryotic cells (e.g., yeast, insect, or mammalian cells). These systems also include, but are not limited to, in vitro transcription/translation systems, many of which are commercially available. The choice of the expression vector and host system depends on the type of application intended for the methods disclosed herein and a person skilled in the art will be able to select a suitable expression host based on known features and application of the different expression hosts. As an example, when it is desired to evaluate the interaction between the macrocyclic peptide(s) generated via the methods disclosed herein with a bacterial, yeast, or a human cell component, a bacterial, yeast, or a human expression host, respectively, can be used. In some embodiments, the expression host system is a cell.

In some embodiments, the formation of the macrocyclic peptides from the biosynthetic polypeptides as defined above is carried out within the cell-based expression host that produces the precursor polypeptides, so that the macrocyclic peptides are produced within this cell-based expression host. This method comprises providing a nucleic acid encoding for the precursor polypeptide, introducing the nucleic acid into the cell-based expression host, inducing the expression of the precursor polypeptide, allowing for the precursor polypeptide to undergo intramolecular cyclization via a bond-forming reaction between the side-chain sulfhydryl group of the cysteine and the $FG_1$ group of the amino acid Z (or between the cysteines and the $FG_1$ and $FG_2$ groups of the amino acid Z2), thereby producing the macrocyclic peptide inside the cell-based expression host. These aspects are illustrated in Examples 4 through 8.

In some embodiments, the formation of the macrocyclic peptides from the biosynthetic polypeptides as defined above is carried out on the surface of a cell or on a viral particle, so that the macrocyclic peptides are produced as tethered to a cell or a viral particle, respectively. This method comprises providing a nucleic acid encoding for the precursor polypeptide, wherein the N- or C-terminal tail comprises a polypeptide component of the cell membrane (e.g., *S. cerevisiae* membrane protein Aga2p) or of the viral particle (e.g., M13 phage pIII protein), introducing the nucleic acid into the expression host, inducing the expression of the precursor polypeptide, allowing for the precursor polypeptide to be integrated into the cell membrane or viral particle, and allowing for the precursor polypeptide to undergo intramolecular cyclization via a bond-forming reaction between the side-chain sulfhydryl group of the cysteine and the $FG_1$ group of the amino acid Z (or between the cysteines and the $FG_1$ and $FG_2$ groups of the amino acid Z2), thereby producing the macrocyclic peptide as tethered to the membrane of the cell or to the viral particle.

In some embodiments, the formation of the macrocyclic peptides from the biosynthetic polypeptides as defined above is carried out within a cell-free expression system, so that the macrocyclic peptides are produced within this cell-free expression system. This method comprises providing a nucleic acid encoding for the precursor polypeptide, introducing the nucleic acid into the cell-free expression host, inducing the expression of the precursor polypeptide, allowing for the precursor polypeptide to undergo intramolecular cyclization via a bond-forming reaction between the side-chain sulfhydryl group of the cysteine and the $FG_1$ group of the amino acid Z (or between the cysteines and the $FG_1$ and $FG_2$ groups of the amino acid Z2), thereby producing the macrocyclic peptide within the cell-free expression host.

A method is also provided for making a library of macrocyclic peptides via cyclization of a plurality of precursor polypeptides of formula (I) or (II) that contain an heterogeneous peptide target sequence $(AA)_n$, or an heterogeneous N-terminal tail $(AA)_m$, or an heterogeneous C-terminal tail $(AA)_p$, or a combination of these. This method comprises: (a) constructing a plurality of nucleic acid molecules encoding for a plurality of precursor polypeptides, said precursor polypeptides having an heterogeneous peptide target sequence $(AA)_n$, or an heterogeneous N-terminal tail $(AA)_m$, or an heterogeneous C-terminal tail $(AA)_p$, or a combination of these; (b) introducing each of the plurality of said nucleic acid molecules into an expression vector, and introducing the resulting vectors into an expression host; (c) expressing the plurality of precursor polypeptides; (d) allowing for the precursor polypeptides to undergo intramolecular cyclization via a bond-forming reaction between the side-chain sulfhydryl group of the cysteine and the $FG_1$ group of the amino acid Z, thereby producing a plurality of macrocyclic peptides.

A method is also provided for making a library of macrocyclic peptides via cyclization of a plurality of precursor polypeptides of formula (V) that contain an heterogeneous peptide target sequence $(AA)_n$, or an heterogeneous second peptide target sequence $(AA)_o$, or an heterogeneous N-terminal tail $(AA)_m$, or an heterogeneous C-terminal tail $(AA)_p$, or a combination of these. This method comprises: (a) constructing a plurality of nucleic acid molecules encoding for a plurality of precursor polypeptides, said precursor polypeptides having an heterogeneous peptide target sequence $(AA)_m$, or an heterogeneous second peptide target sequence $(AA)_o$, or an heterogeneous N-terminal tail $(AA)_m$, or an heterogeneous C-terminal tail $(AA)_p$, or a combination of these; (b) introducing each of the plurality of said nucleic acid molecules into an expression vector, and introducing the resulting vectors into an expression host; (c) expressing the plurality of precursor polypeptides; (d) allowing for the precursor polypeptides to undergo intramolecular cyclization via a bond-forming reaction between the side-chain sulfhydryl group of the cysteines and the $FG_1$ and $FG_2$ group2 of the amino acid Z2, thereby producing a plurality of macrocyclic peptides.

In specific embodiments, each of the plurality of macrocyclic peptides prepared as described above is tethered to a cell component, to a cell membrane component, to a bacteriophage, to a viral particle, or to a DNA molecule, via a polypeptide comprised within the N-terminal tail or within the C-terminal tail of said macrocyclic peptide molecule.

Several methods of making polynucleotides encoding for heterogeneous peptide sequences are known in the art. These include, among many others, methods for site-directed mutagenesis (Botstein, D.; Shortie, D. Science (New York, N.Y., 1985, 229, 1193; Smith, M. Annual review of genetics, 1985, 19, 423; Dale, S. J.; Felix, I. R. Methods in molecular biology (Clifton, N.J., 1996, 57, 55; Ling, M. M.; Robinson, B. H. Analytical biochemistry, 1997, 254, 157), oligonucleotide-directed mutagenesis (Zoller, M. J. Current opinion in biotechnology, 1992, 3, 348; Zoller, M. J.; Smith, M. Methods Enzymol, 1983, 100, 468; Zoller, M. J.; Smith, M. Methods Enzymol, 1987, 154, 329), mutagenesis by total gene synthesis and cassette mutagenesis (Nambiar, K. P.; Stackhouse, J.; Stauffer, D. M.; Kennedy, W. P.; Eldredge, J. K.; Benner, S. A. Science (New York, N.Y., 1984, 223, 1299; Grundstrom, T.; Zenke, W. M.; Wintzerith, M.; Matthes, H. W.; Staub, A.; Chambon, P. Nucleic acids research, 1985, 13, 3305; Wells, J. A.; Vasser, M.; Powers, D. B. Gene, 1985, 34, 315), and the like. Additional methods are described in the following U.S. patents, PCT publications, and EPO publications: U.S. Pat. No. 5,605,793 "Methods for In vitro Recombination", U.S. Pat. No. 5,830,721 "DNA Mutagenesis by Random Fragmentation and Reassembly", WO 95/22625 "Mutagenesis by Random Fragmentation and Reassembly", WO 96/33207 "End Complementary Polymerase Chain Reaction", EP 752008 "DNA Mutagenesis by Random Fragmentation and Reassembly", WO 98/27230 "Methods and Compositions for Polypeptide Engineering", WO 00/00632, "Methods for Generating Highly Diverse Libraries", WO 98/42832 "Recombination of Polynucleotide Sequences Using Random or Defined Primers", WO 99/29902 "Method for Creating Polynucleotide and Polypeptide Sequences". Any of these methods or modifications thereof can be utilized for generating nucleotide molecules that encode for precursor polypeptides of formula (I), (II), or (V) containing an heterogeneous peptide target sequence $(AA)_n$, an heterogeneous second peptide target sequence $(AA)_o$, an heterogeneous N-terminal tail $(AA)_m$, an heterogeneous C-terminal tail $(AA)_p$, or a combination of these.

The compounds provided herein may contain one or more chiral centers. Accordingly, the compounds are intended to include, but not be limited to, racemic mixtures, diastereomers, enantiomers, and mixture enriched in at least one stereoisomer or a plurality of stereoisomers. When a group of substituents is disclosed herein, all the individual members of that group and all subgroups, including any isomers, enantiomers, and diastereomers are intended to be included in the disclosure. Additionally, all isotopic forms of the compounds disclosed herein are intended to be included in the disclosure. For example, it is understood that any one or more hydrogens in a molecule disclosed herein can be replaced with deuterium or tritium.

The terms and expression that are employed herein are used as terms of description and not of limitation, and there is no intention that in the use of such terms and expressions of excluding any equivalents of the features shown and described and portions thereof, but it is recognized that various modifications are possible within the scope of the subject matter claimed herein. Thus, it should be understood that although various embodiments and optional features have been disclosed herein, modification and variation of the concepts herein disclosed may be resorted to those skilled in the art, and that such modifications and variations are considered to be encompassed by the appended claims.

Unless otherwise indicated, the disclosure is not limited to specific molecular structures, substituents, synthetic methods, reaction conditions, or the like, as such may vary. It is to be understood that the embodiments are not limited to particular compositions or biological systems, which can, of course, vary.

A skilled artisan will appreciate that starting materials, biological materials, reagents, synthetic methods, purification methods, analytical methods, assay methods, and biological methods other than those specifically exemplified can be employed in the practice of the methods and compositions disclosed herein. All art-known functional equivalents of any such materials and methods are intended to be included in the methods and compositions disclosed herein.

6. EXAMPLES

The following examples are offered by way of illustration and not by way of limitation.

6.1 Example 1: Synthesis of Cysteine-Reactive Unnatural Amino Acids

This example demonstrates the preparation of various cysteine-reactive unnatural amino acids, i.e., various Z and Z2 amino acids, which can be used for preparation of macrocyclic peptide molecules according to the general methods illustrated in FIGS. 1A-B, 2A-B, 3A-B, 4A-B, and 37A-B.

The unnatural amino acid 4-(2-bromoethoxy)-phenylalanine (1, p-2beF) was prepared according to the synthetic route provide in Scheme 1 of FIG. 5. The unnatural amino acid $N^{\varepsilon}$-((2-bromoethoxy)carbonyl)-lysine (2, 2-becK) was prepared according to the synthetic route provide in Scheme 2 of FIG. 5. The unnatural amino acid 4-(1-bromoethyl)-phenylalanine (3, p-1beF) was prepared according to the synthetic route provide in Scheme 3 of FIG. 5. The unnatural amino acid $N^{\varepsilon}$-((2-chloroethoxy)carbonyl)-lysine (4, 2-cecK) was prepared according to the synthetic route provide in Scheme 4 of FIG. 6. The unnatural amino acid $N^{\varepsilon}$-(buta-2,3-dienoyl)-lysine (5, bdnK) was prepared according to the synthetic route provide in Scheme 5 of FIG. 6. The bifunctional unnatural amino acid O-(2,3-dibromoethyl)-tyrosine (6, OdbpY) was prepared according to the synthetic route provide in Scheme 6 of FIG. 6. A person skilled in the art would readily recognize that many other cysteine-reactive amino acids of general formula (III), (IV), (VI), or (VII) can be prepared in an analogous manner either through modification of naturally occurring amino acids (e.g., p-2beF, 2-becK, 2-cecK, bdnK, ObdpY) or via synthesis ex novo (e.g., p-1beF).

Experimental Details

Synthesis of 4-(2-bromoethoxy)-phenylalanine (p-2beF) (1)

To a reaction flask containing N-tert-butoxycarbonyl-tyrosine (2 g, 7.1 mmol) and potassium carbonate (2.94 g, 21.3 mmol) in dry DMF (20 mL) dibromoethane (1.83 mL, 21.3 mmol) was added dropwise over 20 min. The reaction mixture was stirred at room temperature for 18 h after which the reaction mixture was filtered, diluted with 60 mL of water, acidified with acetic acid to pH 4 and extracted with 2×100 mL of EtOAc. Organic layers were combined and dried over sodium sulfate. The solvent was removed under reduced pressure yielding yellow oil as crude product which was purified by flash column chromatography using 10:9:1 hexane:EtOAc:HOAc acid as solvent system. Fractions of interest were combined and solvent removed under reduced pressure yielding N-Boc-4-(2-bromoethoxy)-phenylalanine as an off-white powder (2.3 g, 84%). $^1H$ NMR (400 MHz, $CD_3OD$) δ 1.39 (s, 9H), 2.8-3.05 (m, 2H), 3.3 (t, 2H), 3.51 (t, 2H), 4.37 (t, 2H), 6.69 (d, 2H), 7.02 (d, 2H); $^{13}C$ NMR (125 MHz, $CD_3OD$) δ 28.73, 29.49, 37.92, 56.82, 65.77, 80.69, 116.27, 128.84, 131.32, 157.39, 157.77, 173.414. MS (ESI) calculated for $C_{14}H_{19}NO_5$ $M^+$: Mk 387.07, found 387.17. Purified N-Boc-4-(2-bromoethoxy)-phenylalanine was treated with 20 mL of 30% TFA/DCM to remove the N-terminal protection. Upon completed reaction (determined by TLC), the solvent was removed under reduced pressure, crude residue dissolved 2× in 10 mL of HOAc followed by solvent evaporation yielding the final product 1 as an off-white solid in quantitative yield (1.7 g). $^1H$ NMR (400 MHz, $CD_3OD$) δ 3.05-3.25 (m, 2H), 3.58 (t, 2H), 4.28 (t, 1H), 4.51 (t, 2H), 6.77 (d, 2H), 7.09 (d, 2H); $^{13}C$ NMR (125 MHz, $CD_3OD$) δ 29.1, 36.9, 55.35, 66.92, 116.92, 125.54, 131.59, 158.41, 169.93. MS (ESI) calculated for $C_{11}H_{14}BrNO_3$ $[M+H]^+$: m/z 288.02, found 288.51.

Synthesis of $N^{\varepsilon}$-((2-bromoethoxy)carbonyl)-lysine (2becK) (2)

To a solution of $N^{\alpha}$-tert-butoxycarbonyl-lysine (1 g, 4.06 mmol) and NaOH (162.4 mg, 4.06 mmol, 1 eq) dissolved in 20 mL of water 2-bromoethylchloroformate (0.435 mL, 4.06 mmol, 1 eq) and, separately, an additional equivalent of NaOH were added simultaneously dropwise over 30 min. The reaction mixture was stirred at room temperature for 18 h. Upon acidification with HOAc, the aqueous phase was extracted with EtOAc (3×80 mL). The combined organic phases were dried over sodium sulfate, solvent was removed under reduced pressure yielding yellow oil as crude product which was purified by flash column chromatography using 10:9:1 hexane:EtOAc:HOAc as solvent system. Fractions of interest were combined and solvent removed under reduced pressure yielding N-Boc-$N^{\varepsilon}$-((2-bromoethoxy)carbonyl)-lysine as an off-white powder (1.1 g, 68%). $^{1}$H NMR (400 MHz, $CD_3OD$) δ 1.43 (s, 9H), 1.5 (m, 2H), 1.65 (m, 2H), 1.79 (m, 2H), 3.09 (t, 2H), 3.54 (t, 2H), 4.05 (t, 1H), 4.29 (t, 2H); $^{13}$C NMR (125 MHz, $CD_3OD$) δ 24.09, 28.78, 30.39, 30.47, 32.434, 41.44, 54.82, 65.51, 80.51, 158.15, 158.44, 176.24; MS (ESI) calculated for $C_{14}H_{19}NO_5$ $[M+H]^+$: m/z 397.1, found 397.47. Purified N-Boc-$N_{\zeta}$-((2-bromoethoxy)carbonyl)-lysine was treated with 20 mL of 30% TFA/DCM to remove the N-terminal protection. Upon completed reaction (determined by TLC), the solvent was removed under reduced pressure, crude residue dissolved 2× in 10 mL of acetic acid followed by solvent evaporation yielding the final product 2 as an off-white solid in quantitative yield (0.82 g). $^{1}$H NMR (400 MHz, $CD_3OD$) δ 1.45 (m, 2H), 1.64 (m, 2H), 1.76 (m, 2H), 2.95 (t, 2H), 3.6 (t, 2H), 3.85 (t, 1H), 4.22 (t, 2H); $^{13}$C NMR (100 MHz, $CD_3OD$) δ 20.74, 23.16, 30.36, 31.16, 41.21, 53.86, 65.54, 158.52, 175.21; MS (ESI) calculated for $C_{11}H_{14}BrNO_3$ $[M+H]^+$: m/z 297.04, found 297.7.

Synthesis of 4-(1-bromoethyl)-phenylalanine (p-1beF) (3)

Solution of 4-acetylphenylalanine (0.5 g, 2.415 mmol), prepared as reported previously (Frost, Vitali et al. 2013), in methanol was placed in an ice bath followed by addition of triethylamine (0.51 mL, 3.63 mmol, 1.5 eq) and dropwise addition of di-tert-butyl dicarbonate (0.665 mL, 2.9 mmol, 1.2 eq) over 30 min. The reaction was left at room temperature for additional 3 h after which the solvent was removed in vacuo. The residue was redissolved in EtOAc and extracted with acidified water (pH 4). Organic phase was dried over sodium sulfate, solvent removed under reduced pressure and the crude yellow oil purified using flash column chromatography with 10:9:1 hexane:EtOAc:HOAc as solvent system. Fractions of interest were combined yielding N-Boc-4-acetylphenylalanine as a yellow powder (0.665 g, 90%) which was dissolved in MeOH, placed in an ice bath and treated with $NaBH_4$ (0.164 g, 4.34 mmol, 2 eq) for 3 h. Following aqueous workup, the crude product was dissolved in DCM, placed in an ice bath and $PBr_3$ (1 M solution in DCM) was added in portions (5.2 mL, 5.2 mmol, 2.4 eq) over 2 h. The reaction was warmed to reach room temperature and left stirring overnight. After workup, the aqueous layer was lyophilized and used as crude product 3 (0.382 g, 65%). $^{1}$H NMR (400 MHz, $CD_3OD$) 1.99 (d, 3H), 2.8-3.2 (m, 2H), 4.31 (t, 1H), 4.78 (q, 1H), 7.18 (d, 2H), 7.27 (d, 2H); MS (ESI) calculated for $C_{11}H_{14}BrNO_2$ $[M+H]^+$: m/z 272.03, found 272.53.

Synthesis of $N^{\varepsilon}$-((2-chloroethoxy)carbonyl)-lysine (2-cecK) (4)

To a solution of $N^{\alpha}$-tert-butoxycarbonyl-lysine 1 (1 g, 4.06 mmol) and NaOH (162.4 mg, 4.06 mmol, 1 eq) dissolved in 20 mL of water 2-chloroethylchloroformate (0.419 mL, 4.06 mmol, 1 eq) and, separately, an additional equivalent of NaOH were added simultaneously dropwise over 30 min. The reaction mixture was stirred at room temperature for 10-12 h. Upon acidification with HOAc, the aqueous phase was extracted with EtOAc (3×80 mL). The combined organic phases were dried over sodium sulfate, solvent was removed under reduced pressure yielding yellow oil as crude product which was purified by flash column chromatography using 10:9:1 hexane:EtOAc:HOAc as solvent system. Fractions of interest were combined and solvent removed under reduced pressure yielding off-white powder as product (1.04 g, 75%). Purified product was treated with 20 mL of 30% TFA/DCM to remove the N-terminal Boc-protection. Upon completed reaction (determined by TLC), the solvent was removed under reduced pressure, yielding the final product 4 as off-white solid in quantitative yield (0.75 g). $^{1}$H NMR (400 MHz, $CD_3OD$) δ 1.45 (m, 2H), 1.64 (m, 2H), 1.76 (m, 2H), 2.95 (t, 2H), 3.6 (t, 2H), 3.85 (t, 1H), 4.22 (t, 2H).

Synthesis of $N^{\varepsilon}$-(buta-2,3-dienoyl)-lysine (bdnK) (5)

3-butynoic acid was prepared by oxidation of 3-butyn-1-ol. About 20 mL of water was added to a 150 mL single neck RBF followed by 65% $HNO_3$ (45 μL, 0.66 mmol, 0.05 eq), $Na_2Cr_2O_7$ (40 mg, 0.132 mmol, 0.01 eq) and $NaIO_4$ (6.22 g, 29 mmol, 2.2 eq) and stirred vigorously on an ice bath. After 15 min 1 mL of 3-butyn-1-ol (1 eq, 13.2 mmol) dissolved in 5 mL of cold water was added dropwise over 30 min The reaction was left stirring overnight followed by product extraction with diethyl ether. Solvent was evaporated to yield off-white/yellow solid (g, %). 1H NMR (400 MHz, CDCl3) δ 3.35 (d, 2H), 2.22 (t, 1H). 3-butynoic acid (0.436 g, 5.2 mmol, 1 eq) was dissolved in dry DCM and 1.5 eq of 2-chloro-1-methylpyridinium iodide was added (2.2 g). The reaction was stirred for 1 h at room temperature followed by dropwise addition of $N^{\alpha}$-tert-butoxycarbonyl-lysine (1.4 g, 5.72 mmol, 1.1 eq) and triethylamine (1.2 mL, 7.8 mmol, 1.5 eq). The reaction was monitored by TLC and upon completion (4-5 h) extracted with water. Organic layer was evaporated and the crude product was purified using flash column chromatography with 10:9:1 hexane:EtOAc:HOAc as solvent system. Fractions containing the desired product were pooled together and the solvent was removed under reduced pressure giving the desired product in 55% yield. $^{1}$H NMR (400 MHz, $CD_3OD$) δ 1.4 (s, 9H), 1.5 (m, 2H), 1.62 (m, 2H), 1.81 (m, 2H), 3.13 (t, 2H), 4.51 (m, 3H), 5.8 (m, 1H). The final Boc-deprotection was achieved using 20 mL of 30% TFA/DCM for 30 min followed by solvent removal resulting in product 5 (g). $^{1}$H NMR (400 MHz, $CD_3OD$) δ 1.48 (m, 2H), 1.63 (m, 2H), 1.82 (m, 2H), 3.12 (t, 2H), 4.21 (t, 1H), 4.51 (d, 2H), 5.8 (m, 1H).

Synthesis of O-(2,3-dibromoethyl)-tyrosine (OdbpY) (6)

To a reaction flask containing $N^{\alpha}$-tert-butoxycarbonyl-tyrosine (2 g, 7.1 mmol) and potassium carbonate (2.94 g, 21.3 mmol, 2 eq) in dry DMF (20 mL) 1,2,3-tribromopropane (0.915 mL, 7.82 mmol, 1.1 eq) was added dropwise over 20 min. The reaction mixture was stirred at room temperature for 8 h after which the reaction mixture was filtered, diluted with 60 mL of water, acidified with acetic acid to pH 4 and extracted with 2×100 mL of EtOAc. Organic layers were combined and dried over sodium sulfate. The solvent was removed under reduced pressure yielding yellow oil as crude product which was purified by flash column chromatography using 10:9:1 hexane:EtOAc: HOAc acid as solvent system. Fractions of interest were combined and solvent removed under reduced pressure yielding off-white powder as product (g, %). $^1$H NMR (400 MHz, $CD_3OD$) δ 1.41 (s, 9H), 2.81-3.07 (m, 2H), 3.6-3.81 (m, 2H), 4.21-4.43 (m, 3H), 4.61-4.72 (m, 1H), 6.71 (d, 2H), 7.04 (d, 2H). Purified product was treated with 20 mL of 30% TFA/DCM to remove the N-terminal protection. Upon completed reaction (determined by TLC), the solvent was removed under reduced pressure yielding the final product 6 as an off-white solid in quantitative yield (g). $^1$H NMR (400 MHz, $CD_3OD$) δ 2.81-3.07 (m, 2H), 3.6-3.81 (m, 2H), 4.12 (t, 1H), 4.21-4.43 (m, 2H), 4.61-4.72 (m, 1H), 6.71 (d, 2H), 7.04 (d, 2H).

6.2 Example 2: Polynucleotides for Expression of Precursor Polypeptides

This example demonstrates procedures for the construction of polynucleotide molecules for the expression of precursor polypeptides of the type (I), (II), or (V) according to the methods described herein.

To illustrate the various embodiments, a series of a plasmid-based vectors were prepared that encode for precursor polypeptides in different formats (Table 1) according to the macrocyclization methods schematically described in FIGS. 1A-B, 2A-B, 3A-B, 4A-B and 37A-B. Specifically, a first series of constructs (Entries 1-9 and 13-15, Table 1) were prepared for the expression of precursor polypeptides of general formula (I), in which (i) the N-terminal tail, $(AA)_m$, consists of a Met-Gly dipeptide; (ii) the target peptide sequence, $(AA)_n$, consists of 1- to 12-amino acid long polypeptides, some of which were designed to include a streptavidin-binding HPQ motif (Katz 1995; Naumann, Savinov et al. 2005) (Entries 13-15, Table 1); and (iii) the C-terminal tail, $(AA)_p$, consists of a short (1 to 8 amino acid-long) polypeptide sequence C-terminally fused to Mxe GyrA intein (SEQ ID NO:1). In these constructs, an amber stop codon was used to enable the introduction of the desired, cysteine-reactive unnatural amino acid Z, upstream of the peptide target sequence via amber stop codon suppression. Moreover, the C-terminal asparagine of Mxe GyrA intein was mutated to an alanine (N198A) to prevent C-terminal splicing and allow for the introduction of a polyhistidine affinity tag at the C-terminus of the polypeptide construct. These constructs were designed to demonstrate the general methods described in FIGS. 1A and 2A.

A second series of constructs (Entries 10-12, Table 1) were prepared for the expression of precursor polypeptides of general formula (II), in which (i) the N-terminal tail, $(AA)_m$, consists of a short (2 to 6 amino acid-long) polypeptide; (ii) the target peptide sequence, $(AA)_n$, consists of a 3 to 7-amino acid long polypeptide; and (iii) the C-terminal tail, $(AA)_p$, consists of the N198A variant of Mxe GyrA intein (SEQ ID NO:1) followed by a polyhistidine tag. In these constructs, an amber stop codon was used to enable the introduction of the desired, cysteine-reactive unnatural amino acid Z, downstream of the peptide target sequence via amber stop codon suppression. These constructs were designed to probe the functionality of the general methods described in FIGS. 1B and 2B.

A third series of constructs (Entries 16-20, Table 1) were prepared for the expression of precursor polypeptides of general formula (I), in which (i) the N-terminal tail, $(AA)_m$, contains the C-domain of *Synechocystis* sp. DnaE split intein (SEQ ID NO:62); (ii) the C-terminal tail, $(AA)_p$, contains the N-domain of *Synechocystis* sp. DnaE split intein (SEQ ID NO:61); and (iii) a streptavidin-binding HPQ motif (Naumann, Savinov et al. 2005) is included within (Entry 18-20, Table 1) or downstream of the target peptide sequence $(AA)_n$ (Entries 16-17, Table 1). In these constructs, an amber stop codon was used to enable the introduction of the desired, cysteine-reactive unnatural amino acid Z, upstream of the peptide target sequence. Furthermore, these constructs contain a CBD (cellulose binding domain) affinity tag fused to the C-terminal end of the split intein N-domain. These constructs were designed to probe the functionality of the general methods described in FIGS. 4A-B.

An additional construct (Entry 21, Table 1) was prepared for the expression of a precursor polypeptide which carries two Cys/Z pairs comprising two different target peptide sequences (HPQF (SEQ ID NO:185) and NTSK (SEQ ID NO:186)) and being separated from each other by an intervening polypeptide sequence (ENLYFQS (SEQ ID NO:187)). This construct is instrumental for demonstrating the possibility to generate polycyclic peptides using the methods disclosed herein.

Finally, a construct (Entry 22, Table 1) was prepared for the expression of a precursor polypeptide which carries a bifunctional cysteine-reactive amino acid (Z2) and two cysteine residues. This construct is instrumental for demonstrating the possibility to generate polycyclic peptides according to the general methods described in FIGS. 37A-B.

TABLE 1

Precursor polypeptide constructs.[a]

| Entry | Construct Name | Peptide Sequence |
|---|---|---|
| 1 | 12 mer-Z1C | MG-(Z)-CGSICLAEYGT-($GyrA_{N198A}$)LEHHHHHH (SEQ ID NO: 159) |
| 2 | 12 mer-Z2C | MG-(Z)-TCSKLAEYGT-($GyrA_{N198A}$)LEHHHHHH (SEQ ID NO: 160) |
| 3 | 12 mer-Z3C | MG-(Z)-TGCKLAEYGT-($GyrA_{N198A}$)LEHHHHHH (SEQ ID NO: 161) |
| 4 | 12 mer-Z4C | MG-(Z)-TGSCLAEYGT-($GyrA_{N198A}$)-LEHHHHHH (SEQ ID NO: 162) |
| 5 | 12 mer-Z5C | MG-(Z)-TGSKCAEYGT-($GyrA_{N198A}$)LEHHHHHH (SEQ ID NO: 163) |

TABLE 1 -continued

Precursor polypeptide constructs.[a]

| Entry | Construct Name | Peptide Sequence |
|---|---|---|
| 6 | 12 mer-Z6C | MG-**(Z)**-TGSKL**C**EYGT-($GyrA_{N198A}$) LEHHHHHH (SEQ ID NO: 164) |
| 7 | 12 mer-Z8C | MG-**(Z)**-TGSKLAE**C**GT-($GyrA_{N198A}$) LEHHHHHH (SEQ ID NO: 165) |
| 8 | 14 mer-Z10C | MG-**(Z)**-TGSKYLNAE**C**GT-($GyrA_{N198A}$) LEHHHHHH (SEQ ID NO: 166) |
| 9 | 16 mer-Z12C | MG-**(Z)**-TGSHKYLRNAE**C**GT-($GyrA_{N198A}$) LEHHHHHH (SEQ ID NO: 167) |
| 10 | 10 mer-C4Z | MGSEAG**C**NIA-**(Z)**-($GyrA_{N198A}$) LEHHHHHH (SEQ ID NO: 168; SEQ ID NO: 169) |
| 11 | 10 mer-C6Z | MGSE**C**GTNIA-**(Z)**-($GyrA_{N198A}$) LEHHHHHH (SEQ ID NO: 170; SEQ ID NO: 169) |
| 12 | 10 mer-C8Z | MG**C**EAGTNIA-**(Z)**-($GyrA_{N198A}$) LEHHHHHH (SEQ ID NO: 171; SEQ ID NO: 169) |
| 13 | Strep1-Z5C | MG-**(Z)**-HPQF**C**GD-($GyrA_{N198A}$) LEHHHHHH (SEQ ID NO: 172) |
| 14 | Strep2-Z7C | MG-**(Z)**-HPQGPP**C**GD-($GyrA_{N198A}$) LEHHHHHH (SEQ ID NO: 173) |
| 15 | Strep3-Z11C | MG-**(Z)**-FTNVHPQFAN**C**D-($GyrA_{N198A}$) LEHHHHHH (SEQ ID NO: 174) |
| 16 | cStrep3(C)-Z3C | ($DnaE_C$)-C-**(Z)**-TN**C**HNFANA-($DnaE_N$)-(CBD) (SEQ ID NO: 175; SEQ ID NO: 176) |
| 17 | cStrep3(S)-Z3C | ($DnaE_C$)-S-**(Z)**-TN**C**HPQFANA-($DnaE_N$)-(CBD) (SEQ ID NO: 177; SEQ ID NO: 178) |
| 18 | cStrep3(C)-Z8C | ($DnaE_C$)-C-**(Z)**-TNVHPQF**C**NA-($DnaE_N$)-(CBD) (SEQ ID NO: 175; SEQ ID NO: 179) |
| 19 | cStrep4(S)-Z8C | ($DnaE_C$)-S-**(Z)**-TNVHPQF**C**NAKGDA-($DnaE_N$)-(CBD) (SEQ ID NO: 177; SEQ ID NO: 180) |
| 20 | cStrep5(S)-Z8C | ($DnaE_C$)-S-**(Z)**-TNVIIPQF**C**NAKGDTQA-($DnaE_N$)-(CBD) (SEQ ID NO: 177; SEQ ID NO: 181) |
| 21 | Strep6_ZAC7C4Z | MG-**(Z)**-HPQF**C**ENLYFQS**C**NTSK-**(Z)**-($GYrA_{N198A}$) LEHHHHHH (SEQ ID NO: 182; SEQ ID NO: 169) |
| 22 | Strep7_C5Z4C | MG**C**AYDSG-**(Z2)**-HPQF**C**GT-($GyrA_{N198A}$) LEHHHHHH (SEQ ID NO: 183; SEQ ID NO: 184) |

[a]$GYrA_{N190A}$ corresponds to the N190A variant of *Mycobacterium xenopi* GyrA (SEQ. ID NO: 1), CBD corresponds to the Chitin Binding Domain (CBD) of *Bacillus circulans* chitinase A1 (SEQ of ID NO: 130), $DnaE_N$ and $DnaE_C$ correspond to the N-domain and C-domain, respectively, *Synechocystis* sp. DnaE split intein (SEQ ID NOS: 61 and 62). The reactive amino acid residues are involved in peptide macrocyclization (i.e., Cys and Z residues; Cys and Z2 residues) are highlighted in bold.

Experimental Details

Cloning and plasmid construction. The plasmid vector pET22b(+) (Novagen) was used as cloning vector to prepare the plasmids for the expression of the precursor polypeptides of Entries 1-15 and 21-22 in Table 1. Briefly, synthetic oligonucleotides (Integrated DNA Technologies) were used for the PCR amplification of a gene encoding for N-terminal peptide and peptide target sequence fused to $GyrA_{N198A}$ intein using a previously described GyrA-containing vector (pBP_MG6) (Smith, Vitali et al. 2011) as template. The resulting PCR product (ca. 0.6 Kbp) was digested with Nde I and Xho I and cloned into pET22b(+) to provide the plasmids for the expression of the precursor polypeptides of Entries 1-15 and 21-22 in Table 1. The cloning process placed the polypeptide-encoding gene under the control of an IPTG-inducible T7 promoter and introduced a poly-histidine tag at the C-terminus of the intein. Plasmids for the expression of the polypeptide constructs of Entries 16 through 20 of Table 1 were prepared in a similar manner but using pBAD plasmid (Life Technologies) as the cloning and expression vector. The genes encoding for $DnaE_N$ and $DnaE_c$ were amplified from Addgene plasmids pSFBAD09 and pJJDuet30. The sequences of the plasmid constructs were confirmed by DNA sequencing.

6.3 Example 3: Identification of tRNA/Aminoacyl-tRNA Synthetase Pairs for Incorporation of Cysteine-Reactive Amino Acids This example illustrates how a suitable tRNA/aminoacyl-tRNA synthetase pair can be identified for the purpose of incorporating a desired cysteine-reactive, unnatural amino acid into a precursor polypeptide of general formula (I), (II), or (V) according to the methods disclosed herein. In particular, this example describes the identification of tRNA/aminoacyl-tRNA synthetase pairs for the incorporation of the unnatural amino acid 4-(2-bromoethoxy)-phenylalanine (p-2beF), $N^{\varepsilon}$-((2-bromoethoxy)carbonyl)-lysine (2becK), 4-(1-bromoethyl)-phenylalanine (p-1beF), $N^{\varepsilon}$-((2-chloroethoxy)carbonyl)-lysine (2cecK), $N^{\varepsilon}$-(buta-2,3-dienoyl)-lysine (bdnK), and O-(2,3-dibromoethyl)-tyrosine (OdbpY), which were synthesized as described in Example 1.

A high-throughput fluorescence-based screen was applied to identify viable tRNA/aminoacyl-tRNA synthetase (AARS) pairs for the ribosomal incorporation of the unnatural amino acid p-2beF, 2becK, p-1beF, 2cecK, bdnK, or OdbpY, in response to an amber stop codon. In this assay, *E. coli* cells are co-transformed with two plasmids with compatible origins of replications and selection markers; one plasmid directs the expression of the tRNA/AARS pair to be tested, whereas the second plasmid contains a gene encoding for a variant of Yellow Fluorescence Protein (YFP), in which an amber stop codon (TAG) is introduced at the second position of the polypeptide sequence following the initial Met residue (called YFP(TAG)). The ability of the tRNA/AARS pair to suppress the amber stop codon with the unnatural amino acid of interest can be thus determined and quantified based on the relative expression of YFP as determined by fluorescence. Using this assay, a panel of engineered aminoacyl-tRNA synthetase (AARS) variants derived from *M. jannaschii* tyrosyl-tRNA synthetase (SEQ ID NO:77), *M. barkeri* pyrrolysyl-tRNA synthetase (SEQ ID NO:79), or *M. mazei* pyrrolysyl-tRNA synthetase (SEQ ID NO:78) in combination with their cognate amber stop codon suppressor tRNA (i.e., $MjtRNA_{CUA}^{Tyr}$ (SEQ ID NO:101) for Mj AARSs and $Mm/MbtRNA_{CUA}^{Pyl}$ (SEQ ID NO:105) for the Mm and Mb AARSs) were tested for their ability to incorporate the target amino acids p-2beF, 2becK, p-1beF, 2cecK, bdnK, or OdbpY into the reporter YFP(TAG) protein. In a representative experiment, this panel of AARS enzymes included the known engineered AARSs Mj-pAcF-RS (SEQ ID NO:81), Mj-pAmF-RS (SEQ ID NO:87), Mb-CrtK-RS (SEQ ID NO:93), and Mm-pXF-RS (SEQ ID NO:91) (Young, Young et al. 2011)) as well as the newly engineered Mj-OpgY2-RS (SEQ ID NO:85). The latter, which is derived from Mj-OpgY-RS (SEQ ID NO:84) (Deiters and Schultz 2005), carries an Ala32G mutation that was designed to facilitate the recognition of 0-substituted tyrosine derivatives such as p-2beF and OdbpY based on the available crystal structure of the parent enzyme Mj-TyrRS (SEQ ID NO:77) (Kobayashi, Nureki et al. 2003). As illustrated by the representative data in FIGS. 7A-B, the AARS/tRNA pair consisting of Mj-pOgY2-RS/$MjtRNA_{CUA}^{Tyr}$ was found to enable the efficient incorporation of p-2beF (FIG. 7A), whereas the AARS/tRNA pair consisting of Mb-CrtK-RS/$Mm/MbtRNA_{CUA}^{Pyl}$ was found to enable the efficient incorporation of 2becK into the reporter YFP(TAG) protein (FIG. 7B). Control experiments with no unnatural amino acid added to the culture medium show no or negligible expression of the reporter YFP protein, evidencing the discriminating selectivity of these AARS/tRNA pairs for the desired unnatural amino acid over the pool of natural amino acids (this property is referred here as "orthogonal reactivity" or simply "orthogonality" of the AARS/tRNA).

Using an analogous procedure, it was established that the Mj-pAcF-RS/$MjtRNA_{CUA}^{Tyr}$ pair can enable efficient amber stop codon suppression with p-1beF; the Mb-CrtK-RS/Mm/$MbtRNA_{CUA}^{Pyl}$ pair can enable efficient amber stop codon suppression with 2cecK or bdnK; and the Mj-pOgY2-RS/$MjtRNA_{CUA}^{Tyr}$ pair can enable efficient amber stop codon suppression with OdbpY. These results provide an exemplary demonstration of viable procedures that can be used to identify suitable AARS/tRNA pairs for the ribosomal incorporation of cysteine-reactive unnatural amino acid into a polypeptide for the purpose of producing macrocyclic peptide according to methods disclosed herein and as illustrated in the following Examples.

Experimental Details

YFP expression assay. Competent BL21(DE3) *E. coli* were cotransformed with a pEVOL-based plasmid (Smith, Vitali et al. 2011) for the expression of the desired AARS/tRNA pair and a pET22-YFP(TAG) plasmid for the expression of the reporter YFP protein. After overnight growth at 37° C. in LB medium supplemented with chloramphenicol (25 μg/mL) and ampicillin (50 μg/mL), cell cultures were used to inoculate 96-well plates containing 0.9 mL of minimal (M9) media (25 μg/mL chloramphenicol, 50 μg/mL ampicillin, 1% glycerol) per well. At $OD_{600}$=0.6, protein expression was induced with 0.05% L-arabinose and 1 mM IPTG. Test wells were supplemented with the desired unnatural amino acid (e.g., 4-(2-bromoethoxy)-phenylalanine (p-2beF) at 2 to 5 mM, whereas no amino acid was added to the negative control wells. Cultures were grown overnight at 27° C. and then diluted 1:100 with phosphate buffer (50 mM KPi (pH 7.5), 150 mM NaCl) into microtiter plates. Fluorescence intensity was measured using a Tecan Infinite 1000 multi-well plate reader ($\lambda_{exc}$: 514 nm; $\lambda_{em}$: 527 nm).

6.4 Example 4: Preparation and Isolation of Macrocyclic Peptides from p-2beF-Containing Precursor Polypeptides of General Formula (I)

This example demonstrates the formation and isolation of macrocyclic peptides produced via the cyclization of ribosomally derived precursor polypeptides of general formula (I) and containing the cysteine-reactive unnatural amino acid p-2beF. In particular, this example demonstrates certain embodiments as schematically described in FIGS. 1A and 2A.

For these experiments, the precursor polypeptides corresponding to Entries 1 through 9 in Table 1 were expressed in BL21(DE3) *E. coli* cells containing a second, pEVOL-based plasmid for the co-expression of Mj-pOgY2-RS and $MjtRNA_{CUA}^{Tyr}$. As described in Example 3, this AARS/tRNA pair was established to allow for the efficient ribosomal incorporation of p-2beF into a polypeptide in response to an amber stop codon. According to our strategy (FIGS. 1A-B), these precursor polypeptides were expected to undergo cyclization via a nucleophilic substitution reaction between the cysteine side-chain thiol group and the p-2beF side-chain bromoalkyl group flanking the target peptide sequence after ribosomal synthesis of the precursor polypeptides in the expression system (*E. coli*) (FIG. 8). To establish the occurrence and efficiency of the cyclization, these proteins were isolated by Ni-affinity chromatography exploiting the C-terminal poly-histidine tag present in these constructs (Table 1). In all the aforementioned constructs, a Thr residue was placed at the site preceding the GyrA intein ("I-1 site"). This substitution minimizes premature hydrolysis of GyrA-fusion proteins during expression in *E. coli* (Frost, Vitali et al. 2013), thereby facilitating analysis of the target peptide sequences after chemically induced splicing of the intein from the purified proteins in vitro (FIG. 8, path A). This procedure would also permit the isolation of any product resulting from the unselective reaction of p-2beF with other nucleophiles in vivo (e.g., glutathione). Accordingly, after purification, the proteins were made react with benzyl mercaptan in order to release the desired macrocyclic peptide (in the form of C-terminal benzyl thioester or the corresponding C-terminal carboxylic acid after thioester hydrolysis) from the GyrA intein via thiol-induced splicing of the intein. The reaction mixtures were then analysed by LC-MS to detect and quantify the amount of the desired thioether-linked macrocyclic product as well as that of any uncyclized linear byproduct, as judged based on the peak areas in the corresponding extracted-ion chromatograms (FIGS. 10A-C, 11A-C, 12A-C, 13A-C, 14A-C and 15A-C). Uncyclized byproducts would appear as unmodified linear peptides or as linear adducts where the bromoalkyl group in p-2beF has undergone nucleophilic substitution with the benzyl mercaptan reagent during the in vitro reaction or with glutathione in vivo.

As summarized in FIG. 9A, these studies revealed that peptide macrocyclization had occurred with very high efficiency (80-95%) across the constructs with Cys and p-2beF being separated by two to eight residues (i.e., Cys at Z+2 to Z+8). Increasing this distance (i.e., with Cys at Z+10 and Z+12, Entries 8-9 in Table 1) resulted in a decrease of the cyclic product (50-20%, FIG. 9A). Interestingly, cyclization could also be achieved also when the Cys was located immediately adjacent to the unnatural amino acid (Entry 1, Table 1), albeit at a lower extent (5%) as compared to the other constructs. This result can be rationalized based on the comparatively less favorable 14-membered macrocycle formed when the p-2beF/Cys pair are in a i/i+1 relationship. For each construct tested, the identity of the macrocyclic product could be further confirmed by analysis of the corresponding MS/MS fragmentation spectrum as illustrated in FIGS. 16A-B.

GyrA intein contains a Cys at its N-terminal end which is crucial for mediating protein splicing in the context of the application of the present methods for producing peptide macrocycles inside the cells (see Example 5). Since this residue is partially buried within the active site (Klabunde, Sharma et al. 1998), we did not expect it to readily react with p-2beF side chain. Notably, quantitative splicing of the GyrA moiety upon treatment of all the aforementioned contructs with benzyl mercaptan indicated that no reaction occurred between p-2beF and the catalytic Cys at the intein I+1 site (see representative results in FIGS. 17*a-d*). Furthermore, no adducts or dimers were observed for any of the constructs described above, including those undergoing only partial cyclization (i.e., Entries 8-9, FIG. 9A). Altogether, these results further highlight the high chemo- and regioselectivity of the macrocyclization reaction.

Experimental Details

Protein Expression and Purification.

The protein constructs were expressed using BL21(DE3) *E. coli* cells co-transformed with a pET22-based vector for the expression of the precursor polypeptide and a pEVOL-based vector for the expression of the Mj-pOgY2-RS/MjtRNA$_{CUA}^{Tyr}$ pair. Cultures of these cells were grown overnight in LB media (50 mg/L ampicillin; 25 mg/L chloramphenicol) and used to inoculate 0.2 L of minimal (M9) media containing the same concentration of antibiotics, 1% glycerol, and 1 mM p-2BeF. At $OD_{600}$=0.6, IPTG (1 mM) and L-arabinose (0.05%) was added to the culture media to induce protein expression. Cultures were grown for 14 h at 27° C. and then harvested by centrifugation. Cell pellets were resuspended in 50 mM Tris, 300 mM NaCl, 20 mM imidazole buffer (pH 7.5) and cells were lysed by sonication. The cell lysate was loaded on a Ni-NTA affinity column and proteins were eluted with 50 mM Tris, 150 mM NaCl, 300 mM imidazole buffer (pH 7.5). Fractions were combined and concentrated followed by buffer exchange with potassium phosphate buffer (50 mM, 150 mM NaCl, pH 7.5). The identity of the isolated proteins was confirmed using MALDI-TOF MS and LC-MS.

Intein Splicing and MS Analysis.

Aliquots of the purified proteins (200 μM) were incubated with 15 mM benzylmercaptan, 20 mM TCEP in 50 mM phosphate buffer (pH 8). The identity of the target macrocycles was confirmed using MALDI-TOF MS and LC-MS analysis. LC-MS analyses were performed on Thermo Scientific LTQ Velos ESI/ion-trap mass spectrometer coupled to an Accela U-HPLC. Macrocycles were analyzed using Thermo Scientific HyPurity C4 column (particle size 5 μm, 100×2.1 mm i.d.) and a linear gradient 5% to 95% ACN (with 0.1% formic acid) in water (with 0.1% formic acid) over 9 mM. MALDI-TOF spectra were acquired on the Bruker Autoflex III mass spectrometer.

6.5 Example 5: In Vivo Production of Macrocyclic Peptides from p-2beF-Containing Precursor Polypeptides of General Formula (I)

This example further demonstrates the formation and isolation of macrocyclic peptides produced via the cyclization of ribosomally derived precursor polypeptides of general formula (I) and containing the cysteine-reactive unnatural amino acid p-2beF. In particular, this example provides a demonstration of the functionality of the methods described herein for the production of macrocyclic peptide within living bacterial cells.

For these studies, the constructs corresponding to Entries 13 through 15 of Table 1 were utilized. The corresponding precursor polypeptides were expressed in BL21(DE3) *E. coli* cells in the presence of the Mj-pOgY2-RS/MjtRNA$_{CUA}^{Tyr}$ to achieve the site-selective incorporation of the unnatural amino acid p-2beF into these proteins via amber stop codon suppression. These constructs were designed to contain an Asp residue in the position preceding the GyrA intein moiety in order to favor premature N-terminal splicing of this intein during expression (FIG. 8). We previously established that certain amino acid substitutions at the level of the I-1 site, and in particular Asp and Lys, can strongly promote premature splicing of GyrA intein during recombinant expression (Frost, Vitali et al. 2013). This effect is likely due to the ability of these residues to favor hydrolysis of the intein-catalyzed thioester linkage through their nucleophilic side-chain groups. This reactivity is leveraged here for mediating the spontaneous release of the macrocyclic peptide from the precursor protein after ribosomal expression as outlined in FIG. 8 (path B). Thus, according to our strategy (FIGS. 1A and 2A), these precursor polypeptides were expected to result in the formation of macrocyclic peptides inside the living cell expression host (*E. coli*) via the intramolecular, thioether bond-forming reaction between the cysteine and p-2beF residue, followed by release of the cyclic peptide via spontaneous N-terminal splicing of the intein moiety. These constructs were also designed to contain a streptavidin-binding motif (HPQ) within the sequence of the resulting macrocyclic peptides (Table 1) in order to allow for the isolation of these peptides via streptavidin-affinity capturing directly from bacterial lysates. Accordingly, *E. coli* cells expressing these precursor polypeptides were grown overnight and lysed by sonication. The cell lysates were then passed over streptavidin-coated beads, from which streptavidin-bound material was eluted. LC-MS analysis of the eluates revealed the occurrence of the expected peptide macrocycle in each case, as illustrated by the LCMS chromatograms and MS/MS spectra in FIGS. 25A-C, 26A-C, and 27A-C. Since the uncyclized peptide could also be captured through this procedure, these analyses also showed that the desired macrocyclic product was formed with high efficiency in each case (i.e., >95% for Strep1-Z5C(p-2beF); 70% for Strep2-Z7C(p-2beF); 85% Strep3-Z11C(p-2beF)). Furthermore, the precursor polypeptides were found to have undergone complete splicing in vivo (FIGS. 33*a-d*). Since p-2beF-mediated alkylation of the intein catalytic cysteine would prevent protein splicing, the latter results further higlighted the high degree of chemo- and regioselectivity of the macrocyclization reaction. Furthremore, the cyclization yield observed with these sequences correlated very well with the reactivity trend measured across the other p-2beF-containing contructs (FIG. 9A), suggesting that this parameter is rather predictable on the sole basis of the Cys/p-2beF distance and in spite of the difference in the composition of the target peptide sequence.

Altogether, these results further demonstrate the versatility of the methods described herein for enabling the ribosomal synthesis of macrocyclic peptides of varying length and compositions. In addition, they demonstrate the possibility to apply these methods to enable the production of macrocyclic peptides in vivo, i.e., inside a living cell. Finally, they demonstrate that these in vivo produced macrocyclic peptides can be functional, that is capable of specifically bind to a target biomolecule (i.e., streptavidin).

Experimental Details

Isolation and Analysis of HPQ-Containing Macrocyclic Peptides.

Protein expression was performed as described above (Example 5). After centrifugation, cells were resuspended in 50 mM Tris, 300 mM NaCl and 20 mM imidazole (pH 7.5) and lysed by sonication. Cell lysates were incubated with streptavidin-coated beads for 1 hour under gentle shaking on ice. Beads were washed two times with the same buffer followed by incubation with acetonitrile:$H_2O$ (70:30 v/v) for one minute to release any streptavidin-bound peptides. Eluates were lyophilized and the identity of the peptides evaluated using MALDI-TOF MS and LC-MS as described above (Example 5).

6.6. Example 6: Preparation and Isolation of Macrocyclic Peptides Generated Via Cysteine Cross-Linking with Different Electrophilic Amino Acids This example further demonstrates the formation and isolation of macrocyclic peptides produced via the cyclization of ribosomally derived precursor polypeptides of general formula (I). In particular, this example demonstrates how different cysteine-reactive unnatural amino acids of general structure (III) can be used for the purpose of generating macrocyclic peptides starting from ribosomally produced polypeptide precursors according to the methods described herein.

As described in Example 3, orthogonal AARS/tRNA pairs could be readily identified to achieve the specific incorporation of the unnatural amino acids 2becK, 2cecK, p-1beF, or bdnK into a precursor polypeptide of choice. Each of these amino acids contains an electrophilic side-chain functionality (i.e., alkylbromide group in 2becK and p-1beF; alkylchloride group in 2cecK; allenamide group in bdnK), which was expected to react chemoselectively with a neighboring cysteine residue within the precursor polypeptide sequence according to the general methods provided herein. To test the ability of 2becK and 2cecK to mediate peptide macrocyclization, the constructs corresponding to Entries 1 through 9 of Table 1 were expressed in *E. coli* as described above (Example 5) using the appropriate AARS/tRNA pairs (Example 3) for the incorporation of either 2becK or 2cecK as the cysteine-reactive residue (Z residue, Table 1). To establish the occurrence of the desired macrocyclization reaction, these proteins were purified by Ni-affinity chromatography and then reacted with benzyl mercaptan to splice the GyrA intein and release the macrocyclic peptide. Detection and quantification of the cyclic product was carried by LC-MS and MS/MS analysis as described in Example 4. These analyses revealed the occurrence of the desired macrocyclic peptide product in each case, as shown by the representative LC-MS extracted-ion chromatograms and MS/MS spectra in FIGS. 18A-C, 19A-B, 20A-C, 21A-C, and 22A-C. As summarized in FIG. 9B, 2becK- and 2cecK-mediated peptide macrocyclization was found to occur very efficiently (>80%) when the cysteine residue is located within a six-residue distance from the electrophilic amino acid (i.e., with constructs 12mer-Z1C through 12mer-Z1C). Beyond this spacing distance, the % cyclization decreases significantly (<20%). Interestingly, the reactivity of 2becK- and 2cecK as cysteine cross-linking residues nicely complement that of p-2beF, as evidenced from comparison of % cyclization data in FIGS. 9A and 9B. For example, whereas the 12mer-Z1C construct undergoes efficient cyclization in the presence of 2becK (or 2cecK) but not p-2beF as the cysteine-reactive residue, the opposite holds true in the context of the large macrocycles formed from the constructs 12mer-Z10C and 12mer-Z12C. Thus, these results show how different cysteine-reactive amino acids can be appropriately chosen and applied to obtain macrocyclic peptides of varying ring size according to the methods provided herein.

To further investigate the generality of the methods presented herein, two additional amino acids, p-1beF and bdnK, were synthesized (Example 1) and tested here for their ability to induce peptide macrocyclization upon reaction with a proximal cysteine in the precursor polypeptide. p-1beF contains a benzylic, secondary alkyl bromide group, thus enabling the formation of more compact peptide ring structures as compared to those generated using p-2beF-mediated cysteine alkylation. On the other hand, bdnK was designed to contain an allenamide group, which is known to react chemoselectively with cysteine via a Michael addition reaction (Abbas, Xing et al. 2014). Using the appropriate AARS/tRNA pair as determined in Example 3, p-1beF was incorporated into the construct 12mer-Z4C (Entry 4, Table 1) to give 12mer-Z4C(p-1beF), whereas bdnK was incorporated into the construct 12mer-Z6C (Entry 6, Table 1) to give 12mer-Z6C(bdnK). After expression in *E. coli* and purification via Ni-affinity chromatography, these proteins were made react with benzyl mercaptan to splice the GyrA intein and release the macrocyclic peptide. The desired macrocyclic peptide product could be observed in each case (FIGS. 23A-C and 24A-C). Altogether, the results included in this example illustrate how a variety of structurally diverse cysteine-reactive amino acids can be designed and applied in the context of the general peptide cyclization methods described in this application.

6.7. Example 7: Preparation and Isolation of Macrocyclic Peptides Precursor Polypeptides of General Formula (II)

This example demonstrates the formation and isolation of macrocyclic peptides produced via the cyclization of ribosomally derived precursor polypeptides of general formula (II). As such, this example demonstrates certain embodiments as schematically described in FIGS. 1B and 2B.

For these studies, the constructs corresponding to Entries 10 through 12 of Table 1 were used. Three different cysteine-reactive amino acids, p-2beF, 2becK, and 2cecK, were tested as the Z residue in these constructs. The corresponding p-2beF-, 2becK-, or 2cecK-containing precursor polypeptides were expressed in BL21(DE3) *E. coli* cells using the appropriate AARS/tRNA pair as determined in Example 3 (Mj-pOgY2-RS/MjtRNA$_{CUA}^{Tyr}$ pair for the p-2beF-containing proteins and Mb-CrtK-RS/Mm/MbtRNA$_{CUA}^{Pyl}$ for the 2becK and 2cecK-containing proteins). In these constructs, the reactive Cys is located upstream of the unnatural amino acid, and specifically at position Z-4, Z-6 and Z-8. Analysis of the p-2beF-containing proteins according to the procedure described above (Example 4) revealed the occurrence of the desired cyclic peptide as the largely predominant product (95-99%) for all of the constructs tested (FIG. 9A, FIGS. 34A-C and 35A-C). For the 2becK- and 2cecK-containing proteins, efficient inter-side-chain cyclization (80-95%) was observed when the cysteine and unnatural amino acid are three (Z-4) and five residue apart, while a lower % of cyclization was noted at the larger spacing distance (Z-8) (FIG. 9B). These data clearly demonstrated that the thioether bond-forming reactivity of the cysteine-reactive amino acids is preserved when the order of Cys and Z residue is reversed, thus enabling structural variation of the resulting macrocyclic peptide products. Furthermore, quantitative thiol-induced splicing of the GyrA intein from the aforementioned proteins indicated that no reaction had occurred between the side-chain of the unnatural amino acid and the catalytic I+1 cysteine residue of the intein (FIGS. 17*a-d*).

6.8 Example 8: In Vivo Production and Isolation of Bicyclic Peptides

This example demonstrates certain embodiments as schematically described in FIG. 4A. In particular, this example demonstrates how bicyclic peptides can be generated from precursor polypeptides of general formula (I) via the combination of a split intein-mediated trans-splicing reaction and inter-side-chain cyclization reaction mediated by a cysteine and a cysteine-reactive unnatural amino acid according to the methods described herein. While split intein-mediated trans-splicing has proven useful for the generation and isolation of head-to-tail cyclic peptides in a variety of context (Scott, Abel-Santos et al. 1999; Tavassoli and Benkovic 2005; Tavassoli and Benkovic 2007; Tavassoli, Lu et al. 2008; Young, Young et al. 2011) (see also U.S. Pat. Nos. 7,354,756, 7,252,952, and 7,105,341), there are reports of the application of this technique (called SICLOPPS) to obtain bicyclic peptides of the general structure described in FIGS. 4A-B. This example demonstrates the possibility to apply the general methods disclosed herein, and specifically in its embodiments as outlined in FIGS. 4A-B, to enable the efficient production of bicyclic peptides inside a living cell. In addition, the advantage conferred by the bicyclic structure and thus by the inter-side-chain thioether linkage toward improving the functional (i.e., protein-binding) properties of the macrocyclic peptide is demonstrated.

For these studies, the constructs corresponding to Entries 16 through 20 of Table 1 were utilized. The corresponding precursor polypeptides were expressed in BL21(DE3) *E. coli* cells in the presence of the Mj-pOgY2-RS/MjtRNA$_{CUA}^{Tyr}$ for incorporation of the unnatural amino acid p-2beY into these proteins via amber stop codon suppression, as described above (Example 5). These constructs were designed to comprise the C-domain and N-domain of split intein DnaE within the N-terminal tail and the C-terminal tail, respectively, of the precursor polypeptide. According to our strategy (FIG. 4A), these precursor polypeptides were expected to result in the formation of bicyclic peptides in *E. coli* by means of an intramolecular, thioether bond-forming reaction between the cysteine and p-2beF residues and a DnaE-catalyzed trans-splicing reaction leading to ring closure (i.e., N-to-C-end cyclization) of the peptide sequence comprised between the C- and N-domain of the split intein. To facilitate the identification and isolation of these bicyclic peptides, a streptavidin-binding motif (HPQ) was included within the sequence targeted for macrocyclization (Table 1). Accordingly, using an analogous procedure as that described in Example 5, lysates of *E. coli* cells expressing the aforementioned precursor polypeptides were passed over streptavidin-coated beads, from which streptavidin-bound material was eluted.

Notably, the desired bicyclic peptide was isolated as the largely predominant product in each case (70-95%), as determined by LC-MS (FIGS. 28A-C, 29A-C, 30A-C, 31A-C, and 32A-C). The bicyclic structure of these compounds was further evidenced by the corresponding MS/MS fragmentation spectra (FIGS. 28A-C, 29A-C, 30A-C, 31A-C, and 32A-C). Treatment of the bicyclic peptide obtained with the thiol-alkylating iodoacetamide resulted in a 57 Da increase in molecular mass and shift of the peptide retention time for the bicyclic product of the cStrep3(C)-Z3C(p-2beF) precursor protein but not for that of cStrep3(S)-Z3C(p-2beF), which is consistent with the presence of a free thiol in the former (from Int$_C$+1 cysteine) but not in the latter. To allow measurement of the extent of post-translational self-processing of these precursor polypeptides in vivo, a chitin-binding domain was included at the C-terminus of the Int$_N$ domain in each construct (Table 1). LC-MS analysis of the protein fraction eluted from chitin beads showed that the split intein-mediated cyclization has occurred nearly quantitatively or nearly quantitatively (>85%) for all the constructs tested (see representative MS spectra in FIGS. 33*a-d*). Overall, the successful generation of bicyclic structures across target sequences of varying length and composition supports the functionality and broad scope of the present methodology for the ribosomal synthesis of bicyclic peptides through the integration of split intein-mediated peptide circularization with inter-side-chain thioether bridge formation.

The increased conformational rigidity imposed by the intra-side-chain thioether bridge is expected to improve the functional and/or stability properties of these bicyclic peptides as compared to the head-to-tail cyclized peptide counterpart. To investigate this aspect, the streptavidin-binding affinity of the bicyclic peptides obtained via cyclization of the cStrep3(S)-Z3C(p-2beF) and cStrep3(C)-Z8C(p-2beF) constructs was measured through an in-solution inhibition assay and compared with that of a 'monocyclic' counterpart (cyclo[S(OpgY)TNCHPQFANA] (SEQ ID NO:189) where OpgY is O-propargyl-tyrosine). In this assay (FIG. 39A), a streptavidin-binding surface is first created by immobilizing the bicyclic peptide obtained from the cStrep3(C)-Z8C(p-2beF) construct on maleimide-coated microtiter plates. Then, a fixed amount of streptavidin-horseradish peroxidase conjugate is added to the plate in the presence of varying amount of the bicyclic or cyclic peptide. After washing, the amount of bound streptavidin is determined based on the residual peroxidase activity using a standard (ABTS) colorimetric assay. Using this assay, the $IC_{50}$ value for the head-to-tail monocyclic peptide cyclo[S(OpgY)TNCHPQFANA (SEQ ID NO:189) was determined to be 1.9 μM, while the thioether-constrained bicyclic peptides from the cStrep3(S)-Z3C(p-2beF) and cStrep3(C)-Z8C(p-2beF) constructs exhibited an $IC_{50}$ of 3.7 and 0.77 μM, respectively (FIG. 39B). The >2-fold increase in streptavidin binding affinity exhibited by the latter as compared to the monocyclic counterpart exemplifies the inherent advantage provided by presence of the additional intramolecular thioether linkage.

Experimental Details

Preparation and Isolation of Bicyclic Macrocycles.

Protein expression of constructs 16-20 was performed as described in the previous Examples with the difference that cells were incubated for additional 3 hours at 37° C. after overnight growth. Cells were harvested, lysed and the cell lysate treated as described above to isolate and analyze the streptavidin-bound peptides by LC-MS. To analyze the amount of protein splicing occurred in vivo, the same cell lysate samples were incubated with chitin beads for 1h on ice. Beads were washed two times with buffer followed by incubation with acetonitrile:$H_2O$ (70:30 v/v) for one minute to release any chitin-bound protein. Eluates were analyzed by LC-MS.

6.9 Example 9: Polycyclic Peptides

This example demonstrates the feasibility of generating polycyclic peptides using the methods provided herein. In particular, it demonstrates the formation and isolation of polycyclic peptides obtained via the post-translational cyclization of precursor polypeptides containing multiple Z/Cys pairs. It also demonstrates the formation and isolation of polycyclic peptides produced via the cyclization of ribosomally derived precursor polypeptides of general formula (V). In particular, this example demonstrates certain embodiments as schematically described in FIGS. 37A-B.

For these studies, the constructs corresponding to Entries 21 and 22 of Table 1 were utilized. In Strep6_Z4C7C4Z, a Z/Cys pair encompassing a four-amino acid target peptide sequence (HPQF (SEQ ID NO:185)) is followed by a second Cys/Z pair encompassing a different target peptide sequence (NTSK) after a spacer sequence (ENLYFQS). To demonstrate the possibility to obtain polycyclic peptides in this manner, the corresponding precursor polypeptide was expressed in BL21(DE3) *E. coli* cells in the presence of the Mj-pOgY2-RS/Mj$tRNA_{CUA}^{Tyr}$ to achieve the site-selective incorporation of the unnatural amino acid p-2beF in correspondence of the two Z residues. Although two possible bicyclic products could be generated via p-2beF-mediated cysteine alkylation, the structure-reactivity studies described in FIG. 9A would predict that each p-2beF would react preferentially or exclusively with its most proximal cysteine residue (i.e., p-2beF3 with Cys8 and p-2beF21 with Cys16, Table 1). Indeed, LC-MS analysis of the small molecular weight products obtained after thiol-induced splicing of purified Strep6_Z4C7C4Z(p-2beF) revealed the occurrence of the expected 2beF3-Cys8/p-2beF21-Cys16 linked product (FIGS. 36A-C) as the only bicyclic product. A small amount of the monocyclic 2beF3-Cys8-linked peptide was also observed. Overall, these studies demonstrate the possibility to generate precursor polypeptides with multiple Z/Cys pairs in order to obtain macrocyclic peptides featuring a polycyclic structure. Whereas this example illustrates the specific case in which two copies of the same cysteine-reactive amino acid are incorporated into the precursor polypeptide, a person skilled in the art would immediately recognize that this approach can be readily extended to the use of two different cysteine-reactive amino acids, such as those described in FIGS. 5 and 6. The ribosomal incorporation of two different cysteine-reactive unnatural amino acids into the precursor polypeptide can be achieved using methods known in the art, i.e., via suppression of two different stop codons (Wan, Huang et al. 2010) or via suppression of a stop codon and a four-based codon (Chatterjee, Sun et al. 2013; Sachdeva, Wang et al. 2014). As shown above, results from structure-reactivity studies such as those described in FIGS. 9A-B can guide the design of appropriate precursor polypeptides for the formation of a polycyclic peptide with the desired pattern of thioether linkages (i.e., through the judicious choice of spacing distances between the different Z and Cys residues).

The successful formation of cyclic peptides via the ribosomal incorporation of cysteine-reactive amino acids into precursor polypeptides as illustrated by the previous Examples suggested that macrocyclic peptide with a polycyclic architecture could also be obtained through the use of amino acids containing more than one cysteine-reactive functional group in their side chain, i.e., using amino acids with the general formula (VI) or (VII). To illustrate this aspect, one such amino acid, ObdpY, was designed and synthesized according to Scheme 6 of FIG. 6. A suitable, orthogonal AARS/tRNA pair for the ribosomal incorporation of ObdpY in response to an amber stop codon was then identified as described in Example 3. Using ObdpY and the Mj-pOgY2-RS/Mj$tRNA_{CUA}^{Tyr}$ pair, the precursor polypeptide corresponding to Entry 22 of Table 1 was expressed in *E. coli* and purified by Ni-affinity chromatography. In this protein (called Strep7_C5Z4C(ObdpY)), two cysteine residues flank the ObdpY residue encompassing two different target peptide sequences (i.e., AYDSG (SEQ ID NO:188) and HPQF (SEQ ID NO:185)). Analysis of the small molecular weight product obtained after thiol-induced splicing of the GyrA intein revealed the occurrence of the desired bicyclic peptide product (FIGS. 38A-C). A small amount of the monocyclic peptide resulting from reaction of ObdpY side chain with only one of the cysteine residue was also observed. Altogether, these studies demonstrate the feasibility of certain embodiments as schematically illustrate in FIGS. 37A-B. As noted above, structure-activity studies such as those presented in FIGS. 9A-B can guide the judicious choice of suitable Z2 residues of general formula (VI) or (VII) and of target sequence lengths in order to the obtain a polycyclic peptide carrying a desired pattern of thioether linkages.

A sample of the methods and cells that are described herein is set forth in the following numbered paragraphs:

1. A method for making a macrocyclic peptide, the method comprising:

a. providing an artificial nucleic acid molecule encoding for a polypeptide of structure:

$(AA)_m$-Z-$(AA)_n$-Cys-$(AA)_p$ (I)

or $(AA)_m$-Cys-$(AA)_n$-Z-$(AA)_p$ (II)

or $(AA)_m$-Cys-$(AA)_n$-Z2-$(AA)_o$-Cys-$(AA)_p$ (V)

wherein:

i. $(AA)_m$ is an N-terminal amino acid or peptide sequence, ii. Z is a non-canonical amino acid carrying a side-chain functional group $FG_1$, $FG_1$ being a functional group selected from the group consisting of —$(CH_2)_n$X, where X is F, Cl, Br, or I and n is an integer number from 1 to 10; —C(O)$CH_2$X, where X is F, Cl, Br, or I; —CH(R')X, where X is F, Cl, Br, or I; —C(O)CH(R')X, where X is F, Cl, Br, or I; —$OCH_2CH_2$X, where X is F, Cl, Br, or I; —C(O)CH═C═C(R')(R"); —$SO_2$C(R')═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$; —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R and R' is independently H, an aliphatic, a substituted aliphatic, an aryl, or a substituted aryl group.

iii. Z2 is a non-canonical amino acid carrying two side-chain functional groups $FG_1$ and $FG_2$, wherein each of $FG_1$ and $FG_2$ is a functional group independently selected from the group consisting of —$(CH_2)_n$X, where X is F, Cl, Br, or I and n is an integer number from 1 to 10; —C(O)$CH_2$X, where X is F, Cl, Br, or I; —CH(R')X, where X is F, Cl, Br, or I; —C(O)CH(R')X, where X is F, Cl, Br, or I; —$OCH_2CH_2$X, where X is F, Cl, Br, or I; —C(O)CH═C═C(R')(R"); —$SO_2$C(R')═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$; —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R' and R' is independently H, an aliphatic, a substituted aliphatic, an aryl, or a substituted aryl group, iv. $(AA)_n$ is a target peptide sequence, v. $(AA)_o$ is a second target peptide sequence, and vi. $(AA)_p$ is a C-terminal amino acid or peptide sequence;

b. introducing the nucleic acid molecule into an expression system and expressing the nucleic acid molecule in the expression system, thereby producing the polypeptide; and c. allowing the functional group $FG_1$, and whenever present, $FG_2$, to react with the side-chain sulfhydryl group (—SH) of the cysteine (Cys) residue(s), thereby producing the macrocyclic peptide.

2. The method of paragraph 1 wherein Z is an amino acid of structure:

(III)

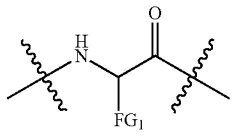

or (IV)

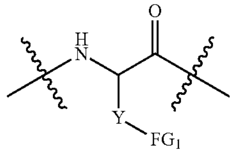

wherein $FG_1$ is a functional group selected from the group consisting of —$(CH_2)_n$X, where X is F, Cl, Br, or I and n is an integer number from 1 to 10; —C(O)$CH_2$X, where X is F, Cl, Br, or I; —CH(R')X, where X is F, Cl, Br, or I; —C(O)CH(R')X, where X is F, Cl, Br, or I; —$OCH_2CH_2$X, where X is F, Cl, Br, or I; —C(O)CH═C═C(R')(R"); —$SO_2$C(R')═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$; —C≡C—C(O)OR'; —C≡C—C(O)N(R')(R"); unsubstituted or substituted oxirane, unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide; where each R and R" is independently H, an aliphatic, a substituted aliphatic, an aryl, or a substituted aryl group;

wherein Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups.

3. The method of paragraph 2 wherein Z is an amino acid of structure (IV) and Y is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, and $C_5$-$C_{24}$ aryloxy groups.

4. The method of paragraph 3 wherein Y is a linker group selected from the group consisting of —$CH_2$—$C_6H_4$—, —$CH_2$—$C_6H_4$—O—, —$CH_2$—$C_6H_4$—NH—, —$(CH_2)_4$—, —$(CH_2)_4$NH—, —$(CH_2)_4$NHC(O)—, and —$(CH_2)_4$NHC(O)O—.

5. The method of paragraph 1 wherein the amino acid Z is selected from the group consisting of 4-(2-bromoethoxy)-phenylalanine, 3-(2-bromoethoxy)-phenylalanine, 4-(2-chloroethoxy)-phenylalanine, 3-(2-chloroethoxy)-phenylalanine, 4-(1-bromoethyl)-phenylalanine, 3-(1-bromoethyl)-phenylalanine, 4-(aziridin-1-yl)-phenylalanine, 3-(aziridin-1-yl)-phenylalanine, 4-acrylamido-phenylalanine, 3-acrylamido-phenylalanine, 4-(2-fluoro-acetamido)-phenylalanine, 3-(2-fluoro-acetamido)-phenylalanine, 4-(2-chloro-acetamido)-phenylalanine, 3-(2-chloro-acetamido)-phenylalanine, 3-(2-fluoro-acetyl)-phenylalanine, 4-(2-fluoro-acetyl)-phenylalanine, $N^{\epsilon}$-((2-bromoethoxy)carbonyl)-lysine, $N^{\epsilon}$-((2-chloroethoxy)carbonyl)-lysine, $N^{\epsilon}$-(buta-2,3-dienoyl)-lysine, $N^{\epsilon}$-acryl-lysine, $N^{\epsilon}$-crotonyl-lysine, $N^{\epsilon}$-(2-fluoro-acetyl)-lysine, and $N^{\epsilon}$-(2-chloro-acetyl)-lysine.

6. The method of paragraph 1 wherein Z2 is an amino acid of structure:

(VI)

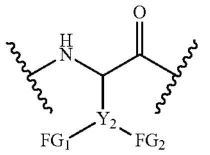

or (VII)

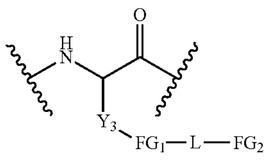

wherein each of $FG_1$ and $FG_2$ is a functional group independently selected from the group consisting of —$(CH_2)_nX$, where X is F, Cl, Br, or I and n is an integer number from 1 to 10; —$C(O)CH_2X$, where X is F, Cl, Br, or I; —CH(R')X, where X is F, Cl, Br, or I; —C(O)CH(R')X, where X is F, Cl, Br, or I; —$OCH_2CH_2X$, where X is F, Cl, Br, or I; —C(O)CH=C=C(R')(R"); —$SO_2C(R')$=C(R')(R"); —C(O)C(R')=C(R')(R"); C(R')=C(R')C(O)OR'; —C(R')=C(R')C(O)N(R')(R"); —C(R')=C(R')—CN; —C(R')=C(R')—$NO_2$, —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R and R' is independently H, an aliphatic, a substituted aliphatic, an aryl, or a substituted aryl group;

wherein $Y_2$, $Y_3$, and L are linker groups selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups.

7. The method of paragraph 6 wherein Z2 is an amino acid of structure (VI) and $Y_2$ is a linker group selected from the group consisting of $C_1$-$C_{24}$ alkyl, $C_1$-$C_{24}$ substituted alkyl, $C_1$-$C_{24}$ substituted heteroatom-containing alkyl, $C_1$-$C_{24}$ substituted heteroatom-containing alkyl, $C_2$-$C_{24}$ alkenyl, $C_2$-$C_{24}$ substituted alkenyl, $C_2$-$C_{24}$ substituted heteroatom-containing alkenyl, $C_2$-$C_{24}$ substituted heteroatom-containing alkenyl, $C_5$-$C_{24}$ aryl, $C_5$-$C_{24}$ substituted aryl, $C_5$-$C_{24}$ substituted heteroatom-containing aryl, $C_5$-$C_{24}$ substituted heteroatom-containing aryl, $C_1$-$C_{24}$ alkoxy, and $C_5$-$C_{24}$ aryloxy groups.

8. The method of paragraph 7 wherein Y is a linker group selected from the group consisting of —$CH_2$—$C_6H_4$—, —$CH_2$—$C_6H_4$—O—, —$CH_2$—$C_6H_4$—NH—, —$CH_2$—$C_6H_4$—$OCH_2$—, —$(CH_2)_4NH$—, —$(CH_2)_4NHC(O)$—, —$(CH_2)_4NHC(O)O$—, —$(CH_2)_4NHC(O)OCH_2$—,

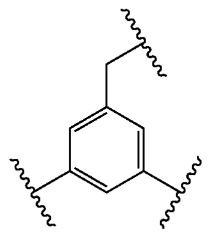

, and

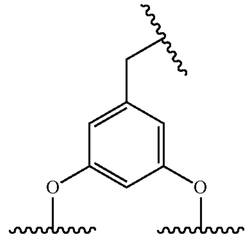

.

9. The method of paragraph 1 wherein the amino acid Z2 is selected from the group consisting of 3,5-bis(2-bromoethoxy)-phenylalanine, 3,5-bis(2-chloroethoxy)-phenylalanine, 3,5-bis(1-bromoethyl)-phenylalanine, 3,5-bis(aziridin-1-yl)-phenylalanine, 3,5-bis-acrylamido-phenylalanine, 3,5-bis(2-fluoro-acetamido)-phenylalanine, 3,5-bis(2-fluoro-acetyl)-phenylalanine, 4-((1,3-dibromopropan-2-yl)oxy)-phenylalanine, 4-((1,3-dichloropropan-2-yl)oxy)-phenylalanine, $N^{\epsilon}$-4(1,3-dibromopropan-2-yl)oxy)carbonyl)-lysine, $N^{\epsilon}$-(((1,3-dichloropropan-2-yl)oxy)carbonyl)-lysine, 4-(2,3-dibromopropoxy)-phenylalanine, 3-(2,3-dibromopropoxy)-phenylalanine, 4-(2,3-dichloropropoxy)-phenylalanine, 3-(2,3-dichloropropoxy)-phenylalanine, $N^{\epsilon}$-((2,3-dibromopropoxy)carbonyl)-lysine, and $N^{\epsilon}$-((2,3-dichloropropoxy)carbonyl)-lysine.

10. The method of paragraph 1 wherein the codon encoding for Z or Z2 is an amber stop codon TAG, an ochre stop codon TAA, an opal stop codon TGA, or a four base codon.

11. The method of paragraph 1, wherein the expression system comprises:

an aminoacyl-tRNA synthetase polypeptide or an engineered variant thereof that is at least 90% identical to SEQ ID NO:77, 78, 79, or 80; and a transfer RNA molecule encoded by a polynucleotide that is at least 90% identical to SEQ ID NO:101, 105, 109, 113, or 117.

12. The method of paragraph 11, wherein:

(a) the engineered variant of the aminoacyl-tRNA synthetase polypeptide of SEQ ID NO:77 comprises an amino acid substitution at a position selected from the group consisting of position: X32, X63, X65, X70, X107, X108, X109, X155, X158, X159, X160, X161, X162, X163, X164, X167, and X286 of SEQ ID NO:77, (b) the engineered variant of the aminoacyl-tRNA synthetase polypeptide of SEQ ID NO:78 comprises an amino acid substitution at a position selected from the group consisting of position: X302, X305, X306, X309, X346, X348, X364, X384, X401, X405, and X417 of SEQ ID NO:78, (c) the engineered variant of the aminoacyl-tRNA synthetase polypeptide of SEQ ID NO:79 comprises an amino acid substitution at a position selected from the group consisting of position: X76, X266, X270, X271, X273, X274, X313, X315, and X349 of SEQ ID NO:79, or (d) the engineered variant of the aminoacyl-tRNA synthetase polypeptide of SEQ ID NO:80 comprises an amino acid substitution at a position selected from the group consisting of position: X37, X182, X183, X186, and X265 of SEQ. ID NO. 204.

13. The method of paragraph 12, wherein:

(a) the engineered variant of the aminoacyl-tRNA synthetase polypeptide of SEQ ID NO:77 comprises at least one of the features selected from the group consisting of: X32 is Tyr, Leu, Ala, Gly, Thr, His, Glu, Val, or Gln; X65 is Leu, His, Tyr, Val, Ser, Thr, Gly, or Glu; X67 is Ala or Gly; X70 is His, Ala, Cys, or Ser; X107 is Glu, Pro, Asn, or Thr; X108 is Phe, Trp, Ala, Ser, Arg, Gly, Tyr, His, Trp, or Glu; X109 is Gln, Met, Asp, Lys, Glu, Pro, His, Gly, Met, or Leu; X155 is Gln, Glu, or Gly; X158 is Asp, Gly, Glu, Ala, Pro, Thr, Ser, or Val; X159 is Ile, Cys, Pro, Leu, Ser, Trp, His, or Ala; X160 is His or Gln; X161 is Tyr or Gly; X162 is Leu, Arg, Ala, Gln, Gly, Lys, Ser, Glu, Tyr, or His; X163 is Gly or Asp; X164 is Val or Ala; X167 is Ala or Val; X286 is Asp or Arg;

(b) the engineered variant of the aminoacyl-tRNA synthetase polypeptide of SEQ ID NO:78 comprises at least one of the features selected from the group consisting of: X302 is Ala or Thr; X305 is Leu or Met; X306 is Tyr, Ala, Met, Ile, Leu, Thr, Gly; X309 is Leu, Ala, Pro, Ser, or Arg; X346 is Asn, Ala, Ser, or Val; X348 is Cys, Ala, Thr, Leu, Lys, Met, or Trp; X364 is Thr or Lys; X384 is Tyr or Phe; X405 is Ile or Arg; X401 is Val or Leu; and X417 is Trp, Thr, or Leu;

(c) the engineered variant of the aminoacyl-tRNA synthetase polypeptide of SEQ ID NO:79 comprises at least one of the features selected from the group consisting of: X76 is Asp or Gly; X266 is Leu, Val, or Met; X270 is Leu or Ile; X271 is Tyr, Phe, Leu, Met, or Ala; X274 is Leu, Ala, Met, or Gly; X313 is Cys, Phe, Ala, Val, or Ile; X315 is Met or Phe; and X349 is Tyr, Phe, or Trp; or (d) the engineered variant of the aminoacyl-tRNA synthetase polypeptide of SEQ ID NO:80 comprises at least one of the features selected from the group consisting of: X37 is Tyr, Ile, Gly, Val, Leu, Thr, or Ser; X182 is Asp, Gly, Ser, or Thr; X183 is Phe, Met, Tyr, or Ala; X186 is Leu, Ala, Met, or Val; and X265 is Asp or Arg.

14. The method of paragraph 1, wherein the expression system comprises:

an aminoacyl-tRNA synthetase selected from the group consisting of SEQ ID NOs. 77, 78, 79, 80, 81, 82, 83, 84, 85, 86, 87, 88, 89, 90, 91, 92, 93, 94, 95, 96, 97, 98, 99 and 100; and a transfer RNA molecule encoded by a polynucleotide selected from the group consisting of SEQ ID NO:101, 102, 103, 104, 105, 106, 107, 108, 109, 110, 111, 112, 113, 114, 115, 116, 117, 118, 119, and 120.

15. The method of paragraph 1, wherein the N-terminal tail polypeptide, $(AA)_m$, or the C-terminal tail polypeptide, $(AA)_p$, or both, of the precursor polypeptides of formula (I), (II), or (V) comprise(s):

a polypeptide affinity tag, a DNA-binding polypeptide, a protein-binding polypeptide, an enzyme, a fluorescent protein, an intein protein, or a combination thereof.

16. The method of paragraph 15, wherein the polypeptide comprised within the N-terminal tail polypeptide, $(AA)_m$, or the C-terminal tail polypeptide, $(AA)_p$, or both, of the precursor polypeptides of formula (I), (II), and (V), is a polypeptide selected from the group of polypeptides consisting of SEQ ID NOs 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, and 158.

17. The method of paragraph 15, wherein the intein polypeptide comprised within the N-terminal tail polypeptide, $(AA)_m$, or the C-terminal tail polypeptide, $(AA)_p$, or both, of the precursor polypeptides of formula (I), (II), or (V), is a selected from the group consisting of a naturally occurring intein, an engineered variant of a naturally occurring intein, a fusion of the N-terminal and C-terminal fragments of a naturally occurring split intein and a fusion of the N-terminal and C-terminal fragments of an engineered split intein.

18. The method of paragraph 17, wherein the intein is selected from the group consisting of Mxe GyrA (SEQ ID NO:1), eDnaB (SEQ ID NO:2), Hsp-NRC1 CDC21 (SEQ ID NO:3), Ceu ClpP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FG-SCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8 (SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:46), Ter RIR1-1 (SEQ ID NO:47), Pab RIR1-1 (SEQ ID NO:48), Pfu RIR1-1 (SEQ ID NO:49), Chy RIR1 (SEQ ID NO:50), Mth RIR1 (SEQ ID NO:51), Pab RIR1-3 (SEQ ID NO:52), Pfu RIR1-2 (SEQ ID NO:53), Ter RIR1-2 (SEQ ID NO:54), Ter RIR1-4 (SEQ ID NO:55), CIV RIR1 (SEQ ID NO:56), Ctr VMA (SEQ ID NO:57), Sce VMA (SEQ ID NO:58), Tac-ATCC25905 VMA (SEQ ID NO:59), Ssp DnaB (SEQ ID NO:60), engineered variant(s) thereof, and engineered variant(s) thereof wherein the N-terminal cysteine or serine residue of the engineered variant is mutated to any natural (or naturally occurring) amino acid residue other than cysteine or serine, or wherein the C-terminal asparagine residue of the engineered variant is mutated to any natural (or naturally occurring) amino acid residue other than asparagine.

19. The method of paragraph 17, wherein the intein is a fusion product of a split intein selected from the group consisting of Ssp DnaE (SEQ ID NO:61-SEQ ID NO:62), Neq Pol (SEQ ID NO:63-SEQ ID NO:64), Asp DnaE (SEQ ID NO:65-SEQ ID NO:66), Npu-PCC73102 DnaE (SEQ ID NO:67-SEQ ID NO:68), Nsp-PCC7120 DnaE (SEQ ID NO:69-SEQ ID NO:70), Oli DnaE (SEQ ID NO:71-SEQ ID NO:72), Ssp-PCC7002 DnaE (SEQ ID NO:73-SEQ ID NO:74), Tvu DnaE (SEQ ID NO:75-SEQ ID NO:76), engineered variant(s) thereof, and engineered variant(s) thereof wherein the N-terminal cysteine or serine residue of the split intein N-domain of the engineered variant is mutated to any of the natural (or naturally occurring) amino acid residues other than cysteine or serine, or wherein the C-terminal asparagine residue of the split intein C-domain of the engineered variant is mutated to any of the natural (or naturally occurring) amino acid residues other than asparagine.

20. The method of paragraph 1, wherein the N-terminal tail polypeptide, $(AA)_m$, of the precursor polypeptide of formula (I), (II), or (V) comprises the C-domain of a split intein, and the C-terminal tail polypeptide, $(AA)_p$, comprises the corresponding N-domain of the split intein.

21. The method of paragraph 20, wherein the split intein C-domain is selected from the group consisting of Ssp DnaE-c (SEQ ID NO:62), Neq Pol-c (SEQ ID NO:64), Asp DnaE-c (SEQ ID NO:66), Npu-PCC73102 DnaE-c (SEQ ID NO:68), Nsp-PCC7120 DnaE-c (SEQ ID NO:70), Oli DnaE-c (SEQ ID NO:72), Ssp-PCC7002 DnaE-c (SEQ ID NO:74), Tvu DnaE-c (SEQ ID NO:76), and engineered variant(s) thereof; and the split intein N-domain is selected from the group consisting of Ssp DnaE-n (SEQ ID NO:61), Neq Pol-n (SEQ ID NO:63), Asp DnaE-n (SEQ ID NO:65), Npu-PCC73102 DnaE-n (SEQ ID NO:67), Nsp-PCC7120 DnaE-n (SEQ ID NO:69), Oli DnaE-n (SEQ ID NO:71), Ssp-PCC7002 DnaE-n (SEQ ID NO:73), Tvu DnaE-n (SEQ ID NO:75), and engineered variant(s) thereof.

22. The method of paragraph 1 wherein the expression system is selected from the group consisting of a prokaryotic cell, an eukaryotic cell, and a cell-free expression system.

23. The method of paragraph 22 wherein the prokaryotic cell is *Escherichia coli.*

24. The method of paragraph 22 wherein the eukaryotic cell is a yeast, a mammalian, an insect or a plant cell.

25. The method of paragraph 1 wherein any of polypeptides $(AA)_n$, $(AA)_o$, $(AA)_m$, or $(AA)_p$, is fully or partially genetically randomized so that a plurality of macrocyclic peptides is obtained upon a thioether bond-forming reaction between the cysteine (Cys) residue and the side-chain functional group $FG_1$ in Z or between the cysteine (Cys) residues and the side-chain functional groups $FG_1$ and $FG_2$ in Z2.

26. The method of paragraph 1 comprising:

fully or partially randomizing any of polypeptides $(AA)_n$, $(AA)_o$, $(AA)_m$, or $(AA)_p$, wherein, upon a thioether bond-forming reaction between the cysteine (Cys) residue and the side-chain functional group $FG_1$ in Z or between the cysteine (Cys) residues and the side-chain functional groups $FG_1$ and $FG_2$ in Z2, a plurality of macrocyclic peptides is produced.

27. A recombinant host cell comprising a polypeptide of structure:

$(AA)_m$-Z-$(AA)_n$-Cys-$(AA)_p$ (I)

or $(AA)_m$-Cys-$(AA)_n$-Z-$(AA)_p$ (II)

or $(AA)_m$-Cys-$(AA)_n$-Z2-$(AA)_o$-Cys-$(AA)_p$ (V)

wherein:

i. $(AA)_m$ is an N-terminal amino acid or peptide sequence, ii. Z is an amino acid of structure:

(III)

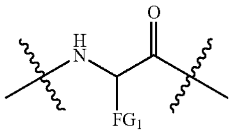

or

-continued (IV)

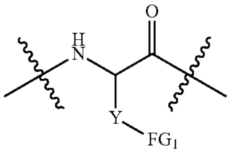

wherein $FG_1$ is a functional group selected from the group consisting of —$(CH_2)_n$X, where X is F, Cl, Br, or I and n is an integer number from 1 to 10; —C(O)$CH_2$X, where X is F, Cl, Br, or I; —CH(R')X, where X is F, Cl, Br, or I; —C(O)CH(R')X, where X is F, Cl, Br, or I; —O$CH_2CH_2$X, where X is F, Cl, Br, or I; —C(O)CH═C═C(R')(R"); —$SO_2$C(R')═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$; —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide; where each R' and R" is independently H, an aliphatic, a substituted aliphatic, an aryl, or a substituted aryl group;

wherein Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups, iii. Z2 is an amino acid of structure:

(VI)

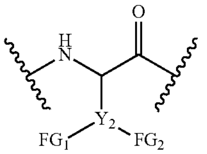

or (VII)

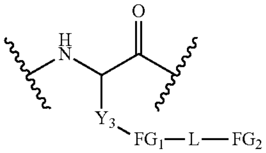

wherein each of $FG_1$ and $FG_2$ is a functional group independently selected from the group consisting of —$(CH_2)_n$X, where X is F, Cl, Br, or I and n is an integer number from 1 to 10; —C(O)$CH_2$X, where X is F, Cl, Br, or I; —CH(R')X, where X is F, Cl, Br, or I; —C(O)CH(R')X, where X is F, Cl, Br, or I; —O$CH_2CH_2$X, where X is F, Cl, Br, or I; —C(O)CH═C═C(R')(R"); —$SO_2$C(R')═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$; —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R' and R' is independently H, an aliphatic, a substituted aliphatic, an aryl, or a substituted aryl group; and wherein $Y_2$, $Y_3$, L are linker groups selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups, iv. $(AA)_n$ is a target peptide sequence, v. $(AA)_o$ is a second target peptide sequence, v. $(AA)_p$ is a C-terminal amino acid or peptide sequence.

28. The cell of paragraph 27, wherein the amino acid Z is selected from the group consisting of 4-(2-bromoethoxy)-phenylalanine, 3-(2-bromoethoxy)-phenylalanine, 4-(2-chloroethoxy)-phenylalanine, 3-(2-chloroethoxy)-phenylalanine, 4-(1-bromoethyl)-phenylalanine, 3-(1-bromoethyl)-phenylalanine, 4-(aziridin-1-yl)-phenylalanine, 3-(aziridin-1-yl)-phenylalanine, 4-acrylamido-phenylalanine, 3-acrylamido-phenylalanine, 4-(2-fluoro-acetamido)-phenylalanine, 3-(2-fluoro-acetamido)-phenylalanine, 4-(2-chloro-acetamido)-phenylalanine, 3-(2-chloro-acetamido)-phenylalanine, 3-(2-fluoro-acetyl)-phenylalanine, 4-(2-fluoro-acetyl)-phenylalanine, $N^{\varepsilon}$-((2-bromoethoxy) carbonyl)-lysine, $N^{\varepsilon}$-((2-chloroethoxy)carbonyl)-lysine, $N^{\varepsilon}$-(buta-2,3-dienoyl)-lysine, $N^{\varepsilon}$-acryl-lysine, $N^{\varepsilon}$-crotonyl-lysine, $N^{\varepsilon}$-(2-fluoro-acetyl)-lysine, and $N^{\varepsilon}$-(2-chloro-acetyl)-lysine.

29. The cell of paragraph 27 wherein the amino acid Z2 is selected from the group consisting of 3,5-bis(2-bromoethoxy)-phenylalanine, 3,5-bis(2-chloroethoxy)-phenylalanine, 3,5-bis(1-bromoethyl)-phenylalanine, 3,5-bis(aziridin-1-yl)-phenylalanine, 3,5-bis-acrylamido-phenylalanine, 3,5-bis(2-fluoro-acetamido)-phenylalanine, 3,5-bis(2-fluoro-acetyl)-phenylalanine, 4-((1,3-dibromopropan-2-yl)oxy)-phenylalanine, 4-((1,3-dichloropropan-2-yl)oxy)-phenylalanine, $N^{\varepsilon}$-4(1,3-dibromopropan-2-yl)oxy) carbonyl)-lysine, $N^{\varepsilon}$-(((1,3-dichloropropan-2-yl)oxy) carbonyl)-lysine, 4-(2,3-dibromopropoxy)-phenylalanine, 3-(2,3-dibromopropoxy)-phenylalanine, 4-(2,3-dichloropropoxy)-phenylalanine, 3-(2,3-dichloropropoxy)-phenylalanine, $N^{\varepsilon}$-((2,3-dibromopropoxy)carbonyl)-lysine, and $N^{\varepsilon}$-((2,3-dichloropropoxy)carbonyl)-lysine.

30. The cell of paragraph 27, wherein the polypeptide comprised within the N-terminal tail polypeptide, $(AA)_m$, or the C-terminal tail polypeptide, $(AA)_p$, or both, of the precursor polypeptides of formula (I), (II), and (V), is a polypeptide selected from the group of polypeptides consisting of SEQ ID NOs 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, and 158.

31. The cell of paragraph 30, wherein the cell comprises a macrocyclic peptide produced by:

a thioether bond-forming reaction between the cysteine (Cys) residue and the $FG_1$ functional group in the amino acid Z or between the cysteine (Cys) residues and the $FG_1$ and $FG_2$ functional groups in the amino acid Z2.

32. The cell of paragraph 27, wherein the N-terminal tail polypeptide, $(AA)_m$, or the C-terminal tail polypeptide, $(AA)_p$, or both, in the precursor polypeptides of formula (I), formula (II), or formula (V) comprise(s) an intein selected from the group consisting of a naturally occurring intein, an engineered variant of a naturally occurring intein, a fusion of the N-terminal and C-terminal fragments of a naturally occurring split intein and a fusion of the N-terminal and C-terminal fragments of an engineered split intein.

33. The cell of paragraph 32, wherein the intein is selected from the group consisting of Mxe GyrA (SEQ ID NO:1), eDnaB (SEQ ID NO:2), Hsp-NRC1 CDC21 (SEQ ID NO:3), Ceu C1pP (SEQ ID NO:4), Tag Pol-1 (SEQ ID NO:5), Tfu Pol-1 (SEQ ID NO:6), Tko Pol-1 (SEQ ID NO:7), Psp-GBD Pol (SEQ ID NO:8), Tag Pol-2 (SEQ ID NO:9), Thy Pol-1 (SEQ ID NO:10), Tko Pol-2 (SEQ ID NO:11), Tli Pol-1 (SEQ ID NO:12), Tma Pol (SEQ ID NO:13), Tsp-GE8 Pol-1 (SEQ ID NO:14), Tthi Pol (SEQ ID NO:15), Tag Pol-3 (SEQ ID NO:16), Tfu Pol-2 (SEQ ID NO:17), Thy Pol-2 (SEQ ID NO:18), Tli Pol-2 (SEQ ID NO:19), Tsp-GE8 Pol-2 (SEQ ID NO:20), Pab Pol-II (SEQ ID NO:21), Mtu-CDC1551 DnaB (SEQ ID NO:22), Mtu-H37Rv DnaB (SEQ ID NO:23), Rma DnaB (SEQ ID NO:24), Ter DnaE-1 (SEQ ID NO:25), Ssp GyrB (SEQ ID NO:26), Mfl GyrA (SEQ ID NO:27), Mgo GyrA (SEQ ID NO:28), Mkas GyrA (SEQ ID NO:29), Mle-TN GyrA (SEQ ID NO:30), Mma GyrA (SEQ ID NO:31), Ssp DnaX (SEQ ID NO:32), Pab Lon (SEQ ID NO:33), Mja PEP (SEQ ID NO:34), Afu-FRR0163 PRP8 (SEQ ID NO:35), Ani-FG-SCA4 PRP8 (SEQ ID NO:36), Cne-A PRP8 (SEQ ID NO:37), Hca PRP8 (SEQ ID NO:38), Pch PRP8 (SEQ ID NO:39), Pex PRP8 (SEQ ID NO:40), Pvu PRP8 (SEQ ID NO:41), Mtu-H37Rv RecA (SEQ ID NO:42), Mtu-So93 RecA (SEQ ID NO:43), Mfl RecA (SEQ ID NO:44), Mle-TN RecA (SEQ ID NO:45), Nsp-PCC7120 RIR1 (SEQ ID NO:46), Ter RIR1-1 (SEQ ID NO:47), Pab RIR1-1 (SEQ ID NO:48), Pfu RIR1-1 (SEQ ID NO:49), Chy RIR1 (SEQ ID NO:50), Mth RIR1 (SEQ ID NO:51), Pab RIR1-3 (SEQ ID NO:52), Pfu RIR1-2 (SEQ ID NO:53), Ter RIR1-2 (SEQ ID NO:54), Ter RIR1-4 (SEQ ID NO:55), CIV RIR1 (SEQ ID NO:56), Ctr VMA (SEQ ID NO:57), Sce VMA (SEQ ID NO:58), Tac-ATCC25905 VMA (SEQ ID NO:59), Ssp DnaB (SEQ ID NO:60), engineered variant(s) thereof, and engineered variant(s) thereof wherein the N-terminal cysteine or serine residue of the engineered variant is mutated to any natural (or naturally occurring) amino acid residue other than cysteine or serine, or wherein the C-terminal asparagine residue of the engineered variant is mutated to any natural (or naturally occurring) amino acid residue other than asparagine.

34. The cell of paragraph 32, wherein the intein is a fusion product of a split intein selected from the group consisting of Ssp DnaE (SEQ ID NO:61-SEQ ID NO:62), Neq Pol (SEQ ID NO:63-SEQ ID NO:64), Asp DnaE (SEQ ID NO:65-SEQ ID NO:66), Npu-PCC73102 DnaE (SEQ ID NO:67-SEQ ID NO:68), Nsp-PCC7120 DnaE (SEQ ID NO:69-SEQ ID NO:70), Oli DnaE (SEQ ID NO:71-SEQ ID NO:72), Ssp-PCC7002 DnaE (SEQ ID NO:73-SEQ ID NO:74), Tvu DnaE (SEQ ID NO:75-SEQ ID NO:76), engineered variant(s) thereof, engineered variant(s) thereof, wherein the N-terminal cysteine or serine residue of the split intein N-domain of the engineered variant is mutated to any natural (or naturally occurring) amino acid residue other than cysteine or serine, or wherein the C-terminal asparagine residue of the split intein C-domain of the engineered variant is mutated to any natural (or naturally occurring) amino acid residue other than asparagine.

35. The cell of paragraph 32, wherein the cell comprises a macrocyclic peptide produced by:

a thioether bond-forming reaction between the cysteine (Cys) residue and the $FG_1$ functional group in the amino acid Z or between the cysteine (Cys) residues and the $FG_1$ and $FG_2$ functional groups in the amino acid Z2, and an intein-catalyzed N-terminal splicing, C-terminal splicing, or self-splicing reaction.

36. The cell of paragraph 27, wherein:

the N-terminal tail polypeptide, $(AA)_m$, comprises the C-domain of a naturally occurring split intein, or of an engineered variant thereof, and the C-terminal tail polypeptide, $(AA)_p$, comprises the N-domain of said split intein.

37. The cell of paragraph 36, wherein the split intein C-domain is selected from the group consisting of Ssp DnaE-c (SEQ ID NO:62), Neq Pol-c (SEQ ID NO:64), Asp DnaE-c (SEQ ID NO:66), Npu-PCC73102 DnaE-c (SEQ ID NO:68), Nsp-PCC7120 DnaE-c (SEQ ID NO:70), Oli DnaE-c (SEQ ID NO:72), Ssp-PCC7002 DnaE-c (SEQ ID NO:74), Tvu DnaE-c (SEQ ID NO:76), and engineered variant(s) thereof; and the split intein N-domain is selected from the group consisting of Ssp DnaE-n (SEQ ID NO:61), Neq Pol-n (SEQ ID NO:63), Asp DnaE-n (SEQ ID NO:65), Npu-PCC73102 DnaE-n (SEQ ID NO:67), Nsp-PCC7120 DnaE-n (SEQ ID NO:69), Oli DnaE-n (SEQ ID NO:71), Ssp-PCC7002 DnaE-n (SEQ ID NO:73), Tvu DnaE-n (SEQ ID NO:75), and engineered variant(s) thereof.

38. The cell of paragraph 36, wherein the cell comprises a polycyclic peptide produced by:

a thioether bond-forming reaction between the cysteine (Cys) residue and the FG1 functional group in the amino acid Z or between the cysteine (Cys) residues and the FG1 and FG2 functional groups in the amino acid Z2, and a split intein-catalyzed trans-splicing reaction.

REFERENCES

Abbas, A., B. G. Xing, et al. (2014). Angewandte Chemie-International Edition 53(29): 7491-7494.

Anderson, J. C., N. Wu, et al. (2004). Proc Natl Acad Sci USA 101(20): 7566-7571.

Bessho, Y., D. R. Hodgson, et al. (2002). Nat Biotechnol 20(7): 723-728.

Chatterjee, A., S. B. Sun, et al. (2013). Biochemistry 52(10): 1828-1837.

Cheng, L., T. A. Naumann, et al. (2007). Protein Sci. 16(8): 1535-1542.

Dedkova, L. M., N. E. Fahmi, et al. (2003). Journal of the American Chemical Society 125(22): 6616-6617.

Deiters, A. and P. G. Schultz (2005). Bioorg Med Chem Lett 15(5): 1521-1524.

Dias, R. L. A., R. Fasan, et al. (2006). J. Am. Chem. Soc. 128(8): 2726-2732.

Driggers, E. M., S. P. Hale, et al. (2008). Nat Rev Drug Discov 7(7): 608-624.

Elleuche, S. and S. Poggeler (2010). Appl Microbiol Biotechnol 87(2): 479-489.

Fairlie, D. P., J. D. A. Tyndall, et al. (2000). J. Med. Chem. 43(7): 1271-1281.

Fekner, T. and M. K. Chan (2011). Current Opinion in Chemical Biology 15(3): 387-391.

Frost, J. R., J. M. Smith, et al. (2013). Curr Opin Struct Biol 23(4): 571-580.

Frost, J. R., F. Vitali, et al. (2013). Chembiochem 14(1): 147-160.

Giebel, L. B., R. T. Cass, et al. (1995). Biochemistry 34(47): 15430-15435.

Hamamoto, T., M. Sisido, et al. (2011). Chem Commun (Camb) 47(32): 9116-9118.

Hartman, M. C., K. Josephson, et al. (2007). PLoS One 2(10): e972.

Hartman, M. C., K. Josephson, et al. (2006). Proc Natl Acad Sci USA 103(12): 4356-4361.

Heinis, C., T. Rutherford, et al. (2009). Nat Chem Biol 5(7): 502-507.

Henchey, L. K., J. R. Porter, et al. (2010). Chembiochem 11(15): 2104-2107.

Horswill, A. R., S. N. Savinov, et al. (2004). Proc Natl Acad Sci USA 101(44): 15591-15596.

Josephson, K., M. C. Hartman, et al. (2005). J Am Chem Soc 127(33): 11727-11735.

Katsara, M., T. Tselios, et al. (2006). Curr Med Chem 13(19): 2221-2232.

Katz, B. A. (1995). Biochemistry 34(47): 15421-15429.

Klabunde, T., S. Sharma, et al. (1998). Nat. Struct. Biol. 5(1): 31-36.

Kobayashi, T., O. Nureki, et al. (2003). Nat. Struct. Biol. 10(6): 425-432.

Kourouklis, D., H. Murakami, et al. (2005). Methods 36(3): 239-244.

Lane, D. P. and C. W. Stephen (1993). Curr. Opin. Immunol. 5: 268-271.

Lang, K. and J. W. Chin (2014). Chem. Rev. 114(9): 4764-4806.

Liu, C. C. and P. G. Schultz (2010). Annu. Rev. Biochem. 79: 413-444.

Marsault, E. and M. L. Peterson (2011). Journal of Medicinal Chemistry 54(7): 1961-2004.

Millward, S. W., T. T. Takahashi, et al. (2005). J Am Chem Soc 127(41): 14142-14143.

Mootz, H. D. (2009). Chembiochem 10(16): 2579-2589.

Murakami, H., A. Ohta, et al. (2006). Nat Methods 3(5): 357-359.

Naumann, T. A., S. N. Savinov, et al. (2005). Biotechnol Bioeng 92(7): 820-830.

Naumann, T. A., A. Tavassoli, et al. (2008). Chembiochem 9(2): 194-197.

Neumann, H., A. L. Slusarczyk, et al. (2010). J Am Chem Soc 132(7): 2142-2144.

Neumann, H., K. Wang, et al. (2010). Nature 464(7287): 441-444.

Obrecht, D., J. A. Robinson, et al. (2009). Current Medicinal Chemistry 16(1): 42-65.

Paulus, H. (2000). Annual Review of Biochemistry 69: 447-496.

Perler, F. B. (2005). IUBMB Life 57(7): 469-476.

Rezai, T., J. E. Bock, et al. (2006). Journal of the American Chemical Society 128(43): 14073-14080.

Rezai, T., B. Yu, et al. (2006). Journal of the American Chemical Society 128(8): 2510-2511.

Rodriguez, E. A., H. A. Lester, et al. (2006). Proc Natl Acad Sci USA 103(23): 8650-8655.

Sachdeva, A., K. Wang, et al. (2014). Journal of the American Chemical Society 136(22): 7785-7788.

Schlippe, Y. V., M. C. Hartman, et al. (2012). J Am Chem Soc 134(25): 10469-10477.

Scott, C. P., E. Abel-Santos, et al. (2001). Chem Biol 8(8): 801-815.

Scott, C. P., E. Abel-Santos, et al. (1999). Proc Natl Acad Sci USA 96(24): 13638-13643.

Seebeck, F. P. and J. W. Szostak (2006). J Am Chem Soc 128(22): 7150-7151.

Sidhu, S. S., H. B. Lowman, et al. (2000). Methods Enzymol. 328: 333-363.

Smith, J. M., J. R. Frost, et al. (2013). J Org Chem 78(8): 3525-3531.

Smith, J. M., F. Vitali, et al. (2011). Angew Chem Int Ed 50(22): 5075-5080.

Tang, Y. Q., J. Yuan, et al. (1999). Science 286(5439): 498-502.
Tavassoli, A. and S. J. Benkovic (2005). Angew Chem Int Ed Engl 44(18): 2760-2763.
Tavassoli, A. and S. J. Benkovic (2007). Nat. Protoc. 2(5): 1126-1133.
Tavassoli, A., Q. Lu, et al. (2008). ACS Chem Biol 3(12): 757-764.
Touati, J., A. Angelini, et al. (2011). Chembiochem 12(1): 38-42.
Walensky, L. D., A. L. Kung, et al. (2004). Science 305 (5689): 1466-1470.
Wan, W., Y. Huang, et al. (2010). Angew Chem Int Ed. 49(18): 3211-3214.
Wang, D., W. Liao, et al. (2005). Angew Chem Int Ed Engl 44(40): 6525-6529.
Wang, L., J. Xie, et al. (2006). Annu Rev Biophys Biomol Struct 35: 225-249.
White, C. J. and A. K. Yudin (2011). Nat Chem 3(7): 509-524.
Wu, X. and P. G. Schultz (2009). J Am Chem Soc 131(35): 12497-12515.
Xu, M. Q. and T. C. Evans, Jr. (2005). Curr Opin Biotechnol 16(4): 440-446.
Xu, M. Q. and F. B. Perler (1996). Embo Journal 15(19): 5146-5153.
Young, D. D., T. S. Young, et al. (2011). Biochemistry 50(11): 1894-1900.
Young, T. S., D. D. Young, et al. (2011). Proc Natl Acad Sci USA 108(27): 11052-11056.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for making a macrocyclic peptide, the method comprising:

(a) providing an artificial nucleic acid molecule encoding for a polypeptide of structure:

$$(AA)_m\text{-Z-}(AA)_n\text{-Cys-}(AA)_p \quad (I)$$

or $$(AA)_m\text{-Cys-}(AA)_n\text{-Z-}(AA)_p \quad (II)$$

or $$(AA)_m\text{-Cys-}(AA)_n\text{-Z2-}(AA)_o\text{-Cys-}(AA)_p \quad (V)$$

wherein:

(i) $(AA)_m$ is an N-terminal amino acid or peptide sequence, (ii) Z is a non-canonical amino acid carrying a side-chain functional group $FG_1$, $FG_1$ being a functional group selected from the group consisting of $-(CH_2)_nX$, where X is F, Cl, Br, or I and n is an integer number from 1 to 10; —$C(O)CH_2X$, where X is F, Cl, Br, or I; —CH(R')X, where X is F, Cl, Br, or I; —C(O)CH(R')X, where X is F, Cl, Br, or I; —$OCH_2CH_2X$, where X is F, Cl, Br, or I; —C(O)CH═C═C(R')(R"); —$SO_2C(R')$═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$; —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R' and R" is independently H, an aliphatic, a substituted aliphatic, an aryl, or a substituted aryl group, (iii) Z2 is a non-canonical amino acid carrying two side-chain functional groups $FG_1$ and $FG_2$, wherein each of $FG_1$ and $FG_2$ is a functional group independently selected from the group consisting of —$(CH_2)_nX$, where X is F, Cl, Br, or I and n is an integer number from 1 to 10; —$C(O)CH_2X$, where X is F, Cl, Br, or I; —CH(R')X, where X is F, Cl, Br, or I; —C(O)CH(R')X, where X is F, Cl, Br, or I; —$OCH_2CH_2X$, where X is F, Cl, Br, or I; —C(O)CH═C═C(R')(R"); —$SO_2C(R')$═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$; —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R' and R" is independently H, an aliphatic, a substituted aliphatic, an aryl, or a substituted aryl group, (iv) $(AA)_n$ is a target peptide sequence, (v) $(AA)_o$ is a second target peptide sequence, and (vi) $(AA)_p$ is a C-terminal amino acid or peptide sequence;

(b) introducing the nucleic acid molecule into an expression system, wherein the expression system is an in vivo cell system, and wherein the in vivo cell system comprises:

an aminoacyl-tRNA synthetase selected from the group consisting of SEQ ID NOs: 77, 78, 79, 80, 81, 82, 83, 84, 85, 86, 87, 88, 89, 90, 91, 92, 93, 94, 95, 96, 97, 98, 99 and 100; and a transfer RNA molecule encoded by a polynucleotide selected from the group consisting of SEQ ID NOs: 101, 102, 103, 104, 105, 106, 107, 108, 109, 110, 111, 112, 113, 114, 115, 116, 117, 118, 119, and 120; and expressing the nucleic acid molecule in the in vivo cell system, thereby producing the polypeptide; and (c) cyclizing the polypeptide via nucleophilic substitution of a peptide side group by a cysteine sulfhydryl group, wherein the cyclizing comprises allowing the functional group $FG_1$, and whenever present, $FG_2$, to react with the side-chain sulfhydryl group (—SH) of the cysteine (Cys) residue(s) in the in vivo cell system, thereby producing the macrocyclic peptide in the in vivo cell system.

2. The method of claim 1 wherein Z is an amino acid of structure:

(III)

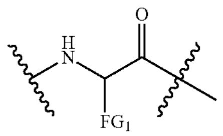

or (IV)

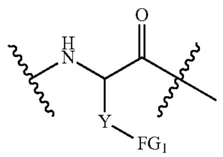

wherein $FG_1$ is a functional group selected from the group consisting of —$(CH_2)_nX$, where X is F, Cl, Br, or I and n is an integer number from 1 to 10; —$C(O)CH_2X$, where X is F, Cl, Br, or I; —CH(R')X, where X is F, Cl, Br, or I; —C(O)CH(R')X, where X is F, Cl, Br, or I; —$OCH_2CH_2X$, where X is F, Cl, Br, or I; —C(O)CH═C═C(R')(R"); —$SO_2C(R')$═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$; —C≡C—C(O)OR'; —C≡C—C(O)N(R')(R"); unsubstituted or substituted oxirane, unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide; where each R' and R" is independently H, an aliphatic, a substituted aliphatic, an aryl, or a substituted aryl group;

wherein Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups.

3. The method of claim 1 wherein the amino acid Z is selected from the group consisting of 4-(2-bromoethoxy)-phenylalanine, 3-(2-bromoethoxy)-phenylalanine, 4-(2-chloroethoxy)-phenylalanine, 3-(2-chloroethoxy)-phenylalanine, 4-(1-bromoethyl)-phenylalanine, 3-(1-bromoethyl)-phenylalanine, 4-(aziridin-1-yl)-phenylalanine, 3-(aziridin-1-yl)-phenylalanine, 4-acrylamido-phenylalanine, 3-acrylamido-phenylalanine, 4-(2-fluoro-acetamido)-phenylalanine, 3-(2-fluoro-acetamido)-phenylalanine, 4-(2-chloro-acetamido)-phenylalanine, 3-(2-chloro-acetamido)-phenylalanine, 3-(2-fluoro-acetyl)-phenylalanine, 4-(2-fluoro-acetyl)-phenylalanine, $N^{\varepsilon}$-((2-bromoethoxy)carbonyl)-lysine, $N^{\varepsilon}$-((2-chloroethoxy)carbonyl)-lysine, $N^{\varepsilon}$-(buta-2,3-dienoyl)-lysine, $N^{\varepsilon}$-acryl-lysine, $N^{\varepsilon}$-crotonyl-lysine, $N^{\varepsilon}$-(2-fluoro-acetyl)-lysine, and $N^{\varepsilon}$-(2-chloro-acetyl)-lysine.

4. The method of claim 1 wherein Z2 is an amino acid of structure:

(VI)

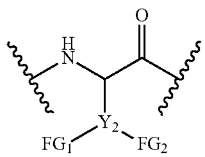

or

-continued (VII)

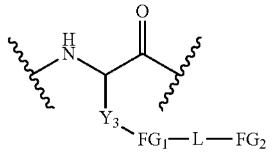

wherein each of $FG_1$ and $FG_2$ is a functional group independently selected from the group consisting of —$(CH_2)_nX$, where X is F, Cl, Br, or I and n is an integer number from 1 to 10; —$C(O)CH_2X$, where X is F, Cl, Br, or I; —CH(R')X, where X is F, Cl, Br, or I; —C(O)CH(R')X, where X is F, Cl, Br, or I; —$OCH_2CH_2X$, where X is F, Cl, Br, or I; —C(O)CH═C═C(R')(R"); —$SO_2C$(R')═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$, —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R' and R" is independently H, an aliphatic, a substituted aliphatic, an aryl, or a substituted aryl group;

wherein $Y_2$, $Y_3$, and L are linker groups selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups.

5. The method of claim 1 wherein the codon encoding for Z or Z2 is an amber stop codon TAG, an ochre stop codon TAA, an opal stop codon TGA, or a four base codon.

6. The method of claim 1, wherein the N-terminal tail polypeptide, $(AA)_m$, or the C-terminal tail polypeptide, $(AA)_p$, or both, of the precursor polypeptides of formula (I), (II), or (V) comprise(s):

a polypeptide affinity tag, a DNA-binding polypeptide, a protein-binding polypeptide, an enzyme, a fluorescent protein, an intein protein, or a combination thereof.

7. The method of claim 1, wherein the N-terminal tail polypeptide, $(AA)_m$, of the precursor polypeptide of formula (I), (II), or (V) comprises the C-domain of a split intein, and the C-terminal tail polypeptide, $(AA)_p$, comprises the corresponding N-domain of the split intein.

8. The method of claim 1 wherein the in vivo cell system is selected from the group consisting of a prokaryotic cell system and an eukaryotic cell system.

9. The method of claim 8 wherein the prokaryotic cell is *Escherichia coli.*

10. The method of claim 8 wherein the eukaryotic cell is a yeast, a mammalian, an insect or a plant cell.

11. The method of claim 1 wherein any of polypeptides $(AA)_n$, $(AA)_o$, $(AA)_m$, or $(AA)_p$, is fully or partially genetically randomized so that a plurality of macrocyclic peptides is obtained upon a thioether bond-forming reaction between the cysteine (Cys) residue and the side-chain functional group $FG_1$ in Z or between the cysteine (Cys) residues and the side-chain functional groups $FG_1$ and $FG_2$ in Z2.

12. The method of claim 1 comprising:

fully or partially randomizing any of polypeptides $(AA)_n$, $(AA)_o$, $(AA)_m$, or $(AA)_p$, wherein, upon a thioether bond-forming reaction between the cysteine (Cys) residue and the side-chain functional group $FG_1$ in Z or between the cysteine (Cys) residues and the side-chain functional groups $FG_1$ and $FG_2$ in Z2, a plurality of macrocyclic peptides is produced.

13. An isolated recombinant host cell comprising a polypeptide of structure:

$(AA)_m$-Z-$(AA)_n$-Cys-$(AA)_p$ (I)

or $(AA)_m$-Cys-$(AA)_n$-Z-$(AA)_p$ (II)

or $(AA)_m$-Cys-$(AA)_n$-Z2-$(AA)_o$-Cys-$(AA)_p$ (V)

wherein:

(i) $(AA)_m$ is an N-terminal amino acid or peptide sequence, (ii) Z is an amino acid of structure:

(III)

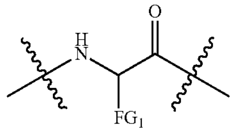

or (IV)

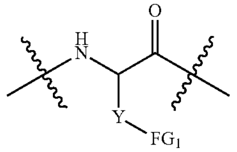

wherein $FG_1$ is a functional group selected from the group consisting of —$(CH_2)_nX$, where X is F, Cl, Br, or I and n is an integer number from 1 to 10; —$C(O)CH_2X$, where X is F, Cl, Br, or I; —CH(R')X, where X is F, Cl, Br, or I; —C(O)CH(R')X, where X is F, Cl, Br, or I; —$OCH_2CH_2X$, where X is F, Cl, Br, or I; —C(O)CH═C═C(R')(R"); —$SO_2C$(R')═C(R')(R"); —C(O)C(R')═C(R')(R"); —C(R')═C(R')C(O)OR'; —C(R')═C(R')C(O)N(R')(R"); —C(R')═C(R')—CN; —C(R')═C(R')—$NO_2$; —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide; where each R' and R" is independently H, an aliphatic, a substituted aliphatic, an aryl, or a substituted aryl group;

wherein Y is a linker group selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups, (iii) Z2 is an amino acid of structure:

(VI)

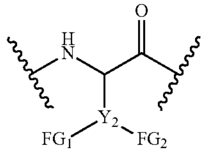

or

-continued (VII)

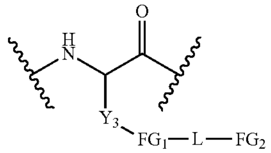

wherein each of $FG_1$ and $FG_2$ is a functional group independently selected from the group consisting of $—(CH_2)_nX$, where X is F, Cl, Br, or I and n is an integer number from 1 to 10; $—C(O)CH_2X$, where X is F, Cl, Br, or I; —CH(R')X, where X is F, Cl, Br, or I; —C(O)CH(R')X, where X is F, Cl, Br, or I; $—OCH_2CH_2X$, where X is F, Cl, Br, or I; —C(O)CH═C═C(R')(R"); $—SO_2C(R')═C(R')(R")$; —C(O)C(R')═C(R')(R"); —C(R')═C(R')C(O)OR'; —C(R')═C(R')C(O)N(R')(R"); —C(R')═C(R')—CN; $—C(R')═C(R')—NO_2$; —C≡C—C(O)OR'; —C≡C—C(O)N(R')(R"); unsubstituted or substituted oxirane; unsubstituted or substituted aziridine; 1,2-oxathiolane 2,2-dioxide; 4-fluoro-1,2-oxathiolane 2,2-dioxide; and 4,4-difluoro-1,2-oxathiolane 2,2-dioxide, where each R' and R" is independently H, an aliphatic, a substituted aliphatic, an aryl, or a substituted aryl group; and wherein $Y_2$, $Y_3$, L are linker groups selected from the group consisting of aliphatic, aryl, substituted aliphatic, substituted aryl, heteroatom-containing aliphatic, heteroatom-containing aryl, substituted heteroatom-containing aliphatic, substituted heteroatom-containing aryl, alkoxy, and aryloxy groups, (iv) $(AA)_n$ is a target peptide sequence, (v) $(AA)_o$ is a second target peptide sequence, and (vi) $(AA)_p$ is a C-terminal amino acid or peptide sequence.

14. The cell of claim 13, wherein the amino acid Z is selected from the group consisting of 4-(2-bromoethoxy)-phenylalanine, 3-(2-bromoethoxy)-phenylalanine, 4-(2-chloroethoxy)-phenylalanine, 3-(2-chloroethoxy)-phenylalanine, 4-(1-bromoethyl)-phenylalanine, 3-(1-bromoethyl)-phenylalanine, 4-(aziridin-1-yl)-phenylalanine, 3-(aziridin-1-yl)-phenylalanine, 4-acrylamido-phenylalanine, 3-acrylamido-phenylalanine, 4-(2-fluoro-acetamido)-phenylalanine, 3-(2-fluoro-acetamido)-phenylalanine, 4-(2-chloro-acetamido)-phenylalanine, 3-(2-chloro-acetamido)-phenylalanine, 3-(2-fluoro-acetyl)-phenylalanine, 4-(2-fluoro-acetyl)-phenylalanine, $N^{\varepsilon}$-((2-bromoethoxy)carbonyl)-lysine, $N^{\varepsilon}$-((2-chloroethoxy)carbonyl)-lysine, $N^{\varepsilon}$-(buta-2,3-dienoyl)-lysine, $N^{\varepsilon}$-acryl-lysine, $N^{\varepsilon}$-crotonyl-lysine, $N^{\varepsilon}$-(2-fluoro-acetyl)-lysine, and $N^{\varepsilon}$-(2-chloro-acetyl)-lysine.

15. The cell of claim 13 wherein the amino acid Z2 is selected from the group consisting of 3,5-bis(2-bromoethoxy)-phenylalanine, 3,5-bis(2-chloroethoxy)-phenylalanine, 3,5-bis(1-bromoethyl)-phenylalanine, 3,5-bis(aziridin-1-yl)-phenylalanine, 3,5-bis-acrylamido-phenylalanine, 3,5-bis(2-fluoro-acetamido)-phenylalanine, 3,5-bis(2-fluoro-acetyl)-phenylalanine, 4-((1,3-dibromopropan-2-yl)oxy)-phenylalanine, 4-((1,3-dichloropropan-2-yl)oxy)-phenylalanine, $N^{\varepsilon}$-(((1,3-dibromopropan-2-yl)oxy)carbonyl)-lysine, $N^{\varepsilon}$-(((1,3-dichloropropan-2-yl)oxy)carbonyl)-lysine, 4-(2,3-dibromopropoxy)-phenylalanine, 3-(2,3-dibromopropoxy)-phenylalanine, 4-(2,3-dichloropropoxy)-phenylalanine, 3-(2,3-dichloropropoxy)-phenylalanine, $N^{\varepsilon}$-((2,3-dibromopropoxy)carbonyl)-lysine, and $N^{\varepsilon}$-((2,3-dichloropropoxy)carbonyl)-lysine.

16. The cell of claim 13, wherein the polypeptide comprised within the N-terminal tail polypeptide, $(AA)_m$, or the C-terminal tail polypeptide, $(AA)_p$, or both, of the precursor polypeptides of formula (I), (II), and (V), is a polypeptide selected from the group of polypeptides consisting of SEQ ID NOs, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, and 158.

17. The cell of claim 13, wherein the N-terminal tail polypeptide, $(AA)_m$, or the C-terminal tail polypeptide, $(AA)_p$, or both, in the precursor polypeptides of formula (I), formula (II), or formula (V) comprise(s) an intein selected from the group consisting of a naturally occurring intein, an engineered variant of a naturally occurring intein, a fusion of the N-terminal and C-terminal fragments of a naturally occurring split intein and a fusion of the N-terminal and C-terminal fragments of an engineered split intein.

18. The cell of claim 13, wherein:

the N-terminal tail polypeptide, $(AA)_m$, comprises the C-domain of a naturally occurring split intein, or of an engineered variant thereof, and the C-terminal tail polypeptide, $(AA)_p$, comprises the N-domain of said split intein.

* * * * *

SEQUENCE LISTING

```
<160> NUMBER OF SEQ ID NOS: 189

<210> SEQ ID NO 1
<211> LENGTH: 198
<212> TYPE: PRT
<213> ORGANISM: Mycobacterium xenopi

<400> SEQUENCE: 1

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95

Ile Lys Pro Gly Asp Tyr Ala Val Ile Gln Arg Ser Ala Phe Ser Val
            100                 105                 110

Asp Cys Ala Gly Phe Ala Arg Gly Lys Pro Glu Phe Ala Pro Thr Thr
        115                 120                 125

Tyr Thr Val Gly Val Pro Gly Leu Val Arg Phe Leu Glu Ala His His
    130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175
```

```
Val Tyr Ser Leu Arg Val Asp Thr Ala Asp His Ala Phe Ile Thr Asn
            180                 185                 190

Gly Phe Val Ser His Asn
        195
```

<210> SEQ ID NO 2
<211> LENGTH: 154
<212> TYPE: PRT
<213> ORGANISM: Artificial Sequence
<220> FEATURE:
<223> OTHER INFORMATION: synthetic or artificial sequence

<400> SEQUENCE: 2

```
Cys Ile Ser Gly Asp Ser Leu Ile Ser Leu Ala Ser Thr Gly Lys Arg
1               5                   10                  15

Val Ser Ile Lys Asp Leu Leu Asp Glu Lys Asp Phe Glu Ile Trp Ala
            20                  25                  30

Ile Asn Glu Gln Thr Met Lys Leu Glu Ser Ala Lys Val Ser Arg Val
        35                  40                  45

Phe Cys Thr Gly Lys Lys Leu Val Tyr Ile Leu Lys Thr Arg Leu Gly
    50                  55                  60

Arg Thr Ile Lys Ala Thr Ala Asn His Arg Phe Leu Thr Ile Asp Gly
65                  70                  75                  80

Trp Lys Arg Leu Asp Glu Leu Ser Leu Lys Glu His Ile Ala Leu Pro
                85                  90                  95

Arg Lys Leu Glu Ser Ser Ser Leu Gln Leu Ser Pro Glu Ile Glu Lys
            100                 105                 110

Leu Ser Gln Ser Asp Ile Tyr Trp Asp Ser Ile Val Ser Ile Thr Glu
        115                 120                 125

Thr Gly Val Glu Glu Val Phe Asp Leu Thr Val Pro Gly Pro His Asn
    130                 135                 140

Phe Val Ala Asn Asp Ile Ile Val His Asn
145                 150
```

<210> SEQ ID NO 3
<211> LENGTH: 182
<212> TYPE: PRT
<213> ORGANISM: Halobacterium sp. NRC1

<400> SEQUENCE: 3

```
Cys Val Arg Gly Asp Thr Thr Val Ala Leu Ala Asp Gly Ser Glu Arg
1               5                   10                  15

Glu Ile Arg Asp Leu Val Glu Ala Asn Leu Asp Asp Pro Arg Pro Val
            20                  25                  30

Asp Asp Gly Val Trp Asp Gly Val Asp Val Ala Val Pro Ser Leu Ala
        35                  40                  45

Ala Asp Gly Arg Leu Val Gln Arg Arg Ala Thr Lys Val Trp Lys Arg
    50                  55                  60

Glu Ala Pro Glu Thr Met Tyr Arg Val Arg Thr Ala Ala Gly His Arg
65                  70                  75                  80

Leu Thr Val Thr Pro Ser His Pro Leu Phe Val Ala Gly Ser His Gly
                85                  90                  95

Pro Asp Ala Val Arg Thr Glu Asp Leu Glu Val Gly Gln Leu Val Gly
            100                 105                 110

Val Ala Pro Asp Gly Asp Gly Ser Gly Gln Val Ala Pro Asp Gly Gly
        115                 120                 125
```

-continued

```
Val Ile Arg Asp Ala Gln Pro Ala Pro Val Gly Asp Ala Glu Thr Val
    130                 135                 140

Ala Trp Ser Ala Ile Glu Ser Ile Thr Glu Val Glu Pro Asp Glu Glu
145                 150                 155                 160

Trp Val Tyr Asp Leu Glu Val Glu Gly Thr His Ser Tyr Leu Thr Asp
                165                 170                 175

Gly Val Val Ser His Asn
            180


<210> SEQ ID NO 4
<211> LENGTH: 456
<212> TYPE: PRT
<213> ORGANISM: Chlamydomonas eugametos

<400> SEQUENCE: 4

Cys Leu Thr Ser Asp His Thr Val Leu Thr Thr Arg Gly Trp Ile Pro
1               5                   10                  15

Ile Ala Asp Val Thr Leu Asp Asp Lys Val Ala Val Leu Asp Asn Asn
            20                  25                  30

Thr Gly Glu Met Ser Tyr Gln Asn Pro Gln Lys Val His Lys Tyr Asp
        35                  40                  45

Tyr Glu Gly Pro Met Tyr Glu Val Lys Thr Ala Gly Val Asp Leu Phe
    50                  55                  60

Val Thr Pro Asn His Arg Met Tyr Val Asn Thr Thr Asn Asn Thr Thr
65                  70                  75                  80

Asn Gln Asn Tyr Asn Leu Val Glu Ala Ser Ser Ile Phe Gly Lys Lys
                85                  90                  95

Val Arg Tyr Lys Asn Asp Ala Ile Trp Asn Lys Thr Asp Tyr Gln Phe
            100                 105                 110

Ile Leu Pro Glu Thr Ala Thr Leu Thr Gly His Thr Asn Lys Ile Ser
        115                 120                 125

Ser Thr Pro Ala Ile Gln Pro Glu Met Asn Ala Trp Leu Thr Phe Phe
    130                 135                 140

Gly Leu Trp Ile Ala Asn Gly His Thr Thr Lys Ile Ala Glu Lys Thr
145                 150                 155                 160

Ala Glu Asn Asn Gln Gln Lys Gln Arg Tyr Lys Val Ile Leu Thr Gln
                165                 170                 175

Val Lys Glu Asp Val Cys Asp Ile Ile Glu Gln Thr Leu Asn Lys Leu
            180                 185                 190

Gly Phe Asn Phe Ile Arg Ser Gly Lys Asp Tyr Thr Ile Glu Asn Lys
        195                 200                 205

Gln Leu Trp Ser Tyr Leu Asn Pro Phe Asp Asn Gly Ala Leu Asn Lys
    210                 215                 220

Tyr Leu Pro Asp Trp Val Trp Glu Leu Ser Ser Gln Gln Cys Lys Ile
225                 230                 235                 240

Leu Leu Asn Ser Leu Cys Leu Gly Asn Cys Leu Phe Thr Lys Asn Asp
                245                 250                 255

Asp Thr Leu His Tyr Phe Ser Thr Ser Glu Arg Phe Ala Asn Asp Val
            260                 265                 270

Ser Arg Leu Ala Leu His Ala Gly Thr Thr Ser Thr Ile Gln Leu Glu
        275                 280                 285

Ala Ala Pro Ser Asn Leu Tyr Asp Thr Ile Ile Gly Leu Pro Val Glu
    290                 295                 300

Val Asn Thr Thr Leu Trp Arg Val Ile Ile Asn Gln Ser Ser Phe Tyr
305                 310                 315                 320
```

```
Ser Tyr Ser Thr Asp Lys Ser Ser Ala Leu Asn Leu Ser Asn Asn Val
                325                 330                 335

Ala Cys Tyr Val Asn Ala Gln Ser Ala Leu Thr Leu Glu Gln Asn Ser
            340                 345                 350

Gln Lys Ile Asn Lys Asn Thr Leu Val Leu Thr Lys Asn Asn Val Lys
        355                 360                 365

Ser Gln Thr Met His Ser Gln Arg Ala Glu Arg Val Asp Thr Ala Leu
    370                 375                 380

Leu Thr Gln Lys Glu Leu Asp Asn Ser Leu Asn His Glu Ile Leu Ile
385                 390                 395                 400

Asn Lys Asn Pro Gly Thr Ser Gln Leu Glu Cys Val Val Asn Pro Glu
                405                 410                 415

Val Asn Asn Thr Ser Thr Asn Asp Arg Phe Val Tyr Tyr Lys Gly Pro
            420                 425                 430

Val Tyr Cys Leu Thr Gly Pro Asn Asn Val Phe Tyr Val Gln Arg Asn
        435                 440                 445

Gly Lys Ala Val Trp Thr Gly Asn
    450                 455


<210> SEQ ID NO 5
<211> LENGTH: 360
<212> TYPE: PRT
<213> ORGANISM: Thermococcus aggregans

<400> SEQUENCE: 5

Cys His Pro Ala Asp Thr Lys Val Ile Val Lys Gly Lys Gly Ile Val
1               5                   10                  15

Asn Ile Ser Asp Val Lys Glu Gly Asp Tyr Ile Leu Gly Ile Asp Gly
            20                  25                  30

Trp Gln Arg Val Lys Lys Val Trp Lys Tyr His Tyr Glu Gly Lys Leu
        35                  40                  45

Ile Asn Ile Asn Gly Leu Lys Cys Thr Pro Asn His Lys Val Pro Val
    50                  55                  60

Val Thr Glu Asn Asp Arg Gln Thr Arg Ile Arg Asp Ser Leu Ala Lys
65                  70                  75                  80

Ser Phe Leu Ser Gly Lys Val Lys Gly Lys Ile Ile Thr Thr Lys Leu
                85                  90                  95

Phe Glu Lys Ile Ala Glu Phe Glu Lys Asn Lys Pro Ser Glu Glu Glu
            100                 105                 110

Ile Leu Lys Gly Glu Leu Ser Gly Ile Ile Leu Ala Glu Gly Thr Leu
        115                 120                 125

Leu Arg Lys Asp Ile Glu Tyr Phe Asp Ser Ser Arg Gly Lys Lys Arg
    130                 135                 140

Ile Ser His Gln Tyr Arg Val Glu Ile Thr Ile Gly Glu Asn Glu Lys
145                 150                 155                 160

Glu Leu Leu Glu Arg Ile Leu Tyr Ile Phe Asp Lys Leu Phe Gly Ile
                165                 170                 175

Arg Pro Ser Val Lys Lys Lys Gly Asp Thr Asn Ala Leu Lys Ile Thr
            180                 185                 190

Thr Ala Lys Lys Ala Val Tyr Leu Gln Ile Glu Glu Leu Leu Lys Asn
        195                 200                 205

Ile Glu Ser Leu Tyr Ala Pro Ala Val Leu Arg Gly Phe Phe Glu Arg
    210                 215                 220

Asp Ala Thr Val Asn Lys Ile Arg Ser Thr Ile Val Val Thr Gln Gly
```

-continued

```
225                 230                 235                 240

Thr Asn Asn Lys Trp Lys Ile Asp Ile Val Ala Lys Leu Leu Asp Ser
                245                 250                 255

Leu Gly Ile Pro Tyr Ser Arg Tyr Glu Tyr Lys Tyr Ile Glu Asn Gly
            260                 265                 270

Lys Glu Leu Thr Lys His Ile Leu Glu Ile Thr Gly Arg Asp Gly Leu
        275                 280                 285

Ile Leu Phe Gln Thr Leu Val Gly Phe Ile Ser Ser Glu Lys Asn Glu
    290                 295                 300

Ala Leu Glu Lys Ala Ile Glu Val Arg Glu Met Asn Arg Leu Lys Asn
305                 310                 315                 320

Asn Ser Phe Tyr Asn Leu Ser Thr Phe Glu Val Ser Ser Glu Tyr Tyr
                325                 330                 335

Lys Gly Glu Val Tyr Asp Leu Thr Leu Glu Gly Asn Pro Tyr Tyr Phe
            340                 345                 350

Ala Asn Gly Ile Leu Thr His Asn
        355                 360


<210> SEQ ID NO 6
<211> LENGTH: 360
<212> TYPE: PRT
<213> ORGANISM: Thermococcus fumicolans

<400> SEQUENCE: 6

Cys His Pro Ala Asp Thr Lys Val Ile Val Lys Gly Lys Gly Val Val
1               5                   10                  15

Asn Ile Ser Glu Val Arg Glu Gly Asp Tyr Val Leu Gly Ile Asp Gly
            20                  25                  30

Trp Gln Lys Val Gln Arg Val Trp Glu Tyr Asp Tyr Glu Gly Glu Leu
        35                  40                  45

Val Asn Ile Asn Gly Leu Lys Cys Thr Pro Asn His Lys Leu Pro Val
    50                  55                  60

Val Arg Arg Thr Glu Arg Gln Thr Ala Ile Arg Asp Ser Leu Ala Lys
65                  70                  75                  80

Ser Phe Leu Thr Lys Lys Val Lys Gly Lys Leu Ile Thr Thr Pro Leu
                85                  90                  95

Phe Glu Lys Ile Gly Lys Ile Glu Arg Glu Asp Val Pro Glu Glu Glu
            100                 105                 110

Ile Leu Lys Gly Glu Leu Ala Gly Ile Ile Leu Ala Glu Gly Thr Leu
        115                 120                 125

Leu Arg Lys Asp Val Glu Tyr Phe Asp Ser Ser Arg Gly Lys Lys Arg
    130                 135                 140

Val Ser His Gln Tyr Arg Val Glu Ile Thr Val Gly Ala Gln Glu Glu
145                 150                 155                 160

Asp Phe Gln Arg Arg Ile Val Tyr Ile Phe Glu Arg Leu Phe Gly Val
                165                 170                 175

Thr Pro Ser Val Tyr Arg Lys Lys Asn Thr Asn Ala Ile Thr Phe Lys
            180                 185                 190

Val Ala Lys Lys Glu Val Tyr Leu Arg Val Arg Glu Ile Met Asp Gly
        195                 200                 205

Ile Glu Asn Leu His Ala Pro Ser Val Leu Arg Gly Phe Phe Glu Gly
    210                 215                 220

Asp Gly Ser Val Asn Lys Val Arg Lys Thr Val Val Val Asn Gln Gly
225                 230                 235                 240
```

```
Thr Asn Asn Glu Trp Lys Ile Glu Val Val Ser Lys Leu Leu Asn Lys
                245                 250                 255

Leu Gly Ile Pro His Arg Arg Tyr Thr Tyr Asp Tyr Thr Glu Arg Glu
            260                 265                 270

Lys Thr Met Thr Thr His Ile Leu Glu Ile Ala Gly Arg Asp Gly Leu
        275                 280                 285

Ile Leu Phe Gln Thr Ile Val Gly Phe Ile Ser Thr Glu Lys Asn Met
    290                 295                 300

Ala Leu Glu Glu Ala Ile Arg Asn Arg Glu Val Asn Arg Leu Glu Asn
305                 310                 315                 320

Asn Ala Phe Tyr Thr Leu Ala Asp Phe Thr Ala Lys Thr Glu Tyr Tyr
                325                 330                 335

Lys Gly Lys Val Tyr Asp Leu Thr Leu Glu Gly Thr Pro Tyr Tyr Phe
            340                 345                 350

Ala Asn Gly Ile Leu Thr His Asn
        355                 360


<210> SEQ ID NO 7
<211> LENGTH: 360
<212> TYPE: PRT
<213> ORGANISM: Thermococcus kodakaraensis

<400> SEQUENCE: 7

Cys His Pro Ala Asp Thr Lys Val Val Val Lys Gly Lys Gly Ile Ile
1               5                   10                  15

Asn Ile Ser Glu Val Gln Glu Gly Asp Tyr Val Leu Gly Ile Asp Gly
            20                  25                  30

Trp Gln Arg Val Arg Lys Val Trp Glu Tyr Asp Tyr Lys Gly Glu Leu
        35                  40                  45

Val Asn Ile Asn Gly Leu Lys Cys Thr Pro Asn His Lys Leu Pro Val
    50                  55                  60

Val Thr Lys Asn Glu Arg Gln Thr Arg Ile Arg Asp Ser Leu Ala Lys
65                  70                  75                  80

Ser Phe Leu Thr Lys Lys Val Lys Gly Lys Ile Ile Thr Thr Pro Leu
                85                  90                  95

Phe Tyr Glu Ile Gly Arg Ala Thr Ser Glu Asn Ile Pro Glu Glu Glu
            100                 105                 110

Val Leu Lys Gly Glu Leu Ala Gly Ile Leu Leu Ala Glu Gly Thr Leu
        115                 120                 125

Leu Arg Lys Asp Val Glu Tyr Phe Asp Ser Ser Arg Lys Lys Arg Arg
    130                 135                 140

Ile Ser His Gln Tyr Arg Val Glu Ile Thr Ile Gly Lys Asp Glu Glu
145                 150                 155                 160

Glu Phe Arg Asp Arg Ile Thr Tyr Ile Phe Glu Arg Leu Phe Gly Ile
                165                 170                 175

Thr Pro Ser Ile Ser Glu Lys Lys Gly Thr Asn Ala Val Thr Leu Lys
            180                 185                 190

Val Ala Lys Lys Asn Val Tyr Leu Lys Val Lys Glu Ile Met Asp Asn
        195                 200                 205

Ile Glu Ser Leu His Ala Pro Ser Val Leu Arg Gly Phe Phe Glu Gly
    210                 215                 220

Asp Gly Ser Val Asn Arg Val Arg Arg Ser Ile Val Ala Thr Gln Gly
225                 230                 235                 240

Thr Lys Asn Glu Trp Lys Ile Lys Leu Val Ser Lys Leu Leu Ser Gln
                245                 250                 255
```

```
Leu Gly Ile Pro His Gln Thr Tyr Thr Tyr Gln Tyr Gln Glu Asn Gly
            260                 265                 270

Lys Asp Arg Ser Arg Tyr Ile Leu Glu Ile Thr Gly Lys Asp Gly Leu
        275                 280                 285

Ile Leu Phe Gln Thr Leu Ile Gly Phe Ile Ser Glu Arg Lys Asn Ala
    290                 295                 300

Leu Leu Asn Lys Ala Ile Ser Gln Arg Glu Met Asn Asn Leu Glu Asn
305                 310                 315                 320

Asn Gly Phe Tyr Arg Leu Ser Glu Phe Asn Val Ser Thr Glu Tyr Tyr
                325                 330                 335

Glu Gly Lys Val Tyr Asp Leu Thr Leu Glu Gly Thr Pro Tyr Tyr Phe
            340                 345                 350

Ala Asn Gly Ile Leu Thr His Asn
        355                 360


<210> SEQ ID NO 8
<211> LENGTH: 537
<212> TYPE: PRT
<213> ORGANISM: Pyrococcus sp. GBD

<400> SEQUENCE: 8

Ser Ile Leu Pro Glu Glu Trp Val Pro Leu Ile Lys Asn Gly Lys Val
1               5                   10                  15

Lys Ile Phe Arg Ile Gly Asp Phe Val Asp Gly Leu Met Lys Ala Asn
            20                  25                  30

Gln Gly Lys Val Lys Lys Thr Gly Asp Thr Glu Val Leu Glu Val Ala
        35                  40                  45

Gly Ile His Ala Phe Ser Phe Asp Arg Lys Ser Lys Lys Ala Arg Val
    50                  55                  60

Met Ala Val Lys Ala Val Ile Arg His Arg Tyr Ser Gly Asn Val Tyr
65                  70                  75                  80

Arg Ile Val Leu Asn Ser Gly Arg Lys Ile Thr Ile Thr Glu Gly His
                85                  90                  95

Ser Leu Phe Val Tyr Arg Asn Gly Asp Leu Val Glu Ala Thr Gly Glu
            100                 105                 110

Asp Val Lys Ile Gly Asp Leu Leu Ala Val Pro Arg Ser Val Asn Leu
        115                 120                 125

Pro Glu Lys Arg Glu Arg Leu Asn Ile Val Glu Leu Leu Leu Asn Leu
    130                 135                 140

Ser Pro Glu Glu Thr Glu Asp Ile Ile Leu Thr Ile Pro Val Lys Gly
145                 150                 155                 160

Arg Lys Asn Phe Phe Lys Gly Met Leu Arg Thr Leu Arg Trp Ile Phe
                165                 170                 175

Gly Glu Glu Lys Arg Val Arg Thr Ala Ser Arg Tyr Leu Arg His Leu
            180                 185                 190

Glu Asn Leu Gly Tyr Ile Arg Leu Arg Lys Ile Gly Tyr Asp Ile Ile
        195                 200                 205

Asp Lys Glu Gly Leu Glu Lys Tyr Arg Thr Leu Tyr Glu Lys Leu Val
    210                 215                 220

Asp Val Val Arg Tyr Asn Gly Asn Lys Arg Glu Tyr Leu Val Glu Phe
225                 230                 235                 240

Asn Ala Val Arg Asp Val Ile Ser Leu Met Pro Glu Glu Glu Leu Lys
                245                 250                 255

Glu Trp Arg Ile Gly Thr Arg Asn Gly Phe Arg Met Gly Thr Phe Val
```

```
            260                 265                 270

Asp Ile Asp Glu Asp Phe Ala Lys Leu Leu Gly Tyr Tyr Val Ser Glu
        275                 280                 285

Gly Ser Ala Arg Lys Trp Lys Asn Gln Thr Gly Gly Trp Ser Tyr Thr
    290                 295                 300

Val Arg Leu Tyr Asn Glu Asn Asp Glu Val Leu Asp Asp Met Glu His
305                 310                 315                 320

Leu Ala Lys Lys Phe Phe Gly Lys Val Lys Arg Gly Lys Asn Tyr Val
                325                 330                 335

Glu Ile Pro Lys Lys Met Ala Tyr Ile Ile Phe Glu Ser Leu Cys Gly
            340                 345                 350

Thr Leu Ala Glu Asn Lys Arg Val Pro Glu Val Ile Phe Thr Ser Ser
        355                 360                 365

Lys Gly Val Arg Trp Ala Phe Leu Glu Gly Tyr Phe Ile Gly Asp Gly
    370                 375                 380

Asp Val His Pro Ser Lys Arg Val Arg Leu Ser Thr Lys Ser Glu Leu
385                 390                 395                 400

Leu Val Asn Gly Leu Val Leu Leu Leu Asn Ser Leu Gly Val Ser Ala
                405                 410                 415

Ile Lys Leu Gly Tyr Asp Ser Gly Val Tyr Arg Val Tyr Val Asn Glu
            420                 425                 430

Glu Leu Lys Phe Thr Glu Tyr Arg Lys Lys Lys Asn Val Tyr His Ser
        435                 440                 445

His Ile Val Pro Lys Asp Ile Leu Lys Glu Thr Phe Gly Lys Val Phe
    450                 455                 460

Gln Lys Asn Ile Ser Tyr Lys Lys Phe Arg Glu Leu Val Glu Asn Gly
465                 470                 475                 480

Lys Leu Asp Arg Glu Lys Ala Lys Arg Ile Glu Trp Leu Leu Asn Gly
                485                 490                 495

Asp Ile Val Leu Asp Arg Val Val Glu Ile Lys Arg Glu Tyr Tyr Asp
            500                 505                 510

Gly Tyr Val Tyr Asp Leu Ser Val Asp Glu Asp Glu Asn Phe Leu Ala
        515                 520                 525

Gly Phe Gly Phe Leu Tyr Ala His Asn
    530                 535


<210> SEQ ID NO 9
<211> LENGTH: 538
<212> TYPE: PRT
<213> ORGANISM: Thermococcus aggregans
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid

<400> SEQUENCE: 9

Ser Ile Leu Pro Asn Glu Trp Leu Pro Ile Ile Glu Asn Gly Glu Val
1               5                   10                  15

Lys Phe Val Lys Ile Gly Glu Phe Ile Asp Arg Tyr Met Glu Glu Gln
            20                  25                  30

Lys Asp Lys Val Arg Thr Val Asp Asn Thr Glu Val Leu Glu Val Asp
        35                  40                  45

Asn Ile Phe Ala Phe Ser Leu Asn Lys Glu Ser Lys Lys Ser Glu Ile
```

-continued

```
    50                  55                  60

Lys Lys Val Lys Ala Leu Ile Arg His Lys Tyr Lys Gly Glu Ala Tyr
65                  70                  75                  80

Glu Val Glu Leu Asn Ser Gly Arg Lys Ile His Ile Thr Arg Gly His
                85                  90                  95

Ser Leu Phe Thr Ile Arg Asn Gly Lys Ile Lys Glu Ile Trp Gly Glu
            100                 105                 110

Glu Val Lys Val Gly Asp Leu Ile Ile Val Pro Lys Lys Val Lys Leu
        115                 120                 125

Asn Glu Lys Glu Ala Val Ile Asn Ile Pro Glu Leu Ile Ser Lys Leu
    130                 135                 140

Pro Asp Glu Asp Thr Ala Asp Val Val Met Thr Thr Pro Val Lys Gly
145                 150                 155                 160

Arg Lys Asn Phe Phe Lys Gly Met Leu Arg Thr Leu Lys Trp Ile Phe
                165                 170                 175

Gly Glu Glu Ser Lys Arg Ile Arg Thr Phe Asn Arg Tyr Leu Phe His
            180                 185                 190

Leu Glu Glu Leu Gly Phe Val Lys Leu Leu Pro Arg Gly Tyr Glu Val
        195                 200                 205

Thr Asp Trp Glu Gly Leu Lys Arg Tyr Arg Gln Leu Tyr Glu Lys Leu
    210                 215                 220

Val Lys Asn Leu Arg Tyr Asn Gly Asn Lys Arg Glu Tyr Leu Val Arg
225                 230                 235                 240

Phe Asn Asp Ile Lys Asp Ser Val Ser Cys Phe Pro Arg Lys Glu Leu
                245                 250                 255

Glu Glu Trp Lys Ile Gly Thr Xaa Lys Gly Phe Arg Xaa Lys Cys Ile
            260                 265                 270

Leu Lys Val Asp Glu Asp Phe Gly Lys Phe Leu Gly Tyr Tyr Val Ser
        275                 280                 285

Glu Gly Tyr Ala Gly Ala Gln Lys Asn Lys Thr Gly Gly Met Ser Tyr
    290                 295                 300

Ser Val Lys Leu Tyr Asn Glu Asn Pro Asn Val Leu Lys Asp Met Lys
305                 310                 315                 320

Asn Ile Ala Glu Lys Phe Phe Gly Lys Val Arg Val Gly Lys Asn Cys
                325                 330                 335

Val Asp Ile Pro Lys Lys Met Ala Tyr Leu Leu Ala Lys Ser Leu Cys
            340                 345                 350

Gly Val Thr Ala Glu Asn Lys Arg Ile Pro Ser Ile Ile Phe Asp Ser
        355                 360                 365

Ser Glu Pro Val Arg Trp Ala Phe Leu Arg Ala Tyr Phe Val Gly Asp
    370                 375                 380

Gly Asp Ile His Pro Ser Lys Arg Leu Arg Leu Ser Thr Lys Ser Glu
385                 390                 395                 400

Leu Leu Ala Asn Gln Leu Val Phe Leu Leu Asn Ser Leu Gly Val Ser
                405                 410                 415

Ser Ile Lys Ile Gly Phe Asp Ser Gly Val Tyr Arg Val Tyr Ile Asn
            420                 425                 430

Glu Asp Leu Pro Phe Leu Gln Thr Ser Arg Gln Lys Asn Thr Tyr Tyr
        435                 440                 445

Pro Asn Leu Ile Pro Lys Glu Val Leu Glu Glu Ile Phe Gly Arg Lys
    450                 455                 460

Phe Gln Lys Asn Ile Thr Phe Glu Lys Phe Lys Glu Leu Ala Asp Ser
465                 470                 475                 480
```

```
Gly Lys Leu Asp Lys Arg Lys Val Lys Leu Leu Asp Phe Leu Leu Asn
                485                 490                 495

Gly Asp Ile Val Leu Asp Arg Val Lys Asn Val Glu Lys Arg Glu Tyr
            500                 505                 510

Glu Gly Tyr Val Tyr Asp Leu Ser Val Glu Asp Asn Glu Asn Phe Leu
        515                 520                 525

Val Gly Phe Gly Leu Leu Tyr Ala His Asn
    530                 535


<210> SEQ ID NO 10
<211> LENGTH: 537
<212> TYPE: PRT
<213> ORGANISM: Thermococcus hydrothermalis

<400> SEQUENCE: 10

Ser Leu Leu Pro Glu Glu Trp Ile Pro Leu Val Glu Asn Gly Lys Val
1               5                   10                  15

Arg Leu His Arg Ile Gly Glu Phe Val Asp Lys Leu Met Glu Thr Asp
            20                  25                  30

Ser Glu Leu Val Lys Arg Asn Gly Asp Thr Glu Val Leu Glu Val Arg
        35                  40                  45

Gly Ile Arg Ala Leu Ser Phe Asp Arg Lys Ser Lys Lys Ala Arg Val
    50                  55                  60

Met Pro Val Lys Ala Val Ile Arg His Arg Tyr Ser Gly Asp Val Tyr
65                  70                  75                  80

Glu Ile Val Leu Gly Ser Gly Arg Arg Ile Thr Val Thr Glu Gly His
                85                  90                  95

Ser Leu Phe Ala Tyr Gly Asp Gly Glu Leu Arg Glu Val Thr Gly Gly
            100                 105                 110

Glu Ile Lys Ala Gly Asp Leu Leu Ala Val Pro Arg Arg Val Asn Leu
        115                 120                 125

Pro Glu Lys Lys Glu Arg Leu Asn Leu Val Glu Leu Leu Arg Arg Leu
    130                 135                 140

Pro Glu Glu Glu Thr Gly Asp Ile Ile Leu Thr Ile Pro Val Lys Gly
145                 150                 155                 160

Arg Lys Asn Phe Phe Lys Gly Met Leu Arg Thr Leu Arg Trp Ile Ser
                165                 170                 175

Gly Glu Glu Lys Arg Pro Arg Thr Ala Arg Arg Tyr Leu Glu His Leu
            180                 185                 190

Glu Gly Leu Gly Tyr Val Arg Leu Lys Lys Ile Gly Tyr Glu Val Thr
        195                 200                 205

Asp Arg Glu Gly Leu Glu Arg Tyr Arg Lys Leu Tyr Glu Arg Leu Val
    210                 215                 220

Glu Ala Val Arg Tyr Asn Gly Asn Lys Arg Glu Tyr Leu Val Glu Phe
225                 230                 235                 240

Asn Ala Val Arg Asp Val Ile Ala Leu Met Pro Glu Glu Glu Leu Arg
                245                 250                 255

Asp Trp Leu Val Gly Thr Arg Asn Gly Phe Arg Met Arg Pro Phe Val
            260                 265                 270

Glu Ile Glu Glu Asp Phe Ala Lys Leu Leu Gly Tyr Tyr Val Ser Glu
        275                 280                 285

Gly Asn Ala Arg Lys Trp Arg Asn Gln Lys Asn Gly Trp Ser Tyr Thr
    290                 295                 300

Val Lys Leu Tyr Asn Glu Asn Gln Arg Val Leu Asp Asp Met Glu Ser
```

```
305                 310                 315                 320

Leu Ala Glu Arg Phe Phe Gly Arg Val Lys Arg Gly Lys Asn Tyr Ile
                325                 330                 335

Glu Ile Pro Arg Lys Met Ala Tyr Ile Ile Phe Glu Asn Leu Cys Gly
            340                 345                 350

Thr Leu Ala Glu Asn Lys Arg Val Pro Glu Ala Ile Phe Thr Ser Pro
        355                 360                 365

Glu Ser Val Arg Trp Ala Phe Ile Glu Gly Tyr Phe Ile Gly Asp Gly
    370                 375                 380

Asp Val His Pro Ser Lys Arg Val Arg Leu Ser Thr Lys Ser Glu Leu
385                 390                 395                 400

Leu Val Asn Gly Leu Val Leu Leu Leu Asn Ser Leu Gly Val Ser Ala
                405                 410                 415

Ile Lys Ile Arg His Asp Ser Gly Val Tyr Arg Val Tyr Val Asn Glu
            420                 425                 430

Glu Leu Pro Phe Thr Asp Tyr Arg Lys Lys Lys Asn Ala Tyr Tyr Ser
        435                 440                 445

His Val Ile Pro Lys Glu Ile Leu Glu Glu Thr Phe Gly Lys Val Phe
    450                 455                 460

Gln Arg Ser Val Ser Tyr Glu Lys Phe Arg Glu Leu Val Lys Ser Glu
465                 470                 475                 480

Lys Leu Asp Gly Glu Lys Ala Lys Arg Ile Glu Trp Leu Leu Asn Gly
                485                 490                 495

Asp Val Val Leu Asp Lys Val Leu Glu Val Lys Lys Arg Pro Tyr Glu
            500                 505                 510

Gly Tyr Val Tyr Asp Leu Ser Val Glu Glu Asp Glu Asn Phe Leu Ala
        515                 520                 525

Gly Phe Gly Leu Leu Tyr Ala His Asn
    530                 535


<210> SEQ ID NO 11
<211> LENGTH: 536
<212> TYPE: PRT
<213> ORGANISM: Thermococcus kodakaraensis

<400> SEQUENCE: 11

Ser Ile Leu Pro Glu Glu Trp Leu Pro Val Leu Glu Glu Gly Glu Val
1               5                   10                  15

His Phe Val Arg Ile Gly Glu Leu Ile Asp Arg Met Met Glu Glu Asn
            20                  25                  30

Ala Gly Lys Val Lys Arg Glu Gly Glu Thr Glu Val Leu Glu Val Ser
        35                  40                  45

Gly Leu Glu Val Pro Ser Phe Asn Arg Arg Thr Asn Lys Ala Glu Leu
    50                  55                  60

Lys Arg Val Lys Ala Leu Ile Arg His Asp Tyr Ser Gly Lys Val Tyr
65                  70                  75                  80

Thr Ile Arg Leu Lys Ser Gly Arg Arg Ile Lys Ile Thr Ser Gly His
                85                  90                  95

Ser Leu Phe Ser Val Arg Asn Gly Glu Leu Val Glu Val Thr Gly Asp
            100                 105                 110

Glu Leu Lys Pro Gly Asp Leu Val Ala Val Pro Arg Arg Leu Glu Leu
        115                 120                 125

Pro Glu Arg Asn His Val Leu Asn Leu Val Glu Leu Leu Leu Gly Thr
    130                 135                 140
```

-continued

```
Pro Glu Glu Glu Thr Leu Asp Ile Val Met Thr Ile Pro Val Lys Gly
145                 150                 155                 160

Lys Lys Asn Phe Phe Lys Gly Met Leu Arg Thr Leu Arg Trp Ile Phe
                165                 170                 175

Gly Glu Glu Lys Arg Pro Arg Thr Ala Arg Arg Tyr Leu Arg His Leu
            180                 185                 190

Glu Asp Leu Gly Tyr Val Arg Leu Lys Lys Ile Gly Tyr Glu Val Leu
        195                 200                 205

Asp Trp Asp Ser Leu Lys Asn Tyr Arg Arg Leu Tyr Glu Ala Leu Val
    210                 215                 220

Glu Asn Val Arg Tyr Asn Gly Asn Lys Arg Glu Tyr Leu Val Glu Phe
225                 230                 235                 240

Asn Ser Ile Arg Asp Ala Val Gly Ile Met Pro Leu Lys Glu Leu Lys
                245                 250                 255

Glu Trp Lys Ile Gly Thr Leu Asn Gly Phe Arg Met Arg Lys Leu Ile
            260                 265                 270

Glu Val Asp Glu Ser Leu Ala Lys Leu Leu Gly Tyr Tyr Val Ser Glu
        275                 280                 285

Gly Tyr Ala Arg Lys Gln Arg Asn Pro Lys Asn Gly Trp Ser Tyr Ser
    290                 295                 300

Val Lys Leu Tyr Asn Glu Asp Pro Glu Val Leu Asp Asp Met Glu Arg
305                 310                 315                 320

Leu Ala Ser Arg Phe Phe Gly Lys Val Arg Arg Gly Arg Asn Tyr Val
                325                 330                 335

Glu Ile Pro Lys Lys Ile Gly Tyr Leu Leu Phe Glu Asn Met Cys Gly
            340                 345                 350

Val Leu Ala Glu Asn Lys Arg Ile Pro Glu Phe Val Phe Thr Ser Pro
        355                 360                 365

Lys Gly Val Arg Leu Ala Phe Leu Glu Gly Tyr Ser Ser Ala Met Ala
    370                 375                 380

Thr Ser Thr Glu Gln Glu Thr Gln Ala Leu Asn Glu Lys Arg Ala Leu
385                 390                 395                 400

Ala Asn Gln Leu Val Leu Leu Leu Asn Ser Val Gly Val Ser Ala Val
                405                 410                 415

Lys Leu Gly His Asp Ser Gly Val Tyr Arg Val Tyr Ile Asn Glu Glu
            420                 425                 430

Leu Pro Phe Val Lys Leu Asp Lys Lys Lys Asn Ala Tyr Tyr Ser His
        435                 440                 445

Val Ile Pro Lys Glu Val Leu Ser Glu Val Phe Gly Lys Val Phe Gln
    450                 455                 460

Lys Asn Val Ser Pro Gln Thr Phe Arg Lys Met Val Glu Asp Gly Arg
465                 470                 475                 480

Leu Asp Pro Glu Lys Ala Gln Arg Leu Ser Trp Leu Ile Glu Gly Asp
                485                 490                 495

Val Val Leu Asp Arg Val Glu Ser Val Asp Val Glu Asp Tyr Asp Gly
            500                 505                 510

Tyr Val Tyr Asp Leu Ser Val Glu Asp Asn Glu Asn Phe Leu Val Gly
        515                 520                 525

Phe Gly Leu Val Tyr Ala His Asn
    530                 535
```

<210> SEQ ID NO 12
<211> LENGTH: 538
<212> TYPE: PRT

-continued

<213> ORGANISM: Thermococcus litoralis

<400> SEQUENCE: 12

Ser Ile Leu Pro Asn Glu Trp Leu Pro Ile Ile Glu Asn Gly Glu Ile
1 5 10 15

Lys Phe Val Lys Ile Gly Glu Phe Ile Asn Ser Tyr Met Glu Lys Gln
20 25 30

Lys Glu Asn Val Lys Thr Val Glu Asn Thr Glu Val Leu Glu Val Asn
35 40 45

Asn Leu Phe Ala Phe Ser Phe Asn Lys Lys Ile Lys Glu Ser Glu Val
50 55 60

Lys Lys Val Lys Ala Leu Ile Arg His Lys Tyr Lys Gly Lys Ala Tyr
65 70 75 80

Glu Ile Gln Leu Ser Ser Gly Arg Lys Ile Asn Ile Thr Ala Gly His
85 90 95

Ser Leu Phe Thr Val Arg Asn Gly Glu Ile Lys Glu Val Ser Gly Asp
100 105 110

Gly Ile Lys Glu Gly Asp Leu Ile Val Ala Pro Lys Lys Ile Lys Leu
115 120 125

Asn Glu Lys Gly Val Ser Ile Asn Ile Pro Glu Leu Ile Ser Asp Leu
130 135 140

Ser Glu Glu Glu Thr Ala Asp Ile Val Met Thr Ile Ser Ala Lys Gly
145 150 155 160

Arg Lys Asn Phe Phe Lys Gly Met Leu Arg Thr Leu Arg Trp Met Phe
165 170 175

Gly Glu Glu Asn Arg Arg Ile Arg Thr Phe Asn Arg Tyr Leu Phe His
180 185 190

Leu Glu Lys Leu Gly Leu Ile Lys Leu Leu Pro Arg Gly Tyr Glu Val
195 200 205

Thr Asp Trp Glu Arg Leu Lys Lys Tyr Lys Gln Leu Tyr Glu Lys Leu
210 215 220

Ala Gly Ser Val Lys Tyr Asn Gly Asn Lys Arg Glu Tyr Leu Val Met
225 230 235 240

Phe Asn Glu Ile Lys Asp Phe Ile Ser Tyr Phe Pro Gln Lys Glu Leu
245 250 255

Glu Glu Trp Lys Ile Gly Thr Leu Asn Gly Phe Arg Thr Asn Cys Ile
260 265 270

Leu Lys Val Asp Glu Asp Phe Gly Lys Leu Leu Gly Tyr Tyr Val Ser
275 280 285

Glu Gly Tyr Ala Gly Ala Gln Lys Asn Lys Thr Gly Gly Ile Ser Tyr
290 295 300

Ser Val Lys Leu Tyr Asn Glu Asp Pro Asn Val Leu Glu Ser Met Lys
305 310 315 320

Asn Val Ala Glu Lys Phe Phe Gly Lys Val Arg Val Asp Arg Asn Cys
325 330 335

Val Ser Ile Ser Lys Lys Met Ala Tyr Leu Val Met Lys Cys Leu Cys
340 345 350

Gly Ala Leu Ala Glu Asn Lys Arg Ile Pro Ser Val Ile Leu Thr Ser
355 360 365

Pro Glu Pro Val Arg Trp Ser Phe Leu Glu Ala Tyr Phe Thr Gly Asp
370 375 380

Gly Asp Ile His Pro Ser Lys Arg Phe Arg Leu Ser Thr Lys Ser Glu
385 390 395 400

-continued

```
Leu Leu Ala Asn Gln Leu Val Phe Leu Leu Asn Ser Leu Gly Ile Ser
                405                 410                 415

Ser Val Lys Ile Gly Phe Asp Ser Gly Val Tyr Arg Val Tyr Ile Asn
            420                 425                 430

Glu Asp Leu Gln Phe Pro Gln Thr Ser Arg Glu Lys Asn Thr Tyr Tyr
        435                 440                 445

Ser Asn Leu Ile Pro Lys Glu Ile Leu Arg Asp Val Phe Gly Lys Glu
    450                 455                 460

Phe Gln Lys Asn Met Thr Phe Lys Lys Phe Lys Glu Leu Val Asp Ser
465                 470                 475                 480

Gly Lys Leu Asn Arg Glu Lys Ala Lys Leu Leu Glu Phe Phe Ile Asn
                485                 490                 495

Gly Asp Ile Val Leu Asp Arg Val Lys Ser Val Lys Glu Lys Asp Tyr
            500                 505                 510

Glu Gly Tyr Val Tyr Asp Leu Ser Val Glu Asp Asn Glu Asn Phe Leu
        515                 520                 525

Val Gly Phe Gly Leu Leu Tyr Ala His Asn
    530                 535


<210> SEQ ID NO 13
<211> LENGTH: 537
<212> TYPE: PRT
<213> ORGANISM: Thermococcus marinus

<400> SEQUENCE: 13

Ser Leu Leu Pro Glu Glu Trp Ile Pro Val Val Glu Asn Gly Lys Val
1               5                   10                  15

Lys Leu Val Arg Ile Gly Glu Phe Val Asp Gly Leu Met Lys Asp Glu
            20                  25                  30

Lys Gly Arg Ala Lys Arg Asp Gly Asn Thr Glu Val Leu Glu Val Ser
        35                  40                  45

Gly Ile Arg Ala Val Ser Phe Asp Arg Lys Thr Lys Lys Ala Arg Leu
    50                  55                  60

Met Pro Val Lys Ala Val Ile Arg His Arg Tyr Ser Gly Asp Val Tyr
65                  70                  75                  80

Lys Ile Thr Leu Ser Ser Gly Arg Lys Ile Thr Val Thr Lys Gly His
                85                  90                  95

Ser Leu Phe Ala Tyr Arg Asn Gly Glu Leu Val Glu Val Pro Gly Glu
            100                 105                 110

Glu Ile Lys Ala Gly Asp Leu Leu Ala Val Pro Arg Arg Val His Leu
        115                 120                 125

Pro Glu Arg Tyr Glu Arg Leu Asp Leu Val Glu Leu Leu Leu Lys Leu
    130                 135                 140

Pro Glu Glu Glu Thr Glu Asp Ile Ile Leu Thr Ile Pro Ala Lys Gly
145                 150                 155                 160

Arg Lys Asn Phe Phe Lys Gly Met Leu Arg Thr Leu Arg Trp Ile Phe
                165                 170                 175

Gly Glu Glu Lys Arg Pro Arg Thr Ala Arg Arg Tyr Leu Arg His Leu
            180                 185                 190

Glu Gly Leu Gly Tyr Val Lys Leu Arg Lys Ile Gly Tyr Glu Ile Ile
        195                 200                 205

Asp Arg Glu Gly Leu Lys Arg Tyr Arg Lys Leu Tyr Glu Arg Leu Ala
    210                 215                 220

Glu Val Val Arg Tyr Asn Gly Asn Lys Arg Glu Tyr Leu Ile Glu Phe
225                 230                 235                 240
```

Asn Ala Val Arg Asp Val Ile Ser Leu Met Pro Glu Glu Glu Leu Asn
245 250 255

Glu Trp Gln Val Gly Thr Arg Asn Gly Phe Arg Ile Lys Pro Leu Ile
260 265 270

Glu Val Asp Glu Asp Phe Ala Lys Leu Leu Gly Tyr Tyr Val Ser Glu
275 280 285

Gly Tyr Ala Gly Lys Gln Arg Asn Gln Lys Asn Gly Trp Ser Tyr Thr
290 295 300

Val Lys Leu Tyr Asn Glu Asp Glu Arg Val Leu Asp Asp Met Glu Asn
305 310 315 320

Leu Ala Arg Glu Phe Phe Gly Lys Ala Arg Arg Gly Arg Asn Tyr Val
325 330 335

Glu Ile Pro Arg Lys Met Ala Tyr Ile Ile Phe Glu Ser Leu Cys Gly
340 345 350

Thr Leu Ala Glu Asn Lys Arg Val Pro Glu Val Ile Phe Thr Ser Pro
355 360 365

Glu Asp Val Arg Trp Ala Phe Leu Glu Gly Tyr Phe Ile Gly Asp Gly
370 375 380

Asp Val His Pro Ser Lys Arg Val Arg Leu Ser Thr Lys Ser Glu Leu
385 390 395 400

Leu Ala Asn Gly Leu Val Leu Leu Leu Asn Ser Leu Gly Val Ser Ala
405 410 415

Val Lys Leu Gly His Asp Ser Gly Val Tyr Arg Val Tyr Val Asn Glu
420 425 430

Glu Leu Pro Phe Thr Gly Tyr Lys Lys Lys Lys Asn Ala Tyr Tyr Ser
435 440 445

His Val Ile Pro Lys Glu Val Leu Glu Glu Thr Phe Gly Lys Val Phe
450 455 460

Gln Arg Asn Met Ser Tyr Glu Lys Phe Gln Glu Leu Val Glu Ser Glu
465 470 475 480

Lys Leu Glu Gly Glu Lys Ala Lys Arg Ile Glu Trp Leu Ile Ser Gly
485 490 495

Asp Ile Ile Leu Asp Lys Val Val Glu Val Lys Lys Met Asn Tyr Glu
500 505 510

Gly Tyr Val Tyr Asp Leu Ser Val Glu Glu Asp Glu Asn Phe Leu Ala
515 520 525

Gly Phe Gly Phe Leu Tyr Ala His Asn
530 535

<210> SEQ ID NO 14
<211> LENGTH: 535
<212> TYPE: PRT
<213> ORGANISM: Thermococcus species GE8

<400> SEQUENCE: 14

Ser Ile Leu Pro Asp Glu Trp Leu Pro Leu Leu Val Asn Gly Arg Leu
1 5 10 15

Lys Leu Val Arg Ile Gly Asp Phe Val Asp Asn Thr Met Lys Lys Gly
20 25 30

Gln Pro Leu Glu Asn Asp Gly Thr Glu Val Leu Glu Val Ser Gly Ile
35 40 45

Glu Ala Ile Ser Phe Asn Arg Lys Thr Lys Ile Ala Glu Ile Lys Pro
50 55 60

Val Lys Ala Leu Ile Arg His Arg Tyr Arg Gly Lys Val Tyr Asp Ile

```
65                  70                  75                  80

Lys Leu Ser Ser Gly Arg Asn Ile Lys Val Thr Glu Gly His Ser Leu
                85                  90                  95

Phe Ala Phe Arg Asp Gly Glu Leu Val Glu Val Thr Gly Gly Glu Ile
            100                 105                 110

Lys Pro Gly Asp Phe Ile Ala Val Pro Arg Arg Val Asn Leu Pro Glu
        115                 120                 125

Arg His Glu Arg Ile Asn Leu Ile Glu Ile Leu Leu Gly Leu Pro Pro
    130                 135                 140

Glu Glu Thr Ser Asp Ile Val Leu Thr Ile Pro Val Lys Gly Arg Lys
145                 150                 155                 160

Asn Phe Phe Lys Gly Met Leu Arg Thr Leu Arg Trp Ile Phe Glu Glu
                165                 170                 175

Glu Gln Arg Pro Arg Thr Ala Arg Arg Tyr Leu Glu His Leu Gln Lys
            180                 185                 190

Leu Gly Tyr Val Lys Leu Met Lys Arg Ala Tyr Glu Ile Val Asn Lys
        195                 200                 205

Glu Ala Leu Arg Asn Tyr Arg Lys Leu Tyr Glu Val Leu Ala Glu Arg
    210                 215                 220

Val Lys Tyr Asn Gly Asn Lys Arg Glu Tyr Leu Val His Phe Asn Asp
225                 230                 235                 240

Leu Arg Asn Glu Ile Lys Phe Met Pro Asp Glu Glu Leu Glu Glu Trp
                245                 250                 255

Lys Val Gly Thr Leu Asn Gly Phe Arg Met Glu Pro Phe Ile Glu Val
            260                 265                 270

Gly Glu Asp Phe Ala Lys Leu Leu Gly Tyr Tyr Val Ser Glu Gly Tyr
        275                 280                 285

Ala Arg Lys Gln Arg Asn Gln Lys Asn Gly Trp Ser Tyr Ser Val Lys
    290                 295                 300

Ile Tyr Asn Asn Asp Gln Arg Val Leu Asp Asp Met Glu Lys Leu Ala
305                 310                 315                 320

Ser Lys Phe Phe Gly Arg Val Arg Arg Gly Lys Asn Tyr Val Glu Ile
                325                 330                 335

Ser Arg Lys Met Ala Tyr Val Leu Phe Glu Ser Leu Cys Gly Thr Leu
            340                 345                 350

Ala Glu Asn Lys Arg Val Pro Glu Val Ile Phe Thr Ser Pro Glu Ser
        355                 360                 365

Val Arg Trp Ala Phe Phe Glu Gly Tyr Phe Ile Gly Asp Gly Asp Leu
    370                 375                 380

His Pro Ser Lys Arg Val Arg Leu Ser Thr Lys Ser Glu Glu Leu Val
385                 390                 395                 400

Asn Gly Leu Val Val Leu Leu Asn Ser Leu Gly Ile Ser Ala Ile Lys
                405                 410                 415

Ile Arg Phe Asp Ser Gly Val Tyr Arg Val Leu Val Asn Glu Glu Leu
            420                 425                 430

Pro Phe Leu Gly Asn Arg Lys Arg Lys Asn Ala Tyr Tyr Ser His Val
        435                 440                 445

Ile Pro Lys Glu Ile Leu Glu Glu Thr Phe Gly Lys Gln Phe Gln Lys
    450                 455                 460

Asn Met Ser Pro Ala Lys Leu Asn Glu Lys Val Glu Lys Gly Glu Leu
465                 470                 475                 480

Asp Ala Gly Lys Ala Arg Arg Ile Ala Trp Leu Leu Glu Gly Asp Ile
                485                 490                 495
```

```
Val Leu Asp Arg Val Glu Lys Val Thr Val Glu Asp Tyr Glu Gly Tyr
            500                 505                 510

Val Tyr Asp Leu Ser Val Glu Glu Asn Glu Asn Phe Leu Ala Gly Phe
        515                 520                 525

Gly Met Leu Tyr Ala His Asn
    530                 535


<210> SEQ ID NO 15
<211> LENGTH: 536
<212> TYPE: PRT
<213> ORGANISM: Thermococcus thioreducens

<400> SEQUENCE: 15

Ser Leu Leu Pro Glu Glu Trp Val Pro Val Ile Val Gly Asp Glu Val
1               5                   10                  15

Lys Pro Val Arg Ile Gly Glu Phe Val Asp Ala Leu Met Lys Thr Asp
            20                  25                  30

Ser Glu Leu Val Arg Arg Asp Gly Asp Thr Glu Val Leu Glu Val Lys
        35                  40                  45

Glu Ile Arg Ala Leu Ser Phe Asn Arg Lys Ser Lys Lys Ala Arg Thr
    50                  55                  60

Met Pro Val Lys Ala Val Ile Arg His Arg Tyr Ala Gly Asp Val Tyr
65                  70                  75                  80

Glu Ile Val Leu Ser Ser Gly Arg Arg Ile Arg Val Thr Thr Gly His
                85                  90                  95

Ser Leu Phe Ala Tyr Arg Asn Gly Glu Leu Val Glu Ile Thr Gly Gly
            100                 105                 110

Glu Val Lys Pro Gly Asp Leu Leu Val Pro Lys Arg Val Ser Leu Pro
        115                 120                 125

Glu Arg Lys Glu Arg Leu Asp Ile Val Glu Leu Leu Leu Lys Leu Pro
    130                 135                 140

Glu Ser Glu Thr Glu Asp Ile Val Met Thr Ile Pro Val Lys Gly Arg
145                 150                 155                 160

Lys Asn Phe Phe Ser Gly Met Leu Arg Thr Leu Arg Trp Ile Phe Gly
                165                 170                 175

Glu Glu Lys Arg Leu Arg Thr Ala Arg Arg Tyr Leu Glu His Leu Glu
            180                 185                 190

Arg Leu Gly Tyr Val Lys Leu Arg Lys Ile Gly Tyr Glu Val Ile Asp
        195                 200                 205

Gly Gly Gly Leu Glu Ser Tyr Arg Lys Leu Tyr Glu Lys Leu Ala Gln
    210                 215                 220

Thr Val Arg Tyr Asn Gly Asn Arg Arg Glu Tyr Leu Val Asp Phe Asn
225                 230                 235                 240

Ala Ile Arg Asp Val Ile Pro Leu Met Pro Val Glu Glu Leu Lys Glu
                245                 250                 255

Trp Leu Ile Gly Thr Arg Asn Gly Phe Arg Met Arg Pro Phe Ile Asp
            260                 265                 270

Val Asn Glu Asp Phe Ala Lys Leu Leu Gly Tyr Tyr Val Ser Glu Gly
        275                 280                 285

Asn Ala Arg Lys Trp Lys Asn His Thr Gly Gly Trp Ser Tyr Ser Val
    290                 295                 300

Lys Leu Tyr Asn Glu Asp Glu Ser Val Leu Asp Asp Met Glu Arg Leu
305                 310                 315                 320

Ala Ser Lys Phe Phe Gly Arg Thr Arg Arg Gly Lys Asn Tyr Val Glu
```

```
                325                 330                 335

Ile Pro Arg Lys Met Ala Tyr Ile Ile Phe Glu Gly Leu Cys Gly Val
            340                 345                 350

Leu Ala Glu Asn Lys Arg Val Pro Glu Val Val Phe Thr Ser Pro Glu
        355                 360                 365

Asn Val Arg Trp Ala Phe Leu Gly Gly Tyr Phe Ile Gly Asp Gly Asp
    370                 375                 380

Val His Pro Gly Lys Arg Val Arg Leu Ser Thr Lys Ser Glu Leu Leu
385                 390                 395                 400

Val Asn Gly Leu Val Leu Leu Leu Asn Ser Leu Gly Ile Ser Ala Ile
                405                 410                 415

Lys Ile Arg His Asp Ser Gly Val His Arg Val Tyr Val Asn Glu Glu
            420                 425                 430

Leu Pro Phe Thr Glu Tyr Arg Lys Lys Lys Asn Val Tyr Tyr Ser His
        435                 440                 445

Val Ile Pro Lys Glu Val Leu Glu Glu Thr Phe Arg Lys Val Phe Gln
    450                 455                 460

Lys Asn Met Ser Arg Glu Lys Phe Arg Glu Leu Val Glu Ser Gly Lys
465                 470                 475                 480

Leu Asp Glu Glu Arg Ala Lys Arg Ile Glu Trp Leu Leu Asp Gly Asp
                485                 490                 495

Ile Ala Leu Asp Lys Val Val Glu Val Lys Arg Glu His Tyr Asp Gly
            500                 505                 510

Tyr Val Tyr Asp Leu Ser Val Glu Glu Asp Glu Asn Phe Leu Ala Gly
        515                 520                 525

Phe Gly Leu Leu Tyr Ala His Asn
    530                 535
```

<210> SEQ ID NO 16
<211> LENGTH: 157
<212> TYPE: PRT
<213> ORGANISM: Thermococcus aggregans

<400> SEQUENCE: 16

```
Ser Val Thr Gly Asp Thr Glu Ile Ile Val Lys Arg Asn Gly Arg Ile
1               5                   10                  15

Glu Phe Val Pro Ile Glu Lys Leu Phe Glu Arg Val Asp Tyr Arg Ile
            20                  25                  30

Gly Glu Lys Glu Tyr Cys Ile Leu Glu Asp Val Glu Ala Leu Thr Leu
        35                  40                  45

Asp Asn Arg Gly Lys Leu Ile Trp Lys Lys Val Pro Tyr Val Met Arg
    50                  55                  60

His Arg Ala Lys Lys Lys Val Tyr Arg Ile Trp Ile Thr Asn Ser Trp
65                  70                  75                  80

Tyr Ile Asp Val Thr Glu Asp His Ser Leu Ile Val Ala Glu Asp Gly
                85                  90                  95

Leu Lys Glu Ala Arg Pro Met Glu Ile Glu Gly Lys Ser Leu Ile Ala
            100                 105                 110

Thr Lys Asp Asp Leu Ser Gly Val Glu Tyr Ile Lys Pro His Ala Ile
        115                 120                 125

Glu Glu Ile Ser Tyr Asn Gly Tyr Val Tyr Asp Ile Glu Val Glu Gly
    130                 135                 140

Thr His Arg Phe Phe Ala Asn Gly Ile Leu Val His Asn
145                 150                 155
```

<210> SEQ ID NO 17
<211> LENGTH: 389
<212> TYPE: PRT
<213> ORGANISM: Thermococcus fumicolans

<400> SEQUENCE: 17

Ser Val Thr Gly Asp Thr Glu Val Thr Ile Arg Arg Asn Gly Arg Ile
1               5                   10                  15

Glu Phe Val Pro Ile Glu Lys Leu Phe Glu Arg Val Asp His Arg Val
            20                  25                  30

Gly Glu Lys Glu Tyr Cys Val Leu Gly Gly Val Glu Ala Leu Thr Leu
        35                  40                  45

Asp Asn Arg Gly Arg Leu Val Trp Lys Lys Val Pro Tyr Val Met Arg
    50                  55                  60

His Lys Thr Asp Lys Arg Ile Tyr Arg Val Trp Phe Thr Asn Ser Trp
65                  70                  75                  80

Tyr Leu Asp Val Thr Glu Asp His Ser Leu Ile Gly Tyr Leu Asn Thr
                85                  90                  95

Ser Lys Val Lys Pro Gly Lys Pro Leu Lys Glu Arg Leu Val Glu Val
            100                 105                 110

Lys Pro Glu Glu Leu Gly Gly Lys Val Lys Ser Leu Ile Thr Pro Asn
        115                 120                 125

Arg Pro Ile Ala Arg Thr Ile Lys Ala Asn Pro Ile Ala Val Lys Leu
    130                 135                 140

Trp Glu Leu Ile Gly Leu Leu Val Gly Asp Gly Asn Trp Gly Gly Gln
145                 150                 155                 160

Ser Asn Trp Ala Lys Tyr Tyr Val Gly Leu Ser Cys Gly Leu Asp Lys
                165                 170                 175

Ala Glu Ile Glu Arg Lys Val Leu Asn Pro Leu Arg Glu Ala Ser Val
            180                 185                 190

Ile Ser Asn Tyr Tyr Asp Lys Ser Lys Lys Gly Asp Val Ser Ile Leu
        195                 200                 205

Ser Lys Trp Leu Ala Gly Phe Met Val Lys Tyr Phe Lys Asp Glu Asn
    210                 215                 220

Gly Asn Lys Ala Ile Pro Ser Phe Met Phe Asn Leu Pro Arg Glu Tyr
225                 230                 235                 240

Ile Glu Ala Phe Leu Arg Gly Leu Phe Ser Ala Asp Gly Thr Val Ser
                245                 250                 255

Leu Arg Arg Gly Ile Pro Glu Ile Arg Leu Thr Ser Val Asn Arg Glu
            260                 265                 270

Leu Ser Asp Ala Val Arg Lys Leu Leu Trp Leu Val Gly Val Ser Asn
        275                 280                 285

Ser Leu Phe Thr Glu Thr Lys Pro Asn Arg Tyr Leu Glu Lys Glu Ser
    290                 295                 300

Gly Thr His Ser Ile His Val Arg Ile Lys Asn Lys His Arg Phe Ala
305                 310                 315                 320

Asp Arg Ile Gly Phe Leu Ile Asp Arg Lys Ser Thr Lys Leu Ser Glu
                325                 330                 335

Asn Leu Gly Gly His Thr Asn Lys Lys Arg Ala Tyr Lys Tyr Asp Phe
            340                 345                 350

Asp Leu Val Tyr Pro Arg Lys Ile Glu Glu Ile Thr Tyr Asp Gly Tyr
        355                 360                 365

Val Tyr Asp Ile Glu Val Glu Gly Thr His Arg Phe Phe Ala Asn Gly
    370                 375                 380

Ile Leu Val His Asn
385

<210> SEQ ID NO 18
<211> LENGTH: 389
<212> TYPE: PRT
<213> ORGANISM: Thermococcus hydrothermalis

<400> SEQUENCE: 18

Ser Val Thr Gly Glu Thr Glu Ile Ile Ile Lys Arg Asn Gly Lys Val
1 5 10 15

Glu Phe Val Ala Ile Glu Glu Leu Phe Gln Arg Val Asp Tyr Arg Ile
20 25 30

Gly Glu Lys Glu Tyr Cys Val Leu Glu Gly Val Glu Ala Leu Thr Leu
35 40 45

Asp Asn Arg Gly Arg Leu Val Trp Lys Ser Val Pro Tyr Val Met Arg
50 55 60

His Arg Thr Asn Lys Arg Ile Tyr Arg Val Trp Phe Thr Asn Ser Trp
65 70 75 80

Tyr Leu Asp Val Thr Glu Asp His Ser Leu Ile Gly Tyr Met Asn Thr
85 90 95

Ser Lys Val Lys Pro Gly Lys Pro Leu Lys Glu Arg Leu Val Glu Val
100 105 110

Lys Pro Gly Glu Leu Gly Glu Ser Val Lys Ser Leu Ile Thr Pro Asn
115 120 125

Arg Ala Ile Ala His Gly Ile Arg Val Asn Pro Ile Ala Val Lys Leu
130 135 140

Trp Glu Leu Ile Gly Leu Leu Val Gly Asp Gly Asn Trp Gly Gly Gln
145 150 155 160

Ser Asn Trp Ala Lys Tyr Asn Val Gly Leu Ser Leu Gly Leu Asp Lys
165 170 175

Glu Glu Ile Glu Glu Lys Ile Leu Lys Pro Leu Lys Asn Thr Gly Ile
180 185 190

Ile Ser Asn Tyr Tyr Asp Lys Ser Lys Lys Gly Asp Val Ser Ile Leu
195 200 205

Ser Lys Trp Leu Ala Arg Phe Met Val Arg Tyr Phe Lys Asp Glu Ser
210 215 220

Gly Ser Lys Arg Ile Pro Glu Phe Met Phe Asn Leu Pro Arg Glu Tyr
225 230 235 240

Ile Glu Ala Phe Leu Arg Gly Leu Phe Ser Ala Asp Gly Thr Val Ser
245 250 255

Leu Arg Lys Gly Val Pro Glu Val Arg Leu Thr Ser Val Asn Pro Glu
260 265 270

Leu Ser Ser Ser Val Arg Lys Leu Leu Trp Leu Val Gly Val Ser Asn
275 280 285

Ser Met Phe Val Glu Thr Asn Pro Asn Arg Tyr Leu Gly Lys Glu Ser
290 295 300

Gly Thr His Ser Val His Val Arg Ile Lys Asp Lys His Arg Phe Ala
305 310 315 320

Glu Arg Ile Gly Phe Leu Leu Asp Arg Lys Ala Thr Lys Leu Ser Glu
325 330 335

Asn Leu Gly Gly His Thr Ser Lys Lys Arg Ala Tyr Lys Tyr Asp Phe
340 345 350

Asp Leu Val Tyr Pro Lys Lys Val Glu Glu Ile Ala Tyr Asp Gly Tyr

```
        355                 360                 365

Val Tyr Asp Ile Glu Val Glu Gly Thr His Arg Phe Phe Ala Asn Gly
    370                 375                 380

Ile Leu Val His Asn
385


<210> SEQ ID NO 19
<211> LENGTH: 390
<212> TYPE: PRT
<213> ORGANISM: Thermococcus litoralis

<400> SEQUENCE: 19

Ser Val Ser Gly Glu Ser Glu Ile Ile Ile Arg Gln Asn Gly Lys Ile
1               5                   10                  15

Arg Phe Val Lys Ile Lys Asp Leu Phe Ser Lys Val Asp Tyr Ser Ile
            20                  25                  30

Gly Glu Lys Glu Tyr Cys Ile Leu Glu Gly Val Glu Ala Leu Thr Leu
        35                  40                  45

Asp Asp Asp Gly Lys Leu Val Trp Lys Pro Val Pro Tyr Val Met Arg
    50                  55                  60

His Arg Ala Asn Lys Arg Met Phe Arg Ile Trp Leu Thr Asn Ser Trp
65                  70                  75                  80

Tyr Ile Asp Val Thr Glu Asp His Ser Leu Ile Gly Tyr Leu Asn Thr
                85                  90                  95

Ser Lys Thr Lys Thr Ala Lys Lys Ile Gly Glu Arg Leu Lys Glu Val
            100                 105                 110

Lys Pro Phe Glu Leu Gly Lys Ala Val Lys Ser Leu Ile Cys Pro Asn
        115                 120                 125

Ala Pro Leu Lys Asp Glu Asn Thr Lys Thr Ser Glu Ile Ala Val Lys
    130                 135                 140

Phe Trp Glu Leu Val Gly Leu Ile Val Gly Asp Gly Asn Trp Gly Gly
145                 150                 155                 160

Asp Ser Arg Trp Ala Glu Tyr Tyr Leu Gly Leu Ser Thr Gly Lys Asp
                165                 170                 175

Ala Glu Glu Ile Lys Gln Lys Leu Leu Glu Pro Leu Lys Thr Tyr Gly
            180                 185                 190

Val Ile Ser Asn Tyr Tyr Pro Lys Asn Glu Lys Gly Asp Phe Asn Ile
        195                 200                 205

Leu Ala Lys Ser Leu Val Lys Phe Met Lys Arg His Phe Lys Asp Glu
    210                 215                 220

Lys Gly Arg Arg Lys Ile Pro Glu Phe Met Tyr Glu Leu Pro Val Thr
225                 230                 235                 240

Tyr Ile Glu Ala Phe Leu Arg Gly Leu Phe Ser Ala Asp Gly Thr Val
                245                 250                 255

Thr Ile Arg Lys Gly Val Pro Glu Ile Arg Leu Thr Asn Ile Asp Ala
            260                 265                 270

Asp Phe Leu Arg Glu Val Arg Lys Leu Leu Trp Ile Val Gly Ile Ser
        275                 280                 285

Asn Ser Ile Phe Ala Glu Thr Thr Pro Asn Arg Tyr Asn Gly Val Ser
    290                 295                 300

Thr Gly Thr Tyr Ser Lys His Leu Arg Ile Lys Asn Lys Trp Arg Phe
305                 310                 315                 320

Ala Glu Arg Ile Gly Phe Leu Ile Glu Arg Lys Gln Lys Arg Leu Leu
                325                 330                 335
```

```
Glu His Leu Lys Ser Ala Arg Val Lys Arg Asn Thr Ile Asp Phe Gly
            340                 345                 350

Phe Asp Leu Val His Val Lys Lys Val Glu Glu Ile Pro Tyr Glu Gly
        355                 360                 365

Tyr Val Tyr Asp Ile Glu Val Glu Glu Thr His Arg Phe Phe Ala Asn
    370                 375                 380

Asn Ile Leu Val His Asn
385                 390


<210> SEQ ID NO 20
<211> LENGTH: 389
<212> TYPE: PRT
<213> ORGANISM: Thermococcus species GE8

<400> SEQUENCE: 20

Ser Val Ala Gly Asn Thr Glu Val Ile Ile Arg Arg Asn Gly Lys Val
1               5                   10                  15

Glu Phe Val Pro Ile Glu Lys Leu Phe Gln Arg Val Asp Tyr Arg Ile
            20                  25                  30

Gly Glu Lys Glu Tyr Cys Ala Leu Glu Gly Val Glu Ala Leu Thr Leu
        35                  40                  45

Asp Asn Arg Gly Arg Leu Val Trp Arg Lys Val Pro Tyr Ile Met Arg
    50                  55                  60

His Lys Thr Asn Lys Lys Ile Tyr Arg Val Trp Phe Thr Asn Ser Trp
65                  70                  75                  80

Tyr Leu Asp Val Thr Glu Asp His Ser Leu Ile Gly Tyr Leu Asn Thr
                85                  90                  95

Ser Lys Val Lys Ser Glu Lys Pro Leu Lys Glu Arg Leu Val Glu Val
            100                 105                 110

Lys Pro Arg Glu Leu Gly Glu Lys Val Lys Ser Leu Ile Thr Leu Asn
        115                 120                 125

Arg Ala Ile Ala Arg Ser Ile Lys Ala Asn Pro Ile Ala Val Arg Leu
    130                 135                 140

Trp Glu Leu Ile Gly Leu Leu Val Gly Asp Gly Asn Trp Gly Gly His
145                 150                 155                 160

Ser Lys Trp Ala Lys Tyr Tyr Val Gly Leu Ser Cys Gly Leu Asp Lys
                165                 170                 175

Ala Glu Ile Glu Glu Lys Val Leu Arg Pro Leu Lys Glu Ala Gly Ile
            180                 185                 190

Ile Ser Asn Tyr Tyr Gly Lys Ser Lys Lys Gly Asp Val Ser Ile Leu
        195                 200                 205

Ser Lys Trp Leu Ala Gly Phe Met Val Lys Tyr Phe Lys Asp Glu Asn
    210                 215                 220

Gly Asn Lys Arg Ile Pro Ser Phe Met Phe Asn Leu Pro Arg Glu Tyr
225                 230                 235                 240

Ile Glu Ala Phe Leu Arg Gly Leu Phe Ser Ala Asp Gly Thr Val Ser
                245                 250                 255

Leu Arg Arg Gly Ile Pro Glu Ile Arg Leu Thr Ser Val Asn Arg Glu
            260                 265                 270

Leu Ser Asn Glu Val Arg Lys Leu Leu Trp Leu Val Gly Val Ser Asn
        275                 280                 285

Ser Met Phe Thr Glu Thr Thr Pro Asn Lys Tyr Leu Gly Asn Glu Ser
    290                 295                 300

Gly Thr Arg Ser Ile His Val Arg Ile Lys Asn Lys His Arg Phe Ala
305                 310                 315                 320
```

Lys Arg Ile Gly Phe Leu Leu Asp Arg Lys Ala Thr Lys Leu Ser Asp
325 330 335

Asn Leu Arg Glu His Thr Asn Lys Lys Met Ala Tyr Arg Tyr Asp Phe
340 345 350

Asp Leu Val Tyr Pro Lys Lys Ile Glu Glu Ile Asn Tyr Asp Arg Tyr
355 360 365

Val Tyr Asp Ile Glu Val Glu Gly Thr His Arg Phe Phe Ala Asn Gly
370 375 380

Ile Leu Val His Asn
385

<210> SEQ ID NO 21
<211> LENGTH: 184
<212> TYPE: PRT
<213> ORGANISM: Pyrococcus abyssi

<400> SEQUENCE: 21

Cys Phe Pro Gly Asp Thr Arg Ile Leu Val Gln Ile Asp Gly Val Pro
1 5 10 15

Gln Lys Ile Thr Leu Arg Glu Leu Tyr Glu Leu Phe Glu Asp Glu Arg
20 25 30

Tyr Glu Asn Met Val Tyr Val Arg Lys Lys Pro Lys Arg Glu Ile Lys
35 40 45

Val Tyr Ser Ile Asp Leu Glu Thr Gly Lys Val Val Leu Thr Asp Ile
50 55 60

Glu Asp Val Ile Lys Ala Pro Ala Thr Asp His Leu Ile Arg Phe Glu
65 70 75 80

Leu Glu Asp Gly Arg Ser Phe Glu Thr Thr Val Asp His Pro Val Leu
85 90 95

Val Tyr Glu Asn Gly Arg Phe Ile Glu Lys Arg Ala Phe Glu Val Lys
100 105 110

Glu Gly Asp Lys Val Leu Val Ser Glu Leu Glu Leu Val Glu Gln Ser
115 120 125

Ser Ser Ser Gln Asp Asn Pro Lys Asn Glu Asn Leu Gly Ser Pro Glu
130 135 140

His Asp Gln Leu Leu Glu Ile Lys Asn Ile Lys Tyr Val Arg Ala Asn
145 150 155 160

Asp Asp Phe Val Phe Ser Leu Asn Ala Lys Lys Tyr His Asn Val Ile
165 170 175

Ile Asn Glu Asn Ile Val Thr His
180

<210> SEQ ID NO 22
<211> LENGTH: 416
<212> TYPE: PRT
<213> ORGANISM: Mycobacterium tuberculosis

<400> SEQUENCE: 22

Cys Leu Thr Ala Ser Thr Arg Ile Leu Arg Ala Asp Thr Gly Ala Glu
1 5 10 15

Val Ala Phe Gly Glu Leu Met Arg Ser Gly Glu Arg Pro Met Val Trp
20 25 30

Ser Leu Asp Glu Arg Leu Arg Met Val Ala Arg Pro Met Ile Asn Val
35 40 45

Phe Pro Ser Gly Arg Lys Glu Val Phe Arg Leu Arg Leu Ala Ser Gly
50 55 60

```
Arg Glu Val Glu Ala Thr Gly Ser His Pro Phe Met Lys Phe Glu Gly
65                  70                  75                  80

Trp Thr Pro Leu Ala Gln Leu Lys Val Gly Asp Arg Ile Ala Ala Pro
                85                  90                  95

Arg Arg Val Pro Glu Pro Ile Asp Thr Gln Arg Met Pro Glu Ser Glu
            100                 105                 110

Leu Ile Ser Leu Ala Arg Met Ile Gly Asp Gly Ser Cys Leu Lys Asn
        115                 120                 125

Gln Pro Ile Arg Tyr Glu Pro Val Asp Glu Ala Asn Leu Ala Ala Val
    130                 135                 140

Thr Val Ser Ala Ala His Ser Asp Gly Ala Ala Ile Arg Asp Asp Tyr
145                 150                 155                 160

Leu Ala Ala Arg Val Pro Ser Leu Arg Pro Ala Arg Gln Arg Leu Pro
                165                 170                 175

Arg Gly Arg Cys Thr Pro Ile Ala Ala Trp Leu Ala Gly Leu Gly Leu
            180                 185                 190

Phe Thr Lys Arg Ser His Glu Lys Cys Val Pro Glu Ala Val Phe Arg
        195                 200                 205

Ala Pro Asn Asp Gln Val Ala Leu Phe Leu Arg His Leu Trp Ser Ala
    210                 215                 220

Gly Gly Ser Val Arg Trp Asp Pro Thr Asn Gly Gln Gly Arg Val Tyr
225                 230                 235                 240

Tyr Gly Ser Thr Ser Arg Arg Leu Ile Asp Asp Val Ala Gln Leu Leu
                245                 250                 255

Leu Arg Val Gly Ile Phe Ser Trp Ile Thr His Ala Pro Lys Leu Gly
            260                 265                 270

Gly His Asp Ser Trp Arg Leu His Ile His Gly Ala Lys Asp Gln Val
        275                 280                 285

Arg Phe Leu Arg His Val Gly Val His Gly Ala Glu Ala Val Ala Ala
    290                 295                 300

Gln Glu Met Leu Arg Gln Leu Lys Gly Pro Val Arg Asn Pro Asn Leu
305                 310                 315                 320

Asp Ser Ala Pro Lys Lys Val Trp Ala Gln Val Arg Asn Arg Leu Ser
                325                 330                 335

Ala Lys Gln Met Met Asp Ile Gln Leu His Glu Pro Thr Met Trp Lys
            340                 345                 350

His Ser Pro Ser Arg Ser Arg Pro His Arg Ala Glu Ala Arg Ile Glu
        355                 360                 365

Asp Arg Ala Ile His Glu Leu Ala Arg Gly Asp Ala Tyr Trp Asp Thr
    370                 375                 380

Val Val Glu Ile Thr Ser Ile Gly Asp Gln His Val Phe Asp Gly Thr
385                 390                 395                 400

Val Ser Gly Thr His Asn Phe Val Ala Asn Gly Ile Ser Leu His Asn
                405                 410                 415
```

<210> SEQ ID NO 23
<211> LENGTH: 416
<212> TYPE: PRT
<213> ORGANISM: Mycobacterium tuberculosis

<400> SEQUENCE: 23

```
Cys Leu Thr Ala Ser Thr Arg Ile Leu Arg Ala Asp Thr Gly Ala Glu
1               5                   10                  15

Val Ala Phe Gly Glu Leu Met Arg Ser Gly Glu Arg Pro Met Val Trp
```

```
            20                  25                  30

Ser Leu Asp Glu Arg Leu Arg Met Val Ala Arg Pro Met Ile Asn Val
        35                  40                  45

Phe Pro Ser Gly Arg Lys Glu Val Phe Arg Leu Arg Leu Ala Ser Gly
    50                  55                  60

Arg Glu Val Glu Ala Thr Gly Ser His Pro Phe Met Lys Phe Glu Gly
65                  70                  75                  80

Trp Thr Pro Leu Ala Gln Leu Lys Val Gly Asp Arg Ile Ala Ala Pro
                85                  90                  95

Arg Arg Val Pro Glu Pro Ile Asp Thr Gln Arg Met Pro Glu Ser Glu
            100                 105                 110

Leu Ile Ser Leu Ala Arg Met Ile Gly Asp Gly Ser Cys Leu Lys Asn
        115                 120                 125

Gln Pro Ile Arg Tyr Glu Pro Val Asp Glu Ala Asn Leu Ala Ala Val
    130                 135                 140

Thr Val Ser Ala Ala His Ser Asp Arg Ala Ala Ile Arg Asp Asp Tyr
145                 150                 155                 160

Leu Ala Ala Arg Val Pro Ser Leu Arg Pro Ala Arg Gln Arg Leu Pro
                165                 170                 175

Arg Gly Arg Cys Thr Pro Ile Ala Ala Trp Leu Ala Gly Leu Gly Leu
            180                 185                 190

Phe Thr Lys Arg Ser His Glu Lys Cys Val Pro Glu Ala Val Phe Arg
        195                 200                 205

Ala Pro Asn Asp Gln Val Ala Leu Phe Leu Arg His Leu Trp Ser Ala
    210                 215                 220

Gly Gly Ser Val Arg Trp Asp Pro Thr Asn Gly Gln Gly Arg Val Tyr
225                 230                 235                 240

Tyr Gly Ser Thr Ser Arg Arg Leu Ile Asp Asp Val Ala Gln Leu Leu
                245                 250                 255

Leu Arg Val Gly Ile Phe Ser Trp Ile Thr His Ala Pro Lys Leu Gly
            260                 265                 270

Gly His Asp Ser Trp Arg Leu His Ile His Gly Ala Lys Asp Gln Val
        275                 280                 285

Arg Phe Leu Arg His Val Gly Val His Gly Ala Glu Ala Val Ala Ala
    290                 295                 300

Gln Glu Met Leu Arg Gln Leu Lys Gly Pro Val Arg Asn Pro Asn Leu
305                 310                 315                 320

Asp Ser Ala Pro Lys Lys Val Trp Ala Gln Val Arg Asn Arg Leu Ser
                325                 330                 335

Ala Lys Gln Met Met Asp Ile Gln Leu His Glu Pro Thr Met Trp Lys
            340                 345                 350

His Ser Pro Ser Arg Ser Arg Pro His Arg Ala Glu Ala Arg Ile Glu
        355                 360                 365

Asp Arg Ala Ile His Glu Leu Ala Arg Gly Asp Ala Tyr Trp Asp Thr
    370                 375                 380

Val Val Glu Ile Thr Ser Ile Gly Asp Gln His Val Phe Asp Gly Thr
385                 390                 395                 400

Val Ser Gly Thr His Asn Phe Val Ala Asn Gly Ile Ser Leu His Asn
                405                 410                 415
```

<210> SEQ ID NO 24
<211> LENGTH: 428
<212> TYPE: PRT
<213> ORGANISM: Rhodothermus marinus

<400> SEQUENCE: 24

Cys Leu Ala Gly Asp Thr Leu Ile Thr Leu Ala Asp Gly Arg Arg Val
1               5                   10                  15

Pro Ile Arg Glu Leu Val Ser Gln Gln Asn Phe Ser Val Trp Ala Leu
            20                  25                  30

Asn Pro Gln Thr Tyr Arg Leu Glu Arg Ala Arg Val Ser Arg Ala Phe
        35                  40                  45

Cys Thr Gly Ile Lys Pro Val Tyr Arg Leu Thr Thr Arg Leu Gly Arg
    50                  55                  60

Ser Ile Arg Ala Thr Ala Asn His Arg Phe Leu Thr Pro Gln Gly Trp
65                  70                  75                  80

Lys Arg Val Asp Glu Leu Gln Pro Gly Asp Tyr Leu Ala Leu Pro Arg
                85                  90                  95

Arg Ile Pro Thr Ala Ser Thr Pro Thr Leu Thr Glu Ala Glu Leu Ala
            100                 105                 110

Leu Leu Gly His Leu Ile Gly Asp Gly Cys Thr Leu Pro His His Val
        115                 120                 125

Ile Gln Tyr Thr Ser Arg Asp Ala Asp Leu Ala Thr Leu Val Ala His
    130                 135                 140

Leu Ala Thr Lys Val Phe Gly Ser Lys Val Thr Pro Gln Ile Arg Lys
145                 150                 155                 160

Glu Leu Arg Trp Tyr Gln Val Tyr Leu Arg Ala Ala Arg Pro Leu Ala
                165                 170                 175

Pro Gly Lys Arg Asn Pro Ile Ser Asp Trp Leu Arg Asp Leu Gly Ile
            180                 185                 190

Phe Gly Leu Arg Ser Tyr Glu Lys Lys Val Pro Ala Leu Leu Phe Cys
        195                 200                 205

Gln Thr Ser Glu Ala Ile Ala Thr Phe Leu Arg His Leu Trp Ala Thr
    210                 215                 220

Asp Gly Cys Ile Gln Met Arg Arg Gly Lys Lys Pro Tyr Pro Ala Val
225                 230                 235                 240

Tyr Tyr Ala Thr Ser Ser Tyr Gln Leu Ala Arg Asp Val Gln Ser Leu
                245                 250                 255

Leu Leu Arg Leu Gly Ile Asn Ala Arg Leu Lys Thr Val Ala Gln Gly
            260                 265                 270

Glu Lys Gly Arg Val Gln Tyr His Val Lys Val Ser Gly Arg Glu Asp
        275                 280                 285

Leu Leu Arg Phe Val Glu Lys Ile Gly Ala Val Gly Ala Arg Gln Arg
    290                 295                 300

Ala Ala Leu Ala Ser Val Tyr Asp Tyr Leu Ser Val Arg Thr Gly Asn
305                 310                 315                 320

Pro Asn Arg Asp Ile Ile Pro Val Ala Leu Trp Tyr Glu Leu Val Arg
                325                 330                 335

Glu Ala Met Tyr Gln Arg Gly Ile Ser His Arg Gln Leu His Ala Asn
            340                 345                 350

Leu Gly Met Ala Tyr Gly Gly Met Thr Leu Phe Arg Gln Asn Leu Ser
        355                 360                 365

Arg Ala Arg Ala Leu Arg Leu Ala Glu Ala Ala Ala Cys Pro Glu Leu
    370                 375                 380

Arg Gln Leu Ala Gln Ser Asp Val Tyr Trp Asp Pro Ile Val Ser Ile
385                 390                 395                 400

Glu Pro Asp Gly Val Glu Glu Val Phe Asp Leu Thr Val Pro Gly Pro

```
            405                 410                 415

His Asn Phe Val Ala Asn Asp Ile Ile Ala His Asn
            420                 425


<210> SEQ ID NO 25
<211> LENGTH: 1365
<212> TYPE: PRT
<213> ORGANISM: Trichodesmium erythraeum

<400> SEQUENCE: 25

Cys Leu Pro Lys Gly Thr Leu Ile Asp Gln Pro Asp Gly Ser Arg Glu
1               5                   10                  15

Ala Ile Glu Asn Ile Lys Ser Gly Glu Val Ile Leu Thr Ser Asp Gly
            20                  25                  30

Arg Lys Val Trp Glu Ala Lys Val Ala Lys Gln Trp Arg Ser Gly Val
        35                  40                  45

Arg Glu Ile Leu Lys Ile Thr Leu Ser Ser Gly Thr Val Ile Tyr Ser
    50                  55                  60

Gly Lys Asn His Arg Phe Leu Thr Pro Glu Gly Asp Lys Phe Ala Trp
65                  70                  75                  80

Glu Leu Gln Pro Gln Val Gly Arg Val Lys Asn Ala Leu Ile Tyr Gly
                85                  90                  95

Ser Ala Val Tyr Glu Lys Trp Gln Val Ser Ser Asn Gln Lys Gln Leu
            100                 105                 110

Arg Lys Asn Asp Ala Tyr Leu Leu Gly Leu Leu Val Gly Lys Ser Asn
        115                 120                 125

Leu Ile Ser Ser Thr Pro Asn Val Ser Phe Ser Thr Gln Gly Ala Ile
    130                 135                 140

Thr Trp Gly Lys Asn Leu Ile Asp Glu Thr Trp Gly Gly Glu Ala Lys
145                 150                 155                 160

His Tyr Phe Asp Thr Ser Arg Arg Gln Val Tyr Leu Asn Phe Asn Thr
                165                 170                 175

Gln Ser Lys Pro Thr Ala Leu Thr Glu Phe Leu Asp Gly Ile Tyr Gly
            180                 185                 190

Ala Gln Asn Trp Gln Val Glu Ser Val Ala Lys His Leu Pro Glu Asp
        195                 200                 205

Ile Leu Asp Tyr Ser Glu Lys Asp Arg Ile Asp Leu Leu Arg Gly Leu
    210                 215                 220

Trp Asp Ser Gly Gly Phe Asp Gly Lys Lys Leu Leu Tyr Tyr Pro Gly
225                 230                 235                 240

Ser Ser Pro Gln Leu Leu Ser Gln Val Cys Gln Leu Leu Gly Ser Leu
                245                 250                 255

Lys Ile Asp Tyr Tyr Leu Ala Asp Asn Ser Val Arg Ile Ser Asp Arg
            260                 265                 270

Ser Arg Phe Ile Asp Ile Leu Glu Asn Tyr Gln Met Ser Ser Gln Gln
        275                 280                 285

Lys Glu Glu Ile Ser Glu Ser Tyr Leu Pro Ala Ser Ser Trp Phe Leu
    290                 295                 300

Lys Gly Gly Ser Glu Asn Asn Ile Gln Lys Thr Asp Ser Ser Ser Arg
305                 310                 315                 320

Lys Thr Gly Glu Ala Ser Gln Gln Lys Ala Thr Leu Phe Thr Gln Asn
                325                 330                 335

Leu Phe Ser Ala Gln Thr Pro Ala Glu Asn Trp Glu Lys Val Gly Glu
            340                 345                 350
```

-continued

```
Asn His Leu Leu Ser Ser Trp Phe Leu Thr Asp Ala Ser Glu Asn Asn
        355                 360                 365

Ile Gln Lys Thr Asp Ser Ser Ser Arg Lys Thr Gly Glu Ala Ser Gln
    370                 375                 380

Gln Lys Ala Thr Leu Phe Thr Gln Asn Leu Phe Ser Ala Gln Thr Pro
385                 390                 395                 400

Ala Glu Asn Trp Glu Lys Val Arg Glu Asn His Leu Leu Ser Ser Trp
                405                 410                 415

Phe Leu Thr Asn Ala Ser Glu Ile Tyr Leu Gln Arg Ile Asp Ser Ser
            420                 425                 430

Ser Arg Lys Thr Gly Glu Ala Ser Gln Gln Lys Ala Thr Leu Phe Thr
        435                 440                 445

Gln Asn Leu Phe Ser Val Gln Thr Pro Ala Glu Asn Trp Glu Lys Val
    450                 455                 460

Arg Glu Asn His Leu Leu Ser Ser Trp Phe Leu Thr Asp Ala Ser Glu
465                 470                 475                 480

Asn Asn Ile Gln Lys Thr Asp Ser Ser Ser Arg Lys Thr Gly Glu Ala
                485                 490                 495

Ser Gln Gln Lys Ala Thr Leu Phe Thr Gln Asn Leu Phe Ser Ala Gln
            500                 505                 510

Thr Pro Ala Glu Asn Trp Glu Lys Val Arg Glu Asn His Leu Leu Ser
        515                 520                 525

Ser Trp Phe Leu Thr Asn Ala Ser Glu Asn Asn Ile Gln Lys Thr Asp
    530                 535                 540

Ser Ser Ser Arg Lys Thr Gly Glu Ala Ser Gln Gln Lys Ala Thr Leu
545                 550                 555                 560

Phe Thr Gln Asn Leu Phe Ser Ala Gln Thr Pro Ala Glu Asn Trp Lys
                565                 570                 575

Lys Ser Arg Lys Asn His Leu Pro Ser Ser Trp Phe Leu Lys Gly Gly
            580                 585                 590

Ser Glu Asn Asn Ile Gln Lys Thr Asp Ser Ser Ser Arg Lys Thr Gly
        595                 600                 605

Glu Ala Ser Gln Gln Lys Ala Thr Leu Phe Thr Gln Asn Leu Phe Ser
    610                 615                 620

Ala Gln Thr Pro Ala Glu Asn Trp Glu Lys Val Arg Glu Asn His Leu
625                 630                 635                 640

Leu Ser Ser Trp Phe Leu Lys Asp Ala Ser Glu Asn Asn Ile Gln Lys
                645                 650                 655

Thr Asp Ser Ser Ser Arg Lys Thr Gly Glu Ala Ser Gln Gln Lys Ala
            660                 665                 670

Thr Leu Phe Thr Gln Asn Leu Phe Ser Ala Gln Thr Pro Ala Glu Asn
        675                 680                 685

Trp Glu Lys Val Arg Glu Asn His Leu Leu Ser Ser Trp Phe Leu Thr
    690                 695                 700

Asp Ala Ser Glu Asn Asn Ile Gln Lys Thr Asp Ser Ser Ser Arg Lys
705                 710                 715                 720

Thr Gly Glu Ala Ser Gln Gln Lys Ala Thr Leu Phe Thr Gln Asn Leu
                725                 730                 735

Phe Ser Ala Gln Thr Pro Ala Glu Asn Trp Glu Lys Val Arg Glu Asn
            740                 745                 750

His Leu Leu Ser Ser Trp Phe Leu Thr Asp Ala Ser Glu Asn Asn Ile
        755                 760                 765

Gln Lys Thr Asp Ser Ser Ser Arg Lys Thr Gly Glu Ala Ser Gln Gln
```

```
    770                 775                 780

Lys Ala Thr Leu Phe Thr Gln Asn Leu Phe Ser Ala Gln Thr Pro Ala
785                 790                 795                 800

Glu Asn Trp Glu Lys Val Arg Glu Asn His Leu Leu Ser Ser Trp Phe
                805                 810                 815

Leu Thr Asn Ala Ser Glu Asn Asn Ile Gln Lys Thr Asp Ser Ser Ser
            820                 825                 830

Arg Lys Thr Gly Glu Ala Ser Gln Gln Lys Ala Thr Leu Phe Thr Gln
        835                 840                 845

Asn Leu Phe Ser Ala Gln Thr Pro Ala Glu Asn Trp Lys Lys Ala Arg
    850                 855                 860

Glu Asn His Leu Leu Ser Ser Trp Phe Leu Thr Asn Ala Ser Glu Ile
865                 870                 875                 880

Tyr Leu Gln Arg Thr Asp Ser Ser Ser Arg Lys Thr Gly Glu Ala Ser
                885                 890                 895

Gln Gln Lys Ala Thr Leu Phe Thr Gln Asn Leu Phe Ser Val Gln Thr
            900                 905                 910

Pro Ala Glu Asn Trp Lys Lys Ala Arg Glu Asn His Leu Leu Ser Ser
        915                 920                 925

Trp Phe Leu Thr Asn Ala Ser Glu Ile Tyr Leu Gln Arg Thr Asp Ser
    930                 935                 940

Ser Ser Arg Lys Thr Gly Gly Ala Ser Gln Gln Lys Ala Thr Leu Phe
945                 950                 955                 960

Asn Gln Asn Leu Phe Ser Val Gln Thr Pro Ala Glu Asn Trp Glu Lys
                965                 970                 975

Val Arg Glu Asn Tyr Leu Leu Ser Ser Trp Phe Leu Thr Asn Ala Ser
            980                 985                 990

Glu Ile Tyr Leu Gln Arg Thr Asp  Ser Ser Ser Arg Lys  Thr Gly Glu
        995                 1000                1005

Ala Ser  Gln Gln Lys Ala Thr  Leu Phe Thr Gln Asn  Leu Phe Ser
    1010                1015                1020

Val Gln  Thr Pro Ala Glu Asn  Trp Lys Lys Ala Arg  Glu Asn His
    1025                1030                1035

Leu Leu  Ser Ser Trp Phe Leu  Thr Asn Ala Ser Glu  Ile Tyr Leu
    1040                1045                1050

Gln Arg  Thr Asp Ser Ser Ser  Arg Lys Thr Gly Gly  Ala Ser Gln
    1055                1060                1065

Gln Lys  Ala Thr Leu Phe Asn  Gln Asn Leu Phe Ser  Val Gln Thr
    1070                1075                1080

Pro Ala  Glu Asn Trp Lys Lys  Ala Arg Glu Asn His  Leu Leu Ser
    1085                1090                1095

Ser Trp  Phe Leu Thr Asn Ala  Ser Glu Ile Tyr Leu  Gln Arg Thr
    1100                1105                1110

Asp Ser  Ser Ser Arg Lys Thr  Val Glu Ala Ser Gln  Gln Lys Ala
    1115                1120                1125

Thr Leu  Phe Thr Gln Asn Leu  Phe Ser Ala Gln Thr  Pro Ala Glu
    1130                1135                1140

Asn Trp  Glu Lys Val Arg Glu  Asn Tyr Leu Leu Ser  Ser Trp Phe
    1145                1150                1155

Leu Thr  Asn Ala Ser Glu Ile  Tyr Leu Gln Arg Ile  Asp Ser Ser
    1160                1165                1170

Ser Arg  Lys Thr Gly Glu Ala  Cys Gln Gln Lys Ala  Thr Leu Phe
    1175                1180                1185
```

Asn Gln Asn Leu Phe Ser Ala Gln Thr Pro Ala Glu Asn Trp Lys
1190 1195 1200

Lys Val Arg Glu Asn His Leu Leu Ser Ser Trp Phe Leu Thr Asp
1205 1210 1215

Ala Ser Glu Asn Asn Ile Gln Lys Thr Asp Ser Ser Ser Arg Lys
1220 1225 1230

Thr Val Glu Ala Ser Gln Gln Lys Ala Thr Leu Phe Thr Gln Asn
1235 1240 1245

Leu Phe Ser Ala Gln Thr Pro Ala Glu Asn Trp Lys Lys Ser Arg
1250 1255 1260

Lys Asn His Leu Pro Ser Ser Trp Phe Leu Thr Asp Ala Ser Glu
1265 1270 1275

Asn Asn Ile Gln Lys Thr Asp Ser Ser Ser Arg Lys Thr Gly Glu
1280 1285 1290

Ala Ser Gln Gln Lys Ala Thr Leu Phe Thr Gln Asn Leu Phe Ser
1295 1300 1305

Val Gln Thr Pro Glu Leu Glu Asn Trp Glu Cys Glu Lys Thr Tyr
1310 1315 1320

Leu Gln Asp Val Arg Val Val His Val Val Ser Val Glu Glu Val
1325 1330 1335

Gly Glu Ala Glu Cys Phe Asp Leu Glu Met Glu Asp Gln Ser Ser
1340 1345 1350

Pro Tyr Phe Leu Ala Glu Gly Val Val Val His Asn
1355 1360 1365

<210> SEQ ID NO 26
<211> LENGTH: 435
<212> TYPE: PRT
<213> ORGANISM: Synechocystis sp. PCC6803

<400> SEQUENCE: 26

Cys Phe Ser Gly Asp Thr Leu Val Ala Leu Thr Asp Gly Arg Ser Val
1 5 10 15

Ser Phe Glu Gln Leu Val Glu Glu Glu Lys Gln Gly Lys Gln Asn Phe
20 25 30

Cys Tyr Thr Ile Arg His Asp Gly Ser Ile Gly Val Glu Lys Ile Ile
35 40 45

Asn Ala Arg Lys Thr Lys Thr Asn Ala Lys Val Ile Lys Val Thr Leu
50 55 60

Asp Asn Gly Glu Ser Ile Ile Cys Thr Pro Asp His Lys Phe Met Leu
65 70 75 80

Arg Asp Gly Ser Tyr Lys Cys Ala Met Asp Leu Thr Leu Asp Asp Ser
85 90 95

Leu Met Pro Leu His Arg Lys Ile Ser Thr Thr Glu Asp Ser Gly Ile
100 105 110

Thr Ile Asp Gly Tyr Glu Met Val Trp Ser Pro Arg Ser Asp Ser Trp
115 120 125

Leu Phe Thr His Leu Val Ala Asp Trp Tyr Asn Arg Trp Gln Gly Ile
130 135 140

Tyr Ile Ala Glu Glu Lys Gln His Cys His His Lys Asp Phe Asn Lys
145 150 155 160

Arg Asn Asn Asn Pro Asp Asn Leu Ile Arg Leu Ser Pro Glu Lys His
165 170 175

Leu Ala Leu His Arg Lys His Ile Ser Lys Thr Leu His Arg Pro Asp

-continued

```
            180                 185                 190

Val Val Glu Lys Cys Arg Arg Ile His Gln Ser Pro Glu Phe Arg Arg
        195                 200                 205

Lys Met Ser Ala Arg Met Gln Ser Pro Glu Thr Arg Ala Ile Leu Ser
    210                 215                 220

Lys Gln Ala Gln Ala Gln Trp Gln Asn Glu Thr Tyr Lys Leu Thr Met
225                 230                 235                 240

Met Glu Ser Trp Arg Ser Phe Tyr Asp Ser Asn Glu Asp Tyr Arg Gln
                245                 250                 255

Gln Asn Ala Glu Gln Leu Asn Arg Ala Gln Gln Glu Tyr Trp Ala Gln
            260                 265                 270

Ala Glu Asn Arg Thr Ala Gln Ala Glu Arg Val Arg Gln His Phe Ala
        275                 280                 285

Gln Asn Pro Gly Leu Arg Gln Gln Tyr Ser Glu Asn Ala Val Lys Gln
    290                 295                 300

Trp Asn Asn Pro Glu Leu Leu Lys Trp Arg Gln Lys Lys Thr Lys Glu
305                 310                 315                 320

Gln Trp Thr Pro Glu Phe Arg Glu Lys Arg Arg Glu Ala Leu Ala Gln
                325                 330                 335

Thr Tyr Tyr Arg Lys Thr Leu Ala Ala Leu Lys Gln Val Glu Ile Glu
            340                 345                 350

Asn Gly Tyr Leu Asp Ile Ser Ala Tyr Asp Ser Tyr Arg Ile Ser Thr
        355                 360                 365

Lys Asp Lys Ser Leu Leu Arg Phe Asp Arg Phe Cys Glu Arg Tyr Phe
    370                 375                 380

Glu Asn Asp Glu Asn Leu Ala Arg Glu Ala Val Leu Asn Tyr Asn His
385                 390                 395                 400

Arg Ile Val Asn Ile Glu Ala Val Ser Glu Thr Ile Asp Val Tyr Asp
                405                 410                 415

Ile Glu Val Pro His Thr His Asn Phe Ala Leu Ala Ser Gly Val Phe
            420                 425                 430

Val His Asn
        435


<210> SEQ ID NO 27
<211> LENGTH: 421
<212> TYPE: PRT
<213> ORGANISM: Mycobacterium flavescens

<400> SEQUENCE: 27

Cys Val Thr Gly Asp Ala Leu Val Arg Leu Pro Phe Gly Gln Ser Val
1               5                   10                  15

Arg Leu Arg Asp Val Val Ala Gly Ala Arg Ser Ser Ser Asp Asn Ala
            20                  25                  30

Ile Asp Leu Lys Val Leu Asn Arg His Gly Asp Pro Val Val Ala Asp
        35                  40                  45

Lys Leu Phe His Ser Gly Glu His Glu Thr Tyr Thr Val Arg Thr Ala
    50                  55                  60

Glu Gly Tyr Glu Val Thr Gly Thr Ala Asn His Pro Leu Leu Cys Leu
65                  70                  75                  80

Val Asp Val Gly Gly Val Pro Thr Leu Leu Trp Lys Leu Thr Glu Glu
                85                  90                  95

Ile Arg Pro Gly Asp His Val Val Leu Gln Arg Thr Pro Pro Thr Glu
            100                 105                 110
```

-continued

```
Phe Gly Pro Ala Asp Trp Gln Asp Ala Phe Glu Ala Leu His Leu Gly
        115                 120                 125

Ala Phe Ile Ser Glu Gly Phe Val Ser Glu Asn Arg Ala Gly Phe Asn
    130                 135                 140

Asn Leu Asp Arg Glu Phe Phe Asn Ala Val Leu Thr Ala Tyr Asp Thr
145                 150                 155                 160

Ile Val Gly Gly Pro Arg Tyr Val Ser Ser Arg Thr Ile Ala Ser Asp
                165                 170                 175

Ser Leu Leu His Glu Leu Asp Val His Asn Leu Thr Ala Leu Lys Lys
            180                 185                 190

Ser Arg Leu Gly Glu Leu Val Gly Gln Arg Ser Ala Asp Lys Ala Val
        195                 200                 205

Pro Glu Trp Leu Trp Lys Ala Pro Ala Val Val Lys Arg Val Phe Leu
    210                 215                 220

Gln Ala Leu Phe Glu Gly Asp Gly Ser Cys Ser Ala Leu Pro Arg Asn
225                 230                 235                 240

Thr Ile Gln Val Ser Tyr Ser Thr Arg Ser Gly Arg Leu Ala Lys Asp
                245                 250                 255

Ile Gln Gln Met Leu Leu Glu Phe Gly Val Ile Ser Arg Arg Tyr Val
            260                 265                 270

His Ala Thr Gly Glu His Lys Val Val Leu Thr Ser Arg Ala Gln Ala
        275                 280                 285

Glu Leu Phe Ala Ala Gln Ile Gly Phe Gly Gly Ile Lys Gln Ala Lys
    290                 295                 300

Leu Gln Gly Leu Leu Asp Ala Leu Pro Gln Ala Ala Ala Gly Arg Asp
305                 310                 315                 320

Gly Asp Tyr Val Pro Gly Leu Ala Gln Phe Val Arg Lys His Ser Gly
                325                 330                 335

Ser Arg Trp Val Asp Lys Asp Trp Leu Asn Arg His Asn Ile Asp Arg
            340                 345                 350

Leu Ser Arg Trp Gln Arg Asp Gly Ala Glu Ile Leu Gly Arg Ile Ala
        355                 360                 365

Asp Pro Asp Val Arg Ala Ile Ala Gln Glu Leu Thr Asp Gly Arg Phe
    370                 375                 380

Tyr Tyr Ala Arg Val Ala Ser Val Thr Asp Ser Gly Val Gln Pro Val
385                 390                 395                 400

Tyr Ser Leu Arg Val Asp Thr Asp Asp His Ser Phe Ile Thr Asn Gly
                405                 410                 415

Phe Val Ser His Asn
            420


<210> SEQ ID NO 28
<211> LENGTH: 420
<212> TYPE: PRT
<213> ORGANISM: Mycobacterium gordonae

<400> SEQUENCE: 28

Cys Leu Thr Gly Asp Ala Leu Val Arg Leu Pro Phe Gly Gln Ser Met
1               5                   10                  15

Arg Ile Gly Asp Val Ala Pro Gly Ala Arg Thr Asn Ser Asp Asn Ala
            20                  25                  30

Gly Glu Leu Lys Val Leu Asp Arg His Gly Asp Pro Val Phe Ala Asp
        35                  40                  45

Arg Leu Phe His Ser Gly Asp His Gln Thr Phe Arg Val Gln Thr Ala
    50                  55                  60
```

```
Glu Gly Tyr Glu Val Thr Gly Thr Ser Asn His Pro Val Leu Cys Leu
65                  70                  75                  80

Val Asn Leu Ala Gly Val Pro Thr Leu Leu Trp Met Leu Ile Glu Glu
                85                  90                  95

Ile Arg Pro Asp Asp Tyr Val Val Leu Gln Arg Ala Pro Pro Val Glu
            100                 105                 110

Ser Gly Pro Ala Asn Trp Arg Asp Ala Met Glu Ala Leu Leu Leu Gly
        115                 120                 125

Ala Phe Ile Ser Glu Gly Phe Met Ser Glu Ser Arg Ala Gly Phe Asn
    130                 135                 140

Asn Val Asp Arg Asp Tyr Phe Asn Ala Val Val Ala Ala Tyr Asp Ala
145                 150                 155                 160

Val Val Gly Gly Lys Arg Tyr Val Ala Gln Arg Thr Ile Ala Ser Gly
                165                 170                 175

Ser Val Leu Asn Glu Leu Asp Ile His Asp Val Ser Ala Leu Lys Gly
            180                 185                 190

Thr Arg Leu Gly Val Leu Cys Gly Gln Arg Ser Ala Asp Lys Ser Val
        195                 200                 205

Pro Glu Trp Leu Trp Gln Ser Pro Ala Ala Val Lys Arg Val Phe Leu
    210                 215                 220

Gln Ala Leu Phe Glu Gly Asp Gly Ser Cys Ser Ala Leu Pro Arg Asn
225                 230                 235                 240

Thr Ile Gln Val Ser Tyr Ser Thr Arg Ser Arg Gln Leu Ala Ile Asp
                245                 250                 255

Val Gln Gln Met Leu Leu Glu Phe Gly Val Ile Ser Arg Arg Tyr Arg
            260                 265                 270

His Ala Val Gly Glu Tyr Lys Val Val Ile Thr Asn Arg Ala Gln Ala
        275                 280                 285

Glu Leu Phe Ala Thr Gln Ile Gly Phe Gly Gly Ala Lys Gln Ser Lys
    290                 295                 300

Leu Thr Arg Ile Leu Gly Ser Leu Pro Pro Cys Ala Gly Met Asp Thr
305                 310                 315                 320

Asn His Val Pro Gly Leu Ala Ala Phe Ile Arg Ser His Cys Asp Ser
                325                 330                 335

Glu Trp Val Asp Lys Glu Trp Leu Arg Lys His Asn Ile Asp Arg Leu
            340                 345                 350

Ser Arg Trp Arg Arg Asp Gly Ala Glu Ile Leu Ser Arg Ile Ala Asn
        355                 360                 365

Pro Asp Val Arg Ala Ile Ala Thr Asp Leu Thr Asp Gly Arg Phe Tyr
    370                 375                 380

Tyr Ala Gln Val Thr Ser Val Thr Glu Ala Gly Val Gln Pro Val Tyr
385                 390                 395                 400

Ser Leu Arg Val Asp Ser Glu Asp His Ala Phe Leu Thr Asn Gly Phe
                405                 410                 415

Val Ser His Asn
            420


<210> SEQ ID NO 29
<211> LENGTH: 420
<212> TYPE: PRT
<213> ORGANISM: Mycobacterium kansasii

<400> SEQUENCE: 29

Cys Val Thr Gly Asp Ala Leu Val Arg Leu Pro Phe Gly Gln Ser Met
```

-continued

```
1               5                   10                  15

Arg Ile Ala Asp Val Val Pro Gly Ala Arg Pro Asn Ser Asp Asn Ala
            20                  25                  30

Val Glu Leu Lys Val Leu Asp Arg His Gly Asn Pro Val Ala Ala Asp
        35                  40                  45

Arg Leu Phe His Ser Gly Asp His Gln Thr Tyr Met Val Arg Thr Ala
    50                  55                  60

Glu Gly Tyr Glu Val Thr Gly Thr Ala Asn His Pro Leu Leu Cys Leu
65                  70                  75                  80

Val Asp Val Gly Gly Val Pro Thr Leu Leu Trp Lys Leu Ile Glu Glu
                85                  90                  95

Ile His Pro Asp Asp Tyr Val Ala Leu Gln Arg Thr Pro Pro Met Glu
            100                 105                 110

Leu Gly Pro Ala Asp Trp His Asp Thr Met Glu Ala Leu Leu Leu Gly
        115                 120                 125

Ala Phe Ile Ser Glu Gly Cys Val Ser Glu Thr Arg Ala Gly Phe Ala
    130                 135                 140

Asn Leu Asp Arg Asp Tyr Phe Thr Met Val Ala Arg Ala Tyr Asp Ala
145                 150                 155                 160

Val Val Gly Asp Lys Arg Asp Val Tyr Gln Gln Thr Ile Ala Ser Gly
                165                 170                 175

Ser Leu Gln His Thr Leu Tyr Thr Gln Asn Val Thr Ala Leu Lys Gln
            180                 185                 190

Ser Arg Leu Trp Gln Ile Leu Gly Met Arg Ser Ala Asp Thr Tyr Val
        195                 200                 205

Pro Glu Trp Met Trp His Ser Pro Ala Ala Val Lys Arg Val Phe Leu
    210                 215                 220

Gln Ala Leu Phe Glu Gly Asp Gly Ser Cys Ser Arg Arg Pro His Asn
225                 230                 235                 240

Thr Ile Gln Ile Ser Tyr Asn Thr Val Ser Lys Gln Leu Ala Met Asp
                245                 250                 255

Val Gln Gln Met Leu Leu Glu Phe Gly Val Ile Ser Arg Arg Tyr Leu
            260                 265                 270

His Ala Ala Gly Glu Tyr Lys Val Val Ile Thr Asp Arg Ala Gln Ala
        275                 280                 285

Glu Leu Phe Pro Lys Gln Ile Gly Phe Gly Gly Ala Lys Gln Thr Glu
    290                 295                 300

Leu Ser Lys Ile Leu Ala Ala Met Pro Pro Cys Ala Gly Arg Asp Ser
305                 310                 315                 320

Asp His Val Pro Gly Leu Ala Arg Phe Ile Arg Arg His Cys Asp Ser
                325                 330                 335

Arg Trp Val Asp Lys Glu Trp Leu His Lys His Asn Ile Asp His Leu
            340                 345                 350

Ser Arg Trp Arg Arg Asp Gly Ala Glu Ile Leu Ser His Ile Ala Asp
        355                 360                 365

Pro Asp Val Arg Thr Ile Ala Thr Asp Leu Thr Asp Gly Arg Phe Tyr
    370                 375                 380

Tyr Ala Arg Val Ala Ser Val Thr Asp Thr Gly Val Gln Pro Val Tyr
385                 390                 395                 400

Ser Leu Arg Val Asp Thr Asp Asp His Ala Phe Leu Thr Asn Gly Phe
                405                 410                 415

Val Ser His Asn
            420
```

<210> SEQ ID NO 30
<211> LENGTH: 420
<212> TYPE: PRT
<213> ORGANISM: Mycobacterium leprae

<400> SEQUENCE: 30

Cys Val Ser Gly Asn Ser Leu Val Arg Leu Leu Phe Gly Lys Ser Ile
1 5 10 15

Arg Ile Gly Asp Ile Val Thr Gly Ala Gln Phe Asn Ser Asp Asn Pro
20 25 30

Ile Asp Leu Lys Val Leu Asp Arg His Gly Asn Pro Val Val Ala Asp
35 40 45

Tyr Leu Phe His Ser Gly Glu His Gln Thr Tyr Thr Val Arg Thr Thr
50 55 60

Glu Gly Tyr Glu Ile Thr Gly Thr Ser Asn His Pro Leu Leu Cys Leu
65 70 75 80

Val Asn Val Gly Gly Ile Pro Thr Leu Leu Trp Lys Leu Ile Gly Glu
85 90 95

Ile Arg Ser Gly Asp Tyr Val Val Leu Gln Arg Ile Pro Pro Val Glu
100 105 110

Phe Gly Pro Ala Asp Trp Tyr Ser Thr Met Glu Ala Leu Leu Phe Gly
115 120 125

Ala Phe Ile Ser Gly Gly Phe Val Phe Gln Asp His Ala Gly Phe Asn
130 135 140

Ser Leu Asp Arg Asp Tyr Phe Thr Met Val Val Asn Ala Tyr Asp Thr
145 150 155 160

Val Val Gly Gly Leu Arg Cys Ile Ser Ser Arg Ile Thr Val Ser Gly
165 170 175

Ser Thr Leu Leu Glu Leu Asp Val Tyr Asn Leu Ile Glu Phe Lys Lys
180 185 190

Thr Arg Leu Ser Gly Leu Cys Gly Gln Arg Ser Ala Asp Lys Leu Val
195 200 205

Pro Asp Trp Leu Trp His Ser Pro Ser Thr Val Lys Arg Ala Phe Leu
210 215 220

Gln Ala Leu Phe Glu Gly Glu Gly Phe Ser Ser Ile Leu Ser Arg Asn
225 230 235 240

Ile Ile Glu Ile Ser Tyr Ser Thr Leu Ser Glu Arg Leu Ala Ala Asp
245 250 255

Val Gln Gln Met Leu Leu Glu Phe Gly Val Val Ser Glu Arg Tyr Cys
260 265 270

His Thr Val Asn Glu Tyr Lys Val Val Ile Ala Asn Arg Ala Gln Val
275 280 285

Glu Met Phe Phe Thr Gln Val Gly Phe Gly Val Thr Lys Gln Ala Lys
290 295 300

Leu Ile Arg Asp Val Val Ser Met Ser Pro Cys Val Gly Met Asp Ile
305 310 315 320

Asn Cys Val Pro Gly Leu Ala Thr Phe Ile Arg Lys His Cys Asp Asn
325 330 335

Arg Trp Val Glu Glu Asp Ser Phe Asn Gln His Asn Val Asp Cys Val
340 345 350

Gln His Trp His His His Ser Ala Glu Ile Val Gly His Ile Ala Asp
355 360 365

Pro Asp Ile Arg Ala Ile Val Thr Asp Leu Thr Asp Gly Arg Phe Tyr 370 375 380

Tyr Ala Arg Val Ala Ser Val Thr Asp Thr Gly Ile Gln Pro Val Phe
385 390 395 400

Ser Leu His Val Asp Thr Glu Asp His Ser Phe Leu Thr Asn Gly Phe
405 410 415

Ile Ser His Asn
420

<210> SEQ ID NO 31
<211> LENGTH: 420
<212> TYPE: PRT
<213> ORGANISM: Mycobacterium malmoense

<400> SEQUENCE: 31

Cys Cys Thr Gly Asp Ala Leu Val Arg Leu Pro Phe Gly His Ser Val
1 5 10 15

Arg Ile Gly Asn Phe Val Pro Ala Ala Cys Pro Asn Ser Asp Asn Ala
20 25 30

Val Asn Leu Lys Val Leu Asp Arg His Gly Asp Pro Val Val Ala Asp
35 40 45

Gln Leu Phe His Ser Gly Glu His Gln Thr Tyr Thr Val Arg Thr Ala
50 55 60

Glu Gly Tyr Glu Val Thr Gly Thr Ser Asn His Pro Leu Leu Cys Leu
65 70 75 80

Val Asp Val Gly Gly Val Pro Thr Leu Leu Trp Lys Leu Ile Glu Glu
85 90 95

Ile Arg Pro Asp Asp His Val Val Leu Gln Arg Thr Pro Pro Val Glu
100 105 110

Phe Gly Pro Ala Asp Trp His Asp Val Met Glu Ala Leu Leu Leu Gly
115 120 125

Ala Phe Ile Ser Glu Gly Phe Val Ser Glu Val Arg Ala Gly Phe Asn
130 135 140

Asn Cys Asp Arg Asp Tyr Phe Ala Met Val Val Gly Ala Tyr Asp Ala
145 150 155 160

Val Val Gly Gly Arg Arg Tyr Val Ser Ser Arg Arg Ile Ala Ser Gly
165 170 175

Ser Thr Leu His Glu Leu Asp Ile Gln Asn Ile Lys Glu Leu Lys Glu
180 185 190

Ala Arg Leu Gly Asp Leu Cys Gly Gln Arg Pro Ala Asp Lys Ser Val
195 200 205

Pro Asp Trp Leu Trp His Ser Pro Ala Ala Val Lys Arg Val Phe Leu
210 215 220

Gln Ala Leu Phe Glu Gly Gly Gly Ser Cys Ser Ala Leu Pro Arg Asn
225 230 235 240

Met Ile Gln Ile Ser Tyr Ser Thr Arg Ser Arg Gln Leu Ala Val Asp
245 250 255

Val Gln Gln Met Leu Leu Glu Phe Gly Ile Ile Thr Arg Arg Tyr Arg
260 265 270

His Ala Val Gly Glu His Lys Val Leu Ile Thr Asn Arg Ala Gln Ala
275 280 285

Glu Leu Phe Ala Thr Arg Val Gly Phe Gly Gly Ala Lys Gln Glu Lys
290 295 300

Leu Thr Lys Ile Leu Gly Ser Met Pro Pro Cys Ala Gly Met Asp Ser
305 310 315 320

```
Asp His Val Pro Gly Leu Ala Arg Phe Ile Arg Lys His Cys Gly Ser
                325                 330                 335

Arg Trp Val Asp Lys Asp Trp Leu Asn Arg His Asn Val Asp Arg Ile
            340                 345                 350

Gln Arg Trp Arg Thr Ser Gly Glu Lys Ile Leu Ser His Ile Ala Asp
        355                 360                 365

Pro Asp Val Arg Ala Ile Ala Thr Asp Leu Thr Asp Gly Arg Phe Tyr
    370                 375                 380

Tyr Ala Lys Val Ala Ser Val Thr Glu Ala Gly Val Gln Pro Val Tyr
385                 390                 395                 400

Ser Leu Arg Val Asp Thr Asp Glu His Ala Phe Leu Thr Asn Gly Phe
                405                 410                 415

Val Ser His Asn
            420


<210> SEQ ID NO 32
<211> LENGTH: 430
<212> TYPE: PRT
<213> ORGANISM: Synechocystis sp. PCC6803

<400> SEQUENCE: 32

Cys Leu Thr Gly Asp Ser Gln Val Leu Thr Arg Asn Gly Leu Met Ser
1               5                   10                  15

Ile Asp Asn Pro Gln Ile Lys Gly Arg Glu Val Leu Ser Tyr Asn Glu
            20                  25                  30

Thr Leu Gln Gln Trp Glu Tyr Lys Lys Val Leu Arg Trp Leu Asp Arg
        35                  40                  45

Gly Glu Lys Gln Thr Leu Ser Ile Lys Thr Lys Asn Ser Thr Val Arg
    50                  55                  60

Cys Thr Ala Asn His Leu Ile Arg Thr Glu Gln Gly Trp Thr Arg Ala
65                  70                  75                  80

Glu Asn Ile Thr Pro Gly Met Lys Ile Leu Ser Pro Ala Ser Val Asp
                85                  90                  95

Val Asp Asn Leu Ser Gln Ser Thr Ala Leu Thr Ala Ser Leu Gly Gly
            100                 105                 110

Leu Ser Gly Ala Ile Asn Tyr Glu Ala Ile Asn Thr Asp Lys Lys Asn
        115                 120                 125

Thr Thr Leu Ser Leu Ser Leu Lys Lys Gln Lys Pro Gln Asp Pro Phe
    130                 135                 140

Val Asn Ala Asp Val Ala Lys Asn Leu Ile Phe Gln His Phe Cys Ser
145                 150                 155                 160

Ala Lys Glu Glu Lys Leu Lys Val Ser Asn Pro Ile Gly Glu Asp Ile
                165                 170                 175

Pro Thr Lys Lys Ala Thr Asp Phe Gly Ile Ser Glu Gln Lys Lys Leu
            180                 185                 190

His Gln Gly Gln Asn Arg Trp Glu Gln Lys Phe Ser Val Leu Ser Thr
        195                 200                 205

Glu Pro Cys Leu Gly Met Glu Val Leu Thr Ile Pro Thr His Ile Ala
    210                 215                 220

Asp Ser Pro Ala Cys Asp Gly Pro Thr Ala Pro Ser Ser Gln Asn Gly
225                 230                 235                 240

Trp Asn Ile Lys Arg Gln Asp Trp Asp Val Cys His Pro Lys Tyr Asp
                245                 250                 255

Ser Gln Pro Ile Lys Ala Met Gly Lys Val Pro Ser Ala Val Lys Pro
            260                 265                 270
```

```
Val Val Pro Gln Thr Leu Leu Met Phe Ser Ala Gln Ser Asn Leu Glu
        275                 280                 285

Val Lys Glu Asn Lys Phe Leu Arg Asn Gly Ser Arg Ile Ser Leu Lys
    290                 295                 300

Lys Glu Trp Leu Gly Gly Thr Trp Thr Thr Val Pro Ser Leu Phe Pro
305                 310                 315                 320

Asn Leu Gly Val His Gln Phe Ser Tyr Thr Gln Arg Ala Phe Ser Arg
                325                 330                 335

Lys Lys Ile Asn Leu Leu Leu Asn Gly Leu Pro Ile Glu Asp Ile Pro
            340                 345                 350

Pro Val Gln Asn Pro Ile Ala Glu Ala Leu Thr Ala Lys Pro Ile Thr
        355                 360                 365

Thr Gln Lys Trp Glu Gln Trp Pro Pro Ala Ser Gly Tyr Arg Thr Trp
    370                 375                 380

Lys Ser Ile Pro Ser Pro Gln Trp His Thr Asn Phe Glu Glu Val Glu
385                 390                 395                 400

Ser Val Thr Lys Gly Gln Val Glu Lys Val Tyr Asp Leu Glu Val Glu
                405                 410                 415

Asp Asn His Asn Phe Val Ala Asn Gly Leu Leu Val His Asn
            420                 425                 430


<210> SEQ ID NO 33
<211> LENGTH: 333
<212> TYPE: PRT
<213> ORGANISM: Pyrococcus abyssi

<400> SEQUENCE: 33

Cys Phe Ser Gly Glu Glu Thr Val Val Ile Arg Glu Asn Gly Glu Val
1               5                   10                  15

Lys Val Leu Arg Leu Lys Asp Phe Val Glu Lys Ala Leu Glu Lys Pro
            20                  25                  30

Ser Gly Glu Gly Leu Asp Gly Asp Val Lys Val Val Tyr His Asp Phe
        35                  40                  45

Arg Asn Glu Asn Val Glu Val Leu Thr Lys Asp Gly Phe Thr Lys Leu
    50                  55                  60

Leu Tyr Ala Asn Lys Arg Ile Gly Lys Gln Lys Leu Arg Arg Val Val
65                  70                  75                  80

Asn Leu Glu Lys Asp Tyr Trp Phe Ala Leu Thr Pro Asp His Lys Val
                85                  90                  95

Tyr Thr Thr Asp Gly Leu Lys Glu Ala Gly Glu Ile Thr Glu Lys Asp
            100                 105                 110

Glu Leu Ile Ser Val Pro Ile Thr Val Phe Asp Cys Glu Asp Glu Asp
        115                 120                 125

Leu Lys Lys Ile Gly Leu Leu Pro Leu Thr Ser Asp Asp Glu Arg Leu
    130                 135                 140

Arg Lys Ile Ala Thr Leu Met Gly Ile Leu Phe Asn Gly Gly Ser Ile
145                 150                 155                 160

Asp Glu Gly Leu Gly Val Leu Thr Leu Lys Ser Glu Arg Ser Val Ile
                165                 170                 175

Glu Lys Phe Val Ile Thr Leu Lys Glu Leu Phe Gly Lys Phe Glu Tyr
            180                 185                 190

Glu Ile Ile Lys Glu Glu Asn Thr Ile Leu Lys Thr Arg Asp Pro Arg
        195                 200                 205

Ile Ile Lys Phe Leu Val Gly Leu Gly Ala Pro Ile Glu Gly Lys Asp
```

```
    210                 215                 220

Leu Lys Met Pro Trp Trp Val Lys Leu Lys Pro Ser Leu Phe Leu Ala
225                 230                 235                 240

Phe Leu Glu Gly Phe Arg Ala His Ile Val Glu Gln Leu Val Asp Asp
                245                 250                 255

Pro Asn Lys Asn Leu Pro Phe Phe Gln Glu Leu Ser Trp Tyr Leu Gly
            260                 265                 270

Leu Phe Gly Ile Lys Ala Asp Ile Lys Val Glu Glu Val Gly Asp Lys
        275                 280                 285

His Lys Ile Ile Phe Asp Ala Gly Arg Leu Asp Val Asp Lys Gln Phe
    290                 295                 300

Ile Glu Thr Trp Glu Asp Val Glu Val Thr Tyr Asn Leu Thr Thr Glu
305                 310                 315                 320

Lys Gly Asn Leu Leu Ala Asn Gly Leu Phe Val Lys Asn
                325                 330


<210> SEQ ID NO 34
<211> LENGTH: 412
<212> TYPE: PRT
<213> ORGANISM: Methanococcus jannaschii

<400> SEQUENCE: 34

Cys Ile Glu Gly Asp Ala Lys Ile Leu Thr Asp Arg Gly Phe Leu Lys
1               5                   10                  15

Met Lys Glu Val Tyr Lys Leu Val Lys Asn Gly Glu Lys Leu Lys Val
            20                  25                  30

Leu Gly Leu Asn Ala Glu Thr Leu Lys Thr Glu Trp Lys Glu Ile Ile
        35                  40                  45

Asp Ala Gln Lys Arg Glu Ala Arg Arg Tyr Glu Ile Gly Val Tyr Arg
    50                  55                  60

Lys Asn Lys Asn Thr Lys Asp Thr Ile Lys Ile Thr Pro Asp His Lys
65                  70                  75                  80

Phe Pro Val Phe Val Asn Gly Glu Leu Ser Lys Val Gln Leu Cys Asp
                85                  90                  95

Ile Ile Asp Asn Asn Leu Ser Val Leu Ser Ile Asp Tyr Ile Pro Met
            100                 105                 110

Ile Glu Glu Lys Tyr Glu Ser Leu Ala Glu Val Met Tyr Leu Gly Gly
        115                 120                 125

Ala Val Leu Ser Asp Gly His Ile Val Arg Arg Asn Gly Lys Pro Ile
    130                 135                 140

Arg Val Arg Phe Thr Gln Lys Asp Thr Glu Glu Lys Lys Asp Phe Ile
145                 150                 155                 160

Glu Lys Val Lys Gly Asp Val Lys Leu Ile Gly Gly Asn Phe Ile Glu
                165                 170                 175

Ile Ser Asn Arg Asn Asn Val Ile Glu Tyr Gln Thr Ser Arg Lys Ile
            180                 185                 190

Pro Ser Glu Ile Leu Gly Phe Ile Glu Val Asn Ile Asn Thr Ile Pro
        195                 200                 205

Leu Tyr Ala Thr Lys Asp Glu Ile Ala Asp Leu Ile Ala Gly Phe Val
    210                 215                 220

Asp Gly Asp Gly Cys Leu Ser Gly Lys Arg Arg Val Glu Ile Tyr Gln
225                 230                 235                 240

Asn Ser Ser His Ile Lys Lys Ile Glu Gly Leu Ile Val Gly Leu Tyr
                245                 250                 255
```

Arg Leu Gly Ile Ile Pro Arg Leu Arg Tyr Lys Arg Ser Ser Thr Ala
260 265 270

Thr Ile Tyr Phe Asn Asn Asn Leu Glu Thr Ile Leu Gln Arg Thr Arg
275 280 285

Arg Ile Lys Leu Asp Lys Leu Lys Glu Phe Lys Lys Pro Val Glu Asp
290 295 300

Lys Lys Leu Ile Asp Ile Ser Gln Ile Leu Pro Glu Leu Lys Glu Phe
305 310 315 320

Asp Tyr Lys Gly Tyr Leu Tyr Lys Thr Tyr Lys Glu Lys Leu Phe Ile
325 330 335

Gly Ile Asn Lys Leu Glu Glu Tyr Leu Ser Lys Ile Asp Lys Asp Gly
340 345 350

Ile Glu Arg Ile Lys Gln Lys Ile Lys Leu Leu Lys Glu Ser Asp Ile
355 360 365

Tyr Ser Ile Arg Ile Lys Lys Val Gly Glu Asp Tyr Gly Glu Val Tyr
370 375 380

Asn Ile Thr Val Lys Ala Glu Asn Glu Phe Asn His Asn Tyr Val Val
385 390 395 400

Trp Thr Lys His Tyr Thr Pro Ile Val Val Phe Asn
405 410

<210> SEQ ID NO 35
<211> LENGTH: 819
<212> TYPE: PRT
<213> ORGANISM: Aspergillus fumigatus

<400> SEQUENCE: 35

Cys Leu Ala Lys Gly Thr Arg Leu Leu Arg Tyr Asp Gly Ser Glu Ile
1 5 10 15

Glu Val Gln Asp Val Lys Glu Gly Asp Leu Leu Leu Gly Pro Asp Gly
20 25 30

Gly Pro Arg Arg Ala Phe Asn Ile Val Asn Gly Lys Asp Arg Leu Tyr
35 40 45

Arg Ile Lys Ile Gly Gly Ser Lys Glu Asp Leu Val Val Thr Pro Asn
50 55 60

His Ile Leu Val Leu His Arg Glu Lys Arg Ala Arg Asn Val Tyr Thr
65 70 75 80

Gly Pro Ser Val Gln Gly His Ile Gln Arg Ser Glu Asn Gly His Gly
85 90 95

Asn Leu Pro Met Leu Ser Ser Ser Pro Ala Ala Ala His His Pro Asn
100 105 110

Asn Leu Val Lys Asn Arg Gly Asp Phe Trp Ser Ala Leu Lys Ser Ala
115 120 125

Ile Ala Trp Val Leu His Ala Glu Arg Ser Ser Thr Gly Ala Asn Met
130 135 140

Val Arg Asn Val Leu Asn Gly Thr Val Gly Leu Thr Ala His Lys Glu
145 150 155 160

Ser Tyr Thr Val Thr Asn Pro Gln Gln Lys Gly Val Tyr Tyr Thr Tyr
165 170 175

Val Trp Gly Asn Pro Gln Arg Thr Ser Ile Lys Gly His Arg Asp His
180 185 190

Pro Pro Val Phe Leu Pro Thr Lys Glu Asp Ala Phe Ser Ala Ala Ile
195 200 205

Ala Lys Ser Arg Glu Leu Tyr Ser Gln Ser Glu Val Thr Leu Ala Thr
210 215 220

```
Leu Arg Gln Arg Phe Leu Ala Lys Ser Ala Asp Gly Lys Gly Gly Glu
225                 230                 235                 240

Ile Leu Val Asp Ala Asn Leu Pro Asn Ile Phe Leu Leu Trp Asp Lys
                245                 250                 255

Asn Arg Ser Asn Leu Lys Phe Arg Val Leu Cys Ser Arg Asn Phe Lys
            260                 265                 270

Thr Tyr Gly Arg Val Tyr Thr Phe Glu Ser Met Pro Ser Thr Asn Ala
        275                 280                 285

Glu Glu Pro Gly Tyr Gly Asp Asp Asp Glu Leu Pro Gln Val Ser Ala
    290                 295                 300

Glu Glu Arg Tyr Asp Thr Val Glu Met Thr Ala Ala Glu Phe Ala Ser
305                 310                 315                 320

Leu Ser Thr Glu Glu Arg Ser Arg Tyr Arg Val Phe Arg Cys Pro Gly
                325                 330                 335

Phe Glu Leu Pro Glu Gln Pro Val Pro Val Asn Pro Tyr Phe Leu Gly
            340                 345                 350

Leu Trp Leu Gly Asp Asp Asn His Glu Lys Thr Thr Asn His Asn Ile
        355                 360                 365

His Glu Glu Asn Val Arg Glu Phe Leu Val Asn His Ala Ala Glu Leu
    370                 375                 380

Asp Met Tyr Leu Ala Trp Gln Gly Leu Ile Asp Tyr Ala Thr Val Ala
385                 390                 395                 400

Asn Pro Ala Pro Met Met Val Arg Leu Pro Pro Thr Asn Pro Asp Thr
                405                 410                 415

Ile Glu His Arg Pro Val Val Cys Gln Ala Arg Gln Ser Ile Arg Lys
            420                 425                 430

Leu Arg Leu Ala Ala Lys Asn Ile Ala Gln Pro Glu Val Val Leu Ser
        435                 440                 445

Thr Ser Pro Arg Pro Glu Ser Gln Met Gln Pro Lys Arg Glu Leu Pro
    450                 455                 460

Ser Asn Thr Glu Thr Ala Leu Arg Ser Glu Ala Glu Ala Ser Ser Ile
465                 470                 475                 480

Ser Ala Ile Leu Asp Ser Lys Ala Gly His Ser Ser Leu Asp Thr Gly
                485                 490                 495

Asp Pro Asn Ser Asp Val Val Pro Glu Ser Ile Pro Asn Asp Val Ala
            500                 505                 510

Asp Phe Gly Leu Asp Gly Val Pro Glu Leu Thr Ser Ser Gly Phe Ser
        515                 520                 525

Glu Leu Thr Ser Asp Ser Glu Leu Met Arg Leu Ile Glu Gln Val Glu
    530                 535                 540

Arg Ser Ser Gln Gly Ser Thr Glu Glu Pro Ser Gln Ala Ser Val Val
545                 550                 555                 560

Glu Gln Glu Ala Asp Leu Asn Leu Leu Glu Thr Asp Ser Glu Asp Glu
                565                 570                 575

Glu Ala Asp Ser Ala Asp Asp Asp Glu Phe Gly Asp Pro Glu Ala Ser
            580                 585                 590

Glu Phe Arg Pro Glu Pro Glu Ser Gln Leu Ser Gln Ser His Phe Ser
        595                 600                 605

Asn Arg Arg Arg Asn His Arg Leu Arg Thr Gly Arg Arg Val Tyr Gly
    610                 615                 620

Asp Leu Asn Gly Glu Glu Glu Gly Ile Leu Leu Asp Gln Ile Val Glu
625                 630                 635                 640
```

-continued

```
Gln Ser Glu Gly Ser Arg Val Asn Ser Leu Leu Arg Ala Leu Asp Ala
                645                 650                 655

Leu Gly Ile Ile Ala Gln Lys Gly Thr Gly Pro Glu Thr Asn Arg Lys
            660                 665                 670

His Ile Pro Ser Ile Tyr Met Lys Asn Ser Arg Ser Val Arg Leu Ala
        675                 680                 685

Val Leu Ala Gly Leu Ile Asp Ser Asp Gly Trp Tyr Val Tyr Pro Glu
    690                 695                 700

Asn Val Leu Gly Phe Ala Gln Ser Glu Arg Trp His Ser Lys Leu Phe
705                 710                 715                 720

Trp Asp Val Val Ala Leu Ala Arg Ser Leu Gly Leu Ser Val Leu Thr
                725                 730                 735

Lys Arg Arg Met Met Trp Asn Pro Ala Arg Thr Glu Arg Tyr Pro Gln
            740                 745                 750

Leu Phe Ala Gln Ile Ser Gly Asn Val Ala Glu Val Pro Cys Leu Ile
        755                 760                 765

Ala Arg Lys Lys Gly Val Glu Arg Leu Ile Pro Gln Thr His Ser Phe
    770                 775                 780

Met Ile Lys Asp Ile Ser Leu Glu Pro Glu Ala Thr Glu Trp Ala Gly
785                 790                 795                 800

Phe Arg Val Asp Lys Asp Gln Leu Tyr Leu Arg His Asp Tyr Leu Val
                805                 810                 815

Leu His Asn


<210> SEQ ID NO 36
<211> LENGTH: 605
<212> TYPE: PRT
<213> ORGANISM: Aspergillus nidulans FGSC A

<400> SEQUENCE: 36

Cys Leu Ala Asn Gly Thr Gln Leu Leu Arg Tyr Asp Gly Thr Lys Val
1               5                   10                  15

Asn Val Glu Asp Val Lys Glu Gly Asp Leu Leu Leu Gly Pro Asp Gly
            20                  25                  30

Gly Pro Arg Arg Ala Phe Asn Val Val Ser Gly Lys Asp Arg Leu Tyr
        35                  40                  45

Arg Ile Lys Ile Asp Gly Asp Lys Glu Asp Leu Val Val Thr Ala Asn
    50                  55                  60

His Ile Leu Val Leu His Arg Ala Lys Ala Met Asn Thr Ser Val Cys
65                  70                  75                  80

Phe Asp Arg Ser Lys Glu Gln Gln Gly Gly Ala Gly Glu Gln Leu Asp
                85                  90                  95

Ile Ser Glu Val Ser Ala Ala Glu Arg Tyr Asp Thr Val Glu Met Thr
            100                 105                 110

Ala Ala Glu Phe Ala Ala Leu His Pro Gln Glu Arg Ser Trp Tyr Arg
        115                 120                 125

Ala Ile Arg Cys Pro Gly Phe Glu Leu Pro Glu Gln Asp Val Pro Val
    130                 135                 140

Asn Pro Tyr Phe Leu Gly Leu Trp Leu Gly Asp Glu Ser Arg Asn Gln
145                 150                 155                 160

Ser Ala Ile Tyr Ser Asn His Glu Glu Ala Leu Arg Glu Phe Leu Val
                165                 170                 175

Ser His Ala Ala Glu Leu Asp Met His Leu Val Tyr His Gly Gln Ser
            180                 185                 190
```

```
Ala Tyr Ser Thr Val Cys Asn Lys Asp Arg Pro Thr Asn Lys Arg Ile
        195                 200                 205

Gly Pro Ala Asn Gln Thr Gln Thr Val Arg Pro Thr Ile Arg Gln Thr
    210                 215                 220

Arg Arg Thr Ile Arg Gln Gln Arg Leu Ala Ala Glu His Ala Ala Ala
225                 230                 235                 240

Glu Tyr Thr Thr Gln Arg Glu Thr Ala Ser Leu Thr Pro Leu Leu Glu
                245                 250                 255

Ser Pro Thr Ser Asp Lys His Gly Leu Leu Ser Ser Val Glu Thr Pro
            260                 265                 270

Gly Arg Leu Ser Asp Ser Val Thr Thr Glu Leu Pro Met Ser Arg Ser
        275                 280                 285

Ala Ser Ala Met Arg Ser Ile Arg Thr Ala Ser Gly Leu Ser Glu Phe
    290                 295                 300

Asn Asp Val Thr Asn Val Ser Ala Ser Met Pro Asp Ile Gln Asn Ser
305                 310                 315                 320

Gly Ile Lys Asn Gln Gly Arg Ile Ala Lys Val Thr Arg Gln Gln Asp
                325                 330                 335

Ser Lys Gly Glu Val Asp Phe Arg Gln Gln Tyr Ser Gln Ala Ile Lys
            340                 345                 350

Asp Asp Leu Glu Leu Leu Glu Thr Asp Ile Glu Asp Asp Val Ala Ser
        355                 360                 365

Ser Asp Glu Ile Glu Asp Val Cys Val Val Gly Ser Glu Asn Glu Leu
    370                 375                 380

Ile Gly Ser Glu Lys Gln Asp Gln Ser Gly Arg Arg Arg Gln Ile His
385                 390                 395                 400

Arg Leu Arg Thr Gly His Arg Gly Tyr Gly Asp Leu Ser Asp Asp Glu
                405                 410                 415

Gln Glu Gln Leu Leu Asp Ser Val Val Glu Arg Tyr Ala Gly Asp Ser
            420                 425                 430

Arg Leu Asn Thr Leu Gln Gln Glu Leu Ser Lys Met Gly Ile Leu Asn
        435                 440                 445

Pro Glu Thr Gly Pro Ile Asn Asp Lys Lys Arg Ile Pro Gln Val Phe
    450                 455                 460

Met Gln Asn Ser Arg Ser Val Arg Leu Ser Val Leu Ala Gly Leu Leu
465                 470                 475                 480

Asp Ser Asp Gly Trp Tyr Ile Tyr Pro Glu Asn Met Phe Gly Phe Ala
                485                 490                 495

Gln Ser Glu Leu Cys His Lys Glu Leu Phe Trp Asp Val Val Thr Leu
            500                 505                 510

Ala Arg Ser Leu Gly Phe Gly Val Trp Thr Lys Lys Arg Met Met Pro
        515                 520                 525

Asp Pro Thr Gly Lys Arg Met Ser Pro Met Leu Val Ala Gln Ile Ser
    530                 535                 540

Gly Asp Leu Ala Glu Ile Pro Cys Val Leu Ala Arg Lys Lys Ala Met
545                 550                 555                 560

Pro Arg Leu Ile Pro Gln Ser His Ser Phe Ala Ile Lys Asp Ile Ser
                565                 570                 575

Leu Glu Ser Glu Ala Thr Glu Trp Ala Gly Phe Arg Val Asp Lys Asp
            580                 585                 590

Gln Leu Tyr Leu Arg His Asp Tyr Val Val Leu His Asn
        595                 600                 605
```

<210> SEQ ID NO 37
<211> LENGTH: 171
<212> TYPE: PRT
<213> ORGANISM: Cryptococcus neoformans

<400> SEQUENCE: 37

Cys Leu Gln Asn Gly Thr Arg Leu Leu Arg Ala Asp Gly Ser Glu Val
1 5 10 15

Leu Val Glu Asp Val Gln Glu Gly Asp Gln Leu Leu Gly Pro Asp Gly
20 25 30

Thr Ser Arg Thr Ala Ser Lys Ile Val Arg Gly Glu Glu Arg Leu Tyr
35 40 45

Arg Ile Lys Thr His Glu Gly Leu Glu Asp Leu Val Cys Thr His Asn
50 55 60

His Ile Leu Ser Met Tyr Lys Glu Arg Phe Gly Arg Glu Gly Ala His
65 70 75 80

Ser Pro Ser Ala Gly Thr Ser Leu Thr Glu Ser His Glu Arg Val Asp
85 90 95

Val Thr Val Asp Asp Phe Val Arg Leu Pro Gln Gln Glu Gln Gln Lys
100 105 110

Tyr Lys Leu Phe Arg Ser Thr Asp Phe Val Arg Arg Glu Gln Pro Ser
115 120 125

Ala Ser Lys Leu Ala Thr Leu Leu His Ile Asn Ser Ile Glu Leu Glu
130 135 140

Glu Glu Pro Thr Lys Trp Ser Gly Phe Val Val Asp Lys Asp Ser Leu
145 150 155 160

Tyr Leu Arg Tyr Asp Tyr Leu Val Leu His Asn
165 170

<210> SEQ ID NO 38
<211> LENGTH: 534
<212> TYPE: PRT
<213> ORGANISM: Histoplasma capsulatum

<400> SEQUENCE: 38

Cys Leu Ala Lys Gly Thr Gln Leu Leu Arg Tyr Asp Gly Thr Lys Val
1 5 10 15

Gly Val Glu Asn Val Arg Glu Gly Asp Leu Leu Leu Gly Pro Asp Gly
20 25 30

Glu Pro Arg Arg Ala Phe Asn Ile Val Ser Gly Arg Asp Arg Leu Tyr
35 40 45

Arg Ile Ser Ile Asp Ala Asp Lys Glu Asp Leu Val Val Thr Pro Asn
50 55 60

His Ile Leu Val Leu His His Glu Lys Glu Asn Gln Lys Arg Gln Ser
65 70 75 80

Glu Leu Ser Ala Ser Ala Thr Glu Arg Tyr Asp Thr Val Glu Met Thr
85 90 95

Ala Ala Asp Phe Ala Ala Leu Asp Pro Glu Glu Arg Arg Trp Tyr Arg
100 105 110

Leu Phe Arg Ser Pro Gly Phe Glu Leu Gly Gln Gln Asn Val Pro Ile
115 120 125

Asp Pro Tyr Phe Val Gly Phe Trp Leu Cys Asp Gly Ile Arg Ala Ser
130 135 140

Thr Thr Ile Tyr Thr Ser Pro Glu Glu Ala Thr Arg Glu Phe Ile Ile
145 150 155 160

Asn His Ala Ala Glu Leu Asp Leu Gln Leu Ala Ser Lys Glu Tyr Met

```
                165                 170                 175

Gln His Pro Val Arg Arg Val Ala Arg Gln Thr Ile Leu Glu Gln Arg
            180                 185                 190

Leu Ala Val Gln Cys Thr Ala Pro Gln Glu Thr Asp Gly Ser Leu Leu
        195                 200                 205

Ser His Ile Leu Gln Lys Ala Ala Lys Ser Gly Leu Ala Ser Ser Thr
    210                 215                 220

Arg Thr Met Ser Thr Ser Arg Asn Arg Gln Pro Leu Ser Glu Thr Ser
225                 230                 235                 240

Ala Ala Thr Ser Met Asn Ile Leu Pro Gly Phe Ala Ser Asn Ser Thr
                245                 250                 255

Ser Val Val Ser Pro Gly Ile Asp Ser His Glu Ile Leu Ser Leu Arg
            260                 265                 270

Asn Ser Cys Ser Gln Leu Val Gln Ile Ala Glu Lys Ser Gly Leu Arg
        275                 280                 285

Glu Glu Cys Met Ile Asn Pro Pro Ser Ser Arg Glu Asp Leu Val Leu
    290                 295                 300

Asp Leu Phe Asp Thr His Ile Glu Ala Asp Glu Ile Gln Gly Leu Asp
305                 310                 315                 320

Glu Asn Leu Thr Gly Gln Lys His Arg Leu Arg Thr Gly Cys Arg Ala
                325                 330                 335

Tyr Gly Asp Leu Thr Val Asp Glu Glu Gly Gln Ile Leu Asp Asn Ile
            340                 345                 350

Ile Ser Arg Pro Val Gly Thr Pro Asp Ile Gly Thr Leu Leu Arg Ala
        355                 360                 365

Leu Glu Glu Leu Gly Leu Pro Thr Asn Arg Thr Glu Gly His Gly Val
    370                 375                 380

Glu Asn Lys Arg Ile Pro Leu Met Tyr Met Lys Ser Ser Arg Ser Ile
385                 390                 395                 400

Arg Leu Ala Leu Leu Ala Gly Leu Ile Asp Ser Asp Gly Trp Tyr Cys
                405                 410                 415

Gln Pro Gln Asn Thr Phe Cys Phe Gly Glu Ser Glu Arg Ile Ser Pro
            420                 425                 430

Thr Leu Phe Trp Asp Ile Val Thr Leu Ala Arg Ser Leu Gly Leu Ser
        435                 440                 445

Val Ser Thr Glu Gln His Thr Met Arg Ser Pro Ala Cys Thr Ala Phe
    450                 455                 460

Lys Pro Arg Phe Val Ala Gln Ile Ser Gly Asn Val Ala Glu Val Thr
465                 470                 475                 480

Cys Leu Leu Ala Arg Lys Arg Gly Val Lys Ser Pro Val Ser Gln Ala
                485                 490                 495

His Ser Phe Thr Ile Lys Gly Ile His Leu Glu Ser Glu Met Thr Glu
            500                 505                 510

Trp Ala Gly Phe Arg Val Asp Lys Asp Gln Leu Tyr Leu Arg His Asp
        515                 520                 525

Phe Leu Val Leu His Asn
    530
```

<210> SEQ ID NO 39
<211> LENGTH: 157
<212> TYPE: PRT
<213> ORGANISM: Penicillium chrysogenum

<400> SEQUENCE: 39

```
Cys Leu Ala Lys Gly Thr Arg Leu Leu Arg Cys Asp Gly Thr Glu Ile
1               5                   10                  15

Asn Val Glu Asp Val Arg Glu Gly Asp Leu Leu Leu Gly Pro Asp Gly
            20                  25                  30

Glu Pro Arg Arg Ala Phe Asn Ile Val Asn Gly Ile Asp Arg Leu Tyr
        35                  40                  45

Arg Ile Lys Ile Gly Gly Glu Lys Glu Asp Leu Val Val Thr Pro Asn
    50                  55                  60

His Ile Leu Val Leu Tyr Arg Glu Asp Gly Ser Lys Asn Val Glu Lys
65                  70                  75                  80

Gln Thr Val Glu Ile Thr Ala Ala Glu Phe Ala Ala Leu Ser Thr Glu
                85                  90                  95

Glu Arg Ser Leu Tyr Ser Ala Phe Thr Ser Pro Arg Ala Glu Lys Gly
            100                 105                 110

Ala Asp Asp Ser Ala Gln Thr His Ser Phe Lys Ile Glu Gln Val Ser
        115                 120                 125

Leu Glu Ser Glu Lys Thr Glu Trp Ala Gly Phe Arg Val Asp Lys Asp
    130                 135                 140

Gln Leu Tyr Leu Arg His Asp Tyr Leu Val Leu His Asn
145                 150                 155


<210> SEQ ID NO 40
<211> LENGTH: 162
<212> TYPE: PRT
<213> ORGANISM: Penicillium expansum

<400> SEQUENCE: 40

Cys Leu Ala Lys Gly Thr Arg Leu Leu Arg Tyr Asp Gly Thr Glu Ile
1               5                   10                  15

Asn Val Glu Asp Val Arg Glu Gly Asp Gln Leu Leu Gly Pro Asp Gly
            20                  25                  30

Glu Pro Arg Arg Ala Phe Asn Ile Val Asn Gly Ile Asp Arg Leu Tyr
        35                  40                  45

Arg Ile Lys Ile Ala Gly Glu Lys Glu Asp Leu Val Val Thr Pro Asn
    50                  55                  60

His Ile Leu Val Leu Tyr Arg Glu Glu Glu Ala Ser Asp Gly Pro Lys
65                  70                  75                  80

Asn Ala Glu Arg Gln Thr Val Glu Ile Thr Ala Ala Glu Phe Ala Ala
                85                  90                  95

Leu Ser Thr Glu Glu Arg Gly Leu His Ser Ala Phe Thr Ser Ser Arg
            100                 105                 110

Val Glu Lys Asp Val Glu Asn Ser Ala Pro Gln Met His Ser Phe Lys
        115                 120                 125

Ile Glu His Ile Asn Leu Glu Tyr Glu Glu Thr Glu Trp Ala Gly Phe
    130                 135                 140

Arg Val Asp Lys Asp Gln Leu Tyr Leu Arg His Asp Tyr Leu Val Leu
145                 150                 155                 160

His Asn


<210> SEQ ID NO 41
<211> LENGTH: 161
<212> TYPE: PRT
<213> ORGANISM: Penicillium vulpinum

<400> SEQUENCE: 41

Cys Leu Ala Lys Gly Thr Arg Leu Leu Arg Tyr Asp Gly Thr Glu Ile
```

```
1               5                   10                  15

Asn Val Glu Asp Val Arg Glu Gly Asp Gln Leu Leu Gly Pro Asp Gly
            20                  25                  30

Glu Pro Arg Arg Ala Phe Asn Ile Val Ser Gly Ile Asp Arg Leu Tyr
        35                  40                  45

Arg Val Lys Ile Gly Gly Glu Lys Glu Asp Leu Val Val Thr Pro Asn
    50                  55                  60

His Ile Leu Val Phe Tyr Arg Glu Gly Pro Ser Asp Gly Pro Glu Asn
65                  70                  75                  80

Ala Glu Arg Gln Thr Val Glu Ile Thr Ala Ala Glu Phe Ala Thr Leu
                85                  90                  95

Ser Thr Glu Glu Arg Ser Leu Tyr Ser Ala Phe Thr Ser Pro Ala Val
            100                 105                 110

Glu Lys Gly Ala Glu Gly Ser Ala Ala Gln Met His Ser Phe Lys Val
        115                 120                 125

Glu Asp Ile Ser Leu Glu Ser Glu Lys Thr Glu Trp Ala Gly Phe Arg
    130                 135                 140

Val Asp Lys Asp Gln Leu Tyr Leu Arg His Asp Tyr Leu Val Leu His
145                 150                 155                 160

Asn


<210> SEQ ID NO 42
<211> LENGTH: 440
<212> TYPE: PRT
<213> ORGANISM: Mycobacterium tuberculosis

<400> SEQUENCE: 42

Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Asp His
            100                 105                 110

Ala Arg Leu Leu Gly Tyr Leu Ile Gly Asp Gly Arg Asp Gly Trp Val
        115                 120                 125

Gly Gly Lys Thr Pro Ile Asn Phe Ile Asn Val Gln Arg Ala Leu Ile
    130                 135                 140

Asp Asp Val Thr Arg Ile Ala Ala Thr Leu Gly Cys Ala Ala His Pro
145                 150                 155                 160

Gln Gly Arg Ile Ser Leu Ala Ile Ala His Arg Pro Gly Glu Arg Asn
                165                 170                 175

Gly Val Ala Asp Leu Cys Gln Gln Ala Gly Ile Tyr Gly Lys Leu Ala
            180                 185                 190

Trp Glu Lys Thr Ile Pro Asn Trp Phe Phe Glu Pro Asp Ile Ala Ala
        195                 200                 205

Asp Ile Val Gly Asn Leu Leu Phe Gly Leu Phe Glu Ser Asp Gly Trp
```

```
    210                 215                 220

Val Ser Arg Glu Gln Thr Gly Ala Leu Arg Val Gly Tyr Thr Thr Thr
225                 230                 235                 240

Ser Glu Gln Leu Ala His Gln Ile His Trp Leu Leu Leu Arg Phe Gly
                245                 250                 255

Val Gly Ser Thr Val Arg Asp Tyr Asp Pro Thr Gln Lys Arg Pro Ser
            260                 265                 270

Ile Val Asn Gly Arg Arg Ile Gln Ser Lys Arg Gln Val Phe Glu Val
        275                 280                 285

Arg Ile Ser Gly Met Asp Asn Val Thr Ala Phe Ala Glu Ser Val Pro
    290                 295                 300

Met Trp Gly Pro Arg Gly Ala Ala Leu Ile Gln Ala Ile Pro Glu Ala
305                 310                 315                 320

Thr Gln Gly Arg Arg Arg Gly Ser Gln Ala Thr Tyr Leu Ala Ala Glu
                325                 330                 335

Met Thr Asp Ala Val Leu Asn Tyr Leu Asp Glu Arg Gly Val Thr Ala
            340                 345                 350

Gln Glu Ala Ala Ala Met Ile Gly Val Ala Ser Gly Asp Pro Arg Gly
        355                 360                 365

Gly Met Lys Gln Val Leu Gly Ala Ser Arg Leu Arg Arg Asp Arg Val
    370                 375                 380

Gln Ala Leu Ala Asp Ala Leu Asp Asp Lys Phe Leu His Asp Met Leu
385                 390                 395                 400

Ala Glu Glu Leu Arg Tyr Ser Val Ile Arg Glu Val Leu Pro Thr Arg
                405                 410                 415

Arg Ala Arg Thr Phe Asp Leu Glu Val Glu Glu Leu His Thr Leu Val
            420                 425                 430

Ala Glu Gly Val Val Val His Asn
        435                 440
```

<210> SEQ ID NO 43
<211> LENGTH: 440
<212> TYPE: PRT
<213> ORGANISM: Mycobacterium tuberculosis

<400> SEQUENCE: 43

```
Cys Leu Ala Glu Gly Thr Arg Ile Phe Asp Pro Val Thr Gly Thr Thr
1               5                   10                  15

His Arg Ile Glu Asp Val Val Asp Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Gln Asp Val Ile Gly Leu Arg Ile Ala Gly Gly
    50                  55                  60

Ala Ile Val Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Asp His
            100                 105                 110

Ala Arg Leu Leu Gly Tyr Leu Ile Gly Asp Gly Arg Asp Gly Trp Val
        115                 120                 125

Gly Gly Lys Thr Pro Ile Asn Phe Ile Asn Val Gln Arg Ala Leu Ile
    130                 135                 140
```

```
Asp Asp Val Thr Arg Ile Ala Ala Thr Leu Gly Cys Ala Ala His Pro
145                 150                 155                 160

Gln Gly Arg Ile Ser Leu Ala Ile Ala His Arg Pro Gly Glu Arg Asn
                165                 170                 175

Gly Val Leu Asp Leu Cys Arg Arg Ala Gly Val His Gly Lys Leu Ala
            180                 185                 190

Trp Glu Lys Thr Ile Pro Asn Trp Phe Phe Glu Pro Asp Ile Ala Ala
        195                 200                 205

Asp Ile Val Gly Asn Leu Leu Phe Gly Leu Phe Glu Ser Asp Gly Trp
    210                 215                 220

Val Ser Arg Glu Gln Thr Gly Ala Leu Arg Val Gly Tyr Thr Thr Thr
225                 230                 235                 240

Ser Glu Gln Leu Ala His Gln Ile His Trp Leu Leu Leu Arg Phe Gly
                245                 250                 255

Val Gly Ser Thr Val Arg Asp Tyr Asp Pro Thr Gln Lys Arg Pro Ser
            260                 265                 270

Ile Val Asn Gly Arg Arg Ile Gln Ser Lys Arg Gln Val Phe Glu Val
        275                 280                 285

Arg Ile Ser Gly Met Asp Asn Val Thr Ala Phe Ala Glu Ser Val Pro
    290                 295                 300

Met Trp Gly Pro Arg Gly Ala Ala Leu Ile Gln Ala Ile Pro Glu Ala
305                 310                 315                 320

Thr Gln Gly Arg Arg Arg Gly Ser Gln Ala Thr Tyr Leu Ala Ala Glu
                325                 330                 335

Met Thr Asp Ala Val Leu Asn Tyr Leu Asp Glu Arg Gly Val Thr Ala
            340                 345                 350

Gln Glu Ala Ala Ala Met Ile Gly Val Ala Ser Gly Asp Pro Arg Gly
        355                 360                 365

Gly Met Lys Gln Val Leu Gly Ala Ser Arg Leu Arg Arg Asp Arg Val
    370                 375                 380

Gln Ala Leu Ala Asp Ala Leu Asp Asp Lys Phe Leu His Asp Met Leu
385                 390                 395                 400

Ala Glu Glu Leu Arg Tyr Ser Val Ile Arg Glu Val Leu Pro Thr Arg
                405                 410                 415

Arg Ala Arg Thr Phe Asp Leu Glu Val Glu Glu Leu His Thr Leu Val
            420                 425                 430

Ala Glu Gly Val Val Val His Asn
        435                 440


<210> SEQ ID NO 44
<211> LENGTH: 364
<212> TYPE: PRT
<213> ORGANISM: Mycobacterium flavescens

<400> SEQUENCE: 44

Cys Phe Ala Tyr Gly Thr Arg Gly Ala Leu Ala Asp Gly Thr Thr Glu
1               5                   10                  15

Lys Ile Gly Lys Ile Val Asn Gln Lys Met Asp Val Glu Val Met Ser
            20                  25                  30

Tyr Asp Pro Asp Thr Asp Gln Val Val Pro Arg Lys Val Val Asn Trp
        35                  40                  45

Phe Asn Asn Gly Pro Ala Glu Gln Phe Leu Gln Phe Thr Val Glu Lys
    50                  55                  60

Ser Gly Gly Asn Gly Lys Ser Gln Phe Ala Ala Thr Pro Asn His Leu
65                  70                  75                  80
```

Ile Arg Thr Pro Ala Gly Trp Thr Glu Ala Gly Asp Leu Val Ala Gly
85 90 95

Asp Arg Val Met Ala Ala Glu Pro His Arg Leu Ser Asp Gln Gln Phe
100 105 110

Gln Val Val Leu Gly Ser Leu Met Gly Asp Gly Asn Leu Ser Pro Asn
115 120 125

Arg Arg Asp Arg Asn Gly Val Arg Phe Arg Met Gly His Gly Ala Lys
130 135 140

Gln Val Asp Tyr Leu Gln Trp Lys Thr Ala Leu Leu Gly Asn Ile Lys
145 150 155 160

His Ser Thr His Val Asn Asp Lys Gly Ala Thr Phe Val Asp Phe Thr
165 170 175

Pro Leu Pro Glu Leu Ala Glu Leu Gln Arg Ala Val Tyr Leu Gly Asp
180 185 190

Gly Lys Lys Phe Leu Ser Glu Glu Asn Phe Lys Ala Leu Thr Pro Leu
195 200 205

Ala Leu Val Phe Trp Tyr Met Asp Asp Gly Pro Phe Thr Val Arg Ser
210 215 220

Lys Gly Leu Gln Glu Arg Thr Ala Gly Gly Ser Gly Arg Ile Glu Ile
225 230 235 240

Cys Val Glu Ala Met Ser Glu Gly Asn Arg Ile Arg Leu Arg Asp Tyr
245 250 255

Leu Arg Asp Thr His Gly Leu Asp Val Arg Leu Arg Leu Ser Gly Ala
260 265 270

Ala Gly Lys Ser Val Leu Val Phe Ser Thr Ala Ser Ser Ala Lys Phe
275 280 285

Gln Glu Leu Val Ala Pro Tyr Ile Thr Pro Ser Met Glu Tyr Lys Leu
290 295 300

Leu Pro Arg Phe Arg Gly Gln Gly Ala Val Thr Pro Gln Phe Val Glu
305 310 315 320

Pro Thr Gln Arg Leu Val Pro Ala Arg Val Leu Asp Val His Val Lys
325 330 335

Pro His Thr Arg Ser Met Asn Arg Phe Asp Ile Glu Val Glu Gly Asn
340 345 350

His Asn Tyr Phe Val Asp Gly Val Met Val His Asn
355 360

<210> SEQ ID NO 45
<211> LENGTH: 365
<212> TYPE: PRT
<213> ORGANISM: Mycobacterium leprae

<400> SEQUENCE: 45

Cys Met Asn Tyr Ser Thr Arg Val Thr Leu Ala Asp Gly Ser Thr Glu
1 5 10 15

Lys Ile Gly Lys Ile Val Asn Asn Lys Met Asp Val Arg Val Leu Ser
20 25 30

Tyr Asp Pro Val Thr Asp Arg Ile Val Pro Arg Lys Val Val Asn Trp
35 40 45

Phe Asn Asn Gly Pro Ala Glu Gln Phe Leu Gln Phe Thr Val Glu Lys
50 55 60

Ser Gly Ser Asn Gly Lys Ser Gln Phe Ala Ala Thr Pro Asn His Leu
65 70 75 80

Ile Arg Thr Pro Gly Gly Trp Thr Glu Ala Gly Asn Leu Ile Ala Gly

-continued

```
                85                  90                  95

Asp Arg Val Leu Ala Val Glu Pro His Met Leu Ser Asp Gln Gln Phe
            100                 105                 110

Gln Val Val Leu Gly Ser Leu Met Gly Asp Gly Asn Leu Ser Pro Asn
        115                 120                 125

Leu Cys Asp Arg Asn Gly Val Arg Phe Arg Leu Leu Gly Tyr Gly Cys
    130                 135                 140

Lys Gln Val Glu Tyr Leu Gln Trp Lys Lys Ala Leu Met Gly Asn Ile
145                 150                 155                 160

Arg His Thr Val Arg Glu Asn Ser Met Gly Ala Ser Phe Ile Asp Phe
                165                 170                 175

Thr Pro Leu Pro Glu Leu Val Glu Leu Gln Arg Ala Val Tyr Leu Gly
            180                 185                 190

Asp Gly Lys Lys Phe Leu Ser Glu Glu Tyr Leu Lys Ala Leu Thr Pro
        195                 200                 205

Leu Val Leu Ala Ile Trp Tyr Met Asp Asp Gly Ser Phe Thr Val Gly
    210                 215                 220

Ser Lys Arg Val Gln Glu Arg Thr Ala Gly Gly Ser Gly Arg Ile Glu
225                 230                 235                 240

Ile Cys Val Asp Ala Met Thr Glu Gly Thr Arg Val Arg Leu Arg Asp
                245                 250                 255

Tyr Leu Cys Asp Thr His Gly Leu Asp Val Arg Leu Arg Glu Val Gly
            260                 265                 270

Ser Ala Gly Lys Ala Val Leu Val Phe Ser Thr Ala Ala Thr Ala Lys
        275                 280                 285

Phe Gln Ser Leu Ile Ala Pro Tyr Val Ala Pro Ser Met Glu Tyr Lys
    290                 295                 300

Leu Leu Pro Gln Phe Arg Gly Arg Gly Ser Val Thr Pro Gln Phe Val
305                 310                 315                 320

Glu Pro Thr Gln Gln Leu Val Pro Ala Arg Val Leu Asp Val His Val
                325                 330                 335

Lys Leu Ser Thr Arg Ser Met Asn Arg Phe Asp Ile Glu Val Glu Gly
            340                 345                 350

Asn His Asn Tyr Phe Val Asp Gly Val Met Val His Asn
        355                 360                 365


<210> SEQ ID NO 46
<211> LENGTH: 407
<212> TYPE: PRT
<213> ORGANISM: Nostoc sp. PCC7120

<400> SEQUENCE: 46

Cys Leu Pro Glu Asp Ala Leu Val His Thr Ala Lys Gly Leu Val Pro
1               5                   10                  15

Ile Arg Asp Val Gln Val Gly Asp Leu Val Gln Thr Pro Leu Gly Phe
            20                  25                  30

Arg Arg Val Val Asp Lys Phe Asp Gln Gly Phe Gln Asp Val Tyr Glu
        35                  40                  45

Ile Glu Thr Asn Ala Thr Tyr Pro Arg Ala Thr Leu Asn His Arg Gln
    50                  55                  60

Ala Val Leu Glu Asp Ala Lys Gly Gly Ile Val Trp Lys His Ile Ala
65                  70                  75                  80

Ser Leu Glu Ala Gly Asp Arg Leu Leu His Asn Lys Gln Val Leu Pro
                85                  90                  95
```

-continued

```
Gly Thr Val Thr His Leu Pro Ala Asp Phe Thr Glu Ser Arg Pro Ser
            100                 105                 110

His Ser Arg Thr Ala Lys Ser Phe Val Val Pro Glu Leu Thr Ala Glu
        115                 120                 125

Val Ala Trp Leu Ile Gly Phe Thr His Gly Asp Gly Tyr Val Ala Leu
    130                 135                 140

Gly Arg Asn Lys Tyr Asp Lys Pro Tyr Gly Arg Val Glu Trp Ser Met
145                 150                 155                 160

Asn Ser Leu Asp Ala Glu Val Thr Ser Arg Ile Gln Ala Lys Ile Asp
                165                 170                 175

Ala Ala Leu Ala Leu Phe Gly Leu Ser Ala Val His Ser Ile Thr Lys
            180                 185                 190

Gly Glu Asn Thr Ala Lys Ser Ile Cys Ser Ser Ile Arg Leu Ala Glu
        195                 200                 205

Tyr Phe His Arg His Ile Lys Gln Pro Asn Ile Pro Leu Thr Val Pro
    210                 215                 220

Ser Phe Ile Leu Gln Gly Ser Val Asp Ile Arg Ala Ala Tyr Leu Ala
225                 230                 235                 240

Gly Leu Met Asp Ser Asp Gly Ala Val Asn Asn Arg Pro Pro His Leu
                245                 250                 255

Ile Thr Ser Val Tyr Arg Ser Phe Ile Arg Gln Val Ser Val Val Leu
            260                 265                 270

Ser Ser Leu Gly Ile Ala Gly Arg Leu Thr Thr Thr Tyr Pro Gln Asn
        275                 280                 285

Ser Asn Trp Gln Val Lys Tyr Asn Leu Thr Ile Pro Ala Leu Lys Glu
    290                 295                 300

Arg Tyr Asn Ala Leu Ile Ser Pro His Ser Ala Lys Gly Glu Leu Arg
305                 310                 315                 320

Gln Gly Leu Lys Met Tyr Gly Phe Thr Val Pro Gly Ala Val Met Arg
                325                 330                 335

Glu Thr Tyr Thr Tyr Ser Glu Met Arg Glu Met Gly Phe Gln Gly Ser
            340                 345                 350

Arg Thr Val Asp Ala Asn Tyr Glu Arg Tyr Val Ala Glu Ala Asp Ile
        355                 360                 365

Ser Leu Asp Ile Pro Val Thr Val Lys Gly Leu Gly Ser Tyr Asp His
    370                 375                 380

Val Gln Thr Tyr Asp Ile Glu Val Asp Glu Ala His Cys Phe Tyr Cys
385                 390                 395                 400

Asp Gly Tyr Leu Thr His Asn
                405


<210> SEQ ID NO 47
<211> LENGTH: 394
<212> TYPE: PRT
<213> ORGANISM: Trichodesmium erythraeum

<400> SEQUENCE: 47

Cys Leu Pro Glu Gly Ala Leu Val His Thr Ala Ser Gly Leu Val Ala
1               5                   10                  15

Ile Glu Lys Ile Arg Ile Gly Asp Arg Val Leu Thr Ser Gln Gly Phe
            20                  25                  30

Tyr Pro Val Thr Asn Phe Phe Asp Gln Gly Ile Gln Ser Leu Cys Arg
        35                  40                  45

Ile Gln Thr Glu Asp Gly Tyr Phe Glu Cys Thr Pro Asp His Lys Val
    50                  55                  60
```

Ala Val Leu Gln Asp Leu Tyr Gly Asn Tyr Lys Met Ile Lys Ala Lys
65 70 75 80

Asp Leu Gln Glu Gly Asp Arg Leu Ile Phe Val Pro Gln Ala Ile Pro
85 90 95

Gly Thr Pro Thr Glu Leu Pro Glu Leu Lys Ala Val Pro Ser Ser Glu
100 105 110

Ala Lys Leu Ile Thr Ile Pro Ala Leu Gln Ser Glu Val Ala Tyr Phe
115 120 125

Leu Gly Tyr Leu Ser Gly Asn Gly Ser Val Gly Ser Asp Gly Gly Gln
130 135 140

Val Arg Phe Arg Val Ser Gln Asp Ser Pro Glu Ile Leu Glu Arg Leu
145 150 155 160

Ile Asn Val Ala Gln Glu Phe Gly Leu Glu Thr His Arg Leu Arg Thr
165 170 175

Leu Glu Gln Phe Gln Thr Gln Ala Tyr Glu Leu Glu Leu Asn Ser Ser
180 185 190

Thr Leu Asn Lys Tyr Leu Ser Gln Phe Lys Gln Pro Ser Asn Ser Val
195 200 205

Cys Ile Pro Glu Cys Ile Leu Met Gly Thr Thr Glu Ile Arg Gln Ala
210 215 220

Tyr Leu Ala Gly Leu Val Asp Ala Asp Gly Cys His Ser Gln Gly Ile
225 230 235 240

Leu Leu Thr Ser Val Asp Gln Gly Phe Leu Arg Gln Val Gln Ala Leu
245 250 255

Tyr Ala Ser Leu Gly Ile Thr Thr Arg Leu Cys Gly Ser Val Gln Lys
260 265 270

Pro Thr Gly Thr Trp Glu Gly Glu Leu Val Thr Val Ser Glu Gly Gly
275 280 285

Tyr Glu Ala Val Glu Lys Leu Met Met Asn Tyr Ser Thr Gln Phe Pro
290 295 300

Val Gln Lys Pro Asn His Leu Lys Phe Phe Pro Asp Gln Gly Phe Pro
305 310 315 320

Lys Glu Met Val Arg Pro Leu Val Lys Thr Ser Gln Asp His Leu Gly
325 330 335

Lys Val His Lys Gln Met Ile Phe Pro Ser Val Lys Lys Phe Val Val
340 345 350

Asp Ala Thr Asp Leu Ile Pro Val Lys Val Lys Lys Val Glu Met Asp
355 360 365

Val Arg Glu Ala Ser Thr Tyr Asp Ile Glu Val Ala Ser Ile His Glu
370 375 380

Phe Val Cys Gln Gly Ile Leu Val Ser Asn
385 390

<210> SEQ ID NO 48
<211> LENGTH: 399
<212> TYPE: PRT
<213> ORGANISM: Pyrococcus abyssi

<400> SEQUENCE: 48

Cys Ile Asp Gly Asn Ala Lys Ile Ile Phe Glu Asn Glu Gly Glu Glu
1 5 10 15

His Leu Thr Thr Met Ala Glu Met Tyr Glu Arg Tyr Arg His Leu Gly
20 25 30

Glu Phe Tyr Asp Glu Asn Tyr Asn Arg Trp Gly Ile Asp Val Ser Ser

-continued

```
        35                  40                  45

Val Pro Ile Tyr Val Lys Ser Phe Asp Pro Glu Thr Arg Arg Val Val
    50                  55                  60

Lys Gly Arg Val Arg Ala Ile Trp Lys Tyr Glu Leu Gly Glu Glu Ile
65                  70                  75                  80

Pro Lys Tyr Glu Ile Arg Thr His Lys Gly Thr Lys Ile Leu Thr Ser
                85                  90                  95

Pro Trp His Pro Phe Phe Val Leu Thr Pro Asp Phe Glu Val Ile Glu
            100                 105                 110

Lys Arg Ala Asp Glu Leu Lys Val Gly Asp Ile Leu Ile Gly Gly Met
        115                 120                 125

Pro Asp Gly Glu Asp His Glu Leu Ile Phe Asp Tyr Trp Leu Ala Gly
    130                 135                 140

Phe Ile Ala Gly Asn Gly Asn Leu Asp Asp Ser Glu Arg Glu Tyr Lys
145                 150                 155                 160

Ala Arg Glu Leu Leu Asp Gly Ile Glu Asn Gly Ile Pro Pro Lys Ile
                165                 170                 175

Leu Arg Lys Gly Lys Asn Ala Val Leu Ser Phe Ile Thr Gly Leu Phe
            180                 185                 190

Asp Ala Glu Gly His Val Asn Asp Lys Ser Gly Ile Glu Leu Gly Met
        195                 200                 205

Val Asn Lys Lys Leu Ile Glu Ala Val Thr His Tyr Leu Asn Ser Leu
    210                 215                 220

Gly Ile Lys Ala Arg Met Arg Glu Lys Arg Arg Lys Asn Gly Ile Asp
225                 230                 235                 240

Tyr Ile Met His Val Glu Glu Tyr Ser Ser Leu Leu Arg Phe Tyr Glu
                245                 250                 255

Leu Ile Gly Lys His Leu Gln Asn Asn Glu Lys Lys Glu Lys Leu Glu
            260                 265                 270

Ile Leu Leu His Lys His Asn Gly Gly Ala Phe Asp Leu Ser Leu Asn
        275                 280                 285

Phe Asn Ala Phe Lys Glu Trp Ala Ser Arg Tyr Gly Val Glu Phe Lys
    290                 295                 300

Thr Asn Gly Asn Gln Ile Leu Ala Ile Ile Gly Asn Glu Lys Val Ser
305                 310                 315                 320

Leu Gly Gln Trp His Ala Arg Gly His Val Ser Lys Ala Val Leu Val
                325                 330                 335

Lys Met Leu Arg Lys Leu Tyr Glu Val Thr Lys Asn Asp Glu Val Lys
            340                 345                 350

Glu Met Leu His Leu Ile Glu Ser Leu Glu Val Val Lys Glu Ile Thr
        355                 360                 365

Ile Thr Asn Glu Pro Lys Thr Phe Tyr Asp Leu Thr Val Asp Lys Tyr
    370                 375                 380

Gln Asn Tyr Leu Ala Gly Glu Asn Gly Met Ile Phe Val His Asn
385                 390                 395


<210> SEQ ID NO 49
<211> LENGTH: 454
<212> TYPE: PRT
<213> ORGANISM: Pyrococcus furiosus

<400> SEQUENCE: 49

Cys Ile Asp Gly Lys Ala Lys Ile Ile Phe Glu Asn Glu Gly Glu Glu
1               5                   10                  15
```

-continued

```
His Leu Thr Thr Met Glu Glu Met Tyr Glu Arg Tyr Lys His Leu Gly
            20                  25                  30

Glu Phe Tyr Asp Glu Glu Tyr Asn Arg Trp Gly Ile Asp Val Ser Asn
        35                  40                  45

Val Pro Ile Tyr Val Lys Ser Phe Asp Pro Glu Ser Lys Arg Val Val
    50                  55                  60

Lys Gly Lys Val Asn Val Ile Trp Lys Tyr Glu Leu Gly Lys Asp Val
65                  70                  75                  80

Thr Lys Tyr Glu Ile Ile Thr Asn Lys Gly Thr Lys Ile Leu Thr Ser
                85                  90                  95

Pro Trp His Pro Phe Phe Val Leu Thr Pro Asp Phe Lys Ile Val Glu
            100                 105                 110

Lys Arg Ala Asp Glu Leu Lys Glu Gly Asp Ile Leu Ile Gly Gly Met
        115                 120                 125

Pro Asp Gly Glu Asp Tyr Lys Phe Ile Phe Asp Tyr Trp Leu Ala Gly
    130                 135                 140

Phe Ile Ala Gly Asp Gly Cys Phe Asp Lys Tyr His Ser His Val Lys
145                 150                 155                 160

Gly His Glu Tyr Ile Tyr Asp Arg Leu Arg Ile Tyr Asp Tyr Arg Ile
                165                 170                 175

Glu Thr Phe Glu Ile Ile Asn Asp Tyr Leu Glu Lys Thr Phe Gly Arg
            180                 185                 190

Lys Tyr Ser Ile Gln Lys Asp Arg Asn Ile Tyr Tyr Ile Asp Ile Lys
        195                 200                 205

Ala Arg Asn Ile Thr Ser His Tyr Leu Lys Leu Leu Glu Gly Ile Asp
    210                 215                 220

Asn Gly Ile Pro Pro Gln Ile Leu Lys Glu Gly Lys Asn Ala Val Leu
225                 230                 235                 240

Ser Phe Ile Ala Gly Leu Phe Asp Ala Glu Gly His Val Ser Asn Lys
                245                 250                 255

Pro Gly Ile Glu Leu Gly Met Val Asn Lys Arg Leu Ile Glu Asp Val
            260                 265                 270

Thr His Tyr Leu Asn Ala Leu Gly Ile Lys Ala Arg Ile Arg Glu Lys
        275                 280                 285

Leu Arg Lys Asp Gly Ile Asp Tyr Val Leu His Val Glu Glu Tyr Ser
    290                 295                 300

Ser Leu Leu Arg Phe Tyr Glu Leu Ile Gly Lys Asn Leu Gln Asn Glu
305                 310                 315                 320

Glu Lys Arg Glu Lys Leu Glu Lys Val Leu Ser Asn His Lys Gly Gly
                325                 330                 335

Asn Phe Gly Leu Pro Leu Asn Phe Asn Ala Phe Lys Glu Trp Ala Ser
            340                 345                 350

Glu Tyr Gly Val Glu Phe Lys Thr Asn Gly Ser Gln Thr Ile Ala Ile
        355                 360                 365

Ile Asn Asp Glu Arg Ile Ser Leu Gly Gln Trp His Thr Arg Asn Arg
    370                 375                 380

Val Ser Lys Ala Val Leu Val Lys Met Leu Arg Lys Leu Tyr Glu Ala
385                 390                 395                 400

Thr Lys Asp Glu Glu Val Lys Arg Met Leu His Leu Ile Glu Gly Leu
                405                 410                 415

Glu Val Val Arg His Ile Thr Thr Thr Asn Glu Pro Arg Thr Phe Tyr
            420                 425                 430

Asp Leu Thr Val Glu Asn Tyr Gln Asn Tyr Leu Ala Gly Glu Asn Gly
```

```
        435                 440                 445

Met Ile Phe Val His Asn
    450


<210> SEQ ID NO 50
<211> LENGTH: 345
<212> TYPE: PRT
<213> ORGANISM: Carboxydothermus hydrogenoformans

<400> SEQUENCE: 50

Cys Val Thr Gly Asp Thr Leu Val Phe Thr Asp Lys Gly Leu Ile Glu
1               5                   10                  15

Ala Arg Lys Leu Glu Val Gly Met Lys Val Trp Ser Gly Asp Gly Trp
            20                  25                  30

Asn Glu Ile Lys Glu Val Ile Asn Asn Gly Val Lys Pro Val Leu Lys
        35                  40                  45

Leu Lys Leu Lys Thr Gly Leu Glu Ile Lys Val Thr Glu Glu His Lys
    50                  55                  60

Ile Phe Thr Gly Glu Gly Trp Lys Glu Ala Lys Asp Leu Lys Val Gly
65                  70                  75                  80

Asp Lys Leu Tyr Leu Pro Val Ser Tyr Pro Glu Leu Asp Phe Pro Val
                85                  90                  95

Lys Glu Glu Asn Asp Phe Tyr Glu Phe Leu Gly Tyr Phe Leu Gly Asp
            100                 105                 110

Gly Ser Leu Ser Val Ser Asn His Val Ser Leu His Val Gly Asn Asp
        115                 120                 125

Lys Glu Leu Ala Leu Tyr Phe Lys Glu Lys Val Glu Lys Tyr Ala Gly
    130                 135                 140

Ala Ala Tyr Leu Ile Glu Arg Asp Gly Gln Tyr Ile Ile Asp Val His
145                 150                 155                 160

Arg Lys Glu Phe Ala Glu Lys Ile Lys Lys Ile Phe Gly Ile Glu Ile
                165                 170                 175

Thr Asp Ser Lys Glu Lys Asp Ile Pro Ser Ser Leu Leu Ala Val Asn
            180                 185                 190

Ser Glu Ala Met Lys Ala Leu Leu Arg Gly Leu Phe Ser Ala Asp Gly
        195                 200                 205

Ser Val Tyr Asp Ala Asn Gly Ser Ile Thr Val Ala Leu Ser Ser Thr
    210                 215                 220

Ser Tyr Pro Leu Leu Arg Lys Val Gln Ile Leu Leu Leu Ser Leu Gly
225                 230                 235                 240

Ile Pro Ser Thr Leu Thr Gly Glu Lys Asp Gln Asp Val Lys Ile Ile
                245                 250                 255

Lys Gly Asn Glu Tyr Glu Thr Leu Pro Thr Tyr Arg Leu Ile Ile Ser
            260                 265                 270

Gly Glu Arg Ala Ser Leu Phe Phe Asn Lys Ile Gly Leu Ile Gly Glu
        275                 280                 285

Lys Lys Lys Lys Phe Leu Glu Leu Met Ala Gly Lys Thr Thr Tyr Ser
    290                 295                 300

Thr Leu Asn Asn His Leu Tyr Gln Glu Ile Val Ser Ile Glu Pro Ala
305                 310                 315                 320

Gly Glu Glu Glu Val Phe Asp Ile Thr Ala Pro Pro Lys Tyr Thr Trp
                325                 330                 335

Ile Thr Asn Gly Ile Leu Ser Leu Asp
            340                 345
```

<210> SEQ ID NO 51
<211> LENGTH: 134
<212> TYPE: PRT
<213> ORGANISM: Methanothermobacter thermautotrophicus

<400> SEQUENCE: 51

Cys Val Ser Gly Asp Thr Ile Val Met Thr Ser Gly Gly Pro Arg Thr
1 5 10 15

Val Ala Glu Leu Glu Gly Lys Pro Phe Thr Ala Leu Ile Arg Gly Ser
20 25 30

Gly Tyr Pro Cys Pro Ser Gly Phe Phe Arg Thr Cys Glu Arg Asp Val
35 40 45

Tyr Asp Leu Arg Thr Arg Glu Gly His Cys Leu Arg Leu Thr His Asp
50 55 60

His Arg Val Leu Val Met Asp Gly Gly Leu Glu Trp Arg Ala Ala Gly
65 70 75 80

Glu Leu Glu Arg Gly Asp Arg Leu Val Met Asp Asp Ala Ala Gly Glu
85 90 95

Phe Pro Ala Leu Ala Thr Phe Arg Gly Leu Arg Gly Ala Gly Arg Gln
100 105 110

Asp Val Tyr Asp Ala Thr Val Tyr Gly Ala Ser Ala Phe Thr Ala Asn
115 120 125

Gly Phe Ile Val His Asn
130

<210> SEQ ID NO 52
<211> LENGTH: 382
<212> TYPE: PRT
<213> ORGANISM: Pyrococcus abyssi

<400> SEQUENCE: 52

Cys Val Val Gly Glu Thr Arg Ile Leu Thr Pro Glu Gly Tyr Ile Lys
1 5 10 15

Ala Glu Glu Leu Phe Lys Leu Ala Lys Glu Arg Gly Lys Met Glu Ala
20 25 30

Ile Ala Val Glu Gly Ile Ala Glu Gly Gly Glu Pro Tyr Ala Tyr Ser
35 40 45

Leu Glu Ile Leu Leu Pro Gly Asp Lys Gln Val Lys Tyr Glu Thr Val
50 55 60

His Gly Asn Ala Val Glu Val Ala Asp Pro Val Ser Val Pro Ala Tyr
65 70 75 80

Val Trp Lys Val Gly Met Lys Glu Val Ala Arg Val Arg Thr Lys Glu
85 90 95

Gly Tyr Glu Ile Thr Ala Thr Leu Asp His Lys Leu Met Thr Pro Glu
100 105 110

Gly Trp Lys Glu Ile Lys Asp Leu Lys Pro Gly Asp Lys Ile Leu Leu
115 120 125

Pro Arg Phe Glu Val Glu Glu Asp Phe Gly Ser Glu Ser Ile Gly Glu
130 135 140

Asp Leu Ala Phe Val Leu Gly Trp Phe Ile Gly Asp Gly Tyr Leu Asn
145 150 155 160

Val Lys Asp Lys Arg Ala Trp Phe Tyr Phe Asn Ala Glu Lys Glu Glu
165 170 175

Glu Ile Ala Trp Lys Ile Arg Glu Ile Leu Ala Lys Arg Phe Glu Ile
180 185 190

```
Lys Ala Glu Pro His Arg Tyr Gly Asn Gln Ile Lys Leu Gly Val Arg
        195                 200                 205

Gly Lys Ala Tyr Glu Trp Leu Glu Ser Ile Val Lys Thr Asn Glu Lys
    210                 215                 220

Arg Ile Pro Glu Ile Val Tyr Arg Leu Lys Pro Asn Glu Ile Ala Ser
225                 230                 235                 240

Phe Leu Arg Gly Leu Phe Ser Ala Asp Gly Tyr Val Asp Asn Asp Met
                245                 250                 255

Ala Ile Arg Leu Thr Ser Lys Ser Arg Glu Leu Leu Arg Glu Val Gln
            260                 265                 270

Asp Leu Leu Leu Leu Phe Gly Ile Leu Ser Lys Ile Tyr Glu Arg Pro
        275                 280                 285

Tyr Lys Arg Glu Phe Lys Tyr Thr Thr Lys Asp Gly Glu Glu Arg Thr
    290                 295                 300

Tyr Thr Thr Glu Gly Tyr Tyr Glu Leu Val Ile Ala Asn Tyr Ser Arg
305                 310                 315                 320

Lys Ile Phe Ala Glu Arg Ile Gly Leu Glu Gly Tyr Lys Met Glu Lys
                325                 330                 335

Leu Ser Leu Glu Lys Ile Lys Val Asp Glu Pro Ile Val Thr Val Glu
            340                 345                 350

Ser Val Glu Ile Leu Gly Lys Lys Leu Val Tyr Asp Phe Thr Val Pro
        355                 360                 365

Glu His His Met Tyr Ile Ser Asn Gly Phe Met Ser His Asn
    370                 375                 380


<210> SEQ ID NO 53
<211> LENGTH: 382
<212> TYPE: PRT
<213> ORGANISM: Pyrococcus furiosus

<400> SEQUENCE: 53

Cys Val Val Gly Asp Thr Arg Ile Leu Thr Pro Glu Gly Tyr Leu Lys
1               5                   10                  15

Ala Glu Glu Ile Phe Ser Leu Ala Lys Glu Arg Gly Lys Lys Glu Ala
            20                  25                  30

Val Ala Val Glu Gly Ile Ala Glu Glu Gly Glu Pro Tyr Ala Tyr Ser
        35                  40                  45

Val Glu Ile Leu Leu Pro Gly Glu Glu Lys Val Glu Tyr Glu Thr Val
    50                  55                  60

His Gly Lys Val Leu Ala Val Ala Asp Pro Val Ala Val Pro Ala Tyr
65                  70                  75                  80

Val Trp Lys Val Gly Arg Lys Lys Val Ala Arg Val Lys Thr Lys Glu
                85                  90                  95

Gly Tyr Glu Ile Thr Ala Thr Leu Asp His Lys Leu Met Thr Pro Glu
            100                 105                 110

Gly Trp Lys Glu Val Gly Lys Leu Lys Glu Gly Asp Lys Ile Leu Leu
        115                 120                 125

Pro Arg Phe Glu Val Glu Glu Glu Phe Gly Ser Glu Ser Ile Gly Glu
    130                 135                 140

Asp Leu Ala Phe Val Leu Gly Trp Phe Ile Gly Asp Gly Tyr Leu Asn
145                 150                 155                 160

Val Asn Asp Lys Arg Ala Trp Phe Tyr Phe Asn Ala Glu Lys Glu Glu
                165                 170                 175

Glu Ile Ala Val Arg Ile Arg Asp Ile Leu Val Lys His Phe Gly Ile
            180                 185                 190
```

```
Lys Ala Glu Leu His Arg Tyr Gly Asn Gln Ile Lys Leu Gly Val Arg
        195                 200                 205

Gly Glu Ala Tyr Arg Trp Leu Glu Asn Ile Val Lys Asn Asn Glu Lys
    210                 215                 220

Arg Ile Pro Glu Ile Val Tyr Arg Leu Lys Pro Arg Glu Ile Ala Ala
225                 230                 235                 240

Phe Leu Arg Gly Leu Phe Ser Ala Asp Gly Tyr Val Asp Lys Asp Met
                245                 250                 255

Ala Ile Arg Leu Thr Ser Lys Ser Arg Glu Leu Leu Arg Glu Val Gln
            260                 265                 270

Asp Leu Leu Leu Leu Phe Gly Ile Leu Ser Lys Ile Tyr Glu Lys Pro
        275                 280                 285

Tyr Glu Ser Glu Phe His Tyr Thr Thr Lys Asn Gly Glu Glu Arg Ile
    290                 295                 300

Tyr Arg Ser Lys Gly Tyr Tyr Glu Leu Val Ile Thr Asn Tyr Ser Arg
305                 310                 315                 320

Lys Leu Phe Ala Glu Lys Ile Gly Leu Glu Gly Tyr Lys Met Glu Lys
                325                 330                 335

Leu Ser Leu Lys Lys Thr Lys Val Asp Gln Pro Ile Val Thr Val Glu
            340                 345                 350

Ser Val Glu Val Leu Gly Glu Glu Ile Val Tyr Asp Phe Thr Val Pro
        355                 360                 365

Asn Tyr His Met Tyr Ile Ser Asn Gly Phe Met Ser His Asn
    370                 375                 380


<210> SEQ ID NO 54
<211> LENGTH: 373
<212> TYPE: PRT
<213> ORGANISM: Trichodesmium erythraeum

<400> SEQUENCE: 54

Cys His Ser Gly Asp Thr Leu Val Ser Thr Asp Gln Gly Leu Ile Ala
1               5                   10                  15

Ile Gln Asp Leu Val Gly Lys Gln Phe Gln Ala Leu Val Asp Leu Arg
            20                  25                  30

Ser Ile Gly Leu Ser Gly Val Arg Leu Thr Asp Ala Ile Ala Phe Ala
        35                  40                  45

Thr Gly Val Lys Thr Thr Tyr Gln Val Ile Leu Asn Asn Gly Met Gln
    50                  55                  60

Met Arg Cys Thr Gly Asp His Gln His Phe Thr Ser Arg Gly Trp Val
65                  70                  75                  80

Ser Thr Arg Asp Leu Thr Asp Asp Asp Asn Ile Tyr Ile Gln Gly Gly
                85                  90                  95

Ala Gly Gln Phe Gly Lys Gly Thr Ile Ser Val Ala Gln Ala Gln Met
            100                 105                 110

Leu Gly Trp Trp Tyr Arg Asp Gly Tyr Asn Val Lys Ile Lys Ala Arg
        115                 120                 125

Ser His Ser His Gly Gly Lys Gln Asp Tyr Phe Ala Thr Gly Phe Val
    130                 135                 140

Phe Asp Gln Asp Asp Tyr Glu Thr Ala Tyr Asn Val Val Glu Lys Ala
145                 150                 155                 160

Val Ala Ser Ile Thr Glu Arg Glu Tyr Val Thr Lys Leu His Lys Gly
                165                 170                 175

Val Tyr Glu Phe Pro Thr Gln Tyr Pro Lys Leu Glu Lys Phe Phe Ala
```

```
            180                 185                 190

Asp Leu Gly Ile Val Gly Lys Glu Glu Leu Pro Asn Asn Phe Leu Ser
        195                 200                 205

Gln Ser Gln Glu Val Leu Ile Gly Phe Leu Gln Gly Ile Phe Ser Ala
    210                 215                 220

Asp Gly Ile Val Tyr Glu Asp Ser Arg Arg Ile Lys Leu Thr Met Val
225                 230                 235                 240

Ser Glu Lys Leu Leu Gln Gln Ile Gln Leu Ile Leu Ser Asn Leu Gly
                245                 250                 255

Ile Ile Ser Thr Val Gly Leu Val Arg Glu Lys Asp Tyr Ile Gly Val
            260                 265                 270

Pro Tyr Arg Thr Val Asn Val Thr His Glu Val Ser Leu Cys Arg Gly
        275                 280                 285

Ser Tyr Glu Leu Leu Ile Ser Ser Phe Ser Phe Ser Leu Phe Gln Gln
    290                 295                 300

Leu Ile Gly Phe Pro Leu Ser Pro Ser Lys Asn Val Lys Ala Glu Lys
305                 310                 315                 320

Leu Leu Val Gln Thr Leu Ala Asn Tyr Ser Glu Ser Thr Ile Asn Ser
                325                 330                 335

Lys Phe Ile Ser Lys Val Lys Lys Val Glu Glu Phe Gly Glu Glu Val
            340                 345                 350

Val Tyr Asp Leu His Val Pro Leu Thr Asn Ser Phe Ile Ala Asn Gly
        355                 360                 365

Cys Leu Thr His Asn
    370


<210> SEQ ID NO 55
<211> LENGTH: 381
<212> TYPE: PRT
<213> ORGANISM: Trichodesmium erythraeum

<400> SEQUENCE: 55

Cys Leu Asp Lys Thr Ala Leu Arg Ile Phe Asn Gln Gly Leu Leu Tyr
1               5                   10                  15

Ala Asp Glu Val Val Thr Pro Gly Ser Gly Glu Thr Val Gly Leu Gly
            20                  25                  30

Leu Thr Val Arg Asn Gly Ile Gly Ala Ser Thr Ala Ile Ala Asn Gln
        35                  40                  45

Pro Met Glu Leu Val Glu Ile Lys Leu Ala Asn Gly Arg Lys Leu Arg
    50                  55                  60

Met Thr Pro Asn His Arg Met Ser Val Lys Gly Lys Trp Ile His Ala
65                  70                  75                  80

Cys Asn Leu Lys Pro Gly Met Leu Leu Asp Tyr Ser Ile Gly Glu Tyr
                85                  90                  95

Gln Lys Arg Glu Asp Thr Leu Leu Ile Pro Leu Gln Leu Glu Asp Tyr
            100                 105                 110

Thr Glu Val Asn Asn Ser Gln Thr Leu Gly His Asn Gly Gly Val Leu
        115                 120                 125

Thr Lys Lys Ile Met Thr Pro Ala Ser Met Thr Ser Asp Leu Ala Tyr
    130                 135                 140

Phe Leu Gly Cys Leu Phe Gly Asn Gly Cys Ile Val Gln Asn Lys Tyr
145                 150                 155                 160

Gln Val Cys Phe Tyr His Ser Arg Leu Asp Val Leu Tyr Gly Leu Gln
                165                 170                 175
```

-continued

```
Glu Lys Gly Lys Lys Leu Phe Gly Ile Lys Gly Ser Leu Asn Asp Phe
            180                 185                 190

Ala Asn Gly Arg Phe Glu Leu Cys Phe Ala Ser Arg Gln Leu Phe Tyr
        195                 200                 205

Trp Leu His Leu Asn Gln Leu Val Lys Thr Gln Lys Ser Glu Asp Leu
    210                 215                 220

Glu Arg Ile Pro Leu Ser Leu Arg Arg Ser Ser Arg Val Thr Leu Leu
225                 230                 235                 240

Ser Phe Phe Cys Gly Leu Ile Asp Thr Asn Gly Tyr Val Pro Gln Asp
                245                 250                 255

Gly Lys Leu Ser Ile Ala Ser Ala Ser Ser Asp Phe Ile His Asn Leu
            260                 265                 270

Gln Gln Ile Gly Glu Ser Ile Gly Leu Cys Phe Ser Ile Tyr Gln Asn
        275                 280                 285

Thr Lys Gly Glu Asn Leu Gln Asn Gln His Asn Asn Thr Trp Gly Leu
    290                 295                 300

Cys Leu Ser Pro Met Leu Ser Asn Val Asp Ala Leu Asp Tyr Leu Asn
305                 310                 315                 320

His Asn Ser Ile Lys Cys Gln Glu Gly Pro Val Val Ile Ser Lys Cys
                325                 330                 335

Val Leu Asn Tyr Ser Pro Tyr Lys Ile Glu Ser Val Asn Ile Gly Ala
            340                 345                 350

Val Cys Asp Tyr Ser Tyr Asp Phe Ala Ile Glu Gly Ile Asn Asp Asn
        355                 360                 365

Asp Ser Trp Tyr Trp Gln Gly Ala Leu Lys Ser His Asn
    370                 375                 380


<210> SEQ ID NO 56
<211> LENGTH: 339
<212> TYPE: PRT
<213> ORGANISM: Chilo iridescent virus

<400> SEQUENCE: 56

Cys Val Ala Pro Glu Thr Met Ile Leu Thr Glu Asp Gly Gln Phe Pro
1               5                   10                  15

Ile Lys Asp Leu Glu Gly Lys Ile Ile Lys Val Trp Asn Gly Asn Glu
            20                  25                  30

Phe Ser Ser Val Thr Val Val Lys Thr Gly Thr Glu Lys Glu Leu Leu
        35                  40                  45

Glu Val Glu Leu Ser Asn Gly Cys Thr Leu Ser Cys Thr Pro Glu His
    50                  55                  60

Lys Phe Ile Ile Val Lys Ser Tyr Thr Glu Ala Lys Lys Gln Lys Thr
65                  70                  75                  80

Asp Asp Asn Ala Ile Ala Asn Ala Glu Arg Val Asp Ala Gln Asp Leu
                85                  90                  95

Lys Pro Arg Met Lys Leu Ile Lys Phe Asp Leu Pro Thr Leu Phe Gly
            100                 105                 110

Asn Ser Glu His Asp Ile Lys Tyr Pro Tyr Thr His Gly Phe Phe Cys
        115                 120                 125

Gly Asp Gly Thr Tyr Thr Lys Tyr Gly Lys Pro Gln Leu Ser Leu Tyr
    130                 135                 140

Gly Asp Lys Lys Glu Leu Leu Thr Tyr Leu Asp Val Arg Thr Met Thr
145                 150                 155                 160

Gly Leu Glu Asp Ala Ser Gly Arg Leu Asn Thr Trp Leu Pro Leu Asp
                165                 170                 175
```

```
Leu Ala Pro Lys Phe Asp Val Pro Ile Asn Ser Ser Leu Glu Cys Arg
            180                 185                 190

Met Glu Trp Leu Ala Gly Tyr Leu Asp Ala Asp Gly Cys Val Phe Arg
        195                 200                 205

Asn Gly Thr Asn Glu Ser Ile Gln Val Ser Cys Ile His Leu Asp Phe
    210                 215                 220

Leu Lys Arg Ile Gln Leu Leu Leu Ile Gly Met Gly Val Thr Ser Lys
225                 230                 235                 240

Ile Thr Lys Leu His Asp Glu Lys Ile Thr Thr Met Pro Asp Gly Lys
                245                 250                 255

Gly Gly Gln Lys Pro Tyr Ser Cys Lys Pro Ile Trp Arg Leu Phe Ile
            260                 265                 270

Ser Ser Ser Gly Leu Tyr His Leu Ser Glu Gln Gly Phe Glu Thr Arg
        275                 280                 285

Arg Leu Lys Trp Glu Pro Arg Gln Pro Gln Arg Asn Ala Glu Arg Phe
    290                 295                 300

Val Glu Val Leu Lys Val Asn Lys Thr Gly Arg Val Asp Asp Thr Tyr
305                 310                 315                 320

Cys Phe Thr Glu Pro Ile Asn His Ala Gly Val Phe Asn Gly Ile Leu
                325                 330                 335

Thr Gly Gln


<210> SEQ ID NO 57
<211> LENGTH: 471
<212> TYPE: PRT
<213> ORGANISM: Candida tropicalis

<400> SEQUENCE: 57

Cys Phe Thr Lys Gly Thr Gln Val Met Met Ala Asp Gly Ala Asp Lys
1               5                   10                  15

Ser Ile Glu Ser Ile Glu Val Gly Asp Lys Val Met Gly Lys Asp Gly
            20                  25                  30

Met Pro Arg Glu Val Val Gly Leu Pro Arg Gly Tyr Asp Asp Met Tyr
        35                  40                  45

Lys Val Arg Gln Leu Ser Ser Thr Arg Arg Asn Ala Lys Ser Glu Gly
    50                  55                  60

Leu Met Asp Phe Thr Val Ser Ala Asp His Lys Leu Ile Leu Lys Thr
65                  70                  75                  80

Lys Gln Asp Val Lys Ile Ala Thr Arg Lys Ile Gly Gly Asn Thr Tyr
                85                  90                  95

Thr Gly Val Thr Phe Tyr Val Leu Glu Lys Thr Lys Thr Gly Ile Glu
            100                 105                 110

Leu Val Lys Ala Lys Thr Lys Val Phe Gly His His Ile His Gly Gln
        115                 120                 125

Asn Gly Ala Glu Glu Lys Ala Ala Thr Phe Ala Ala Gly Ile Asp Ser
    130                 135                 140

Lys Glu Tyr Ile Asp Trp Ile Ile Glu Ala Arg Asp Tyr Val Gln Val
145                 150                 155                 160

Asp Glu Ile Val Lys Thr Ser Thr Thr Gln Met Ile Asn Pro Val His
                165                 170                 175

Phe Glu Ser Gly Lys Leu Gly Asn Trp Leu His Glu His Lys Gln Asn
            180                 185                 190

Lys Ser Leu Ala Pro Gln Leu Gly Tyr Leu Leu Gly Thr Trp Ala Gly
        195                 200                 205
```

Ile Gly Asn Val Lys Ser Ser Ala Phe Thr Met Asn Ser Lys Asp Asp
    210                 215                 220

Val Lys Leu Ala Thr Arg Ile Met Asn Tyr Ser Ser Lys Leu Gly Met
225                 230                 235                 240

Thr Cys Ser Ser Thr Glu Ser Gly Glu Leu Asn Val Ala Glu Asn Glu
                245                 250                 255

Glu Glu Phe Phe Asn Asn Leu Gly Ala Glu Lys Asp Glu Ala Gly Asp
            260                 265                 270

Phe Thr Phe Asp Glu Phe Thr Asp Ala Met Asp Glu Leu Thr Ile Asn
        275                 280                 285

Val His Gly Ala Ala Ala Ser Lys Lys Asn Asn Leu Leu Trp Asn Ala
    290                 295                 300

Leu Lys Ser Leu Gly Phe Arg Ala Lys Ser Thr Asp Ile Val Lys Ser
305                 310                 315                 320

Ile Pro Gln His Ile Ala Val Asp Asp Ile Val Val Arg Glu Ser Leu
                325                 330                 335

Ile Ala Gly Leu Val Asp Ala Ala Gly Asn Val Glu Thr Lys Ser Asn
            340                 345                 350

Gly Ser Ile Glu Ala Val Val Arg Thr Ser Phe Arg His Val Ala Arg
        355                 360                 365

Gly Leu Val Lys Ile Ala His Ser Leu Gly Ile Glu Ser Ser Ile Asn
    370                 375                 380

Ile Lys Asp Thr His Ile Asp Ala Ala Gly Val Arg Gln Glu Phe Ala
385                 390                 395                 400

Cys Ile Val Asn Leu Thr Gly Ala Pro Leu Ala Gly Val Leu Ser Lys
                405                 410                 415

Cys Ala Leu Ala Arg Asn Gln Thr Pro Val Val Lys Phe Thr Arg Asp
            420                 425                 430

Pro Val Leu Phe Asn Phe Asp Leu Ile Lys Ser Ala Lys Glu Asn Tyr
        435                 440                 445

Tyr Gly Ile Thr Leu Ala Glu Glu Thr Asp His Gln Phe Leu Leu Ser
    450                 455                 460

Asn Met Ala Leu Val His Asn
465                 470

<210> SEQ ID NO 58
<211> LENGTH: 454
<212> TYPE: PRT
<213> ORGANISM: Saccharomyces cerevisiae

<400> SEQUENCE: 58

Cys Phe Ala Lys Gly Thr Asn Val Leu Met Ala Asp Gly Ser Ile Glu
1               5                   10                  15

Cys Ile Glu Asn Ile Glu Val Gly Asn Lys Val Met Gly Lys Asp Gly
            20                  25                  30

Arg Pro Arg Glu Val Ile Lys Leu Pro Arg Gly Arg Glu Thr Met Tyr
        35                  40                  45

Ser Val Val Gln Lys Ser Gln His Arg Ala His Lys Ser Asp Ser Ser
    50                  55                  60

Arg Glu Val Pro Glu Leu Leu Lys Phe Thr Cys Asn Ala Thr His Glu
65                  70                  75                  80

Leu Val Val Arg Thr Pro Arg Ser Val Arg Arg Leu Ser Arg Thr Ile
                85                  90                  95

Lys Gly Val Glu Tyr Phe Glu Val Ile Thr Phe Glu Met Gly Gln Lys

```
            100                 105                 110

Lys Ala Pro Asp Gly Arg Ile Val Glu Leu Val Lys Glu Val Ser Lys
        115                 120                 125

Ser Tyr Pro Ile Ser Glu Gly Pro Glu Arg Ala Asn Glu Leu Val Glu
    130                 135                 140

Ser Tyr Arg Lys Ala Ser Asn Lys Ala Tyr Phe Glu Trp Thr Ile Glu
145                 150                 155                 160

Ala Arg Asp Leu Ser Leu Leu Gly Ser His Val Arg Lys Ala Thr Tyr
                165                 170                 175

Gln Thr Tyr Ala Pro Ile Leu Tyr Glu Asn Asp His Phe Phe Asp Tyr
            180                 185                 190

Met Gln Lys Ser Lys Phe His Leu Thr Ile Glu Gly Pro Lys Val Leu
        195                 200                 205

Ala Tyr Leu Leu Gly Leu Trp Ile Gly Asp Gly Leu Ser Asp Arg Ala
    210                 215                 220

Thr Phe Ser Val Asp Ser Arg Asp Thr Ser Leu Met Glu Arg Val Thr
225                 230                 235                 240

Glu Tyr Ala Glu Lys Leu Asn Leu Cys Ala Glu Tyr Lys Asp Arg Lys
                245                 250                 255

Glu Pro Gln Val Ala Lys Thr Val Asn Leu Tyr Ser Lys Val Val Arg
            260                 265                 270

Gly Asn Gly Ile Arg Asn Asn Leu Asn Thr Glu Asn Pro Leu Trp Asp
        275                 280                 285

Ala Ile Val Gly Leu Gly Phe Leu Lys Asp Gly Val Lys Asn Ile Pro
    290                 295                 300

Ser Phe Leu Ser Thr Asp Asn Ile Gly Thr Arg Glu Thr Phe Leu Ala
305                 310                 315                 320

Gly Leu Ile Asp Ser Asp Gly Tyr Val Thr Asp Glu His Gly Ile Lys
                325                 330                 335

Ala Thr Ile Lys Thr Ile His Thr Ser Val Arg Asp Gly Leu Val Ser
            340                 345                 350

Leu Ala Arg Ser Leu Gly Leu Val Val Ser Val Asn Ala Glu Pro Ala
        355                 360                 365

Lys Val Asp Met Asn Gly Thr Lys His Lys Ile Ser Tyr Ala Ile Tyr
    370                 375                 380

Met Ser Gly Gly Asp Val Leu Leu Asn Val Leu Ser Lys Cys Ala Gly
385                 390                 395                 400

Ser Lys Lys Phe Arg Pro Ala Pro Ala Ala Ala Phe Ala Arg Glu Cys
                405                 410                 415

Arg Gly Phe Tyr Phe Glu Leu Gln Glu Leu Lys Glu Asp Asp Tyr Tyr
            420                 425                 430

Gly Ile Thr Leu Ser Asp Asp Ser Asp His Gln Phe Leu Leu Ala Asn
        435                 440                 445

Gln Val Val Val His Asn
    450


<210> SEQ ID NO 59
<211> LENGTH: 173
<212> TYPE: PRT
<213> ORGANISM: Thermoplasma acidophilum

<400> SEQUENCE: 59

Cys Val Ser Gly Asp Thr Pro Val Leu Leu Asp Ala Gly Glu Arg Arg
1               5                   10                  15
```

-continued

```
Ile Gly Asp Leu Phe Met Glu Ala Ile Arg Pro Lys Glu Arg Gly Glu
            20                  25                  30

Ile Gly Gln Asn Glu Glu Ile Val Arg Leu His Asp Ser Trp Arg Ile
        35                  40                  45

Tyr Ser Met Val Gly Ser Glu Ile Val Glu Thr Val Ser His Ala Ile
    50                  55                  60

Tyr His Gly Lys Ser Asn Ala Ile Val Asn Val Arg Thr Glu Asn Gly
65                  70                  75                  80

Arg Glu Val Arg Val Thr Pro Val His Lys Leu Phe Val Lys Ile Gly
                85                  90                  95

Asn Ser Val Ile Glu Arg Pro Ala Ser Glu Val Asn Glu Gly Asp Glu
            100                 105                 110

Ile Ala Trp Pro Ser Val Ser Glu Asn Gly Asp Ser Gln Thr Val Thr
        115                 120                 125

Thr Thr Leu Val Leu Thr Phe Asp Arg Val Val Ser Lys Glu Met His
    130                 135                 140

Ser Gly Val Phe Asp Val Tyr Asp Leu Met Val Pro Asp Tyr Gly Tyr
145                 150                 155                 160

Asn Phe Ile Gly Gly Asn Gly Leu Ile Val Leu His Asn
                165                 170


<210> SEQ ID NO 60
<211> LENGTH: 429
<212> TYPE: PRT
<213> ORGANISM: Synechocystis sp. PCC6803

<400> SEQUENCE: 60

Cys Ile Ser Gly Asp Ser Leu Ile Ser Leu Ala Ser Thr Gly Lys Arg
1               5                   10                  15

Val Ser Ile Lys Asp Leu Leu Asp Glu Lys Asp Phe Glu Ile Trp Ala
            20                  25                  30

Ile Asn Glu Gln Thr Met Lys Leu Glu Ser Ala Lys Val Ser Arg Val
        35                  40                  45

Phe Cys Thr Gly Lys Lys Leu Val Tyr Ile Leu Lys Thr Arg Leu Gly
    50                  55                  60

Arg Thr Ile Lys Ala Thr Ala Asn His Arg Phe Leu Thr Ile Asp Gly
65                  70                  75                  80

Trp Lys Arg Leu Asp Glu Leu Ser Leu Lys Glu His Ile Ala Leu Pro
                85                  90                  95

Arg Lys Leu Glu Ser Ser Ser Leu Gln Leu Met Ser Asp Glu Glu Leu
            100                 105                 110

Gly Leu Leu Gly His Leu Ile Gly Asp Gly Cys Thr Leu Pro Arg His
        115                 120                 125

Ala Ile Gln Tyr Thr Ser Asn Lys Ile Glu Leu Ala Glu Lys Val Val
    130                 135                 140

Glu Leu Ala Lys Ala Val Phe Gly Asp Gln Ile Asn Pro Arg Ile Ser
145                 150                 155                 160

Gln Glu Arg Gln Trp Tyr Gln Val Tyr Ile Pro Ala Ser Tyr Arg Leu
                165                 170                 175

Thr His Asn Lys Lys Asn Pro Ile Thr Lys Trp Leu Glu Asn Leu Asp
            180                 185                 190

Val Phe Gly Leu Arg Ser Tyr Glu Lys Phe Val Pro Asn Gln Val Phe
        195                 200                 205

Glu Gln Pro Gln Arg Ala Ile Ala Ile Phe Leu Arg His Leu Trp Ser
    210                 215                 220
```

Thr Asp Gly Cys Val Lys Leu Ile Val Glu Lys Ser Ser Arg Pro Val
225 230 235 240

Ala Tyr Tyr Ala Thr Ser Ser Glu Lys Leu Ala Lys Asp Val Gln Ser
245 250 255

Leu Leu Leu Lys Leu Gly Ile Asn Ala Arg Leu Ser Lys Ile Ser Gln
260 265 270

Asn Gly Lys Gly Arg Asp Asn Tyr His Val Thr Ile Thr Gly Gln Ala
275 280 285

Asp Leu Gln Ile Phe Val Asp Gln Ile Gly Ala Val Asp Lys Asp Lys
290 295 300

Gln Ala Ser Val Glu Glu Ile Lys Thr His Ile Ala Gln His Gln Ala
305 310 315 320

Asn Thr Asn Arg Asp Val Ile Pro Lys Gln Ile Trp Lys Thr Tyr Val
325 330 335

Leu Pro Gln Ile Gln Ile Lys Gly Ile Thr Thr Arg Asp Leu Gln Met
340 345 350

Arg Leu Gly Asn Ala Tyr Cys Gly Thr Ala Leu Tyr Lys His Asn Leu
355 360 365

Ser Arg Glu Arg Ala Ala Lys Ile Ala Thr Ile Thr Gln Ser Pro Glu
370 375 380

Ile Glu Lys Leu Ser Gln Ser Asp Ile Tyr Trp Asp Ser Ile Val Ser
385 390 395 400

Ile Thr Glu Thr Gly Val Glu Glu Val Phe Asp Leu Thr Val Pro Gly
405 410 415

Pro His Asn Phe Val Ala Asn Asp Ile Ile Val His Asn
420 425

<210> SEQ ID NO 61
<211> LENGTH: 123
<212> TYPE: PRT
<213> ORGANISM: Synechocystis sp. PCC6803

<400> SEQUENCE: 61

Cys Leu Ser Phe Gly Thr Glu Ile Leu Thr Val Glu Tyr Gly Pro Leu
1 5 10 15

Pro Ile Gly Lys Ile Val Ser Glu Glu Ile Asn Cys Ser Val Tyr Ser
20 25 30

Val Asp Pro Glu Gly Arg Val Tyr Thr Gln Ala Ile Ala Gln Trp His
35 40 45

Asp Arg Gly Glu Gln Glu Val Leu Glu Tyr Glu Leu Glu Asp Gly Ser
50 55 60

Val Ile Arg Ala Thr Ser Asp His Arg Phe Leu Thr Thr Asp Tyr Gln
65 70 75 80

Leu Leu Ala Ile Glu Glu Ile Phe Ala Arg Gln Leu Asp Leu Leu Thr
85 90 95

Leu Glu Asn Ile Lys Gln Thr Glu Glu Ala Leu Asp Asn His Arg Leu
100 105 110

Pro Phe Pro Leu Leu Asp Ala Gly Thr Ile Lys
115 120

<210> SEQ ID NO 62
<211> LENGTH: 36
<212> TYPE: PRT
<213> ORGANISM: Synechocystis sp. PCC6803

<400> SEQUENCE: 62

```
Met Val Lys Val Ile Gly Arg Arg Ser Leu Gly Val Gln Arg Ile Phe
1               5                   10                  15

Asp Ile Gly Leu Pro Gln Asp His Asn Phe Leu Leu Ala Asn Gly Ala
            20                  25                  30

Ile Ala Ala Asn
        35


<210> SEQ ID NO 63
<211> LENGTH: 98
<212> TYPE: PRT
<213> ORGANISM: Nanoarchaeum equitans Kin4-M

<400> SEQUENCE: 63

Ser Ile Met Asp Thr Glu Ile Glu Val Ile Glu Asn Gly Ile Lys Lys
1               5                   10                  15

Lys Glu Lys Leu Ser Asp Leu Phe Asn Lys Tyr Tyr Ala Gly Phe Gln
            20                  25                  30

Ile Gly Glu Lys His Tyr Ala Phe Pro Pro Asp Leu Tyr Val Tyr Asp
        35                  40                  45

Gly Glu Arg Trp Val Lys Val Tyr Ser Ile Ile Lys His Glu Thr Glu
    50                  55                  60

Thr Asp Leu Tyr Glu Ile Asn Gly Ile Thr Leu Ser Ala Asn His Leu
65                  70                  75                  80

Val Leu Ser Lys Gly Asn Trp Val Lys Ala Lys Glu Tyr Glu Asn Lys
                85                  90                  95

Asn Asn


<210> SEQ ID NO 64
<211> LENGTH: 30
<212> TYPE: PRT
<213> ORGANISM: Nanoarchaeum equitans Kin4-M

<400> SEQUENCE: 64

Met Arg Tyr Leu Gly Lys Lys Arg Val Ile Leu Tyr Asp Leu Ser Thr
1               5                   10                  15

Glu Ser Gly Lys Phe Tyr Val Asn Gly Leu Val Leu His Asn
            20                  25                  30


<210> SEQ ID NO 65
<211> LENGTH: 102
<212> TYPE: PRT
<213> ORGANISM: Anabaena sp. PCC7120

<400> SEQUENCE: 65

Cys Leu Ser Tyr Asp Thr Glu Val Leu Thr Val Glu Tyr Gly Phe Val
1               5                   10                  15

Pro Ile Gly Glu Ile Val Glu Lys Gly Ile Glu Cys Ser Val Phe Ser
            20                  25                  30

Ile Asn Asn Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
```

100

<210> SEQ ID NO 66
<211> LENGTH: 36
<212> TYPE: PRT
<213> ORGANISM: Anabaena sp. PCC7120

<400> SEQUENCE: 66

Met Ile Lys Ile Ala Ser Arg Lys Phe Leu Gly Val Glu Asn Val Tyr
1 5 10 15

Asp Ile Gly Val Arg Arg Asp His Asn Phe Phe Ile Lys Asn Gly Leu
20 25 30

Ile Ala Ser Asn
35

<210> SEQ ID NO 67
<211> LENGTH: 102
<212> TYPE: PRT
<213> ORGANISM: Nostoc punctiforme PCC73102

<400> SEQUENCE: 67

Cys Leu Ser Tyr Glu Thr Glu Ile Leu Thr Val Glu Tyr Gly Leu Leu
1 5 10 15

Pro Ile Gly Lys Ile Val Glu Lys Arg Ile Glu Cys Thr Val Tyr Ser
20 25 30

Val Asp Asn Asn Gly Asn Ile Tyr Thr Gln Pro Val Ala Gln Trp His
35 40 45

Asp Arg Gly Glu Gln Glu Val Phe Glu Tyr Cys Leu Glu Asp Gly Ser
50 55 60

Leu Ile Arg Ala Thr Lys Asp His Lys Phe Met Thr Val Asp Gly Gln
65 70 75 80

Met Leu Pro Ile Asp Glu Ile Phe Glu Arg Glu Leu Asp Leu Met Arg
85 90 95

Val Asp Asn Leu Pro Asn
100

<210> SEQ ID NO 68
<211> LENGTH: 36
<212> TYPE: PRT
<213> ORGANISM: Nostoc punctiforme PCC73102

<400> SEQUENCE: 68

Met Ile Lys Ile Ala Thr Arg Lys Tyr Leu Gly Lys Gln Asn Val Tyr
1 5 10 15

Asp Ile Gly Val Glu Arg Asp His Asn Phe Ala Leu Lys Asn Gly Phe
20 25 30

Ile Ala Ser Asn
35

<210> SEQ ID NO 69
<211> LENGTH: 102
<212> TYPE: PRT
<213> ORGANISM: Nostoc sp. PCC7120

<400> SEQUENCE: 69

Cys Leu Ser Tyr Asp Thr Glu Val Leu Thr Val Glu Tyr Gly Phe Val
1 5 10 15

Pro Ile Gly Glu Ile Val Glu Lys Gly Ile Glu Cys Ser Val Phe Ser
20 25 30

-continued

Ile Asn Asn Asn Gly Ile Val Tyr Thr Gln Pro Ile Ala Gln Trp His
        35                  40                  45

His Arg Gly Lys Gln Glu Val Phe Glu Tyr Cys Leu Glu Asp Gly Ser
    50                  55                  60

Ile Ile Lys Ala Thr Lys Asp His Lys Phe Met Thr Gln Asp Gly Lys
65                  70                  75                  80

Met Leu Pro Ile Asp Glu Ile Phe Glu Gln Glu Leu Asp Leu Leu Gln
                85                  90                  95

Val Lys Gly Leu Pro Glu
            100

<210> SEQ ID NO 70
<211> LENGTH: 36
<212> TYPE: PRT
<213> ORGANISM: Nostoc sp. PCC7120

<400> SEQUENCE: 70

Met Ile Lys Ile Ala Ser Arg Lys Phe Leu Gly Val Glu Asn Val Tyr
1               5                   10                  15

Asp Ile Gly Val Arg Arg Asp His Asn Phe Phe Ile Lys Asn Gly Leu
            20                  25                  30

Ile Ala Ser Asn
        35

<210> SEQ ID NO 71
<211> LENGTH: 112
<212> TYPE: PRT
<213> ORGANISM: Oscillatoria limnetica

<400> SEQUENCE: 71

Cys Leu Ser Tyr Asn Thr Glu Val Leu Thr Val Glu Tyr Gly Pro Leu
1               5                   10                  15

Pro Ile Gly Lys Ile Val Asp Glu Gln Ile His Cys Arg Val Tyr Ser
            20                  25                  30

Val Asp Glu Asn Gly Phe Val Tyr Thr Gln Ala Ile Ala Gln Trp His
        35                  40                  45

Asp Arg Gly Tyr Gln Glu Ile Phe Ala Tyr Glu Leu Ala Asp Gly Ser
    50                  55                  60

Val Ile Arg Ala Thr Lys Asp His Gln Phe Met Thr Glu Asp Gly Gln
65                  70                  75                  80

Met Phe Pro Ile Asp Glu Ile Trp Glu Lys Gly Leu Asp Leu Lys Lys
                85                  90                  95

Leu Pro Thr Val Gln Asp Leu Pro Ala Ala Val Gly Tyr Thr Val Ser
            100                 105                 110

<210> SEQ ID NO 72
<211> LENGTH: 36
<212> TYPE: PRT
<213> ORGANISM: Oscillatoria limnetica

<400> SEQUENCE: 72

Met Val Lys Ile Val Arg Arg Gln Ser Leu Gly Val Gln Asn Val Tyr
1               5                   10                  15

Asp Ile Gly Val Glu Lys Asp His Asn Phe Cys Leu Ala Ser Gly Glu
            20                  25                  30

Ile Ala Ser Asn
        35

<210> SEQ ID NO 73
<211> LENGTH: 107
<212> TYPE: PRT
<213> ORGANISM: Synechocystis sp. PCC 7002

<400> SEQUENCE: 73

```
Cys Leu Ala Gly Gly Thr Pro Val Val Thr Val Glu Tyr Gly Val Leu
1               5                   10                  15

Pro Ile Gln Thr Ile Val Glu Gln Glu Leu Leu Cys His Val Tyr Ser
            20                  25                  30

Val Asp Ala Gln Gly Leu Ile Tyr Ala Gln Leu Ile Glu Gln Trp His
        35                  40                  45

Gln Arg Gly Asp Arg Leu Leu Tyr Glu Tyr Glu Leu Glu Asn Gly Gln
    50                  55                  60

Met Ile Arg Ala Thr Pro Asp His Arg Phe Leu Thr Thr Thr Gly Glu
65                  70                  75                  80

Leu Leu Pro Ile Asp Glu Ile Phe Thr Gln Asn Leu Asp Leu Ala Ala
                85                  90                  95

Trp Ala Val Pro Asp Ser Leu Pro Arg Thr Ala
            100                 105
```

<210> SEQ ID NO 74
<211> LENGTH: 36
<212> TYPE: PRT
<213> ORGANISM: Synechocystis sp. PCC 7002

<400> SEQUENCE: 74

```
Met Val Lys Ile Ile Arg Arg Lys Phe Ile Gly His Ala Pro Thr Tyr
1               5                   10                  15

Asp Ile Gly Leu Ser Gln Asp His Asn Phe Leu Leu Gly Gln Gly Leu
            20                  25                  30

Ile Ala Ala Asn
        35
```

<210> SEQ ID NO 75
<211> LENGTH: 117
<212> TYPE: PRT
<213> ORGANISM: Thermosynechococcus vulcanus

<400> SEQUENCE: 75

```
Cys Leu Ser Gly Glu Thr Ala Val Met Thr Val Glu Tyr Gly Ala Ile
1               5                   10                  15

Pro Ile Arg Arg Leu Val Gln Glu Arg Leu Ile Cys Gln Val Tyr Ser
            20                  25                  30

Leu Asp Pro Gln Gly His Leu Tyr Thr Gln Pro Ile Ala Gln Trp His
        35                  40                  45

Phe Gln Gly Phe Arg Pro Val Tyr Ala Tyr Gln Leu Glu Asp Gly Ser
    50                  55                  60

Thr Ile Cys Ala Thr Pro Asp His Arg Phe Met Thr Thr Ser Gly Gln
65                  70                  75                  80

Met Leu Pro Ile Glu Gln Ile Phe Arg Glu Gly Leu Glu Leu Trp Gln
                85                  90                  95

Val Ala Ile Ala Pro Pro Gly Ala Leu Ala Gln Gly Leu Lys Pro Ala
            100                 105                 110

Val Gln Met Ser Cys
        115
```

<210> SEQ ID NO 76

-continued

<211> LENGTH: 35
<212> TYPE: PRT
<213> ORGANISM: Thermosynechococcus vulcanus

<400> SEQUENCE: 76

Met Lys Ile Val Gly Arg Arg Leu Val Gly Trp Gln Ala Val Tyr Asp
1 5 10 15

Ile Gly Leu Ala Gly Asp His Asn Phe Leu Leu Ala Asn Gly Ala Ile
20 25 30

Ala Ala Asn
35

<210> SEQ ID NO 77
<211> LENGTH: 306
<212> TYPE: PRT
<213> ORGANISM: Methanococcus jannaschii

<400> SEQUENCE: 77

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Tyr
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Leu Leu Ala Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Phe Gln Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Asp Ile His
145 150 155 160

Tyr Leu Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Asp Leu Lys
275 280 285

Asn Ala Val Ala Glu Glu Leu Ile Lys Ile Leu Glu Pro Ile Arg Lys
290 295 300

```
Arg Leu
305


<210> SEQ ID NO 78
<211> LENGTH: 454
<212> TYPE: PRT
<213> ORGANISM: Methanosarcina mazeii

<400> SEQUENCE: 78

Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Ser Arg Thr Ala Arg Ala Leu Arg His His Lys
    50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Tyr Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
```

```
        355                 360                 365

His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Gly Ser Tyr Tyr Asn
        435                 440                 445

Gly Ile Ser Thr Asn Leu
    450


<210> SEQ ID NO 79
<211> LENGTH: 419
<212> TYPE: PRT
<213> ORGANISM: Methanosarcina barkeri

<400> SEQUENCE: 79

Met Asp Lys Lys Pro Leu Asp Val Leu Ile Ser Ala Thr Gly Leu Gly
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270
```

```
Tyr Leu Arg Lys Leu Asp Arg Ile Leu Pro Gly Pro Ile Lys Val Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Cys Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu


<210> SEQ ID NO 80
<211> LENGTH: 424
<212> TYPE: PRT
<213> ORGANISM: Escherichia coli

<400> SEQUENCE: 80

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Tyr Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Asp Phe Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220
```

```
Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Asp Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420


<210> SEQ ID NO 81
<211> LENGTH: 306
<212> TYPE: PRT
<213> ORGANISM: Artificial Sequence
<220> FEATURE:
<223> OTHER INFORMATION: Engineered sequence

<400> SEQUENCE: 81

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160
```

```
Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 82
<211> LENGTH: 306
<212> TYPE: PRT
<213> ORGANISM: Artificial Sequence
<220> FEATURE:
<223> OTHER INFORMATION: Engineered sequence

<400> SEQUENCE: 82

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Gln
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Glu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Gly Leu Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ser Ile His
145                 150                 155                 160

Tyr Tyr Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205
```

```
Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 83
<211> LENGTH: 306
<212> TYPE: PRT
<213> ORGANISM: Artificial Sequence
<220> FEATURE:
<223> OTHER INFORMATION: Engineered sequence

<400> SEQUENCE: 83

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Ala His
145                 150                 155                 160

Tyr Gln Gly Val Asp Val Val Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255
```

-continued

```
Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305


<210> SEQ ID NO 84
<211> LENGTH: 306
<212> TYPE: PRT
<213> ORGANISM: Artificial Sequence
<220> FEATURE:
<223> OTHER INFORMATION: Engineered sequence

<400> SEQUENCE: 84

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Ala
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Ala Ile His
145                 150                 155                 160

Tyr Ala Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300
```

Arg Leu
305

<210> SEQ ID NO 85
<211> LENGTH: 306
<212> TYPE: PRT
<213> ORGANISM: Artificial Sequence
<220> FEATURE:
<223> OTHER INFORMATION: Engineered sequence

<400> SEQUENCE: 85

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Gly
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Leu Leu Ala Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Pro Phe Gln Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Ala Ile His
145 150 155 160

Tyr Ala Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Arg Leu Lys
275 280 285

Asn Ala Val Ala Glu Glu Leu Ile Lys Ile Leu Glu Pro Ile Arg Lys
290 295 300

Arg Leu
305

<210> SEQ ID NO 86
<211> LENGTH: 306
<212> TYPE: PRT
<213> ORGANISM: Artificial Sequence
<220> FEATURE:

<223> OTHER INFORMATION: Engineered sequence

<400> SEQUENCE: 86

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 87
<211> LENGTH: 306
<212> TYPE: PRT
<213> ORGANISM: Artificial Sequence
<220> FEATURE:
<223> OTHER INFORMATION: Engineered sequence

<400> SEQUENCE: 87

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30
```

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Leu Leu Ala Asp Leu His Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Thr Phe Gln Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Pro Leu His
145 150 155 160

Tyr Ala Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Arg Leu Lys
275 280 285

Asn Ala Val Ala Glu Glu Leu Ile Lys Ile Leu Glu Pro Ile Arg Lys
290 295 300

Arg Leu
305

<210> SEQ ID NO 88
<211> LENGTH: 306
<212> TYPE: PRT
<213> ORGANISM: Artificial Sequence
<220> FEATURE:
<223> OTHER INFORMATION: Engineered sequence

<400> SEQUENCE: 88

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Gly
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

Leu Leu Ala Asp Leu His Ala Tyr Leu Asn Gln Lys Gly Glu Leu Asp
65 70 75 80

```
Glu Ile Arg Lys Ile Gly Asp Tyr Asn Lys Lys Val Phe Glu Ala Met
                85                  90                  95

Gly Leu Lys Ala Lys Tyr Val Tyr Gly Ser Pro Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Thr Ser His
145                 150                 155                 160

Tyr Leu Gly Ala Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 89
<211> LENGTH: 306
<212> TYPE: PRT
<213> ORGANISM: Artificial Sequence
<220> FEATURE:
<223> OTHER INFORMATION: Engineered sequence

<400> SEQUENCE: 89

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Trp Met Leu Asp Lys
            100                 105                 110

Asp Tyr Thr Leu Asn Val Tyr Arg Leu Ala Leu Lys Thr Thr Leu Lys
        115                 120                 125
```

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Gly Ala His
145 150 155 160

Tyr Leu Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Asp Leu Lys
275 280 285

Asn Ala Val Ala Glu Glu Leu Ile Lys Ile Leu Glu Pro Ile Arg Lys
290 295 300

Arg Leu
305

<210> SEQ ID NO 90
<211> LENGTH: 306
<212> TYPE: PRT
<213> ORGANISM: Artificial Sequence
<220> FEATURE:
<223> OTHER INFORMATION: Engineered sequence

<400> SEQUENCE: 90

Met Asp Glu Phe Glu Met Ile Lys Arg Asn Thr Ser Glu Ile Ile Ser
1 5 10 15

Glu Glu Glu Leu Arg Glu Val Leu Lys Lys Asp Glu Lys Ser Ala Glu
20 25 30

Ile Gly Phe Glu Pro Ser Gly Lys Ile His Leu Gly His Tyr Leu Gln
35 40 45

Ile Lys Lys Met Ile Asp Leu Gln Asn Ala Gly Phe Asp Ile Ile Ile
50 55 60

His Leu Gly Asp Leu Gly Ala Tyr Leu Asn Gln Lys Gly Glu Leu Asp
65 70 75 80

Glu Ile Arg Lys Ile Gly Asp Tyr Asn Lys Lys Val Phe Glu Ala Met
85 90 95

Gly Leu Lys Ala Lys Tyr Val Tyr Gly Ser Glu Tyr His Leu Asp Lys
100 105 110

Asp Tyr Thr Leu Asn Val Tyr Arg Leu Ala Leu Lys Thr Thr Leu Lys
115 120 125

Arg Ala Arg Arg Ser Met Glu Leu Ile Ala Arg Glu Asp Glu Asn Pro
130 135 140

Lys Val Ala Glu Val Ile Tyr Pro Ile Met Gln Val Asn Gly Ile His
145 150 155 160

Tyr Gly Gly Val Asp Val Ala Val Gly Gly Met Glu Gln Arg Lys Ile
165 170 175

His Met Leu Ala Arg Glu Leu Leu Pro Lys Lys Val Val Cys Ile His
180 185 190

Asn Pro Val Leu Thr Gly Leu Asp Gly Glu Gly Lys Met Ser Ser Ser
195 200 205

Lys Gly Asn Phe Ile Ala Val Asp Asp Ser Pro Glu Glu Ile Arg Ala
210 215 220

Lys Ile Lys Lys Ala Tyr Cys Pro Ala Gly Val Val Glu Gly Asn Pro
225 230 235 240

Ile Met Glu Ile Ala Lys Tyr Phe Leu Glu Tyr Pro Leu Thr Ile Lys
245 250 255

Arg Pro Glu Lys Phe Gly Gly Asp Leu Thr Val Asn Ser Tyr Glu Glu
260 265 270

Leu Glu Ser Leu Phe Lys Asn Lys Glu Leu His Pro Met Asp Leu Lys
275 280 285

Asn Ala Val Ala Glu Glu Leu Ile Lys Ile Leu Glu Pro Ile Arg Lys
290 295 300

Arg Leu
305

<210> SEQ ID NO 91
<211> LENGTH: 454
<212> TYPE: PRT
<213> ORGANISM: Artificial Sequence
<220> FEATURE:
<223> OTHER INFORMATION: Engineered sequence

<400> SEQUENCE: 91

Met Asp Lys Lys Pro Leu Asn Thr Leu Ile Ser Ala Thr Gly Leu Trp
1 5 10 15

Met Ser Arg Thr Gly Thr Ile His Lys Ile Lys His His Glu Val Ser
20 25 30

Arg Ser Lys Ile Tyr Ile Glu Met Ala Cys Gly Asp His Leu Val Val
35 40 45

Asn Asn Ser Arg Ser Ser Arg Thr Ala Arg Ala Leu Arg His His Lys
50 55 60

Tyr Arg Lys Thr Cys Lys Arg Cys Arg Val Ser Asp Glu Asp Leu Asn
65 70 75 80

Lys Phe Leu Thr Lys Ala Asn Glu Asp Gln Thr Ser Val Lys Val Lys
85 90 95

Val Val Ser Ala Pro Thr Arg Thr Lys Lys Ala Met Pro Lys Ser Val
100 105 110

Ala Arg Ala Pro Lys Pro Leu Glu Asn Thr Glu Ala Ala Gln Ala Gln
115 120 125

Pro Ser Gly Ser Lys Phe Ser Pro Ala Ile Pro Val Ser Thr Gln Glu
130 135 140

Ser Val Ser Val Pro Ala Ser Val Ser Thr Ser Ile Ser Ser Ile Ser
145 150 155 160

Thr Gly Ala Thr Ala Ser Ala Leu Val Lys Gly Asn Thr Asn Pro Ile
165 170 175

Thr Ser Met Ser Ala Pro Val Gln Ala Ser Ala Pro Ala Leu Thr Lys
180 185 190

Ser Gln Thr Asp Arg Leu Glu Val Leu Leu Asn Pro Lys Asp Glu Ile
195 200 205

Ser Leu Asn Ser Gly Lys Pro Phe Arg Glu Leu Glu Ser Glu Leu Leu
210 215 220

Ser Arg Arg Lys Lys Asp Leu Gln Gln Ile Tyr Ala Glu Glu Arg Glu
225 230 235 240

Asn Tyr Leu Gly Lys Leu Glu Arg Glu Ile Thr Arg Phe Phe Val Asp
245 250 255

Arg Gly Phe Leu Glu Ile Lys Ser Pro Ile Leu Ile Pro Leu Glu Tyr
260 265 270

Ile Glu Arg Met Gly Ile Asp Asn Asp Thr Glu Leu Ser Lys Gln Ile
275 280 285

Phe Arg Val Asp Lys Asn Phe Cys Leu Arg Pro Met Leu Ala Pro Asn
290 295 300

Leu Tyr Asn Tyr Leu Arg Lys Leu Asp Arg Ala Leu Pro Asp Pro Ile
305 310 315 320

Lys Ile Phe Glu Ile Gly Pro Cys Tyr Arg Lys Glu Ser Asp Gly Lys
325 330 335

Glu His Leu Glu Glu Phe Thr Met Leu Ala Phe Ala Gln Met Gly Ser
340 345 350

Gly Cys Thr Arg Glu Asn Leu Glu Ser Ile Ile Thr Asp Phe Leu Asn
355 360 365

His Leu Gly Ile Asp Phe Lys Ile Val Gly Asp Ser Cys Met Val Tyr
370 375 380

Gly Asp Thr Leu Asp Val Met His Gly Asp Leu Glu Leu Ser Ser Ala
385 390 395 400

Val Val Gly Pro Ile Pro Leu Asp Arg Glu Trp Gly Ile Asp Lys Pro
405 410 415

Trp Ile Gly Ala Gly Phe Gly Leu Glu Arg Leu Leu Lys Val Lys His
420 425 430

Asp Phe Lys Asn Ile Lys Arg Ala Ala Arg Ser Gly Ser Tyr Tyr Asn
435 440 445

Gly Ile Ser Thr Asn Leu
450

<210> SEQ ID NO 92
<211> LENGTH: 454
<212> TYPE: PRT
<213> ORGANISM: Artificial Sequence
<220> FEATURE:
<223> OTHER INFORMATION: Engineered sequence

<400> SEQUENCE: 92

Met Asp Lys Lys Pro Leu Asn Thr Leu Ile Ser Ala Thr Gly Leu Trp
1 5 10 15

Met Ser Arg Thr Gly Thr Ile His Lys Ile Lys His His Glu Val Ser
20 25 30

Arg Ser Lys Ile Tyr Ile Glu Met Ala Cys Gly Asp His Leu Val Val
35 40 45

Asn Asn Ser Arg Ser Ser Arg Thr Ala Arg Ala Leu Arg His His Lys
50 55 60

Tyr Arg Lys Thr Cys Lys Arg Cys Arg Val Ser Asp Glu Asp Leu Asn
65 70 75 80

Lys Phe Leu Thr Lys Ala Asn Glu Asp Gln Thr Ser Val Lys Val Lys
85 90 95

Val Val Ser Ala Pro Thr Arg Thr Lys Lys Ala Met Pro Lys Ser Val
100 105 110

Ala Arg Ala Pro Lys Pro Leu Glu Asn Thr Glu Ala Ala Gln Ala Gln
115 120 125

```
Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ala Pro Asn
    290                 295                 300

Leu Ala Asn Tyr Leu Arg Lys Leu Asp Arg Ala Leu Pro Asp Pro Ile
305                 310                 315                 320

Lys Ile Phe Glu Ile Gly Pro Cys Tyr Arg Lys Glu Ser Asp Gly Lys
                325                 330                 335

Glu His Leu Glu Glu Phe Thr Met Leu Asn Phe Cys Gln Met Gly Ser
            340                 345                 350

Gly Cys Thr Arg Glu Asn Leu Glu Ser Ile Ile Thr Asp Phe Leu Asn
        355                 360                 365

His Leu Gly Ile Asp Phe Lys Ile Val Gly Asp Ser Cys Met Val Phe
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Trp Ile Gly Ala Gly Phe Gly Leu Glu Arg Leu Leu Lys Val Lys His
            420                 425                 430

Asp Phe Lys Asn Ile Lys Arg Ala Ala Arg Ser Gly Ser Tyr Tyr Asn
        435                 440                 445

Gly Ile Ser Thr Asn Leu
    450
```

<210> SEQ ID NO 93
<211> LENGTH: 419
<212> TYPE: PRT
<213> ORGANISM: Artificial Sequence
<220> FEATURE:
<223> OTHER INFORMATION: Engineered sequence

<400> SEQUENCE: 93

```
Met Asp Lys Lys Pro Leu Asp Val Leu Ile Ser Ala Thr Gly Leu Gly
1               5                   10                  15

Met Ser Arg Thr Gly Thr Leu His Lys Ile Lys His His Glu Val Ser
            20                  25                  30
```

```
Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270

Tyr Ala Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Phe Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Phe Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu
```

<210> SEQ ID NO 94
<211> LENGTH: 419
<212> TYPE: PRT

<213> ORGANISM: Artificial Sequence
<220> FEATURE:
<223> OTHER INFORMATION: Engineered sequence

<400> SEQUENCE: 94

```
Met Asp Lys Lys Pro Leu Asp Val Leu Ile Ser Ala Thr Gly Leu Gly
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Met Asn
            260                 265                 270

Tyr Gly Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Ala Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Phe Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
```

385 390 395 400

Asn Ile Lys Arg Ala Ser Arg Ser Glu Ser Tyr Tyr Asn Gly Ile Ser
405 410 415

Thr Asn Leu

<210> SEQ ID NO 95
<211> LENGTH: 419
<212> TYPE: PRT
<213> ORGANISM: Artificial Sequence
<220> FEATURE:
<223> OTHER INFORMATION: Engineered sequence

<400> SEQUENCE: 95

Met Asp Lys Lys Pro Leu Asp Val Leu Ile Ser Ala Thr Gly Leu Gly
1 5 10 15

Met Ser Arg Thr Gly Thr Leu His Lys Ile Lys His His Glu Val Ser
20 25 30

Arg Ser Lys Ile Tyr Ile Glu Met Ala Cys Gly Asp His Leu Val Val
35 40 45

Asn Asn Ser Arg Ser Cys Arg Thr Ala Arg Ala Phe Arg His His Lys
50 55 60

Tyr Arg Lys Thr Cys Lys Arg Cys Arg Val Ser Asp Glu Asp Ile Asn
65 70 75 80

Asn Phe Leu Thr Arg Ser Thr Glu Ser Lys Asn Ser Val Lys Val Arg
85 90 95

Val Val Ser Ala Pro Lys Val Lys Lys Ala Met Pro Lys Ser Val Ser
100 105 110

Arg Ala Pro Lys Pro Leu Glu Asn Ser Val Ser Ala Lys Ala Ser Thr
115 120 125

Asn Thr Ser Arg Ser Val Pro Ser Pro Ala Lys Ser Thr Pro Asn Ser
130 135 140

Ser Val Pro Ala Ser Ala Pro Ala Pro Ser Leu Thr Arg Ser Gln Leu
145 150 155 160

Asp Arg Val Glu Ala Leu Leu Ser Pro Glu Asp Lys Ile Ser Leu Asn
165 170 175

Met Ala Lys Pro Phe Arg Glu Leu Glu Pro Glu Leu Val Thr Arg Arg
180 185 190

Lys Asn Asp Phe Gln Arg Leu Tyr Thr Asn Asp Arg Glu Asp Tyr Leu
195 200 205

Gly Lys Leu Glu Arg Asp Ile Thr Lys Phe Phe Val Asp Arg Gly Phe
210 215 220

Leu Glu Ile Lys Ser Pro Ile Leu Ile Pro Ala Glu Tyr Val Glu Arg
225 230 235 240

Met Gly Ile Asn Asn Asp Thr Glu Leu Ser Lys Gln Ile Phe Arg Val
245 250 255

Asp Lys Asn Leu Cys Leu Arg Pro Met Leu Ala Pro Thr Leu Met Asn
260 265 270

Tyr Gly Arg Lys Leu Asp Arg Ile Leu Pro Gly Pro Ile Lys Val Phe
275 280 285

Glu Val Gly Pro Cys Tyr Arg Lys Glu Ser Asp Gly Lys Glu His Leu
290 295 300

Glu Glu Phe Thr Met Val Asn Phe Ala Gln Met Gly Ser Gly Cys Thr
305 310 315 320

Arg Glu Asn Leu Glu Ala Leu Ile Lys Glu Phe Leu Asp Tyr Leu Glu
325 330 335

```
Ile Asp Phe Glu Ile Val Gly Asp Ser Cys Met Val Trp Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu


<210> SEQ ID NO 96
<211> LENGTH: 419
<212> TYPE: PRT
<213> ORGANISM: Artificial Sequence
<220> FEATURE:
<223> OTHER INFORMATION: Engineered sequence

<400> SEQUENCE: 96

Met Asp Lys Lys Pro Leu Asp Val Leu Ile Ser Ala Thr Gly Leu Gly
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
                85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220

Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ala Pro Thr Leu Tyr Asn
            260                 265                 270
```

```
Tyr Ala Arg Lys Leu Asp Arg Ile Leu Pro Gly Pro Ile Lys Ile Phe
        275                 280                 285

Glu Val Gly Pro Cys Tyr Arg Lys Glu Ser Asp Gly Lys Glu His Leu
    290                 295                 300

Glu Glu Phe Thr Met Val Asn Phe Val Gln Met Gly Ser Gly Cys Thr
305                 310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Phe Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Trp Ile Gly
    370                 375                 380

Ala Gly Phe Gly Leu Glu Arg Leu Leu Lys Val Met His Gly Phe Lys
385                 390                 395                 400

Asn Ile Lys Arg Ala Ser Arg Ser Glu Ser Tyr Tyr Asn Gly Ile Ser
                405                 410                 415

Thr Asn Leu


<210> SEQ ID NO 97
<211> LENGTH: 424
<212> TYPE: PRT
<213> ORGANISM: Artificial Sequence
<220> FEATURE:
<223> OTHER INFORMATION: Engineered sequence

<400> SEQUENCE: 97

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Leu Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
```

```
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Arg Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420


<210> SEQ ID NO 98
<211> LENGTH: 424
<212> TYPE: PRT
<213> ORGANISM: Artificial Sequence
<220> FEATURE:
<223> OTHER INFORMATION: Engineered sequence

<400> SEQUENCE: 98

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Val Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
```

-continued

```
145                 150                 155                 160

Leu Asn Arg Glu Asp Gln Gly Ile Ser Phe Thr Glu Phe Ser Tyr Asn
                165                 170                 175

Leu Leu Gln Gly Tyr Ser Met Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Arg Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420


<210> SEQ ID NO 99
<211> LENGTH: 424
<212> TYPE: PRT
<213> ORGANISM: Artificial Sequence
<220> FEATURE:
<223> OTHER INFORMATION: Engineered sequence

<400> SEQUENCE: 99

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
            20                  25                  30

Pro Ile Ala Leu Ser Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
```

```
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Thr Met Ala Cys Val Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Arg Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420


<210> SEQ ID NO 100
<211> LENGTH: 424
<212> TYPE: PRT
<213> ORGANISM: Artificial Sequence
<220> FEATURE:
<223> OTHER INFORMATION: Engineered sequence

<400> SEQUENCE: 100

Met Ala Ser Ser Asn Leu Ile Lys Gln Leu Gln Glu Arg Gly Leu Val
1               5                   10                  15

Ala Gln Val Thr Asp Glu Glu Ala Leu Ala Glu Arg Leu Ala Gln Gly
```

```
            20                  25                  30

Pro Ile Ala Leu Ile Cys Gly Phe Asp Pro Thr Ala Asp Ser Leu His
        35                  40                  45

Leu Gly His Leu Val Pro Leu Leu Cys Leu Lys Arg Phe Gln Gln Ala
    50                  55                  60

Gly His Lys Pro Val Ala Leu Val Gly Gly Ala Thr Gly Leu Ile Gly
65                  70                  75                  80

Asp Pro Ser Phe Lys Ala Ala Glu Arg Lys Leu Asn Thr Glu Glu Thr
                85                  90                  95

Val Gln Glu Trp Val Asp Lys Ile Arg Lys Gln Val Ala Pro Phe Leu
            100                 105                 110

Asp Phe Asp Cys Gly Glu Asn Ser Ala Ile Ala Ala Asn Asn Tyr Asp
        115                 120                 125

Trp Phe Gly Asn Met Asn Val Leu Thr Phe Leu Arg Asp Ile Gly Lys
    130                 135                 140

His Phe Ser Val Asn Gln Met Ile Asn Lys Glu Ala Val Lys Gln Arg
145                 150                 155                 160

Leu Asn Arg Glu Asp Gln Gly Ile Ser Phe Thr Glu Phe Ser Tyr Asn
                165                 170                 175

Leu Leu Gln Gly Tyr Gly Met Ala Cys Ala Asn Lys Gln Tyr Gly Val
            180                 185                 190

Val Leu Gln Ile Gly Gly Ser Asp Gln Trp Gly Asn Ile Thr Ser Gly
        195                 200                 205

Ile Asp Leu Thr Arg Arg Leu His Gln Asn Gln Val Phe Gly Leu Thr
    210                 215                 220

Val Pro Leu Ile Thr Lys Ala Asp Gly Thr Lys Phe Gly Lys Thr Glu
225                 230                 235                 240

Gly Gly Ala Val Trp Leu Asp Pro Lys Lys Thr Ser Pro Tyr Lys Phe
                245                 250                 255

Tyr Gln Phe Trp Ile Asn Thr Ala Arg Ala Asp Val Tyr Arg Phe Leu
            260                 265                 270

Lys Phe Phe Thr Phe Met Ser Ile Glu Glu Ile Asn Ala Leu Glu Glu
        275                 280                 285

Glu Asp Lys Asn Ser Gly Lys Ala Pro Arg Ala Gln Tyr Val Leu Ala
    290                 295                 300

Glu Gln Val Thr Arg Leu Val His Gly Glu Glu Gly Leu Gln Ala Ala
305                 310                 315                 320

Lys Arg Ile Thr Glu Cys Leu Phe Ser Gly Ser Leu Ser Ala Leu Ser
                325                 330                 335

Glu Ala Asp Phe Glu Gln Leu Ala Gln Asp Gly Val Pro Met Val Glu
            340                 345                 350

Met Glu Lys Gly Ala Asp Leu Met Gln Ala Leu Val Asp Ser Glu Leu
        355                 360                 365

Gln Pro Ser Arg Gly Gln Ala Arg Lys Thr Ile Ala Ser Asn Ala Ile
    370                 375                 380

Thr Ile Asn Gly Glu Lys Gln Ser Asp Pro Glu Tyr Phe Phe Lys Glu
385                 390                 395                 400

Glu Asp Arg Leu Phe Gly Arg Phe Thr Leu Leu Arg Arg Gly Lys Lys
                405                 410                 415

Asn Tyr Cys Leu Ile Cys Trp Lys
            420
```

<210> SEQ ID NO 101

<211> LENGTH: 77
<212> TYPE: DNA
<213> ORGANISM: Artificial Sequence
<220> FEATURE:
<223> OTHER INFORMATION: Engineered sequence.

<400> SEQUENCE: 101
ccggcggtag ttcagcaggg cagaacggcg gactctaaat ccgcatggca ggggttcaaa 60
tcccctccgc cggacca 77

<210> SEQ ID NO 102
<211> LENGTH: 77
<212> TYPE: DNA
<213> ORGANISM: Artificial Sequence
<220> FEATURE:
<223> OTHER INFORMATION: Engineered sequence.

<400> SEQUENCE: 102
ccggcggtag ttcagcaggg cagaacggcg gactttaaat ccgcatggca ggggttcaaa 60
tcccctccgc cggacca 77

<210> SEQ ID NO 103
<211> LENGTH: 77
<212> TYPE: DNA
<213> ORGANISM: Artificial Sequence
<220> FEATURE:
<223> OTHER INFORMATION: Engineered sequence.

<400> SEQUENCE: 103
ccggcggtag ttcagcaggg cagaacggcg gacttcaaat ccgcatggca ggggttcaaa 60
tcccctccgc cggacca 77

<210> SEQ ID NO 104
<211> LENGTH: 78
<212> TYPE: DNA
<213> ORGANISM: Artificial Sequence
<220> FEATURE:
<223> OTHER INFORMATION: Engineered sequence.

<400> SEQUENCE: 104
ccggcggtag ttcagcaggg cagaacggcg gacttctaaa tccgcatggc aggggttcaa 60
atcccctccg ccggacca 78

<210> SEQ ID NO 105
<211> LENGTH: 72
<212> TYPE: DNA
<213> ORGANISM: Artificial Sequence
<220> FEATURE:
<223> OTHER INFORMATION: Engineered sequence.

<400> SEQUENCE: 105
ggaaacctga tcatgtagat cgaatggact ctaaatccgt tcagccgggt tagattcccg 60
gggtttccgc ca 72

<210> SEQ ID NO 106
<211> LENGTH: 72
<212> TYPE: DNA
<213> ORGANISM: Artificial Sequence
<220> FEATURE:
<223> OTHER INFORMATION: Engineered sequence.

<400> SEQUENCE: 106
ggaaacctga tcatgtagat cgaatggact ttaaatccgt tcagccgggt tagattcccg 60
gggtttccgc ca 72

<210> SEQ ID NO 107
<211> LENGTH: 72
<212> TYPE: DNA
<213> ORGANISM: Artificial Sequence
<220> FEATURE:
<223> OTHER INFORMATION: Engineered sequence.

<400> SEQUENCE: 107
ggaaacctga tcatgtagat cgaatggact tcaaatccgt tcagccgggt tagattcccg 60
gggtttccgc ca 72

<210> SEQ ID NO 108
<211> LENGTH: 73
<212> TYPE: DNA
<213> ORGANISM: Artificial Sequence
<220> FEATURE:
<223> OTHER INFORMATION: Engineered sequence.

<400> SEQUENCE: 108
ggaaacctga tcatgtagat cgaatggact tctaaatccg ttcagccggg ttagattccc 60
ggggtttccg cca 73

<210> SEQ ID NO 109
<211> LENGTH: 72
<212> TYPE: DNA
<213> ORGANISM: Artificial Sequence
<220> FEATURE:
<223> OTHER INFORMATION: Engineered sequence.

<400> SEQUENCE: 109
ggggggtgga tcgaatagat cacacggact ctaaattcgt gcaggcgggt gaaactcccg 60
tactccccgc ca 72

<210> SEQ ID NO 110
<211> LENGTH: 72
<212> TYPE: DNA
<213> ORGANISM: Artificial Sequence
<220> FEATURE:
<223> OTHER INFORMATION: Engineered sequence.

<400> SEQUENCE: 110
ggggggtgga tcgaatagat cacacggact ttaaattcgt gcaggcgggt gaaactcccg 60
tactccccgc ca 72

<210> SEQ ID NO 111
<211> LENGTH: 72
<212> TYPE: DNA
<213> ORGANISM: Artificial Sequence
<220> FEATURE:
<223> OTHER INFORMATION: Engineered sequence.

<400> SEQUENCE: 111
ggggggtgga tcgaatagat cacacggact tcaaattcgt gcaggcgggt gaaactcccg 60
tactccccgc ca 72

<210> SEQ ID NO 112
<211> LENGTH: 73
<212> TYPE: DNA
<213> ORGANISM: Artificial Sequence
<220> FEATURE:

<223> OTHER INFORMATION: Engineered sequence

<400> SEQUENCE: 112 gggggtgga tcgaatagat cacacggact tctaaattcg tgcaggcggg tgaaactccc 60
gtactccccg cca 73

<210> SEQ ID NO 113
<211> LENGTH: 85
<212> TYPE: DNA
<213> ORGANISM: Artificial Sequence
<220> FEATURE:
<223> OTHER INFORMATION: Engineered sequence

<400> SEQUENCE: 113
ggtggggttc ccgagcggcc aaagggagca gactctaaat ctgccgtcac agacttcgaa 60
ggttcgaatc cttcccccac cacca 85

<210> SEQ ID NO 114
<211> LENGTH: 85
<212> TYPE: DNA
<213> ORGANISM: Artificial Sequence
<220> FEATURE:
<223> OTHER INFORMATION: Engineered sequence

<400> SEQUENCE: 114
ggtggggttc ccgagcggcc aaagggagca gactttaaat ctgccgtcac agacttcgaa 60
ggttcgaatc cttcccccac cacca 85

<210> SEQ ID NO 115
<211> LENGTH: 85
<212> TYPE: DNA
<213> ORGANISM: Artificial Sequence
<220> FEATURE:
<223> OTHER INFORMATION: Engineered sequence

<400> SEQUENCE: 115
ggtggggttc ccgagcggcc aaagggagca gacttcaaat ctgccgtcac agacttcgaa 60
ggttcgaatc cttcccccac cacca 85

<210> SEQ ID NO 116
<211> LENGTH: 86
<212> TYPE: DNA
<213> ORGANISM: Artificial Sequence
<220> FEATURE:
<223> OTHER INFORMATION: Engineered sequence

<400> SEQUENCE: 116
ggtggggttc ccgagcggcc aaagggagca gacttctaaa tctgccgtca cagacttcga 60
aggttcgaat ccttccccca ccacca 86

<210> SEQ ID NO 117
<211> LENGTH: 85
<212> TYPE: DNA
<213> ORGANISM: Artificial Sequence
<220> FEATURE:
<223> OTHER INFORMATION: Engineered sequence

<400> SEQUENCE: 117
ggaggggtag cgaagtggct aaacgcggcg gactctaaat ccgctccctc agggttcggc 60
agttcgaatc tgcccccctc cacca 85

<210> SEQ ID NO 118
<211> LENGTH: 85
<212> TYPE: DNA
<213> ORGANISM: Artificial Sequence
<220> FEATURE:
<223> OTHER INFORMATION: Engineered sequence

<400> SEQUENCE: 118
ggaggggtag cgaagtggct aaacgcggcg gactttaaat ccgctccctc agggttcggc 60
agttcgaatc tgcccccctc cacca 85

<210> SEQ ID NO 119
<211> LENGTH: 85
<212> TYPE: DNA
<213> ORGANISM: Artificial Sequence
<220> FEATURE:
<223> OTHER INFORMATION: Engineered sequence

<400> SEQUENCE: 119
ggaggggtag cgaagtggct aaacgcggcg gacttcaaat ccgctccctc agggttcggc 60
agttcgaatc tgcccccctc cacca 85

<210> SEQ ID NO 120
<211> LENGTH: 86
<212> TYPE: DNA
<213> ORGANISM: Artificial Sequence
<220> FEATURE:
<223> OTHER INFORMATION: Engineered sequence

<400> SEQUENCE: 120
ggaggggtag cgaagtggct aaacgcggcg gacttctaaa tccgctccct cagggttcgg 60
cagttcgaat ctgcccccct ccacca 86

<210> SEQ ID NO 121
<211> LENGTH: 5
<212> TYPE: PRT
<213> ORGANISM: Artificial Sequence
<220> FEATURE:
<223> OTHER INFORMATION: synthetic or artificial sequence

<400> SEQUENCE: 121

Arg Arg Arg Arg Arg
1               5

<210> SEQ ID NO 122
<211> LENGTH: 6
<212> TYPE: PRT
<213> ORGANISM: Artificial Sequence
<220> FEATURE:
<223> OTHER INFORMATION: synthetic or artificial sequence

<400> SEQUENCE: 122

His His His His His His
1               5

<210> SEQ ID NO 123
<211> LENGTH: 19
<212> TYPE: PRT
<213> ORGANISM: Artificial Sequence
<220> FEATURE:
<223> OTHER INFORMATION: synthetic or artificial sequence

<400> SEQUENCE: 123

Ser Gly Leu Asn Asp Ile Phe Glu Ala Gln Lys Ile Glu Trp His Glu
1               5                   10                  15

Leu Glu Leu

<210> SEQ ID NO 124
<211> LENGTH: 8
<212> TYPE: PRT
<213> ORGANISM: Artificial Sequence
<220> FEATURE:
<223> OTHER INFORMATION: synthetic or artificial sequence

<400> SEQUENCE: 124

Asp Tyr Lys Asp Asp Asp Asp Lys
1               5

<210> SEQ ID NO 125
<211> LENGTH: 8
<212> TYPE: PRT
<213> ORGANISM: Artificial Sequence
<220> FEATURE:
<223> OTHER INFORMATION: synthetic or artificial sequence

<400> SEQUENCE: 125

Trp Ser His Pro Gln Phe Glu Lys
1               5

<210> SEQ ID NO 126
<211> LENGTH: 10
<212> TYPE: PRT
<213> ORGANISM: Artificial Sequence
<220> FEATURE:
<223> OTHER INFORMATION: synthetic or artificial sequence

<400> SEQUENCE: 126

Glu Gln Lys Leu Ile Ser Glu Glu Asp Leu
1               5                   10

<210> SEQ ID NO 127
<211> LENGTH: 15
<212> TYPE: PRT
<213> ORGANISM: Artificial Sequence
<220> FEATURE:
<223> OTHER INFORMATION: synthetic or artificial sequence

<400> SEQUENCE: 127

Lys Glu Thr Ala Ala Ala Lys Phe Glu Arg Gln His Met Asp Ser
1               5                   10                  15

<210> SEQ ID NO 128
<211> LENGTH: 26
<212> TYPE: PRT
<213> ORGANISM: Artificial Sequence
<220> FEATURE:
<223> OTHER INFORMATION: synthetic or artificial sequence

<400> SEQUENCE: 128

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 129
<211> LENGTH: 38
<212> TYPE: PRT
<213> ORGANISM: Artificial Sequence
<220> FEATURE:
<223> OTHER INFORMATION: synthetic or artificial sequence

<400> SEQUENCE: 129

Met Asp Glu Lys Thr Thr Gly Trp Arg Gly Gly His Val Val Glu Gly
1 5 10 15

Leu Ala Gly Glu Leu Glu Gln Leu Arg Ala Arg Leu Glu His His Pro
20 25 30

Gln Gly Gln Arg Glu Pro
35

<210> SEQ ID NO 130
<211> LENGTH: 71
<212> TYPE: PRT
<213> ORGANISM: Bacillus circulans

<400> SEQUENCE: 130

Met Lys Ile Glu Glu Gly Lys Leu Thr Asn Pro Gly Val Ser Ala Trp
1 5 10 15

Gln Val Asn Thr Ala Tyr Thr Ala Gly Gln Leu Val Thr Tyr Asn Gly
20 25 30

Lys Thr Tyr Lys Cys Leu Gln Pro His Thr Ser Leu Ala Gly Trp Glu
35 40 45

Pro Ser Asn Val Pro Ala Leu Trp Gln Leu Gln Asn Asn Gly Asn Asn
50 55 60

Gly Leu Glu Leu Arg His Gly
65 70

<210> SEQ ID NO 131
<211> LENGTH: 220
<212> TYPE: PRT
<213> ORGANISM: Artificial Sequence
<220> FEATURE:
<223> OTHER INFORMATION: synthetic or artificial sequence

<400> SEQUENCE: 131

Met Ser Pro Ile Leu Gly Tyr Trp Lys Ile Lys Gly Leu Val Gln Pro
1 5 10 15

Thr Arg Leu Leu Leu Glu Tyr Leu Glu Glu Lys Tyr Glu Glu His Leu
20 25 30

Tyr Glu Arg Asp Glu Gly Asp Lys Trp Arg Asn Lys Lys Phe Glu Leu
35 40 45

Gly Leu Glu Phe Pro Asn Leu Pro Tyr Tyr Ile Asp Gly Asp Val Lys
50 55 60

Leu Thr Gln Ser Met Ala Ile Ile Arg Tyr Ile Ala Asp Lys His Asn
65 70 75 80

Met Leu Gly Gly Cys Pro Lys Glu Arg Ala Glu Ile Ser Met Leu Glu
85 90 95

Gly Ala Val Leu Asp Ile Arg Tyr Gly Val Ser Arg Ile Ala Tyr Ser
100 105 110

Lys Asp Phe Glu Thr Leu Lys Val Asp Phe Leu Ser Lys Leu Pro Glu
115 120 125

Met Leu Lys Met Phe Glu Asp Arg Leu Cys His Lys Thr Tyr Leu Asn
130 135 140

Gly Asp His Val Thr His Pro Asp Phe Met Leu Tyr Asp Ala Leu Asp
145 150 155 160

Val Val Leu Tyr Met Asp Pro Met Cys Leu Asp Ala Phe Pro Lys Leu
165 170 175

Val Cys Phe Lys Lys Arg Ile Glu Ala Ile Pro Gln Ile Asp Lys Tyr
180 185 190

```
Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp
    210                 215                 220


<210> SEQ ID NO 132
<211> LENGTH: 368
<212> TYPE: PRT
<213> ORGANISM: Artificial Sequence
<220> FEATURE:
<223> OTHER INFORMATION: synthetic or artificial sequence

<400> SEQUENCE: 132

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335
```

```
Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365


<210> SEQ ID NO 133
<211> LENGTH: 128
<212> TYPE: PRT
<213> ORGANISM: Artificial Sequence
<220> FEATURE:
<223> OTHER INFORMATION: synthetic or artificial sequence

<400> SEQUENCE: 133

Met Ala Glu Ala Gly Ile Thr Gly Thr Trp Tyr Asn Gln Leu Gly Ser
1               5                   10                  15

Thr Phe Ile Val Thr Ala Gly Ala Asp Gly Ala Leu Thr Gly Thr Tyr
            20                  25                  30

Glu Ser Ala Val Gly Asn Ala Glu Ser Arg Tyr Val Leu Thr Gly Arg
        35                  40                  45

Tyr Asp Ser Ala Pro Ala Thr Asp Gly Ser Gly Thr Ala Leu Gly Trp
    50                  55                  60

Thr Val Ala Trp Lys Asn Asn Tyr Arg Asn Ala His Ser Ala Thr Thr
65                  70                  75                  80

Trp Ser Gly Gln Tyr Val Gly Gly Ala Glu Ala Arg Ile Asn Thr Gln
                85                  90                  95

Trp Leu Leu Thr Ser Gly Thr Thr Glu Ala Asn Ala Trp Lys Ser Thr
            100                 105                 110

Leu Val Gly His Asp Thr Phe Thr Lys Val Lys Pro Ser Ala Ala Ser
        115                 120                 125


<210> SEQ ID NO 134
<211> LENGTH: 239
<212> TYPE: PRT
<213> ORGANISM: Artificial Sequence
<220> FEATURE:
<223> OTHER INFORMATION: synthetic or artificial sequence

<400> SEQUENCE: 134

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Ser Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
```

```
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235


<210> SEQ ID NO 135
<211> LENGTH: 550
<212> TYPE: PRT
<213> ORGANISM: Artificial Sequence
<220> FEATURE:
<223> OTHER INFORMATION: synthetic or artificial sequence

<400> SEQUENCE: 135

Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asn Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
```

275 280 285

Pro Thr Leu Phe Ser Phe Phe Ala Lys Ser Thr Leu Ile Asp Lys Tyr
290 295 300

Asp Leu Ser Asn Leu His Glu Ile Ala Ser Gly Gly Ala Pro Leu Ser
305 310 315 320

Lys Glu Val Gly Glu Ala Val Ala Lys Arg Phe His Leu Pro Gly Ile
325 330 335

Arg Gln Gly Tyr Gly Leu Thr Glu Thr Thr Ser Ala Ile Leu Ile Thr
340 345 350

Pro Glu Gly Asp Asp Lys Pro Gly Ala Val Gly Lys Val Val Pro Phe
355 360 365

Phe Glu Ala Lys Val Val Asp Leu Asp Thr Gly Lys Thr Leu Gly Val
370 375 380

Asn Gln Arg Gly Glu Leu Cys Val Arg Gly Pro Met Ile Met Ser Gly
385 390 395 400

Tyr Val Asn Asn Pro Glu Ala Thr Asn Ala Leu Ile Asp Lys Asp Gly
405 410 415

Trp Leu His Ser Gly Asp Ile Ala Tyr Trp Asp Glu Asp Glu His Phe
420 425 430

Phe Ile Val Asp Arg Leu Lys Ser Leu Ile Lys Tyr Lys Gly Tyr Gln
435 440 445

Val Ala Pro Ala Glu Leu Glu Ser Ile Leu Leu Gln His Pro Asn Ile
450 455 460

Phe Asp Ala Gly Val Ala Gly Leu Pro Asp Asp Asp Ala Gly Glu Leu
465 470 475 480

Pro Ala Ala Val Val Val Leu Glu His Gly Lys Thr Met Thr Glu Lys
485 490 495

Glu Ile Val Asp Tyr Val Ala Ser Gln Val Thr Thr Ala Lys Lys Leu
500 505 510

Arg Gly Gly Val Val Phe Val Asp Glu Val Pro Lys Gly Leu Thr Gly
515 520 525

Lys Leu Asp Ala Arg Lys Ile Arg Glu Ile Leu Ile Lys Ala Lys Lys
530 535 540

Gly Gly Lys Ser Lys Leu
545 550

<210> SEQ ID NO 136
<211> LENGTH: 524
<212> TYPE: PRT
<213> ORGANISM: Bos taurus

<400> SEQUENCE: 136

Met Ile Ser Pro Phe Leu Leu Leu Ala Ile Gly Thr Cys Phe Ala Ser
1 5 10 15

Ser Leu Val Pro Glu Lys Glu Lys Asp Pro Lys Tyr Trp Arg Asp Gln
20 25 30

Ala Gln Gln Thr Leu Lys Asn Ala Leu Arg Leu Gln Thr Leu Asn Thr
35 40 45

Asn Val Ala Lys Asn Val Ile Met Phe Leu Gly Asp Gly Met Gly Val
50 55 60

Ser Thr Val Thr Ala Ala Arg Ile Leu Lys Gly Gln Leu His His Ser
65 70 75 80

Pro Gly Glu Glu Thr Lys Leu Glu Met Asp Lys Phe Pro Tyr Val Ala
85 90 95

-continued

```
Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Gln Arg Ser Gln Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ser Tyr Ala His Ser Ala Asp Arg Asp Trp Tyr Ser Asp Asn Glu Met
            180                 185                 190

Pro Pro Glu Ala Leu Ser Gln Gly Cys Lys Asp Ile Ala Tyr Gln Leu
        195                 200                 205

Met Tyr Asn Ile Lys Asp Ile Glu Val Ile Met Gly Gly Gly Arg Lys
    210                 215                 220

Tyr Met Phe Pro Lys Asn Arg Thr Asp Val Glu Tyr Glu Leu Asp Glu
225                 230                 235                 240

Lys Ala Arg Gly Thr Arg Leu Asp Gly Leu Asn Leu Ile Asp Ile Trp
                245                 250                 255

Lys Ser Phe Lys Pro Lys His Lys His Ser His Tyr Val Trp Asn Arg
            260                 265                 270

Thr Asp Leu Leu Ala Leu Asp Pro His Ser Val Asp Tyr Leu Leu Gly
        275                 280                 285

Leu Phe Glu Pro Gly Asp Met Gln Tyr Glu Leu Asn Arg Asn Asn Ala
    290                 295                 300

Thr Asp Pro Ser Leu Ser Glu Met Val Glu Met Ala Ile Arg Ile Leu
305                 310                 315                 320

Asn Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
            340                 345                 350

Val Glu Met Asp Gln Ala Ile Gly Gln Ala Gly Ala Met Thr Ser Val
        355                 360                 365

Glu Asp Thr Leu Thr Val Val Thr Ala Asp His Ser His Val Phe Thr
    370                 375                 380

Phe Gly Gly Tyr Thr Pro Arg Gly Asn Ser Ile Phe Gly Leu Ala Pro
385                 390                 395                 400

Met Val Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
            420                 425                 430

Met Val Asp Tyr Ala His Asn Asn Tyr Gln Ala Gln Ser Ala Val Pro
        435                 440                 445

Leu Arg His Glu Thr His Gly Gly Glu Asp Val Ala Val Phe Ala Lys
    450                 455                 460

Gly Pro Met Ala His Leu Leu His Gly Val Gln Glu Gln Asn Tyr Ile
465                 470                 475                 480

Pro His Val Met Ala Tyr Ala Ala Cys Ile Gly Ala Asn Arg Asp His
                485                 490                 495

Cys Ala Ser Ala Ser Ser Ser Gly Ser Pro Ser Pro Gly Pro Leu Leu
            500                 505                 510

Leu Leu Leu Ala Leu Leu Pro Leu Gly Ser Leu Phe
```

515 520

<210> SEQ ID NO 137
<211> LENGTH: 112
<212> TYPE: PRT
<213> ORGANISM: phage M13

<400> SEQUENCE: 137

Met Pro Val Leu Leu Gly Ile Pro Leu Leu Leu Arg Phe Leu Gly Phe
1 5 10 15

Leu Leu Val Thr Leu Phe Gly Tyr Leu Leu Thr Phe Leu Lys Lys Gly
20 25 30

Phe Gly Lys Ile Ala Ile Ala Ile Ser Leu Phe Leu Ala Leu Ile Ile
35 40 45

Gly Leu Asn Ser Ile Leu Val Gly Tyr Leu Ser Asp Ile Ser Ala Gln
50 55 60

Leu Pro Ser Asp Phe Val Gln Gly Val Gln Leu Ile Leu Pro Ser Asn
65 70 75 80

Ala Leu Pro Cys Phe Tyr Val Ile Leu Ser Val Lys Ala Ala Ile Phe
85 90 95

Ile Phe Asp Val Lys Gln Lys Ile Val Ser Tyr Leu Asp Trp Asp Lys
100 105 110

<210> SEQ ID NO 138
<211> LENGTH: 345
<212> TYPE: PRT
<213> ORGANISM: phage T7

<400> SEQUENCE: 138

Met Ala Ser Met Thr Gly Gly Gln Gln Met Gly Thr Asn Gln Gly Lys
1 5 10 15

Gly Val Val Ala Ala Gly Asp Lys Leu Ala Leu Phe Leu Lys Val Phe
20 25 30

Gly Gly Glu Val Leu Thr Ala Phe Ala Arg Thr Ser Val Thr Thr Ser
35 40 45

Arg His Met Val Arg Ser Ile Ser Ser Gly Lys Ser Ala Gln Phe Pro
50 55 60

Val Leu Gly Arg Thr Gln Ala Ala Tyr Leu Ala Pro Gly Glu Asn Leu
65 70 75 80

Asp Asp Lys Arg Lys Asp Ile Lys His Thr Glu Lys Val Ile Thr Ile
85 90 95

Asp Gly Leu Leu Thr Ala Asp Val Leu Ile Tyr Asp Ile Glu Asp Ala
100 105 110

Met Asn His Tyr Asp Val Arg Ser Glu Tyr Thr Ser Gln Leu Gly Glu
115 120 125

Ser Leu Ala Met Ala Ala Asp Gly Ala Val Leu Ala Glu Ile Ala Gly
130 135 140

Leu Cys Asn Val Glu Ser Lys Tyr Asn Glu Asn Ile Glu Gly Leu Gly
145 150 155 160

Thr Ala Thr Val Ile Glu Thr Thr Gln Asn Lys Ala Ala Leu Thr Asp
165 170 175

Gln Val Ala Leu Gly Lys Glu Ile Ile Ala Ala Leu Thr Lys Ala Arg
180 185 190

Ala Ala Leu Thr Lys Asn Tyr Val Pro Ala Ala Asp Arg Val Phe Tyr
195 200 205

Cys Asp Pro Asp Ser Tyr Ser Ala Ile Leu Ala Ala Leu Met Pro Asn

```
    210                 215                 220

Ala Ala Asn Tyr Ala Ala Leu Ile Asp Pro Glu Lys Gly Ser Ile Arg
225                 230                 235                 240

Asn Val Met Gly Phe Glu Val Val Glu Val Pro His Leu Thr Ala Gly
                245                 250                 255

Gly Ala Gly Thr Ala Arg Glu Gly Thr Thr Gly Gln Lys His Val Phe
            260                 265                 270

Pro Ala Asn Lys Gly Glu Gly Asn Val Lys Val Ala Lys Asp Asn Val
        275                 280                 285

Ile Gly Leu Phe Met His Arg Ser Ala Val Gly Thr Val Lys Leu Arg
    290                 295                 300

Asp Leu Ala Leu Glu Arg Ala Arg Arg Ala Asn Phe Gln Ala Asp Gln
305                 310                 315                 320

Ile Ile Ala Lys Tyr Ala Met Gly His Gly Gly Leu Arg Pro Glu Ala
                325                 330                 335

Ala Gly Ala Val Val Phe Lys Val Glu
            340                 345


<210> SEQ ID NO 139
<211> LENGTH: 398
<212> TYPE: PRT
<213> ORGANISM: phage T7

<400> SEQUENCE: 139

Met Ala Ser Met Thr Gly Gly Gln Gln Met Gly Thr Asn Gln Gly Lys
1               5                   10                  15

Gly Val Val Ala Ala Gly Asp Lys Leu Ala Leu Phe Leu Lys Val Phe
            20                  25                  30

Gly Gly Glu Val Leu Thr Ala Phe Ala Arg Thr Ser Val Thr Thr Ser
        35                  40                  45

Arg His Met Val Arg Ser Ile Ser Ser Gly Lys Ser Ala Gln Phe Pro
    50                  55                  60

Val Leu Gly Arg Thr Gln Ala Ala Tyr Leu Ala Pro Gly Glu Asn Leu
65                  70                  75                  80

Asp Asp Lys Arg Lys Asp Ile Lys His Thr Glu Lys Val Ile Thr Ile
                85                  90                  95

Asp Gly Leu Leu Thr Ala Asp Val Leu Ile Tyr Asp Ile Glu Asp Ala
            100                 105                 110

Met Asn His Tyr Asp Val Arg Ser Glu Tyr Thr Ser Gln Leu Gly Glu
        115                 120                 125

Ser Leu Ala Met Ala Ala Asp Gly Ala Val Leu Ala Glu Ile Ala Gly
    130                 135                 140

Leu Cys Asn Val Glu Ser Lys Tyr Asn Glu Asn Ile Glu Gly Leu Gly
145                 150                 155                 160

Thr Ala Thr Val Ile Glu Thr Thr Gln Asn Lys Ala Ala Leu Thr Asp
                165                 170                 175

Gln Val Ala Leu Gly Lys Glu Ile Ile Ala Ala Leu Thr Lys Ala Arg
            180                 185                 190

Ala Ala Leu Thr Lys Asn Tyr Val Pro Ala Ala Asp Arg Val Phe Tyr
        195                 200                 205

Cys Asp Pro Asp Ser Tyr Ser Ala Ile Leu Ala Ala Leu Met Pro Asn
    210                 215                 220

Ala Ala Asn Tyr Ala Ala Leu Ile Asp Pro Glu Lys Gly Ser Ile Arg
225                 230                 235                 240
```

-continued

```
Asn Val Met Gly Phe Glu Val Val Glu Val Pro His Leu Thr Ala Gly
                245                 250                 255

Gly Ala Gly Thr Ala Arg Glu Gly Thr Thr Gly Gln Lys His Val Phe
            260                 265                 270

Pro Ala Asn Lys Gly Glu Gly Asn Val Lys Val Ala Lys Asp Asn Val
        275                 280                 285

Ile Gly Leu Phe Met His Arg Ser Ala Val Gly Thr Val Lys Leu Arg
    290                 295                 300

Asp Leu Ala Leu Glu Arg Ala Arg Arg Ala Asn Phe Gln Ala Asp Gln
305                 310                 315                 320

Ile Ile Ala Lys Tyr Ala Met Gly His Gly Gly Leu Arg Pro Glu Ala
                325                 330                 335

Ala Gly Ala Val Val Phe Gln Ser Gly Val Met Leu Gly Val Ala Ser
            340                 345                 350

Thr Val Ala Ala Ser Pro Glu Glu Ala Ser Val Thr Ser Thr Glu Glu
        355                 360                 365

Thr Leu Thr Pro Ala Gln Glu Ala Ala Arg Thr Arg Ala Ala Asn Lys
    370                 375                 380

Ala Arg Lys Glu Ala Glu Leu Ala Ala Ala Thr Ala Glu Gln
385                 390                 395


<210> SEQ ID NO 140
<211> LENGTH: 29
<212> TYPE: PRT
<213> ORGANISM: Escherichia coli

<400> SEQUENCE: 140

Met Lys Leu Thr Thr His His Leu Arg Thr Gly Ala Ala Leu Leu Leu
1               5                   10                  15

Ala Gly Ile Leu Leu Ala Gly Cys Asp Gln Ser Ser Ser
            20                  25


<210> SEQ ID NO 141
<211> LENGTH: 190
<212> TYPE: PRT
<213> ORGANISM: Escherichia coli

<400> SEQUENCE: 141

Asn Asn Gly Arg Gly Ala Leu Arg Gln Asn Gly Asp Gly Val Gly Gly
1               5                   10                  15

Ser Ile Thr Tyr Asp Tyr Glu Gly Phe Gly Ile Gly Ala Ala Val Ser
            20                  25                  30

Ser Ser Lys Arg Thr Asp Asp Gln Asn Gly Ser Tyr Thr Ser Asn Gly
        35                  40                  45

Val Val Arg Asn Tyr Ile Gly Thr Gly Asp Arg Ala Glu Thr Tyr Thr
    50                  55                  60

Gly Gly Leu Lys Tyr Asp Ala Asn Asn Ile Tyr Leu Ala Ala Gln Tyr
65                  70                  75                  80

Thr Gln Thr Tyr Asn Ala Thr Arg Val Gly Ser Leu Gly Trp Ala Asn
                85                  90                  95

Lys Ala Gln Asn Phe Glu Ala Val Ala Gln Tyr Gln Phe Asp Phe Gly
            100                 105                 110

Leu Arg Pro Ser Leu Ala Tyr Leu Gln Ser Lys Gly Lys Asn Leu Gly
        115                 120                 125

Val Ile Asn Gly Arg Asn Tyr Asp Asp Glu Asp Ile Leu Lys Tyr Val
    130                 135                 140
```

Asp Val Gly Ala Thr Tyr Tyr Phe Asn Lys Asn Met Ser Thr Tyr Val
145 150 155 160

Asp Tyr Lys Ile Asn Leu Leu Asp Asp Asn Gln Phe Thr Arg Asp Ala
165 170 175

Gly Ile Asn Thr Asp Asn Ile Val Ala Leu Gly Leu Val Tyr
180 185 190

<210> SEQ ID NO 142
<211> LENGTH: 448
<212> TYPE: PRT
<213> ORGANISM: Escherichia coli

<400> SEQUENCE: 142

Met Val Met Ser Gln Lys Thr Leu Phe Thr Lys Ser Ala Leu Ala Val
1 5 10 15

Ala Val Ala Leu Ile Ser Thr Gln Ala Trp Ser Ala Gly Phe Gln Leu
20 25 30

Asn Glu Phe Ser Ser Ser Gly Leu Gly Arg Ala Tyr Ser Gly Glu Gly
35 40 45

Ala Ile Ala Asp Asp Ala Gly Asn Val Ser Arg Asn Pro Ala Leu Ile
50 55 60

Thr Met Phe Asp Arg Pro Thr Phe Ser Ala Gly Ala Val Tyr Ile Asp
65 70 75 80

Pro Asp Val Asn Ile Ser Gly Thr Ser Pro Ser Gly Arg Ser Leu Lys
85 90 95

Ala Asp Asn Ile Ala Pro Thr Ala Trp Val Pro Asn Met His Phe Val
100 105 110

Ala Pro Ile Asn Asp Gln Phe Gly Trp Gly Ala Ser Ile Thr Ser Asn
115 120 125

Tyr Gly Leu Ala Thr Glu Phe Asn Asp Thr Tyr Ala Gly Gly Ser Val
130 135 140

Gly Gly Thr Thr Asp Leu Glu Thr Met Asn Leu Asn Leu Ser Gly Ala
145 150 155 160

Tyr Arg Leu Asn Asn Ala Trp Ser Phe Gly Leu Gly Phe Asn Ala Val
165 170 175

Tyr Ala Arg Ala Lys Ile Glu Arg Phe Ala Gly Asp Leu Gly Gln Leu
180 185 190

Val Ala Gly Gln Ile Met Gln Ser Pro Ala Gly Lys Thr Pro Gln Gly
195 200 205

Gln Ala Leu Ala Ala Thr Ala Asn Gly Ile Asp Ser Asn Thr Lys Ile
210 215 220

Ala His Leu Asn Gly Asn Gln Trp Gly Phe Gly Trp Asn Ala Gly Ile
225 230 235 240

Leu Tyr Glu Leu Asp Lys Asn Asn Arg Tyr Ala Leu Thr Tyr Arg Ser
245 250 255

Glu Val Lys Ile Asp Phe Lys Gly Asn Tyr Ser Ser Asp Leu Asn Arg
260 265 270

Val Phe Asn Asn Tyr Gly Leu Pro Ile Pro Thr Ala Thr Gly Gly Ala
275 280 285

Thr Gln Ser Gly Tyr Leu Thr Leu Asn Leu Pro Glu Met Trp Glu Val
290 295 300

Ser Gly Tyr Asn Arg Val Asp Pro Gln Trp Ala Ile His Tyr Ser Leu
305 310 315 320

Ala Tyr Thr Ser Trp Ser Gln Phe Gln Gln Leu Lys Ala Thr Ser Thr
325 330 335

```
Ser Gly Asp Thr Leu Phe Gln Lys His Glu Gly Phe Lys Asp Ala Tyr
            340                 345                 350

Arg Ile Ala Leu Gly Thr Thr Tyr Tyr Tyr Asp Asp Asn Trp Thr Phe
        355                 360                 365

Arg Thr Gly Ile Ala Phe Asp Asp Ser Pro Val Pro Ala Gln Asn Arg
    370                 375                 380

Ser Ile Ser Ile Pro Asp Gln Asp Arg Phe Trp Leu Ser Ala Gly Thr
385                 390                 395                 400

Thr Tyr Ala Phe Asn Lys Asp Ala Ser Val Asp Val Gly Val Ser Tyr
                405                 410                 415

Met His Gly Gln Ser Val Lys Ile Asn Glu Gly Pro Tyr Gln Phe Glu
            420                 425                 430

Ser Glu Gly Lys Ala Trp Leu Phe Gly Thr Asn Phe Asn Tyr Ala Phe
        435                 440                 445
```

<210> SEQ ID NO 143
<211> LENGTH: 122
<212> TYPE: PRT
<213> ORGANISM: Escherichia coli

<400> SEQUENCE: 143

```
Cys Ser Ser Asn Ala Lys Ile Asp Gln Pro Tyr Val Gly Phe Glu Met
1               5                   10                  15

Gly Tyr Asp Trp Leu Gly Arg Met Pro Tyr Lys Gly Ser Val Glu Asn
            20                  25                  30

Gly Ala Tyr Lys Ala Gln Gly Val Gln Leu Thr Ala Lys Leu Gly Tyr
        35                  40                  45

Pro Ile Thr Asp Asp Leu Asp Ile Tyr Thr Arg Leu Gly Gly Met Val
    50                  55                  60

Trp Arg Ala Asp Thr Lys Ser Asn Val Tyr Gly Lys Asn His Asp Thr
65                  70                  75                  80

Gly Val Ser Pro Val Phe Ala Gly Gly Val Glu Tyr Ala Ile Thr Pro
                85                  90                  95

Glu Ile Ala Thr Arg Leu Glu Tyr Gln Trp Thr Asn Asn Ile Gly Asp
            100                 105                 110

Ala His Thr Ile Gly Thr Arg Pro Asp Asn
        115                 120
```

<210> SEQ ID NO 144
<211> LENGTH: 182
<212> TYPE: PRT
<213> ORGANISM: Escherichia coli

<400> SEQUENCE: 144

```
Met Gln Phe Asn Ile Pro Thr Leu Leu Thr Leu Phe Arg Val Ile Leu
1               5                   10                  15

Ile Pro Phe Phe Val Leu Val Phe Tyr Leu Pro Val Thr Trp Ser Pro
            20                  25                  30

Phe Ala Ala Ala Leu Ile Phe Cys Val Ala Ala Val Thr Asp Trp Phe
        35                  40                  45

Asp Gly Phe Leu Ala Arg Arg Trp Asn Gln Ser Thr Arg Phe Gly Ala
    50                  55                  60

Phe Leu Asp Pro Val Ala Asp Lys Val Leu Val Ala Ile Ala Met Val
65                  70                  75                  80

Leu Val Thr Glu His Tyr His Ser Trp Trp Val Thr Leu Pro Ala Ala
                85                  90                  95
```

Thr Met Ile Ala Arg Glu Ile Ile Ile Ser Ala Leu Arg Glu Trp Met
100 105 110

Ala Glu Leu Gly Lys Arg Ser Ser Val Ala Val Ser Trp Ile Gly Lys
115 120 125

Val Lys Thr Thr Ala Gln Met Val Ala Leu Ala Trp Leu Leu Trp Arg
130 135 140

Pro Asn Ile Trp Val Glu Tyr Ala Gly Ile Ala Leu Phe Phe Val Ala
145 150 155 160

Ala Val Leu Thr Leu Trp Ser Met Leu Gln Tyr Leu Ser Ala Ala Arg
165 170 175

Ala Asp Leu Leu Asp Gln
180

<210> SEQ ID NO 145
<211> LENGTH: 948
<212> TYPE: PRT
<213> ORGANISM: Escherichia coli

<400> SEQUENCE: 145

Met Ile Thr His Gly Phe Tyr Ala Arg Thr Arg His Lys His Lys Leu
1 5 10 15

Lys Lys Thr Phe Ile Met Leu Ser Ala Gly Leu Gly Leu Phe Phe Tyr
20 25 30

Val Asn Gln Asn Ser Phe Ala Asn Gly Glu Asn Tyr Phe Lys Leu Gly
35 40 45

Ser Asp Ser Lys Leu Leu Thr His Asp Ser Tyr Gln Asn Arg Leu Phe
50 55 60

Tyr Thr Leu Lys Thr Gly Glu Thr Val Ala Asp Leu Ser Lys Ser Gln
65 70 75 80

Asp Ile Asn Leu Ser Thr Ile Trp Ser Leu Asn Lys His Leu Tyr Ser
85 90 95

Ser Glu Ser Glu Met Met Lys Ala Ala Pro Gly Gln Gln Ile Ile Leu
100 105 110

Pro Leu Lys Lys Leu Pro Phe Glu Tyr Ser Ala Leu Pro Leu Leu Gly
115 120 125

Ser Ala Pro Leu Val Ala Ala Gly Gly Val Ala Gly His Thr Asn Lys
130 135 140

Leu Thr Lys Met Ser Pro Asp Val Thr Lys Ser Asn Met Thr Asp Asp
145 150 155 160

Lys Ala Leu Asn Tyr Ala Ala Gln Gln Ala Ala Ser Leu Gly Ser Gln
165 170 175

Leu Gln Ser Arg Ser Leu Asn Gly Asp Tyr Ala Lys Asp Thr Ala Leu
180 185 190

Gly Ile Ala Gly Asn Gln Ala Ser Ser Gln Leu Gln Ala Trp Leu Gln
195 200 205

His Tyr Gly Thr Ala Glu Val Asn Leu Gln Ser Gly Asn Asn Phe Asp
210 215 220

Gly Ser Ser Leu Asp Phe Leu Leu Pro Phe Tyr Asp Ser Glu Lys Met
225 230 235 240

Leu Ala Phe Gly Gln Val Gly Ala Arg Tyr Ile Asp Ser Arg Phe Thr
245 250 255

Ala Asn Leu Gly Ala Gly Gln Arg Phe Phe Leu Pro Glu Asn Met Leu
260 265 270

Gly Tyr Asn Val Phe Ile Asp Gln Asp Phe Ser Gly Asp Asn Thr Arg

```
        275                 280                 285

Leu Gly Ile Gly Gly Glu Tyr Trp Arg Asp Tyr Phe Lys Ser Ser Val
    290                 295                 300

Asn Gly Tyr Phe Arg Met Ser Gly Trp His Glu Ser Tyr Asn Lys Lys
305                 310                 315                 320

Asp Tyr Asp Glu Arg Pro Ala Asn Gly Phe Asp Ile Arg Phe Asn Gly
                325                 330                 335

Tyr Leu Pro Ser Tyr Pro Ala Leu Gly Ala Arg Leu Met Tyr Glu Gln
            340                 345                 350

Tyr Tyr Gly Asp Asn Val Ala Leu Phe Asn Ser Asp Lys Leu Gln Ser
        355                 360                 365

Asn Pro Gly Ala Ala Thr Val Gly Val Asn Tyr Thr Pro Ile Pro Leu
    370                 375                 380

Val Thr Met Gly Ile Asp Tyr Arg His Gly Thr Gly Asn Glu Asn Asp
385                 390                 395                 400

Leu Leu Tyr Ser Met Gln Phe Arg Tyr Gln Phe Asp Lys Pro Trp Ser
                405                 410                 415

Gln Gln Ile Glu Pro Gln Tyr Val Asn Glu Leu Arg Thr Leu Ser Gly
            420                 425                 430

Ser Arg Tyr Asp Leu Val Gln Arg Asn Asn Asn Ile Ile Leu Glu Tyr
        435                 440                 445

Lys Lys Gln Asp Ile Leu Ser Leu Asn Ile Pro His Asp Ile Asn Gly
    450                 455                 460

Thr Glu Arg Ser Thr Gln Lys Ile Gln Leu Ile Val Lys Ser Lys Tyr
465                 470                 475                 480

Gly Leu Asp Arg Ile Val Trp Asp Asp Ser Ser Leu Arg Ser Gln Gly
                485                 490                 495

Gly Gln Ile Gln His Ser Gly Ser Gln Ser Ala Gln Asp Tyr Gln Ala
            500                 505                 510

Ile Leu Pro Ala Tyr Val Gln Gly Gly Ser Asn Val Tyr Lys Val Thr
        515                 520                 525

Ala Arg Ala Tyr Asp Arg Asn Gly Asn Ser Ser Asn Asn Val Gln Leu
    530                 535                 540

Thr Ile Thr Val Leu Ser Asn Gly Gln Val Val Asp Gln Val Gly Val
545                 550                 555                 560

Thr Asp Phe Thr Ala Asp Lys Thr Ser Ala Lys Ala Asp Asn Thr Asp
                565                 570                 575

Thr Ile Thr Tyr Thr Ala Met Val Lys Lys Asn Gly Val Thr Gln Ala
            580                 585                 590

Asn Val Pro Val Ser Phe Asn Ile Val Ser Gly Thr Ala Thr Leu Gly
        595                 600                 605

Ala Asn Ser Ala Lys Thr Asp Ala Asn Gly Lys Ala Thr Val Thr Leu
    610                 615                 620

Lys Ser Ser Thr Pro Gly Gln Val Val Val Ser Ala Lys Thr Ala Glu
625                 630                 635                 640

Met Thr Ser Ala Leu Asn Ala Ser Ala Val Ile Phe Val Asp Gln Thr
                645                 650                 655

Lys Ala Ser Ile Thr Glu Ile Lys Ala Asp Lys Thr Thr Ala Lys Ala
            660                 665                 670

Asn Gly Ser Asp Ala Ile Thr Tyr Thr Val Lys Val Met Lys Asn Asn
        675                 680                 685

Gln Pro Glu Val Asn His Ser Val Thr Phe Ser Thr Asn Phe Gly Asn
    690                 695                 700
```

```
Leu Gly Gly Asn Ser Gln Thr Gln Ile Val Gln Thr Asp Lys Asp Gly
705                 710                 715                 720

Lys Ala Thr Val Lys Leu Thr Ser Gly Ser Glu Gly Ser Ala Val Val
                725                 730                 735

Ser Ala Lys Val Ser Glu Val Asn Thr Glu Val Lys Ala Ser Glu Val
            740                 745                 750

Lys Phe Phe Ser Val Leu Ser Ile Gly Asn Asn Val Asn Ile Ile Gly
        755                 760                 765

Thr Ser Ala Asp Gly Ala Leu Pro Asn Ile Trp Leu Gln Tyr Gly Gln
    770                 775                 780

Phe Lys Leu Thr Ala Lys Gly Gly Asp Gly Lys Tyr Lys Trp His Ser
785                 790                 795                 800

Lys Asp Thr Ser Val Ala Ser Val Asp Ala Ser Thr Gly Gln Val Thr
                805                 810                 815

Leu Leu Lys Lys Gly Thr Thr Thr Ile Glu Val Val Ser Gly Asp Asn
            820                 825                 830

Gln Thr Ala Thr Tyr Thr Ile Asn Gln Pro Glu Asn Ile Ile Thr Val
        835                 840                 845

Glu Thr Gln Asp Lys Val Leu Tyr Asn Val Ala Lys Thr Lys Cys Glu
    850                 855                 860

Met Asn Ser Gly Arg Leu Pro Ser Ser Thr Ser Glu Leu Lys Asp Val
865                 870                 875                 880

Tyr Asn Gln Trp Gly Pro Ala Asn Ser Tyr Asp Gly Tyr Lys Gly Lys
                885                 890                 895

Asn Thr Ile Thr Ala Trp Thr Gln Gln Thr Ala Asp Asp Ile Pro Lys
            900                 905                 910

Gly Trp Thr Ser Thr Phe Asp Ile Val Thr Lys Asn Glu Ile Pro Asn
        915                 920                 925

Asn Gly Ile Lys Val Lys Val Asn Val Asp Ala Ala Asn Ala Phe Ala
    930                 935                 940

Val Cys Val Lys
945


<210> SEQ ID NO 146
<211> LENGTH: 87
<212> TYPE: PRT
<213> ORGANISM: Saccharomyces cerevisiae

<400> SEQUENCE: 146

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe
                85


<210> SEQ ID NO 147
<211> LENGTH: 1537
<212> TYPE: PRT
```

<213> ORGANISM: Saccharomyces cerevisiae

<400> SEQUENCE: 147

Met Thr Met Pro His Arg Tyr Met Phe Leu Ala Val Phe Thr Leu Leu
1 5 10 15

Ala Leu Thr Ser Val Ala Ser Gly Ala Thr Glu Ala Cys Leu Pro Ala
20 25 30

Gly Gln Arg Lys Ser Gly Met Asn Ile Asn Phe Tyr Gln Tyr Ser Leu
35 40 45

Lys Asp Ser Ser Thr Tyr Ser Asn Ala Ala Tyr Met Ala Tyr Gly Tyr
50 55 60

Ala Ser Lys Thr Lys Leu Gly Ser Val Gly Gly Gln Thr Asp Ile Ser
65 70 75 80

Ile Asp Tyr Asn Ile Pro Cys Val Ser Ser Ser Gly Thr Phe Pro Cys
85 90 95

Pro Gln Glu Asp Ser Tyr Gly Asn Trp Gly Cys Lys Gly Met Gly Ala
100 105 110

Cys Ser Asn Ser Gln Gly Ile Ala Tyr Trp Ser Thr Asp Leu Phe Gly
115 120 125

Phe Tyr Thr Thr Pro Thr Asn Val Thr Leu Glu Met Thr Gly Tyr Phe
130 135 140

Leu Pro Pro Gln Thr Gly Ser Tyr Thr Phe Lys Phe Ala Thr Val Asp
145 150 155 160

Asp Ser Ala Ile Leu Ser Val Gly Gly Ala Thr Ala Phe Asn Cys Cys
165 170 175

Ala Gln Gln Gln Pro Pro Ile Thr Ser Thr Asn Phe Thr Ile Asp Gly
180 185 190

Ile Lys Pro Trp Gly Gly Ser Leu Pro Pro Asn Ile Glu Gly Thr Val
195 200 205

Tyr Met Tyr Ala Gly Tyr Tyr Tyr Pro Met Lys Val Val Tyr Ser Asn
210 215 220

Ala Val Ser Trp Gly Thr Leu Pro Ile Ser Val Thr Leu Pro Asp Gly
225 230 235 240

Thr Thr Val Ser Asp Asp Phe Glu Gly Tyr Val Tyr Ser Phe Asp Asp
245 250 255

Asp Leu Ser Gln Ser Asn Cys Thr Val Pro Asp Pro Ser Asn Tyr Ala
260 265 270

Val Ser Thr Thr Thr Thr Thr Thr Glu Pro Trp Thr Gly Thr Phe Thr
275 280 285

Ser Thr Ser Thr Glu Met Thr Thr Val Thr Gly Thr Asn Gly Val Pro
290 295 300

Thr Asp Glu Thr Val Ile Val Ile Arg Thr Pro Thr Thr Ala Ser Thr
305 310 315 320

Ile Ile Thr Thr Thr Glu Pro Trp Asn Ser Thr Phe Thr Ser Thr Ser
325 330 335

Thr Glu Leu Thr Thr Val Thr Gly Thr Asn Gly Val Arg Thr Asp Glu
340 345 350

Thr Ile Ile Val Ile Arg Thr Pro Thr Thr Ala Thr Thr Ala Ile Thr
355 360 365

Thr Thr Glu Pro Trp Asn Ser Thr Phe Thr Ser Thr Ser Thr Glu Leu
370 375 380

Thr Thr Val Thr Gly Thr Asn Gly Leu Pro Thr Asp Glu Thr Ile Ile
385 390 395 400

```
Val Ile Arg Thr Pro Thr Thr Ala Thr Thr Ala Met Thr Thr Thr Gln
                405                 410                 415

Pro Trp Asn Asp Thr Phe Thr Ser Thr Ser Thr Glu Leu Thr Thr Val
            420                 425                 430

Thr Gly Thr Asn Gly Leu Pro Thr Asp Glu Thr Ile Ile Val Ile Arg
        435                 440                 445

Thr Pro Thr Thr Ala Thr Thr Ala Met Thr Thr Thr Gln Pro Trp Asn
    450                 455                 460

Asp Thr Phe Thr Ser Thr Ser Thr Glu Leu Thr Thr Val Thr Gly Thr
465                 470                 475                 480

Asn Gly Leu Pro Thr Asp Glu Thr Ile Ile Val Ile Arg Thr Pro Thr
                485                 490                 495

Thr Ala Thr Thr Ala Met Thr Thr Thr Gln Pro Trp Asn Asp Thr Phe
            500                 505                 510

Thr Ser Thr Ser Thr Glu Ile Thr Thr Val Thr Gly Thr Asn Gly Leu
        515                 520                 525

Pro Thr Asp Glu Thr Ile Ile Val Ile Arg Thr Pro Thr Thr Ala Thr
    530                 535                 540

Thr Ala Met Thr Thr Pro Gln Pro Trp Asn Asp Thr Phe Thr Ser Thr
545                 550                 555                 560

Ser Thr Glu Met Thr Thr Val Thr Gly Thr Asn Gly Leu Pro Thr Asp
                565                 570                 575

Glu Thr Ile Ile Val Ile Arg Thr Pro Thr Thr Ala Thr Thr Ala Ile
            580                 585                 590

Thr Thr Thr Glu Pro Trp Asn Ser Thr Phe Thr Ser Thr Ser Thr Glu
        595                 600                 605

Met Thr Thr Val Thr Gly Thr Asn Gly Leu Pro Thr Asp Glu Thr Ile
    610                 615                 620

Ile Val Ile Arg Thr Pro Thr Thr Ala Thr Thr Ala Ile Thr Thr Thr
625                 630                 635                 640

Gln Pro Trp Asn Asp Thr Phe Thr Ser Thr Ser Thr Glu Met Thr Thr
                645                 650                 655

Val Thr Gly Thr Asn Gly Leu Pro Thr Asp Glu Thr Ile Ile Val Ile
            660                 665                 670

Arg Thr Pro Thr Thr Ala Thr Thr Ala Met Thr Thr Thr Gln Pro Trp
        675                 680                 685

Asn Asp Thr Phe Thr Ser Thr Ser Thr Glu Ile Thr Thr Val Thr Gly
    690                 695                 700

Thr Thr Gly Leu Pro Thr Asp Glu Thr Ile Ile Val Ile Arg Thr Pro
705                 710                 715                 720

Thr Thr Ala Thr Thr Ala Met Thr Thr Thr Gln Pro Trp Asn Asp Thr
                725                 730                 735

Phe Thr Ser Thr Ser Thr Glu Met Thr Thr Val Thr Gly Thr Asn Gly
            740                 745                 750

Val Pro Thr Asp Glu Thr Val Ile Val Ile Arg Thr Pro Thr Ser Glu
        755                 760                 765

Gly Leu Ile Ser Thr Thr Thr Glu Pro Trp Thr Gly Thr Phe Thr Ser
    770                 775                 780

Thr Ser Thr Glu Met Thr Thr Val Thr Gly Thr Asn Gly Gln Pro Thr
785                 790                 795                 800

Asp Glu Thr Val Ile Val Ile Arg Thr Pro Thr Ser Glu Gly Leu Val
                805                 810                 815

Thr Thr Thr Thr Glu Pro Trp Thr Gly Thr Phe Thr Ser Thr Ser Thr
```

```
            820                 825                 830

Glu Met Thr Thr Ile Thr Gly Thr Asn Gly Val Pro Thr Asp Glu Thr
        835                 840                 845

Val Ile Val Ile Arg Thr Pro Thr Ser Glu Gly Leu Ile Ser Thr Thr
    850                 855                 860

Thr Glu Pro Trp Thr Gly Thr Phe Thr Ser Thr Ser Thr Glu Met Thr
865                 870                 875                 880

Thr Ile Thr Gly Thr Asn Gly Gln Pro Thr Asp Glu Thr Val Ile Val
                885                 890                 895

Ile Arg Thr Pro Thr Ser Glu Gly Leu Ile Ser Thr Thr Thr Glu Pro
            900                 905                 910

Trp Thr Gly Thr Phe Thr Ser Thr Ser Thr Glu Met Thr His Val Thr
        915                 920                 925

Gly Thr Asn Gly Val Pro Thr Asp Glu Thr Val Ile Val Ile Arg Thr
    930                 935                 940

Pro Thr Ser Glu Gly Leu Ile Ser Thr Thr Thr Glu Pro Trp Thr Gly
945                 950                 955                 960

Thr Phe Thr Ser Thr Ser Thr Glu Val Thr Thr Ile Thr Gly Thr Asn
                965                 970                 975

Gly Gln Pro Thr Asp Glu Thr Val Ile Val Ile Arg Thr Pro Thr Ser
            980                 985                 990

Glu Gly Leu Ile Ser Thr Thr Thr  Glu Pro Trp Thr Gly  Thr Phe Thr
        995                 1000                1005

Ser Thr  Ser Thr Glu Met Thr  Thr Val Thr Gly Thr  Asn Gly Gln
    1010                1015                1020

Pro Thr  Asp Glu Thr Val Ile  Val Ile Arg Thr Pro  Thr Ser Glu
    1025                1030                1035

Gly Leu  Val Thr Thr Thr Thr  Glu Pro Trp Thr Gly  Thr Phe Thr
    1040                1045                1050

Ser Thr  Ser Thr Glu Met Ser  Thr Val Thr Gly Thr  Asn Gly Leu
    1055                1060                1065

Pro Thr  Asp Glu Thr Val Ile  Val Val Lys Thr Pro  Thr Thr Ala
    1070                1075                1080

Ile Ser  Ser Ser Leu Ser Ser  Ser Ser Ser Gly Gln  Ile Thr Ser
    1085                1090                1095

Ser Ile  Thr Ser Ser Arg Pro  Ile Ile Thr Pro Phe  Tyr Pro Ser
    1100                1105                1110

Asn Gly  Thr Ser Val Ile Ser  Ser Ser Val Ile Ser  Ser Ser Val
    1115                1120                1125

Thr Ser  Ser Leu Phe Thr Ser  Ser Pro Val Ile Ser  Ser Ser Val
    1130                1135                1140

Ile Ser  Ser Ser Thr Thr Thr  Ser Thr Ser Ile Phe  Ser Glu Ser
    1145                1150                1155

Ser Lys  Ser Ser Val Ile Pro  Thr Ser Ser Ser Thr  Ser Gly Ser
    1160                1165                1170

Ser Glu  Ser Glu Thr Ser Ser  Ala Gly Ser Val Ser  Ser Ser Ser
    1175                1180                1185

Phe Ile  Ser Ser Glu Ser Ser  Lys Ser Pro Thr Tyr  Ser Ser Ser
    1190                1195                1200

Ser Leu  Pro Leu Val Thr Ser  Ala Thr Thr Ser Gln  Glu Thr Ala
    1205                1210                1215

Ser Ser  Leu Pro Pro Ala Thr  Thr Thr Lys Thr Ser  Glu Gln Thr
    1220                1225                1230
```

Thr Leu Val Thr Val Thr Ser Cys Glu Ser His Val Cys Thr Glu
1235 1240 1245

Ser Ile Ser Pro Ala Ile Val Ser Thr Ala Thr Val Thr Val Ser
1250 1255 1260

Gly Val Thr Thr Glu Tyr Thr Thr Trp Cys Pro Ile Ser Thr Thr
1265 1270 1275

Glu Thr Thr Lys Gln Thr Lys Gly Thr Thr Glu Gln Thr Thr Glu
1280 1285 1290

Thr Thr Lys Gln Thr Thr Val Val Thr Ile Ser Ser Cys Glu Ser
1295 1300 1305

Asp Val Cys Ser Lys Thr Ala Ser Pro Ala Ile Val Ser Thr Ser
1310 1315 1320

Thr Ala Thr Ile Asn Gly Val Thr Thr Glu Tyr Thr Thr Trp Cys
1325 1330 1335

Pro Ile Ser Thr Thr Glu Ser Arg Gln Gln Thr Thr Leu Val Thr
1340 1345 1350

Val Thr Ser Cys Glu Ser Gly Val Cys Ser Glu Thr Ala Ser Pro
1355 1360 1365

Ala Ile Val Ser Thr Ala Thr Ala Thr Val Asn Asp Val Val Thr
1370 1375 1380

Val Tyr Pro Thr Trp Arg Pro Gln Thr Ala Asn Glu Glu Ser Val
1385 1390 1395

Ser Ser Lys Met Asn Ser Ala Thr Gly Glu Thr Thr Thr Asn Thr
1400 1405 1410

Leu Ala Ala Glu Thr Thr Thr Asn Thr Val Ala Ala Glu Thr Ile
1415 1420 1425

Thr Asn Thr Gly Ala Ala Glu Thr Lys Thr Val Val Thr Ser Ser
1430 1435 1440

Leu Ser Arg Ser Asn His Ala Glu Thr Gln Thr Ala Ser Ala Thr
1445 1450 1455

Asp Val Ile Gly His Ser Ser Ser Val Val Ser Val Ser Glu Thr
1460 1465 1470

Gly Asn Thr Lys Ser Leu Thr Ser Ser Gly Leu Ser Thr Met Ser
1475 1480 1485

Gln Gln Pro Arg Ser Thr Pro Ala Ser Ser Met Val Gly Tyr Ser
1490 1495 1500

Thr Ala Ser Leu Glu Ile Ser Thr Tyr Ala Gly Ser Ala Asn Ser
1505 1510 1515

Leu Leu Ala Gly Ser Gly Leu Ser Val Phe Ile Ala Ser Leu Leu
1520 1525 1530

Leu Ala Ile Ile
1535

<210> SEQ ID NO 148
<211> LENGTH: 335
<212> TYPE: PRT
<213> ORGANISM: Homo sapiens

<400> SEQUENCE: 148

Met Ala Asp Gly Pro Tyr Leu Gln Ile Leu Glu Gln Pro Lys Gln Arg
1 5 10 15

Gly Phe Arg Phe Arg Tyr Val Cys Glu Gly Pro Ser His Gly Gly Leu
20 25 30

Pro Gly Ala Ser Ser Glu Lys Asn Lys Lys Ser Tyr Pro Gln Val Lys

```
        35                  40                  45

Ile Cys Asn Tyr Val Gly Pro Ala Lys Val Ile Val Gln Leu Val Thr
    50                  55                  60

Asn Gly Lys Asn Ile His Leu His Ala His Ser Leu Val Gly Lys His
65                  70                  75                  80

Cys Glu Asp Gly Ile Cys Thr Val Thr Ala Gly Pro Lys Asp Met Val
                85                  90                  95

Val Gly Phe Ala Asn Leu Gly Ile Leu His Val Thr Lys Lys Lys Val
            100                 105                 110

Phe Glu Thr Leu Glu Ala Arg Met Thr Glu Ala Cys Ile Arg Gly Tyr
        115                 120                 125

Asn Pro Gly Leu Leu Val His Pro Asp Leu Ala Tyr Leu Gln Ala Glu
    130                 135                 140

Gly Gly Gly Asp Arg Gln Leu Gly Asp Arg Glu Lys Glu Leu Ile Arg
145                 150                 155                 160

Gln Ala Ala Leu Gln Gln Thr Lys Glu Met Asp Leu Ser Val Val Arg
                165                 170                 175

Leu Met Phe Thr Ala Phe Leu Pro Asp Ser Thr Gly Ser Phe Thr Arg
            180                 185                 190

Arg Leu Glu Pro Val Val Ser Asp Ala Ile Tyr Asp Ser Lys Ala Pro
        195                 200                 205

Asn Ala Ser Asn Leu Lys Ile Val Arg Met Asp Arg Thr Ala Gly Cys
    210                 215                 220

Val Thr Gly Gly Glu Glu Ile Tyr Leu Leu Cys Asp Lys Val Gln Lys
225                 230                 235                 240

Asp Asp Ile Gln Ile Arg Phe Tyr Glu Glu Glu Glu Asn Gly Gly Val
                245                 250                 255

Trp Glu Gly Phe Gly Asp Phe Ser Pro Thr Asp Val His Arg Gln Phe
            260                 265                 270

Ala Ile Val Phe Lys Thr Pro Lys Tyr Lys Asp Ile Asn Ile Thr Lys
        275                 280                 285

Pro Ala Ser Val Phe Val Gln Leu Arg Arg Lys Ser Asp Leu Glu Thr
    290                 295                 300

Ser Glu Pro Lys Pro Phe Leu Tyr Tyr Pro Glu Ile Lys Asp Lys Glu
305                 310                 315                 320

Glu Val Gln Arg Lys Arg Gln Lys Val Gln Arg Lys Arg Gln Lys
                325                 330                 335


<210> SEQ ID NO 149
<211> LENGTH: 18
<212> TYPE: PRT
<213> ORGANISM: phage M13

<400> SEQUENCE: 149

Met Lys Lys Leu Leu Phe Ala Ile Pro Leu Val Val Pro Phe Tyr Ser
1               5                   10                  15

His Ser


<210> SEQ ID NO 150
<211> LENGTH: 23
<212> TYPE: PRT
<213> ORGANISM: phage M13

<400> SEQUENCE: 150

Met Lys Lys Ser Leu Val Leu Lys Ala Ser Val Ala Val Ala Thr Leu
1               5                   10                  15
```

Val Pro Met Leu Ser Phe Ala
20

<210> SEQ ID NO 151
<211> LENGTH: 112
<212> TYPE: PRT
<213> ORGANISM: phage M13

<400> SEQUENCE: 151

Met Pro Val Leu Leu Gly Ile Pro Leu Leu Leu Arg Phe Leu Gly Phe
1 5 10 15

Leu Leu Val Thr Leu Phe Gly Tyr Leu Leu Thr Phe Leu Lys Lys Gly
20 25 30

Phe Gly Lys Ile Ala Ile Ala Ile Ser Leu Phe Leu Ala Leu Ile Ile
35 40 45

Gly Leu Asn Ser Ile Leu Val Gly Tyr Leu Ser Asp Ile Ser Ala Gln
50 55 60

Leu Pro Ser Asp Phe Val Gln Gly Val Gln Leu Ile Leu Pro Ser Asn
65 70 75 80

Ala Leu Pro Cys Phe Tyr Val Ile Leu Ser Val Lys Ala Ala Ile Phe
85 90 95

Ile Phe Asp Val Lys Gln Lys Ile Val Ser Tyr Leu Asp Trp Asp Lys
100 105 110

<210> SEQ ID NO 152
<211> LENGTH: 207
<212> TYPE: PRT
<213> ORGANISM: Artificial Sequence
<220> FEATURE:
<223> OTHER INFORMATION: Engineered sequence

<400> SEQUENCE: 152

Met Asp Lys Asp Cys Glu Met Lys Arg Thr Thr Leu Asp Ser Pro Leu
1 5 10 15

Gly Lys Leu Glu Leu Ser Gly Cys Glu Gln Gly Leu His Glu Ile Lys
20 25 30

Leu Leu Gly Lys Gly Thr Ser Ala Ala Asp Ala Val Glu Val Pro Ala
35 40 45

Pro Ala Ala Val Leu Gly Gly Pro Glu Pro Leu Met Gln Cys Thr Ala
50 55 60

Trp Leu Asn Ala Tyr Phe His Gln Pro Glu Ala Ile Glu Glu Phe Pro
65 70 75 80

Val Pro Ala Leu His His Pro Val Phe Gln Gln Glu Ser Phe Thr Arg
85 90 95

Gln Val Leu Trp Lys Leu Leu Lys Val Val Lys Phe Gly Glu Val Ile
100 105 110

Ser Tyr Gln Gln Leu Ala Ala Leu Ala Gly Asn Pro Lys Ala Ala Arg
115 120 125

Ala Val Gly Gly Ala Met Arg Gly Asn Pro Val Pro Ile Leu Ile Pro
130 135 140

Cys His Arg Val Val Cys Ser Ser Gly Ala Val Gly Asn Tyr Ser Trp
145 150 155 160

Gly Leu Ala Val Lys Glu Trp Leu Leu Ala His Glu Gly His Arg Leu
165 170 175

Gly Lys Pro Gly Leu Gly Gly Ser Ser Gly Leu Ala Gly Ala Trp Leu
180 185 190

```
Lys Gly Ala Gly Ala Thr Ser Gly Ser Pro Pro Ala Gly Arg Asn
        195                 200                 205


<210> SEQ ID NO 153
<211> LENGTH: 207
<212> TYPE: PRT
<213> ORGANISM: Artificial Sequence
<220> FEATURE:
<223> OTHER INFORMATION: Engineered sequence

<400> SEQUENCE: 153

Met Asp Lys Asp Cys Glu Met Lys Arg Thr Thr Leu Asp Ser Pro Leu
1               5                   10                  15

Gly Lys Leu Glu Leu Ser Gly Cys Glu Gln Gly Leu His Glu Ile Lys
            20                  25                  30

Leu Leu Gly Lys Gly Thr Ser Ala Ala Asp Ala Val Glu Val Pro Ala
        35                  40                  45

Pro Ala Ala Val Leu Gly Gly Pro Glu Pro Leu Ile Gln Cys Thr Ala
    50                  55                  60

Trp Leu Asn Ala Tyr Phe His Gln Pro Glu Ala Ile Glu Glu Phe Pro
65                  70                  75                  80

Val Pro Ala Leu His His Pro Val Phe Gln Gln Glu Ser Phe Thr Arg
                85                  90                  95

Gln Val Leu Trp Lys Leu Leu Lys Val Val Lys Phe Gly Glu Val Ile
            100                 105                 110

Ser Glu Gln Gln Leu Ala Ala Leu Val Gly Asn Pro Lys Ala Ala Arg
        115                 120                 125

Ala Val Asn Gly Ala Met Asp Gly Asn Pro Val Pro Ile Leu Ile Pro
    130                 135                 140

Cys His Arg Val Val Cys Ser Ser Ser Ala Val Gly Pro Tyr Leu Trp
145                 150                 155                 160

Gly Leu Ala Val Lys Glu Trp Leu Leu Ala His Glu Gly His Arg Leu
                165                 170                 175

Gly Lys Pro Gly Leu Gly Gly Ser Ser Gly Leu Ala Gly Ala Trp Leu
            180                 185                 190

Lys Gly Ala Gly Ala Thr Ser Gly Ser Pro Pro Ala Gly Arg Asn
        195                 200                 205


<210> SEQ ID NO 154
<211> LENGTH: 407
<212> TYPE: PRT
<213> ORGANISM: phage M13

<400> SEQUENCE: 154

Ser Ala Glu Thr Val Glu Ser Cys Leu Ala Lys Ser His Thr Glu Asn
1               5                   10                  15

Ser Phe Thr Asn Val Trp Lys Asp Asp Lys Thr Leu Asp Arg Tyr Ala
            20                  25                  30

Asn Tyr Glu Gly Cys Leu Trp Asn Ala Thr Gly Val Val Val Cys Thr
        35                  40                  45

Gly Asp Glu Thr Gln Cys Tyr Gly Thr Trp Val Pro Ile Gly Leu Ala
    50                  55                  60

Ile Pro Glu Asn Glu Gly Gly Gly Ser Glu Gly Gly Gly Ser Glu Gly
65                  70                  75                  80

Gly Gly Ser Glu Gly Gly Gly Thr Lys Pro Pro Glu Tyr Gly Asp Thr
                85                  90                  95

Pro Ile Pro Gly Tyr Thr Tyr Ile Asn Pro Leu Asp Gly Thr Tyr Pro
```

```
            100                 105                 110

Pro Gly Thr Glu Gln Asn Pro Ala Asn Pro Asn Pro Ser Leu Glu Glu
        115                 120                 125

Ser Gln Pro Leu Asn Thr Phe Met Phe Gln Asn Asn Arg Phe Arg Asn
    130                 135                 140

Arg Gln Gly Ala Leu Thr Val Tyr Thr Gly Thr Val Thr Gln Gly Thr
145                 150                 155                 160

Asp Pro Val Lys Thr Tyr Tyr Gln Tyr Thr Pro Val Ser Ser Lys Ala
                165                 170                 175

Met Tyr Asp Ala Tyr Trp Asn Gly Lys Phe Arg Asp Cys Ala Phe His
            180                 185                 190

Ser Gly Phe Asn Glu Asp Pro Phe Val Cys Glu Tyr Gln Gly Gln Ser
        195                 200                 205

Ser Asp Leu Pro Gln Pro Pro Val Asn Ala Gly Gly Gly Ser Gly Gly
    210                 215                 220

Gly Ser Gly Gly Gly Ser Glu Gly Gly Gly Ser Glu Gly Gly Gly Ser
225                 230                 235                 240

Glu Gly Gly Gly Ser Glu Gly Gly Gly Ser Gly Gly Gly Ser Gly Ser
                245                 250                 255

Gly Asp Phe Asp Tyr Glu Lys Met Ala Asn Ala Asn Lys Gly Ala Met
            260                 265                 270

Thr Glu Asn Ala Asp Glu Asn Ala Leu Gln Ser Asp Ala Lys Gly Lys
        275                 280                 285

Leu Asp Ser Val Ala Thr Asp Tyr Gly Ala Ala Ile Asp Gly Phe Ile
    290                 295                 300

Gly Asp Val Ser Gly Leu Ala Asn Gly Asn Gly Ala Thr Gly Asp Phe
305                 310                 315                 320

Ala Gly Ser Asn Ser Gln Met Ala Gln Val Gly Asp Gly Asp Asn Ser
                325                 330                 335

Pro Leu Met Asn Asn Phe Arg Gln Tyr Leu Pro Ser Leu Pro Gln Ser
            340                 345                 350

Val Glu Cys Arg Pro Phe Val Phe Ser Ala Gly Lys Pro Tyr Glu Phe
        355                 360                 365

Ser Ile Asp Cys Asp Lys Ile Asn Leu Phe Arg Gly Val Phe Ala Phe
    370                 375                 380

Leu Leu Tyr Val Ala Thr Phe Met Tyr Val Phe Ser Thr Phe Ala Asn
385                 390                 395                 400

Ile Leu Arg Asn Lys Glu Ser
                405


<210> SEQ ID NO 155
<211> LENGTH: 50
<212> TYPE: PRT
<213> ORGANISM: phage M13

<400> SEQUENCE: 155

Ala Glu Gly Asp Asp Pro Ala Lys Ala Ala Phe Asn Ser Leu Gln Ala
1               5                   10                  15

Ser Ala Thr Glu Tyr Ile Gly Tyr Ala Trp Ala Met Val Val Val Ile
            20                  25                  30

Val Gly Ala Thr Ile Gly Ile Lys Leu Phe Lys Lys Phe Thr Ser Lys
        35                  40                  45

Ala Ser
    50
```

<210> SEQ ID NO 156
<211> LENGTH: 285
<212> TYPE: PRT
<213> ORGANISM: Escherichia coli

<400> SEQUENCE: 156

```
Met Thr Asp Leu His Gln Thr Tyr Tyr Arg Gln Val Lys Asn Pro Asn
1               5                   10                  15

Pro Val Phe Thr Pro Arg Glu Gly Ala Gly Thr Leu Lys Phe Cys Glu
            20                  25                  30

Lys Leu Met Glu Lys Ala Val Gly Phe Thr Ser Arg Phe Asp Phe Ala
        35                  40                  45

Ile His Val Ala His Ala Arg Ser Arg Gly Leu Arg Arg Arg Met Pro
    50                  55                  60

Pro Val Leu Arg Arg Arg Ala Ile Asp Ala Leu Leu Gln Gly Leu Cys
65                  70                  75                  80

Phe His Tyr Asp Pro Leu Ala Asn Arg Val Gln Cys Ser Ile Thr Thr
                85                  90                  95

Leu Ala Ile Glu Cys Gly Leu Ala Thr Glu Ser Ala Ala Gly Lys Leu
            100                 105                 110

Ser Ile Thr Arg Ala Thr Arg Ala Leu Thr Phe Leu Ser Glu Leu Gly
        115                 120                 125

Leu Ile Thr Tyr Gln Thr Glu Tyr Asp Pro Leu Ile Gly Cys Tyr Ile
    130                 135                 140

Pro Thr Asp Ile Thr Phe Thr Ser Ala Leu Phe Ala Ala Leu Asp Val
145                 150                 155                 160

Ser Glu Glu Ala Val Ala Ala Ala Arg Arg Ser Arg Val Val Trp Glu
                165                 170                 175

Asn Lys Gln Arg Lys Lys Gln Gly Leu Asp Thr Leu Gly Met Asp Glu
            180                 185                 190

Leu Ile Ala Lys Ala Trp Arg Phe Val Arg Glu Arg Phe Arg Ser Tyr
        195                 200                 205

Gln Thr Glu Leu Lys Ser Arg Gly Ile Lys Arg Ala Arg Ala Arg Arg
    210                 215                 220

Asp Ala Asp Arg Glu Arg Gln Asp Ile Val Thr Leu Val Lys Arg Gln
225                 230                 235                 240

Leu Thr Arg Glu Ile Ala Glu Gly Arg Phe Thr Ala Asn Arg Glu Ala
                245                 250                 255

Val Lys Arg Glu Val Glu Arg Arg Val Lys Glu Arg Met Ile Leu Ser
            260                 265                 270

Arg Asn Arg Asn Tyr Ser Arg Leu Ala Thr Ala Ser Pro
        275                 280                 285
```

<210> SEQ ID NO 157
<211> LENGTH: 725
<212> TYPE: PRT
<213> ORGANISM: Saccharomyces cerevisiae

<400> SEQUENCE: 157

```
Met Thr Leu Ser Phe Ala His Phe Thr Tyr Leu Phe Thr Ile Leu Leu
1               5                   10                  15

Gly Leu Thr Asn Ile Ala Leu Ala Ser Asp Pro Glu Thr Ile Leu Val
            20                  25                  30

Thr Ile Thr Lys Thr Asn Asp Ala Asn Gly Val Val Thr Thr Thr Val
        35                  40                  45
```

-continued

```
Ser Pro Ala Leu Val Ser Thr Ser Thr Ile Val Gln Ala Gly Thr Thr
    50                  55                  60

Thr Leu Tyr Thr Thr Trp Cys Pro Leu Thr Val Ser Thr Ser Ser Ala
65                  70                  75                  80

Ala Glu Ile Ser Pro Ser Ile Ser Tyr Ala Thr Thr Leu Ser Arg Phe
                85                  90                  95

Ser Thr Leu Thr Leu Ser Thr Glu Val Cys Ser His Glu Ala Cys Pro
            100                 105                 110

Ser Ser Ser Thr Leu Pro Thr Thr Thr Leu Ser Val Thr Ser Lys Phe
        115                 120                 125

Thr Ser Tyr Ile Cys Pro Thr Cys His Thr Thr Ala Ile Ser Ser Leu
    130                 135                 140

Ser Glu Val Gly Thr Thr Thr Val Val Ser Ser Ser Ala Ile Glu Pro
145                 150                 155                 160

Ser Ser Ala Ser Ile Ile Ser Pro Val Thr Ser Thr Leu Ser Ser Thr
                165                 170                 175

Thr Ser Ser Asn Pro Thr Thr Thr Ser Leu Ser Ser Thr Ser Thr Ser
            180                 185                 190

Pro Ser Ser Thr Ser Thr Ser Pro Ser Ser Thr Ser Thr Ser Ser Ser
        195                 200                 205

Ser Thr Ser Thr Ser Ser Ser Ser Thr Ser Thr Ser Ser Ser Ser Thr
    210                 215                 220

Ser Thr Ser Pro Ser Ser Thr Ser Thr Ser Ser Ser Leu Thr Ser Thr
225                 230                 235                 240

Ser Ser Ser Ser Thr Ser Thr Ser Gln Ser Ser Thr Ser Thr Ser Ser
                245                 250                 255

Ser Ser Thr Ser Thr Ser Pro Ser Ser Thr Ser Thr Ser Ser Ser Ser
            260                 265                 270

Thr Ser Thr Ser Pro Ser Ser Lys Ser Thr Ser Ala Ser Ser Thr Ser
        275                 280                 285

Thr Ser Ser Tyr Ser Thr Ser Thr Ser Pro Ser Leu Thr Ser Ser Ser
    290                 295                 300

Pro Thr Leu Ala Ser Thr Ser Pro Ser Ser Thr Ser Ile Ser Ser Thr
305                 310                 315                 320

Phe Thr Asp Ser Thr Ser Ser Leu Gly Ser Ser Ile Ala Ser Ser Ser
                325                 330                 335

Thr Ser Val Ser Leu Tyr Ser Pro Ser Thr Pro Val Tyr Ser Val Pro
            340                 345                 350

Ser Thr Ser Ser Asn Val Ala Thr Pro Ser Met Thr Ser Ser Thr Val
        355                 360                 365

Glu Thr Thr Val Ser Ser Gln Ser Ser Ser Glu Tyr Ile Thr Lys Ser
    370                 375                 380

Ser Ile Ser Thr Thr Ile Pro Ser Phe Ser Met Ser Thr Tyr Phe Thr
385                 390                 395                 400

Thr Val Ser Gly Val Thr Thr Met Tyr Thr Thr Trp Cys Pro Tyr Ser
                405                 410                 415

Ser Glu Ser Glu Thr Ser Thr Leu Thr Ser Met His Glu Thr Val Thr
            420                 425                 430

Thr Asp Ala Thr Val Cys Thr His Glu Ser Cys Met Pro Ser Gln Thr
        435                 440                 445

Thr Ser Leu Ile Thr Ser Ser Ile Lys Met Ser Thr Lys Asn Val Ala
    450                 455                 460

Thr Ser Val Ser Thr Ser Thr Val Glu Ser Ser Tyr Ala Cys Ser Thr
```

```
465                 470                 475                 480

Cys Ala Glu Thr Ser His Ser Tyr Ser Ser Val Gln Thr Ala Ser Ser
                485                 490                 495

Ser Ser Val Thr Gln Gln Thr Thr Ser Thr Lys Ser Trp Val Ser Ser
            500                 505                 510

Met Thr Thr Ser Asp Glu Asp Phe Asn Lys His Ala Thr Gly Lys Tyr
        515                 520                 525

His Val Thr Ser Ser Gly Thr Ser Thr Ile Ser Thr Ser Val Ser Glu
    530                 535                 540

Ala Thr Ser Thr Ser Ser Ile Asp Ser Glu Ser Gln Glu Gln Ser Ser
545                 550                 555                 560

His Leu Leu Ser Thr Ser Val Leu Ser Ser Ser Ser Leu Ser Ala Thr
                565                 570                 575

Leu Ser Ser Asp Ser Thr Ile Leu Leu Phe Ser Ser Val Ser Ser Leu
            580                 585                 590

Ser Val Glu Gln Ser Pro Val Thr Thr Leu Gln Ile Ser Ser Thr Ser
        595                 600                 605

Glu Ile Leu Gln Pro Thr Ser Ser Thr Ala Ile Ala Thr Ile Ser Ala
    610                 615                 620

Ser Thr Ser Ser Leu Ser Ala Thr Ser Ile Ser Thr Pro Ser Thr Ser
625                 630                 635                 640

Val Glu Ser Thr Ile Glu Ser Ser Ser Leu Thr Pro Thr Val Ser Ser
                645                 650                 655

Ile Phe Leu Ser Ser Ser Ser Ala Pro Ser Ser Leu Gln Thr Ser Val
            660                 665                 670

Thr Thr Thr Glu Val Ser Thr Thr Ser Ile Ser Ile Gln Tyr Gln Thr
        675                 680                 685

Ser Ser Met Val Thr Ile Ser Gln Tyr Met Gly Ser Gly Ser Gln Thr
    690                 695                 700

Arg Leu Pro Leu Gly Lys Leu Val Phe Ala Ile Met Ala Val Ala Cys
705                 710                 715                 720

Asn Val Ile Phe Ser
                725


<210> SEQ ID NO 158
<211> LENGTH: 761
<212> TYPE: PRT
<213> ORGANISM: phage P2

<400> SEQUENCE: 158

Met Ala Val Lys Ala Ser Gly Arg Phe Val Pro Pro Ser Ala Phe Ala
1               5                   10                  15

Ala Gly Thr Gly Lys Met Phe Thr Gly Ala Tyr Ala Trp Asn Ala Pro
            20                  25                  30

Arg Glu Ala Val Gly Arg Glu Arg Pro Leu Thr Arg Asp Glu Met Arg
        35                  40                  45

Gln Val Gln Gly Val Leu Ser Thr Ile Asn Arg Leu Pro Tyr Phe Leu
    50                  55                  60

Arg Ser Leu Phe Thr Ser Arg Tyr Asp Tyr Ile Arg Arg Asn Lys Ser
65                  70                  75                  80

Pro Val His Gly Phe Tyr Phe Leu Thr Ser Thr Phe Gln Arg Arg Leu
                85                  90                  95

Trp Pro Arg Ile Glu Arg Val Asn Gln Arg His Glu Met Asn Thr Asp
            100                 105                 110
```

```
Ala Ser Leu Leu Phe Leu Ala Glu Arg Asp Gln Tyr Ala Arg Leu Pro
        115                 120                 125

Gly Met Asn Asp Lys Glu Leu Lys Lys Phe Ala Ala Arg Ile Ser Ser
    130                 135                 140

Gln Leu Phe Met Met Tyr Glu Glu Leu Cys Asp Ala Trp Val Asp Ala
145                 150                 155                 160

His Gly Glu Lys Glu Ser Leu Phe Thr Asp Glu Ala Gln Ala His Leu
                165                 170                 175

Tyr Gly His Val Ala Gly Ala Ala Arg Ala Phe Asn Ile Ser Pro Leu
            180                 185                 190

Tyr Trp Lys Lys Tyr Arg Lys Gly Gln Met Thr Thr Arg Gln Ala Tyr
        195                 200                 205

Ser Ala Ile Ala Arg Leu Phe Asn Asp Glu Trp Trp Thr His Gln Leu
    210                 215                 220

Lys Gly Gln Arg Met Arg Trp His Glu Ala Leu Leu Ile Ala Val Gly
225                 230                 235                 240

Glu Val Asn Lys Asp Arg Ser Pro Tyr Ala Ser Lys His Ala Ile Arg
                245                 250                 255

Asp Val Arg Ala Arg Arg Gln Ala Asn Leu Glu Phe Leu Lys Ser Cys
            260                 265                 270

Asp Leu Glu Asn Arg Glu Thr Gly Glu Arg Ile Asp Leu Ile Ser Lys
        275                 280                 285

Val Met Gly Ser Ile Ser Asn Pro Glu Ile Arg Arg Met Glu Leu Met
    290                 295                 300

Asn Thr Ile Ala Gly Ile Glu Arg Tyr Ala Ala Ala Glu Gly Asp Val
305                 310                 315                 320

Gly Met Phe Ile Thr Leu Thr Ala Pro Ser Lys Tyr His Pro Thr Arg
                325                 330                 335

Gln Val Gly Lys Gly Glu Ser Lys Thr Val Gln Leu Asn His Gly Trp
            340                 345                 350

Asn Asp Glu Ala Phe Asn Pro Lys Asp Ala Gln Arg Tyr Leu Cys Arg
        355                 360                 365

Ile Trp Ser Leu Met Arg Thr Ala Phe Lys Asp Asn Asp Leu Gln Val
    370                 375                 380

Tyr Gly Leu Arg Val Val Glu Pro His His Asp Gly Thr Pro His Trp
385                 390                 395                 400

His Met Met Leu Phe Cys His Pro Arg Gln Arg Asn Gln Ile Ile Glu
                405                 410                 415

Ile Met Arg Arg Tyr Ala Leu Lys Glu Asp Gly Asp Glu Arg Gly Ala
            420                 425                 430

Ala Arg Asn Arg Phe Gln Ala Lys His Leu Asn Arg Gly Gly Ala Ala
        435                 440                 445

Gly Tyr Ile Ala Lys Tyr Ile Ser Lys Asn Ile Asp Gly Tyr Ala Leu
    450                 455                 460

Asp Gly Gln Leu Asp Asn Asp Thr Gly Arg Pro Leu Lys Asp Thr Ala
465                 470                 475                 480

Ala Ala Val Thr Ala Trp Ala Ser Thr Trp Arg Ile Pro Gln Phe Lys
                485                 490                 495

Thr Val Gly Leu Pro Thr Met Gly Ala Tyr Arg Glu Leu Arg Lys Leu
            500                 505                 510

Pro Arg Gly Val Ser Ile Ala Asp Glu Phe Asp Glu Arg Val Glu Ala
        515                 520                 525

Ala Arg Ala Ala Ala Asp Ser Gly Asp Phe Ala Leu Tyr Ile Ser Ala
```

```
    530                 535                 540

Gln Gly Gly Ala Asn Val Pro Arg Asp Cys Gln Thr Val Arg Val Ala
545                 550                 555                 560

Arg Ser Leu Ser Asp Asp Val Asn Glu Tyr Glu Glu Glu Val Glu Arg
                565                 570                 575

Val Val Gly Ile Tyr Ala Pro His Leu Gly Ala Arg His Ile His Ile
            580                 585                 590

Thr Arg Thr Thr Asp Trp Arg Ile Val Pro Lys Val Pro Val Val Glu
        595                 600                 605

Pro Leu Thr Leu Lys Ser Gly Ile Ala Ala Pro Arg Ser Pro Val Asn
    610                 615                 620

Asn Cys Gly Lys Leu Thr Gly Ser Asp Thr Ser Leu Pro Ala Pro Thr
625                 630                 635                 640

Pro Tyr Glu His Ala Ala Ala Val Leu Asn Leu Val Asp Asp Gly Val
                645                 650                 655

Ile Glu Trp Asn Glu Pro Glu Val Val Arg Ala Leu Arg Gly Ala Leu
            660                 665                 670

Lys His Glu Leu Arg Thr Pro Asn Arg Gln Gln Arg Asn Gly Ser Pro
        675                 680                 685

Leu Lys Pro His Glu Ile Ala Pro Ser Thr Arg Leu Thr Arg Ser Glu
    690                 695                 700

Arg Thr Gln Ile Thr Arg Ile Arg Val Asp Leu Ala Gln Asn Gly Ile
705                 710                 715                 720

Arg Pro Gln Arg Trp Glu Leu Glu Ala Leu Ala Arg Gly Ala Thr Val
                725                 730                 735

Asn Tyr Asp Gly Lys Lys Phe Thr Tyr Pro Val Ala Asp Glu Trp Pro
            740                 745                 750

Gly Phe Ser Thr Val Met Glu Trp Thr
        755                 760


<210> SEQ ID NO 159
<211> LENGTH: 216
<212> TYPE: PRT
<213> ORGANISM: Artificial Sequence
<220> FEATURE:
<223> OTHER INFORMATION: Synthetic or artificial sequence

<400> SEQUENCE: 159

Cys Gly Ser Lys Leu Ala Glu Tyr Gly Thr Cys Ile Thr Gly Asp Ala
1               5                   10                  15

Leu Val Ala Leu Pro Glu Gly Glu Ser Val Arg Ile Ala Asp Ile Val
            20                  25                  30

Pro Gly Ala Arg Pro Asn Ser Asp Asn Ala Ile Asp Leu Lys Val Leu
        35                  40                  45

Asp Arg His Gly Asn Pro Val Leu Ala Asp Arg Leu Phe His Ser Gly
    50                  55                  60

Glu His Pro Val Tyr Thr Val Arg Thr Val Glu Gly Leu Arg Val Thr
65                  70                  75                  80

Gly Thr Ala Asn His Pro Leu Leu Cys Leu Val Asp Val Ala Gly Val
                85                  90                  95

Pro Thr Leu Leu Trp Lys Leu Ile Asp Glu Ile Lys Pro Gly Asp Tyr
            100                 105                 110

Ala Val Ile Gln Arg Ser Ala Phe Ser Val Asp Cys Ala Gly Phe Ala
        115                 120                 125

Arg Gly Lys Pro Glu Phe Ala Pro Thr Thr Tyr Thr Val Gly Val Pro
```

130 135 140

Gly Leu Val Arg Phe Leu Glu Ala His His Arg Asp Pro Asp Ala Gln
145 150 155 160

Ala Ile Ala Asp Glu Leu Thr Asp Gly Arg Phe Tyr Tyr Ala Lys Val
165 170 175

Ala Ser Val Thr Asp Ala Gly Val Gln Pro Val Tyr Ser Leu Arg Val
180 185 190

Asp Thr Ala Asp His Ala Phe Ile Thr Asn Gly Phe Val Ser His Ala
195 200 205

Leu Glu His His His His His His
210 215

<210> SEQ ID NO 160
<211> LENGTH: 216
<212> TYPE: PRT
<213> ORGANISM: Artificial Sequence
<220> FEATURE:
<223> OTHER INFORMATION: Synthetic or artificial sequence

<400> SEQUENCE: 160

Thr Cys Ser Lys Leu Ala Glu Tyr Gly Thr Cys Ile Thr Gly Asp Ala
1 5 10 15

Leu Val Ala Leu Pro Glu Gly Glu Ser Val Arg Ile Ala Asp Ile Val
20 25 30

Pro Gly Ala Arg Pro Asn Ser Asp Asn Ala Ile Asp Leu Lys Val Leu
35 40 45

Asp Arg His Gly Asn Pro Val Leu Ala Asp Arg Leu Phe His Ser Gly
50 55 60

Glu His Pro Val Tyr Thr Val Arg Thr Val Glu Gly Leu Arg Val Thr
65 70 75 80

Gly Thr Ala Asn His Pro Leu Leu Cys Leu Val Asp Val Ala Gly Val
85 90 95

Pro Thr Leu Leu Trp Lys Leu Ile Asp Glu Ile Lys Pro Gly Asp Tyr
100 105 110

Ala Val Ile Gln Arg Ser Ala Phe Ser Val Asp Cys Ala Gly Phe Ala
115 120 125

Arg Gly Lys Pro Glu Phe Ala Pro Thr Thr Tyr Thr Val Gly Val Pro
130 135 140

Gly Leu Val Arg Phe Leu Glu Ala His His Arg Asp Pro Asp Ala Gln
145 150 155 160

Ala Ile Ala Asp Glu Leu Thr Asp Gly Arg Phe Tyr Tyr Ala Lys Val
165 170 175

Ala Ser Val Thr Asp Ala Gly Val Gln Pro Val Tyr Ser Leu Arg Val
180 185 190

Asp Thr Ala Asp His Ala Phe Ile Thr Asn Gly Phe Val Ser His Ala
195 200 205

Leu Glu His His His His His His
210 215

<210> SEQ ID NO 161
<211> LENGTH: 216
<212> TYPE: PRT
<213> ORGANISM: Artificial Sequence
<220> FEATURE:
<223> OTHER INFORMATION: Synthetic or artificial sequence

<400> SEQUENCE: 161

```
Thr Gly Cys Lys Leu Ala Glu Tyr Gly Thr Cys Ile Thr Gly Asp Ala
1               5                   10                  15

Leu Val Ala Leu Pro Glu Gly Glu Ser Val Arg Ile Ala Asp Ile Val
            20                  25                  30

Pro Gly Ala Arg Pro Asn Ser Asp Asn Ala Ile Asp Leu Lys Val Leu
        35                  40                  45

Asp Arg His Gly Asn Pro Val Leu Ala Asp Arg Leu Phe His Ser Gly
    50                  55                  60

Glu His Pro Val Tyr Thr Val Arg Thr Val Glu Gly Leu Arg Val Thr
65                  70                  75                  80

Gly Thr Ala Asn His Pro Leu Leu Cys Leu Val Asp Val Ala Gly Val
                85                  90                  95

Pro Thr Leu Leu Trp Lys Leu Ile Asp Glu Ile Lys Pro Gly Asp Tyr
            100                 105                 110

Ala Val Ile Gln Arg Ser Ala Phe Ser Val Asp Cys Ala Gly Phe Ala
        115                 120                 125

Arg Gly Lys Pro Glu Phe Ala Pro Thr Thr Tyr Thr Val Gly Val Pro
    130                 135                 140

Gly Leu Val Arg Phe Leu Glu Ala His His Arg Asp Pro Asp Ala Gln
145                 150                 155                 160

Ala Ile Ala Asp Glu Leu Thr Asp Gly Arg Phe Tyr Tyr Ala Lys Val
                165                 170                 175

Ala Ser Val Thr Asp Ala Gly Val Gln Pro Val Tyr Ser Leu Arg Val
            180                 185                 190

Asp Thr Ala Asp His Ala Phe Ile Thr Asn Gly Phe Val Ser His Ala
        195                 200                 205

Leu Glu His His His His His His
    210                 215


<210> SEQ ID NO 162
<211> LENGTH: 216
<212> TYPE: PRT
<213> ORGANISM: Artificial Sequence
<220> FEATURE:
<223> OTHER INFORMATION: Synthetic or artificial sequence

<400> SEQUENCE: 162

Thr Gly Ser Cys Leu Ala Glu Tyr Gly Thr Cys Ile Thr Gly Asp Ala
1               5                   10                  15

Leu Val Ala Leu Pro Glu Gly Glu Ser Val Arg Ile Ala Asp Ile Val
            20                  25                  30

Pro Gly Ala Arg Pro Asn Ser Asp Asn Ala Ile Asp Leu Lys Val Leu
        35                  40                  45

Asp Arg His Gly Asn Pro Val Leu Ala Asp Arg Leu Phe His Ser Gly
    50                  55                  60

Glu His Pro Val Tyr Thr Val Arg Thr Val Glu Gly Leu Arg Val Thr
65                  70                  75                  80

Gly Thr Ala Asn His Pro Leu Leu Cys Leu Val Asp Val Ala Gly Val
                85                  90                  95

Pro Thr Leu Leu Trp Lys Leu Ile Asp Glu Ile Lys Pro Gly Asp Tyr
            100                 105                 110

Ala Val Ile Gln Arg Ser Ala Phe Ser Val Asp Cys Ala Gly Phe Ala
        115                 120                 125

Arg Gly Lys Pro Glu Phe Ala Pro Thr Thr Tyr Thr Val Gly Val Pro
    130                 135                 140
```

Gly Leu Val Arg Phe Leu Glu Ala His His Arg Asp Pro Asp Ala Gln
145 150 155 160

Ala Ile Ala Asp Glu Leu Thr Asp Gly Arg Phe Tyr Tyr Ala Lys Val
165 170 175

Ala Ser Val Thr Asp Ala Gly Val Gln Pro Val Tyr Ser Leu Arg Val
180 185 190

Asp Thr Ala Asp His Ala Phe Ile Thr Asn Gly Phe Val Ser His Ala
195 200 205

Leu Glu His His His His His His
210 215

<210> SEQ ID NO 163
<211> LENGTH: 216
<212> TYPE: PRT
<213> ORGANISM: Artificial Sequence
<220> FEATURE:
<223> OTHER INFORMATION: Synthetic or artificial sequence

<400> SEQUENCE: 163

Thr Gly Ser Lys Cys Ala Glu Tyr Gly Thr Cys Ile Thr Gly Asp Ala
1 5 10 15

Leu Val Ala Leu Pro Glu Gly Glu Ser Val Arg Ile Ala Asp Ile Val
20 25 30

Pro Gly Ala Arg Pro Asn Ser Asp Asn Ala Ile Asp Leu Lys Val Leu
35 40 45

Asp Arg His Gly Asn Pro Val Leu Ala Asp Arg Leu Phe His Ser Gly
50 55 60

Glu His Pro Val Tyr Thr Val Arg Thr Val Glu Gly Leu Arg Val Thr
65 70 75 80

Gly Thr Ala Asn His Pro Leu Leu Cys Leu Val Asp Val Ala Gly Val
85 90 95

Pro Thr Leu Leu Trp Lys Leu Ile Asp Glu Ile Lys Pro Gly Asp Tyr
100 105 110

Ala Val Ile Gln Arg Ser Ala Phe Ser Val Asp Cys Ala Gly Phe Ala
115 120 125

Arg Gly Lys Pro Glu Phe Ala Pro Thr Thr Tyr Thr Val Gly Val Pro
130 135 140

Gly Leu Val Arg Phe Leu Glu Ala His His Arg Asp Pro Asp Ala Gln
145 150 155 160

Ala Ile Ala Asp Glu Leu Thr Asp Gly Arg Phe Tyr Tyr Ala Lys Val
165 170 175

Ala Ser Val Thr Asp Ala Gly Val Gln Pro Val Tyr Ser Leu Arg Val
180 185 190

Asp Thr Ala Asp His Ala Phe Ile Thr Asn Gly Phe Val Ser His Ala
195 200 205

Leu Glu His His His His His His
210 215

<210> SEQ ID NO 164
<211> LENGTH: 216
<212> TYPE: PRT
<213> ORGANISM: Artificial Sequence
<220> FEATURE:
<223> OTHER INFORMATION: Synthetic or artificial sequence

<400> SEQUENCE: 164

Thr Gly Ser Lys Leu Cys Glu Tyr Gly Thr Cys Ile Thr Gly Asp Ala
1 5 10 15

```
Leu Val Ala Leu Pro Glu Gly Glu Ser Val Arg Ile Ala Asp Ile Val
            20                  25                  30

Pro Gly Ala Arg Pro Asn Ser Asp Asn Ala Ile Asp Leu Lys Val Leu
        35                  40                  45

Asp Arg His Gly Asn Pro Val Leu Ala Asp Arg Leu Phe His Ser Gly
    50                  55                  60

Glu His Pro Val Tyr Thr Val Arg Thr Val Glu Gly Leu Arg Val Thr
65                  70                  75                  80

Gly Thr Ala Asn His Pro Leu Leu Cys Leu Val Asp Val Ala Gly Val
                85                  90                  95

Pro Thr Leu Leu Trp Lys Leu Ile Asp Glu Ile Lys Pro Gly Asp Tyr
            100                 105                 110

Ala Val Ile Gln Arg Ser Ala Phe Ser Val Asp Cys Ala Gly Phe Ala
        115                 120                 125

Arg Gly Lys Pro Glu Phe Ala Pro Thr Thr Tyr Thr Val Gly Val Pro
    130                 135                 140

Gly Leu Val Arg Phe Leu Glu Ala His His Arg Asp Pro Asp Ala Gln
145                 150                 155                 160

Ala Ile Ala Asp Glu Leu Thr Asp Gly Arg Phe Tyr Tyr Ala Lys Val
                165                 170                 175

Ala Ser Val Thr Asp Ala Gly Val Gln Pro Val Tyr Ser Leu Arg Val
            180                 185                 190

Asp Thr Ala Asp His Ala Phe Ile Thr Asn Gly Phe Val Ser His Ala
        195                 200                 205

Leu Glu His His His His His His
    210                 215


<210> SEQ ID NO 165
<211> LENGTH: 216
<212> TYPE: PRT
<213> ORGANISM: Artificial Sequence
<220> FEATURE:
<223> OTHER INFORMATION: Synthetic or artificial sequence

<400> SEQUENCE: 165

Thr Gly Ser Lys Leu Ala Glu Cys Gly Thr Cys Ile Thr Gly Asp Ala
1               5                   10                  15

Leu Val Ala Leu Pro Glu Gly Glu Ser Val Arg Ile Ala Asp Ile Val
            20                  25                  30

Pro Gly Ala Arg Pro Asn Ser Asp Asn Ala Ile Asp Leu Lys Val Leu
        35                  40                  45

Asp Arg His Gly Asn Pro Val Leu Ala Asp Arg Leu Phe His Ser Gly
    50                  55                  60

Glu His Pro Val Tyr Thr Val Arg Thr Val Glu Gly Leu Arg Val Thr
65                  70                  75                  80

Gly Thr Ala Asn His Pro Leu Leu Cys Leu Val Asp Val Ala Gly Val
                85                  90                  95

Pro Thr Leu Leu Trp Lys Leu Ile Asp Glu Ile Lys Pro Gly Asp Tyr
            100                 105                 110

Ala Val Ile Gln Arg Ser Ala Phe Ser Val Asp Cys Ala Gly Phe Ala
        115                 120                 125

Arg Gly Lys Pro Glu Phe Ala Pro Thr Thr Tyr Thr Val Gly Val Pro
    130                 135                 140

Gly Leu Val Arg Phe Leu Glu Ala His His Arg Asp Pro Asp Ala Gln
145                 150                 155                 160
```

```
Ala Ile Ala Asp Glu Leu Thr Asp Gly Arg Phe Tyr Tyr Ala Lys Val
                165                 170                 175

Ala Ser Val Thr Asp Ala Gly Val Gln Pro Val Tyr Ser Leu Arg Val
            180                 185                 190

Asp Thr Ala Asp His Ala Phe Ile Thr Asn Gly Phe Val Ser His Ala
        195                 200                 205

Leu Glu His His His His His His
    210                 215
```

<210> SEQ ID NO 166
<211> LENGTH: 218
<212> TYPE: PRT
<213> ORGANISM: Artificial Sequence
<220> FEATURE:
<223> OTHER INFORMATION: Synthetic or artificial sequence

<400> SEQUENCE: 166

```
Thr Gly Ser Lys Tyr Leu Asn Ala Glu Cys Gly Thr Cys Ile Thr Gly
1               5                   10                  15

Asp Ala Leu Val Ala Leu Pro Glu Gly Glu Ser Val Arg Ile Ala Asp
            20                  25                  30

Ile Val Pro Gly Ala Arg Pro Asn Ser Asp Asn Ala Ile Asp Leu Lys
        35                  40                  45

Val Leu Asp Arg His Gly Asn Pro Val Leu Ala Asp Arg Leu Phe His
    50                  55                  60

Ser Gly Glu His Pro Val Tyr Thr Val Arg Thr Val Glu Gly Leu Arg
65                  70                  75                  80

Val Thr Gly Thr Ala Asn His Pro Leu Leu Cys Leu Val Asp Val Ala
                85                  90                  95

Gly Val Pro Thr Leu Leu Trp Lys Leu Ile Asp Glu Ile Lys Pro Gly
            100                 105                 110

Asp Tyr Ala Val Ile Gln Arg Ser Ala Phe Ser Val Asp Cys Ala Gly
        115                 120                 125

Phe Ala Arg Gly Lys Pro Glu Phe Ala Pro Thr Thr Tyr Thr Val Gly
    130                 135                 140

Val Pro Gly Leu Val Arg Phe Leu Glu Ala His His Arg Asp Pro Asp
145                 150                 155                 160

Ala Gln Ala Ile Ala Asp Glu Leu Thr Asp Gly Arg Phe Tyr Tyr Ala
                165                 170                 175

Lys Val Ala Ser Val Thr Asp Ala Gly Val Gln Pro Val Tyr Ser Leu
            180                 185                 190

Arg Val Asp Thr Ala Asp His Ala Phe Ile Thr Asn Gly Phe Val Ser
        195                 200                 205

His Ala Leu Glu His His His His His His
    210                 215
```

<210> SEQ ID NO 167
<211> LENGTH: 220
<212> TYPE: PRT
<213> ORGANISM: Artificial Sequence
<220> FEATURE:
<223> OTHER INFORMATION: Synthetic or artificial sequence

<400> SEQUENCE: 167

```
Thr Gly Ser His Lys Tyr Leu Arg Asn Ala Glu Cys Gly Thr Cys Ile
1               5                   10                  15

Thr Gly Asp Ala Leu Val Ala Leu Pro Glu Gly Glu Ser Val Arg Ile
```

```
            20                  25                  30

Ala Asp Ile Val Pro Gly Ala Arg Pro Asn Ser Asp Asn Ala Ile Asp
        35                  40                  45

Leu Lys Val Leu Asp Arg His Gly Asn Pro Val Leu Ala Asp Arg Leu
    50                  55                  60

Phe His Ser Gly Glu His Pro Val Tyr Thr Val Arg Thr Val Glu Gly
65                  70                  75                  80

Leu Arg Val Thr Gly Thr Ala Asn His Pro Leu Leu Cys Leu Val Asp
                85                  90                  95

Val Ala Gly Val Pro Thr Leu Leu Trp Lys Leu Ile Asp Glu Ile Lys
            100                 105                 110

Pro Gly Asp Tyr Ala Val Ile Gln Arg Ser Ala Phe Ser Val Asp Cys
        115                 120                 125

Ala Gly Phe Ala Arg Gly Lys Pro Glu Phe Ala Pro Thr Thr Tyr Thr
    130                 135                 140

Val Gly Val Pro Gly Leu Val Arg Phe Leu Glu Ala His His Arg Asp
145                 150                 155                 160

Pro Asp Ala Gln Ala Ile Ala Asp Glu Leu Thr Asp Gly Arg Phe Tyr
                165                 170                 175

Tyr Ala Lys Val Ala Ser Val Thr Asp Ala Gly Val Gln Pro Val Tyr
            180                 185                 190

Ser Leu Arg Val Asp Thr Ala Asp His Ala Phe Ile Thr Asn Gly Phe
        195                 200                 205

Val Ser His Ala Leu Glu His His His His His His
    210                 215                 220


<210> SEQ ID NO 168
<211> LENGTH: 10
<212> TYPE: PRT
<213> ORGANISM: Artificial Sequence
<220> FEATURE:
<223> OTHER INFORMATION: Synthetic or artificial sequence

<400> SEQUENCE: 168

Met Gly Ser Glu Ala Gly Cys Asn Ile Ala
1               5                   10


<210> SEQ ID NO 169
<211> LENGTH: 206
<212> TYPE: PRT
<213> ORGANISM: Artificial Sequence
<220> FEATURE:
<223> OTHER INFORMATION: Synthetic or artificial sequence

<400> SEQUENCE: 169

Cys Ile Thr Gly Asp Ala Leu Val Ala Leu Pro Glu Gly Glu Ser Val
1               5                   10                  15

Arg Ile Ala Asp Ile Val Pro Gly Ala Arg Pro Asn Ser Asp Asn Ala
            20                  25                  30

Ile Asp Leu Lys Val Leu Asp Arg His Gly Asn Pro Val Leu Ala Asp
        35                  40                  45

Arg Leu Phe His Ser Gly Glu His Pro Val Tyr Thr Val Arg Thr Val
    50                  55                  60

Glu Gly Leu Arg Val Thr Gly Thr Ala Asn His Pro Leu Leu Cys Leu
65                  70                  75                  80

Val Asp Val Ala Gly Val Pro Thr Leu Leu Trp Lys Leu Ile Asp Glu
                85                  90                  95
```

```
Ile Lys Pro Gly Asp Tyr Ala Val Ile Gln Arg Ser Ala Phe Ser Val
            100                 105                 110

Asp Cys Ala Gly Phe Ala Arg Gly Lys Pro Glu Phe Ala Pro Thr Thr
        115                 120                 125

Tyr Thr Val Gly Val Pro Gly Leu Val Arg Phe Leu Glu Ala His His
    130                 135                 140

Arg Asp Pro Asp Ala Gln Ala Ile Ala Asp Glu Leu Thr Asp Gly Arg
145                 150                 155                 160

Phe Tyr Tyr Ala Lys Val Ala Ser Val Thr Asp Ala Gly Val Gln Pro
                165                 170                 175

Val Tyr Ser Leu Arg Val Asp Thr Ala Asp His Ala Phe Ile Thr Asn
            180                 185                 190

Gly Phe Val Ser His Ala Leu Glu His His His His His His
        195                 200                 205


<210> SEQ ID NO 170
<211> LENGTH: 10
<212> TYPE: PRT
<213> ORGANISM: Artificial Sequence
<220> FEATURE:
<223> OTHER INFORMATION: Synthetic or artificial sequence

<400> SEQUENCE: 170

Met Gly Ser Glu Cys Gly Thr Asn Ile Ala
1               5                   10


<210> SEQ ID NO 171
<211> LENGTH: 10
<212> TYPE: PRT
<213> ORGANISM: Artificial Sequence
<220> FEATURE:
<223> OTHER INFORMATION: Synthetic or artificial sequence

<400> SEQUENCE: 171

Met Gly Cys Glu Ala Gly Thr Asn Ile Ala
1               5                   10


<210> SEQ ID NO 172
<211> LENGTH: 213
<212> TYPE: PRT
<213> ORGANISM: Artificial Sequence
<220> FEATURE:
<223> OTHER INFORMATION: Synthetic or artificial sequence

<400> SEQUENCE: 172

His Pro Gln Phe Cys Gly Asp Cys Ile Thr Gly Asp Ala Leu Val Ala
1               5                   10                  15

Leu Pro Glu Gly Glu Ser Val Arg Ile Ala Asp Ile Val Pro Gly Ala
            20                  25                  30

Arg Pro Asn Ser Asp Asn Ala Ile Asp Leu Lys Val Leu Asp Arg His
        35                  40                  45

Gly Asn Pro Val Leu Ala Asp Arg Leu Phe His Ser Gly Glu His Pro
    50                  55                  60

Val Tyr Thr Val Arg Thr Val Glu Gly Leu Arg Val Thr Gly Thr Ala
65                  70                  75                  80

Asn His Pro Leu Leu Cys Leu Val Asp Val Ala Gly Val Pro Thr Leu
                85                  90                  95

Leu Trp Lys Leu Ile Asp Glu Ile Lys Pro Gly Asp Tyr Ala Val Ile
            100                 105                 110

Gln Arg Ser Ala Phe Ser Val Asp Cys Ala Gly Phe Ala Arg Gly Lys
```

```
        115                 120                 125

Pro Glu Phe Ala Pro Thr Thr Tyr Thr Val Gly Val Pro Gly Leu Val
    130                 135                 140

Arg Phe Leu Glu Ala His His Arg Asp Pro Asp Ala Gln Ala Ile Ala
145                 150                 155                 160

Asp Glu Leu Thr Asp Gly Arg Phe Tyr Tyr Ala Lys Val Ala Ser Val
                165                 170                 175

Thr Asp Ala Gly Val Gln Pro Val Tyr Ser Leu Arg Val Asp Thr Ala
            180                 185                 190

Asp His Ala Phe Ile Thr Asn Gly Phe Val Ser His Ala Leu Glu His
        195                 200                 205

His His His His His
    210


<210> SEQ ID NO 173
<211> LENGTH: 215
<212> TYPE: PRT
<213> ORGANISM: Artificial Sequence
<220> FEATURE:
<223> OTHER INFORMATION: Synthetic or artificial sequence

<400> SEQUENCE: 173

His Pro Gln Gly Pro Pro Cys Gly Asp Cys Ile Thr Gly Asp Ala Leu
1               5                   10                  15

Val Ala Leu Pro Glu Gly Glu Ser Val Arg Ile Ala Asp Ile Val Pro
            20                  25                  30

Gly Ala Arg Pro Asn Ser Asp Asn Ala Ile Asp Leu Lys Val Leu Asp
        35                  40                  45

Arg His Gly Asn Pro Val Leu Ala Asp Arg Leu Phe His Ser Gly Glu
    50                  55                  60

His Pro Val Tyr Thr Val Arg Thr Val Glu Gly Leu Arg Val Thr Gly
65                  70                  75                  80

Thr Ala Asn His Pro Leu Leu Cys Leu Val Asp Val Ala Gly Val Pro
                85                  90                  95

Thr Leu Leu Trp Lys Leu Ile Asp Glu Ile Lys Pro Gly Asp Tyr Ala
            100                 105                 110

Val Ile Gln Arg Ser Ala Phe Ser Val Asp Cys Ala Gly Phe Ala Arg
        115                 120                 125

Gly Lys Pro Glu Phe Ala Pro Thr Thr Tyr Thr Val Gly Val Pro Gly
    130                 135                 140

Leu Val Arg Phe Leu Glu Ala His His Arg Asp Pro Asp Ala Gln Ala
145                 150                 155                 160

Ile Ala Asp Glu Leu Thr Asp Gly Arg Phe Tyr Tyr Ala Lys Val Ala
                165                 170                 175

Ser Val Thr Asp Ala Gly Val Gln Pro Val Tyr Ser Leu Arg Val Asp
            180                 185                 190

Thr Ala Asp His Ala Phe Ile Thr Asn Gly Phe Val Ser His Ala Leu
        195                 200                 205

Glu His His His His His His
    210                 215


<210> SEQ ID NO 174
<211> LENGTH: 218
<212> TYPE: PRT
<213> ORGANISM: Artificial Sequence
<220> FEATURE:
<223> OTHER INFORMATION: Synthetic or artificial sequence
```

<400> SEQUENCE: 174

Phe Thr Asn Val His Pro Gln Phe Ala Asn Cys Asp Cys Ile Thr Gly
1 5 10 15

Asp Ala Leu Val Ala Leu Pro Glu Gly Glu Ser Val Arg Ile Ala Asp
20 25 30

Ile Val Pro Gly Ala Arg Pro Asn Ser Asp Asn Ala Ile Asp Leu Lys
35 40 45

Val Leu Asp Arg His Gly Asn Pro Val Leu Ala Asp Arg Leu Phe His
50 55 60

Ser Gly Glu His Pro Val Tyr Thr Val Arg Thr Val Glu Gly Leu Arg
65 70 75 80

Val Thr Gly Thr Ala Asn His Pro Leu Leu Cys Leu Val Asp Val Ala
85 90 95

Gly Val Pro Thr Leu Leu Trp Lys Leu Ile Asp Glu Ile Lys Pro Gly
100 105 110

Asp Tyr Ala Val Ile Gln Arg Ser Ala Phe Ser Val Asp Cys Ala Gly
115 120 125

Phe Ala Arg Gly Lys Pro Glu Phe Ala Pro Thr Thr Tyr Thr Val Gly
130 135 140

Val Pro Gly Leu Val Arg Phe Leu Glu Ala His His Arg Asp Pro Asp
145 150 155 160

Ala Gln Ala Ile Ala Asp Glu Leu Thr Asp Gly Arg Phe Tyr Tyr Ala
165 170 175

Lys Val Ala Ser Val Thr Asp Ala Gly Val Gln Pro Val Tyr Ser Leu
180 185 190

Arg Val Asp Thr Ala Asp His Ala Phe Ile Thr Asn Gly Phe Val Ser
195 200 205

His Ala Leu Glu His His His His His His
210 215

<210> SEQ ID NO 175
<211> LENGTH: 37
<212> TYPE: PRT
<213> ORGANISM: Artificial Sequence
<220> FEATURE:
<223> OTHER INFORMATION: Synthetic or artificial sequence

<400> SEQUENCE: 175

Met Val Lys Val Ile Gly Arg Arg Ser Leu Gly Val Gln Arg Ile Phe
1 5 10 15

Asp Ile Gly Leu Pro Gln Asp His Asn Phe Leu Leu Ala Asn Gly Ala
20 25 30

Ile Ala His Asn Cys
35

<210> SEQ ID NO 176
<211> LENGTH: 186
<212> TYPE: PRT
<213> ORGANISM: Artificial Sequence
<220> FEATURE:
<223> OTHER INFORMATION: Synthetic or artificial sequence

<400> SEQUENCE: 176

Thr Asn Cys His Pro Gln Phe Ala Asn Ala Cys Leu Ser Phe Gly Thr
1 5 10 15

Glu Ile Leu Thr Val Glu Tyr Gly Pro Leu Pro Ile Gly Lys Ile Val
20 25 30

Ser Glu Glu Ile Asn Cys Ser Val Tyr Ser Val Asp Pro Glu Gly Arg
35 40 45

Val Tyr Thr Gln Ala Ile Ala Gln Trp His Asp Arg Gly Glu Gln Glu
50 55 60

Val Leu Glu Tyr Glu Leu Glu Asp Gly Ser Val Ile Arg Ala Thr Ser
65 70 75 80

Asp His Arg Phe Leu Thr Thr Asp Tyr Gln Leu Leu Ala Ile Glu Glu
85 90 95

Ile Phe Ala Arg Gln Leu Asp Leu Leu Thr Leu Glu Asn Ile Lys Gln
100 105 110

Thr Glu Glu Ala Leu Asp Asn His Arg Leu Pro Phe Pro Leu Leu Asp
115 120 125

Ala Gly Thr Ile Lys Gly Thr Thr Asn Pro Gly Val Ser Ala Trp Gln
130 135 140

Val Asn Thr Ala Tyr Thr Ala Gly Gln Leu Val Thr Tyr Asn Gly Lys
145 150 155 160

Thr Tyr Lys Cys Leu Gln Pro His Thr Ser Leu Ala Gly Trp Glu Pro
165 170 175

Ser Asn Val Pro Ala Leu Trp Gln Leu Gln
180 185

<210> SEQ ID NO 177
<211> LENGTH: 37
<212> TYPE: PRT
<213> ORGANISM: Artificial Sequence
<220> FEATURE:
<223> OTHER INFORMATION: Synthetic or artificial sequence

<400> SEQUENCE: 177

Met Val Lys Val Ile Gly Arg Arg Ser Leu Gly Val Gln Arg Ile Phe
1 5 10 15

Asp Ile Gly Leu Pro Gln Asp His Asn Phe Leu Leu Ala Asn Gly Ala
20 25 30

Ile Ala His Asn Ser
35

<210> SEQ ID NO 178
<211> LENGTH: 186
<212> TYPE: PRT
<213> ORGANISM: Artificial Sequence
<220> FEATURE:
<223> OTHER INFORMATION: Synthetic or artificial sequence

<400> SEQUENCE: 178

Thr Asn Cys His Pro Gln Phe Ala Asn Ala Cys Leu Ser Phe Gly Thr
1 5 10 15

Glu Ile Leu Thr Val Glu Tyr Gly Pro Leu Pro Ile Gly Lys Ile Val
20 25 30

Ser Glu Glu Ile Asn Cys Ser Val Tyr Ser Val Asp Pro Glu Gly Arg
35 40 45

Val Tyr Thr Gln Ala Ile Ala Gln Trp His Asp Arg Gly Glu Gln Glu
50 55 60

Val Leu Glu Tyr Glu Leu Glu Asp Gly Ser Val Ile Arg Ala Thr Ser
65 70 75 80

Asp His Arg Phe Leu Thr Thr Asp Tyr Gln Leu Leu Ala Ile Glu Glu
85 90 95

Ile Phe Ala Arg Gln Leu Asp Leu Leu Thr Leu Glu Asn Ile Lys Gln

```
            100                 105                 110

Thr Glu Glu Ala Leu Asp Asn His Arg Leu Pro Phe Pro Leu Leu Asp
        115                 120                 125

Ala Gly Thr Ile Lys Gly Thr Thr Asn Pro Gly Val Ser Ala Trp Gln
    130                 135                 140

Val Asn Thr Ala Tyr Thr Ala Gly Gln Leu Val Thr Tyr Asn Gly Lys
145                 150                 155                 160

Thr Tyr Lys Cys Leu Gln Pro His Thr Ser Leu Ala Gly Trp Glu Pro
                165                 170                 175

Ser Asn Val Pro Ala Leu Trp Gln Leu Gln
            180                 185


<210> SEQ ID NO 179
<211> LENGTH: 186
<212> TYPE: PRT
<213> ORGANISM: Artificial Sequence
<220> FEATURE:
<223> OTHER INFORMATION: Synthetic or artificial sequence

<400> SEQUENCE: 179

Thr Asn Cys His Pro Gln Phe Ala Asn Ala Cys Leu Ser Phe Gly Thr
1               5                   10                  15

Glu Ile Leu Thr Val Glu Tyr Gly Pro Leu Pro Ile Gly Lys Ile Val
            20                  25                  30

Ser Glu Glu Ile Asn Cys Ser Val Tyr Ser Val Asp Pro Glu Gly Arg
        35                  40                  45

Val Tyr Thr Gln Ala Ile Ala Gln Trp His Asp Arg Gly Glu Gln Glu
    50                  55                  60

Val Leu Glu Tyr Glu Leu Glu Asp Gly Ser Val Ile Arg Ala Thr Ser
65                  70                  75                  80

Asp His Arg Phe Leu Thr Thr Asp Tyr Gln Leu Leu Ala Ile Glu Glu
                85                  90                  95

Ile Phe Ala Arg Gln Leu Asp Leu Leu Thr Leu Glu Asn Ile Lys Gln
            100                 105                 110

Thr Glu Glu Ala Leu Asp Asn His Arg Leu Pro Phe Pro Leu Leu Asp
        115                 120                 125

Ala Gly Thr Ile Lys Gly Thr Thr Asn Pro Gly Val Ser Ala Trp Gln
    130                 135                 140

Val Asn Thr Ala Tyr Thr Ala Gly Gln Leu Val Thr Tyr Asn Gly Lys
145                 150                 155                 160

Thr Tyr Lys Cys Leu Gln Pro His Thr Ser Leu Ala Gly Trp Glu Pro
                165                 170                 175

Ser Asn Val Pro Ala Leu Trp Gln Leu Gln
            180                 185


<210> SEQ ID NO 180
<211> LENGTH: 190
<212> TYPE: PRT
<213> ORGANISM: Artificial Sequence
<220> FEATURE:
<223> OTHER INFORMATION: Synthetic or artificial sequence

<400> SEQUENCE: 180

Thr Asn Val His Pro Gln Phe Cys Asn Ala Lys Gly Asp Ala Cys Leu
1               5                   10                  15

Ser Phe Gly Thr Glu Ile Leu Thr Val Glu Tyr Gly Pro Leu Pro Ile
            20                  25                  30
```

```
Gly Lys Ile Val Ser Glu Glu Ile Asn Cys Ser Val Tyr Ser Val Asp
        35                  40                  45

Pro Glu Gly Arg Val Tyr Thr Gln Ala Ile Ala Gln Trp His Asp Arg
    50                  55                  60

Gly Glu Gln Glu Val Leu Glu Tyr Glu Leu Glu Asp Gly Ser Val Ile
65                  70                  75                  80

Arg Ala Thr Ser Asp His Arg Phe Leu Thr Thr Asp Tyr Gln Leu Leu
                85                  90                  95

Ala Ile Glu Glu Ile Phe Ala Arg Gln Leu Asp Leu Leu Thr Leu Glu
            100                 105                 110

Asn Ile Lys Gln Thr Glu Glu Ala Leu Asp Asn His Arg Leu Pro Phe
        115                 120                 125

Pro Leu Leu Asp Ala Gly Thr Ile Lys Gly Thr Thr Asn Pro Gly Val
    130                 135                 140

Ser Ala Trp Gln Val Asn Thr Ala Tyr Thr Ala Gly Gln Leu Val Thr
145                 150                 155                 160

Tyr Asn Gly Lys Thr Tyr Lys Cys Leu Gln Pro His Thr Ser Leu Ala
                165                 170                 175

Gly Trp Glu Pro Ser Asn Val Pro Ala Leu Trp Gln Leu Gln
            180                 185                 190
```

<210> SEQ ID NO 181
<211> LENGTH: 192
<212> TYPE: PRT
<213> ORGANISM: Artificial Sequence
<220> FEATURE:
<223> OTHER INFORMATION: Synthetic or artificial sequence

<400> SEQUENCE: 181

```
Thr Asn Val His Pro Gln Phe Cys Asn Ala Lys Gly Asp Thr Gln Ala
1               5                   10                  15

Cys Leu Ser Phe Gly Thr Glu Ile Leu Thr Val Glu Tyr Gly Pro Leu
            20                  25                  30

Pro Ile Gly Lys Ile Val Ser Glu Glu Ile Asn Cys Ser Val Tyr Ser
        35                  40                  45

Val Asp Pro Glu Gly Arg Val Tyr Thr Gln Ala Ile Ala Gln Trp His
    50                  55                  60

Asp Arg Gly Glu Gln Glu Val Leu Glu Tyr Glu Leu Glu Asp Gly Ser
65                  70                  75                  80

Val Ile Arg Ala Thr Ser Asp His Arg Phe Leu Thr Thr Asp Tyr Gln
                85                  90                  95

Leu Leu Ala Ile Glu Glu Ile Phe Ala Arg Gln Leu Asp Leu Leu Thr
            100                 105                 110

Leu Glu Asn Ile Lys Gln Thr Glu Glu Ala Leu Asp Asn His Arg Leu
        115                 120                 125

Pro Phe Pro Leu Leu Asp Ala Gly Thr Ile Lys Gly Thr Thr Asn Pro
    130                 135                 140

Gly Val Ser Ala Trp Gln Val Asn Thr Ala Tyr Thr Ala Gly Gln Leu
145                 150                 155                 160

Val Thr Tyr Asn Gly Lys Thr Tyr Lys Cys Leu Gln Pro His Thr Ser
                165                 170                 175

Leu Ala Gly Trp Glu Pro Ser Asn Val Pro Ala Leu Trp Gln Leu Gln
            180                 185                 190
```

<210> SEQ ID NO 182
<211> LENGTH: 17
<212> TYPE: PRT
<213> ORGANISM: Artificial Sequence
<220> FEATURE:
<223> OTHER INFORMATION: Synthetic or artificial sequence

<400> SEQUENCE: 182

His Pro Gln Phe Cys Glu Asn Leu Tyr Phe Gln Ser Cys Asn Thr Ser
1 5 10 15

Lys

<210> SEQ ID NO 183
<211> LENGTH: 8
<212> TYPE: PRT
<213> ORGANISM: Artificial Sequence
<220> FEATURE:
<223> OTHER INFORMATION: Synthetic or artificial sequence

<400> SEQUENCE: 183

Met Gly Cys Ala Tyr Asp Ser Gly
1 5

<210> SEQ ID NO 184
<211> LENGTH: 213
<212> TYPE: PRT
<213> ORGANISM: Artificial Sequence
<220> FEATURE:
<223> OTHER INFORMATION: Synthetic or artificial sequence

<400> SEQUENCE: 184

His Pro Gln Phe Cys Gly Thr Cys Ile Thr Gly Asp Ala Leu Val Ala
1 5 10 15

Leu Pro Glu Gly Glu Ser Val Arg Ile Ala Asp Ile Val Pro Gly Ala
20 25 30

Arg Pro Asn Ser Asp Asn Ala Ile Asp Leu Lys Val Leu Asp Arg His
35 40 45

Gly Asn Pro Val Leu Ala Asp Arg Leu Phe His Ser Gly Glu His Pro
50 55 60

Val Tyr Thr Val Arg Thr Val Glu Gly Leu Arg Val Thr Gly Thr Ala
65 70 75 80

Asn His Pro Leu Leu Cys Leu Val Asp Val Ala Gly Val Pro Thr Leu
85 90 95

Leu Trp Lys Leu Ile Asp Glu Ile Lys Pro Gly Asp Tyr Ala Val Ile
100 105 110

Gln Arg Ser Ala Phe Ser Val Asp Cys Ala Gly Phe Ala Arg Gly Lys
115 120 125

Pro Glu Phe Ala Pro Thr Thr Tyr Thr Val Gly Val Pro Gly Leu Val
130 135 140

Arg Phe Leu Glu Ala His His Arg Asp Pro Asp Ala Gln Ala Ile Ala
145 150 155 160

Asp Glu Leu Thr Asp Gly Arg Phe Tyr Tyr Ala Lys Val Ala Ser Val
165 170 175

Thr Asp Ala Gly Val Gln Pro Val Tyr Ser Leu Arg Val Asp Thr Ala
180 185 190

Asp His Ala Phe Ile Thr Asn Gly Phe Val Ser His Ala Leu Glu His
195 200 205

His His His His His
210

-continued

```
<210> SEQ ID NO 185
<211> LENGTH: 4
<212> TYPE: PRT
<213> ORGANISM: Artificial Sequence
<220> FEATURE:
<223> OTHER INFORMATION: Synthetic or artificial sequence

<400> SEQUENCE: 185

His Pro Gln Phe
1


<210> SEQ ID NO 186
<211> LENGTH: 4
<212> TYPE: PRT
<213> ORGANISM: Artificial Sequence
<220> FEATURE:
<223> OTHER INFORMATION: Synthetic or artificial sequence

<400> SEQUENCE: 186

Asn Thr Ser Lys
1


<210> SEQ ID NO 187
<211> LENGTH: 7
<212> TYPE: PRT
<213> ORGANISM: Artificial Sequence
<220> FEATURE:
<223> OTHER INFORMATION: Synthetic or artificial sequence

<400> SEQUENCE: 187

Glu Asn Leu Tyr Phe Gln Ser
1               5


<210> SEQ ID NO 188
<211> LENGTH: 5
<212> TYPE: PRT
<213> ORGANISM: Artificial Sequence
<220> FEATURE:
<223> OTHER INFORMATION: Synthetic or artificial sequence

<400> SEQUENCE: 188

Ala Tyr Asp Ser Gly
1               5


<210> SEQ ID NO 189
<211> LENGTH: 10
<212> TYPE: PRT
<213> ORGANISM: Artificial Sequence
<220> FEATURE:
<223> OTHER INFORMATION: synthetic or artificial sequence

<400> SEQUENCE: 189

Thr Asn Cys His Pro Gln Phe Ala Asn Ala
1               5                   10
```